United States Patent
Kayakiri et al.

(10) Patent No.: US 6,348,474 B1
(45) Date of Patent: Feb. 19, 2002

(54) SULFONAMIDE COMPOUNDS AND MEDICINAL USE THEREOF

(75) Inventors: Hiroshi Kayakiri, Suita; Yoshito Abe, Tsukuba; Hitoshi Hamashima, Kyoto; Hitoshi Sawada; Tsuyoshi Mizutani, both of Tsukuba; Teruo Oku, Takatsuki; Noritsugu Yamasaki, Himeji; Osamu Onomura, Nagasaki; Masahiro Nishikawa, Arai; Takahiro Hiramura, Arai; Takafumi Imoto, Arai, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/446,110

(22) PCT Filed: Jun. 24, 1998

(86) PCT No.: PCT/JP98/02877

§ 371 Date: Feb. 14, 2000

§ 102(e) Date: Feb. 14, 2000

(87) PCT Pub. No.: WO99/00372

PCT Pub. Date: Jan. 7, 1999

(30) Foreign Application Priority Data

Jun. 27, 1997 (JP) ................................. 9-208295
Apr. 24, 1998 (JP) ................................. 10-114718

(51) Int. Cl.[7] ..................... A61K 31/435; C07D 471/04
(52) U.S. Cl. .................. 514/303; 514/299; 514/300; 546/112; 546/113; 546/118; 546/119
(58) Field of Search .................. 546/112, 113, 546/118, 119; 514/299, 300, 303

(56) References Cited

U.S. PATENT DOCUMENTS 4,606,753 A    8/1986   Powell ...................... 71/88

FOREIGN PATENT DOCUMENTS

| EP | 0 468 785 | 1/1992 |
|----|-----------|--------|
| EP | 0 507 594 | 10/1992 |
| EP | 0 844 245 | 5/1998 |
| HU | P9500685 | 2/1996 |
| WO | 93/19067 | * 9/1993 |
| WO | WO 93/19067 | 9/1993 |
| WO | WO 94/05639 | 3/1994 |
| WO | WO 96/26195 | 8/1996 |
| WO | WO 96/33190 | 10/1996 |
| WO | WO 97/24334 | 7/1997 |

OTHER PUBLICATIONS

H. T. Beauchamp, et al., "In Vivo Receptor Occupancy Of The Angiotensin II Receptor By Nonpeptide Antagonists: Relationship To In Vitro Affinities And In Vivo Pharmacologic Potency", *The Journal of Pharmacology and Experimental Therapeutics*, 1995, vol. 272, No. 2, pp. 612–618.

* cited by examiner

Primary Examiner—Bernard Dentz
(74) Attorney, Agent, or Firm—Oblon, Spivak, McClelland, Maier & Neustadt, P.C.

(57) ABSTRACT

A sulfonamide compound of the formula (I):

$$R^1\text{—}SO_2NHCO\text{—}A\text{—}R^2 \qquad (I)$$

wherein $R^1$ is alkyl, alkenyl, alkynyl and the like; A is an optionally substituted heteropolycyclic group except benzimidazolyl, indolyl, 4,7-dihydrobenzimidazolyl and 2,3-dihydrobenzoxazinyl; X is alkylene, oxa, oxa(lower) alkylene and the like; and $R^2$ is optionally substituted aryl, substituted biphenylyl and the like, a salt thereof and a pharmaceutical composition comprising the same. The sulfonamide compound is effective for the diseases treatable based on their blood sugar level-depressing activity, cGMP-PDE (especially PDE-V)-inhibiting activity, smooth muscle relaxing activity, bronchodilating activity, vasodilating activity, smooth muscle cell suppressing activity, and antiallergic activity.

11 Claims, No Drawings

SULFONAMIDE COMPOUNDS AND MEDICINAL USE THEREOF

This application is a 371 of PCT/JP98/02877 filed Jun. 24, 1998.

TECHNICAL FIELD OF THE INVENTION

The present invention relates to novel sulfonamide compounds. More particularly, the present invention relates to novel sulfonamide compounds and salts thereof having hypoglycemic activity or PDE-V inhibitory activity. Moreover, the present invention relates to a method for producing the above-mentioned sulfonamide compound and salts thereof. The present invention also relates to pharmaceutical compositions comprising the above-mentioned sulfonamide compound or a salt thereof as an active ingredient.

BACKGROUND OF THE INVENTION

The present invention aims at providing novel sulfonamide compounds, pharmaceutically acceptable salts thereof and pharmaceutical preparations comprising the above-mentioned sulfonamide compound or a pharmaceutically acceptable salt thereof as an active ingredient, which can be used for the prophylaxis and treatment of impaired glucose tolerance disorder, diabetes (e.g., type II diabetes), diabetic complications (e.g, diabetic gangrene, diabetic arthropathy, diabetic bone resorption, diabetic glomerulosclerosis, diabetic nephropathy, diabetic dermatopathy, diabetic neuropathy, diabetic cataract, diabetic retinopathy and the like), insulin resistant syndrome (e.g., insulin receptor disorders, Rabson-Mendenhall syndrome, leprechaunism, Kobberling-Dunnign syndrome, Seip syndrome, Lawrence syndrome, Cushing syndrome, acromegaly and the like), polycystic ovary syndrome, hyperlipideria, atherosclerosis, cardiovascular disorders (e.g., stenocadia, cardiac fildure and the like), hyperglycemia (e.g., those characterrred by abnormal saccharometabolism such as feeding disorders), hypertension, pulmonary hypertension, congestive heart failure, glomerulopathy (e.g., diabetic glomerulosclerosis), tubulointerstitial disorders (e.g, kidney diseases induced by FK506, cyclosporine and the like), renal failure, angiostenosis (e.g, after percutaneous arterioplasty), distal angiopathy, cerebral apoplexy, chronic reversible obstructions (e.g, bronchitiss, asthma inclusive of chronic asthma and allergic asthma), autoimmune diseases, allergic rhinitis, urticaria, glaucoma, diseases characterized by enteromotility (e.g., hypersensitive enteropathy), impotence (e.g., organic impotence, psychic impotence and the like), nephritis, cancer cachexia or restenosis after PTCA, pancreatitis, cachexia (e.g., progressive weight loss due to lipolysis, myolsis, anemia, edema, anorexia and the like in chronic diseases such as cancer, tuberculosis, endocrine diseases and AIDS), and the like.

SUMMARY OF THE INVENTION

The novel sulfonamide compound of the present invention has the following formula (I):

$$R^1\text{—}SO_2NHCO\text{—}A\text{—}X\text{—}R^2 \tag{I}$$

wherein $R^1$ is an optionally substituted allyl, an optionally substituted alkenyl, an optionaly substituted alkynyl, an optionally substituted cyclo(lower)alkyl, an optionally substituted aryl or an optionally substituted hetercyic group;

A is an optionally substituted heterxpolycyclic group except benzimidazolyl, indolyl, 4,7-dihydrobenzimidazolyl and 2,3-dihydrobenzoxazinyl;

X is an alkylene, an oxa, an oxa(lower)alkylene, a lower alkyleneoxa, a carbonyl, a lower alkenylene, an optionally substituted imino, an optionally N-substituted imino(lower)alkylene, an optionally N-substituted lower alkyleneimino, a thioxa(lower)alyklene or a lower alkylenethioxa; and $R^2$ is an optionally substituted aryl, an optionally substituted heterocyclic group or a substituted biphenylyl;

provided that when A is 3H-imidazo[4,5-b]pyridyl substituted by lower alkyl, $R^2$ is an optionally substituted aryl an optionally substituted heterocylic group, or a biphenylyl substituted by a group other than tetrazolyl, and when A is quinolyl substituted by lower allyl, $R^2$ is an optionaly substituted aryl, an optionally substituted heterocyclic group, or a biphenylyl substituted by at least one group selected from the group consisting of alkyl, cyclo(lower)alkyl, alkenyl, alkynyl, lower alkanoyl, lower alkoxy, phenyl, heterocycle(lower)alkyl other than substituted tetrazolylmethyl, halogen, amino, substituted amino, lower alkylsulfonyl, lower alkylsulfinyl, lower alkylthio, cyano, carbamoyl, mono(lower)alkylcarbamoyl, di(lower)alkylcarbamoyl, nitro, halo(lower)alkyl, aryl(lower)alkyl, aryl(lower)alkenyl, ary(lower)alkoxy, lower alkoxy substituted by substituted amino, cyclo(lower)alkyl(lower)alkyxoy, cyclo(lower)alkyl(lower)alkyl, aryloxy(lower)alkyl, acyloxy(lower)alkyl, hydroxy(lower)alkyl, mono- or di(lower)alkylamino(lower)alkyl, aryl(lower)alkoxy(lower)alkyl, arylthio(lower)alkyl, heterocycle(lower)alkoxy, heterocycle-oxy(lower)alkyl, aryl(lower)alkythio, arylureido, lower alkoxy(lower)alkoxy, aryl(lower)alkynyl, lower alkyl substituted by optionally substituted divalent heterocyclic group and optionaly substituted heterocyclic group, (hereinafter also referred to as objective compound (I)).

Preferred salts of the objective compound (I) are conventional salts that are non-toxic and acceptable for use as phamraceuticals. Examples thereof include salts of alkali metal such as sodium and potassium, salts of alkaline earth metal such as calcium and magnesium, salts with inorganic base such as ammonium salt, salts with organic amine such as triethylamine, pyridine, picoline, ethanolamine and triethanolamine, salts with inorganic acid such as hydrochloric acid, hydrobromic acid, sulfuric acid and phosphoric acid, salts with organic carboxylic acid such as formic acid, acetic acid, trifluoroacetic acid, maleic acid and tartaric acid, addition salts with sulfonic acid such as methanesulfonic acid, benzenesulfonic acid and p-toluenesulfonic acid, addition salts with basic amino acid such as arginine, and addition salts with acidic amino acid such as aspartic acid and glutamic acid.

The objective compound (I) and a salt thereof can be produced by the method shown by the following reaction formula.

Production Method 1:

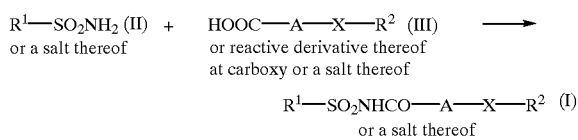

wherein each symbol in the formula is as defined above.

The objective compound (I) and a salt thereof can be also produced by the methods shown by the following reaction formulas.

Production Method 2:

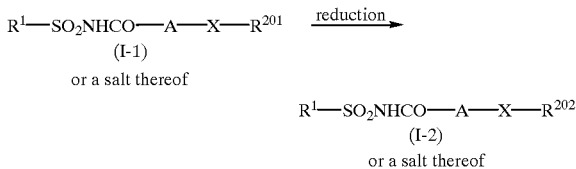

wherein $R^{201}$ is an optionally substituted aryl, an optionally substituted heterocyclic group or a substituted biphenylyl, all of which having at least alkynyl, aryl(lower)alkenyl, terminal nitro or terminal formyl, $R^{202}$ is an optionaly substituted aryl, an optionally substituted heterocyclic group or a substituted biphenyl, all of which having at least alkyl, aryl(lower)alkyl, terminal amino or hydroxymethyl, and other symbols are as defined above.

Production Method 3:

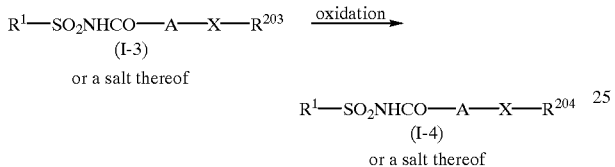

wherein $R^{203}$ is an optionally substituted aryl, an optionally substituted heterocyclic group or a substituted biphenylyl, all of which having at least terminal formyl, $R^{204}$ is an optionally substituted aryl, an optionally substituted heterocyclic group or a substituted biphenylyl, all of which having at least carboxy, and other symbols are as defined above.

Production Method 4:

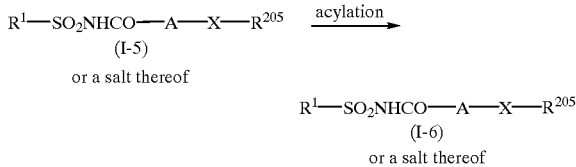

wherein $R^{205}$ is an optionally substituted aryl, an optionally substituted heterocyclic group or a substituted biphenylyl, all of which having at least hydroxy(lower)alkyl, $R^{206}$ is an optionaly substituted aryl, an optionally substituted heterocyclic group or a substituted biphenylyl, all of which having at least acyloxy(lower)alkyl, and other symbols are as defined above.

Production Method 5:

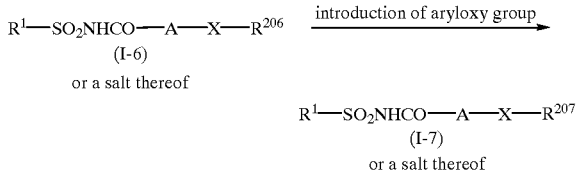

wherein $R^{207}$ is an optionally substituted aryl, an optionally substituted heterocyclic group or a substituted biphenylyl, all of which having at least aryloxy(lower)alkyl, and other symbols are as defined above.

Production Method 6:

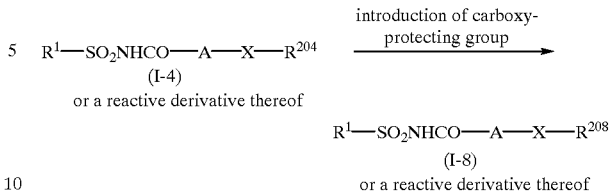

wherein $R^{208}$ is an optionally substituted aryl, an optionally substituted heterocyclic group or a substituted biphenylyl, all of which having at least protected carboxy, and other symbols are as defined above.

Production Method 7:

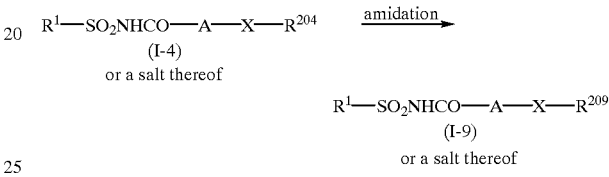

wherein $R^{209}$ is an optionally substituted aryl, an optionally substituted heterocyclic group or a substituted biphenylyl, all of which having at least optionally substituted amide, and other symbols are as defined above.

Production Method 8:

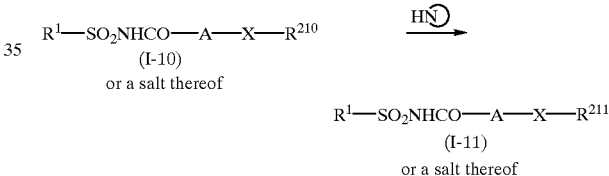

wherein $R^{210}$ is an optionally substituted aryl having at least a halogen atom,

is a heterocyclic group having nitrogen, $R^{211}$ is an aryl substituted by at least heterocyclic group having nitrogen, and other symbols are as defined above.

Various definitions included in the entire specification are explained in detail in the following.

"Lower" means 1 to 6 carbon atoms, unless otherwise specified.

"Higher" means 7 to 20 carbon atoms, unless otherwise specified.

"Alkyl" and "alkyl moiety" are preferably linear or branched lower alkyl and higher alkyl, respectively. Specific examples include methyl, ethyl n-propyl, i-propyl, n-butyl, i-butyl, t-butyl, sec-butyl, n-pentyl, i-pentyl, sec-pentyl, t-pentyl, methylbutyl 1,1-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 2,2-dimethylbutyl, 3,3-dimethylbutyl, 1-ethyl-1-methylpropyl, n-heptyl 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1,1-dimethylpentyl, 2,2-dimethylpentyl, 3,3-dimethylpentyl, 4,4-dimethylpentyl, 1-propylbutyl, n-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 5-ethylhexyl, 5-ethylhexyl, 1,1-dimethylhexyl, 2,2-dimethylhexyl, 3,3-dimethylhexyl, 4,4-dimethylhexyl, 5,5-dimethylhexyl, 1-propylpentyl, 1-propylpentyl and the like.

Of these, particularly preferred is alkyl having 2 to 8 carbon atoms.

"Alkenyl" and "lower alkenyl moiety" are preferably exemplified by linear or branched lower alkenyl and higher alkenyl such as ethenyl 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl and the like.

Of these, particularly preferred is alkenyl having 2 to 8 carbon atoms.

"Alkynyl" is preferably a linear or branched lower allynyl or higher alkynyl, such as ethynyl, 1-propynyl, 2-propynyl, 1-butynyl, 2-butynyl, 3-butynyl, 1-pentynyl, 2-pentynyl, 3-pentynyl, 4-pentynyl, 2-methyl-3-butynyl, 1,1-dimethyl-2-butynyl, 1-hexynyl, 5-hexynyl, and the like.

Of these, particularly preferred is alkynyl having 2 to 8 carbon atoms.

"Cyclo(lower)alkyl" is cycloalkyl having 3 to 10, preferably 3 to 7, carbon atoms. Examples thereof include cyclopropyl, cyclobutyl, cyclopentyl, cyclohexyl and cycloheptyl, with preference given to cyclopropyl, cyclobutyl and cyclohexyl.

Examples of preferable aryl include aryl having 6 to 10 carbon atoms, such as phenyl, naphthyl and pentalenyl.

Of these, particularly preferred are phenyl and naphthyl.

"Heterocyclic group" is a saturated or unsaturated, heteromonocyclic or heteropolycyclic group having at least one hetero atom, such as oxygen atom, sulfur atom, nitrogen atom and selenium atom. Particularly, heteropolycyclic group (specifically heterobicyclic group) and unsaturated 3- to 8-membered heteromonocyclic group having 1 or 2 sulfur atom(s) are preferable.

Preferred heterocyclic group includes the following.

Heteromonocyclic group includes the following.

Unsaturated 3 to 8-membered (more preferably 5 or 6-membered) heteromonocyclic group having 1 to 4 nitrogen atoms, such as pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl and 2H-1,2,3-triazolyl), tetrazolyl (e.g., 1H-tetrazolyl and 2H-tetrazolyl) and the like.

Saturated 3 to 8-membered (more preferably 5- or 6-membered) heteromonocyclic group having 1 to 4 nitrogen atoms, such as pyrrolidinyl, imidazolidinyl, piperidyl, piperazinyl and the like.

Unsaturated 3 to 8-membered (more preferably 5 or 6-membered) heteromonocyclic group having 1 or 2 oxygen atoms and 1 to 3 nitrogen atoms, such as oxazolyl, isooxazolyl, oxadiazolyl (e.g., 1,2,4-oxadiazolyl, 1,3,4-oxadiazolyl and 1,2,5-oxadiazolyl) and the like.

Saturated 3 to 8-membered (more preferably 5 or 6-membered) heteromonocyclic having 1 or 2 oxygen atoms and 1 to 3 nitrogen atoms, such as morpholinyl, sydnonyl and the like.

Unsaturated 3 to 8-membered (more preferably 5- or 6-membered) heteromonocyclic group having 1 or 2 sulfur atoms and 1 to 3 nitrogen atoms, such as thiazolyl, isothiazolyl, thiadiazolyl (e.g., 1,2,3-thiadiazolyl, 1,2,4-thiadiazolyl, 1,3,4-thiadiazolyl and 1,2,5-thiadiazolyl), dihydrothiazinyl and the like.

Saturated 3 to 8-membered (more preferably 5- or 6-membered) heteromonocyclic group having 1 or 2 sulfur atoms and 1 to 3 nitrogen atoms, such as thiazolidinyl and the like.

Unsaturated 3 to 8-membered (more preferably 5- or 6-membered) heteromonocyclic group having 1 or 2 sulfur atoms, such as thienyl, dihydrodithiinyl, dihydrodithionyl and the like.

Unsaturated 3 to 8-membered (more preferably 5- or 6-membered) heteromonocyclic group having 1 or 2 oxygen atoms, such as tetrahydrofuryl, tetrahydropyranyl and the like.

Unsaturated 3 to 8-membered (more preferably 5- or 6-membered) heteromonocyclic group having one oxygen atom, such as furyl and the like.

Spiroheterocyclic group having 1 or 2 oxygen atoms, such as dioxaspiroundecanyl (e.g, 1,5-dioxaspiro[5,5]undecanyl) and the like.

Unsaturated 3 to 8-membered (more preferably 5 or 6-membered) heteromonocyclic group having one oxygen atom and 1 or 2 sulfur atoms, such as dihydroxathinyl.

Examples of heteropolycyclic group include the following.

Saturated or unsaturated 7 to 12-membered (more preferably 8 to 10-membered) heteropolycyclic (more preferably heterodicyclic) group having 1 to 4 nitrogen atoms, exclusive of benzimidazolyl and indolyl.

Specific examples thereof include 2,3-dihydrobenzimidazolyl, pyrazolopyrimidinyl (e.g, pyrazolo[1,5-a]pyrimidinyl), tetrahydropyrazolopyrimidinyl (e.g, 4,5,6,7-tetrahydropyrazolo[1,5-a]pyrimidinyl), imidazopyrazolyl (e.g., 4H-imidazo[1,2-b]pyrazolyl), dihydroimidazopyrazolyl (e.g., 2,3-dihydroimidazo[1,2-b]pyrazolyl), imidazopyridyl (e.g., imidazo[1,5-a] (or [1,2-a] or [3,4-a]) pyridyl, 1H (or 3H)-imidazo[4,5-b] (or [4,5-c])pyridyl), pyrrolopyridyl (e.g., 1H-pyrrolo[3,2-b]pyridyl), pyrazolopyridyl (e.g., pyrazolo[1,5a] (or [2,3-a]pyridyl, 1H (or 2H)-pyrazolo[4,3-b]pyridyl), benzopyrazolyl (e.g., 1H (or 2H)-benzo[c]pyrazolyl), dihydrobenzimidazolyl, benzotriazolyl (e.g., benzo[d][1H-1,2,3]triazolyl), indolizinyl, isoindolyl (e.g., 1H-isoindolyl), indazolyl (e.g, 1H (or 2H or 3H)-indazolyl), indolinyl, isoindolinyl, purinyl, quinolizinyl (e.g., 4H-quinolizinyl), isoquinolyl, quinolyl phthalazinyl, naphthalidinyl (e.g., 1,8-naphthalidinyl), quinoxalinyl, dihydroquinoxalinyl (e.g., 1,2-dihydroquinoxalinyl), tetrahydroquinoxalinyl (e.g., 1,2,3,4-tetrahydroquinoxalinyl), quinazolinyl, dihydroquinazolinyl (e.g., 1,4 (or 3,4)-dihydroquinazolinyl), tetrahydroquinazolinyl (e.g., 1,2,3,4-tetrahydroquinazolinyl), cinnolinyl, pteridinyl, pyrazinopyridazinyl (e.g., pyrazino[2,3-d]pyridazinyl), imidazotriazinyl (e.g., imidazo[1,2-b][1,2,4]triazinyl, imidazopyrazinyl (e.g, 1H-imidazo[4,5-b]pyrazinyl), imidazopyrimidine (e.g., 3H-purine and imidazo[1,5a] (or [3,4-a])pyrimidine), imidazopyridazinyl (e.g., imidazo[2,3-b] (or [3,4-b])pyridazinyl), 1H-1- (or 2)pyrinedinyl and the like.

Saturated or unsaturated 7 to 12-membered (more preferably 8 to 10-membered) heteropolycyclic (more preferably hyeterodicyclic) group having 1 to 3 oxygen atoms.

Specifc examples thereof include benzofuranyl (e.g., benzo[b] (or [c])furanyl), isobenzofuranyl, furopyridyl, chromenyl (e.g., 2H-chromenyl), chromanyl, isochromanyl, benzoxepinyl (e.g., 3-benzoxepinyl), cyclopentapyranyl (e.g., cyclopenta[b]pyranyl), furopyranyl (e.g., 2H-furo[3,2-b]pyranyl), and the like.

Saturated or unsaturated 7 to 12-membered (more preferably 8 to 10-membered) heteropolycyclic (more preferably heterodicylic) group having 1 to 3 sulfur atoms.

Specific examples thereof include benzothiophenyl (e.g., benzo[b]thiophenyl), dihydrodithianaphthalenyl (e.g, 4H-1,3-dithianaphthalenyl), dithianaphthalenyl (e.g, 1,4-dithianaphthalenyl) and the like.

Saturated or unsaturated 7 to 12-membered (more preferably 8 to 10-membered) heteropolycyclic (more preferably heterodicyclic) group having 1 to 3 nitrogen atoms and 1 or 2 oxygen atoms.

Specific examples thereof include dioxoloimidazolyl (e.g., 4H-1,3-dioxolo[4,5-d]imidazolyl, benzoxazinyl (e.g., 4H-3,1-benzoxazinyl), pyridooxazinyl (e.g., 5H-pyrido[2,3-d]oxazinyl), pyrazolooxazolyl (e.g., 1H-pyrazolo[4,3-d]oxazolyl), furopyridyl, and the like.

Saturated or unsaturated 7 to 12-membered (more preferably 8 to 10-membered) heteropolycyclic (more preferably heterodicyclic) group having 1 to 3 nitrogen atoms and 1 or 2 sulfur atoms.

Specific examples thereof include thienoimidazolyl (e.g., thieno[2,3-d]imidazolyl), thienopyridyl, dithiadiazaindanyl (e.g., 2,3-dithia-1,5-diazaindanyl) and the like.

Saturated or unsaturated 7 to 12-membered (more preferably 8 to 10-membered) heteropolycyclic (more preferably heterodiclic) group having 1 to 3 oxygen atoms and 1 or 2 sulfur atoms.

Specific examples thereof include thienofuranyl (e.g., thieno[2,3-b]furanyl), and the like.

Saturated or unsaturated 7 to 12-membered (more preferably 8 to 10-membered) heteropolycyclic (more preferably heterodicyclic) group having 1 nitrogen atom, 1 oxygen atom and 1 sulfur atom.

Specific examples thereof include oxathiolopyrrolyl (e.g., 4H[1,3]-oxathiolo[5,4-b]pyrrolyl, and the like.

Saturated or unsaturated 7 to 12-membered (more preferably 8 to 10-membered) heteropolycyclic (more preferably heterodicyclic) group having 1 or 2 selenium atoms.

Specific examples thereof include benzoselenophenyl (e.g., benzo[b] (or [c])selenophenyl), and the like.

Saturated or unsaturated 7 to 12-membered (more preferably 8 to 10-membered) heteropolycyclic (more preferably heterodicyclic) group having 1 or 2 selenium atoms and 1 to 3 nitrogen atoms.

Specific examples thereof include selenopyridyl (e.g., seleno[3,2-b]pyridyl), and the like.

Examples of preferable lower alkylene include methylene, ethylene, propylene, butylene, pentylene, hexylene and the like, with preference given to alkylene having up to 4 carbon atoms.

Examples of preferable lower alkenylene include ethenylene, 1-propenylene, 2-propenylene, 1-butenylene, 2-butenylene, 3-butenylene, 1-pentenylene, 2-pentenylene, 3-pentenylene, 4-pentenylene, 1-hexenylene, 2-hexenylene, 3-hexenylene, 4-hexenylene, 5-hexenylene and the like, with preference given to alkenylene having up to 4 carbon atoms.

The lower alkylene moiety of oxa(lower)alkylene, lower alkyleneoxa, imino(lower)alkylene, lower alkyleneimino, thioxa(lower)alkylene and lower alkylenethioxa is the same as that of the above-mentioned alkylene.

Lower alkanoyl is a linear or branched alkylcarbonyl having up to 6 carbon atoms Examples thereof include acetyl, propionyl, n-butyryl, isobutyryl, valeryl, isovaleryl, sec-butylcarbonyl, t-butylcarbonyl, n-pentylcarbonyl, i-pentylcarbonyl, sec-pentylcarbonyl, t-pentylcarbonyl, 2-methylbutylcarbonyl and the like.

More preferred is alkanoyl having up to 4 carbon atoms.

Lower alkoy is a linear or branched alkyloxy having up to 6 carbon atoms. Examples thereof include methoxy, ethoxy, n-propyloxy, i-propyloxy, n-butyloxy, i-butyloxy, sec-butyloxy, t-butyloxy, n-pentyloxy, i-pentyloxy, sec-pentyloxy, t-pentyloxy, 2-methylbutoxy, n-hexyloxy, i-hexyloxy, t-hexyloxy, sec-hexyloxy, 2-methylpentyloxy, 3-methylpentyloxy, 1-ethylbutyloxy, 2-ethylbutyloxy, 1,1-dimethylbutyloxy, 2,2-dimethylbutyloxy, 3,3-dimethylbutyloxy, 1-ethyl-1-methylpropyloxy, and the like.

More preferred is alkoxy having up to 4 carbon atoms, such as methoxy, ethoxy, n-propyloxy, i-propyloxy, n-butyloxy, i-butyloxy, sec-butyloxy, t-butyloxy, and the like.

Heterocycle(lower)alkyl means lower alkyl substituted by the above-mentioned heterocyclic group.

Halogen is exemplified by fluorine atom, chlorine atom, bromine atom and iodine atom.

The substituted amino of "substituted amino" and "optionally substituted amino" is, for example, lower alkanoylamino, mono(lower)alkylamino, di(lower)alkylamino, N-(lower)alkyl-N-acylamino, lower alkylsulfonylamino, ary(lower)alkylamino, N-heterocycle-N-(lower)alkylamino, arylsulfonylamino, arylcarbonylamino and the like. Examples of N-(lower)alkyl-N-acylamino include N-(lower)alkyl-N-(arylcarbonyl)amino and the like.

"Lower alkanoylamino" is amino substituted by the above-mentioned lower alkanoyl.

"Mono or di(lower)alkylamino" is amino substituted by linear or branched alkyl having up to 6 carbon atoms. Examples thereof include methylamino, ethylamino, n-propylamino, i-propylamino, n-butylamino, i-butylamino, sec-butylamino, t-butylamino, n-pentylamino, i-pentylamino, sec-pentylamino, t-pentylamino, 2-methylbutylamino, n-hexylamino, 1-methylpentylamino, 2-methylpentylamino, 3-methylpentamino, 4-methylpentylamino, 1-ethylbutylamino, 2-ethylbutylamino, 3-ethylbutylamino, 1,1-dimethylbutylamino, 2,2-dimethylbutylamino, 3,3-dimethylbutylamino, 1-ethyl-1-methylpropylamino and the like.

Prefened is alkylamino having up to 4 carbon atoms, such as methylamino, ethylamino, n-propylamino, i-propylamino, n-butylamino, i-butylamino, sec-butylamino, t-butylamino and the like.

Preferable "acyl" in "N-(lower)alkyl-N-acylamino" is exemplified by carbamoyl, aliphatic acyl, aromatic acyl, and acyl having a heterocycle, such as heterocyclic acyl.

Examples of the above-mentioned acyl include carbamoyl; lower or higher (having not less than 7, preferbly 7 to 25, carbon atoms) alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tidecanoyl, tetradecanoyl, pentadecanoyl, hexadecanoyl, heptadecanoyl, octadecanoyl, nonadecanoyl, icosanoyl and the like; lower or higher alkoxycarbonyl, such as methoxycarbonyl, ethoxycarbonyl, t-butoxycarbonyl, t-pentyloxycarbonyl, heptloxycarbonyl and the like; lower or higher alkanesulfonyl, such as methanesulfonyl, ethanesulfonyl and the like; aliphatic acyl such as lower or higher alkoxysulfonyl (e.g., methoxysulfonyl and ethoxysulfonyl); aroyl such as benzoyl, toluoyl, naphthoyl and the like; phenyl(lower)alkanoyl, such as phenylacetyl, phenylpropanoyl, phenylbutanoyl, phenylisobutyryl, phenylpentanoyl, phenylhexanoyl and the like and aryl(lower)alkanoyl (e.g., naphthyl(lower)alkanoyl such as naphthylacetyl, naphthylpropanoyl and naphthylbutanoyl); phenyl(lower)alkenoyl such as phenylpropenoyl, phenylbutenoyl, phenylmethacryloyl, phenylpentenoyl, phenylhexenoyl and the like and aryl(lower)alkenoyl such as naphthyl(lower)alkenoyl (e.g., naphthyl propenoyl, naphthyl butenoyl and naphthyl pentenoyl; aryl(lower)alkoxycarbonyl such as phenyl(lower)alkoxycarbonyl (e.g., benzyloxycarbonyl); aryloxycarbonyl such as phenoxycarbonyl, naphthyloxycarbonyl and the like; aryloxy(lower)alkanoyl such as phenoxyacetyl, phenoxypropionyl and the like; arylcarbamoyl such as phenylcarbamoyl and the like; arylthiocarbamoyl such as phenylthiocarbamoyl and the like; arylglyoxyloyl such as phenylglyoxyloyl, naphthylglyoxyloyl and the like; aromatic acyl such as arenesulfonyl (e.g., benzenesulfonyl and p-toluenesulfonyl); heterocyclecarbonyl; heterocycle(lower)alkanoyl such as thienylacetyl, thienylpropanoyl, thienylbutanoyl, thienylpentanoyl, thienylhexanoyl, thiazolylacetyl, tetrazolylacetyl and the like; heterocycle (lower)alkenoyl such as heterocycle propenoyl, heterocyclebutenoyl, heterocyclepentenoyl, heterocyclehexenoyl and the like; heterocycleglyoxyloyl such as thiazolylglyoxyloyl, thienylglyoxyloyl and the like.

The preferable heterocycle moiety of the above-mentioned "heterocycle carbonyl", "heterocycle(lower)alkanoyl", "heterocycle(lower)alkenoyl" and "heterocycleglyoxyloyl" is a saturated or unsaturated heteromonocyclic or heteropolycyclic group having at least one hetero atom such as oxygen atom, sulfur atom, nitrogen atom and the like, with preference given to the heterocyclic groups mentioned above.

The aforementioned acyl moiety may have 1 to 10 same or different suitable substituent(s), such as halogen (e.g., fluorine, chlorine, bromine and iodine), hydroxy, nitro, lower alkyl (e.g., methyl, ethyl, propyl, isopropyl, butyl, isobutyl, t-butyl, pentyl and hexyl), amino, protected amino, heterocycle(lower)alkylamino having the above-mentioned heterocycle moiety and lower alkyl moiety, lower alkoxy (e.g., methoxy, ethoxy, propoxy, butyloxy, t-butyloxy, pentyloxy and hexyloxy), carboxy, protected carboxy, N,N-di (lower)alkylamino(lower)alkyl (e.g., N,N-dimethylaminomethyl, N,N-diethylaminomethyl, N,N-dipropylaminomethyl, N,N-dimethylaminoethyl, N,N-diethylaminoethyl, N,N-dipropylaminoethyl, N,N-dimethylaminopropyl, N,N-diethylaminopropyl, N,N-dipropylaminopropyl, N,N-dibutylaminomethyl, N,N-dipentylaminomethyl and N,N-dihexylaminomethyl), hydroxyimino(lower)alkyl (e.g., hydroxyiminomethyl, hydroxyiminoethyl, hydroxyiminopropyl, hydroxyiminobutyl, hydroxyiminopentyl and hydroxyiminohexyl), arylimino(lower)alkyl such as phenylimino(lower)alkyl (e.g., phenyliminomethyl, phenyliminoethyl, phenyliminopropyl, phenyliminobutyl, phenyliminopentyl and phenyliminohexyl), acyl such as lower alkanoyl (e.g., formyl, acetyl, propanoyl, butanoyl, pentanoyl and hexanoyl), hydroxy(lower)alkylheterocycle (lower)alkyl having the above-mentioned lower alkyl moiety and heterocyclic moiety, mono- (or di- or tri-)halo (lower)alkyl, arylamino (e.g., phenylamino) and the like.

"Lower alkylsulfonyl" and "lower alkylsulfinyl" are sulfonyl and sulfinyl respectively substituted by the above-mentioned lower alkyl.

"Lower alkylthio" is a linear or branched alkylthio having up to 6 carbon atoms. Examples thereof include methylthio, ethylthio, n-propylthio, i-propylthio, n-butylthio, i-butylthio, sec-butylthio, t-butylthio, n-pentylthio, i-pentylthio, sec-pentylthio, t-pentylthio, 2-methylbutylthio, n-hexylthio, i-hexylthio, t-hexylthio, sec-hexylthio, 2-methylpentylthio, 3-methylpentylthio, 1-ethylbutylthio, 2-ethylbutylthio, 1,1-dimethylbutylthio, 2,2-dimethylbutylthio, 3,3-dimethylbutylthio, 1-ethyl-1-methylpropylthio and the like.

More preferred is alkylthio having up to 4 carbon atoms, such as methylthio, ethylthio, n-propylthio, i-propylthio, n-butylthio, i-butylthio, sec-butylthio, t-butylthio and the like.

"Mono- or di(lower)alkylcarbamoyl" is carbamoyl mono- or di-substituted by the above-mentioned lower alkyl, "Halo(lower)alkyl" is a linear or branched alkyl having up to 6 carbon atoms, which is substituted by fluorine atom, chlorine atom, bromine atom or iodine atom, and is preferably exemplified by a linear or branched alkyl having up to 6 carbon atoms, which is substituted by fluorine atom, chlorine atom or bromine aton. Examples therof include fluoromethyl, difluoromethyl, trifluoromethyl, chloromethyl, dichloromethyl, trichloromethyl, bromomethyl, dibromomethyl, tribromomethyl, 1-fluoroethyl, 1-chloroethyl, 1-bromoethyl, 2-fluoroethyl, 2-chloroethyl, 2-bromoethyl, 1,2-difluoroethyl, 1,2-dichloroethyl, 1,2-dibromoethyl, 2,2,2-trifluoroethyl, heptafluoroethyl, 1-fluoropropyl, 1-chloropropyl, 1-bromopropyl, 2-fluoropropyl, 2-chloropropyl, 2-bromopropyl, 3-fluoropropyl, 3-chloropropyl, 3-bromopropyl, 1,2-difluoropropyl, 1,2-dichloropropyl, 1,2-dibromopropyl, 2,3-difluoropropyl, 2,3-dichloropropyl, 2,3-dibromopropyl, 3,3,3-trifluoropropyl, 2,2,3,3,3-pentafluoropropyl, 2-fluorobutyl, 2-chlorobutyl, 2-bromobutyl, 4-fluorobutyl, 4-chlorobutyl, 4-bromobutyl, 4,4,4-trifluorobutyl, 2,2,3,3,4,4,4-heptafluorobutyl, perfluorobutyl, 2-fluoropentyl, 2-chloropentyl, 2-bromopentyl, 5-fluoropentyl, 5-chloropentyl, 5-bromopentyl, perfluoropentyl, 2-fluorohexyl, 2-chlorohexyl, 2-bromohexyl, 6-fluorohexyl, 6-chlorohexyl, 6-bromohexyl, perfluorohexyl, 2-fluoroheptyl, 2-chloroheptyl, 2-bromoheptyl, 7-fluoroheptyl, 7-fluoroheptyl, 7-chloroheptyl, 7-bromoheptyl, perfluoroheptyl and the like.

Examples of preferable aryl(lower)alkyl include $C_6$–$C_{10}$aryl($C_1$–$C_6$)alkyl such as benzyl, phenylethyl, phenylpropyl, phenylbutyl, phenylpentyl, phenylhexyl, naphthylmethyl, naphthylethyl, naphthylpropyl, naphthylbutyl, naphthylpentyl, naphthylhexyl and the like.

"Aryl(lower)alkenyl" and "aryl(lower)alkoxy" are respectively the above-mentioned lower alkenyl and lower alkoxy substituted by the above-mentioned aryl.

"Protected carboxy" is preferably esterified carboxy.

Examples of prefetable ester moiety of the esterified carboxy include lower alkyl esters such as methyl ester, ethyl ester, propyl ester, isopropyl ester, butyl ester, isobutyl ester, t-butyl ester, pentyl ester and hexyl ester. These groups may have at least one appropriate substituent, which is exemplified by (lower)alkanoyloxy-(lower)alkyl ester such as acetoxymethyl ester, propionyloxymethyl ester, butyryloxymethyl ester, valeryloxymethyl ester, pivaloyloxymethyl ester, hexanoyloxymethyl ester, 1 (or 2)-acetoxyethyl ester, 1 (or 2 or 3)-acetoxypropyl ester, 1 (or 2 or 3 or 4)-acetoxybutyl ester, 1 (or 2)-propionyloxymethyl ester, 1 (or 2 or 3)-propionyloxypropyl ester, 1 (or 2)-butyryloxyethyl ester, 1 (or 2)-isobutyryloxyethyl ester, 1 (or 2)-pivaloyloxyethyl ester, 1 (or 2)-hexanoyloxyethyl ester, isobutyryloxy-methyl ester, 2-ethylbutyryloxymethyl ester, 3,3-dimethylbutyryloxymethyl ester, 1 (or 2)-pentanoyloxyethyl ester), and the like, lower alkanesulfonyl(lower)alkyl ester (e.g., 2-mesylethyl ester), mono- (or di- or tri)halo(lower)alkyl ester (e.g., 2-iodoethyl ester and 2,2,2-trichloroethyl ester), lower alkoxycarbonyloxy(lower)alkyl ester (e.g., methoxycarbonyloxymethyl ester, ethoxycarbonyloxymethyl methyl ester, 2-methoxycarbonyloxyethyl ester, 1-ethoxycarbonyloxyethyl ester and 1-isopropoxycarbonyloxyethyl ester), phthalidylidene(lower)alkyl ester and (5-lower)alkyl-2-oxo1,3-dioxol-4-yl(lower)alkyl ester (e.g., (5-methyl-2-oxo-1,3-dioxol-4-yl)methyl ester, (5ethyl-2-oxo-1,3-dioxol-4-yl)methyl ester and (5-propyl-2-oxo-1,3-dixol-4-yl)ethyl ester); lower alkenyl ester (e.g., vinyl ester and allyl ester); lower alkynyl ester (e.g., ethynyl ester and propynyl ester); aryl(lower)alkyl ester optionally having at least one suitable substituent, such as mono- (or di- or tri-)phenyl(lower)alkyl ester optionally having at least one suitable substituent, which is exemplified by benzyl ester, 4-methoxybenzyl ester, 4-nitrobenzyl ester, phenylethyl ester, trityl ester, benzhydryl ester, bis(methoxyphenyl) methyl ester, 3,4-dimethoxybenzyl ester and 4-hydroxy-3,5-di-t-butyl ester; aryl ester optionally having at least one suitable substituent, such as phenyl ester, 4-chlorophenyl ester, tolyl ester, t-butylphenyl ester, xylyl ester, mesityl ester and cumenyl ester, cyclo(lower)alkyl ester (e.g., cyclohexyl ester); phthalidyl ester; and the like.

The heterocyclic group having nitrogen, which is represented by

is exemplified by the above-mentioned heterocyclic group having nitrogen.

The preferable ojective compound (I) is a compound of the formula (I) having the following groups and pharmaceutically acceptable salts thereof. $R^1$ is an optionally substituted alkyl, an optionally substituted alkenyl, an optionally substituted alkynyl, an optionally substituted cyclo (lower)alkyl, an optionally substituted aryl or an optionally substituted heterocyclic group, wherein, when the above groups are substituted, the substituent is at least one member selected from the group consistng of alkyl, cyclo(lower) alkyl, alkenyl, alkynyl, lower alkanoyl, lower alkoxy, aryl, heterocycle(lower)alkyl, halogen, amino, substituted amino, lower alkylsulfonyl, lower alkylsulfinyl, lower alkylthio, cyano, carboxy, protected carboxy, carbamoyl, mono(lower) alkylcarbamoyl, di(lower)alkylcarbamoyl, nitro, halo (lower)alkyl, aryl(lower)alkyl, aryl(lower)alkenyl, aryl (lower)alkoxy, lower alkoxy substituted by substituted amino, cyclo(lower)alkyl(lower)alkoxy, cyclo(lower)alkyl-(lower)alkyl, aryloxy(lower)alkyl, acyloxy(lower)alkyl, hydroxy(lower)alkyl, mono- or di(lower)alkylamino(lower) alkyl, aryl(lower)alkoxy(lower)alkyl, arylthio(lower)alkyl, heterocycle(lower)alkoxy, heterocycleoxy(lower)alkyl, aryl (lower)alkylthio, arylureido, lower alkoxy(lower)alkoxy, aryl(lower)alkynyl, lower alkyl substituted by optionally substituted divalent heterocyclic group and optionally substituted heterocyclic group. A is a heteropolylcylic group having at least one hetero atom, such as oxygen atom, sulfur atom, selenium atom and nitrogen atom, exclusive of bezimidazolyl indolyl, 4,7-dihydrobenzimidazolyl and 2,3-dihydrobenzoxazinyl, said heteroyclic group being optionally substituted by at least one member selected from the group consisting of alkyl, oxo, thioxo, halogen, lower alkoxy, lower alkylthio, cyclo(lower)alkyl, optionally substituted amino, aryl, heterocyclic group, lower alkylsulfonyl and lower alkylsulfinyl. $R^2$ is optionally substituted aryl optionally substituted heterocyclic group or substituted biphenylyl, wherein, when these groups are substituted, the substituent is at least one member selected from the group consisting of alkyl cyclo(lower)alkyl, alkenyl, alkynyl, lower alkanoyl, lower alkyoxy, aryl, heterocycle(lower) alkyl, halogen, amino, substituted amino, lower alkylsulfonyl, lower alkylsulfinyl, lower alkylthio, cyano, carboxy, protected carboxy, carbamoyl, mono(lower) alkylcarbamoyl, di(lower)alkylcarbamoyl, nitro, halo (lower)alkyl, aryl(lower)alkyl, aryl(lower)alkenyl, aryl (lower)alkoxy, lower alkoxy substituted by substituted amino, cyclo(lower)alkyl-(lower)alkoxy, cyclo(lower)alkyl (lower)alkyl, aryloxy(lower)alkyl, acyloxy(lower)alkyl, hydroxy(lower)alkyl, mono- or di(lower)alkylamino(lower) alkyl, aryl(lower)alkoxy-(lower)alkyl, arylthio(lower)alkyl, heterocycle(lower)alkoxy, heterocycleoxy(lower)alkyl, aryl (lower)alkylthio, arylureido, lower alkoxy(lower)alkoxy, aryl(lower)alkynyl, lower alkyl substituted by optionally substituted divalent heterocyclic group and optionally substituted heterocyic group, provided that when A is 3H-imidazo[4,5-b]pyridyl substituted by lower alkyl, $R^2$ is optionally substituted aryl, optionally substituted heterocyclic group or biphenylyl substituted by a substituent other than tetrazolyl, and when A is quinolyl substituted by lower alkyl, $R^2$ is optionally substituted aryl, optionally substituted heterocyclic group or substituted biphenylyl.

When the above-mentioned aryl and heterocyclic group are substituted, the substituent is at least one member selected from the group consisting of alkyl, cyclo(lower) alkyl, alkenyl, alkynyl, lower alkanoyl, lower alkoxy, phenyl, heterocycle(lower)alkyl, halogen, amino, substituted amino, lower alkylsulfonyl, lower alkylsulfinyl, lower alkylthio, cyano, carboxy, protected carboxy, carbamoyl, mono(lower)alkylcarbamoyl, di(lower)alkylcarbamoyl, nitro, halo(lower)alkyl, aryl(lower)alkyl, aryl(lower) alkenyl, aryl(lower)alkoxy, lower alkoxy substituted by substituted amino, cyclo(lower)alkyl(lower)alkoxy, cyclo (lower)alkyl(lower)alkyl, aryloxy(lower)alkyl, acyloxy (lower)alkyl, hydroxy(lower)alkyl, mono- or di(lower) alkylamino(lower)alkyl, aryl(lower)alkoxy(lower)alkyl, arylthio(lower)alkyl, heterocycle(lower)alkoxy, heterocycle-oxy(lower)alkyl, aryl(lower)alkylthio, arylureido, lower alkoxy(lower)alkoxy, aryl(lower)alkynyl, lower alkyl substituted by optionally substituted divalent heterocyclic group and optionally substituted heterocyclic group.

The substituent for the above-mentioned biphenylyl is at least one member selected from the group consisting of alkyl, cyclo(lower)alkyl, alkenyl, alkynyl, lower alkanoyl, lower alkoxy, phenyl, heterocycle(lower)alkyl other than substituted tetrazolylmethyl, halogen, amino, substituted amino, lower alkylsulfonyl, lower alkylsulfinyl, lower alkylthio, cyano, carbamoyl, mono(lower)alkylcarbamoyl, di(lower)alkylcarbamoyl, nitro, halo(lower)alkyl, aryl (lower)alkyl, aryl(lower)alkenyl, aryl(lower)alkoxy, lower alkoxy substituted by substituted amino, cyclo(lower)alkyl-(lower)alkoxy, cyclo(lower)alkyl(lower)alkyl, aryloxy (lower)alkyl, acyloxy(lower)alkyl, hydroxy(lower)alkyl, mono- or di(lower)alkylamino(lower)alkyl, aryl(lower) alkoxy-(lower)alkyl, arylthio(lower)alkyl, heterocycle (lower)alkoxy, heterocycle-oxy(lower)alkyl, aryl(lower) alkythio, arylureido, lower alkoxy(lower)alkoxy, aryl (lower)alkynyl, lower alkyl substituted by optionally substituted divalent heterocyclic group and optionally substituted heterocyclic group.

Of the above-mentioned compounds, a compound of the formula (I) having the following and pharmaceuticaly acceptable salts thereof are particularly preferable. $R^1$ is an optionally substituted alkyl, an optionally substituted alkenyl, an optionally substituted alkynyl, an optionally substituted cyclo(lower)alkyl, an optionally substituted phenyl or an optionally substituted heterocyclic group, wherein, when these groups are substituted, the substituent is at least one member selected from the group consisting of alkyl, cyclo(lower)alkyl, alkenyl, alkynyl, lower alkanoy, lower alkoxy, phenyl, heterocycle(lower)alkyl, halogen, amino, lower alkanoylamino, mono(lower)alkylamino, di(lower) alkylamino, N-(lower)alkyl-N-acylamino, lower alkylsulfonylamino, aryl(lower)alkylamino, N-heterocycle-N-(lower)alkylamino, arylsulfonylamino, arylcarbonylamino, lower alkylsulfonyl, lower alkylsulfinyl, lower alkylthio, cyano, carboxy, protected carboxy, carbamyl, mono(lower)alkylcarbamoyl, di(lower) alkylcarbamoyl, nitro, halo(lower)alkyl, aryl(lower)alkyl, aryl(lower)alkenyl, aryl(lower)alkoxy, lower alknoylamino (lower)alkoxy, mono(lower)alkylamino-(lower)alkoxy, di(lower)alkylamino(lower)alkoxy, N-(lower)alkyl-N-acylamino(lower)-alkoxy, lower alkylsulfonylamino(lower) alkoxy, aryl(lower)alkylamino(lower)alkoxy, N-heterocycle-N-(lower)alkylamino(lower)alkoxy, arylsulfonylamino(lower)alkoxy, arylcarbonylamino(lower) alkoxy, cyclo(lower)alkyl(lower)alkoxy, cyclo(lower)alkyl-(lower)alkyl, aryloxy(lower)alkyl, acyloxy(lower)alkyl, hydroxy(lower)alkyl, mono- or di(lower)alkylamino(lower) alkyl, aryl(lower)alkoxy(lower)alkyl, arylthio(lower)alkyl, heterocycle(lower)alkoxy, heterocycle-oxy(lower)alkyl, aryl(lower)alkylthio, arylureido, lower alkoxy(lower) alkoxy, aryl(lower)alkynyl, lower alkyl substituted by optionally substituted divalent heterocyclic group and optionally substituted heterocyclic group. A is a heterodicyclic group of the following (A) to (I) exclusive of benzimidazolyl, indolyl, 4,7-dihydrobenzimidazolyl and 2,3-dihydrobenzoxazinyl, wherein said heterocyclic group may be substituted by at least one member selected from the group consisting of alkyl, oxo, thioxo, halogen, lower, lower alkylthio, cyclo(lower)alkyl, amino, lower alkanoylamino, mono(lower)alkylamino, di(lower)alkylamino, N-(lower) alkyl-N-acylamino, lower alkylsulfonylamino, aryl(lower) alkylamino, N-heterocycle-N-(lower)alkylamino, arylsulfonylamino, arylcarbonylamino, aryl, heterocyclic group, lower alkylsulfonyl and lower alkylsulfinyl, provided that when A is 3H-imidazo[4,5-b]pyridyl substituted by lower alkyl, $R^2$ is an optionally substituted aryl optionally substituted heterocyclic group or biphenylyl substituted by a group other than tetrazolyl, and when A is quinolyl substituted by lower alkyl, $R^2$ is an optionally substituted phenyl, optionally substituted naphthyl, optionally substituted heterocyclic group or substituted biphenylyl.

The substituent for the above-mentioned phenyl, naphthyl and heterocyclic group is at least one member selected from the group consisting of alkyl, cyclo(lower)alkyl, alkenyl, alkynyl, lower alkanoyl, lower alkoxy, phenyl, heterocycle (lower)alkyl, halogen, amino, lower alkanoylamino, mono (lower)-alkylamino, di(lower)alkylamino, N-(lower)alkyl-N-acylamino, lower alkylsulfonyl-amino, aryl(lower) alkylamino, N-heterocycle-N-(lower)alkylamino, arylsulfonylamino, arylcarbonylamino, lower alkylsulfonyl, lower alkylsulfinyl, lower alkylthio, cyano, carboxy, protected carboxy, carbamoyl, mono(lower)alkylcarbamoyl, di(lower)alkyl-carbamoyl, nitro, halo(lower)alkyl, aryl (lower)alkyl, aryl(lower)alkenyl, aryl(lower)alkoxy, lower alkanoylamino(lower)alkoxy, mono(lower)alkylamino (lower)alkoxy, di(lower)alkylamino(lower)alkyl, N-(lower) alkyl-N-acylamino(lower)alkoxy, lower alkylsulfonylamino (lower)alkoxy, aryl(lower)alkylamino(lower)alkoxy, N-heterocycle-N-(lower)alkylamino(lower)alkoxy, arylsulfonylamino(lower)aloxy, arylcarbonyl-amino(lower) alkoxy, cyclo(lower)alkyl(lower)alkoxy, cyclo(lower)alkyl (lower)alkyl, aryloxy(lower)alkyl, acyloxy(lower)alkyl, hydroxy(lower)alkyl, mono- or di(lower)alkyl-amino (lower)alkyl, aryl(lower)alkoxy(lower)alkyl, arylthio (lower)alkyl, heterocyle-(lower)alkoxy, heterocyle-oxy (lower)alkyl, aryl(lower)alkylthio, arylureido, lower alkoxy (lower)alkoxy, aryl(lower)alkynyl, lower alkyl substituted by optionally substituted divalent heterocyclic group and optionally substituted heterocyclic group.

The substituent for the above-mentioned biphenylyl is at least one member selected from the group consisting of alkyl, cyclo(lower)alkyl, alkenyl, alkynyl, lower alkanoyl lower alkoxy, phenyl, heterocycle(lower)alkyl other than substituted tetrazolylmethyl, halogen, amino, lower alkanoylamino, mono(lower)alkylamino, di(lower) alkylamino, N-(lower)alkyl-N-acylamino, lower alkylsulfonylamino, aryl(lower)alkylamino, N-heterocycle-N-(lower)alkylamino, arylsulfonylamino, arylcarbonylamnio, lower alkylsulfonyl, lower alkylsulfinyl, lower alkythio, cyano, carbamoyl, mono(lower) alkylcarbamoyl, di(lower)alkylcarbamoyl, nitro, halo (lower)-alkyl, aryl(lower)alkyl, aryl(lower)alkenyl, aryl (lower)alkoxy, lower alkanoylamino-(lower)alkoxy, mono (lower)alkylamino(lower)alkoxy, di(lower)alkylamino (lower)alkoxy, N-(lower)alkyl-N-acylamino(lower)alkoxy, lower alkylsulfonylamino(lower)alkoxy, aryl(lower) alkylamino(lower)alkoy, N-heterocycle-N-(lower) alkylamino(lower)alkoxy, arylsulfonylamino(lower)alkoxy, arylcarbonylamino(lower)alkoxy, cyclo(lower)alkyl-(lower) alkoxy, cyclo(lower)alkyl(lower)alkyl, aryloxy(lower)alkyl, acyloxy(lower)alkyl, hydroxy(lower)alkyl, mono- or di(lower)alkylamino(lower)alkyl, aryl(lower)alkoxy-(lower)alkyl, arylthio(lower)alkyl, hetereocycle(lower) alkoxy, heterocycle-oxy(lower)alkyl, aryl(lower)alkythio, arylureido, lower alkoxy(lower)alkoxy, aryl(lower)alkynyl, lower alkyl substituted by optionally substituted divalent heterocyclic group and optionally substituted heterocyclic group.

The above-mentioned hetecyclic group means the following (A) to (T):

(A) saturated or unsaturated 7 to 12-membered heterobicyclic group having 1 to 4 nitrogen atoms (B) saturated or unsaturated 7 to 12-membered heterobicyclic group having 1 to 3 oxygen atoms (C) saturated or unsaturated 7 to 12-membered heterobicyclic group having 1 to 3 sulfur atoms (D) saturated or unsaturated 7 to 12-membered heterobicyclic group having 1 to 3 nitrogen atoms and 1 or 2 oxygen atoms (E) saturated or unsaturated 7 to 12-membered heterobicyclic group having 1 to 3 nitrogen atoms and 1 or 2 sulfur atoms (F) saturated or unsaturated 7 to 12-membered heterobicyclic group having 1 or 2 oxyge atoms and 1 or 2 sulfur atoms (G) saturated or unsaturated 7 to 12-membered heterobicyclic group having 1 nitrogen atom, 1 oxygen atom and 1 sulfur atom (H) saturated or unsaturated 7 to 12-membered heterobicyclic group having 1 or 2 selenium atoms (I) saturated or unsaturated 7 to 12-membered heterobicyclic group having 1 or 2 selenium atoms and 1 to 3 nitrogen atoms (J) unsaturated 3 to 8-membered heteromonocyclic group having 1 to 4 nitrogen atoms (K) saturated 3 to 8-membered heteromonocyclic group having 1 to 4 nitrogen atoms
(L) unsaturated 3 to 8-membered heteromonocyclic group having 1 or 2 oxygen atoms and 1 to 3 nitrogen atoms
(M) saturated 3 to 8-membered heteromonocyclic group having 1 or 2 oxygen atoms and 1 to 3 nitrogen atoms
(N) unsaturated 3 to 8-membered heteromonocyclic group having 1 or 2 sulfur atoms and 1 to 3 nitrogen atoms
(O) saturated 3 to 8-membered heteromonocyclic group having 1 or 2 sulfur atoms and 1 to 3 nitrogen atoms
(P) unsaturated 3 to 8-membered heteromonocyclic group having 1 or 2 sulfur atoms
(Q) unsaturated 3- to 8-membered heteromonocyclic group having 1 or 2 oxygen atoms
(R) unsaturated 3 to 8-membered heteromonocylic group having 1 oxygen atom
(S) spiroheteocyclic group having 1 or 2 oxygen atoms
(T) unsaturated 3 to 8-membered heteromonocycic group having 1 oxygen atom and 1 or 2 sulfur atoms Of the above-mentioned compounds, a compound of the formula (I) wherein A is a heterocyclic group selected from the group consisting of 2,3-dihydrobenzimidazolyl, pyrazolopyrimidinyl, tetrahydropyrazolopyrimidinyl, imidazopyrazolyl, dihydroimidazopyrzolyl, imidazopyridyl, pyrrolopridyl, pyrazolopyridyl, benzopyrazolyl, dihydrobenzimidazolyl, benzotriazolyl, indolizinyl, isoindolyl, indazolyl, indolinyl, isoindolinyl purinyl, quinolizinyl, isoquinolyl, quinolyl, phthalazinyl, naphthalidinyl, quinoxalinyl, dihydroquinoxalinyl, tetrahydroquinoxalinyl, quinazolinyl, dihydroquinazolinyl, tetrahydroquinazolinyl, cinnolinyl, pteridinyl, pyrazinopyridazinyl, imidazotriazinyl, imidazopyrazinyl, imidazopyrimidinyl, imidazopyridazinyl, 1H-1-(or 2)pyridazinyl, benzofuranyl, isobenzofuranyl, furopyridyl chromenyl, chromanyl, isochromanyl, benzoxepinyl, cyclopentapyranyl, furopyranyl, benzothiophenyl, dihydrodithianaphthalenyl, dithianaphthalenyl, dioxoloimidazolyl benzoxazinyl, pyridoxazinyl, pyrazolooxazolyl, furopyridyl, thienoimidazolyl, thienopyridyl, dithiadiazaindanyl, thienofuranyl, oxathiolopyrrolyl, benzoselenophenyl, selenopyridyl, benzoselenol, selenopyridyl and cyclopentadienopyridyl. These heterocyic groups are preferably optionally substituted by lower alkyl and/or oxo.

Of the above-mentioned compounds, preferably exemplified is a compound of the formula (I) wherein $R^1$ is an alkyl, an alkenyl, a phenyl(lower)alkenyl, a quinolyl, a phenyl optionally substituted by a substituent selected from the group consisting of nitro, alkyl and alkenyl, or a thienyl optionally substituted by halogen; A is a heterocyclic group selected from the group consisting of 2,3-dihydrobenzimidazolyl, imidazopyrazolyl, imidazopyridyl, pyrrolopyridyl, pyrazolopyridyl, benzotriazolyl, indolizinyl, indazoyl, quinolyl, dihydroquinoxalinyl, tetrahydroquinoxalinyl, dihydroquinazolinyl, tetrahydroquinazolinyl, benzofuranyl, benzothiophenyl and thienoimidazolyl, said heterocyclic group being optionally substituted by alkyl or oxo; X is a lower alkylene, an oxa(lower)alkylene or an oxa; and $R^2$ is a phenyl optionally substituted by a substituent selcedted from the group consisting of alkyl, alkenyl, alkynyl, lower alkanoyl, lower alkoxy, phenyl, imidazolyl(lower)alkyl, piperidinyl-(lower)alkyl, halogen, amino, lower alkanoylamino, mono(lower)alkylamino, di(lower)alkylamino, N-(lower)alkyl-N-(lower)alkanoylamino, N-(lower)alkyl-N-benzoylamino, lower alkylsulfonylamino, phenyl(lower)alkylamino, phenylsulfonylamino, benzoylamino, lower alkysulfonyl, lower alkylsulfinyl, lower alkylthio, cyano, carboxy, lower alkoxycarbonyl, cyclo(lower)alkyloxycarbonyl, mono(lower)-alkylcarbamoyl, nitro, halo(lower)alkyl, phenyl(lower)alkyl, phenyl(lower)alkenyl, phenyl(lower)alkoxy, (N-pyridyl-N-(lower)alkylamino)(lower)alkoxy, cyclo(lower)alkyl(lower)alkoxy, cyclo(lower)alkyl(lower)alkyl, phenoxy(lower)alkyl, lower alkylsulfonyloxy(lower)alkyl, hydroxy(lower)alkyl, di(lower)alkylamino-(lower)alkyl, phenyl(lower)alkoxy(lower)alkyl, phenylthio(lower)alkyl, thienyl(lower)-alkoxy, pyridyloxy(lower)alkyl, phenyl(lower)alkylthio, phenylureido, lower alkoxy(lower)alkoxy, phenyl(lower)alkynyl, dioxothiazolidylidene(lower)alkyl and thienyl optionally substituted by halogen; a naphthyl optionally substituted by halogen; a 4-phenylphenyl substituted by halogen; a thienyl optionally substituted by halogen; a benzothienyl optionally substituted by halogen; a quinolyl optionally substituted by halogen; or a benzooxolanyl optionally substituted by halogen.

Of the above-mentioned compounds, preferred is a compound of the formula (I) wherein $R^1$ is an alkyl, an alkenyl, a phenyl(lower)alkenyl, a phenyl optionally substituted by a substituent selected from the group consisting of alkyl and alkenyl or a thienyl optionally substituted by halogen; A is a heterocyclic group selected from the group consisting of 3H-imidazo[4,5-b]pyridyl, pyrazolo[1,5-a]pyridyl, indolizinyl, 1H-indazolyl, benzo[b]furanyl and benzo[m]thiophenyl, said heterocyclic group being optionally substituted by one or two alkyl; X is an alkylene; and $R^2$ is a phenyl optionally substituted by a substituent selected from the group consisting of alkyl, lower alkoxy, phenyl, halogen, di(lower)alkylamino, lower alkylthio, lower alkoxycarbonyl, nitro, halo(lower)alkyl, phenyl(lower)alkyl, phenyl(lower)alkenyl, phenyl(lower)alkoxy, cyclo(lower)alkyl(lower)alkoxy, phenoxy(lower)alkyl, phenyl(lower)alkoxy(lower)alkyl and thienyl optionally substituted by halogen; a naphthyl optionally substituted by halogen; or a 4-phenylphenyl substituted by halogen.

Of the above-mentioned compounds, preferred is a sulfonamide compound (I) wherein A is a 3H-imidazo[4,5-b]pyridyl, a 1H-indazolyl or a benzo[b]furnyl, these heterocyclic groups being optionally substituted by alkyl; and $R^2$ is a phenyl substituted by halogen, said phenyl being optionally substituted by a substituent selected from the group consisting of alkyl, alkenyl, alkynyl, lower alkoxy, phenyl, halogen, di(lower)alkylamino, lower alkylthio, lower alkoxycarbonyl, nitro, halo(lower)alkyl, phenyl(lower)alkyl, phenyl(lower)alkenyl, phenyl(lower)alkoxy, cyclo(lower)alkyl(lower)alkoxy, phenoxy(lower)alkyl, phenyl(lower)alkoxy(lower)alkyl, phenyl(lower)alkynyl and thienyl optionally substituted by halogen, or a naphthyl substituted by halogen, or a salt thereof. Above all, a sulfonamide compound (I) wherein A is 3H-imidazo[4,5-b]pyridyl substituted by one or two lower alkyl, 1H-indazolyl substituted by one lower alkyl or benzo[b]furanyl substituted by one lower alkyl is preferable.

Paticularly preferable groups are as follows.

$R^1$: phenyl, 2-nitrophenyl, o- or p-tolyl, n-pentenyl, n-butyl, n-pentyl, n-hexyl, thienyl, 8-quinolyl, (E)-2-phenylethenyl, 4-pentenyl, 4-vinylphenyl, 5-chlorothiophen-2-yl, 5-bromothiophen-2-yl, 4-ethylphenyl, X: methylene, —OCH$_2$—, oxa $R^2$: 2,4-dichlorophenyl, 2-chlorophenyl, 4-bromo-2-chlorophenyl, 2,4-dichloro-5-fluorophenyl, 3,4-chlorophenyl, 2,3-dichlorophenyl, 2,5-dichlorophenyl, 2-bromo-4-chlorophenyl, 4-chloro-2-methoxyphenyl, 4-chloro-2-methylphenyl, 4-phenyl-phenyl, 2-chloro-4-phenylphenyl, 1-bromo-2-naphthyl, 3-chlorobenzo[b]thiophen-2-yl, 2-chloro-4-(thiophen-2-yl)phenyl, 2-chloro-4-(5-chlorothiophen-2-yl)phenyl, 2-chloro-4-ethylphenyl, 2-chloro-4-vinylphenyl, 2-chloro-4-methylphenyl, 2-chloro-4-(n-pentyl)phenyl, 2-chloro-4-(i-butyl)phenyl, 2-chloro-4-(cylohexylmethyl)phenyl, (E)-2-chloro-4-(2-phenylethenyl)phenyl, 4-benzyloxy-2-chlorophenyl, 2-chloro-4-methoxyphenyl, 2-chloro-4-isopropoxyphenyl, 2-chloro-4-(n-butoxy)phenyl, 2-chloro-4-((cylohexylmethyl)oxy)phenyl, 2-chloro-4-((2-(N-methyl-N-(2-pyridinyl)amino)ethyl)oxy)phenyl, 2-chloro-4-(methylthio)phenyl, 2-chloro-4-(methylsulfinyl)-phenyl, 2-chloro-4-(methanesulfonyl)phenyl, 4-(benzylamino)-2-chlorophenyl, 4-(n-butylamino)-2-chlorophenyl, 2-chloro-4-(N,N-dimethylamino)phenyl, 4-acetylamino-2-chlorophenyl, 2-chloro-4-(methanesulfonylamino)phenyl, 2-chloro-4-nitrphenyl, 2-chloro-4-formylphenyl, 2-chloro-4-[(2,4-dioxo-1,3-thiazolidin-5-ylidene)methyl]-phenyl, 2-chloro-fluorophenyl, 2,4,6-trichlorophenyl, 2,3,4-trichlorophenyl, 2-chloro-4-iodophenyl, 2,5-dichlorothiophen-3-yl, 2-chloro-4,5-(methylenedioxy)-phenyl, 2-chloroquinolin-3-yl, 2-chloro-4-(trifluoromethyl)phenyl, 2-chloro-4-cyanophenyl, 2-chloro-4-(2-phenylethyl)phenyl, 2-chloro-4-aminophenyl, 2-chloro-4-(hydroxymethyl)phenyl, 4-carboxy-2-chlorophenyl, 2-chloro-4-((methanesulfonyloxy)methyl)phenyl, 2-chloro-4-((phenyloxy)methyl)phenyl, 2-chloro-4-(ethoxycarbonyl)phenyl, 2-chloro-4-(methylcarbamoyl)phenyl, 2-chloro-4-(dimethylaminomethyl)phenyl, 2-chloro-4-((imidazol-1-yl)methyl)phenyl, 2-chlor4-((piperidin-1-yl)methyl)phenyl, 2-chloro-4(phenylthiomethyl)phenyl, 4-((benzyloxy)-methyl)-2-chlorophenyl, 4-(benzimidazol-2-yl)-2-chlorophenyl, 4-(1-methylbenzimidazol-2-yl)-2-chlorophenyl, 1-ethylbenzimidazol-2-yl, 2-chloro-4-(n-pentanethio)-phenyl, 4-(benzylthio)-2-chlorophenyl, 2-chloro-4-((3-pyridyloxy)methyl)phenyl, 2-chloro-4-ethylthiophenyl, 4-(N-butyrylamino)-2-chlorophenyl, 4-(N-benzoylamino)-2-chlorophenyl, 4-(N-benzoyl-N-methylamino)-2-chlorophenyl, 4-(N-butyryl-N-methylamino)-2-chlorophenyl, 2-chloro-(N-(n-pentyl)amino)phenyl, 2chloro-4-(N-methyl-N-(n-pentyl)amino)phenyl, 4-(N-benzenesulfonylamino)-2-chlorophenyl, 2-chloro-4-(isopropoxylcarbonyl)phenyl, 2-chloro-4-(cyclohexyloxycarbonyl)phenyl, 2-chloro-4-(3-phenylureido)phenyl, 2-chloro-4-propoxyphenyl, 2-chloro-4-(n-pentoxy)phenyl, 2-chloro-4-ethoxyphenyl, 2-chloro-4-(2-methoxyethoxy)phenyl, 2-chloro-4-[(thiophen-2-yl)methyloxy]phenyl, 2-chloro-4-[(thiophen-3-yl)methyloxy]phenyl, 2-chloro-4-phenylethynylphenyl, 2-chloro-4-(cyclopentylmethyloxy)phenyl, 2-chloro-4-(1-hexynyl)phenyl, 2-chloro-4-hexylphenyl, 2-chloro-4-piperidinophenyl, 2-chloro-4-morpholinophenyl, 2-chloro-4-(hexamethyleneimino)phenyl, 2-chloro-4-pyrrolidinophenyl, 2-chloro-4-(4-methylpiperazin-1-yl)phenyl A: 4H-imidazo[1,2-b]pyrazolyl, 3H-thieno[2,3-d]imidazolyl, 1H-thieno[2,3-d]imidazolyl, imidazo[1,2-a]pyridyl, H-pyrrolo[3,2-b]pyridyl, 2,3-dihydrobenzo-[d]imidazolyl, 1H-indazolyl, indolizinyl, benzotriazolyl, 1H-imidazo[4,5-b]pyridyl, 3H-imidazo[4,5-b]pyridyl, pyrazolo[1,5a]pyridyl, benzo[b]furanyl, benzo[b]thiophenyl, 3,4-dihydroquinazolinyl, 1,2-dihydroquinoxalinyl, 1,2,3,4-tetrahydroquinoxalinyl quinolyl, 1,2,3,4-tetrahydroquinazolinyl, 1,4-dihydroquinazolinyl, 2H-indazolyl Substitutent of A: methyl, ethyl, n-propyl,oxo Preferred objective compounds (I) are as follows.

3-(3,4-dichlorobenzyl)-2-methyl-5-(n-pentanesulfonylcarbamoyl)benzo[b]thiophene
3-(2,3-dichlorobenzyl)-2-methyl-5-(n-pentanesulfonylcarbamoyl)benzo[b]thiophene
3-(2,5-dichlorobenzyl)-2-methyl-5-(n-pentanesulfonylcarbamoyl)benzo[b]thiophene
3-(2,4-dichlorobenzyl)-2-methyl-5-(n-pentanesulfonylcarbamoyl)pyrazolo[1,5-a]pyridine
3-(2,4-dichlorobenzyl)-2-methyl-5-benzenesulfonylcarbamoyl)pyrazolo[1,5-a]pyridine
1-(2,4-dichlorobenzyl)-2-methyl-7-(n-pentanesulfonylcarbamoyl)indolizine
7-n-butanesulfonylcarbamoyl-1-(2,4-dichlorobenzyl)-2-methylindolizne
1-(2,4-dichlorobenzyl)-2-methyl-7-(benzenesulfonylcarbamoyl)indolizine
2-methyl-7-(n-pentanesulfonylcarbamoyl)-1-(4-phenylbenzyl)indolizne
6-(n-pentanesulfonylcarbamoyl)-4-(4-phenylbenzyl)quinoline
3-(2,4-dichlorobenzyl)-2-methyl-5-(n-pentanesulfonylcarbamoyl)-3H-imidazo[4,5-b]pyridine
5-(n-butanesulfonylcarbamoyl)-3-(2,4-dichlorobenzyl)-2-methyl-3H-imidazo[4,5-b]pyridine
5-benzenesulfonylcarbamoyl-3-(2,4-dichlorobenzyl)-2-methyl-3H-imidazo[4,5-b]pyridine
3-(2-chloro-4-phenylbenzyl)-2-methyl-5-(n-pentanesulfonylcarbamoyl)-3H-imidazo[4,5-b]pyridine
3-(1-bromo-2-naphthyl)methyl-2-methyl-5-(n-pentanesulfonylcarbamoyl)-3H-imidazo[4,5-b]pyridine
2-methyl-5-(n-pentanesulfonylcarbamoyl)-3-(4-phenylbenzyl)-3H-imidazo[4,5-b]pyridine
3-(4-bromo-2-chlorobenzyl)-2-methyl-5-(n-pentanesulfonylcarbamoyl)-3H-imlidazo[4,5-b]pryidine
3-(4-bromo-2-chlorobenzyl)-5-(n-butanesulfonylcarbamoyl)-2-methyl-3H-[4,5-b]pyridine
5-(benzenesulfonylcarbamoyl)-3-(4-bromo-2-chorobenzyl)-2-metyl-3H-imidazo[4,5-b]pyridine
3-(2-bromo-4-chlorobenzyl)-2-methyl-5-(n-pentanesulfonylcarbamoyl)-3H-imidazo[4,5-b]pyridine
5-(benzenesulfonylcarbamoyl)-3-(2-bromo-4-chlorobenzyl)-2-methyl-3H-imidazo[4,5-b]pyridine
3-(2-bromo-4-chlorobenzyl)-5-(n-butanesulfonylcarbamoyl)-2-methyl-3H-imidazo[4,5-b]pyridine
3-(2,4-dichlorobenzyl)-2-methyl-6-(n-pentanesulfonylcarbamoyl)indolizine
3-(2,4-dichlorobenzyl)-2-methyl-6-(n-butanesulfonylcarbamoyl)indolizine
3-(2,4-dichlorobenzyl)-2-methyl-6-(benzenesulfonylcarbamoyl)indolizine
3-(2,4-dichlorobenzyl)-2-ethyl-7-methyl-5-(n-pentanesulfonylcarbamoyl)-3H-imidazo[4,5-b]pyridine
2-ethyl-7-methyl-5-(n-pentanesulfonylcarbamoyl)-3-(4-phenylbenzyl)-3H-imidazo[4,5-b]pyridine
3-(2,4-dichlorobenzyl)-2-methyl-5-(benzenesulfonylcarbamoyl)benzo[b]thiophene
3-(2,4-dichlorobenzyl)-2-methyl-5-(n-butanesulfonylcarbamoyl)benzo[b]thiophene
3-(4-phenylbenzyl)-2-methyl-5-(n-pentanesulfonylcarbamoyl)benzo[b]thiophene 3-(2-chlorobenzyl)-2-methyl-5-(n-pentanesulfonylcarbamoyl)benzo[b]thiophene
3-(4-bromo-2-chlorobenzyl)-2-methyl-5-(n-pentanesulfonylcarbamoyl)-benzo[b]thiophene
3-(2,4-dichloro-5-fluorobenzyl)-2-methyl-5-(n-pentanesulfonylcarbamoyl)-benzo[b]thiophene
3-((3-chlorobenzo[b]thiophen-2-yl)methyl)-2-methyl-5-(n-pentanesulfonyl-carbamoyl)benzo[b]thiophene
3-(1-bromonaphthalen-2-yl)methyl-2-methyl-5-(n-pentanesulfonyl-carbamoyl)benzo[b]thiophene
1-(2,4-dichlorobenzyl)-2-methyl-5-n-pentanesulfonylcarbamoyl-1H-thieno[2,3-d]imidazole
3-(2,4-dichlorobenzyl)-2-methyl-5-(n-pentanesulfonylcarbamoyl)-3H-thieno[2,3-d]imidazole
1-(2,4-dichlorobenzyl)-2-methyl-6-(n-pentanesulfonylcarbamoyl)-1H-imidazo[4,5-b]pyridine
3-(2,4-dichlorobenzyl)-2-methyl-5-(n-pentanesulfonylcarbamoyl)pyrrolo[3,2-b]pyridine
3-(2,4-dichlorobenzyl)-2-methyl-5-(benzesulfonylcarbamoyl)pyrrolo[3,2-b]pyridine
3-(4-chloro-2-methoxybenzyl)-2-methyl-5-(n-pentanesulfonylcarbamoyl)-3H-imidazo[4,5-b]pyridine
3-(4-chloro-2-methylbenzyl)-2-methyl-5-(n-pentanesulfonylcarbamoyl)-3H-imidazo[4,5-b]pyridine
5-benzenesulfonylcarbamoyl-3-(4-chloro-2-methylbenzyl)-2-methyl-3H-imidazo[4,5-b]pyridine
5-benzenesulfonylcarbamoyl-3-(2-chloro-4-phenylbenzyl)-2-methyl-3H-imidazo[4,5-b]pyridine
5-(n-butanesulfonylcarbamoyl)-3-(2-chloro-4-phenylbenzyl)-2-methyl-3H-imidazo[4,5-b]pyridine
3-(2,4-dichlorobenzyl)-2-methyl-5-(1-n-pentanesulfonylcarbamoyl)benzo[b]furan
5-(benzenesulfonylcarbamoyl)-3-(2,4-dichlorobenzyl)-2-methylbenzo[b]furan
2-(2,4-dichlorbenzyl)-3,5-dimethyl-7-(1-n-pentanesulfonylcarbamoyl)benzo[b]furan
7-(benzenesulfonylcarbamoyl)-2-(2,4-dichlorobenzyl)-3,5-dimethylbenzo[b]furan
2-methyl-5-(1-n-pentanesulfonylcarbamoyl)-3-(4-phenylbenzyl)benzo[b]furan
5-(1-benzenesulfonylcarbamoyl)-2-methyl-3-(4-phenylbenzyl)benzo[b]furan
5-(1-n-butanesulfonylcarbamoyl)-3-(2,4-dichlorobenzyl)-2-methylbenzo[b]furan
3-(2,4-dichlorobenzyl)-5-(1-n-hexanesulfonylcarbamoyl)-2-methylbenzo[b]furan
3-(2,4-dichlorobenzyl)-2-methyl-5-(2-thiophenesulfonylcarbamoyl)benzo[9]furan
3-(2,4-dichlorobenzy)-2ethyl-5-(1-n-pentanesulfonylcarbamoyl)benzo[b]furan
5-(benzenesulfonylcarbamoyl)-3-(2,4-dichlorobenzyl)-2-ethylbenzo[b]furan
3-(2,4-dichlorobenzyl)-2-ethyl-5-(8-quinolinesulfonylcarbamoyl)benzo[b]furan
3-(2,4-dichlorobenzyl)-2-ethyl-5-((2-methylbenzene)sulfonylcarbamaoyl)-benzo[b]furan
3-(2,4-dichlorobenzyl)-5-(1-n-pentanesulfonylcarbamoyl)-2-propylbenzo[b]furan
5-(benzenesulfonylcarbamoyl)-3-(2,4-dichlorobenzyl)-2-propylbenzo[b]furan
3-(2,4-dichlorobenzyl)-5-ethyl-(2-nitrobenzenesulfonylcarbamoyl)-2-propylbenzo[b]furan
3-(2,4-dichlorobenzyl)-5-(1-n-pentanesulfonylcarbamoyl)benzo[b]furan
3-(2,4-dichlorobenzyl)-2-methyl-5-(1-n-pentanesulfonylcarbamoyl)-benzo[b]thiophene
2-(2,4-dichlorobenzyl)-3-ethyl-7-(1-n-pentanesulfonylcarbamoyl)benzo[b]thiophene
7-(benzesulfonylcarbamoyl)-2-(2,4-dichlorobenzyl)-3-ethylbenzo[b]thiophene
6-(1-n-butanesulfonylcarbamoyl)-1-(2,4-dichlorobenzyl)-3-methyl-2-benzimidazolone
1-(2,4-dichlorobenzyl)-3-methyl-6-(1-pentanesulfonylcarbamoyl)-1H-indazole
6-(benzenesulfonylcarbamonyl)-1-(2,4-dichlorobenzyl)-3-methyl-1H-indazole
(E)-1-(2,4-dichlorobenzyl)-3-methyl-6-((2-phenylethenyl)sulfonylcarbamoyl)-1H-indazole
6-(1-n-butanesulfonylcarbamoyl)-1-(2,4-dichlorobenzyl)benzotriazole
6-(1-n-butanesulfonylcarbamoyl)-1-(2,4-dichlorobenzyl)-3-methyl-1H-indazole
7-(1-n-butanesulfonylcarbamoyl)-1-(2,4-dichlorobenzyl)-3-ethyl-4(3H)-quinazoline 7-(1n-butanesulfonylcarbamoyl)-3-(2,4-dichlorobenzyl)-1-methyl-4(3H)-quinazoline
7-(1-n-butanesulfonylcarbamoyl)-3-(2,4-dichlorobenzyl)-4-(3H)-quinazolinone
7-(1-n-butanesulfonylcarbamoyl)-2-(2,4-dichlorobenzyl)-3-methyl-4-(3H)quinazoline
6-(1-n-butanesulfonylcarbamoyl)-3-(2,4-dichlorobenzyl)-3,4-dihydro-2-methylquinazoline.hydrochloride
1-(2,1-dichlorobenzyl)-2-methyl-7-(1-n-pentanesulfonylcarbamoyl)-4-(1H)-quinazolinone
7-(benzenesulfonylcarbamoyl)-1-(2,4-dichlorobenzyl)-2-methyl-4-(1-H)-quinazolinone
1-(2,4-dichlorobenzyl)-1,4-dihydro-2-methyl-7-(1-n-pentanesulfonyl-carbamoyl)quinazoline.hydochloride
7-(1-n-butanesulfonylcarbamoyl)-1-(2,4-dichlorobenzyl)-3-methyl-2-(1H)-quinoxalinone
7-(1-n-butanesulfonylcarbamoyl)-1-(2,4-dichlorobenzyl)-4methyl-2,3-(1H,4H)-quinoxalinedione
4-(2,4-dichlorobenzyl)-5-ethyl-3-(1-n-pentanesulfonylcarbamoyl)imidazo[1,2-b]pyrazole
3-(2,4-dichlorobenzyl)-2-methyl-6-(1-n-pentanesulfonylcarbamoyl)imidazo[1,2-a]pyridine
6-(n-pentanesulfonylcarbamoyl)-4-(4-phenylphenyloxy)quinoline
6-(n-pentanesulfonylcarbamoyl)-4-(4-phenylbenzloxy)quinoline
3-(2,4-dichlorobenzyl)-2-ethyl-5-(((E)-pentene-1-sulfonyl)carbamoyl)benzo[b]furan
1-(2,4-dichlorobenzyl)-3-ethyl-6-(1-n-pentanesulfonylcarbamoyl)-1H-indazole
6-(benzenesulfonylcarbamoyl)-1-(2,4-dichlorobenzyl)-3-ethyl-1H-indazole
6-(benzenesulfonylcarbamoyl)-3-(2,4-dichlorobeznyl)-2-methylimidazol[1,2-a]pyridine
3-(2,3-dichlorobenzyl)-2-methyl-5-(n-pentanesulfonylcarbamoyl)-3H-imidazo[4,5-b]pyridine
3-((3-chlorobenzo[b]thiophen-2-yl)methyl)-2-methyl-5-n-pentanesulfonyl-carbamoyl-3H-imidazo[4,5-b]pyridine
3-(2-chloro-4-phenylbenzyl)-2-methyl-5-(n-pentanesulfonylcarbamoyl)-benzo[b]thiophene
3-(2-chloro-4-phenylbenzyl)-2-methyl-5-(((E)-1-pentene-1sulfonyl)carbamoyl)-3H-imidazo[4,5-b]pyrine
1-(2-chloro-4-phenylbenzyl-3-methyl-6-(1-pentanesulfonylcarbamyl)-1H-indazole
6(benzenesulfonylcarbamoyl)-1-(2-chloro-4-phenylbenzyl)-3-methyl-1H-indazole
(E)-1-(2-chloro-4-phenylbenzyl)-3-methyl-6-((2-phenylethenyl)sulfonylcarbamoyl)-1H-indazole
1-(2-chloro-4-phenylbenzyl)-3-methyl-6-(((E)-1-pentene-1-sulfonyl)carbamoyl)-1H-indazole
1-(2-chloro-4-phenylbenzyl)-3-methyl-6-((4-vinylbenzene)sulfonylcarbamoyl-1H-indazole 1-(2-chloro-4-phenylbenzyl)-3-methyl-6-((4-methylbenzene)sulfonylcarbamoyl-1H-indazole
1-(4-bromo-2-chlorobenzyl)-3-methyl-6-(1-pentanesulfonylcarbamoyl)-1H-indazole
6-(benzenesulfonylcarbamoyl)-1-(4-bromo-2-chlorobenzyl)-3-methyl-1H-indazole
(E)-1-(4-bromo-2-chlorobenzyl)-3-methyl-6-((2-phenylethenyl)sulfonylcarbamoyl)-1H-indazole
3-(2,4-dichlorobenzyl)-2-methyl-5-(((E)-1-pentene-1-sulfonyl)carbamoyl)-benzo[b]furan
(E)-3-(2,4-dichlorobenzyl)-2-methyl-5-((2-phenylethenyl)sulfonylcarbamoyl)-benzo[b]furan
3-(2,4-dichlorobenzyl)-2-methyl-5-((4-vinylbenzene)sulfonylcarbamoyl)-bezno[b]furan
3-(2chloro-4-phenylbenzyl)-2-methyl-5-(1-pentanesulfonylcarbmoyl)-benzo[b]furan
5-(benzenesulfonylcarbamoyl)-3-(2-chloro-4-phenylbenzyl)-2-methylbenzo[b]furan
(E)-3-(2-chloro-4-phenylbenzyl)-2-methyl-5-((2-phenylethenyl)sulfonyl-carbamoyl)benzo[b]furan
3-(2-chloro-4-phenylbenzyl)-2-methyl-5-(4-vinylbenzenesulfonylcarbamoyl)-benzo[b]furan
3-(2-chloro-phenylbenzyl)-2-methyl-5-(((E)-1-pentene-1-sulfonyl)carbamoyl)-benzo[b]furan
3-(4-bromo-2-chlorobenzyl)-2-methyl-5-(1-pentanesulfonylcarbamoyl)-benzo[b]furan
5-(benzenesulfonylcarbamoyl)-3-(4-bromo-2-chlorobenzyl)-2-methylbenzo[b]furan
(E)-3-(4-bromo-2-chlorobenzyl)-2-methyl-5-((2-phenylethenyl)sulfonylcarbamoyl)-benzo[b]furan
3-(2,4dichlorobenzyl)-2-methyl-5-[(4-methylbenzene)sulfonylcarbamoyl]-3H-imidazo[4,5-b]pyridine
3-(2,4-dichlorobenzyl)-2-methyl-5-1-[(4-vinylbenzene)sulfonylcarbamoyl]-3H-imidazo[4,5-b]pyridine
(E)-3-(2,4-dichlorobenzyl)-2-methyl-5-[(2-phenylethenyl)sulfonylcarbamoyl-3H-imidazo[4,5-b]pyridine
5-((5-chlorothiophen-2-yl)sulfonylcarbamoyl)-3-(2,4-chlorobenzyl)-2-methyl-3H-imidazo[4,5-b]pyridine
5-((5-bromothiophen-2-yl)sulfonylcarbamoyl)-3-(2,4-dichlorobenzyl)-2-methyl-3H-imidazo[4,5-b]pyridine
(E)-3-(4-bromo-2chlorobenzyl)-2-methyl-5-[(2-phenylethenyl)sulfonylcarbamoyl]-3H-imidazo[4,5-b]pyridine
3-(4-bromo-2-chlorobenzyl)-2-methyl-5-[(4-vinylbenzene)sulfonylcarbamoyl]-3H-imidazo[4,5-b]pyridine
3-(2-chloro-4-phenylbenzyl)-2-methyl-5-[(4-vinylbenzene)sulfonylcarbamoyl]-3H-imidazo[4,5-b]pyridine
(E)-3-(2-chloro-4-phenylbenzyl)-2-methyl-5[(2-phenylethenyl)sulfonylcarbamoyl]-3H-imidazo[4,5-b]pyridine
3-(2-chloro-4-phenylbenzyl)-5-[(5-chlorothiophen-2-yl)sulfonylcarbamoyl]-2-methyl-3H-imidazo[4,5-b]pyridine
3-(2-chloro-4-phenylbenzyl)-2-methyl-5-[(4-methylbenzene)sulfonylcarbamoy]-3H-imidazo[4,5-b]pyridine
5-[(5-bromothiophen-2-yl)sulfonylcarbamoyl]-3-(2-chloro-4-phenylbenzyl)-2-methyl-3H-imidazol[4,5-b]pyridine
3-(2-chloro-4-phenylbenzyl)-5-[(4-ethylbenzene)sulfonylcarbamoyl]-2-methyl-3H-imidazo[4,5-b]pyridine
5-(benzenesulfonylcarbamoyl)-3-[2-chloro-4-(thiophen-2-yl)benzyl]-2-methyl-3H-imidazo[4,5-b]pyridine
5-(benzenesulfonylcarbamoyl)-3-[2-chloro-4-(5-chlorothiophen-2-yl)benzyl]-2-methyl-3H-imidazo[4,5-b]pyridine
3-(2-chloro-4-ethylbenzyl)-2-methyl-5-(1-pentanesulfonylcarbamoyl)-3H-imidazo[4,5-b]pyridine
5-(benzenesulfonylcarbamoyl)-3-(2-chloro4-ethylbenzyl)-2-methyl-3H-imidazo[4,5-b]pyridine 3-(2-chloro-4-ethylbenzyl)-2-methyl-5-[(4-methylbenzene)sulfonylcarbamoyl]-3H-imidazo[4,5-b]pyridine
(E)-3-(2-chloro-4-ethylbenzyl)-2-methyl-5-[(2-phenylethenyl)sulfonylcarbamoyl]-3H-imidazo[4,5-b]pyridine
5-(benzenesulfonylcarbamoyl)-3-(2-chloro-4-vinylbenzyl)-2-methyl-3H-imidazo[4,5-b]pyridine
5-(benzenesulfonylcarbamoyl)-3-(2-chloro-4-methylbenzyl)-2-methyl-3H-imidazo[4,5-b]pyridine
5-(benzenesulfonylcarbamoyl)-3-(2-chloro-4-(n-pentyl)benzyl)-2-methyl-3H-imidazo[4,5-b]pyridine
5-(benzenesulfonylcarbamoyl)-3-(2-chloro-4-isobutylbenzyl)-2-methyl-3H-imidazo[4,5-b]pyridine
5-(benzenesulfonylcarbamoyl)-3-(2-chloro-4-(cyclohexylmethy)benzyl)-2-methyl-3H-imidazo[4,5-b]pyridine
(E)-5-(benzenesulfonylcarbamoyl)-3-(2-chloro-4-(2-phenylethenlyl)benzyl)-2-methyl-3-3H-imidazo[4,5-b]pyridine
5-(benzenesulfonylcarbamoyl)-3-(4-benzyloxy-2-chlorobenzyl)-2-methyl-3H-imidazo[4,5-b]pyridine
5-(benzenesulfonylcarbamoyl)-3-(2-chloro-4-methoxybenzyl)-2-methyl-3H-imidazo[4,5-b]pyridine
5-(benzenesulfonylcarbamoyl)-3-(2-chloro-4-isopropoxybenzyl)-2-methyl-3H-imidazo[4,5-b]pyridine
5-(benzenesulfonylcarbamoyl)-3-(4(n-butoxy)-2-chlorobenzyl)-2-methyl-3H-imidazo[4,5-b]pyridine
5-(benzenesulfonylcarbamoyl)-3-(2-chloro-4-((cyclohexylmethyl)oxy)benzyl)-2-methyl-3H-imidazo[4,5-b]pyridine
5-(benzenesulfonylcarbamoyl)-3(2chloro-4((2-(N-methyl-N-(2-pyridinyl)amino)ethyl)oxy)benzyl)-2-methyl-3H-imidazo[4,5-b]pyridine
5-(benzenesulfonylcarbamoyl)-3-(2-chloro-4-(methylthio)benzyl)-2-methyl-3H-imidazo[4,5-b]pyridine
5-(benzenesulfonylcarbamoyl)-3-(2-chloro-4-(methylsulfinyl)benzyl)-2-methyl-3H-imidazo[4,5-b]pyridine
5-(benzenesulfonylcarbamoyl)-3-(2-chloro-4-(methanesulfonyl)benzyl)-2-methyl-3H-imidazo[4,5-b]pyridine
5-(benzenesulfonylcarbamoyl)-3-(4-(benzylamino)-2-chlorobenzyl)-2-methyl-3H-imidazo[4,5-b]pyridine
5-(benzenesulfonylcarbamoyl)-3-(4-(n-butylamino)-2-chlorobenzyl)-2-methyl-3H-imidazo[4,5-b]pyridine
5-(benzenesulfonylcarbamoyl)-3-(2-chloro-4-(N,N-dimethylamino)benzyl)-2-methyl-3H-imidazo[4,5-b]pyridine
3-(4-(acetamide)-2-chlorobenzyl)-5-(benzenesulfonylcarbamoyl)-2-methyl-3H-imidazo[4,5-b]pyridine
5-(benzenesulfonylcarbamoyl)-3-(2-chloro-4-(methanesulfonylamino)benzyl)-2-methyl-3H-imidazo[4,5-b]pyridine
5-(benzenesulfonylcarbamoyl)-3-(2-chloro-4-nitrobenzyl)-2-methyl-3H-imidazo[4,5-b]pyridine
5-(benzenesulfonylcarbamoyl)-3-(2-chloro-4-formylbenzyl)-2-methyl-3H-[4,5-b]pyridine
5-(benzenesulfonylcarbamoyl)-3-[2-chloro-4-[(2,4-dioxo-1,3-thiazolidin-5-ylidene)methyl]benzyl]-2-methyl-3H-imidazo[4,5-b]pyridine
5-(benzenesulfonylcarbamoyl)-3-(2-chloro-4-fuorobenzyl)-2-methyl-3H-imidazo[4,5-b]pyridine
5-(benzenesulfonylcarbamoyl)-2-methyl-3-(2,4,6-trichlorobenzyl)-3H-imidazo[4,5-b]pyridine
5-(benzenesulfonylcarbamoyl)-2-methyl-3-(2,3,4-trichlorobenzyl)-3H-imidazo[4,5-b]pyridine 5-(benzenesulfonylcarbamoyl)-3-(2,4-dichloro-5-fluorobenzyl)-2-methyl-3H-imidazo[4,5-b]pyridine 5-(benzenesulfonylcarbamoyl)-3-(2-chloro-4-iodobenzyl)-2-methyl-3H-imidazo[4,5-b]pyridine 5-(benzenesulfonylcarbamoyl)-3-((2,5-dichlorothiophen-3-yl)methyl)-2-methyl-3H-imidazo[4,5-b]pyridine 5-(benzenesulfonylcarbamoyl)-3-(2-chloro-4,5-(methylenedioxy)benzyl)-2-methyl-3H-imidazo[4,5-b]pyridine 5-(benzenesulfonylcarbamoyl)-3-((2-chloroquinolin-3-yl)methyl)-2-methyl-3H-imidazo[4,5-b]pyridine 5-(benzenesulfonylcarbamoyl)-3-(4-chloro-4-(trifluoromethyl)benzyl)-2-methyl-3H-imidazo[4,5-b]pyridine 3-[2-chloro-4-(trifluoromethyl)benzyl]-2-methyl-5-(1-pentanesulfonylcarbamoyl)-3H-imidazo[4,5-b]pyridine 3-[2-chloro-4-(trifluoromethyl)benzyl]-2-methyl-5-[(4-methylbenzene)sulfonyl-carbamoyl]-3H-imidazo[4,5-b]pyridine 5-(benzenesulfonylcarbamoyl)-3-(1-bromonaphthalen-2-ylmethyl)-2-methyl-3H-imidazo[4,5-b]pyridine 3-(1-bromonaphthalen-2-ylmethyl)-2,7-dimethyl-5-(pentanesulfonylcarbamoyl)-3H-imidazo[4,5-b]pyridine 5-(benzenesulfonylcarbamoyl)-3-(1-bromonaphthalen-2-ylmethyl)-2,7-dimethyl-3H-imidazo[4,5-b]pridine (E)-3-(1-bromonaphthalen-2-ylmethyl)-2,7-dimethyl-5-((2-phenylethenyl)-sulfonylcarbamoyl)-3H-imidazo[4,5-b]pyridine 3-(1-bromonaphthalen-2-ylmethyl)-2,7-diethyl-5-((4-methylbenzene)sulfonyl-carbamoyl)-3H-imidazo[4,5-b]pyridine 3-(1-bromonaphthalen-2-ylmethyl)-2,7-dimethyl-5-((4-vinylbenzne)sulfony-carbamoyl)-3H-imidazo[4,5-b]pyridine 3-(1-bromonaphthalen-2-ylmethyl)-2,7-dimethyl-5-((5-chlorothiophen-2-yl)sulfonylcarbamoyl)-3H-imidazo[4,5-b]pyridine 3-(4-bromo-2-chlorobenzyl)-2,7-dimethyl-5-(1-pentanesulfonylcarbamoyl)-3H-imidazo[4,5-b]pyridine 3-(4-bromo-2-chlorobenzyl)-2,7-dimethyl-5-[(4-methylbenzene)sulfonylcarbamoyl]-3H-imidazo[4,5-b]pyridine (E)-3-(4-bromo-2-chlorobenzyl)-2,7-dimethyl-5-[(2-phenylethenyl)sulfonyl-carbamoyl]-3H-imidazo[4,5-b]pyridine 3-(4-bromo-2-chlorobenzyl)-5-[(5-chlorothiophen-2-yl)sulfonylcarbamoyl]-2,7-dimethyl-3H-imidazo[4,5-b]pyridine 3-(4-bromo-2-chlorobenzyl)-2,7-dimethyl-5-[(4-vinylbenzene)sulfonylcarbamoyl]-3H-imidazo[4,5-b]pyridine 3-(4-bromo-2-chlorobenzyl)-5-[(5-bromothiophen-2-yl)sulfonylcarbamoyl]-2,7-dimethyl-3H-imidazo[4,5-b]pyridine 5-(benzenesulfonylcarbamoyl)-3-(2-chloro-4-nitrobenzyl)-2,7-dimethyl-3H-imidazo[4,5-b]pyridine 3-(2-chloro-4-nitrobenzyl)-2,7-dimethyl-5-((4-methylbenzene)sulfonylcarbamoyl)-3H-imidazo[4,5-b]pyridine (E)-3-(2-chloro-4-nitrobenzyl)-2,7-dimethyl-5-((2-phenylethenyl)sulfonylcarbamoyl)-3H-imidazo[4,5-b]pyridine 3-(2-chloro-4-nitrobenzyl)-2,7-dimethyl-5-((4-vinylbenzene)sulfonylcarbamoyl)-3H-imidazo[4,5-b]pyridine 5-(benzenesulfonylcarbamoyl)-3-(2-chloro-4-cyanobenzyl)-2-methyl-3H-imidlazo[4,5-b]pyrdine (E)-3-(2-chloro-4-(trifluoromethyl)benzyl)-2-methyl-5-((2-phenylethenyl)-sulfonylcarbamoyl)-3H-imidazo[4,5-b]pyridine 3-(2-chloro-4-(triflouromethyl)benzyl)-2-methyl-5-((4-vinylbenzene)sulfonyl-carbamoyl)-3H-imidazo[4,5-b]pyridine 3-(2-chloro-4-(trifluoromethyl)benzyl)-5-((5-chlorothiophen-2-yl)sulfonyl-carbamoyl)-2-methyl-3H-imidazo[4,5-b]pyridine 5-((5-bromothiophen-2-yl)sulfonylcarbamoyl)-3-(2-chloro-4-(trifluoromethyl)benzyl)-2-methyl-3H-imidazo[4,5-b]pyridine 5-benzenesulfonylcarbamoyl)-3-(2-chloro-4-phenylbenzyl)-2-methylbenzo-[4]thiophene 1-(2-chloro-4-phenylbenzyl)-6-((5-chlorothiophen-2-yl)sulfonylcarbamoyl)-3-methyl-1H-indazole 6-((5-bromothiophen-2-yl)sulfonylcarbamoyl)-1-(2-chloro-4-phenylbenzyl)-3-methyl-1H-indazole 3-(1-bromonaphthalen-2-ylmethyl)-5-((5-bromothiophen-2-yl)sulfonylcarbamoyl)-2,7-dimethyl-3H-imidiazo[4,5-b]pyridine 5-(benzenesulfonylcarbamoyl)-3-(2-chloro-4-(2-phenylethyl)benzyl)-2-methyl-3H-imidazo[4,5-b]pyridine 3-(4-amino2-chlorobenzyl)-5-(benzenesulfonylcarbamoyl)-2-methyl-3H-imidazo[4,5-b]pyridine 5-(benzenesulfonylcarbamoyl)-3-(2-chloro-4-(hydroxymethyl)benzyl)-2-methyl-3H-imidazo[4,5-b]pyridine 5-(benzesulfonylcarbamoyl)-3-(4-carboxy-2-chlorobenzyl)-2-methyl-3H-imidazo[4,5-b]pyridine 5-(benzenesulfonylcarbamoyl)-3-(2-chloro-4-((methanesulfonyloxy)methyl)benzyl)-2-methyl-3H-imidazo[4,-b]pyridine 5-(benzenesulfonylcarbamoyl)-3-(2-chloro-4-((phenyloxy)benzyl)-2-methyl-3H-imidazo[4,5-b]pyridine 5-(benzenesulfonylcarbamoyl)-3-(2-chloro-4-(ethoxycarbonyl)benzyl)-2-methyl-3H-imidazo[4,5-b]pyridine 5-(benzenesulfonylcarbamoyl)-3-(2-chloro-4-(methylcarbamoyl)benzyl)-2-methyl-3H-imidazo[4,5-b]pyridine 3-(2-chloro-4-(E)-(2-phenylethenyl)benzyl)-2-methyl-5-((4-methylbenzene)-sulfonylcarbamoyl)-3H-imidazo[4,5-b]pyridine 3-(2-chloro-4-(E)-(2-phenylethenyl)benzyl)-2-methyl-5-((4-vinylbenzene)sulfonylcarbamoyl)-3H-imidazo[4,5-b]pyridine 3-(2-chloro-4-(E)-(2-phenyletheny)benzyl)-2-methyl-5-(E)-((2-phenylethenyl)sulfonylcarbamoyl)-3H-imidazo[4,5-b]pyridine 3-(2-chloro-4-(E)-(2-phenylethenyl)benzyl)-5-((5-chlorothiophen-2-yl)sulfonyl-carbamoyl)-2-methyl-3H-imidazo[4,5-b]pyridine 5-((5-bromothiophen-2-yl)sulfonylcarbamoyl)-3-(E)-(2-chloro-4-(2-phenylethenyl)-benzyl)-2-methyl-3H-imidazo[4,5-b]pyridine 3-(2-chloro-4-(E)-(2-phenylethenyl)benzyl)-2-methyl-5-(1-pentanesulfonyl-carbamoyl)-3H-imidazo[4,5-b]pyridine 3-(2-chloro-4-(2-phenylethyl)benzyl)-2-methyl-5-((4-methylbenzene)sulfonyl-carbamoyl)-3H-imidazo[4,5-b]pyridine 3-(2-chloro-4-(2-phenylethyl)benzyl)-2-methyl-5-((4-vinylbenzene)sulfonyl-carbamoyl)-3H-imidazo[4,5-b]pyridine 3-(2-chloro-4-(2-phenylethyl)benzyl)-2-methyl-5-(E)-((2-phenylethenyl)sulfonylcarbamoyl)-3H-imidazo[4,5-b]pyridine 3-(2-chloro-4-(2-phenylethyl)benzyl)-5-((5-chlorothiophen-2-yl)sulfonylcarbamoyl)-2-methyl-3H-imidazo[4,5-b]pyridine 5-((5-bromothiophen-2-yl)sulfonylcarbanoyl)-3-(2-chloro-4-(2-phenylethyl)benzyl)-2-methyl-3H-imidazo[4,5-b]pyridine 3-(2-chloro-4-(2-phenylethyl)benzyl)-2-methyl-5-(1-pentanesulfonylcarbamoyl-3H-imidazo[4,5-b]pyridine 3-(4-benzyloxy-2-chlorobenzyl)-2-methyl-5-((4-methylbenzene)sulfonylcarbamoyl)-3H-imidamzo[4,5-b]pyridine 3-(4-benzyloxy-2-chlorobenzyl)-2-methyl-5-((4-vinylbenzene)sulfonylcarbamoyl)-3H-imidazo[4,5-b]pyridine 3-(4-benzyloxy-2-chlorobenzyl)-2-methyl-5-(E)-((2-phenylethenyl)sulfonyl-carbamoyl)-3H-imidazo[4,5-b]pyridine 3-(4-benzyloxy-2-chlorobenzyl)-5-((5-chlorothiophen-2-yl)sulfonylcarbamoyl)-2-methyl-3H-imidazo[4,5-b]pyridine 3-(4-benzyloxy-2-chlorobenzyl)-5-((5-bromothiophen-2-yl)sulfonylcarbamoyl)-2-methyl-3H-imidazo[4,5-b]pyridine 3-(4-benzyloxy-2-chlorobenzyl)-2-methyl-5-(1-pentanesulfonylcarbamoyl)-3H-imidazo[4,5-b]pyridine 3-(2chloro-4-((cyclohexlmethyl)oxy)benzyl)-2-methyl-5-((4-methylbenzene)-sulfonylcarbamoyl)-3H-imidazo[4,5-b]pyridine 3-(2-chloro-4-((cyclohexymethyl)benzyl)-2-methyl-5-((4-vinylbenzene)sulfonylcarbamoyl)-3H-imidazo[4,5-b]pyridine 3-(2-chloro-4-((cyclohexylmethyl)oxy)benzyl)-2-methyl-5-(E)-((2-phenylethenyl)-sulfonylcarbamoyl)-3H-imidazo[4,5-b]pyridine 3-(2-chloro-4-((cyclohexylmethyl)oxy)benzyl)-5-((5-chlorothiophen-2-yl)sulfonylcarbamoyl)-2-methyl-3H-imidazo[4,5-b]pyridine 5-((5-bromothiophen-2-yl)sulfonylcarbamoyl)-3-(2-chloro-4-((cyclohexylemthyl)-oxy)benzyl)-2-methyl-3H-imidazo[4,5-b]pyridine 3-(2-chloro-4-((cyclohexylmethyl)oxy)benzyl)-2-methyl-5-(1-pentanesulfonyl-carbamoyl)-3H-imidazo[4,5-b]pyridine 3-(2-chloro-4-(methylthio)benzyl)-2-methyl-5-[(4-methylbenzene)-sulfonylcarbamoyl]-3H-imidazo[4,5-b]pyridine 3-(2-chloro-4-(methylthio)benzyl)-2-methyl-5-[(4-vinylbenzene)sulfonylcarbamoyl]-3H-imidazo[4,5-b]pyridine 3-(2-chloro-4-(methylthio)benzyl)-2-methyl-5-(E)-[(2-phenylethenyl)-sulfonylcarbamoyl]-3H-imidazo[4,5-b]pyridine 3-(2-chloro-4-(methylthio)benzyl)-5-[(5-chlorothiophen-2-yl)sulfonylcarbamoyl]-2-methyl-3H-imidazo[4,5-b]pyridine 3-[2-chloro-4-(methylthio)benzyl]-5-[(5-bromothiophen-2-yl)sulfonylcarbamoyl]-2-methyl-3H-imidazo[4,5-b]pyridine 3-(2-chloro-4-(methylthio)benzyl)-2-methyl-5-(1-pentanesulfonylcarbamoyl)-3H-imidazo[4,5-b]pyridine 3-(2-chloro-4-(ethoxycarbonyl)benzyl)-2-methyl-5-((4-methylbenzenl)-sulfonylcarbamoyl)-3H-imidazo[4,5-b]pyridine 3-(2-chloro-4-(ethoxycarbonyl)benzyl)-2-methyl-5-((4-vinylbenzene)sulfonylcarbamoyl)-3H-imidazo[4,5-b]pyridine 3-(2-chloro-4-(ethoxycarbonyl)benzyl)-2-methyl-5-(E)-(2-phenylethenyl)sulfonylcarbamoyl)-3H-imidazo[4,5-b]pyridine 3-(2-chloro-4-(ethoxycarbonyl)benzyl)-5-((5-chlorothiophen-2-yl)sulfonyl-carbamoyl)-2-methyl-3H-imidazo[4,5b]pyridine 5-((5-bromothiophen-2-yl)sulfonylcarbamoyl-3-(2-chloro-4-(ethoxycarbonyl)-benzyl)-2-methyl-3H-imidazo[4,5b]pyridine 3-(2-chloro-4-(ethoxycarbonyl)benzyl)-2-methyl-5-(1-pentanesulfonylcarbamoyl)-3H-imidazo[4,5-b]pyridine 3-(2-chloro-4-((phenyloxy)methyl)benzyl)-2-methyl-5-[(4-methylbenzene)-sulfonylcarbamoyl]-3H-imidazo[4,5-b]pyridine 3-(2-chloro-4-((phenyloxy)methyl)benzyl-2-methyl-5-[(4-vinylbenzene)sulfonylcarbamoyl]-3H-imidazo[4,5-b]pyridine 3-(2-chloro-4-((phenyloxy)methyl)benzyl)-2-methyl-5-[(E)-(2-phenylethenyl)sulfonylcarbamoyl]-3H-imidazo[4,5-b]pyridine 3-(2-chloro-4-((phenyloxy)methyl)benzyl)-5-[(5-chlorothiophen-2-yl)sulfonyl-carbamoyl]-2-methyl-3H-imidazo[4,5-b]pyridine 5-[(5-bromothiophen-2-yl)sulfonylcarbamoyl]-3-(2-chloro((phenyloxy)methyl)-benzyl)-2-metyl-3H-imidazo[4,5-b]pyridine 3-(2-chloro-4-((phenyloxy)methyl)benzyl)-2-methyl-5-(1-pentanesulfonyl-carbamoyl)-3H-imidazo[4,5-b]pyridine 3-[2-chloro-4-(dimethlyaminomethyl)benzyl]-2-methyl-5[(4-methylbenzene)-sulfonylcarbamoyl]-3H-imidazo[4,5-b]pyridine 3-[2-chloro-((imidazol-1-yl)methyl)benzyl]-2-methyl-5-[(4-methylbenzene)-sulfonylcarbamoyl]-3H-imidazo[4,5b]pyridine 3-[2-chloro-4-((piperidin-1-yl)methyl)benzyl]-2-methyl-5-[(4-methylbenzene)-sulfonylcarbamoyl]-3H-imidazo[4,5-b]pyridine 3-[2-chloro-4-(phenylthiomethyl)benzyl]-2-methyl-5-[(4-methylbezene)-sulfonylcarbamoyl]-3H-imidazo[4,5-b]pyridine 3-(4-(benzyloxy)methyl)-2-chlorobenzyl)-2-methyl-5-[(4-methylbenzene)-sulfonylcarbamoyl]-3H-imidazo[4,5-b]pyridine 3-[4-(benzimidazol-2-yl)-2-chlorobenzyl]-2-methyl-5-[(4-methylbenzene)-sulfonylcarbamoyl]-3H-imidazol4,5-b]pyridine 2-methyl-5-[(4-methylbenzene)sulfonylcarbamoyl]-3-[4-(1-methylbenzimidazol-2-yl)-2-chlorobenzyl]-3H-imidazo[4,5-b]pyridine 3-[1-ethylbenzimidazol-2-yl)methyl]-2-methyl-5-[(4-methylbenzene)-sulfonylcarbamoyl]-3H-imidazo[4,5-b]pyridine 3-(2-chloro-4-(thiophen-2-yl) )-2-methyl-5-(1-pentanesulfonylcarbamoyl)-3H-imidazo[4,5-b]pyridine 3-(2-chloro-4-(thiophen-2-yl)benzyl)-2-methyl-5-[(4-methylbenzene)-sulfonylcarbamoyl]-3H-imidazo[4,5-b]pyridine 3-(2-chloro-4-(thiophen-2-yl)benzyl)-5-[(5-chlorothiophen-2-yl)sulfonylcarbamoyl]-2-methyl-3H-imidazo[4,5-b]pyridine 5-[(5-bromothiophen-2-yl)sulfonylcarbamoyl]-3-(2-chloro-4-(thiophen-2-yl)benzyl)-2-methyl-3H-imidazo[4,5-b]pyridine 3-(2-chloro-4-(thiophen-2-yl)benzyl)-2-methyl-5-[(E)-(2-phenylethene)sulfonylcarbamoyl]-3H-imidazo[4,5-b]pyridine 3-(2-chloro-4-(thiophen-2-yl)benzyl)-2-methyl-5-[(4-vinylbenzene)sulfonyl-carbamoyl]-3H-imidazo[4,5-b]pyridine 3-(2-chloro-4-(5-chlorothiophen-2-yl)benzyl)-2-methyl-5-(1-pentanesulfonyl-carbamoyl)-3H-imidazo[4,5-b]pyridine 3-(2-chloro-4-(5-chlorothiophen-2-yl)benzyl)-2-methyl-5-[(4-methylbenzene)-sulfonylcarbamoyl]-3H-imidazo[4,5-b]pyridine 3-(2-chloro-4-(5-chlorothiophen-2-yl)benzyl)-5-[(5-chlorothiophen-2-yl)sulfonylcarbamoyl]-2-methyl-3H-imidazo[4,5-b]pyridine 5-[(5-bromothiophen-2-y)sulfonylcarbamoyl]-3-(2-chloro-4-(5-chlorothiophen-2-yl)benzyl)-2-methyl-3H-imidazo[4,5-b]pyridine 3-(2-chloro-4-(5-chlorothiophen-2-yl)benzyl)-2-methyl-5-[(E)-(2-phenylethene)sulfonylcarbamoyl]-3H-imidazo[4,5-b]pyridine 3-(2-chloro-4-(5-chlorothiophen-2-yl)benzyl)-2-methyl-5-[(4-vinylbenzene)sulfonylcarbamoyl]-3H-imidazo[4,5-b]pyridine 3-(2-chloro-4-phenylbenzyl)-2,7-dimethyl-5-(1-pentanesulfonylcarbamoyl)-3H-imidazo[4,5-b]pyridine 3-(2-chloro-4-phenylbenzyl)-5-[(5-chlorothiophen-2-yl)sulfonylcarbamoyl]-2,7-dimethyl-3H-imidazo[4,5-b]pyridine 5-[(5-bromothiophen-2-yl)sulfonylcarbamoyl]-3-(2-chloro-4-phenylbenzyl)-2,7-dimethyl-3H-imidazo[4,5-b]pyridine 3-(2-chloro-4-phenylbenzyl)-2,7-methyl-5-[(4-vinylbenzene)sulfonylcarbamoyl]-3H-imidazo[4,5-b]pyridine 3-[2-chloro-4(thiophen-2-yl)benzyl]-2,7-dimethyl-5-(1-pentanesulfonylcarbamoyl)-3H-imidazo[4,5-b]pyridine 3-[2-chloro-4-(thiophen-2-yl)benzyl]-2,7-dimethyl-5-[(4-methylbenzene)-sulfonylcarbamoyl]-3H-imidazo[4,5-b]pyridine 5-[(5-bromothiophen-2-yl)sulfonylcarbamoyl]-3-[2-chloro-4-(thiophen-2-yl)benzyl]-2,7-dimethyl-3H-imidazo[4,5-b]pyridine 3-[2-chloro-4-(thiophen-2-yl)benzyl]-2,7-dimethyl-5-[(E)-(2-phenylethenyl)-sulfonylcarbamoyl]-3H-imidazo[4,5-b]pyridine 3-[2-chloro-4-(thiophen-2-yl)benzyl]-2,7-dimethyl-5-[(4-vinylbenzene)sulfonylcarbamoyl]-3H-imidazo[4,5-b]pyridine 3-[2-chloro-4-(5-chlorothiophen-2-yl)benzyl]-2,7-dimethyl-5-(1-pentanesulfonyl-carbamoyl)-3H-imidazo[4,5-b]pyridine 3-[2-chloro-4-(5-chlorothiophen-2-yl)benzyl-2,7-dimethyl-5-[(4-methylbenzene)-sulfonylcarbamoyl]-3H-imidazo[4,5-b]pyridine 5-[(5-bromothiophen-2-yl)sulfonylcarbamoyl]-3-[2-chloro-4(5-chlorothiophen-2-yl)benzyl]-2,7-dimethyl-3H-imidazo[4,5-b]pyridine 3-[2-chloro-4-(5-chlorothiophen-2-yl)benzyl]-2,7-dimethyl-5-[(E)-(2-phenylethenyl)sulfonylcarbamoyl]-3H-imidazo[4,5-b]pyridine 3-[2-chloro-4-(5-chlorothiophen-2-yl)benzyl-4-2,7-dimethyl-5-[(4-vinylbenzene)sulfonylcarbamoyl]-3H-imidazo[4,5-b]pyridine 3-(2-chloro-4-(n-pentanethio)benzyl)-2-methyl-5-[(4-methylbenzene)-sulfonylcarbamoyl]-3H-imidazo[4,5-b]pyridine 3-4-(benzylthio)-2-chloro-]benzyl-2-methyl-5-[(4-methylbenzene)sulfonyl-carbamoyl-3H-imidazo[4,5-b]pyridine 3-(2-chloro-4-((3-pyridyloxy)methyl)benzyl)-2-methyl-5-[(4-methylbenzene)-sulfonyl-carbamoyl-3H-imidazo[4, 5b]pyridine 3-(2-chloro-4-ethylthiobenzyl)-2-methyl-5-[(4-methylbenzene)sulfonylcarbamoyl]-3H-imidazo[4,5-b]pyridine 3-(4-(N-butyrylamino)-2-chlorobenzyl)-2-methyl-5-((4-methylbenzene)-sulfonylcarbamoyl)-3H-imidazo[4,5-b]pyridine 3-(4-(N-benzoylamino)-2-chlorobenzyl)-2-methyl-5-((4-methylbenzene)-sulfonylcarbamoyl)-3H-imidazo[4,5-b]pyridine 3-(4-(N-benzoyl-N-methylamino)-2-chlorobenzyl)-2-methyl-5-((4-methylbenzene)-sulfonylcarbamoyl)-3H-imidazo[4,5-b]pyridine 5-benzenesulfonylcarbamoyl)-3-(2-chloro-4-phenylbenzyl)-2-methyl-3H-imidazo[4,5-b]pyridine sodium salt 5-[(4-vinylbenzene)sulfonylcarbamoyl]-3-(2-chloro-4-phenylbenzyl)-2-methyl-3H-imidazo[4,5-b]pyridine sodium salt 5-[(5-bromothiophen-2-yl)sulfonylcarbamoyl]-3-(2-chloro-4-phenylbenzyl)-2-methyl-3H-imidazo[4,5-b]pyridine sodium salt 3-(4-bromo-2-chlorobenzyl)-2,7-dimethyl-5-[(4-methylbenzene)sulfonylcarbamoyl]-3H-imidazo[4,5-b]pyridine sodium salt 3-(4-(N-butyryl-N-methylamino)-2-chlorobenzyl)-2-methyl-5-((4-methylbenzene)-sulfonylcarbamoyl)-3H-imidazo[4,5-b]pyridine 3-(2-chloro-4-(N-(n-pentyl)amino)benzyl)-2-methyl-5-((4-methylbenzene)-sulfonylcarbamoyl)-3H-imidazo[4,5-b]pyridine 3-(2-chloro-4-(N-methyl-N-(n-pentyl)amino)benzyl)-2-methyl-5-((4-methylbenzene)-sulfonylcarbamoyl)-3H-imidazo[4,5-b]pyridine 3-(4-(N-benzenesulfonylamino)-2-chlorobenzyl)-2-methyl-5-((4-methylbenzene)-sulfonylcarbamoyl)-3H-imidazo[4,5-b]pyridine 3-(2-chloro-4-(isopropoxylcarbonyl)benzyl)-2-methyl-5-((4-methylbenzene)-sulfonylcarbamoyl)-3H-imidazo[4,5-b]pyridine 3-(2-chloro-4-(cyclohexyloxycarbonyl)benzyl)-2-methyl-5-((4-methylbenzene)-sulfonylcarbamoyl)-3H-imidazo[4,5-b]pyridine 3-(2-chloro-4-(3-phenylureido)benzyl)-2-methyl-5-((4-methylbenzene)sulfonyl-carbamoyl)-3H-idazo[4,5-b]pyridine 3-[2-chloro-4-propoxybenzyl]-2-methyl-5-[(4-methylbenzene)sulfonylcarbamoyl]-3H-imidazo[4,5-b]pyridine 3-[2-chloro-4-(n-pentoxy)benzyl]-2-methyl-5-[(4-methylbenzene)sulonyl-carbamoyl]-3H-imidazo[4, 5-b]pyridine 3-(2-chloro-4-ethoxy)benzyl-2-methyl-5-[(4-methylbenzene)sulfonylcarbamoyl]-3H-imidazo[4,5-b]pyridine 3-chloro-4-(2-methoxyethoxy)benzyl]-2-methyl-5-[(4-metlylbenzene)-sulfonylcarbamoyl]-3H-imidazo[4,5-b]pyridine 3-[2-4-[(thiophen-2-yl)methyloxy)benzyl]-2-methyl-5-[(4-methylbenzene)-sulfonylcarbamoyl]-3H-imidazo[4,5-b]pyridine 3-[2-chloro-4-[(thiophene-3-yl)methyloxy]benzyl]-2-methyl-5-[(4-methylbenzene)-sulfonylcarbamoyl]-3H-imidazo[4,5-b]pyridine 3-(2-chloro-4-phenylethynyl)benzyl-2,7-dimethyl-5-[(4-methylbenzene)-sulfonylcarbamayol]-3H-imidazo[4,5-b]pyridine 3-[2-chloro-4-(cyclopentylmethyloxy)benzyl]-2-methyl-5-[(4-methylbenzene)-sulfonylcarbamoyl]-3H-imidazo[4, 5-b]pyridine 3-(2-chloro-4-phenylethynyl)benzyl-2,7-dimethyl-5-(1-pentanesulfonylcarbamayl)-3H-imidazo[4,5-b]pyridine 3-(2-chloro-4-(1-hexynyl)benzyl-2-methyl-5N-(4-methylphenylsulfonyl)carbamoyl-3H-imidazo[4,5-b]pyridine 3-(2-chloro-4-(cyclohexylmethyloxy)benzyl)-2,7-dimethyl-5-((1-pentanesulfonyl-carbamoyl)-3H-imidazo[4,5-b]pyridine 3-(2-chloro-4-(cyclohexylmethyloxy)benzyl)-2,7-dimethyl-5-[(4-methylbenzene)-sulfonylcarbamoyl]-3H-imidazo[4,5-b]pyridine 3-(2-chloro-4-ethylbenzyl)-2,7-dimethyl-5-(1-pentanesulfonycarbamoyl)-3H-imidazo[4,5-b]pyridine 3-(2-chloro-4-ethylbenzyl)-2,7-dimethyl-5-[(4-methylbenzene)sulfonylcarbamoyl]-3H-imidazo[4,5-b]pyridine 3-(2-chloro-4-(trifluoromethyl)benzyl)-2,7-dimethyl-5-(1-pentanesulfonyl-carbamoyl)-3H-imidazo[4,5-b]pyridine 3-(2-chloro-4-(trifluoromethyl)benzyl)-2,7-dimethyl-5-[(4-methylbenzene)-sulfonylcarbamoyl]-3H-imidazo[4,5-b]pyridine 3-(2-chloro-4-ethoxybenzyl)-2,7-dimethyl-5-(1-pentanesulfonylcarbamoyl]-3H-imidazo[4,5-b]pyridine 3-(2-chloro-4-ethoxybenzyl)-2,7-dimethyl-5-[(4-methylbenzene)sulfonylcarbamoyl]-3H-imidazo[4,5-b]pyridine 3-(2,4-dichlorobenzyl)-2-methyl-5-(p-toluenesulfonylcarbamoyl)benzo[b]furan 5-((5-bromothiophen-2-yl)sulfonylcarbamoyl)-3-(2,4-dichlorobenzyl)-2-methylbenzo[b]furan 5-((5-chlorothiophen-2-yl)sulfonylcarbamoyl)-3-(2,4-dichlorobenzyl)-2-methylbenzo[b]furan 3-(2-chloro-4-phenylbenzyl)-2-methyl-5-((4-pentene)sulfonylcarbamoyl)-3H-imidazo[4,5-b]pyridine 2-(2-chloro-4-phenylbenzyl)-3-methyl-6-(p-toluenesulfonylcarbamoyl)-2H-indazole 3-(2-chloro-4-hexylbenzyl)-2-methyl-5-(N-(4-methylphenylsulfonyl)carbamoyl-3H-imidazo[4,5-b]pyridine 3-(2-chloro-4-piperidinobenzyl)-2,7-dimethyl-5-((4-methylbenzene)sulfonyl-carbamoyl)-3H-imidazo[4,5-b]pyridine 3-(2-chloro-4-morpholinobenzyl)-2,7-dimethyl-5-((4-methylbenzene)sulfonylcarbamoyl)-3H-imidazo[4,5-b]pyridine 3-(2-chloro-4-(hexamethyleneimino)benzyl)-2,7-dimethyl-5-((4-methylbenzene)-sulfonylcarbamoyl)-3H-imidazo[4,5-b]pyridine 3-(2-chloro-4-(1-pyrrolidinyl)benzyl)-2,7-dimethyl-5-((4-methylbenzene)-sulfonylcarbamoyl)-3H-imidazo[4,5-b]pyridine 3-(2-chloro-4-(4-methylpiperazin-1-yl)benzyl)-2,7-dimethyl-5-((4-methylbenzene)-sulfonylcarbamoyl)-3H-imidazo[4,5-b]pyridine 3-(2-chloro-4-methylthiobenzyl)-2,7-dimethyl-5-[(4-methylbenzene)sulfonyl-carbamoyl]-3H-imidazo[4,5-b]pyridine 3-(2-chloro-4-methylthiobenzyl)-2,7-dimethyl-5-(1-pentanesulfonylcarbamoyl)-3H-imidazo[4,5-b]pyridine The methods for producing the objective compound (I) are descrbed in detail in the following.

Production Method 1

The objective compound (I) and a salt thereof can be produced by reacting compound (II) or a salt thereofwith compound (III) or a reactive derivative thereof at its carboxy group or a salt thereof.

The compound (II), compound (III) and reactive derivative at carboxyl group thereof are exemplified by those shown with regard to compound (I).

Preferable reactive derivative at carboxy of compound (III) is acid halide, acid anhydride such as intramolecular acid anhydride, intermolecular acid anhydride and mixed acid anhydride, active amide, active ester and the like. Preferable examples thereof include add chloride, acid azide, mixed acid anhydride with acid such as substituted phosphoric acid (e.g., diaphosphinic acid, phenylphosphonic acid, diphenylphosphinic acid, dibenzylphosphinic acid and halogenated phosphoric acid), dialklphosphinic acid, sulfurous acid, thiosulfuric acid, sulfuric acid, sulfonic acid (e.g., methanesulfonic acid), aliphatic carboxyhlic acid (e.g., acetic acid, propionic acid, butyric acid, isobutyric acid, pivalic acid, pentanoic acid, isopentanoic acid, 2-ethylbutric acid and trichloroacetic acid), aromatic carboxylic acid (e.g., benzoic acid), and the like; symmetric acid anhydride; active amide with imidazole, 4-substituted imidazole, dimethylpyrazloe, triazole or tetrazole; active ester (e.g., cyanomethyl ester, methoxymethyl ester, dimethyliminomethyl $[(CH_3)_2N^+=CH-]$ ester, vinyl ester, progargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester and 8-quinolylthio ester); esters with N-hydroxy compound (eg., N,N-dimethylhydroxylamine, 1-hydroxy-2-1H-pyridone, N-hydroxoysuccinimide and 1-hydoxy-1H-benzotriazole); and the like. These reactive derivatives can be appropriatey selected according to the kind of compound (III) to be used.

The reaction generalky proceeds in a conventional solvent such as water, alcohol (e.g., methanol and ethanol), acetone, dioxane, acetonitrile, chlorform, methylene chloride, ethylene chloride, tetrahydrofuran, ethyl acetate, N,N-dimethylformamide and pyridine, or in a solvent which does not adversely affect the reaction. These conventional solvents may be used alone or in combination.

When compound (III) is used in the from of a free acid or a salt thereof in this reaction, the reaction is preferably cartied out in a conventional condensing agent such as N,N'-dicyclohexylcarbodiimide, N-cylohexyl-N'-morpholinoethyl-carbodiimide, N-cyclohexyl-N'-(4-diethylaminocyclohexyl)-carbodiimide, N,N'-diethylcarbidiimide, N,N'-diisopropylcarbodimiide, N-ethyl-N'-(3-dimethylamino-propyl)carbodiimide, N,N'-carbonylbis(2-methylimidazole), pentamethylenelketen-N-cyclohexylimine, diphenylketen-N-cyclohexylimine, ethoxyacetylene, 1-alkoxy-1-chloroethylene, trialkyl phosphite, ethyl polyphosphorate, isopropyl polyphosphorate, phosphorous oxychloride (phosphoryl chloride), phosphorous trichloride, diphenylphosphoryl azide, diphenyl chlorophosphate, diphenylphosphinic acid chloride, thionyl chloride, oxalyl chloride, lower alkyl haloformate (e.g., methyl chloroformate and isopropyl chloroformate), triphenylphosphine, 2-ethyl-7-hydroxybenzoisoxazolium salt, intramolecular salt of 2-ethyl-5-(m-sulfophenyl)isoxazolium hydroxide, 1-(p-chlorobenzensulfonyloxy)-6-chloro-1H-benzotriazole, and so called Vilsmeier reagent(prepared from N,N-dimethylformamide with thionyl chloride, phosgene, trichloromethyl chloroformate, or phosphoryl chloride, and so on), and the like.

The reaction can be carried out in the presence of an inorganic or organic base such as alkali metal bicarbonate, tri(lower)alkylamine, pyridine, 4-methyl-aminopyridine, N-(lower)alkylmorpholine, N,N-di(lower)alkylamniline (e.g., N,N-dimethylaniline), N,N-di(lower)alkylbenzylamine, and the like.

The reaction temperature is not particularly limited, and the reaction is generally carried out from under cooling to heating.

Production Method 2

The objective compound (I-2) and a salt thereof can be prepared by reducing compound (I-1) or a salt thereof.

The method for producing objective compound (I-2) by reduction includes chemical reduction and catalytic reduction.

The preferable reducing agent used in the chemical reduction is, for example, metal such as tin, zinc and iron, or a combination of a metal compound, such as chromium chloride and chromium acetate, and an organic acid or inorganic acid such as formic acid, acetic acid, propionic acid, trifluoroacetic acid, p-toluenesulfonic acid, hydrochloric acid and hydrobromic acid.

The preferable reducing agent used in the cataltic reduction is, for example, platinum catalyst such as platinum plate, platinum sponge, platinum black, platinum colloid, platinum oxide and platinum wire, palladium catalyst such as palladium sponge, palladium black, palladium oxide, palladium-carbon, palladium colloid, palladium-barium sulfate and palladium-barium carbonate, nickel catalyst such as reduced nickel and Raney-nickel, cobalt catalyst such as reduced cobalt and Raney cobalt, iron catalyst such as reduced iron and Raney iron, copper catalyst such as reduced copper, Raney copper and Ulmann copper, and the like.

The reducion is generally carried out in a conventional solvent that does not adversely influence the reaction, such as water, methanol, ethanol, propanol and N,N-dimethylformamide, or a mixed solvent thereof. When the above-mentioned acid to be used for the chemical reduction is liquid, it can be used as a solvent.

The preferable solvent to be used for the catalytic reduction includes, besides the above-mentioned solvents, other conventional solvents such as diethyl ether, dioxane and tetrahydrofuran and mitures thereof.

The reaction temperature of the reduction is not particularly limited, and the reaction is generally carried out from under cooling to heating.

Production Method 3

The objective compound (I-4) and a salt thereof can be produced by oxidizing compound (I-3) or a salt thereof.

When objective compound (I-4) is produced by oxidation, an oxidizing agent such as sodium chlorite, chronic anhydride and potassium permanganate, and a solvent such as water and acetone are used. The reaction temperature is not particularly limited, and the reaction is generally carried out from under cooling to heating.

Production Method 4

The objective compound (I-6) and a salt thereof can be produced by acylation of compound (I-5) or a salt thereof.

When objective compound (I-6) is to be obtained by acylation, compound (I-5) having terminal hydroxy is reacted with an acylating agent Examples of the acylating agent include lower alkanesulfonyl halide (e.g., methanesulfonyl chloride) and lower alkanesulfonic anhydride (e.g., methanesulfonic anhydride). The solvent may be dichloromethane, tetrahydrofuran and the like, and the reaction proceeds from under fom ice-cooling to heating.

Production Method 5

The objective compound (I-7) and a salt thereof can be produced by introducing an aryloxy group into compound (I-6) or a salt thereof. For the introduction of the aryloxy group, compound (I-6) having terminal acyloxy(lower)alkyl is reacted with hydroxyaryl compound (e.g., phenol) in the presence of a base such as sodium hydride. As the solvent, N,N-dimethylformamide, tetrahydrofuran and the like can be used, and the reaction proceeds form under ice-cooling to heating.

Production Method 6

The objective compound (I-8) and a salt thereof can be produced by introducing a carboxy-protecting group into compound (I-4) or a reactive derivative thereof.

The carboxy-protecting group can be introduced by, for example, reacting compound (I-4) having terminal carboxyl or a reactive derivative thereof with an alkyl alcohol such as ethanol. As the solvent, N,N-dimethylformamide, dichloromethane and the like can be used, and the reaction proceeds from under ice-cooling to heating.

The preferable reactive derivative at carboxy includes acid halide, acid anhydride, active amide, active ester and the like. Preferable examples thereof are acid chloride, acid azide, mixed acid anhydride with acid such as substituted phosphoric acid (e.g., dialkyl phosphoric acid, phenylphosphonic acid, diphenyl-phosphonic acid, dibenzylphosphinic acid and halogenated phosphoric acid), dialkyphosphinic acid, sulfurous acid, thiosulfuric acid, sulfuric acid, sulfonic acid (e.g., methanesulfonic acid), aliphatic carboxylic acid (e.g., acetic acid, propionic acid, butyric acid, isobutyric acid, pivalic acid, pentanoic acid, isopentanoic acid, 2-ethylbutyric acid and trichloroacetic acid), aromatic carboxylic acid (e.g., benzoic acid), and the like; symmetric acid anhydride; active amide with imidazole, 4-substituted imidazole, dimethylpyrazole, triazole or tetrazole; active ester (e.g., cyanomethyl ester, methoxymethyl ester, dimethyliminomethyl $[(CH_3)_2N^+=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester and 8-quinolyl ester, esters with N-hydroxy compound (e.g., N,N-dimethylhydroxylamine, 1-hydroxy-2-1H-pyridone, N-hydroxysuccinmide, N-hydroxyphthalimide and 1-hydroxy-1H-benzotriazole), and the like. These reactive derivatives can be selected according to the kind of compound to be used.

Production Method 7

The objective compound (I-9) and a salt thereof can be produced by introducing a carboxy-protecting group into compound (I-4) or a salt thereof.

When compound (I-4) is reacted with alkylamine such as methylamine and ethylamine, this compound is amidated. The solvent to be used is, for example, tetrahydrofuran, dichloromethane, N,N-dimethylformamide and the like, and the reaction proceeds from under ice-cooling to heating.

Production Method 8

The objective compound (I-11) and a salt thereof can be produced by aciding a heterocylic group containing nitrogen to compound (I-10) or a salt thereof.

This reaction is preferably carried out in the presence of a base such as sodium tert-butylate and the above-mentioned inorganic or organic base. The reaction is preferably carried out in the presence of a cat such as tris (dibenzylideneacetone)-dipalladium(O), (R)-(+)-BINAP [2,2'-bis(diphenyl-phosphino)-1,1'-binaphthyl] and the like.

While the reaction temperature is not particulary limited, the reaction is carried out from room temperature to heating, and the reaction can be also carried out in the presence of a solvent such as toluene, which does not adversy affect the reaction.

The above-mentioned compounds can be purified as necessary according to a conventional method for purifying an organic compound, such as recyrstallization, column chromatography, thin-layer chromatography, high performance liquid chromatography and the like. The compound can be identified by NMR spectrometric analysis, mass spectrometric analysis, IR spectrometric analysis, elemental analysis, melting point measurement and the like.

The compound of the present invention may have one or more chiral centers and includes enantiomers and diastereomers. Some compounds having alkenyl may be present as a cis or trans isomer. The present invention encompasses such mixtures and respective isomers.

The inventive compound and a salt thereof may be in the form of a solvate, which is also encompassed in the present invention. The solvate is preferably exemplified by hydrate and ethanolate.

The pharmaceutical data of compound (I) are shown in the following to demonstrate the utility of the objective compound (I).

Experimental Example 1
(Blood Sugar Level Depressing Activity in dd/db Mice)
Test Compound
Compound A
3-(2,4-Dichlorobenzyl)-2-methyl-5-(1-n-pentanesulfonylcarbamoyl)-benzo[b]furan (compound of Example 30-1)
Test Animal Female C57BL/KsJ-dbm db+/db+, C57BL/KsJ-dbm +m/+m (Jackson Laboratory) mice (5 weeks old) were purchased and subjected to the test after 2–3 weeks of acclimating period.
Drug Administration The test drug was mixed with a powder diet (CE2, Clea Japan, Inc.) in a mortar. In the case of administration in 100 mg/kg, the mixing proportion of the test drug to the diet was 0.1%, in the case of 30 mg/kg, the proportion was 0.03% and in the case of 10 mg/kg, the proportion was 0.01%. The diet was changed twice a week. The amount of the diet given and the amount left were recorded and the diet intake was calculated by determining the difference.
Test Schedule The female db/db mice were grouped according to body weight, blood sugar level and triglyceride concentration in blood. Then, the drug-mixed diet was given for 14 days, during which period the mice were 8 to 10 weeks of age. At day 7 and day 14 in the morning, blood was taken from supraorbital plexus venosus using a heparinized glass capilary tube (Chase Heparinized capillary tube), and centrifuged to give plasma fractions. The blood sugar value, triglyceride concentration in plasma and insulin concentration in plasma were measured at day 0 and day 14, and blood sugar value and triglyceride concentration in blood were measured at day 7. Body weight was measured at day 0, day 7 and day 14. After final blood sampling, the mice were slaughtered with $CO_2$ gas.
Measurement Method Blood sugar value was measured using 10–15 µl of plasma and in accord with glucose oxidase method (glucose CII-test Waco, Waco Pure Chemicals Co., Ltd.). The triglyceride concentration in plasme was measured using 10–15 µl of plasma and in accord with GPO-p-chlorophenol method (triglyceride G-test Waco) or GPO-DAOS method (triglyceride E-test Waco). The measurement was done promptly after blood sampling. The insulin concentration in plasme was measured using 20 µl of plasma (preservable at −20° C.) and in accord with an antibody method (Phadesef Insulin RIA kit, Kabi Pharmacia).

Result

Using the difference between db/db mice control group and +/+ mice in blood sugar value and triglyceride concentration in plasma as 100%, the proportion (%) of decrease in the blood sugar value and triglyceride concentration in plasma of the group administred with the test drug was determined. The results are shown in Table 1.

TABLE 1

| Test compound | Dose (mg/kg) | Blood sugar decrease (%) |
|---|---|---|
| Compound A | 10 | 71 |

The compound (I) of the present invention can be used for therapeutic purposes in the form of a pharmaceutical preparation. This pharmaceutical preparation contains any one of the compounds (I) as an active ingredient in admixture with a pharmaceutically acceptable organic or inorganic excipient which is a solid, semi-solid or liquid and which is suitable for oral, parenteral or external (local) administration. Examples of the dosage form include capsules, tablets, sugar coating tablets, granules, suppositories, liquid, lotion, suspension, emulsion, ointment, gel and the like. When desired, these preparations may contain adjuvant auxiliary, auxiliary substance, stabilizer, moistening agent, emulsifier, buffering agent, and other conventional additives.

While the dose of the compound (I) varies depending on the age and symptom of patients, compound (I) is administered for the therapy of the above-mentioned diseases in an average single dose amount of about 0.1 mg, 1 mg, 10 mg, 50 mg, 100 mg, 250 mg, 500 mg or 1000 mg. In general, its daily dose is about 0.1 mg/patient to about 1000 mg/patient.

EXAMPLES

The present invention is described in more detail by way of Preparation Examples and Examples.

Preparation Example 1-1

Methyl 3-(3,4-dichlorobenzoyl)-2-methylbenzo[b]thiophene-5-carboxylate

In the same manner as in Preparation Example 16-2 to be described later, the objective compound was obtained from methyl 2-methylbenzo[b]thiophene-5-carboxylate and 3,4-dichlorobenzoyl chloride.

$^1$H-NMR(CDCl$_3$): 2.48(3H, s), 3.89(3H, s), 7.52–7.68 (2H, m), 7.79–8.04(3H, m), 8.23(1H,s) Mass(ESI): m/e 377(M−H)$^-$ Preparation Example 1-2

Methyl 3-(3,4-Dichlorobenzyl)-2-methylbenzo[b]thiophene-5-carboxylate

To a solution of methyl 3-(3,4-diclorobenzyoyl)-2-methylbenzo[b]thiophene-5-carboxylate (259 mg) in tetrahydrofuran (2.6 ml)-methanol (0.26 ml) was added sodium borohydride (36 mg) under ice-cooling, and the mixture was stirred for 10 min. Trifluoroacetic acid (15 ml) was placed in a different reaction vessel, and sodium borohydride (255 mg) was portionwise added with stirring under ice-cooling. Thereto was added the above-mentioned reaction mixture and the mixture was stirred for 3 hr at room temperature. The reaction mixture was concentrated, diluted with water under ice-cooling and neutralized with a 15% aqueous sodium hydroxide solution. The resulting product was extracted with ethyl acetate. The obtained organic layer was washed with brine and dried over anhydrous magnesium sulfate. The solvent was evaporated to give the objective compound (224 mg) as a white powder.

$^1$H-NMR(CDCl$_3$): 2.51(3H, s), 3.91(3H, s), 4.14(2H, s), 6.97(1H, dd, J=8 and 2 Hz), 7.20(1H, d, J=2 Hz), 7.31(1H, d, J=8 Hz), 7.82(1H, d, J=8 Hz), 7.93(1H, dd, J=8 and 2 Hz) Mass(ESI): m/e 363(M−H)$^-$

Preparation Method 1-3

3-(3,4-Dichlorobenzyl)-2-methylbenzo[b]thiophene-5-carboxylic acid

In the same manner as in Preparation Example 4-7 to be described later, the objective compound was obtained from methyl 3-(3,4-dichlorobenzyl)-2-methylbenzo[b]thiophene-5-carboxylate.

$^1$H-NMR(DMSO-d$_6$): 2.56(3H, s), 4.24(2H, s), 7.10(1H, d, J=8Hz), 7.43 (1H, s), 7.51(1H, d, J=8 Hz), 7.82(1H, d, J=8), 7.95(1H, d, J=8 Hz), 8.14(1H, d, J=8 Hz) Mass(ESI): m/e 349(M−H)$^-$

Preparation Example 2-1

Methyl 3-(2,3-dichlorobenzoyl)-2-methylbenzo[b]thiophene-5-carboxylate

In the same manner as in Preparation Example 1-1, the objective compound was obtained using 2,3-dichlorobenzoyl chloride.

$^1$H-NMR(CDCl$_3$): 2.40(3H, s), 3.90(3H, s), 7.31–7.41 (2H, m), 7.58–7.69(1H, m), 7.81(1H, d, J=8 Hz), 8.01(1H, d, J=8 Hz), 8.59(1H, s)

Mass(ESI): m/e 377(M−H)$^-$

Preparation Example 2-2

Methyl 3-(2,3-dichlorobenzyl)-2-methylbenzo[b]thiophene-5-carboxylate

In the same manner as in Preparation Example 1-2, the objective compound was obtained from the obtained methyl ester.

$^1$H-NMR(CDCl$_3$): 2.45(3H, s), 3.89(3H, s), 4.27(2H, s), 6.57(1H, d, J=8 Hz), 6.97(1H, t, J=8 Hz), 7.31(1H, d, J=8 Hz), 7.82(1H, d, J=8 Hz), 7.94(1H, d, J=8 Hz), 8.11(1H, s)

Mass(ESI): m/e 363(M−H)$^-$

Preparation Example 2-3

3-(2,3-Dichlorobenzyl)-2-methylbenzo[b]thiophene-5-carboxylic acid

In the same manner as in Preparation Example 1-3, the objective compound was obtained from the obtained methyl ester.

$^1$H-NMR(DMSO-d$_6$): 2.50(3H, s), 4.32(2H, s), 6.71(1H, d, J=8 Hz), 7.19(1H, t, J=8 Hz), 7.51(1H, d, J=8 Hz), 7.83(1H, d, J=8 Hz), 8.01(1H, s), 8.02(1H, d, J=8 Hz)

Mass(ESI): m/e 349(M−H)$^-$

Preparation Example 3-1

Methyl 3-(2,5-dichlorobenzoyl)-2-methylbenzo[b]thiophene-5-carboxylate

On the same manner as in Preparation Example 1-1, the objective compound was obtained using 2,5-dichlorobenzoyl chloride.

$^1$H-NMR(CDCl$_3$): 2.42(3H, s), 3.90(3H, s), 7.35–7.51 (3H, m), 7.81(1H, d, J=8 Hz), 8.01(1H, d, J=8 Hz), 8.06(1H, s)

Mass(ESI): m/e 377(M−H)$^-$

Preparation Example 3-2

Methyl 3-(2,5-dichlorobenzyl)-2-methylbenzo[b]thiophene-5-carboxylate

In the same manner as in Preparation Example 1-2, the objective compound was obtained from the obtained methyl ester.

$^1$H-NMR(CDCl$_3$): 2.48(3H, s), 3.90(3H, s), 4.21(2H, s), 6.64(1H, s), 7.11(1H, d, J=8 Hz), 7.34(1H, d, J=8 Hz), 7.83(1H, d, J=8 Hz), 7.95(1H, d, J=8 Hz), 8.13(1H, s)

Mass(ESI): m/e 363(M−H)$^-$

Preparation Example 3-3

3-(2,5-Dichlorobenzyl)-2-methylbenzo[b]thiophene-5-carboxylic acid

In the same manner as in Preparation Example 1-3, the objective compound was obtained from the obtained methyl ester.

$^1$H-NMR (DMSO-d$_6$): 2.52(3H, s), 4.28(2H, s), 6.75(1H, d, J=2 Hz), 7.33(1H, dd, J=8 and 2 Hz), 7.55(1H, d, J=8 Hz), 7.84(1H, d, J=8 Hz), 7.89–8.11(2H, m)

Mass(ESI): m/e 349(M−H)$^-$

Preparation Example 4-1

Ethyl N-aminoisonicotinate 2,4-dinitrophenol salt

Ethyl isonicotinate (10.0 g) was dissolved in tetrahydrofuran (100 ml), and O-(2,4-dinitrophenyl)hydroxylamine (11.9 g) was added at room temperature, which was followed by refluxing under heating for 2 hr. The solvent was evaporated under reduced pressure, and the obtained residue was washed with diethyl ether and ethyl acetate to give the objective compound (10.5 g) as an amber-colored powder.

$^1$H-NMR(DMSO-d$_6$): 1.36(3H, t, J=6 Hz), 4.40(2H, q, J=6 Hz), 6.32(1H, d, J=9 Hz), 7.78(1H, dd, J=9, 2 Hz), 8.34(1H, d, J=8 Hz), 8.59(1H, d, J=2 Hz), 8.84(1H, d, J=8 Hz)

Preparation Example 4-2

Diethyl-2-methylpyrazolo[1,5-a]pyridine-3,5-dicarboxylate

Ethyl N-aminoisonicotinate 2,4-dinitrophenol salt (10.2 g) was suspended in ethanol (147 ml), and potassium carbonate (3.77 g) was added, which was followed by stirring at room temperature for 30 min. To the mixture was added ethyl acetoacetate (3.69 ml), and the mixture was stirred at 60° C. for 5 hr with heating. The insoluble matter was filtered off and the filtrate was concentrated to dryness under reduced pressure. The residue was purified by silica gel column chromatography (eluent: hexane/ethyl acetate= 7/1) to give the objective compound (2.70 g) as an amber-colored solid.

$^1$H-NMR(CDCl$_3$): 1.42(3H, t, J=6 Hz), 1.46(3H, t, J=6 Hz), 2.70(3H, s), 4.36–4.50(4H, m), 7.46(1H, d, J=8 Hz, 7.78(1H, dd, J=9, 2 Hz), 8.43(1H, d, J=8 Hz), 8.78(1H, s)

Preparation Example 4-3

2-Methylpyrazolo[1,5-a]pyridine-3,5-dicarboxylic acid

A mixture of diethyl 2-methylpyrazolo[1,5-a]pyridine-3, 5-dicarboxylate (100 mg), a 50% aqueous sodium hydroxide solution (160 mg), water (0.5 ml) and ethanol (1.0 ml) was refluxed under heating for 30 min. Then, the reaction mixture was adjusted to pH 4 under ice-cooling and stirred at the same temperature for 30 min. The precipitate was collected by filtration and washed with water to give the objective compound (50 mg) as a pale-brown powder.

$^1$H-NMR(DMSO-d$_6$): 2.55(3H, s), 7.43(1H, d, J=8 Hz), 8.46(1H, s), 8.56 (1H, d, J=8 Hz)

Preparation Example 4-4

2-Methylpyrazolo[1,5-a]pyridine-5-carboxylic acid

A mixture of 2-methylpyrazolo[1,5-a]pyridine-3,5-dicarboxylic acid (1.39 g) and polyphosphoric acid (13.9 g) was stirred at 150° C. with heating for 2 hr, and ice (14 g) was added under ice-cooling, which was followed by shaking to give a homogeneous solution. The reaction mixture was adjusted to pH 4 at the same temperature and diluted with dichloromethane/methanol (4:1) and water. The precipitate was collected by filtration to give the objective compound (610 mg) as a pale-brown powder. The organic layer of the mother liquor was taken, and the aqueous layer was extracted with dichloromethane/methanol (4:1). Both organic layers were combined, dried over magnesium sulfate and concentrated to dryness under reduced pressure. The residue was washed with ether to give second crystals (200 mg) as a pale-brown powder.

$^1$H-NMR(DMSO-d$_6$): 2.42(3H, s), 6.67(1H, s), 7.18(1H, d, J=8 Hz), 8.21 (1H, s), 8.62(1H, d, J=8 Hz)

Preparation Example 4-5

Ethyl 2-methylpyrazolo[1,5-a]pyridine-5-carboxylate

2-Methylpyrazolo[1,5-a]pyridine-5-carboxylic acid (723 mg) was dissolved in 10% sulfuric acid/ethanol (20 ml) and the mixture was refluxed under heating for 2.5 hr. The reaction mixture was neutralized under ice-cooling, extracted with ethyl acetate and dried over magnesium sulfate. The residue was concentrated to dryness under reduced pressure. The residue was purified by silica gel column chromatography (hexane/ethyl acetate=4:1) to give the objective compound (707 mg) as a pale-brown powder.

$^1$H-NMR(CDCl$_3$): 1.41(3H, t J=7 Hz), 2.52(3H, s), 4.40 (2H, q, J=7 Hz), 6.49(1H, s), 7.25(1H, d, J=8 Hz), 8.19(1H, s), 8.40(1H, d, J=8 Hz)

Preparation Example 4-6

Ethyl 3-(2,4-dichlorobenzyl)-2-methylpyrazolo[1,5-a]pyridine-5-carboxylate

To a solution of trifluoroacetic acid (558 mg) and triethylsilane (1.14 g) in dry dichloromethane (2.0 ml) were added ethyl 2-methylpyrazolo[1,5-a]pyridine-5-carboxylate (200 mg) and 2,4-dichlorobenzaldehyde (189 mg), and the mixture was stirred at room temperature for 3 days. To the reaction mixture was added 2,4-dichlorobenzaldehyde (189 mg) and the mixture was stirred at room temperature for one day. This step was repeated three times. The reaction mixture was diluted with dichloromethane and washed with a saturated aqueous sodium hydrogencarbonate solution. The aqueous layer was extracted with dichloromethane. The organic layers were combined, dried over magnesium sulfate, and concentrated to dryness under reduced pressure. The residue was purified by silica gel column chromatography (hexane/ethyl acetate=9:1) and washed with isopropyl ether to give the objective compound (233 mg) as a white powder.

$^1$H-NMR(CDCl$_3$): 1.40(3H, t, J=7 Hz), 2.38(3H, s), 4.12 (2H, s), 4.38(2H, q, J=7 Hz), 6.84(1H, d, J=8 Hz), 7.10(1H, d, J=8 Hz), 7.27(1H, d, J=8 Hz), 7.42(1H, s), 8.00(1H, s), 8.40(1H, d, J=8 Hz)

Preparation Example 4-7

3-(2,4-Dichlorobenzyl)-2-methylpyrazolo[1,5-a]pyridine-5-carboxylic acid

A mixture of ethyl 3-(2,4-dichlorobenzyl)-2-methylpyrazolo[1,5-a]pyridine-5-carboxylate (230 mg), a 1N aqueous sodium hydroxide solution (2.0 ml) and ethanol (2.3 ml) was refluxed under heating for 25 min. The reaction mixture was adjusted to pH 4 under ice-cooling with 1N hydrochloric acid. The precipitate was collected by filtration and washed with water to give the objective compound (208 mg) as a white powder.

$^1$H-NMR(DMSO-d$_6$): 2.30(3H, s), 4.19(2H, s), 7.10(1H, d, J=8 Hz), 7.16(1H, d, J=8 Hz), 7.34(1H, d, J=8 Hz), 7.62(1H, s), 8.06(1H, s), 8.62(1H, d, J=8 Hz)

Preparation Example 5-1

1-(2,4-Dichlorophenyl)-1-trimethylsilyloxyethene

Diisopropylamine (16.2 g) was dissolved in tetrahydrofuran (133 ml), and 1.6N n-butyl lithium (100 ml) was dropwise added thereto under ice-cooling. The reaction mixture was stirred at the same temperature for 10 min, and a solution of 2,4-dichoroacetophenone (25.2 g) in tetrahydrofuran (133 ml) was dropwise added under cooling in a dry ice-acetone bath. Hexamethylphosphoramide (26.7 ml) was added little by little. The mixture was stirred at the same temperature for 5 min, and chlorotrimethylsilane (20.3 ml) was dropwise added, which was followed by stirring at room temperature for 30 min. The reaction mixture was partitioned between ice-cooled n-hexane and ice-cooled water. The organic layer was washed twice with ice-cooling water and then once with saturated brine, dried over sodium sulfate and concentrated under reduced pressure to dryness to give a crude product (37.5 g) of the objective compound as a pale-yellow oil.

Preparation Example 5-2

1-(2,4-Dichlorophenyl)-3-hydroxy-3-methylbutanone

To a solution of titanium tetrachloride (17.8 ml) in dichloromethane (160 ml) was dropwise added acetone (10 ml) under cooling in a dry ice-acetone bath, and one minutes later, a solution of the crude product (37.5g) of 1-(2,4-dichlorophenyl)-1-trimethylsilyloxyethene in dichloromethane (160 ml) was added. The mixture was stirred under cooling in a dry ice-acetone bath overnight and at room temperature for 3 hr. The ration mixture was washed with water, and the aqueous layer was extracted once with dichloromethane. The organic layers were combined, washed with a saturated aqueous sodium hydrogencarbonate solution and saturated brine, dried over magnesium sulfate and concentrated under reduced pressure to dryness to give a brown oily residue. The obtained residue was purified by silica gel column chromatography (eluent: hexane/ethyl acetate=9/1-4/1) to give the objective compound (16.2 g) as a pale-yellow oil.

$^1$H-NMR(CDCl$_3$): 1.34(6H, s), 3.13(2H, s), 7.33(1H, d, J=8 Hz), 7.44(1H, d, J=8 Hz), 7.47(1H, s)

Preparation Example 5-3

1-(2,4-Dichlorophenyl)-3-methyl-3-trifluoroacetoxybutanone

To a solution of 1-(2,4-dichlorophenyl)-3-hydroxy-3-methylbutanone (16.16 g) and triethylamine (27.4 ml) in dichloromethane (160 ml) was added trifluoroacetic anhydride (13.9 ml) under ice-cooling. The mixture was stirred at the same temperature for 10 min, and at room temperature for 1 hr. The reaction mix was washed with water and a saturated aqueous sodium hydrogencarbonate solution, dried over sodium sulfate, and concentrated under reduced pressure to dryness to give a crude product of the objective compound (19.9 g) as a brown oil.

Preparation Example 5-4

1-(2,4-Dichlorophenyl)-3-methyl-2-butenone

To a solution of the crude product (19.9 g) of 1-(2,4-dichlorophenyl)-3-methyl-3-trifluoroacetoxybutanone in toluene (100 ml) was added 1,8-diazabicyclo[5,4,0]-undec-7-ene (4.0 ml), and the mixture was stirred at room temperature for 30 min. The reaction mixture was washed successively with ice-water, 1N hydrochloric acid, saturated brine, a saturated aqueous sodium hydrogencarbonate solution and saturated brine, dried over magnesium sulfate, and concentrated under reduced pressure to dryness. The residue was purified by silica gel column chromatography (eluent: hemane/ethyl acetate=49/1) to give the objective compound (12.5 g) as a pale-brown oil.

$^1$H-NMR(CDCl$_3$): 2.00(3H, s), 2.24(3H, s), 6.43(1H, s), 7.29(1H, d, J=8 Hz), 7.39–7.46(2H)

Preparation Example 5-5

(E) 4-Bromo-1-(2,4-dichlorophenyl)-3-methyl-2-butenone

To a solution of 1-(2,4-dichlorophenyl)-3-methyl-2-butenone (9.30 g) in carbon tertachloride (93 ml) were added N-bromosuccinimide (7.95 g) and benzoyl peroxide (983 mg), and the mixture was refluxed under heating for 1 hr. The reaction mixture was ice-cooled and the precipitate was filtered off. The filtrate and washing solution were combined and washed three times with a saturated aqueous sodium hydrogencarbonate solution and then once with saturated brine. The organic layer was dried over magnesium sulfate, concentrated under reduced pressure to dryness to give a crude product (14.6 g) of the objective compound as a black oil.

Preparation Example 5-6

(E) 1-(2,4-Dichlorophenyl)-4-(4-ethoxycarbonylpyridyl)-3-methyl-2-butenone

The crude product of (E) 4-bromo-1-(2,4-dichlorophenyl)-3-methyl-2-butenone (14.6g) was dissolved in acetone (140 ml), and ethyl isonicotinate (12.1 ml) was added. The mixture was refluxed under heating for 6 hr. The reaction mixture was concentrated under reduced pressure to dryness to give a crude product (22.0 g) of the objective compound as a brown solid.

Preparation Example 5-7

Ethyl 1-(2,4-dichlorobenzoyl)-2-methylindolizine-7-carboxylate

The crude product of (E) 1-(2,4-dichlorophenyl)-4-(4-ethoxycarbonylpyridyl)-3-methyl-2-butenone (22.0 g) was dissolved in ethanol (146 ml), and potassium carbonate (5.61 g) was added. The mixture was refluxed under heating for 12 hr. The reaction mixture was partitioned between ethyl acetate and saturated brine, and the organic layer was dried over magnesium sulfate and concentrated under reduced pressure to dryness to give an amber-colored solid. The residue was pulverized in ether to give the objective compound (3.54 g) as a yellow powder.

$^1$H-NMR(CDCl$_3$): 1.38(3H, t, J=6 Hz), 2.16(3H, s), 4.35 (2H, q, J=6 Hz), 7.22(1H, s), 7.30–7.42(3H), 7.52(1H, s), 7.97(1H, d, J=8 Hz), 8.36(1H, s)

Preparation Example 5-8

Ethyl 1-(2,4-dichlorobenzyl)-2-methylindolizine-7-carboxylate

Ethyl 1-(2,4-dichorobenzoyl)-2-methylindolizine-7-carboxylate (3.17 g) was dissolved in tetrahydrofuran (32 ml), and a 10M borane-dimethyl sulfide complex (9.5 ml) was dropwise added under ice-cooling. The mixture was stirred at room temperature for 3.5 hr, neutralized and partitioned between ethyl acetate and water. The organic layer was washed three times with water and then with saturated brine, dried over magnesium sulfate and concentrated under reduced pressure to dryness. The residue was purified by silica gel column chromatography (eluent: hexane/ethyl acetate=19/1) to give the objective compound (1.81 g) as a pale-yellow oil.

$^1$H-NMR(CDCl$_3$): 1.38(3H, t J=6 Hz), 2.13(3H, s), 4.16 (2H, s), 4.33(2H, q, J=6 Hz), 6.71(1H, d, J=8 Hz), 6.99(1H, d, J=8 Hz), 7.03(1H, dd, J=8, 2 Hz), 7.29(1H, s), 7.40(1H, s), 7.80(1H, d, J=8 Hz), 7.98(1H, s).

Preparation Example 5-9

1-(2,4-Dichlorobenzyl)-2-methylindolizine-7-carboxylic acid

In the same manner as in Preparation Example 4-7, the objective compound (1.63 g) was obtained from ethyl 1-(2,4-dichlorobenzyl)-2-methylindolizine-7-carboxylate (1.81 g) as a yellow powder.

$^1$H-NMR(DMSO-d$_6$): 2.10(3H, s), 4.17(2H, s), 6.84–6.91 (2H), 7.28(1H, d, J=8 Hz), 7.60(2H, s), 7.93(1H, s), 8.19 (1H, d, J=8 Hz)

Preparation Example 6-1

(E)-4-Methyl-2-(4-phenylphenyl)ethenylpyridine

A mixture of 4-phenyl benzaldehyde (6.45 g), 2,4-lutidine (7.59 g) and acetic anhydride (10 ml) was heated at a bath temperature of 150° C. for 12 hr, and refluxed under heating for 12 hr. The reaction mixture was concentrated under reduced pressure to dryness. The residue was purified by silica gel column chromatography (eluent: hexane/ethyl acetate=9/1-5/1) to give the objective compound (4.35 g) as a yellow solid.

$^1$H-NMR(CDCl$_3$): 2.38(3H, s), 6.98(1H, d, J=5 Hz), 7.12–7.28(2H), 7.34(1H, t, J=8 Hz), 7.44(2H, t, J=8 Hz), 7.57–7.71(7H), 8.47(1H, d, J=5 Hz)

Preparation Example 6-2

(E)-2-(4-Phenylphenyl)ethenylpyridine-4-carboxylic acid

A mixture of (E)-4-methyl-2-(4-phenylphenyl) ethenylpyridine (4.24 g), selenium diode (2.08 g) and pyridine (43 ml) was refluxed under heating for 24 hr. The reaction mixture was concentrated under reduced pressure to dryness. The residue was extracted with chloroform/ methanol/aqueous ammonium (65:25:4). The extract was concentrated under reduced pressure to dryness. The residue was pulverized in ethyl acetate to give the objective compound (3.81 g) as a brown powder.

$^1$H-NMR(DMSO-d$_6$): 7.32–7.53(4H), 7.63(1H, d, J=5 Hz), 7.70–7.84(8H), 7.96(1H, s), 8.66(1H, d, J=5 Hz)

Preparation Example 6-3

Ethyl (E)-2-(4-phenylphenyl)ethenylpyridine-4-carboxylate (E)-2-(4-Phenylphenyl)ethenylpyridine-4-carboxylic acid (3.60 g) and a mixture of concentrated sulfuric acid/ethanol (9:1) were refluxed under heating for 2 hr, and neutralized under ice cooling. The reaction mixture was partitioned between dichloromethane and water, and the aqueous layer was extracted once with dichloromethane. The organic layers were combined, dried over magnesium sulfite and concentrated to dryness under reduced pressure. The residue was purified by silica gel column chromatography (eluent: hexane/ethyl acetate=9/1-4/1) to give the objective compound (3.14 g) as a white solid.

$^1$H-NMR(CDCl$_3$): 1.43(3H, t, J=6 Hz), 4.45(2H, q, J=6 Hz), 7.22–7.50(4H), 7.60–7.79(8H), 7.97(1H, s), 8.74(1H, d, J=5 Hz)

Preparation Example 6-4

Ethyl 2-(4-phenylphenyl)ethylpyridine-4-carboxylate

A mixture of ethyl (E)-2-(4-phenylphenyl)ethenylpyridine-4-carboxylate (1.84 g), 10% palladium/active carbon (184 mg), dioxane (18 ml) and ethanol (9.0 ml) was stirred at 40° C. for 5 hr under a hydrogen atmosphere at 5 atm. To this reaction mixture were added dioxane (9.0 ml) and ethanol (9.0 ml), and the mite was stirred at 50° C. for 3 hr under a hydrogen atmosphere at 5 atm. To the mixture was added 10% palladium/active carbon (184 mg, and the mixture was stirred for 3 hr under the same conditions. The reaction mixture was filtered through Celite and washed with chloroform/methanol (4:1). The filtrate and the washing were combined and concentrated to dryness under reduced pressure to give a crude product of the objective compound (1.97 g) as a pale-yellow solid.

$^1$H-NMR(CDCl$_3$): 1.40(3H, t, J=6 Hz), 3.12(2H, m), 3.22(2H, m), 4.40(2H, q, J=6 Hz), 7.22–7.36(3H), 7.43(2H, t, J=8 Hz), 7.52(2H, d, J=8 Hz), 7.58(2H, d, J=8 Hz), 7.67–7.72(2H), 8.72(1H, d, J=5 Hz)

Preparation Example 6-5

Ethyl 2-methyl-1-(4-phenylbenzyl)indolizine-7-carboxylate

The crude product of ethyl 2-(4-phenylphenyl) ethylpyridine-4-carboxylate (1.62 g) and bromoacetone (803 mg) were dissolved in acetone (32 ml). The mixture was refluxed under heating for 24 hr and concentrated to dryness under reduced pressure. The residue was dissolved in ethanol (16 ml). Sodium hydrogen-carbonate was added, and the mixture was refluxed under heating for 12 hr. The reaction mixture was diluted with ethyl acetate and washed with water. The organic layer was dried over magnesium sulfate and concentrated to dryness under reduced pressure. The residue was purified by silica gel column chromatography (eluent: hexane/ethyl acetate=19/1) to give the objective compound (383 mg) as a yellow-green solid. The unreacted starting compound, ethyl 2-(4-phenylphenyl)-ethylpyridine-4-carboxylate, (1.04 g) was recovered.

$^1$H-NMR(CDCl$_3$): 1.38(3H, t, J=6 Hz), 2.21(3H, s), 4.19 (2H, s), 4.35(2H, q, J=6 Hz), 6.98(1H, d, J=8 Hz), 7.18–7.36 (4H), 7.40(2H, t, J=8 Hz), 7.48(2H, d, J=8 Hz), 7.56(2H, d, J=8 Hz), 7.78(1H, d, J=8 Hz), 8.12(1H, s)

Preparation Example 6-6

2-Methyl-1-(4-phenylbenzyl)indolizine-7-carboxylic acid

In the same manner as in Preparation Example 4-7, the objective compound (612 mg) was obtained as a yellow powder from ethyl 2-methyl-1-(4-phenylbenzyl)-indolizine-7-carboxylate 710 mg).

$^1$H-NMR(DMSO-d$_6$): 2.20(3H, s), 4.16(2H, s), 6.86(1H, d, J=8 Hz), 7.22(2H, d, J=8 Hz), 7.33(1H, t, J=8 Hz), 7.43(2H, t, J=8 Hz), 7.52–7.64(5H), 8.06(1H, s), 8.17(1H, d, J=8 Hz)

Preparation Example 7-1

6-(4,5-Dihydro-4,4-dimethyloxazol-2-yl)quinoline

A mxiture of quinoline-6-carboxylic acid (4.00 g) and thionyl chloride (10.1 ml) was stirred for 3 hr at room temperature and concentrated to dryness under reduced pressure. To the residue were added dichloromethane (60 ml) and triethylamine (16 ml), and then 2-amino-2-methylpropanol (4.12 g) with stirring in an ice bath. The reaction mixture was stirred for 3 hr at room temperature. Water was added to separate the organic layer. The aqueous layer was extracted twice with dichloromethane. The organic layers were combined, dried over anhydrous magnesium sulfate and concentrated to dryness under reduced pressure to give a pale-brown solid (5.55 g). To this was added thionyl chloride (16.8 ml) while stirring under cooling with ice water under a nitrogen atmosphere, and the mixture was stirred for 3 hr at room temperature. The reaction mixture was concentrated to dryness under reduced pressure. Water and 1N aqueous sodium hydroxide solution were added to basicify and the mixture was extracted three times with ethyl acetate. The extract was dried over anhydrous magnesium sulfate and concentrated to dryness under reduced pressure. The residue was purified by silica gel column chromatography (eluent: ethyl acetate) to give the objective compound (3.26 g) as a light-brown solid.

$^1$H-NMR(CDCl$_3$):1.43(6H, s), 4.20(2H, s), 7.45(1H, dd, J=4 Hz, 8 Hz), 8.11(1H, d, J=8 Hz), 8.21(1H, d, J=8 Hz), 8.26 (1H, d, J=8 Hz), 8.43(1H, s), 8.97 (1H, m)

Preparation Example 7-2

1-Ethoxycarbonyl-6-(4,5-dihydro-4,4-dimethyloxazol-2-yl)-2-dimethoxyphosphoryl-1,2-dihydroquinoline A mixture of 6-(4,5-dihydro-4,4-dimethyloxazol-2-yl) quinoline (543 mg) and ethyl chloroformate (0.275 ml) was stirred for 3 hr at room temperature. Trimethyl phosphonate (0.340 ml) was added under ice water-cooling and the mixture was stirred for 15 hr at room temperature. The reaction mixture was concentrated to dryness under reduced pressure. The residue was purified by silica gel column chromatography (eluent: ethyl acetate, ethyl acetate/methanol=20/1) to give the objective compound (974 mg) as a pale-yellow oil.

$^1$H-NMR(CDCl$_3$): 1.33(3H, t, J=7 Hz), 1.39(6H, s), 3.52 (3H, d, J=10 Hz), 3.64(3H, d, J=10 Hz), 4.12(2H, s), 4.26–4.38(2H, br), 5.61–5.75(1H, br), 6.06–6.14(1H, m), 6.62(1H, m), 7.68(1H, s), 7.78(1H, dd, J=4 Hz, 8 Hz)

Preparation Example 7-3

1-Ethoxycarbonyl-6-(4,5-dihydro-4,4-dimethyloxazol-2-yl)-2-dimethoxyphosphoryl-4-(4-phenylbenezyl)-1,2-dihydroquinoline 1-Ethoxycarbonyl-6-(4,5-dihydro-4,4-dimethyloxazol-2-yl)-2-dimethoxyphosphoryl-1,2-dihydroquioline (934 mg) was dissolved in THF (10 ml), and a 1.6 M n-butyllithiumhexane solution (1.8 ml) was added under cooling with dry ice-acetone. The mixture was stirred for 1 hr at the same temperature. 4-(Iodomethyl)biphenyl (740 mg, 2.52 mmol) was added under cooling with dry ice-acetone, and the mixture was stirred at −20° C. for 1 hr and at 0° C. for 1 hr. Then, water was added, and the mixture was stirred for 0.5 hr at room temperature and extracted three times with ethyl acetate. The extract was dried over anhydrous magnesium sulfate and concentrated to dryness under reduced pressure. The residue was purified by silica gel column chromatography (eluent: ethyl acetate, ethyl acetate/methanol=20/1) to give the objective compound (738 mg) as a yellow powder.

$^1$H-NMR(CDCl$_3$): 1.32(3H, t, J=7 Hz), 1.38(6H, s), 3.49 (3H, d, J=10 Hz), 3.61(3H, d, J=10 Hz), 3.99(2H, br), 4.10(2H, m), 4.30(2H, m), 5.54–5.74(2H, br), 7.29–7.60 (10H, m), 7.84(1H, m), 7.91(1H, s)

MS (m/z) 575.

Preparation Example 7-4

6-(4,5-Dihydro-4,4-dimethyloxazol-2-yl)-4-(4-phenylbenzyl)quinoline

A mixture of 1-ethoxycarbonyl-6-(4,5-dihydro-4,4-dimethyloxazol-2-yl)-2-dimethoxyphosphoryl-4-(4-phenylbenzyl)-1,2-dihydroquinoline (738 mg), ethanol (20 ml) and 1N aqueous sodium hydroxide solution (4 ml) was refluxed under heating for 2 hr. The reaction mixture was concentrated to dryness under reduced pressure. Water was added and the mixture was extracted twice with ethyl acetate. The organic layers were combined, washed once with saturated brine, dried over anhydrous magnesium sulfate and concentrated to dryness under reduced pressure. The residue was purified by silica gel column chromatography (eluent: ethyl acetate) to give the objective compound (140 mg) as a white solid.

$^1$H-NMR(CDCl$_3$): 1.42(6H, s), 4.18(2H, s), 4.54(2H, s), 7.18(1H, br), 7.27–7.46(5H, m), 7.52–7.60(4H, m), 8.16 (1H, d, J=8 Hz), 8.29(1H, d, J=8 Hz), 8.73(1H, br), 8.83(1H, d, J=7 Hz)

Preparation Example 7-5

4-(4-Phenylbenzyl)quinoline-6-carboxylic acid

A mixture of 6-(4,5-dihydro-4,4-dimethyloxazol-2-yl)-4-(4-phenylbenzyl)-quinoline (132 mg), ethanol (1 ml) and 3N hydrochloric acid (3 ml) was refluxed under heating for 2 hr. Then 6N hydrochloric acid (3 ml) was added and the mixtured was refluxed for 4 hr. The mixture was basified with aqueous sodium hydroxide solution, and washed once with chloroform. The aqueous layer was adjusted to pH 4 with 1N hydrochloric acid. The resulting precipitate was collected by filtration and washed with water to give the objective compound (87 mg) as a white powder.

$^1$H-NMR(DMSO-d$_6$): 4.61(2H, s), 7.30–7.50(6H, m), 7.57–7.68(4H, m), 8.12(1H, d, J=8 Hz), 8.21(1H, d, J=8 Hz), 8.83(1H, s), 8.94 (1H, d, J=4 Hz)

Preparation Example 8-1

2,3-Diamino-6-chloropyridine

In the same manner as in the following Preparation Example 9-2, the objective compound (8.3 g) was obtained from 2-amino-6-chloro-3-nitropyridine (10.2 g) as a red-brown solid.

$^1$H-NMR(DMSO-d$_6$): 4.77(2H, br s), 5.79(2H, br s), 6.34(1H, d, J=8 Hz), 6.69(1H, d, J=8 Hz)

MASS(ESI): m/z 142(M−1)

Preparation Example 8-2

5-Chloro-2-methyl-1H-imidazo[4,5-b]pyridine

In the same manner as in the following Preparation Example 9-3, the objective compound (6.64 g) was obtained from 2,3-diamino-6-chloropyridine (8.1 g) as light brown crystals.

$^1$H-NMR(DMSO-d$_6$): 2.52(3H, s), 7.22(1H, d, J=8 Hz), 7.91(1H, d, J=8 Hz)

MASS(ESI): m/z 166(M−1)

mp 254–255° C.

Preparation Example 8-3

5-Bromo-2-methyl-1H-imidazo[4,5-b]pyridine

In the same manner as in the following Preparation Example 9-1, the objective compound (7.54 g) was obtained from 5-chloro-2-methyl-1H-imidazo[4,5-b]pyridine (6.54 g) as pale-purple crystals.

$^1$H-NMR(DMSO-d$_6$): 2.51(3H, s), 7.32(1H, d, J=8 Hz), 7.83(1H, d, J=8 Hz)

MASS(ESI): m/z 210(M−1)

mp 239–241° C.

Preparation Example 8-4

2-Methylimidazol[4,5-b]pyridine-5-carbonitrile

To a solution of 5-bromo-2-methyl-1H-imidazo[4,5-b]pyridine (1.92 g) in N,N-dimethylformamide (48 ml) was added Copper (I) cyanide (2.04 g), and the mixture was stirred for 9 hr at 150° C. After evaporation of the solvent under reduced pressure, water (45 ml) and ethylenediamine (2.7 g) were added to the residue, and the mixture was heated at 70° C. for 15 min. The solution was concentrated under reduced pressure and the residue was purified by a short silica gel column to give the objective compound (927 mg) as a brown powder. Purification by silica gel column chromatography (dichloromethane/methanol=10/1) gave a purer compound.

$^1$H-NMR(DMSO-d$_6$): 2.58(3H, s), 7.76(1H, d, J=8 Hz), 8.05(1H, d, J=8 Hz)

Mass(ESI): m/e 157(M−H)$^-$

Preparation Example 9-1

2-Amino-6-bromo-3-nitropyridine

A 30% solution of hydrogen bromide in acetic acid (10 ml) was added to 2-amino-6-chloro-3-nitropyridine (1.0 g) at room temperature and the mixture was heated at 100° C. After 24 hr, a 30% solution of hydrogen bromide in acetic acid (5 ml) was added. After 48 hr, the reaction mixture was cooled and concentrated. The residue was neutralized with 28% aqueous ammonia and extracted three times with ethyl acetate. The organic layer was dried over anhydrous magnesium sulfate, filtered and concentrated. The residue was crystallized from isopropyl ether to give the objective compound (1.14 g) as yellow crystals.

$^1$H-NMR(DMSO-d$_6$): 6.90(1H, d, J=8 Hz), 8.25(1H, d, J=8 Hz)

MASS(ESI): m/z 217(M−1)

Preparation Example 9-2

2,3-Diamino-6-bromopyridine

To a suspension of 2-amino-6-bromo-3-nitropyridine (21.8 g) in ethanol (220 ml) in water (22 ml) was added iron powder (39.0 g) at room temperature. Concentrated hydrochloric acid (0.8 ml) was added and the mixture was slowly heated with stirring to start the reaction. The mixture was refluxed under heating for 2 hr and the insoluble matter was filtered off while it was hot. The solvent was evaporated under reduced pressure and water (200 ml) and active carbon were added to the remaining solid, which was followed by heating. The insoluble matter was filtered off while it was hot. Water was evaporated under reduced pressure from the filtrate to give the objective compound (9.00 g) as a green-brown powder. Ethanol (100 ml)-water (100 ml) was added to the solid from the above operation and the mixture was heated for dissolution, and the insoluble matter was filtered off. The solvent was evaporated under reduced pressure and the residue was purified by silica gel column chromatograhy (hexane/ethyl acetate=1/3) to give the objective compound (8.25 g) as a black powder.

$^1$H-NMR(DMSO-d$_6$): 4.78(2H, br s), 5.80(2H, br s), 6.47(1H, d, J=8 Hz), 6.61(1H, d, J=8 Hz)

Mass(ESI): m/e 188, 190 (M+H)$^+$

Preparation Example 9-3

5-Bromo-2-methyl-1H-imidazo[4,5-b]pyridine 2,3-Diamino-6-bromopyridine (8.16 g) and triethyl orthoacetate (12.0 ml) were mixed in acetic acid (41 ml), and the mixture was refluxed under heating for 29 hr. The mixture was allowed to cool and the solvent was evaporated to give a crude product (10 g). This was dissolved in a sufficient amount of dichloromethane. Anhydrous potassium carbonate and active carbon were added and the mixture was stirred at room temperature. The insoluble matter was filtered off and the solvent was evaporated to give the objective compound (7.59 g) as a pale-yellow powder.

$^1$H-NMR(DMSO-d$_6$): 2.51(3H, s), 7.31(1H, d, J=8 Hz), 7.82(1H, d, J=8 Hz)

Mass(ESI): m/e 212, 214 (M+H)$^+$

Preparation Example 10-1

3-(2,4-Dichlorobenzyl)-2-methyl-3H-imidazo[4,5-b]pyridine-5-carbonitrile and 1-(2,4-dichlorobenzyl)-2-methyl-1H-imidazo[4,5-b]pyridine-5-carbonitrile In the same manner as in the following Preparation Example 14-2, two isomers, 3-(2,4-dichlorobenzyl)-2-methyl-3H-imidazo[4,5-b]pyridine-5-carbonitrile (138 mg) and 1-(2,4-dichlorobenzyl)-2-methyl-1H-imidazo[4,5-b]pyridine-5-carbonitrile (67 mg were respectively obtained as pale-brown crystals from 2-methyl-1H-imidazo[4,5-b]pyridine-5-carbonitrile (200 mg).

3-(2,4-Dichlorobenzyl)-2-methyl-3H-imidazo[4,5-b]pyridine-5-carbonitrile $^1$H-NMR(CDCl$_3$): 2.60(3H, s), 5.55(2H, s), 6.64(1H, d, J=8 Hz), 7.14(1H, dd, J=8, 2 Hz), 7.48(1H, br s), 7.65(1H, d, J=8 Hz), 8.09(1H, br d, J=8 Hz)

MASS(ESI): m/z 317(M+1), mp 180–182° C.

1-(2,4-Dichlorobenzyl)-2-methyl-1H-imidazo[4,5-b]pyridine-5-carbonitrile $^1$H-NMR(CDCl$_3$): 2.67(3H, br s), 5.42(2H, s), 6.46(1H, d, J=8 Hz), 7.18(1H, d, J=8 Hz), 7.49–7.60(3H, m)

MASS(ESI): m/z 317(M+1)

Preparation Example 10-2

3-(2,4-Dichlorobenzyl)-2-methyl-3H-imidazo[4,5-b]pyridine-5-carboxylic acid

To a suspension of 3-(2,4-dichlorobenzyl)-2-methyl-3H-imidazo[4,5-b]pyridine-5-carbonitrile (113 mg) in ethanol (0.6 ml) was added a 30% aqueous sodium hydroxide solution (0.3 ml), and the mixture was refluxed under heating for 12 hr. After 12 hr, a 30% aqueous sodium hydroxide solution (0.5 ml) was added and the mixture was refluxed under heating 3 hr. The reaction mixture was cooled, adjusted to pH 1 with 6N hydrochloric acid, stirred for 1 hr and adjusted to pH 4 with a saturated aqueous sodium hydrogencarbonate solution. The precipitated crystals were collected by filtration to give the objective compound (144 mg) as colorless crystals.

$^1$H-NMR(DMSO-d$_6$): 2.51(3H, s), 5.60(2H, s), 6.60(1H, d, J=8 Hz), 7.31(1H, br d, J=8 Hz), 7.76(1H, br s), 8.00(1H, d, J=8 Hz), 8.12(1H, d, J=8 Hz)

MASS(ESI): m/z 334(M−1)

mp >260° C.

Preparation Example 11-1

2-Chloro-4-phenylbenzyl alcohol

To a suspension of lithium chloride (482 mg) in anhydrous 1,4-dioxane (12 ml) were added 4-bromo-2-chlorobenzyl alcohol (1.05 g), phenyl tributyl tin (1.74 g) and tetrakis(triphenylphosphine)palladium(O) (110 mg) under a nitrogen atmosphere, and the mixture was refluxed under heating. After 5 hr, the reaction mixture was cooled and water was added. The mixture was extracted with ethyl acetate. The organic layer was washed with a saturated aqueous sodium hydrogencarbonate solution and saturated brine, and dried over anhydrous magnesium sulfate. The filtrate was concentrated, and the residue was subjected to flash silica gel column chromatography (silica gel, 50 ml, eluent: hexane-ethyl acetate=2-1). The eluate was washed with hexane to give the objective compound (220 mg) as colorless crystals.

$^1$H-NMR(CDCl$_3$): 4.72(2H, s), 7.32–7.61(8H, m)

mp 69–70° C.

Preparation Example 11-2

2-Chloro-4-phenylbenzyl alcohol

To a suspension of tetrakis(triphenylphosphine)palladium (O) (16 mg) in toluene (1 ml) was added 4bromo-2-chlorobenzyl alcohol (100 mg) at room temperature, and the mixture was stirred. After 10 min, to the reaction mixture were added a solution of phenylboric acid (83 mg) in ethanol (0.1 ml) and a 2M aqueous sodium carbonate solution (0.9 ml), and the mixture was refluxed under heating. After 1 hr, the reaction mixture was cooled, ethyl acetate was added, and the mixture was filtered through Celite. The organic layer was washed with saturated brine and dried over anhydrous magnesium sulfate. The filtrate was concentrated, and the residue was subjected to flash silica gel column chromatography (silica gel, 40 ml, eluent: hexane-ethyl acetate=3-1) to give crude crystals. The crystals were washed with hexane to give the objective compound (76 mg) as colorless crystals.

$^1$H-NMR(CDCl$_3$): 4.72(2H, s), 7.32–7.61(8H, m)
mp 69–70° C.

Preparation Example 11-3

2-Chloro-1-methanesulfonyloxymethyl-4-phenylbenzene

In the same manner as in the following Preparation Example 14-1, the objective compound (422 mg) was obtained from 2-chloro-4-phenylbenzyl alcohol (305 mg) as a colorless oil.

$^1$H-NMR(CDCl$_3$): 3.05(3H, s), 5.39(2H, s), 7.34–7.60 (7H, m), 7.66(1H, br s)

Preparation Example 11-4

3-(2-Chloro-4-phenylbenzyl)-2-methyl-3H-imidazo[4,5-b]pyridine-5-carbonitrile and 1-(2-chloro-4-phenylbenzyl)-2-methyl-1H-imidazo[4,5-b]pyridine-5-carbonitrile In the same manner as in the following Preparation Example 14-2, 3-(2-chloro-4-phenylbenzyl)-2-methyl-3H-imidazo[4,5-b]pyridine-5-carbonitrile (163 mg and 1-(2-chloro-4-phenylbenzyl)-2-methyl-1H-imidazo-[4,5-b]pyridine-5-carbonitrile (113 mg) were respectively obtained as pale-yellow crystals and pale-yellow amorphous from 2-methyl-1H-imidazo[4,5-b]pyridine-5-carbonitrile (200 mg).

3-(2-Chloro-4-phenylbenzyl)-2-methyl-3H-imidazo[4,5-b]pyridine-5-carbonitrile $^1$H-NMR(CDCl$_3$): 2.62(3H, s), 5.64(2H, s), 6.74(1H, d, J=8 Hz), 7.31–7.56(6H, m), 7.62–7.70(2H, m), 8.10(1H, br d, J=8 Hz)

MASS(ESI): m/z 359(M+1), mp 202–205° C.

1-(2-Chloro-4-phenylbenzyl)-2-methyl-1H-imidazo[4,5-b]pyridine-5-carbonitrile $^1$H-NMR(CDCl$_3$): 2.70(3H, br s), 5.52(2H, s), 6.60(1H, d, J=8 Hz), 7.31–7.60(8H, m), 7.70(1H, br d, J=1 Hz)

MASS(ESI): m/z 359(M+1)

Preparation Example 11-5

3-(2-Chloro-4-phenylbenzyl)-2-methyl-3H-imidazo[4,5-b]pyridine-5-carboxylic acid In the same manner as in Preparation Example 10-2, the objective compound (168 mg) was obtained from 3-(2-chloro-4-phenylbenzyl)-2-methyl-3H-imidazo[4,5-b]pyridine-5-carbonitrile (159 mg) as colorless crystals.

$^1$H-NMR(DMSO-d$_6$): 2.55(3H, s), 5.65(2H, s), 6.60(1H, d, J=8 Hz), 7.33–7.55(3H, m), 7.65(2H, br d, J=8 Hz), 7.85(1H, d, J=1 Hz), 8.00(1H, d, J=8 Hz), 8.11(1H, d, J=8 Hz)

MASS(ESI): m/z 376(M−1)
mp 238–243° C.

Preparation Example 12-1

3-(1-Bromonaphthalen-2-yl)methyl-2-methyl-3H-imidazo[4,5-b]pyridine-5-carbonitrile and 1-(1-bromonaphthalen-2-yl)methyl-2-methyl-H-imidazo[4,5-b]pyridine-5-carbonitrile In the same manner as in the following Preparation Example 14-2, 3-(1-bromonaphthalen-2-yl)methyl-2-methyl-3H-imidazo[4,5-b]pyridine-5-carbonitrile (139 mg) and 1-(1-bromo-naphthalen-2-yl)methyl-2-methyl-1H-imidazo[4,5-b]pyridine-5-carbonitrile (96 mg) were respectively obtained as pale-brown crystals and pale-brown amorphous from 2-methyl-1H-imidazo[4,5-b]pyridine-5-carbonitrile (200 mg).

3-(1-Bromonaphthlen-2-yl)methyl-2-methyl-3H-imidazo[4,5-b]pyridine-5-carbonitrile $^1$H-NMR(CDCl$_3$): 2.58(3H, s), 5.85(2H, s), 6.70(1H, d, J=8 Hz), 7.58(1H, br t, J=8 Hz), 7.62–7.71(3H, m), 7.81(1H, br d, J=8 Hz), 8.10(1H, d, J=8 Hz), 8.39(1H, br d, J=8 Hz)

MASS(ESI): m/z 377(M+1)
mp 215–218° C.

1-(1-Bromonaphthalen-2-yl)methyl-2-methyl-1H-imidazo[4,5-b]pyridine-5-carbonitrile $^1$H-NMR(CDCl$_3$): 2.70(3H, s), 5.69(2H, s), 6.56(1H, d, J=8 Hz), 7.49–7.74(5H, m), 7.82(1H, d, J=8 Hz), 8.37(1H, d, J=8 Hz)

MASS(ESI): m/z 377(M+1)

Preparation Example 12-2

3-(1-Bromonaphthalen-2-yl)methyl-2-methyl-3H-imidazo[4,5-b]pyridine-5-carboxylic acid In the same manner as in Preparation Example 10-2, the objective compound (235 mg) was obtained from 3-(1-bromonaphthalen-2-yl)methyl-2-methyl-3H-imidazo[4,5-b]pyridine-5-carbonitrile (138 mg) as pale-yellow crystals.

$^1$H-NMR(DMSO-d$_6$): 2.40(3H, s), 5.80(2H, s), 6.51(1H, d, J=8 Hz), 7.61(1H, br t, J=8 Hz), 7.75(1H, br t, J=8 Hz), 7.84(1H, d, J=8 Hz), 8.30(1H, d, J=8 Hz)

MASS(ESI): m/z 394(M−1)
mp >250° C.

Preparation Example 13-1

2-Methyl-3-(4-phenylbenzyl)-3H-imidazo[4,5-b]pyridine-5-carbonitrile and 2-methyl-1-(4-phenylbenzyl)-1H-imidazo[4,5-b]pyridine-5-carbonitrile In the same manner as in the following Preparation Example 14-2, 2-methyl-3-(4-phenylbenzyl)-3H-imidazo[4,5-b]pyridine-5-carbonitrile (140 mg) and 2-methyl-1-(4-phenylbenzyl)-1H-imidazo[4,5-b]pyridine-5-carbonitrile (113 mg) were respectively obtained as pale-brown crystals and pale-yellow amorphous from 2-methyl-1H-imidazo[4,5-b]pyridine-5-carbonitrile (200 mg).

2-Methyl-3-(4-phenylbenzyl)-3H-imidazo[4,5-b]pyridine-5-carbonitrile $^1$H-NMR(CDCl$_6$): 2.65(3H, s), 5.52(2H, s), 7.22–7.59 (9H, m), 7.65(1H. d, J=8 Hz), 8.05(1H. d, J=8 Hz)

MASS(ESI): m/z 325(M+1)
mp 225–226° C.

2-Methyl-1-(4-phenylbenzyl)-1H-imidazo[4,5-b]pyridine-5-carbonitrile $^1$H-NMR(CDCl$_3$):2.72(3H, br s), 5.41(2H, s), 7.10(2H. d, J=8 Hz), 7.32–7.68(9H, m)

MASS(ESI): m/z 325(M+1)

Preparation Example 13-2

2-Methyl-3-(4-phenylbenzyl)-3H-imidazo[4,5-b]pyridine-5-carboxylic acid

In the same manner as in Preparation Example 14-2, the objective compound (133 mg) was obtained as colorless crystals from 2-methyl-3-(4-phenylbenzyl)-3H-imidazo[4,5-b]pyridine-5-carbonitrile (135 mg).

$^1$H-NMR(DMSO-d$_6$): 2.58(3H, s), 5.61(2H, s), 7.30(2H, d, J=8 Hz), 7.35 (1H, d, J=8 Hz), 7.40–7.49(2H, m), 7.59–7.68(4H, m), 8.00(1H, d, J=8 Hz), 8.10(1H. d, J=8 Hz)

MASS(ESI): m/z 342(M−1)

mp >250° C.

Preparation Example 14-1

4-Bromo-2-chloro-1-methanesulfonyloxymethyl

To a solution of 4-bromo-2-chlorobenzyl alcohol (3.56 g) and anhydrous triethylamine (3 ml) in anhydrous dichloromethane (36 ml) was dropwise added methanesulfonyl chloride (1.4 ml) under a nitrogen atmosphere and ice-cooling. The reaction mixture was stirred for 1 hr, washed with water, a saturated aqueous sodium hydrogencarbonate solution and saturated brine, and dried over anhydrous magnesium sulfate. The filtrate was concentrated to give the objective compound (4.77 g) as a light brown sold.

$^1$H-NMR(CDCl$_3$): 3.03(3H, s), 5.29(2H, s), 7.37(1H, d, J=8 Hz), 7.47(1H, dd, J=8, 1 Hz), 7.60(1H, d, J=1 Hz)

MASS(ESI): m/z 298(M−1)

Preparation Example 14-2

3-(4-Bromo-2-chlorobenzyl)-2-methyl-3H-imidazo[4,5-b]pyridine-5-carbonitrile and 1-(4-bromo-2-chlorobenzyl)-2-methyl-1H-imidazo[4,5-b]pyridine-5-carbonitrile To a suspension of 2-methylimidazo[4,5-b]pyridine-5-carbonitrile (200 mg) in N,N-dimethylformamide (2 ml) was added sodium hydride (70% in mineral oil, 55 mg) under ice-cooling, and the mixture was stirred for 30 min. To this reaction mixture was added 4-bromo-2-chlorobenzyl methanesulfonate (450 mg), and the mixture was stirred for 2 hr at room temperature. The reaction mixture was poured into water and the product was extracted three times with ethyl acetate. The organic layers were combined and washed successively with water and saturated brine, dried over anhydrous magnesium sulfate and the solvent was evaporated. The residue was subjected to silica gel column chromatography (dichloromethane/ethyl acetate=5/1) to give two isomers, 3-(4-bromo-2-chlorobenzyl)-2-methyl-3H-imidazo[4,5-b]pyridine-5-carbonitrile (Rf 0.4, 233 mg) and 1-(4-bromo-2-chlorobenzyl)-2-methyl-1H-imidazo[4,5-b]pyridine-5-carbonitrile (Rf 0.1, 163 mg) as a white powder and a pale-yellow powder.

3-(4-Bromo-2-chlorobenzyl)-2-methyl-3H-imidazo[4,5-b]pyridine-5-carbonitrile $^1$H-NMR(CDCl$_3$): 2.58(3H, s), 5.52(2H, s), 6.55(1H, d, J=8 Hz), 7.27(1H, dd, J=8 and 2 Hz), 7.61(1H, d, J=2 Hz), 7.64(1H, d, J=8.06(1H, d, J=8 Hz)

Mass(ESI): m/e 359, 361 (M−H)⁻

1-(4-Bromo-2-chlorobenzyl)-2-methyl-1H-imidazo[4,5-b]pyridine-5-carbonitrile $^1$H-NMR(CDDl$_3$): 2.67(3H, s), 5.39(2H, s), 6.39(1H, d, J=8 Hz), 7.31(1H, dd, J=8 Hz), 7.31(1H, dd, J=8 and 2 Hz), 7.53(2H, s), 7.65(1H, d, J=2 Hz)

Mass(ESI): m/e 359, 361 (M−H)⁻

Preparation Example 14-3

3-(4Bromo-2-chlorobenzyl)-2-methyl-3H-imidazo[4,5-b]pyridine-5-carboxylic acid

To 3-(4-bromo-2-chlorobenzyl)-2-methyl-3H-imidazo[4,5-b]pyridine-5-carbonitrile (226 mg) was added 6N hydrochloric acid (2.5 ml) and the mixture was refluxed under heating for 1.5 hr. The reaction mixture was cooled with ice and adjusted to pH 5 with a 1N aqueous sodium hydroxide solution. The precipitate was collected by filtration. This was dried under reduced pressure to give the objective compound (226 mg) as a white powder.

$^1$H-NMR(DMSO-d$_6$): 2.51(3H, s), 5.58(2H, s), 6.52(1H, d, J=8 Hz), 7.43 (1H, dd, J=8 and 2 Hz), 7.85(1H, d, J=2 Hz), 8.00(1H, d, J=82, 8.12(1H, d, J=8 Hz)

Mass(ESI): m/e 378, 380 (M−H)⁻

Preparation Example 15-1

5-Bromo-3-(2-bromo-4-chlorobenzyl)-2-methyl-3H-imidazo[4,5-b]pyridine and 5-bromo-1-(2-bromo-4-chlorobenzyl)-2-methyl-1H-imidazo[4,5-b]pyridine In the same manner as in Preparation Example 14-2, 5-bromo-3-(2-bromo-4-chlorobenzyl-2-methyl-3H-imidazo[4,5-b]pyridine (2.30 g) and 5-bromo-1-(2-bromo-4-chlorobenzyl)-2-methyl-1H-imidazo[4,5-b]pyridine (1.32 g) were obtained as white powders from 5-bromo-2-methyl-1H-imidazo[4,5-b]pyridine (2.12 g).

5-Bromo-3-(2-bromo-4-chlorobenzyl)-2-methyl-3H-[4,5-b]pyridine $^1$H-NMR(CDCl$_3$): 2.51(3H, s), 5.49(2H, s), 6.48 (1H, d, J=8 Hz), 7.16(1H, dd, J=8 and 2 Hz), 7.43(1H, d, J=8 Hz), 7.65(1H, d, J=2 Hz), 7.89(1H, d, J=8 Hz)

Mass(ESI): m/e 414, 416, 418 (1:2:1, (M+H)⁺

5-Bromo-1-(2-bromo-4-chlorobenzyl)-2-methyl-1H-imidazo[4,5-b]pyridine $^1$H-NMR(CDCl$_3$): 2.62(3H, s), 5.34(2H, s), 6.37(1H, d, J=8 Hz), 7.19(1H, dd, J=8 and 2 Hz), 7.29(2H, s), 7.68(1H, d, J=2 Hz)

Mass(ESI): m/e 414, 416, 418 (1:2:1, (M+H)⁺

Preparation Example 15-2

3-(2-Bromo-4-chlorobenzyl)-2-methyl-3H-imidazo[4,5-b]pyridine-5-carbonitrile

In the same manner as in Preparation example 8-4, the objective compound (268 mg) was obtained as a pale-yellow powder from 5bromo-3-(2-bromo-4-chlorobenzyl)-2-methyl-3H-imidazo[4,5-b]pyridine (2.07 g).

$^1$H-NMR(CDCl$_3$): 2.59(3H, s), 5.04(2H, s), 6.51(1H, d, J=8 Hz), 7.17(1H, dd, J=8 and 2 Hz), 7.66(1H, d, J=8 Hz), 7.68(1H, d, J=2 Hz), 8.10(1H, d, J=8 Hz)

Mass(ESI): m/e 361, 363 (M+H)⁺

Preparation Example 15-3

3-(2-Bromo-4-chlorobenzyl)-2-methyl-3H-imidazo[4,5-b]pyridine-5-carboxylic acid

In the same manner as in Preparation Example 14-3, the objective compound (214 mg) was obtained as a pale-yellow powder from 3-(2-bromo-4-chlorobenzyl)-2-methyl-3H-imidazo[4,5-b]pyridine-5-carbonitrile (253 mg).

$^1$H-NMR(DMSO-d$_6$): 2.54(3H, s), 5.56(2H, s), 6.55(1H, d, J=8 Hz), 7.34(1H, dd, J=8 and 2 Hz), 7.90(1H, d, J=2 Hz), 8.04(1H, d, J=8 Hz), 8.18(1H, d, J=8 Hz)

Mass(ESI): m/e 378, 380 (M−H)⁻

Preparation Example 16-1

Methyl 2-methylindolizine-6-carboxylate

Methyl 6-methyl-3-pyridinecarboxylate (9.83 g) and bromoacetone (11.8 g) were mixed in acetone (98 ml) and the mixture was refluxed under heating for 20 hr. The solvent was evaporated under reduced pressure and the residue was dissolved in methanol (98 ml). Sodium hydrogencarbonate (16.4 g) was added and the mixture was refluxed under heating for 24 hr. The reaction mixture was concentrated under reduced pressure, water was added and the precipitate was collected by filtration. This was recrystallized from hexane-ethyl acetate to give the objective compound (5.94 g) as a pale-yellow solid.

$^1$H-NMR(CDCl$_3$): 2.31(3H, s), 3.89(3H, s), 6.29(1H, s), 7.06–7.29(3H, m), 8.63(1H, s)

Mass(ESI): m/e 190(M+H)$^+$

Preparation Example 16-2

Methyl 3-(2,4-dichlorobenzyl)-2-methylindolizine-6-carboxylate

To a suspension of anhydrous aluminum chloride (3.18 g) in dichloromethane (19 ml) was added 2,4-dichlorobenzoyl chloride (2.93 g) under ice-cooling, and the mixture was stirred for 10 min. To this solution was added methyl 2-methylindolizine-6-carboxylate (1.89 g) and the mixture was stirred for 4 hr at room temperature. The reaction mixture was slowly poured into ice water and the resulting product was extracted with ethyl acetate. The organic layer was washed successively with water, a saturated aqueous sodium hydrogencarbonate solution and saturated brine, and dried over anhydrous magnesium sulfate. The solvent was evaporated and the residue was purified by silica gel column chromatography (hexane/ethyl acetate=5/1) to give the objective compound (2.39 g) as a pale-yellow solid.

$^1$H-NMR(CDCl$_3$): 1.85(3H, s), 3.95(3H, s), 6.39(1H, s), 7.25(1H, s), 7.29(1H, d, J=8 Hz), 7.37(1H, d, J=8 Hz), 7.41–7.52(2H, m), 7.76(1H, d, J=8 Hz),

Mass(ESI): m/e 362(M−H)$^-$

Preparation Example 16-3

Methyl 3-(2,4-dichlorobenzyl)-2-methylindolizine-6-carboxylate

To a solution of methyl 3-(2,4-dichlorobenzoyl)-2-methylindolizine-6-carboxylate (2.34 g) in tetrahydrofuran (47 ml) was dropwise added a borane-dimethylsulfide complex (10.0 M, 6.5 ml) under ice-cooling. The mixture was stirred for 4 hr at room temperature. To this reaction mixture was carefully added dropwise 1N hydrochloric acid (6.5 ml) under ice-cooling, and the mixture was stirred for 30 min at room temperature. The reaction mixture was neutralized with saturated aqueous sodium hydrogencarbonate solution, and the resulting product was extracted three times with ethyl acetate. The organic layers were combined, washed with saturated brine and dried over magnesium sulfate. The solvent was evaporated and the residue was purified by silica gel column chromatography (hexane/ethyl acetate=5/1) to give the objective compound (490.4 mg) as a pale-yellow solid.

$^1$H-NMR(CDCl$_3$): 2.27(3H, s), 3.83(3H, s), 4.28(2H, s), 6.42(1H, d, J=8 Hz), 7.01(1H, dd, J=8 and 2 Hz), 7.13(1H, d, J=8 Hz), 7.24(1H, s), 7.30(1H, d, J=8 Hz), 7.44(1H, d, J=2 Hz), 8.29(1H, s)

Mass(ESI): m/e 348 (M+H)$^+$

Preparation Example 16-4

3-(2,4-Dichlorobenzyl)-2-methylindolizine-6-carboxylic acid

In the same manner as in Preparation Example 4-7, the objective compound (487 mg) was obtained as a yellow powder from methyl 3-(2,4-dichlorobenzyl)-2-methylindolizine carboxylate (460 mg).

$^1$H-NMR(DMSO-d$_6$): 2.24(3H, s), 4.38(2H, s), 6.46(1H, s), 6.58(1H, d, J=8 Hz), 7.03(1H, d, J=8 Hz), 7.27(1H, dd, J=8 and 3 Hz), 7.40(1H, d, J=8 Hz), 7.67(1H, d, J=3 Hz), 8.33(1H, s)

Preparation Example 17-1

Ethyl 3-(2,4-dichlorobenzyl)-2-ethyl-7-methyl-3H-imidazo[4,5-b]pyridine-5-carboxylate In the same manner as in Preparation Example 14-2, the objective compound (210 mg) was obtained from ethyl 2-ethyl-7-methyl-3H-imidazo[4,5-b]pyridine-5-carboxylate (300 mg).

$^1$H-NMR(CDCl$_3$): 1.36(3H, t, J=7 Hz), 1.42(3H, t, J=7 Hz), 2.73(3H, s), 2.79(2H, q, J=7 Hz), 4.45(2H, q, J=7 Hz), 5.61(2H, s), 6.55(1H, d, J=8 Hz), 7.07(1H, dd, J=8, 1 Hz), 7.45(1H, d, J=1 Hz), 7.95(1H, s)

Mass(ESI): m/e 394(M+1)

mp: 143–144° C.

Preparation Example 17-2

3-(2,4-Dichlorobenzyl)-2-ethyl-7-methyl-3H-imidazo[4,5-b]pyridine-5-carboxylic acid In the same manner as in Preparation Example 4-7, the objective compound (181 mg) was obtained from ethyl 3-(2,4-dichlorobenzyl)-2-ethyl-7-methyl-3H-[4,5-b]pyridine-5-carboxylate (200 mg).

$^1$H-NMR(CDCl$_3$): 1.40(3H, t, J=7 Hz), 2.76(3H, s), 2.87 (2H, q, J=7 Hz), 5.53(2H, s), 6.49(1H, d, J=8 Hz), 7.11(1H, br d, J=8 Hz), 7.49(1H, br s), 8.05(1H, s)

Mass(ESI): m/e 362(M−1)

mp: 214–216° C.

Preparation Example 18-1

Ethyl 2-ethyl-7-methyl-3-(4-phenylbenzyl)-3H-imidazo[4,5-b]pyridine-5-carboxylate In the same manner as in Preparation Example 14-2, the objective compound (294 mg) was obtained from ethyl 2-ethyl-7-methyl-3H-imidazo[4,5-b]pyridine-5-carboxylate (292 mg).

$^1$H-NMR(CDCl$_3$): 1.36(3H, t, J=7 Hz), 1.45(3H, t, J=7 Hz), 2.73(3H, s), 2.78(2H, q, J=7 Hz), 4.48(2H, q, J=7 Hz), 5.61(2H, s), 7.19–7.29(2H, m), 7.30–7.45(3H, m), 7.49–7.57(4H, m), 7.95(1H, s)

Mass(ESI): m/e 400(M+1)

mp: 153–154° C.

Preparation Example 18-2

2-Ethyl-7-methyl-3-(4-phenylbenzyl)-3H-imidazo[4,5-b]pyridine-5-carboxylic acid

In the same manner as in Preparation Example 4-7, the objective compound (249 mg) was obtained from ethyl 2yl-7-methyl-3-(4-phenylbenzyl)-3H-imidazo[4,5-b]pyridine-5-carboxylate (287 mg).

$^1$H-NMR(DMSO-d$_6$): 1.28(3H, t, J=7 Hz), 2.63(3H, s), 2.90(2H, q, J=7 Hz), 5.61(2H, s), 7.24(2H, d, J=8 Hz), 7.30–7.48(3H, m), 7.59–7.68(4H, m), 7.78(1H, s)

Mass(ESI): m/e 370(M−1)

mp 171–174° C.

Preparation Example 19-1

Methyl 3-(4bromo-2-chlorobenzoyl)-2-methylbenzo[b]thiophene-5-carboxylate

In the same manner as in Preparation Example 1-1, the objective compound (297 mg) was obtained as palegreen crystals from methyl 2-methylbenzo[b]-thiophene-5-carboxylate (191 mg).

$^1$H-NMR(CDCl$_3$): 2.43(3H, s), 3.92(3H, s), 7.38(1H, d, J=8 Hz), 7.56(1H, d, J=8 Hz), 7.65(1H, s), 7.80(1H, d, J=8 Hz), 8.00(1H, d, J=8 Hz), 8.49(1H, s)

Preparation Example 19-2

Methyl 3-(4-bromo-2chlorobenzyl)-2-methylbenzo[b]thiophene-5-carboxylate

In the same manner as in Preparation Example 1-2, the objective compound (271 mg) was obtained as white crystals from methyl 3-(4bromo-2-chlorobenzyl)-2-methylbenzo[b]thiophene-5-carboxylate (280 mg).

$^1$H-NMR(CDCl$_3$): 2.47(3H, s), 3.90(3H, s), 4.20(2H, s), 6.55(1H, d, J=8 Hz), 7.14(1H, dd, J=2, 8 Hz), 7.58(1H, d, J=3 Hz), 7.83(1H, d, J=8 Hz), 7.93(1H, d, J=8 Hz), 8.13(1H, s)

Preparation Example 19-3

3-(4Bromo-2-chlorobenzyl)-2-methylbenzo[b]thiophene-5-carboxylic acid

In the same manner as in Preparation Example 4-7, the objective compound (237 mg) was obtained as white crystals from methyl 3-(4-bromo-2-chlorobenzyl)-2-methylbenzo[b]thiophene-5-carboxylate (255 mg).

$^1$H-NMR(DMSO-d$_6$): 2.52(3H, s), 4.22(2H, s), 6.72(1H, d, J=8 Hz), 7.39(1H, dd, J=2, 8 Hz), 7.77(1H, s), 7.82(1H, d, J=8 Hz), 8.01(1H, s), 8.03(1H, d, J=8 Hz)

Preparation Example 20-1

Methyl 3-(2,4-dichloro-5-fluorobenzoyl)-2-methylbenzo[b]thiophene-5-carboxylate

In the same manner as in Preparation Example 16-2, the objective compound (341 mg) was obtained as pale-green crystals from methyl 2-methylbenzo[b]-thiophene-5-carboxylmethylate (200 mg).

$^1$H-NMR(CDCl$_3$): 2.47(3H, s), 3.92(3H, s), 7.32(1H, d, J=8 Hz), 7.56(1H, d, J=4 Hz), 7.82(1H, d, J=8 Hz), 8.03(1H, d, J=8 Hz), 8.51(1H, s)

Preparation Example 20-2

Methyl 3-(2,4-dichloro-5-fluorobenzyl)-2-methylbenzo[b]thiophene-5-carboxylate

In the same manner as in Preparation Example 1-2, the objective compound (307 mg) was obtained as white crystals fom methyl 3-(2,4-chloro-5-fluorobenzyl)-2-methylbenzo[b]thiophene-5-carboxylate (318 mg).

$^1$H-NMR(CDCl$_3$): 2.48(3H, s), 3.91(3H, s), 4.19(2H, s), 6.43(1H, d, J=8 Hz), 7.50(1H, dd, J=2, 7 Hz), 7.84(1H, d, J=8 Hz), 7.96(1H, dd, J=2, 8 Hz), 8.10(1H, s)

Preparation Example 20-3

3-(2,4-Dichloro-5-fluorobenzyl-2-methylbenzo[b]thiophene-5-carboxylic acid

In the same manner as in Preparation Example 4-7, the objective compound (241 mg) was obtained as white crystals from methyl 3-(2,4-dichloro-5-fluorobenzyl)-2-methylbenzo[b]thiophene-5-carboxylate (290 mg).

$^1$H-NMR(DMSO-d$_6$): 2.52(3H, s), 4.27(2H, s), 6.78(1H, d, J=9 Hz), 7.84(1H, d, J=8 Hz), 7.89(1H, d, J=7 Hz), 8.03(1H, d, J=7 Hz), 8.04(1H, s)

Preparation Example 21-1

Methyl 3-((3-chlorobenzo[b]thiophen-2-yl)carbonyl)-2-methylbenzo[b]thiophene-5-carboxylate In the same manner as in Preparation Example 16-2, the objective compound (389 mg) was obtained as pale-yellow crystals from methyl 2-methylbenzo-[b]thiophene-5-carboxylate (200 mg).

$^1$H-NMR(CDCl$_3$): 2.56(3H, s), 3.87(3H, s), 7.48–7.63 (2H, m), 7.82–8.05(4H, m), 8.37(1H, s)

Preparation Example 21-2

Methyl 3-((3-chlorobenzo[b]thiophen-2-yl)hydroxymethyl)-2-methylbenzo-[b]thiophene-5-carboxylate In the same manner as in the following Preparation Example 35-5, the objective compound (297 mg) was obtained as white crystals from methyl 3-((3-chlorobenzo-[b]thiophen-2-yl)carbonyl)-2-methylbenzo[b]thiophene-5-carboxylate (380 mg).

$^1$H-NMR(CDCl$_3$): 2.70(3H, s), 3.91(3H, s), 6.72(1H, s), 7.32–7.43(2H, m), 7.72–7.77(3H, m), 7.90(1H, d, J=8 Hz), 8.84(1H, s)

Preparation Example 21-3

Methyl 3-((3-chlorobenzo[b]thiophen-2-yl)methyl)-2-methylbenzo[b]thiophene-5-carboxylate In the same manner as in the following Preparation Example 35-6, the objective compound (266 mg) was obtained as white crystals from methyl 3-((3-chlorobenzo-[b]thiophen-2-yl)hydroxymethyl)-2-methylbenzo[b]thiophene-5-carboxylate (280 mg).

$^1$H-NMR(CDCl$_3$): 2.61(3H, s), 3.92(3H, s), 2.47(2H, s), 7.30(1H, d, J=8 Hz), 7.41(1H, t, J=8 Hz), 7.60(1H, d, J=7 Hz), 7.78–7.82(2H, m), 7.94(1H, dd, J=2, 8 Hz), 8.41(1H, s)

Preparation Example 21-4

3-((3-Chlorobenzo[b]thiophen-2-yl)methyl)-2-methylbenzo[b]thiophene-5-carboxylic acid In the same manner as in Preparation Example 4-7, the objective compound (243 mg) was obtained as white crystals from methyl 3-((3-chlorobenzo[b]thiophen-2-yl)methyl)-2-methylbenzo[b]thiophene-5-carboxylate (250 mg).

$^1$H-NMR(DMSO-d$_6$): 2.64(3H, s), 4.57(2H, s), 7.39(1H, t J=8 Hz), 7.49(1H, t J=8 Hz), 7.76(1H, d, J=7 Hz), 7.84(1H, d, J=7 Hz), 7.87(1H, d, J=7 Hz), 8.02(1H, d, J=8 Hz), 7.30(1H, s)

Preparation Example 22-1

Methyl 3-(1-bromonaphthalen-2-yl)carbonyl-2-methylbenzo[b]thiophene-5-carboxylate In the same manner as in Preparation Example 16-2, the objective compound (358 mg) was obtained as pale-green crystals from methyl 2-methylbenzo[b]thiophene-5-carboxylate (200 mg).

¹H-NMR(CDCl₃): 2.30(3H, s), 3.83(3H, s), 7.48(1H, d, J=8 Hz,) 7.62–7.72(2H, m), 7.80(1H, d, J=8 Hz), 7.90–8.03 (3H, m), 8.38(1H, d, J=8 Hz), 8.73(1H, s)

Preparation Example 22-2

Methyl 3-(1-bromonaphthalen-2-yl)methyl-2-methylbenzo[b]thiophene-5-carboxylate

In the same manner as in Preparation Example 1-2, the objective compound (331 mg) was obtained as white crystals from methyl 3-(1-bromonaphtho-2-yl)-2-methylbenzo[b]thiophene-5-carboxylate (342 mg).

¹H-NMR(CDCl₃): 2.49(3H, s), 3.85(3H, s), 4.52(2H, s), 6.84(1H, d, J=8 Hz), 7.48(1H, t, J=8 Hz), 7.55–7.63(2H, m), 7.74(1H, d, J=8 Hz), 7.83(1H, d, J=8 Hz), 7.93(1H, d, J=8 Hz), 8.23(1H, s), 8.39(1H, d, J=8 Hz)

Preparation Example 22-3

3-(1-Bromonaphthalen-2-yl)methyl-2-methylbenzo[b]thiophene-5-carboxylic acid

In the same manner as in Preparation Example 4-7, the objective compound (284 mg) was obtained as white crystals from methyl 3-(1-bromonaphthalen-2-yl)methyl-2-methylbenzo[b]thiophene-5-carboxylate (315 mg).

¹H-NMR(DMSO-d₆): 2.57(3H, s), 4.53(2H, s), 6.94(1H, d, J=8 Hz), 7.57(1H, t, J=7 Hz), 7.70(1H, t, J=7 Hz), 7.78(1H, d, J=8 Hz), 7.83(1H, d, J=8 Hz), 7.90(1H, d, J=8 Hz), 8.03(1H, d, J=8 Hz), 8.08(1H, s), 8.30(1H, d, J=8 Hz)

Preparation Example 23-1

4,5-Dibromo-2-methyl-1-(2-(trimethylsilyl)ethoxymethyl)imidazol 4,5-Dibromo-2-methylimidazol (4.91 g) was dissolved in N,N-dimethyl-formamide (50 ml) and 60% sodium hydride (901 mg) was gradually added under ice-cooling. The mixture was stirred for 1 hr at room temperature, and 2-(trimethylsilyl)ethoxymethyl chloride (3.75 g) was gradually added dropwise under ice-cooling and the mixture was stirred at room temperature overnight. The solvent was evaporated under reduced pressure and ethyl acetate was added to the residue. The residue was washed with a saturated aqueous sodium hydrogencarbonate solution, and then with brine. The organic layer was dried over anhydrous magnesium sulfate and evaporated under reduced pressure to remove the solvent. The residue was purified by silica gel column chromatography (hexane/ethyl acetate=3/1) to give the objective compound (7.6 g) as a colorless oil.

¹H-NMR(CDCl₃): 0.00(9H, s), 0.92(2H, t, J=8 Hz), 2.47 (3H, s), 3.55(2H, t, J=8 Hz), 5.24(2H, s)

Preparation Example 23-2

4-Bromo-2-methyl-1-(2-(trimethysilyl)ethoxymethyl)imidazol-5-carboxaldehyde 4,5-Dibromo-2-methyl-1-(2-(trimethylsilyl)ethoxymethyl)imidazo (29.2 g) was dissolved in tetrahydrofurane (250 ml) and a 1.63N n-butyl lithium/hexane solution (58.1 ml) was dropwise added over 20 min at −55° C. to −60° C. The mixture was stirred at −60° C. for 30 min and N,N-dimethylformamide (58 g) was dropwise added at −55° C. to −60° C., and the mixture was stirred at room temperature for 1 hr. Saturated brine was added and the mixture was extracted with ethyl acetate. The organic layer was dried over anhydrous sodium sulfate and the solvent was evaporated under reduced pressure. The residue was purified by silica gel column chromatography (hexane/ethyl acetate=3/1) to give the objective compound (18.5 g) as a pale-yellow oil.

¹H-NMR(CDCl₃): 0.00(9H, s), 0.91(2H, t, J=8 Hz), 2.52 (3H, s), 3.58(2H, t, J=8 Hz), 5.70(2H, s), 9.71(1H, s)

Preparation Example 23-3

Ethyl 2-methyl-1-(2-(trimethylsilyl)ethoxymethyl)-1H-thieno[2,3-d]imidazol-5-carboxylate 2.68 M Sodium ethylate was dissolved in ethanol (50 ml) and a solution (25 ml) of ethyl thioglycolate in ethanol was added. Thereto was added a solution (150 ml) of 4-bromo-2-methyl-1-(2-(trimethylsilyl)ethoxymethyl)imidazol-5-carboxaldehyde (3.16 g) in ethanol and the mixture was stirred at 80° C. for 2 hr. The solvent was evaporated under reduced pressure and water was added. The mixture was extracted twice with ethyl acetate. The organic layer was washed with brine and dried over anhydrous magnesium sulfate, and the solvent was evaporated under reduced pressure. The residue was obtained by silica gel column chromatograhy (hexane/ethyl acetate=9/1). Hexane was added to the purified product and crystals were collected by filtration to give the objective compound (765 mg) as pale-brown crystals.

¹H-NMR(CDCl₃): 0.00(9H, s), 0.94(2H, t, 8 Hz), 1.43 (3H, t, 8 Hz), 2.15(3H, s), 3.56(2H, t, 8 Hz), 4.40(2H, q, 8 Hz), 5.42(2H, s), 7.64(1H, s)

Preparation Example 23-4

Ethyl 2-methylthieno[2,3-d]imidazol-5-carboxylate

Ethyl 2-methyl-1-(2-(trimethylsilyl)ethoxymethyl)-1H-thieno[2,3-d]imidazol-5-carboxlate (745 mg) was dissolved in ethanol (10 ml) and 6N hydrochloric acid (10 ml) was added, which was followed by reflux under heating for 1 hr. A saturated aqueous sodium hydrogencarbonate solution was added under ice-cooling until the solution became weak alkaline, and the mixture was stirred with ethyl acetate. The organic layer was washed with a saturated aqueous sodium hydrogencarbonate solution and brine, and dried over anhydrous sodium sulfate. The solvent was evaporated under reduced pressure to give the objective compound (370 mg) as white crystals.

¹H-NMR(CDCl₃): 1.39(3H, t, 7 Hz), 2.56(3H, s), 4.36 (2H, q, 7 Hz), 7.62(1H, s)

Preparation Example 23-5

Ethyl 1-(2,4-dichlorobenzyl)-2-methyl-1H-thieno[2,3-d]imidazol-5-carboxylate and ethyl 3-(2,4-dichlorobenzyl)-2-methyl-3H-thieno[2,3-d]imidazol-5-carboxylate In the same manner as in Preparation Example 14-2, ethyl 1-(2,4-dichlorobenzyl)-2-methyl-1H-thieno[2,3-d]imidazol-5-carboxylate (340 mg) and ethyl 3-(2,4-dichlorobenzyl)-2-methyl-3H-thieno[2,3-d]imidazol-5-carboxylate (168 mg) were obtained both as white crystals from ethyl 2-methylthieno[2,3]imidazol-5-caboxylate (350 mg). The structures of the both were determined by NOE.

Ethyl 1-(2,4-dichlorobenzyl)-2-methyl-1H-thieno[2,3-d]imidazol-5-carboxylate

¹H-NMR(CDCl₃): 1.36(3H, t, 7 Hz), 2.54(3H, s, 4.32(2H, q, 8 Hz), 5.29(2H, s) 6.62(1H, d, 8 Hz), 7.17(1H, dd, 2, 8 Hz), 7.38(1H, s), 7.47(1H, d, 2 Hz)

Ethyl 3-(2,4-dichlorobenzyl)-2-methyl-3H-thieno[2,3-d]imidazol-5-carboxylate $^1$H-NMR(CDCl$_3$): 1.36(3H, t, 8 Hz), 2.60(3H, s), 4.32 (2H, q, 8 Hz), 5.23(2H, s), 6.97(1H, d, 8 Hz), 7.29(1H, dd, 2, 8 Hz), 7.47(1H, d, 2 Hz), 7.80(1H, d, 2 Hz)

Preparation Example 23-6

1-(2,4-Dichlorobenzyl)-2-methyl-1H-thieno[2,3-d]imidazol-5-carboxylic acid

In the same manner as in Preparation Example 4-7, the objective compound (151 mg) was obtained as white crystals from ethyl 1-(2,4-dichlorobenzyl)-2-methyl-1H-thieno[2,3-d]imidazol-5-carboxylate (170 mg) was obtained.

$^1$H-NMR(DMSO-d$_6$): 2.48(3H, s), 5.48(2H, s), 6.97(1H, d, 8 Hz), 7.44(1H, dd, 2, 8 Hz), 7.50(1H, s) 7.73(1H, d, 2 Hz)

Preparation Example 23-7

3-(2,4-Dichlorobenzyl)-2-methyl-3H-thieno[2,3-d]imidazol-5-carboxylic acid

In the same manner as in Preparation Example 4-7, the objective compound (112 mg) was obtained as white crystals from ethyl 3-(2,4-dichlorobenzyl)-2-methyl-3H-thieno[2,3-d]imidazol-5-carboxylate (130 mg).

$^1$H-NMR(DMSO-d$_6$): 2.57(3H, s), 5.40(2H, s), 7.50(1H, d, 8 Hz), 7.56(1H, dd, 2, 8 Hz), 7.65(1H, s), 7.77(1H, d, 2 Hz)

Preparation Example 24-1

Ethyl 6-amino-5-nitronicotinate

In the same manner as in Preparation Example 4-5, the objective compound (9.2 g) was obtained as yellow crystals from 6-amino-5-nitronicotinic acid (18.2 g).

$^1$H-NMR(CDCl$_3$): 1.41(3H, t, J=7 Hz), 4.40(2H, q, J=7 Hz), 8.95(1H, d, J=2 Hz), 9.01(1H, s).

MASS(ESI): m/z 210(M−1)

Preparation Example 24-2

Ethyl 5,6-diaminonicotinate

To a suspension of ethyl 6-amino-5-nitro-5-nicotinate (500 mg) and ammonium chloride (50 mg) in water (0.5 ml) and ethanol (4.5 ml) was added reduced iron (496 mg) at 50° C. and the mixture was refluxed under heating. Three hours later, reduced iron (200 mg) was added and the mixture was refluxed under heating for 3 hr. The reaction mixture was cooled, filtered through Celite and washed with chloroform. The filtrate was washed with water and the organic layer was dried over anhydrous magnesium sulfate, filtrated and concentrated. The residue was crystal from isopropyl ether to give the objective compound (307 mg) as red-brown crystals.

$^1$H-NMR(CDCl$_3$): 1.38(3H, t, J=7 Hz), 3.30(2H, br s), 4.32(2H, q, J=7 Hz), 4.70(2H, br s), 7.49(1H, d, J=1 Hz), 8.37(1H, d, J=1 Hz)

MASS(ESI): m/z 182(M+1)

Preparation Example 24-3

Ethyl 6-amino-5-(1-aza-2-(2,4-dichlorophenyl)vinyl)nicotinate

A mixture of ethyl 5,6-diaminonicotinate (3.17 g), benzaldehyde (4 g) and molecular sieves 4 Å (15 g) in tetrahydrofurane (60 ml) was refluxed with heating for 2 days. The reaction mixture was filtrated and the residue was concentrated and crystallized from ethyl acetate to give the objective compound (2.89 g) as yellow crystals.

$^1$H-NMR(CDCl$_3$): 1.38(3H, t, J=7 Hz), 3.30(2H, br s), 4.32(2H, q, J=7 Hz), 4.70(2H, br s), 7.49(1H, d, J=1 Hz), 8.37(1H, d, J=1 Hz)

MASS(ESI): m/z 182(M+1)

Preparation Example 24-4

Ethyl 6-amino-5-(2,4-dichlorobenzylamino)nicotinate

To a suspension of ethyl 6-amino-(1-aza-2-(2,4-dichlorophenyl)vinyl)nicotinate (2.88 g) in ethanol (30 ml) was added sodium borohydride (644 mg) at room temperature, and the mixture was stirred. Three hours later, water was added to the reaction mixture and the mixture was extracted with chloroform. The organic layer was washed with water, dried over anhydrous magnesium sulfate and filtrated. The filtrate was concentrated and the residue was crystallized from ethyl acetate to give the objective compound (1.68 g) as yellow crystals. The mother liquor was concentrated and crystallize from isopropyl ether to give the objective compound (594 mg) as yellow crystals.

$^1$H-NMR(CDCl$_3$): 1.37(3H, t, J=7 Hz), 3.49(1H, br t, J=6 Hz), 4.32(2H, q, J=7 Hz), 4.40(2H, d, J=6 Hz), 4.69(2H, br s), 7.22(1H, d, J=8 Hz), 7.31(1H, d, J=8 Hz), 7.39(1H, br s), 7.45(1H, d, J=1 Hz), 8.35(1H, d, J=1 Hz)

MASS(ESI): m/z 340(M+1)

Preparation Example 24-5

Ethyl 1-(2,4-dichlorobenzyl)-2-methyl-1H-imidazo[4,5-b]pyridine-6-carboxylate

A suspension of ethyl 6-amino-5-(2,4-dichlorobenzylamino)nicotinate (300 mg) and acetic acid (132 mg) in polphosphoric acid (6 g) was heated to 100° C. Two hours later, the reaction mixture was cooled and ice (5 g) was added. The mixture was neutralized with a saturated aqueous sodium hydrogencarbonate and extracted with dichloromethane. The organic layer was washed with water, dried over anhydrous sulfate and filtrated. The filtrate was concentrated and the residue was crystallized from isopropyl ether to give the objective compound (288 mg) as pale-brown crystals.

$^1$H-NMR(CDCl$_3$): 1.40(3H, t, J=7 Hz), 2.64(3H, s), 4.41 (2H, q, J=7 Hz), 5.41(2H, s), 6.39(1H, d, J=8 Hz), 7.11(1H, dd, J=8, 2 Hz), 7.50(1H,s), 8.12(1H, br s), 9.20(1H, d, J=2 Hz)

MASS(ESI): m/z 364(M+1)

Preparation Example 24-6

1-(2,4-Dichlorobenzyl)-2-methyl-1H-imidazo[4,5-b]pyridine-6-carboxylic acid

In the same manner as in Preparation Example 4-7, the objective compound (309 mg) was obtained as pale-brown crystals from ethyl 1-(2,4-dichlorobenzyl)-2-methyl-1H-imidazo[4,5-b]pyridine-6-carboxylate (337 mg).

$^1$H-NMR(DMSO-d$_6$): 2.57(3H, s), 5.68(2H, s), 6.68(1H, d, J=8 Hz), 7.34(1H, dd, J=8, 2 Hz), 7.74(1H,d, J=2 Hz), 8.35(1H, d, J=2 Hz), 8.91(1H, s)

MASS(ESI): m/z 334(M−1)

Preparation Example 25-1

Ethyl-2-chloro-3-pyridyl carbamate

To a mixture of 3-amino-2-chloropyridine (10 g) in a 1N aqueous sodium hydroxide solution (156 ml) and 1,4- dioxane (100 ml) was dropwise added ethyl chlorocarbonate (9 ml) at 10–20° C. under ice-cooling. The mixture was stirred at room temperature for 10 minutes. Two hours later, ethyl chlorocarbonate (4 ml) was added. At 4, 5 and 6 hours later, ethyl chlorocarbonate (4 ml) and an aqueous sodium hydroxide solution (40 ml) were added at each time. After standing the mixture overnight, water was added to the reaction mixture and the mixture was extracted with ethyl acetate. The organic layer was washed with water and saturated brine, and dried over anhydrous magnesium sulfate. The extract was concentrated and the residue was subjected to flash silica gel chromatography (silica gel 400 ml), eluent: hexane-ethyl acetate=5-1) to give the objective compound (14.8 g) as a colorless solid.

$^1$H-NMR(CDCl$_3$): 1.34(3H, t, J=7 Hz), 4.28(2H, q, J=7 Hz), 7.11(1H, br s), 7.25(1H, dd, J=8, 5 Hz), 8.08(1H, d, J=5 Hz), 8.50(1H, d, J=8 Hz)

MASS(ESI): m/z 199(M−1)

Preparation Example 25-2

Ethyl-2-(1-propyn-1-yl)-3-pyridyl carbamate

To a suspension of lithium chloride (7 g) in 1,4-dioxane (135 ml) were added ethyl-2-chloro-3-pyridylcarbamate (13.5 g), tributyl (1-propyn-1-yl)tin (22 g) and tetrakis(triphenylphosphine)palladium(O) (1.56 g), and the mixture was refluxed with heating. After 1.5 hr, the reaction mixture was cooled and water was added, which was followed by extraction with ethyl acetate. The organic layer was washed with a saturated aqueous solution of sodium hydrogencarbonate and saturated brine, and dried over anhydrous magnesium sulfate. The extract was concentrated and the residue was subjected to flash silica gel chromatography (silica gel 400 ml, eluent: hexane-ethyl acetate=2-1) to give the objective compound (10.9 g) as a pale-yellow solid.

$^1$H-NMR(CDCl$_3$): 1.36(3H, t, J=7 Hz), 2.19(3H, s), 4.25 (2H, q, J=7 Hz), 7.20(1H, dd, J=8, 5 Hz), 7.33(1H, br s), 8.20(1H, d, J=5 Hz), 8.45(1H, br d, J=8 Hz)

MASS(ESI): m/z 205(M+1)

mp 90–91° C.

Preparation Example 25-3

2-Methylpyrrolo[3,2-b]pyridine

To a solution of ethyl-2-(1-propyn-1-yl)-3-pyridyl carbamate (10.9 g) in ethanol was added a 21% solution (50 ml) of sodium ethylate in ethanol and the mixture was refluxed under heating. After 1.5 hr, the reaction mixture was cooled and water was added, which was followed by three times of extraction with dichloromethane. The organic layer was dried over anhydrous magnesium sulfate, and filtrated. The filtrate was concentrated and the residue was crystallized from ethyl acetate to give the objective compound (6.5 g) as pale-brown crystals.

$^1$H-NMR(CDCl$_3$): 2.41(3H, s), 6.23(1H, s), 6.97(1H, dd, J=8, 5 Hz), 7.60(1H, d, J=8 Hz), 8.19(1H, br d, J=5 Hz)

MASS(ESI): m/z 133(M+1)

mp 193–195° C.

Preparation Example 25-4

3-(2,4-Dichlorobenzoyl)-2-methylpyrrolo[3,2-b]pyridine

In the same manner as in Preparation Example 16-2, the objective compound (1.23 g) was obtained as a colorless solid from 2-methylpyrrolo[3,2-b]pyridine (500 mg).

$^1$H-NMR(DMSO-d$_6$): 2.75(3H, s), 7.07(1H, dd, J=8, 5 Hz), 7.38(1H, d, J=8 Hz), 7.48(1H, d, J=8 Hz), 7.65(1H, s), 7.74(1H, d, J=8 Hz), 8.14(1H, d, J=5 Hz).

MASS(ESI): m/z 303(M−1)

Preparation Example 25-5

3-((2,4-Dichlorophenyl)hydroxymethyl)-2-methylpyrrolo[3,2-b]pyridine

In the same manner as in Preparation Example 35-5 to be described later, the objective compound (850 mg) was obtained as a colorless solid from 3-(2,4-dichlorobenzoyl)-2-methylpyrrolo[3,2-b]pyridine (1.11 g).

$^1$H-NMR(DMSO-d$_6$): 2.28(3H, s), 5.69(1H, d, J=5 Hz), 6.30(1H, d, J=5 Hz), 6.98(1H, dd, J=8, 5 Hz), 7.41–7.48(2H, m), 7.58(1H, d, J=8 Hz), 8.05(1H, d, J=8 Hz), 8.20(1H, d, J=5 Hz)

MASS(ESI): m/z 307(M+1)

mp 195–197° C.

Preparation Example 25-6

3-(2,4-Dichlorobenzyl)-2-methylpyrrolo[3,2-b]pyridine

In the same manner as in Preparation Example 35-6 to be described later, the objective compound (580 mg) was obtained as a colorless solid from 3-((2,4-dichlorophenyl)hydroxymethyl)-2-methylpyrrolo[3,2-b]pyridine (840 mg).

$^1$H-NMR(DMSO-d$_6$): 2.39(3H, s), 4.18(2H, s) 6.98(1H, dd, J=8,5 Hz), 7.21–7.33(2H, m), 7.62(1H, d, J=2 Hz), 8.06(1H, br d, J=8 Hz), 8.38(1H, d, J=5 Hz)

MASS(ESI): m/z 291(M+1)

mp 228–229° C.

Preparation Example 25-7

Ethyl 3-(2,4-dichlorobenzyl)-2-methylpyrrolo[3,2-b]pyridine-1-carboxylate

In the same manner as in Preparation Example 14-2, the objective compound (405 mg) was obtained as colorless crystals from 3-(2,4-dichlorobenzyl)-2-methylpyrrolo[3,2-b]pyridine (528 mg).

$^1$H-NMR(CDCl$_3$): 1.50(3H, t, J=7 Hz), 2.58(3H, s), 4.21 (2H, s), 4.52(2H, q, J=7 Hz), 6.96(1H, d, J=8 Hz), 7.02(1H, dd, J=8, 1 Hz), 7.19(1H, dd, J=8, 5 Hz), 7.39(1H, d, J=1 Hz), 8.32(1H, d, J=8 Hz), 8.49(1H, d, J=5 Hz)

MASS(ESI): m/z 363(M+1)

mp 92–93° C.

Preparation Example 25-8

Ethyl 3-(2,4-dichlorobenzyl)-2-methylpyrrolo[3,2-b]pyridine-1-carboxylate N-oxide To a solution of ethyl 3-(2,4-dichlorobenzyl)-2-methylpyrrolo[3,2-b]pyridine-1-carboxylate (400 mg) in chloroform (6 ml) was added m-chloroperbenzoic acid (462 mg) at room temperature, and the mixture was stirred overnight. The reaction mixture was subjected to silica gel chromatography (silica gel, 40 ml, eluted with ethyl acetate and then with ethyl acetate-methanol=10-1), and crystallized from ether to give the objective compound (417 mg) as colorless crystals.

$^1$H-NMR(CDCl$_3$): 1.50(3H, t, J=7 Hz), 2.51(3H, s), 4.53 (2H, q, J=7 Hz), 4.61(2H, s), 6.96(1H, d, J=8 Hz), 7.01–7.11 (2H, m), 7.39(1H, s), 8.00–8.09(2H, m)

MASS(ESI): m/z 379(M+1)
mp 126–127° C.

Preparation Example 25-9

Ethyl 3-(2,4-dichlorobenzyl)-5-cyano-2-mehtylpyrrolo[3,2-b]pyridine-1-carboxylate To a suspension of ethyl 3-(2,4-dichlorobenzyl)-2-methylpyrrolo[3,2-b]pyridine-1-carboxylate N-oxide (414 mg) in anhydrous triethylamine (4 ml) was added trimethylsilylcyanide (704 mg) at room temperature in a nitrogen atmosphere, and the mixture was refluxed with heating overnight. The reaction mixture was cooled and a saturated aqueous sodium hydrogencarbonate solution was added. The mixture was extracted with ethyl acetate, and washed with water and saturated brine. The organic layer was dried over anhydrous magnesium sulfate. After filtration, the filtrate was concentrated, and the residue was subjected to flash silica gel chromatography (silica gel, 80 ml, eluted with hexane-ethyl acetate=5-1) and crystallized from isopropyl ether to give the objective compound (204 mg) as colorless crystals.

$^1$H-NMR(CDCl$_3$): 1.51(3H, t, J=7 Hz), 2.62(3H, s), 4.21 (2H, s), 4.55(2H, q, J=7 Hz), 7.05–7.15(2H, m), 7.58(1H, d, J=8 Hz), 8.31(1H, d, J=8 Hz)

MASS(ESI): m/z 388(M+1)
mp 112–113° C.

Preparation Example 25-10

3-(2,4-Dichlorobenzyl)-2-methylpyrrolo[3,2-b]pyridine-5-carboxylic acid

A solution of ethyl 3-(2,4-dichlorobenzyl)-5-cyano-2-methylpyrrolo[3,2-b]pyridine-1-carboxylate (180 mg) in acetic acid (1 ml) and concentrated hydrochloric acid (1 ml) was refluxed under heating. The mixture was allowed to react overnight, and concentrated hydrochloric acid (1 ml) was added, which was followed by reflux under heating for 10 hr. The reaction mixture was cooled and adjusted to pH 7 with a 30% aqueous solution of sodium hydride. After stirring for 2 hr, crystals were collected by filtration to give the object compound (135 mg) as yellow crystals.

$^1$H-NMR(DMSO-d$_6$): 2.37(3H, s), 4.19(2H, s), 7.05(1H, d, J=8 Hz), 7.23(1H, dd, J=8, 1 Hz), 7.60(1H, d, J=1 Hz), 7.85(2H, s)

MASS(ESI): m/z 333(M−1)
mp 235–236° C.

Preparation Example 26-1

5-Bromo-3-(4-chloro-2-methoxybenzyl-2-methyl-3H-imidazo[4,5-b]pyridine and 5-bromo-1-(4-chloro-2-methoxybenzyl)-2-methyl-1H-imidazo[4,5-b]pyridine In the same manner as in Preparation Example 14-2, the objective compounds of 5-bromo-3-(4-chloro-2-methoybenzyl)-2-methyl-3H-imidazo[4,5-b]pyridine (200 mg) and 5-bromo-1-(4-chloro-2-methoxybenzyl)-2-methyl-1H-imidazo[4,5-b]pyridine (138 mg) were respectively obtained as pale-yellow crystals and a pale-brown oil from 5-bromo-2-methyl-1H-imidazo[4,5-b]pyridine (305 mg).

5-Bromo-3-(4-chloro-2-methoxybenzyl)-2-methyl-3H-imidazo[4,5-b]pyridine $^1$H-NMR(CDCl$_3$): 2.69(3H, s), 3.86(3H, s), 5.41(2H, s), 6.85–6.95(3H, m), 7.45(1H, d, J=8 Hz), 7.92(1H, d, J=8 Hz)

MASS(ESI): m/z 368(M+1)
mp 149–150° C.

5-Bromo-1-(4-chloro-2-methoxybenzyl)-2-methyl-1H-imidazo[4,5-b]pyridine $^1$H-NMR(CDCl$_3$): 2.67(3H, s), 3.81(3H, s), 5.25(2H, s), 6.68(1H, d, J=8 Hz), 6.84–6.91(2H, m), 7.26(1H, d, J=8 Hz), 7.38(1H, d, J=8 Hz)

MASS(ESI): m/z 368(M+1)

Preparation Example 26-2

Methyl 3-(4-chloro-2-methoxybenzyl)-2-methyl-3H-imidazo[4,5-b]pyridine-5-carboxylate To a solution of 5-bromo-3-(4-chloro-2-methoxybenzyl)-2-methyl-3H-imidazo[4,5-b]pyridine (200 mg) in anhydrous methanol (1.8 ml) and an anhydrous N,N-dimethylformamide (2 ml) were added anhydrous triethylamine (129 mg), palladium acetate (35 mg) and 1,3-bis(diphenylphosiphino)propane (72 mg) and the mixture was placed in an autoclave. After replacing with carbon monoxide 4 times, the mixture was stirred at 85° C. and 10 atm. After 18 hr, the reaction mixture was cooled and water was added. The mixture was extracted with ethyl acetate. The organic layer was washed with water (three times) and saturated brine, then dried over anhydrous magnesium sulfate. The residue was subjected to flash silica gel chromatography (silica gel, 40 ml, eluent: dichloromethane-methanol=50-1) and crystallized from ethanol to give the objective compound (148 mg) as pale-yellow crystals.

$^1$H-NMR(CDCl$_3$): 2.70(3H, s), 3.86(3H, s), 4.00(3H, s), 5.53(2H, s), 6.81–6.90(2H, m), 6.98(1H, br d, J=8 Hz), 8.10(1H, d, J=8 Hz), 8.17(1H, d, J=8 Hz)

MASS(ESI): m/z 346(M+1), mp 166–168° C.

Preparation Example 26-3

3-(4-Chloro-2-methoxybenzyl)-2-methyl-3H-imidazo[4,5-b]pyridine-5-carboxylic acid In the same manner as in Preparation Example 4-7, the objective compound (105 mg) was obtained as colorless crystal from methyl 3-(4-chloro-2-methoxybenzyl)-2-methyl-3H-imidazo[4,5-b]pyridine-5-carboxylate (144 mg).

$^1$H-NMR(DMSO-d$_6$): 2.52(3H, s), 3.90(3H, s), 5.44(2H, s), 6.62(1H, d, J=8 Hz), 6.89(1H, dd, J=8, 1 Hz), 7.15(1H, d, J=1 Hz), 7.98(1H, d, J=8 Hz), 8.09(1H, d, J=8 Hz)

MASS(ESI): m/z 330(M−1)
mp 243–246° C.

Preparation Example 27-1

5-Bromo-3-(4-chloro-2-methylbenzyl)-2-methyl-3H-imidazo[4,5-b]pyridine and 5-bromo-1-(4-chloro-2-methylbenzyl)-2-methyl-1H-imidazo[4,5-b]pyridine In the same manner as in Preparation Example 14-2, a mixture (399 mg) of 5-bromo-3-(4-chloro-2-methylbenzyl)-2-methyl-3H-imidazo[4,5-b]pyridine and 5-bromo-1-(4-chloro-2-methylbenzyl)-2-methyl-1H-imidazo[4,5-b]pyridine was obtained as a pale-brown solid from 5-bromo-2-methyl-1H-imidazo[4,5-b]pyridine (305 mg). The isomers were used in the next reaction without separation.

Preparation Example 27-2

Methyl 3-(4-chloro-2-methylbenzyl)-2-methyl-3H-imidazo[4,5-b]pyridine-5-carboxylate and methyl 1-(4-chloro-2-methylbenzyl)-2-methyl-1H-imidazo[4,5-b]pyridine-5-carboxylate In the same manner as in Preparation Example 26-2, methyl 3-(4-chloro-2-methylbenzyl)-2-methyl-3H-imidazo

[4,5-b]pyridine-5-carboxylate (148 mg) was obtained as colorless crystals and methyl 1-(4-chloro-2-methylbenzyl)-2-methyl-1H-imidazo[4,5-b]pyridine-5-carboxylate (87 mg) as a brown powder from a mixture (390 mg) of 5-bromo-3-(4-chloro-2-methylbenzyl)-2-methyl-3H-imidazo[4,5-b]pyridine and 5-bromo-1-(4-chloro-2-methylbenzyl)-2-methyl-1H-imidazo[4,5-b]pyridine.

Methyl 3-(4-chloro-2-methylbenzyl)-2-methyl-3H-imidazo[4,5-b]pyridine-5-carboxylate $^1$H-NMR(CDCl$_3$): 2.41(3H, s), 2.56(3H, s), 4.00(3H, s), 5.53(2H, s), 6.44(1H, d, J=8 Hz), 7.03(1H, br d, J=8 Hz), 7.22(1H, br s), 8.12(1H, d, J=8 Hz), 8.19(1H, d, J=8 Hz)

MASS(ESI): m/z 330(M+1)

mp 175–176° C.

Methyl 1-(4-chloro-2-methylbenzyl)-2-methyl-1H-imidazo[4,5-b]pyridine-5-carboxylate $^1$H-NMR(CDCl$_3$): 2.38(3H, s), 2.65(3H, s), 4.01(3H, s), 5.30(2H, s), 6.48(1H, d, J=8 Hz), 7.05(1H, br d, J=8 Hz), 7.26(1H, br s), 7.48(1H, d, J=8 Hz), 8.06(1H, d, J=8 Hz)

MASS(ESI): m/z 330(M+1)

Preparation Example 27-3

3-(4-Chloro-2-methylbenzyl)-2-methyl-3H-imidazo[4,5-b]pyridine-5-carboxylic acid In the same manner as in Preparation Example 4-7, the objective compound (144 mg) was obtained as colorless crystals from methyl 3-(4-chloro-2-methylbenzyl)-2-methyl-3H-imidazo[4,5-b]pyridine-5-carboxylate (163 mg).

$^1$H-NMR(DMSO-d$_6$): 2.52(3H, s), 2.45(3H, s), 2.49(3H, s), 5.51(2H, s), 6.31(1H, d, J=8 Hz), 7.10(1H, br d, J=8 Hz), 7.37(1H, br s), 8.00(1H, d, J=8 Hz), 8.11(1H, d, J=8 Hz)

MASS(ESI): m/z 314(M−1)

mp 219–212° C.

Preparation Example 28-1

5-Bromo-3-(2-chloro-4-phenylbenzyl)-2-methyl-3H-imidazo[4,5-b]pyridine and 5-bromo-1-(2-chloro-4-phenylbenzyl)-2-methyl-1H-imidazo[4,5-b]pyridine In the same manner as in Preparation Example 14-2, 5-bromo-3-(2-chloro-4-phenylbenzyl)-2-methyl-3H-imidazo[4,5-b]pyridine (883 mg) was obtained as colorless crystals and 5-bromo-1-(2-chloro-4-phenylbenzyl)-2-methyl-1H-imidazo[4,5-b]pyridine (681 mg) as pale-yellow crystals from 5-bromo-2-methyl-1H-imidazo[4,5-b]pyridine (800 mg).

5-Bromo-3-(2-chloro-4-phenylbenzyl)-2-methyl-3H-imidazo[4,5-b]pyridine $^1$H-NMR(CDCl$_3$): 2.52(3H, s), 5.59(2H, s), 6.64(1H, br d, J=8 Hz), 7.30–7.47(5H, m), 7.49– 7.54(2H, m), 7.66(1H, br s), 7.85(1H, d, J=8 Hz)

MASS(ESI): m/z 414(M+1), mp 150–155° C.

5-Bromo-1-(2-chloro-4-phenylbenzyl)-2-methyl-1H-imidazo[4,5-b]pyridine $^1$H-NMR(CDCl$_3$): 2.67(3H, s), 5.44(2H, s), 6.57(1H, d, J=8 Hz), 7.24–7.55(8H, m), 7.69(1H, s)

MASS(ESI): m/z 414(M+1)

mp 181–185° C.

Preparation Example 28-2

Methyl 3-(2-chloro-4-phenylbenzyl)-2-methyl-3H-imidazo[4,5-b]pyridine-5-carboxylate In the same manner as in Preparation Example 26-2, the objective compound (504 mg) was obtained as pale yellow crystals from 5-bromo-3-(2-chloro-4-phenylbenzyl)-2-methyl-3H-imidazo[4,5-b]pyridine (822 mg).

$^1$H-NMR(CDCl$_3$): 2.60(3H, s), 4.00(3H, s), 5.73(2H, s), 6.71(1H, d, J=8 Hz), 7.30–7.54(6H, m), 7.67(1H, br s), 8.10(1H, d, J=8 Hz), 8.18(1H, d, J=8 Hz)

MASS(ESI): m/z 392(M+1)

mp 200–201° C.

Preparation Example 28-3

3-(2-Chloro-4-phenylbenzyl)-2-methyl-3H-imidazo[4,5-b]pyridine-5-carboxylic acid In the same manner as in Preparation Example 4-7, the objective compound (403 mg) was obtained as colorless crystals from methyl 3-(2-chloro-4-phenylbenzyl)-2-methyl-3H-imidazo[4,5-b]pyridine-5-carboxylate (500 mg).

$^1$H-NMR(DMSO-d$_6$): 2.55(3H, s), 5.65(2H, s), 6.60(1H, d, J=8 Hz), 7.33–7.55(3H, m), 7.65(2H, br d, J=8 Hz), 7.85(1H, d, J=1 Hz), 8.00(1H, d, J=8 Hz), 8.11(1H, d, J=8 Hz)

MASS(ESI): m/z 376(M−1)

mp 238–243° C.

Preparation Example 29-1

5-Bromo anisaldehyde

5-Bromosalicylaldehyde (25 g, 124 mmol) was dissolved in acetone (300 ml) and anhydrous potassium carbonate (17.2 g, 124 nmmol) was added. The mixture was heated and dimethyl sulfate (15.7 g, 124 mmol) was dropwise added over 45 min with gentle reflux. After the dropwise addition, the mixture was refluxed for 1 hr and cooled. Acetone was evaporated under reduced pressure. Toluene and water were added to the residue and the toluene layer was separated. The aqueous layer was extracted with toluene. The combined organic layer was washed with water and dried over anhydrous sodium sulfate. The desiccant was filtered off and the filtrate was concentrated under reduced pressure to give the objective compound (27.3 g, quantitative) as colorless crystals.

Preparation Example 29-2

(5-Bromo-2-methoxyphenyl)acetone

A mixture of 5-bromoanisaldehyde (19.4 g, 90 mmol), toluene (25 ml), nitroethane (8.1 g, 108 mmol) and butylamine (2.0 g, 27 mmol) was vigorously refluxed under heating while removing water generated by the reaction with a Dean-Stark distilling tube. During the reflux, N-butylamine (4.5 ml) and nitroethane (4 ml) were added in several portions and the reaction proceeded for 6 hr. Then, the reaction mixture was cooled and extracted with toluene and 3N hydrochloric acid. The organic layer was washed with saturated brine, and dried over anhydrous sodium sulfate. The desiccant was filtered off and the filtrate was concentrated under reduced pressure to give a brown oil containing 3-(2-nitropropen-1-yl)-4-methoxybromobenzene. The oil was dissolved in toluene (30 ml) and an aqueous solution (30 ml) of iron(III) chloride hexahydrate (1.0 g) was added. Thereto was added iron powder (15.1 g, 270 mmol) and the mixture was heated to 75° C. While vigorously stirring the mixture, concentrated hydrochloric acid (37.5 ml, 450 mmol) was dropwise added over 2 hr. After the dropwise addition, the mixture was stirred for 1 hr at 75° C. After cooling, the insoluble matter was filtered off and the filtrate was partitioned. The aqueous layer was extracted with toluene. The organic layers were combined, washed with 3N hydrochloric acid, and dried over anhydrous sodium sulfate. The desiccant was filtered off and the filtrate was concentrated under reduced pressure. The residue was purified by silica gel column chromatography (eluent: hexane/ethyl acetate=4/1) to give the objective compound (6.9 g, 33%) as a colorless oil.

$^1$H-NMR(CDCl$_3$, δ ppm): 7.36(1H, dd, J=2.4 and 8.7 Hz), 7.24(1H, d, J=2.4 Hz), 6.75(1H, d, J=9.0 Hz), 3.78(3H, s), 3.63(2H, s), 2.15(3H, s)

Preparation Example 29-3

5-Bromo-2-methylbenzo[b]furan (5-Bromo-2-methoxyphenyl)acetone (6.6 g, 28.6 mmol) was dissolved in methylene chloride (50 ml) and cooled to −70° C. Thereto was dropwise added a 1 M solution (28.6 ml, 28.6 mmol) of boron tribromide in methylene chloride over 15 min. After the dropwise addition, the mixture was heated to room temperature and stirred for 1.5 hr. Then, the reaction mixture was ice-cooled and water (50 ml) was added. The insoluble matter was filtered off and the filtrate was partitioned. The aqueous layer was extracted with methylene chloride. The organic layers were combined, and dried over anhydrous sodium sulfate. The desiccant was filtered off and the filtrate was concentrated under reduced pressure. The residue was purified by silica gel column chromatography (eluent: hexane/ethyl acetate=30/1) to give the objective compound (3.45 g, 57%) as a colorless liquid.

$^1$H-NMR(CDCl$_3$, δ ppm): 7.58(1H, d, J=1.8 Hz), 7.29 (1H, dd, J=1.8 and 8.6 Hz), 7.26(1H, d, J=8.3 Hz), 6.31(1H, d, J=0.7 Hz), 2.45(3H, s).

Preparation Example 29-4

5-Carboxy-2-methylbenzo[b]furan

Magnesium (2.34 g, 97 mmol) was suspended in diethyl ether and a solution of 5-bromo-2-methylbenzo[b]furan (3.4 g, 16.1 mmol) and methyl iodide (6.86 g, 48.3 mmol) in diethyl ether (50 ml) was dropwise added over about 50 min in such a manner that mild reflux could be maintained. After the dropwise addition, the mixture was refluxed under heating for 30 min and cooled in a dry ice—acetone bath. The reaction mixture was slowly added with stirring into diethyl ether containing pulverized dry ice. 2N Hydrochloric acid was added to the reaction mixture and the mixture was stirred. The partitioned organic layer was extracted with a 2N aqueous sodium hydroxide solution (100 ml). The aqueous layer was acidified with concentrated hydrochloric acid and precipitated crystals were dissolved in diethyl ether. The organic layer was washed with saturated brine, and dried over anhydrous sodium sulfate. The desiccant was filtered off and the filtrate was concentrated under reduced pressure to give the objective compound (1.9 g, 67%) colorless crystals.

$^1$H-NMR(DMSO-d$_6$, δ ppm): 8.28(1H, d, J=1.5 Hz), 8.01(1H, dd, J=1.7 and 8.5 Hz), 7.45(1H, d, J=8.6 Hz), 6.46(1H, s), 2.48(3H, s)

Preparation Example 29-5

5-(Methoxycarbonyl)-2-methylbenzo[b]furan

5-Carboxy-2-methylbenzo[b]furan (1.9 g, 10.7 mmol) was suspended in methanol (50 ml) and concentrated sulfuric acid (0.1 ml) was added, which was followed by reflux under heating for 14 hr. After cooling, a saturated aqueous sodium hydrogencarbonate solution was added. Methanol was evaporated under reduced pressure, and the residue was extracted with methyl t-butyl ether. The organic layer was washed with saturated brine, and dried over anhydrous sodium sulfate. The desiccant was filtered off and the filtrate was concentrated under reduced pressure. The residue was purified by silica gel column chromatography (eluent: hexane/ethyl acetate=9/1) to give the objective compound (1.66 g, 81%) as colorless crystals.

$^1$H-NMR(CDCl$_3$, δ ppm): 8.20(1H, d, J=1.4 Hz), 7.93 (1H, dd, J=1.5 and 8.5 Hz), 7.42(1H, d, J=8.5 Hz), 6.43(1H, d, J=1 Hz), 3.93(3H, s), 2.47(3H, d, J=0.6 Hz)

Preparation Example 29-6

3-(2,4-Dichlorobenzoyl)-5-(methoxycarbonyl)-2-methylbenzo[b]furan

Aluminum chloride (2.52 g, 18.9 mmol) was suspended in methylene chloride (25 ml) and 2,4-dichlorobenzoyl chloride (1.98 g, 9.5 mmol) was added. Then, 5-(methoxycarbonyl)-2-methylbenzo[b]furan (1.5 g, 7.9 mmol) was added and the mixture was stirred at room temperature for 1.5 hr. The reaction mixture was poured into ice water and extracted with ethyl acetate. The organic layer was washed with a saturated aqueous solution of sodium hydrogencarbonate (twice) and then saturated brine, and dried over anhydrous sodium sulfate. The desiccant was filtered off and the filtrate was concentrated under reduced pressure to give the objective compound (2.9 g, quantitative) as colorless crystals.

$^1$H-NMR(CDCl$_3$, δ ppm): 8.28(1H, d, J=1.4 Hz), 8.04 (1H, dd, J=1.5 and 8.4 Hz), 7.54(1H, d, J=1.8 Hz), 7.49(1H, dd, J=0.6 and 8.3 Hz), 7.43(1H, dd, J=1.9 and 7.9 Hz), 7.37(1H, d, J=8.1 Hz), 3.91(3H, s), 2.43(3H, s)

Preparation Example 29-7

3-((2,4-Dichlorophenyl)hydroxymethyl)-5-(methoxycarbonyl)-2-methylbenzo[b]furan 3-(2,4-Dichlorobenzoyl)-5-(methoxycarbonyl)-2-methylbenzo[b]furan (0.84 g, 2.31 mmol) was dissolved in tetrahydrofuran (20 ml) and a solution (1.0 M, 5 ml, 5 mmol) of a borane-tetrahydrofuran complex in tetrahydrofuran was added. The mixture was stirred at room temperature for 30 min and then at 50° C. for 2 hr. The reaction mixture was concentrated under reduced pressure and a saturated aqueous ammonium chloride solution was added to the residue. The mixture was extracted with ethyl acetate. The organic layer was washed with saturated brine, and dried over anhydrous magnesium sulfate. The desiccant was filtered off and the filtrate was concentrated under reduced pressure to give the objective compound (0.8 g) as a colorless oil. This crude product was used in the next reaction as it was.

$^1$H-NMR(CDCl$_3$, δ ppm): 8.27(1H, s),7.92(1H, dd, J=1.6 and 8.4 Hz), 7.86(1H, d, J=9.2 Hz), 7.39(1H, d, J=8.9 Hz), 7.36(2H, m), 6.27(1H, d, J=2.9 Hz), 3.90(3H, s), 2.46(3H, s), 2.04(1H, brs)

Preparation Example 29-8

3-(2,4-Dichlorobenzyl)-5-(methoxycarbonyl)-2-methylbenzo[b]furan

Trifluoroacetic acid (50 ml) was ice-cooled and sodium borohydride (873 mg, 23.1 mmol) was gradually added over 20 min under a nitrogen atmosphere at 5–7° C. Thereto was dropwise added a solution of 3-((2,4-dichlorophenyl) hydroxymethyl)-5-(methoxycarbonyl)-2-methylbenzo[b] furan in methylene chloride over 20 min, and the mixture was stirred at room temperature for 45 min. After the completion of the reaction, the reaction mixture was poured into ice water and a 25% aqueous sodium hydroxide solution was added to make an alkali solution. The solution was extracted with ethyl acetate. The organic layer was washed with saturated brine, and dried over anhydrous magnesium sulfate. The desiccant was filtered off and the filtrate was concentrated under reduced pressure. The crystalline residue was purified by silica gel column chromatography to give the objective compound (0.58 g, 72% in 2 steps) as colorless crystals.

$^1$H-NMR(CDCl$_3$, δ ppm): 7.98(1H, d, J=1.5 Hz), 7.95 (1H, dd, J=1.8 and 8.7 Hz), 7.43(1H, d, J=8.2 Hz), 7.42(1H, d, J=2.2 Hz), 7.10(1H, dd, J=2.2 and 8.3 Hz), 6.96(1H, d, J=8.3 Hz), 4.03(2H, s), 3.89(3H, s), 2.40(3H, s)

Preparation Example 29-9

5-Carboxy-3-(2,4-dichlorobenzyl)-2-methylbenzo[b] furan

A mixture of 3-(2,4-dichlorobenzoyl)-5-(methoxycarbonyl)-2-methylbenzo-[b]furan (0.57 g, 1.6 mmol), methanol (6 ml), tetrahydrofuran (6 ml) and a 2M aqueous sodium hydroxide solution (8.5 ml) was refluxed under heating for 40 min. The reaction mixture was concentrated under reduced pressure and water was added to the residue. The mixture was acidified with 3N hydrochloric acid and the precipitated solid was extracted with hot ethyl acetate. The organic layer was washed with saturated brine, and dried over anhydrous magnesium sulfate. The desiccant was filtered offhand the filtrate was concentrated under reduced pressure to give the objective compound (0.54 g, quantitative) as colorless crystals.

$^1$H-NMR(DMSO-d$_6$, δ ppm): 12.70(1H, brs), 7.88(1H, d, J=1.6 Hz), 7.81(1H, dd, J=1.8 and 8.7 Hz), 7.62(1H, d, J=2.1 Hz), 7.55(1H, d, J=8.8 Hz), 7.34(1H, dd, J=2.1 and 8.3 Hz), 7.25(1H, d, J=8.3 Hz), 4.09(2H, s), 2.44(3H, s).

Preparation Example 30-1

Ethyl 5-methylsalicylate

To a solution of 5-methyl salicylic acid (9.90 g) in ethanol (100 ml) was added concentrated sulfuric acid (1.0 g) and the mixture was refluxed under heating for 21 hr. The reaction mixture was concentrated to give an oil mainly containing the objective compound.

$^1$H-NMR(CDCl$_3$, δ ppm): 1.40 (3H, t, J=7.1 Hz), 2.26 (3H, s), 4.38(2H, quartet, J=7.1 Hz), 6.86(1H, d, J=8.5 Hz), 7.23(1H, dd, J=8.4 and 2.3 Hz), 7.61(1H, d, J=1.8 Hz), 10.66(1H, s)

Preparation Example 30-2

Ethyl 2-acetoxy-5-methylbenzoate

To this oil were added acetic acid (40 ml) and acetic anhydride (40 ml), and the mixture was heated at 100° C. for 20 min. After concentration, ether was added, and the mixture was washed with water and a saturated aqueous solution of sodium hydrorgencarbonate, and dried over magnesium sulfate. Concentration of the residue gave the objective compound (9.66 g) as a yellow oil.

$^1$H-NMR(CDCl$_3$, δ ppm): 1.37(3H, t, J=7.2 Hz), 2.33(3H, s), 2.38(3H, s), 4.33(2H, quartet, J=7.4 Hz), 6.98(1H, d, J=8.2 Hz), 7.34(1H, d, J=8.6 Hz), 7.82(1H, s)

Preparation Example 30-3

Ethyl 3-acetyl-5-methylsalicylate

Aluminum chloride (8.80 g) was added to a solution of ethyl 2-acetoxy-5-methylbenzoate (8.50 g) in 1,2-dichloroethane (25 ml), and the mixture was stirred at room temperature for 30 min. Ice was added to the reaction mixture and the mixture was extracted with ethyl acetate. The extract was washed with water, dried over magnesium sulfate and concentrated. The residue was purified by silica gel column chromatography to give the objective compound (2.28 g) as a white solid.

$^1$H-NMR(CDCl$_3$, δ ppm): 1.43(3H, t, J=7.2 Hz), 2.32(3H, s), 2.69(3H, s), 3.92(2H, quartet, J=7.2 Hz), 7.79(1H, s), 7.86(1H, d, J=2.3 Hz), 12.08(1H, s)

Preparation Example 30-4

2-(2,4-Dichlorobenzoyl)-7-(ethoxycarbonyl)-3,5-dimethylbenzo[b]furan

Ethyl 3-acetyl-5-methyl salicylate (2.40 g), 2,2',4'-trichloro acetophenone (2.10 g), potassium iodide (1.50 g) and potassium carbonate (2.76 g) were stirred in acetone (70 ml) at room temperature for 7 hr. Acetone (ca. 50 ml) was evaporated from the reaction mixture. Water (20 ml) was added and the precipitated solid was collected by filtration. The solid was washed with diisopropyl ether and dried to give the objective compound (0.80 g) as a white solid.

$^1$H-NMR(CDCl$_3$, δ ppm): 1.20(3H, t, J=7.2 Hz), 2.52(3H, s), 2.65(3H, s), 4.32(2H, quartet, J=7.2 Hz), 7.39(1H, d, J=8.4 Hz), 7.50(1H, s), 7.53 (1H, d, J=8.3 Hz), 7.67(1H, s), 7.99(1H, s)

Preparation Example 30-5

7-Carboxy-2-(2,4-dichlorobenzyl)-3,5-dimethylbenzo[b]furan 2-(2,4-Dichlorobenzoyl)-7-(ethoxycarbonyl)-3,5-dimethylbenzo[b]furan (0.78 g) and hydrazine monohydrate (0.70 g) were stirred in ethylene glycol (6.5 ml) at 140° C. for 2 hr. After cooling, potassium hydroroxide (0.75 g) was added and the mixture was stirred at 150° C. for 4 hr. After cooling, ice and concentrated hydrochloric acid were added and precipitate was collected by filtration. The precipitate was washed with water and diisopropyl ether and dried to give the objective compound (0.66 g) as white crystals.

$^1$H-NMR(DMSO-d$_6$, δ ppm): 2.16(3H, s), 2.42(3H, s), 4.23(2H, s), 7.27(1H, d, J=8.3 Hz), 7.38(1H, dd, J=8.3 and 2.1 Hz), 7.57 (2H, 2s), 7.63(1H, d, J=2.1 Hz)

Preparation Example 31-1

5-(Methoxycarbonyl)-2-methylbenzo[b]furan

Methyl 4-hydroxybenzoate (25.51 g), 2,3-dichloropropene (22.33 g) and potassium carbonate (27.65 g) were heated in 2-butanone (150 ml) at 70° C. for 20 hr. The reaction mixture was concentrated, and water was added, which was followed by extraction with toluene. The extract was washed with saturated brine and concentrated. To the concentrate (34.5 g) was added diethyl aniline (100 ml) and the mixture was stirred at 200° C. for 89 hr. After cooing, toluene and concentrated hydrochloric acid were added and the toluene layer was washed with saturated brine, and dried over sodium sulfate. After concentration, formic acid (80 ml) was added to the residue (34.5 g) and the mixture was refluxed for 25 hr. After concentration, ethyl acetate and water were added. The separated toluene layer was washed with a saturated aqueous solution of sodium hydrogencarbonate, dried over magnesium sulfate and concentrated. The residue was purified by silica gel column chromatography to give the objective compound (3.30 g).

$^1$H-NMR(CDCl$_3$, δ ppm): 2.47(3H, s), 3.93(3H, s), 6.44 (1H, s), 7.41 (1H, d, J=8.8 Hz), 7.94(1H, dd, J=8.6 and 1.7 Hz), 8.20(1H, d, J=1.6 Hz)

Preparation Example 31-2

5-(Methoxycarbonyl)-2-methyl-3-(4-phenylbenzoyl) benzo[b]furan

Aluminum chloride (0.80 g) was stirred in methylene chloride (10 ml) at room temperature. Thereto was added 4-phenylbenzoyl chlodide (0.67 g), and then a solution of 5-(methoxycarbonyl)-2-methylbenzo[b]furan (0.67 g) in methylene chloride (5 ml), and the mixture was stirred for 4 hr. Ice was added to the reaction mixture and the mixture was extracted with ethyl acetate. The extract was washed with a saturated aqueous solution of sodium hydrogencarbonate (twice) and saturated brine (once), dried over sodium sulfate and concentrated to give the objective compound (1.36 g).

$^1$H-NMR(CDCl$_3$, δ ppm): 2.58(3H, s), 3.88(3H, s), 7.39–8.28(12H, m)

Preparation Example 31-3

5-(Methoxycarbonyl)-2-methyl-3-(4-phenylbenzyl) benzo[b]furan

While a 1 M borane-tetrahydrofuran solution (8 ml) was stirred at room temperature, a solution of 5-(methoxycarbonyl)-2-methyl-3-(4-phenylbenzoyl)-benzo [b]furan (1.36 g) in tetrahydrofuran (20 ml) was dropwise added thereto over 20 min, which was followed by stirring at 50° C. for 50 min. After cooling, ethyl acetate and a 10% aqueous solution of ammonium chloride were added and the separated organic layer was dried over sodium sulfate and concentrated.

In a different container, sodium borohydride (1.51 g) was added to trifluoroacetic acid (50 ml) over 10 min under cooling in an ice water bath. Then, a solution of the residue (1.51 g) after the above-mentioned concentration in methylene chloride (20 ml) was dropwise added over 40 min. After the dropwise addition, the bath was removed and the reaction mixture was stirred at room temperature for 15 min. Ethyl acetate and a 10% aqueous sodium hydroxide solution were added to the reaction mixture and the separated ethyl acetate layer was washed with a 10% aqueous solution of sodium hydroxide to basify the solution. The solution was dried over sodium sulfate and concentrated to give the objective compound (1.31 g).

$^1$H-NMR(CDCl$_3$, δ ppm): 2.46(3H, s), 3.89(3H, s), 4.04 (2H, s), 7.22–7.58(10H, m), 7.94(1H, d, J=8.6 Hz), 8.09(1H, s)

Preparation Example 31-4

5-Carboxy-2-methyl-3-(4-phenylbenzyl)benzo[b] furan 5-(Methoxycarbonyl)-2-methyl-3-(4-phenylbenzyl)benzo [b]furan (1.31 g) was refluxed for 1 hr in a mixed solution of a 10% aqueous solution (10 ml) of sodium hydroxide, methanol (10 ml) and tetrahydrofuran (10 ml). The reaction mixture was concentrated and concentrated hydrochloric acid was added to acidify the solution. The precipitated solid was collected by filtration, washed with water and diisopropyl ether and dried to give the objective compound (0.68 g).

$^1$H-NMR(DMSO-d$_6$, δ ppm): 2.52(3H, s), 4.07(2H, s), 7.29–7.36(3H, m), 7.42 (2H, t, J=7.8 Hz), 7.53–7.63(5H, m), 7.81(1H, d, J=8.6 Hz), 7.99(1H, s)

Preparation Example 32-1

2-Acetyl-5-bromobenzo[b]furan

5-Bromo salicylaldehyde (10.05 g), bromo acetone (8.0 g) and potassium carbonate (13.80 g) were refluxed for 1 hr in 2-butanone (100 ml). 2-Butanone (ca. 50 ml) was evaporated and ice was added. The precipitate was collected by filtration and washed with water and hexane to give the objective compound (10.50 g).

$^1$H-NMR(CDCl$_3$, δ ppm): 2.62(3H, s), 7.44(1H, s), 7.47 (1H, d, J=8.9 Hz), 7.57(1H, dd, J=8.9 and 2.0 Hz), 7.86(1H, d, J=2.0 Hz)

Preparation Example 32-2

5-Bromo-2-ethylbenzo[b]furan

2-Acetyl-5-bromobenzo[b]furan (10.00 g) and hydrazine monohydrate (8.00 g) were stirred in ethylene glycol (60 ml) at 150° C. for 2 hr. After cooling, potassium hydroxide (9.00 g) was added and the mixture was stirred at 150° C. for 2 hr. After cooling, toluene (200 ml) and water (100 ml) were added and the separated toluene layer was washed with 10% aqueous solution (100 ml) of ammonium chloride, dried over magnesium sulfate and concentrated to give the objective compound (8.30 g).

$^1$H-NMR(CDCl$_3$, δ ppm): 1.33(3H, t, J=7.5 Hz), 2.79(2H, quartet, J=7.5 Hz), 6.32(1H, s), 7.24–7.31(2H, m), 7.59(1H, d, J=1.8 Hz)

Preparation Example 32-3

5-Carboxy-2-ethylbenzo[b]furan

Magnesium (1.50 g) was stirred in ether (30 ml) at room temperature. Thereto was dropwise added a solution of 5-bromo-2-ethylbenzo[b]furan (8.30 g) and methyl iodide (0.55 g) in ether (30 ml) over 30 min. Then, the mixture was refluxed for 50 min and cooled in an ice water bath. In a different container, pulverized dry ice was stirred in ether and the Grignard reagent prepared above was transferred over about 5 min. 2N Hydrochloric acid was added to the reaction mixture to acidify the solution, and the ether layer was separated. The solution was basified with a 5% aqueous solution of sodium hydroxide and the separated aqueous layer was acidified with 2N hydrochloric acid. After extraction with ether, the extract was dried over sodium sulfate and concentrated to give the objective compound (2.48 g).

$^1$H-NMR(DMSO-d$_6$, δ ppm): 1.26(3H, t, J=7.6 Hz), 2.80 (2H, quartet, J=7.5 Hz), 6.69(1H, s), 7.56(1H, dd, J=8.6 Hz), 7.83(1H, dd, J=8.6 and 1.8 Hz), 8.16(1H, d, J=1.7 Hz), 12.73(1H, s)

Preparation Example 32-4

2-Ethyl-5-(methoxycarbonyl)benzo[b]furan

5-Carboxy-2-ethylbenzo[b]furan (2.48 g) and concentrated sulfuric acid (0.30 g) were stirred with heating in methanol (50 ml) at 60° C. for 16 hr. The reaction mixture was concentrated and chloroform mixture was added. The mixture was washed with a saturated aqueous solution of sodium hydrogencarbonate. The chloroform layer was separated, dried over magnesium sulfate and concentrated to give the objective compound (2.40 g).

$^1$H-NMR(CDCl$_3$, δ ppm): 1.35(3H, t, J=7.6 Hz), 2.82(2H, quartet., J=7.6 Hz), 3.93(3H, s), 6.44(1H, s), 7.42(1H, dd, J=8.8 Hz), 7.94(1H, dd, J=8.6 and 1.8 Hz), 8.22(1H, d, J=1.6 Hz)

Preparation Example 32-5

3-(2,4-Dichlorobenzoyl)-2-ethyl-5-(methoxycarbonyl)benzo[b]furan

In the same manner as in Preparation Example 31-2, the objective compound (2.28 g) was obtained from 2-ethyl-5-(methoxycarbonyl)benzo[b]furan (2.40 g), aluminum chloride (3.33 g) and 2,4-dichlorobenzoyl chloride (2.80 g).

$^1$H-NMR(CDCl$_3$, δ ppm): 1.30(3H, t, J=7.6 Hz), 2.79(2H, quartet, J=7.5 Hz), 3.91(3H, s), 7.38(1H, d, J=8.2 Hz), 7.42(1H, dd, J=8.1 and 1.9 Hz), 7.50(1H, d, J=8.8 Hz), 7.54(1H, d, J=1.8 Hz), 8.05(1H, dd, J=8.6 and 1.8 Hz), 8.18(1H, d, J=1.8 Hz)

Preparation Example 32-6

3-(2,4-Dichlorobenzyl)-2-ethyl-5-(methoxycarbonyl)benzo[b]furan

In the same manner as in Preparation Example 31-3, the objective compound (2.20 g) was obtained from 3-(2,4-dichlorobenzoyl)-2-ethyl-5-(methoxycarbonyl)benzo[b]furan (2.28 g).

$^1$H-NMR(CDCl$_3$, δ ppm): 1.28(3H, t, J=7.6 Hz), 2.76(2H, quartet, J=7.6 Hz), 3.90(3H, s), 4.04(2H, s), 6.92(1H, d, J=8.4 Hz), 7.09 (1H, dd, J=8.4 and 2.2 Hz), 7.42–7.46(2H, m), 7.96(1H, dd, J=8.6 and 1.7 Hz), 7.98(1H, d, J=1.5 Hz)

Preparation Example 32-7

5-Carboxy-3-(2,4-dichlorobenzyl)-2-ethylbenzo[b]furan

In the same manner as in Preparation Example 31-4, the objective compound (1.50 g) was obtained from 3-(2,4-dichlorobenzyl)-2-ethyl-5-(methoxycarbonyl)benzo[b]furan (2.20 g).

$^1$H-NMR(DMSO-d$_6$, δ ppm): 1.20(3H, t, J=7.5 Hz), 2.81 (2H, quartet, J=7.5 Hz), 4.11(2H, s), 7.20(1H, d, J=8.4 Hz), 7.34 (1H, dd, J=8.3 and 2.2 Hz), 7.58 (1H, d, J=8.5 Hz), 7.63(1H, d, J=2.2 Hz), 7.83(1H, dd, J=8.6 and 1.7 Hz), 7.89(1H, d, J=1.6 Hz), 12.78(1H, brs)

Preparation Example 33-1

5-Bromo-2-propionylbenzo[b]furan

In the same manner as in Preparation Example 32-1, the objective compound (7.10 g) was obtained from 5-bromo salicylaldehyde (5.50 g), 1-bromo-2-butanone (5.00 g) and potassium carbonate (8.00 g).

$^1$H-NMR(CDCl$_3$, δ ppm): 1.26(3H, t, J=7.3 Hz), 3.00(2H, quartet, J=7.3 Hz), 7.42(1H, s), 7.46(1H, d, J=8.9 Hz), 7.56(1H, dd, J=8.8 and 2.0 Hz), 7.84(1H, d, J=2.0 Hz)

Preparation Example 33-2

5-Bromo-2-propylbenzo[b]furan

In the same manner as in Preparation Example 32-2, the objective compound (5.85 g) was obtained from 5-bromo-2-propylbenzo[b]furan (7.00 g), hydrazine monohydrate (5.00 g) and potassium hydroxide (6.00 g).

$^1$H-NMR(CDCl$_3$, δ ppm): 1.01(3H, t, J=7.4 Hz), 1.72–1.81(2H, m), 2.73(2H, t, J=7.3 Hz), 6.32(1H, s), 7.25–7.30(2H, m), 7.59(1H, d, J=1.8 Hz)

Preparation Example 33-3

5-Carboxy-2-propylbenzo[b]furan

In the same manner as in Preparation Example 32-3, the objective compound (3.01 g) was obtained from 5-bromo-2-propylbenzo[b]furan (5.85 g), methyl iodide (10.0 g), magnesium (2.67 g) and dry ice.

$^1$H-NMR(DMSO-d$_6$, δ ppm): 0.95(3H, t, J=7.4 Hz), 1.67–1.75(2H, m), 2.76(2H, t, J=7.4 Hz), 6.70(1H, d, J=0.70 Hz), 7.56(1H, d, J=8.5 Hz), 7.83(1H, dd, J=8.6 and 1.7 Hz), 8.15(1H, d, J=1.5 Hz)

Preparation Example 33-4

5-(Methoxycarbonyl)-2-propylbenzo[b]furan

In the same manner as in Preparation Example 32-4, the objective compound (3.22 g) was obtained from 5-carboxy-2-propylbenzo[b]furan (3.00 g).

$^1$H-NMR(CDCl$_3$, δ ppm): 1.02(3H, t, J=7.4 Hz), 1.76–1.81(2H, m), 2.76(2H, t, J=7.5 Hz), 3.93(3H, s), 6.44 (1H, s), 7.42(1H, dd, J=8.2 Hz), 7.94(1H, dd, J=8.6 and 1.7 Hz), 8.21(1H, s).

Preparation Example 33-5

3-(2,4-Dichlorobenzoyl)-5-(methoxycarbonyl)-2-propylbenzo[b]furan

In the same manner as in Preparation Example 31-2, the objective compound (4.29 g) was obtained from 5-(methoxycarbonyl)-2-propylbenzo[b]furan (3.20 g), aluminum chloride (4.00 g) and 2,4-dichlorobenzoyl chloride (3.84 g).

$^1$H-NMR(CDCl$_3$, δ ppm): 0.91(3H, t, J=7.4 Hz), 1.72–1.80(2H, m), 2.76(2H, t, J=7.5 Hz), 3.91(3H, s), 7.38 (1H, d, J=8.1 Hz), 7.42(1H, dd, J=8.2 and 1.9 Hz), 7.50(1H, d, J=8.3 Hz), 7.54(1H, d, J=2.0 Hz), 8.04(1H, dd, J=8.7 and 1.8 Hz), 8.15(1H, d, J=1.9 Hz)

Preparation Example 33-6

3-(2,4-Dichlorobenzyl)-5-(methoxycarbonyl)-2-propylbenzo[b]furan

In the same manner as in Preparation Example 31-3, the objective compound (2.27 g) was obtained from 3-(2,4-dichlorobenzoyl)-5-(methoxycarbonyl)-2-propylbenzo[b]furan (2.42 g).

$^1$H-NMR(CDCl$_3$, δ ppm): 0.94(3H, t, J=7.4 Hz), 1.69–1.77(2H, m), 2.71(2H, t, J=7.5 Hz), 3.89(3H, s), 4.04 (2H, s), 6.91(1H, d, J=8.4 Hz), 7.08 (1H, dd, J=8.3 and 2.1 Hz), 7.43–7.46(2H, m), 7.94–7.98(2H, m)

Preparation Example 33-7

5-Carboxy-3-(2,4-dichlorobenzyl)-2-propylbenzo[b]furan

In the same manner as in Preparation Example 31-4, the objective compound (2.04 g) was obtained from 3-(2,4-dichlorobenzyl)-5-(methoxycarbonyl)-2-propylbenzo[b]furan (2.25 g).

¹H-NMR(DMSO-d₆, δ ppm) 0.87(3H, t, J=7.4 Hz), 1.60–1.68(2H, m), 2.76(2H, t, J=7.4 Hz), 4.11(2H, s), 7.18 (1H, d, J=8.4 Hz), 7.34 (1H, dd, J=8.3 and 2.2 Hz), 7.58 (1H, d, J=8.7 Hz), 7.63(1H, d, J=2.1 Hz), 7.83(1H, dd, J=8.6 and 1.7 Hz), 7.89(1H, d, J=1.6 Hz), 12.75(1H, brs).

Preparation Example 34-1

Methyl 4-((2,2-dimethoxy)ethoxy)benzoate

Methyl 4-hydroxybenzoate (15.52 g), bromoacetaldehyde dimethyl acetal (16.90 g) and 60% sodium hydride (5.00 g) were heated in dimethyl formamide (50 ml) at 80° C. for 18 hr. Dimethyl formamide was distilled away from the reaction mixture, and toluene and water were added. The separated toluene layer was dried over magnesium sulfate, and the solvent was distilled away to give the objective compound (16.00 g).

¹H-NMR(CDCl₃, δ ppm): 3.47(6H, s), 3.89(3H, s), 4.06 (1H, d, J=5.3 Hz), 4.73(1H, d, J=5.2 Hz), 6.94(2H, d, J=8.9 Hz), 7.99(2H, d, J=8.9 Hz)

Preparation Example 34-2

5-(Methoxycarbonyl)benzo[b]furan

Methyl 4-((2,2-dimethoxy)ethoxy)benzoate (10.00 g) and polyphosphoric acid (20.00 g) were refluxed in 1,2-dichloroethane (50 ml) for 1 hr. After cooling, ice was added, and the separated organic layer was washed with 10% hydrochloric acid. The mixture was dried over magnesium sulfate, concentrated and purified by column chromatography to give the objective compound (0.86 g).

¹H-NMR(CDCl₃, δ ppm): 3.94(3H, s), 6.85(1H, dd, J=2.4 and 0.8 Hz), 7.53(1H, d, J=8.6 Hz), 7.69(1H, d, J=2.2 Hz), 8.03(1H, dd, J=8.7 and 1.7 Hz), 8.35(1H, d, J=1.7 Hz)

Preparation Example 34-3

3-(2,4-Dichlorobenzoyl)-5-(methoxycarbonyl)-2-propylbenzo[b]furan

In the same manner as in Preparation Example 31-2, the objective compound (0.34 g) was obtained from 5-(methoxycarbonyl)benzo[b]furan (0.85 g), aluminum chloride (1.11 g) and 2,4-dichlorobenzoyl chloride (1.00 g).

¹H-NMR(CDCl₃, δ ppm): 3.96(3H, s), 7.38(1H, dd, J=8.3 and 1.9 Hz), 7.46(1H, d, J=8.2 Hz), 7.50(1H, d, J=2.0 Hz), 7.57(1H, d, J=8.9 Hz), 7.94(1H, s), 8.13(1H, dd, J=8.7 and 1.8 Hz), 8.94(1H, d, J=1.4 Hz)

Preparation Example 34-4

3-(2,4-Dichlorobenzyl)-5-(methoxycarbonyl)benzo[b]furan

In the same manner as in Preparation Example 16-2, the objective compound (0.28 g) was obtained from 3-(2,4-dichlorobenzoyl)-5-(methoxycarbonyl)benzo[b]furan(0.34 g).

¹H-NMR(CDCl₃, δ ppm): 3.93(3H, s), 4.11(2H, s), 7.13–7.18(2H, m), 7.41 (1H, s), 7.50(1H, d, J=8.8 Hz), 8.03(1H, dd, J=8.7 and 1.8 Hz), 8.21(1H, d, J=1.7 Hz).

Preparation Example 34-5

5-Carboxy-3-(2,4-dichlorobenzyl)benzo[b]furan

In the same manner as in Preparation Example 35-5 to be mentioned below, the objective compound (0.26 g) was obtained from 3-(2,4-dichlorobenzyl)-5-(methoxycarbonyl)benzo[b]furan (0.28 g).

¹H-NMR(CDCl₃, δ ppm): 4.13(2H, s), 7.17–7.18(2H, m), 7.43–7.55 (2H, m), 7.54(1H, d, J=8.8 Hz), 8.10(1H, dd, J=8.7 and 1.7 Hz), 8.30(1H, d, J=1.6 Hz).

Preparation Example 35-1

5-Bromo-2-methylbenzo[b]thiophene

4-Bromobenzenethiol (10.0 g, 52.8 mmol) was dissolved in acetone (100 ml), and anhydrous potassium carbonate (8.8 g, 63 mmol), and 2,3-dichloropropene (7.0 g, 63 mmol) were added. The mixture was stirred at room temperature for 14 hr. Acetone was distilled away under reduced pressure and toluene and water were added to the residue. The toluene layer was separated. The organic layer was washed with water, and dried over anhydrous sodium sulfate. The desiccant was filtered away and the filtrate was concentrated under reduced pressure to give a pale-yellow oil (13.9 g). This oil was dissolved in diethyl aniline (45 ml), and the mixture was stirred at 205° C. for 50 hr with heating. Diethyl aniline was distilled away under reduced pressure, and 3N hydrochloric acid and toluene were added to the residue. After the toluene layer was separated, the organic layer was dried over anhydrous sodium sulfate. The desiccant was filtered off, and the filtrate was concentrated under reduced pressure. The residual crystalline oil was dissolved in hexane, and the insoluble oil was removed by decantation. After concentration under reduced pressure, the residue was recrystallized from a small amount of hot hexane to give the objective compound (5.9 g, 58%) as colorless crystals.

¹H-NMR(CDCl₃, δ ppm): 7.77(1H, d, J=1.9 Hz), 7.58 (1H, d, J=8.4 Hz), 7.33(1H, dd, J=1.9 8.4 Hz), 6.90(1H, s), 2.58(1H, d, J=1.0 Hz)

Preparation Example 35-2

5-Carboxy-2-methylbenzo[b]thiophene

Magnesium (1.93 g, 79 mmol) was dispersed in diethyl ether, and diethyl ether (50 ml) solution of 5-bromo-2-methylbenzo[b]thiophene (3.0 g, 13.2 mmol) and methyl iodide (5.62 g, 40 mmol) was added dropwise thereto over about 30 min in such a manner that mild refluxing could be maintained. After the completion of the addition, the mixture was refluxed under heating for about 50 min, and the reaction mixture was cooled with ice. The reaction mixture was gradually added with stirring to diethyl ether containing pulverized dry ice. The reaction mixture containing oil was extracted with 2N hydrochloric acid, and the organic layer was extracted with 1M aqueous sodium hydroxide solution. The aqueous layer was acidified with 3M hydrochloric acid, and the precipitated crystals were extracted with diethyl ether. The organic layer was washed with saturated brine and dried over anhydrous magnesium sulfate. The desiccant was filtered off, and the filtrate was concentrated under reduced pressure to give the objective compound (2.1 g, 82%) as colorless crystals.

¹H-NMR(DMSO-d₆, δ ppm): 12.84(1H, brs), 8.30(1H, d, J=1.3 Hz), 7.96(1H, d, J=8.4 Hz), 7.80(1H, dd, J=1.6 and 8.4 Hz), 7.26(1H, s), 2.57(1H, d, J=1.1 Hz)

Preparation Example 35-3

5-(Methoxycarbonyl)-2-methylbenzo[b]thiophene

5-Carboxy-2-methylbenzo[b]thiophene (2.1 g, 10.9 mmol) was dispersed in methanol (50 ml), and concentrated sulfuric acid was added. The mixture was refluxed with heating for 6 hr. After cooling, a saturated aqueous solution of sodium hydrogencarbonate was added, and methanol was distilled away under reduced pressure. The residue was extracted with methyl t-butyl ether. The organic layer was washed with saturated brine, and dried over anhydrous sodium sulfate. The desiccant was filtered off, and the filtrate was concentrated under reduced pressure to give the objective compound (2.0 g, 89%) as colorless crystals.

$^1$H-NMR(CDCl$_3$, δ ppm): 8.35(1H, d, J=1.5 Hz), 7.91 (1H, dd, J=1.5 and 8.4 Hz), 7.78(1H, d, J=8.4 Hz), 7.04(1H, m), 3.94(3H, s), 2.60(3H, d, J=1.2 Hz)

Preparation Example 35-4

3-(2,4-Dichlorobenzoyl)-5-(methoxycarbonyl)-2-methylbenzo[b]thiophene

Aluminum chloride (1.24 g, 9.3 mmol) was dispersed in methylene chloride (10 ml), and 2,4-dichlorobenzoyl chloride (0.97 g, 4.7 mmol) and then 5-(methoxycarbonyl)-2-methylbenzo[b]thiophene(0.8 g, 3.9 mml) were added thereto. The mixture was stirred at room temperature for 4 hr. The reaction mixture was poured into ice water and ethyl acetate was added. The mixture was extracted. The organic layer was washed twice with a saturated aqueous solution of sodium hydrogencarbonate and once with brine, and dried over anhydrous sodium sulfate. The desiccant was filtered off, and the filtrate was concentrated under reduced pressure to give the objective compound (1.5 g, quantitative) as pale yellow crystals.

$^1$H-NMR(DMSO-d$_6$, δ ppm): 8.49(1H, d, J=1.3 Hz), 8.00(1H, dd, J=1.4 and 8.4 Hz), 7.81(1H, d, J=8.4 Hz), 7.49(1H, d, J=1.8 Hz), 7.47(1H, d, J=8.3 Hz), 7.40(1H, dd, J=1.9 and 8.3 Hz), 3.90(3H, s), 2.43(3H, s)

Preparation Example 35-5

3-((2,4-Dichlorophenyl)hydroxymethyl)-5-(methoxycarbonyl)-2-methylbenzo[b]thiophene 3-(2,4-Dichlorobenzoyl)-5-(methoxycarbonyl)-2-methylbenzo[b]-thiophene (600 mg, 1.58 mmol) was dissolved in a mixed solvent of tetrahydrofuran (10 ml) and methanol (1 ml), and sodium borohydride (72 mg, 1.9 mmol) was added thereto under ice-cooling. The mixture was stirred for 40 min under ice-cooling. Water was added to the reaction mixture, and the mixture was extracted with ethyl acetate. The organic layer was washed with saturated brine, and dried over anhydrous magnesium sulfate. The desiccant was filtered off, and the filtrate was concentrated under reduced pressure to give the objective compound (580 mg, 96%) as colorless crystals.

$^1$H-NMR(CDCl$_3$, δ ppm): 8.46(1H, d, J=1.3 Hz), 7.90 (1H, dd, J=1.5 and 8.4 Hz), 7.77(1H, d, J=8.4 Hz), 7.70(1H, d, J=8.4 Hz), 7.37(1H, d, J=2.1 Hz), 7.29(1H, dd, J=2.1 and 8.4 Hz), 6.44(1H, d, J=2.8 Hz), 3.90(3H, s), 2.52(3H, s), 2.04(1H, brs)

Preparation Example 35-6

3-(2,4-Dichlorobenzyl)-5-(methoxycarbonyl)-2-methylbenzo[b]thiophene

Trifluoroacetic acid (30 ml) was cooled with ice, and sodium borohydride (537 mg, 14.2 mmol) was gradually added at 5–7° C. for 20 min under a nitrogen atmosphere. A solution of 3-((2,4-dichlorophenyl)hydroxymethyl)-5-(methoxycarbonyl)-2-methylbenzo[b]thiophene in methylene chloride was added dropwise for 50 min and the mixture was stirred at room temperature for 70 min. After the completion of the reaction, the reaction mixture was poured into ice water, and trifluoroacetic acid was neutralized with 25% aqueous solution of sodium hydroxide to make the solution alkaline. The solution was extracted with ethyl acetate, and the organic layer was washed with saturated brine and dried over anhydrous magnesium sulfate. The desiccant was filtered off, and the filtrate was concentrated under reduced pressure to give the objective compound (0.52 g) as colorless crystals.

$^1$H-NMR(CDCl$_3$, δ ppm): 8.13(1H, d, J=1.4 Hz), 7.94 (1H, dd, J=1.5 and 8.3 Hz), 7.83(1H, d, J=8.3 Hz), 7.44(1H, d, J=2.2 Hz), 7.01(1H, dd, J=2.1 and 8.3 Hz), 6.61(1H, J=8.3 Hz), 4.20(2H, s), 3.90(3H, s). 2.46(3H, s)

Preparation Example 35-7

5-Carboxy-3-(2,4-dichlorobenzyl)-2-methylbenzo[b]thiophene

A mixture of 3-(2,4-Dichlorobenzyl)-5-(methoxycarbonyl)-2-methylbenzo-[b]thiophene (0.52 g, 1.42 mmol), methanol (5 ml), tetrahydrofuran (5 ml) and 2 ml aqueous sodium hydroxide solution (7 ml) was refluxed under heating for 1 hr. The reaction mixture was concentrated under reduced pressure, and water was added to the residue. Then, the mixture was acidified with 3N hydrochloric acid and the precipitate was extracted from hot ethyl acetate. The organic layer was washed with saturated brine, and dried over anhydrous magnesium sulfate. The desiccant was ffitered off, and the filtrate was concentrated under reduced pressure to give the objective compound (0.45 g, 90% by two steps) as colorless crystals.

$^1$H-NMR(DMSO-d$_6$, δ ppm): 12.91 ((1H, brs), 8.01 (1H, d, J=8.5 Hz), 8.00(1H, s), 7.82(1H, dd, J=1.7 and 8.3 Hz), 7.66(1H, d, J=2.0 Hz), 7.25(1H, dd, J=2.1 and 8.4 Hz), 6.77(1H, d, J=8.4 Hz), 4.24(2H, s), 2.50(3H, s)

Preparation Example 36-1

2-Bromophenyl (n-butane-2-on-1-yl)thioether

2-Bromothiophenol (3.5 ml), 1-bromo-2-butanone (3.1 ml) and potassium carbonate (6.90 g) were stirred in acetone at room temperature for 30 min. The reaction mixture was added to water (100 ml). The mixture was extracted with toluene (100 ml), dried over magnesium sulfate, and concentrated to give the objective compound (8.46 g) as an oil.

$^1$H-NMR(CDCl$_3$, δ ppm): 1.07 (3H, t, J=7.3 Hz), 2.66 (2H, quartet, J=7.3 Hz), 7.05–7.09(1H, m), 7.27–7.29(2H, m), 7.55(1H, d, J=8.4 Hz)

Preparation Example 36-2

7-Bromo-3-ethylbenzo[b]thiophene

Polyphosphoric acid (15.0 g) was added to 2-bromophenyl(n-butane-2-on-1-yl)thioether (6.81 g), and the mixture was stirred at 160° C. for 2 hr. Ice was added to the reaction mixture and the mixture was extracted with toluene. The extract was washed with 10% aqueous ammonium chloride and a saturated aqueous solution of sodium hydrogencarbonate, dried over magnesium sulfate and concentrated to give the objective compound (4.43 g) as an oil.

$^1$H-NMR(CDCl$_3$, δ ppm): 1.36(3H, t, J=7.5 Hz), 2.84(2H, quartet, J=7.5 Hz), 7.16(1H, s), 7.27(1H, t, J=7.8 Hz), 7.50(1H, d, J=7.6 Hz), 7.70(1H, d, J=7.9 Hz)

Preparation Example 36-3

7-Carboxy-3-ethylbenzo[b]thiophene

Magnesium (2.67 g) was stirred in ether (15 ml) at room temperature. A solution of 7-bromo-3-ethylbenzo[b]thiophene (4.40 g) and methyl iodide (7.76 g) in ether (50 ml) were added dropwise over 30 min. Then, refluxing was conducted for 50 min and the reaction mixture was cooled in ice water bath. Using a separate reaction vessel, pulverized dry ice was stirred in ether, and the Grignard reagent prepared above was transferred to the vessel for about 5 min. To the reaction mixture was added 2N hydrochloric acid to acidify the solution, and the ether layer was separated. The solution was made alkaline with a 5% aqueous sodium hydroxide solution. The separated aqueous layer was acidified with 2N hydrochloric acid. After extraction with ether, the extract was dried over sodium sulfate and concentrated to give the objective compound (3.22 g) as crystals.

$^1$H-NMR(CDCl$_3$, δ ppm): 1.40(3H, t, J=7.3 Hz), 2.91(2H, quartet, J=7.5 Hz), 7.25(1H, s), 7.52(1H, t, J=7.6 Hz), 8.02(1H, dd, J=7.9 and 0.9 Hz), 8.25(1H, d, J=7.4 Hz)

Preparation Example 36-4

3-Ethyl-7-(methoxycarbonyl)benzo[b]thiophene

7-Carboxy-3-ethylbenzo[b]thiophene (3.20 g) and concentrated sulfuric acid were stirred in methanol (100 ml) at 60° C. for 16 hr. The reaction mixture was concentrated and chloroform mixture was added thereto. The mixture was washed with a saturated aqueous solution of sodium hydrogencarbonate. The chloroform was separated, and the residue was dried over magnesium sulfate, and concentrated to give the objective compound (3.04 g).

$^1$H-NMR(CDCl$_3$, δ ppm): 1.39(3H, t, J=7.5 Hz), 2.89(2H, quartet, J=7.5 Hz), 4.02(3H, s), 7.22(1H, s), 7.47(1H, t, J=7.8 Hz), 7.95(1H, dd, J=7.9 and 0.9 Hz), 8.12(1H, d, J=7.5 Hz)

Preparation Example 36-5

2-(2,4-Dichlorobenzoyl)-3-ethyl-7-(methoxycarbonyl)benzo[b]thiophene

Aluminum chloride (2.48 g) was stirred in methylene chloride (10 ml) and a solution of 2,4-dichlorobenzoyl chloride (1.94 g) in methylene chloride (10 ml) was added dropwise over 5 min. After stirring for 2 hr, ice was added to the reaction mixture, and the mixture was extracted with ethyl acetate. The extract was washed twice with a saturated aqueous solution of sodium hydrogencarbonate and once with a saturated aqueous solution of ammonium chloride and sodium sulfate. The concentration gave the objective compound (3.12 g).

$^1$H-NMR(CDCl$_3$, δ ppm): 1.32(3H, t, J=7.5 Hz), 3.28(2H, quartet, J=7.5 Hz), 3.99(3H, s), 7.37(1H, dd, J=8.3 and 2.0 Hz), 7.45(1H, d, J=8.2 Hz), 7.49(1H, d, J=1.9 Hz), 7.56(1H, t, J=7.9 Hz), 8.16(1H, d, J=8.2 Hz), 8.26(1H, d, J=7.4 Hz)

Preparation Example 36-6

7-Carboxy-2-(2,4-dichlorobenzyl)-3-ethylbenzo[b]thiophene 2-(2,4-Dichlorobenzoyl)-3-ethyl-7-(methoxycarbonyl)benzo[b]thiophene (2.85 g) and hydrazine hydrate (3.50 g) were stirred in ethylene glycol (30 ml) at 160° C. for 1 hr. After cooling, potassium hydroxide (3.30 g) was added, and the mixture was stirred at 160° C. for 2 hr. After cooling, ice and concentrated hydrochloric acid were added, and the mixture was extracted with ethyl acetate. The extract was dried over sodium sulfate and concentrated, and the residue was purified by silica gel column chromatography to give the objective compound (1.98 g) as white crystals.

$^1$H-NMR(CDCl$_3$, δ ppm): 1.20(3H, t, J=7.6 Hz), 2.88(2H, quartet, J=7.6 Hz), 4.31(2H, s), 7.12(1H, d, J=8.4 Hz), 7.17(1H, dd, J=8.4 and 2.1 Hz), 7.42(1H, d, J=2.1 Hz), 7.50(1H, t, J=7.8 Hz), 7.95 (1H, dd, J=7.9 and 0.8 Hz), 8.16(1H, dd, J=7.8 and 0.8 Hz).

Preparation Example 37-1

Ethyl 3-(2,4-dichlorobenzylamino)-4-nitrobenzoate

A mixture of 3-fluoro-4-nitrobenzoic acid (5.20 g), 2,4-dichlorobenzyl-amine (14.8 g) and toluene (35 ml) was refluxed under heating for 24 hr. The mixture was heated to room temperature, and water and ethyl acetate were added. The mixture was stirred and precipitated crystals were collected by filtration. The chloroform layer of the filtrate was separated and the solvent was distilled away. Ether was added to the residue and the precipitated crystals were collected by filtration. The crystals were combined, washed with ether and dried to give 3-(2,4-dichlorobenzyl-amino)-4-nitrobenzoic acid. Sulfuric acid (2.3 g) was added thereto, and the mixture was refluxed under heating in ethanol for 6 hr. The reaction mixture was concentrated and poured into a saturated aqueous solution of sodium hydrogencarbonate. The mixture was extracted with ethyl acetate, washed with saturated brine and dried. The solvent was distilled away and the residue was crystallized from a mixed solvent of ethyl acetate and hexane. The crystals were collected by filtration and dried to give the objective compound (4.0 g).

$^1$H-NMR(CDCl$_3$, δ ppm): 1.38(3H, t, J=7.1 Hz), 4.37(2H, q, J=7.1 Hz), 4.66(2H, d, J=5.9 Hz), 7.22–7.32(3H, m), 7.46(1H, d, J=2.0 Hz), 7.48(1H, d, J=1.7 Hz), 8.25(1H, d, J=8.8 Hz), 8.37(1H, brs).

Preparation Example 37-2

Ethyl 4-amino3-(2,4-dichlorobenzylamino)benzoate

Ethanol (7 ml), tetrahydrofuran (7 ml) and water (28 ml) were added to ethyl 3-(2,4-dichlorobenzylamino)-4-nitrobenzoate (1.40 g), and sodium hydrosulfite (4.50 g) was added at room temperature. The mixture was stirred at 50° C. for 20 min. The reaction mixture was extracted with chloroform and water, and the organic layer was washed with saturated brine, dried and concentrated to give the objective compound (1.4 g, as a crude product). The crude product was used in the following reaction as it was.

Preparation Example 37-3

1-(2,4-Dichlorobenzylamino)-2-hydroxy-6-(ethoxycarbonyl)benzimidazol

A solution of crude ethyl 4-amino-3-(2,4-dichlorobenzylamino)benzoate (1.4 g) and tetramethoxymethane (2.60 g) in acetic acid (4 ml) was stirred at 60° C. for 5 hr. The reaction mixture was concentrated, and ethanol (10 ml) and concentrated hydrochloric acid (0.5 g) were added to the residue obtained. The mixture was refluxed under heating for 2 hr. The mixture was heated to room temperature, and neutralized with a saturated aqueous solution of sodium hydrogencarbonate. The solvent was distilled away under reduced pressure. Precipitated gum was gathered, and suspended in ethanol, filtered and dried to give the objective compound (0.400 g).

$^1$H-NMR(DMSO-d$_6$, δ ppm): 1.27(3H, t, J=7.1 Hz), 4.24 (2H, q, J=7.1 Hz), 5.12(2H, s), 7.04(1H, d, J=8.4 Hz), 7.12(1H, d, J=8.2 Hz), 7.37(1H, dd, J=2.1 and 8.4 Hz), 7.51(1H, s), 7.67–7.72(2H, m), 11.37(1H, brs)

Preparation Example 37-4

1-(2,4-Dichlorobenzylamino)-6-(ethoxycarbonyl)-3-methyl-2-benzimidazolone

Sodium hydrite (0.080 g, 60% suspension in oil) was added to a solution of 1-(2,4-dichlorobenzylamino)-2-hydroxy-6-(ethoxycarbonyl)benzimidazole (0.396 g) in N,N'-dimethylformamide (4 ml), and the mixture was stirred at room temperature for 1 hr. Methyl iodide (0.307 g) was added, and the mixture was stirred for 2 hr. The precipitated crystals were collected by filtration, washed with water and ethanol and dried to give the objective compound (0.348 g).

$^1$H-NMR(DMSO-d$_6$, δ ppm): 1.28(3H, t, J=7.1 Hz), 3.41 (3H, s), 4.25(2H, q, J=7.1 Hz), 5.17(2H, s), 7.05(1H, d, J=8.4 Hz), 7.32(1H, d, J=8.3 Hz), 7.36(1H, d, J=8.4 Hz), 7.57(1H, s), 7.69(1H, s), 7.76(1H, d, J=8.3 Hz)

Preparation Example 37-5

6-Carboxy-1-(2,4-dichlorobenzylamino)-3-methyl-2-benzimidazolone

Ten percent sodium hydroxide (0.650 g) was added to a mixture of 1-(2,4-dichlorobenzylamino)-6-(ethoxycarbonyl)-3-methyl-2-benzimidazolone (0.308 g), ethanol (4 ml), tetrahydrofuran (8 ml) and water (4 ml), and the mixture was stirred at 60° C. for 2.5 hr. A part of the reaction mixture was concentrated, and neutralized with a saturated aqueous solution of sodium hydrogencarbonate. The crystals precipitated were filtered and dried to give the objective compound (0.276 g).

$^1$H-NMR(DMSO-d$_6$, δ ppm): 3.41(3H, s), 5.16(2H, s), 7.03(1H, d, J=8.4 Hz), 7.29(1H, d, J=8.2 Hz), 7.36(1H, dd, J=2.1 and 8.4 Hz), 7.55(1H, d, J=1.4 Hz), 7.69(1H, d, J=2.1 Hz), 7.75(1H, dd, J=1.4 and 8.3 Hz)

Preparation Example 38-1

1-(2,4-Dichlorobenzyl)-6-(ethoxycarbonyl) benzotriazole

Ethyl 4-amino-3-(2,4-dichlorobenzylamino)benzoate (0.89 g), concentrated sulfuric acid (1.0 g) were stirred in a mixed solvent of acetic acid (20 ml), water (10 ml) and tetrahydrofuran (20 ml). Sodium nitrite (3.0 g) was added thereto, and the mixture was stirred at room temperature for 30 min. The solvent was distilled away, and water was added to separate the toluene layer. The mixture was washed with a saturated aqueous solution of sodium hydrogencarbonate. The toluene layer was concentrated to give the objective compound (0.64 g) as a crude product.

$^1$H-NMR(CDCl$_3$, δ ppm): 1.43(3H, t, J=7.2 Hz), 4.43(2H, quartet, J=7.1 Hz), 5.97(2H, s), 6.94 (1H, d, J=8.4 Hz), 7.18(1H, dd, J=8.4 and 2.1 Hz), 7.48(1H, d, J=2.0 Hz), 8.06(1H, dd, J=8.7 and 1.3 Hz), 8.12(1H, dd, J=8.9 and 0.9 Hz), 8.23(1H, d, J=1.0 Hz)

Preparation Example 38-2

6-Carboxy-1-(2,4-dichlorobenzyl)benzotriazole 1-(2,4-Dichlorobenzyl)-6-(ethoxycarbonyl)benzotriazole (0.60 g) was refluxed under heating in a mixed solvent of 5% aqueous solution of sodium hydroxide (6 g) and ethanol (20 g) for 0.5 hr. After cooling, concentrated hydrochloric acid (4 ml) and water (10 ml) were added to the reaction mixture, and the mixture was extracted with ethyl acetate, concentrated and dried to give the objective compound (0.50 g) as a crude product.

$^1$H-NMR(DMSO-d$_6$, δ ppm): 6.13(2H, s), 7.24(1H, d, J=8.3 Hz), 7.43–7.46(1H, m), 7.70–7.72(1H, m), 7.95(1H, d, J=8.8 Hz), 8.14(1H, d, J=8.6 Hz), 8.47(1H, s)

Preparation Example 39-1

4-Ethyl-3-nitrobenzoic acid

4-Ethylbenzoic acid (20 g, 133 mmol) was ice-cooled and fuming nitric acid (94%, d=1.50, 50 ml) was dropwise added thereto for 40 min. The mixture was stirred at 4–5° C. for 1.25 hr. The resulting yellow suspension was poured into ice-water and the precipitated crystals were collected by filtration. The crystals were dissolved in ethanol, and water was added for recrystallization to give the objective compound (24.6 g, 94.8%) as colorless crystals.

$^1$H-NMR(CDCl$_3$, δ ppm): 8.59(1H, d, J=1.6 Hz), 8.24 (1H, dd, J=1.6 and 8.0 Hz), 7.52(1H, d, J=8.0 Hz), 3.00(2H, quartet, J=7.5 Hz), 1.33(3H, t, J=7.5 Hz)

Preparation Example 39-2

3-Amino-4-ethylbenzoic acid

4-Ethyl-3-nitrobenzoic acid (5.0 g, 27.4 mmol) was dissolved in methanol (50 ml) and a Pd-C catalyst (5%, 250 mg) was added thereto. The mixture was stirred under a hydrogen atmosphere from 0° C. to room temperature for 1 hr. After the completion of the reaction, the catalyst was filtered off and the filtrate was concentrated under reduced pressure. The obtained crystals were washed with methyl t-butyl ether/hexane and dried to give the object compound (3.2 g, 70.6%).

$^1$H-NMR(DMSO-d$_6$, δ ppm): 12.40(1H, brs), 7.21(1H, d, J=1.6 Hz), 7.07(1H, dd, J=1.6 and 7.6 Hz), 6.99(1H, d, J=7.7 Hz), 5.06(2H, brs), 2.45(2H, quartet, J=7.4 Hz), 1.11(3H, t, J=7.4 Hz).

Preparation Example 39-3

6-Carboxy-3-methyl-1H-indazole

To chloroform (75 ml), which had been passed through an alumina column, was added boron trifluoride diethyl ether complex (3.75 g, 26.4 mmol) and the mixture was cooled at −12° C. A solution of 3-amino-4-ethylbenzoic acid (2.5 g, 15.1 mmol) in tetrahydrofuran (25 ml) was dropwise added thereto for 20 min. After the completion of the addition, t-butyl nitrite (1.87 g, 18.1 mmol) was added and the mixture was heated to 5° C. The mixture was stirred at 5° C. for 1.5 hr. Then potassium acetate (7.4 g, 75.4 mmol) and 18-crown-6-ether (400 mg, 1.51 mmol) were added and the mixture was stirred at room temperature for 40 hr. The brown reaction mixture was concentrated under reduced pressure. Ethyl acetate/acetone (7/3, 100 ml) and 1N hydrochloric acid (25 ml) was added to the residue and the mixture was stirred at room temperature for 1 hr. Saturated brine (25 ml) was added thereto. The insoluble matter was filtered off and the filtrate was partitioned. The water layers were extracted with ethyl acetate/acetone (7/3, 40 ml) and the combined organic layer was dried over anhydrous magnesium sulfate. The drying agent was filtered off and the filtrate was concentrated under reduced pressure. The obtained brown oil (4.3 g) was dissolved in ethyl acetate, and then hydrogen chloride-diethyl ether (61 of hydrogen chloride in 40 ml of ether) and diethyl ether (100 ml) were added. The precipitated solid was collected by filtration. The obtained solid was extracted with ethyl acetate/acetone (7/3, 100 ml) and saturated brine (25 ml), and the aqueous layer was further extracted with ethyl acetate. The combined organic layers were dried over anhydrous magnesium sulfate. The drying agent was filtered off and the filtrate was concentrated under reduced pressure. The obtained solid was washed with diethyl ether to give the objective compound (0.46 g, 17%) as brown crystals.

$^1$H-NMR(DMSO-$d_6$, δ ppm): 12.94(2H, brs), 8.04(1H, s), 7.77(1H, d, J=8.3 Hz), 7.62(1H, dd, J=1.1 and 8.4 Hz), 2.48(3H, s).

Preparation Example 39-4

6-(Methoxycarbonyl)-3-methyl-1H-indazole

6-Carboxy-3-methyl-1H-indazole (359 mg, 2.11 mmol) was dissolved in methanol (50 ml), and concentrated sulfuric acid (0.1 ml) was added. The mixture was heated under reflux for 22 hr. After cooling, a saturated aqueous sodium hydrogencarbonate solution was added and the methanol was distilled away under reduced pressure. The residue was extracted with ethyl acetate, and the organic layer was washed with saturated brine and dried over anhydrous sodium sulfate. The drying agent was filtered off and the filtrate was concentrated under reduced pressure to give the objective compound (340 mg, 87%) as brown crystals.

$^1$H-NMR(CDCl$_3$, δ ppm): 8.18(1H, s), 7.82(1H, d, J=8.4 Hz), 7.72(1H, d, J=8.4 Hz), 3.96(3H, s), 2.61(3H, s).

Preparation Example 39-5

1-(2,4-Dichlorobenzyl)-6-(methoxycarbonyl)-3-methyl-1H-indazole 6-(Methoxycarbonyl)-3-methyl-1H-indazole (0.40 g, 2.1 mmol) was dissolved in dimethylformamide (15 ml) and the mixture was ice-cooled. Sodium hydride (85 mg, 60% suspension in oil, 2.1 mmol as NaH) was added and the mixture was stirred at 0° C. for 30 min. 2,4-Dichlorobenzyl chloride (0.45 g, 2.3 mmol) was added and the mixture was stirred at room temperature for 18 hr. The reaction mixture was extracted with ethyl acetate/water. The organic layer was washed with saturated brine and dried over anhydrous sodium sulfate. The drying agent was filtered off and the filtrate was concentrated under reduced pressure. The obtained crystalline residue was separated and purified by silica gel column chromatography (eluent: hexane/ethyl acetate=9/1) to give the objective compound (0.54 g, 74%) as colorless crystals.

$^1$H-NMR(CDCl$_3$, δ ppm): 8.06(1H, d, J=1.1 Hz), 7.82 (1H, dd, J=1.1 and 8.4 Hz), 7.72(1H, d, J=8.3 Hz), 7.42(1H, d, J=2.0 Hz), 7.08(1H, dd, J=2.0 and 8.3 Hz), 6.60(1H, d, J=8.4 Hz), 5.63(2H, s), 3.94(3H, s), 2.61(3H, s)

Preparation Example 39-6

6-Carboxy-1-(2,4-dichlorobenzyl)-3-methyl-1H-indazole 1-(2,4-Dichlorobenzyl)-6-(methoxycarbonyl)-3-methyl-1H-indazole (0.2 g, 0.57 mmol) was suspended in ethanol (10 ml), and a 1M aqueous sodium hydroxide solution (2 ml) was added. The mixture was stirred under heating at 90° C. for 40 min. After the starting compound disappeared, the ethanol was distilled away under reduced pressure. The residue was acidified with 1N hydrochloric acid (3 ml) and extracted with ethyl acetate. The organic layer was washed with saturated brine and dried over anhydrous sodium sulfate. The drying agent was filtered off and the filtrate was concentrated under reduced pressure to give the objective compound (0.19 g, 99%) as colorless crystals.

$^1$H-NMR(CDCl$_3$, δ ppm):8.14(1H, s), 7.87(1H, dd, J=1.1 and 8.4 Hz), 7.76(1H, d, J=8.2 Hz), 7.43(1H, d, J=2.1 Hz), 7.10(1H, dd, J=2.1 and 8.3 Hz), 6.67(1H, d, J=8.3 Hz), 5.65(2H, s), 2.63(3H, s)

Preparation Example 40-1

3-Ethyl-7-(methoxycarbonyl)-2,4-(1H,3H)-quinazolinedione

A mixture of dimethyl 2-aminoterephthalate (4.18 g), ethyl isocyanate (2.58 ml) and triethylamine (1.0 ml) in toluene (20 ml) was heated at 70° C. for 15 hr. After concentration, methanol (50 ml) and concentrated hydrochloric acid (10 ml) was added and the mixture was stirred at room temperature for 5 hr. After concentration, the residue was washed with water (50 ml) and methanol (50 ml) and dried to give the object compound (2.23 g).

$^1$H-NMR(DMSO-$d_6$, δ ppm): 1.14(3H, t, J=7.1 Hz), 3.88 (3H, s), 3.92(2H, quartet, J=7.1 Hz), 7.69(1H, dd, J=8.3 and 1.4 Hz), 7.75(1H, d, J=1.2 Hz), 8.03(1H, d, J=8.2 Hz), 11.58(1H, brs)

Preparation Example 40-2

1-(2,4-Dichlorobenzyl)-3-ethyl-7-(methoxycarbonyl)-2,4(1H,3H)-quinazolinedione

A mixture of 3-ethyl-7-(methoxycarbonyl)-2,4(1H,3H)-quinazolinedione (2.17 g), 2,4-dichlorobenzyl chloride (2.05 g), potassium iodide (1.45 g) and potassium carbonate (5.0 g) in acetone (80 ml) was heated under reflux for 1.5 hr. After cooling, water (50 ml) was added to the reaction mixture and the precipitate was collected by filtration. The precipitate was washed with water (30 ml) and methyl t-butyl ether (30 ml) and dried to give the object compound (2.60 g).

$^1$H-NMR(DMSO-$d_6$, δ ppm): 1.20(3H, t, J=7.0 Hz), 3.83 (3H, s), 4.02(2H, quartet, J=7.0 Hz), 5.38(2H, s), 7.16(1H, d, J=8.5 Hz), 7.29–7.31(1H, m), 7.51(1H, s), 7.75(1H, d, J=2.0 Hz), 7.80(1H, d, J=8.1 Hz), 8.22(1H, d, J=8.1 Hz)

Preparation Example 40-3

7-Carboxy-1-(2,4-dichlorobenzyl)-3-ethyl-2,4-(1H,3H)-quinazolinedione 1-(2,4-Dichlorobenzyl)-3-ethyl-7-(methoxycarbonyl)-2,4 (1H,3H)-quinazolinedione (2.36 g) in a mixture of a 5% aqueous sodium hydroxide solution (10 g) and methanol (30 g) was heated under reflux for 1 hr. After cooling, concentrated hydrochloric acid (3.9 g) was added to the reaction mixture and the precipitate was collected by filtration. The precipitate was washed with water (100 g) and toluene (20 ml) and dried to give the objective compound (2.27 g) as white crystals.

$^1$H-NMR(DMSO-$d_6$, δ ppm): 1.19(3H, t, J=7.0 Hz), 4.02 (2H, quartet, J=7.0 Hz), 5.37(2H, s), 7.14(1H, d, J=8.4 Hz), 7.30(1H, dd, J=8.4 and 2.1 Hz), 7.48(1H, s), 7.75(1H, d, J=2.1 Hz), 7.78(1H, d, J=8.0 Hz), 8.20(1H, d, J=8.1 Hz)

IR(Nujol): 1724, 1704, 1662 cm$^{-1}$ mp: 238–240° C.

Preparation Example 41-1

3-(2,4-Dichlorobenzyl)-7-(methoxycarbonyl)-2,4 (1H,3H)-quinazolinedione

A mixture of dimethyl 2-aminoterephthalate (4.18 g), N,N'-carbonyldiimidazole (3.89 g) and N-methylmorpholine (4.0 ml) in tetrahydrofuran (30 ml) was stirred at room temperature for 21 hr. After concentration of the reaction mixture, acetonitrile (70 ml) and 2,4-dichlorobenzylamino (5.47 g) were added and the mixture was stirred at reflux temperature for 2 hr. The precipitated solid was washed with water (50 ml) and acetonitrile (50 ml) and dried to give the objective compound (4.64 g).

$^1$H-NMR(DMSO-$d_6$, δ ppm): 3.90(3H, s), 5.09(2H, s), 7.15(1H, d, J=8.4 Hz), 7.30(1H, dd, J=8.4 and 2.1 Hz), 7.65(1H, d, J=2.2 Hz), 7.71(1H, dd, J=8.3 and 1.4 Hz), 7.81(1H, s), 8.06(1H, d, J=8.4 Hz), 11.8(1H, brs)

Preparation Example 41-2

3-(2,4-Dichlorobenzyl)-7-(methoxycarbonyl)-1-methyl-2,4(1H,3H)-quinazolinedione A mixture of 3-(2,4-dichlorobenzyl)-7-(methoxycarbonyl)-2,4-(1H,3H)-quinazolinedione (2.30 g), methyl iodide (2.13 g) and potassium carbonate (2.07 g) in acetone (30 ml) was heated under reflux for 2 hr. After cooling, the reaction mixture was concentrated, and the residue was washed with water (60 ml) and methyl t-butyl ether (20 ml) and dried to give the objective compound (2.25 g) as white crystals.

$^1$H-NMR(DMSO-$d_6$, δ ppm): 3.58(3H, s), 3.93(3H, s), 5.14(2H, s), 7.17(1H, d, J=8.4 Hz), 7.29 (1H, dd, J=8.4 and 2.0 Hz), 7.65(1H, d, J=2.0 Hz), 7.84(1H, dd, J=8.2 and 1.2 Hz), 7.91(1H, s), 8.18(1H, d, J=8.2 Hz)

Preparation Example 41-3

7-Carboxy-3-(2,4-dichlorobenzyl)-1-methyl-2,4(1H, 3H)-quinazolinedione 3-(2,4-Dichlorobenzyl)-7-(methoxycarbonyl)-1-methyl-2,4-(1H,3H)-quinazolinedione (2.02 g) in a mixture of a 5% aqueous sodium hydroxide solution (10 g) and methanol (30 g) was heated under reflux for 1 hr. After cooling, concentrated hydrochloric acid (5.5 g) was added to the reaction mixture and the precipitate was collected by filtration. The precipitate was washed with water (50 g) and methanol (50 g) and dried to give the objective compound (1.90 g) as white crystals.

$^1$H-NMR(DMSO-$d_6$, δ ppm): 3.58(3H, s), 5.14(2H, s), 7.16(1H, d, J=8.5 Hz), 7.29 (1H, dd, J=8.4 and 2.1 Hz), 7.65(1H, d, J=2.1 Hz), 7.82(1H, d, J=8.2 Hz), 7.91(1H, s), 8.16(1H, d, J=8.2 Hz)

IR(Nujol): 1712, 1691, 1667 cm$^{-1}$ mp: 308–310° C.

Preparation Example 42-1

3-(2,4-Dichlorobenzyl)-7-(methoxycarbonyl)-4(3H)-quinazolinone

A solution of dimethyl 2-aminoterephthalate (4.18 g) and N,N-dimethylformamide dimethyl acetal (4.77 g) in dimethylformamide (20 ml) was heated at 135° C. for 2 hr. The reaction mixture was concentrated to give an oil (5.40 g). To 2.70 g of the oil, 2,4-dichlorobenzylamine (3.52 g) was added and the mixture was heated for at 100° C. for 5 min. After cooling, the residue was washed with water (50 ml) and 2-propanol (50 ml) and dried to give the objective compound (3.10 g) as white crystals.

$^1$H-NMR(DMSO-$d_6$, δ ppm): 3.99(3H, s), 5.26(2H, s), 7.24–7.27(2H, m), 7.42 (1H, d, J=8.4 Hz), 7.44(1H, d, J=2.2 Hz), 8.12(1H, dd, J=8.3 and 1.7 Hz), 8.25(1H, s), 8.35(1H, d, 8.4 Hz), 8.39(1H, d, 1.4 Hz)

Preparation Example 42-2

7-Carboxy-3-(2,4-dichlorobenzyl)-4(3H)-quinazolinone 3-(2,4-Dichlorobenzyl)-7-(methoxycarbonyl)-4(3H)-quinazolinone (2.00 g) in a mixture of a 5% aqueous sodium hydroxide solution (20 ml) and methanol (20 ml) was heated under reflux for 1 hr. After cooling, concentrated hydrochloric acid was added to the reaction mixture and the precipitate was collected by filtration. The precipitate was washed with water (50 g) and toluene (30 ml) and dried to give the objective compound (1.50 g) as white crystals.

$^1$H-NMR(DMSO-$d_6$, δ ppm): 5.25(2H, s), 7.19(1H, d, J=8.4 Hz), 7.37(1H, dd, J=8.4 and 2.3 Hz), 7.68(1H, d, J=2.1 Hz), 8.03(1H, dd, J=8.2 and 1.5 Hz), 8.18(1H, s), 8.23(1H, d, J=8.4 Hz), 8.58(1H, s)

IR(Nujol): 1724, 1679, 1660 cm$^{-1}$.

mp: 244–246° C.

Preparation Example 43-1

Dimethyl 2-((2,4-dichlorophenyl)acetylamino) terephthalate

A mixture of dimethyl 2-aminoterephthalate (2.09 g), 2,4-dichlorophenylacetic acid (2.05 g), N,N-dimethylaminopyridine (1.32 g) and dicyclohexylcarbodiimide (2.22 g) in tetrahydrofuran (20 ml) was stirred at room temperature for 2 hr and then at 80° C. for 4 hr. After cooling, the precipitate was filtered off and the filtrate was washed with 1N hydrochloric acid. Chloroform mixture was added to the obtained organic layer, and the mixture was washed with a saturated aqueous sodium hydrogencarbonate solution and dried over sodium sulfate. The solvent was distilled away and the residue was washed with water and methanol to give the object compound (2.54 g) as white crystals.

$^1$H-NMR(DMSO-$d_6$, δ ppm): 3.81(3H, s), 3.86(3H, s), 3.93(2H, s), 7.45 (1H, dd, J=8.3 and 2.1 Hz), 7.51(1H, d, J=8.3 Hz), 7.73(1H, dd, J=8.2 and 1.7 Hz), 7.97(1H, d, J=8.2 Hz), 8.74(1H, d, 1.7 Hz), 10.64(1H, s).

Preparation Example 43-2

2-(2,4-Dichlorobenzyl)-3-methyl-7-(methylcarbamoyl)-4(3H)-quinazolinone

Dimethyl 2-((2,4-dichlorophenyl)acetylamino) terephthalate (0.96 g) and a 40% aqueous methylamine solution (5 ml) in a mixture of methanol (20 ml) and tetrahydrofuran (20 ml) were stirred at room temperature for 1 hr. After concentration of the reaction mixture, methanol (20 ml) and concentrated hydrochloric acid (5 ml) were added to the residue and the mixture was stirred at 50° C. for 30 min. The reaction mixture was concentrated to give the objective compound (0.90 g) as white crystals.

$^1$H-NMR(CDCl$_3$, δ ppm): 3.05(3H, d, J=4.9 Hz), 3.56 (3H, s), 4.28(2H, s), 6.24(1H, brs), 7.12(1H, d, J=8.4 Hz), 7.22(1H, dd, J=8.3 and 2.1 Hz), 7.48(1H, d, J=2.2 Hz), 7.86(1H, dd, J=8.2 and 1.7 Hz), 7.90(1H, d, J=1.6 Hz), 8.32(1H, d, J=8.4 Hz).

Preparation Example 43-3

7-Carboxy-2-(2,4-dichlorobenzyl)-3-methyl-4(3H)-quinazolinone 2-(2,4-Dichlorobenzyl)-3-methyl-7-(methylcarbamoyl)-4 (3H)-quinazolinone (0.88 g) in a mixture of concentrated sulfuric acid (2.0 g) and water (2.0 g) was stirred at 100° C. for 7 hr. After cooling of the reaction mixture, water (5 ml) was added. The precipitate was collected by filtration, washed with methanol and dried to give the objective compound (0.69 g) as white crystals.

$^1$H-NMR(DMSO-$d_6$, δ ppm): 3.58(3H, s), 4.37(2H, s), 7.37–7.44(2H, m), 7.66(1H, d, J=2.0 Hz), 7.87(1H, d, J=1.4 Hz), 7.94(1H, dd, J=8.2 and 1.6 Hz), 8.20(1H, d, J=8.3 Hz)

IR(Nujol): 1719, 1676 cm$^{-1}$ mp: 266–271° C.

Preparation Example 44-1

6-(Ethoxycarbonyl)-3-(2,4-dichlorobenzyl)-3,4-dihydro-2-methylquinazoline hydrochloride A mixture of ethyl 3-methyl-4-nitrobenzoate (2.09 g), N-bromosuccinimide (2.78 g) and AIBN (0.12 g) in carbon tetrachloride (10 ml) was heated under reflux for 12 hr. After cooling, precipitate was filtered off and the filtrate was concentrated. 2,4-Dichlorobenzylamine (2.76 g), the potassium carbonate (2.76 g) and toluene (20 ml) were added to the residue and the mixture was stirred under heating at 100° C. for 1.5 hr. After cooling, the reaction mixture was washed with water and concentrated hydrochloric acid (5 ml) was added to the toluene layer. The resulting solid was collected by filtration, washed with water and toluene and dried to give a crude product of ethyl 3-(2,4-dichlorobenzylamino) methyl-4-nitrobenzoate hydrochloride (2.74 g).

To the crude product were added sodium hydrosulfite (17 g), tetrahydrofuran (20 ml), ethanol (20 ml) and water (80 ml) and the mixture was heated under reflux for 1 hr. After cooling, the tetrahydrofuran layer was separated and concentrated. To the residue containing ethyl 4-amino-3-(2,4-dichlorobenzyl-amino)methylbenzoate as a main component, acetic acid (20 ml) and acetic anhydride (20 ml) were added and the mixture was heated at 100° C. for 1 hr. After concentration of the reaction mixture containing ethyl 4-acetylamino-3-(2,4-dichlorobenzylamino)methylbenzoate as a main component, methanol (20 ml) and concentrated hydrochloric acid (5 ml) were added and the mixture was heated under reflux for 1 hr. The reaction mixture was concentrated to give a crude product of the object compound (0.68 g).

Preparation Example 44-2

6-Carboxy-3-(2,4-dichlorobenzyl)-3,4-dihydro-2-methylquinazoline hydrochloride 6-(Ethoxycarbonyl)-3-(2,4-dichlorobenzyl)-3,4-dihydro-2-methylquinazoline hydrochloride (0.68 g) in a mixture of a 10% aqueous sodium hydroxide solution (5 ml) and ethanol (10 ml) was stirred at 60° C. for 1 hr. After standing cool the reaction mixture, concentrated hydrochloric acid (5 ml) was added and the precipitate was collected by filtration. The precipitated was washed with toluene and 2-propanol and dried to give the objective compound (0.41 g) as white crystals.

$^1$H-NMR(DMSO-$d_6$, δ ppm): 3.55(3H, s), 4.74(2H, s), 4.90(2H, s), 7.31(1H, d, J=8.3 Hz), 7.49 (1H, dd, J=8.4 and 2.2 Hz), 7.64(1H, d, J=8.4 Hz), 7.71(1H, s), 7.76(1H, d, J=2.0 Hz), 7.89(1H, d, J=8.3 Hz), 12.96(1H, brs)

IR(Nujol): 1718 cm$^{-1}$ mp: 277° C. (decomposition)

Preparation Example 45-1

Dimethyl 2-((2,4-dichlorobenzyl)amino) terephthalate

Dimethyl 2-aminoterephthalate (10.45 g), 2,4-dichlorobenzyl chloride (11.74 g), potassium iodide (8.33 g) and potassium carbonate (13.82 g) in a mixed solvent of toluene (50 ml) and water (30 ml) were heated under reflux for 20 hr. After cooling, toluene (50 ml) was added and the precipitated yellow crystals were collected by filtration. The crystals were washed with water and toluene and dried to give the objective compound (7.87 g). The mother liquor was concentrated and crystallized from ethyl acetate to give the second crystals (4.43 g).

$^1$H-NMR(CDCl$_3$, δ ppm): 3.88(3H, s), 3.90(3H, s), 7.19–7.27(4H, m), 7.42(1H, d, J=2.0 Hz), 7.99(1H, d, J=8.8 Hz), 8.20–8.28(1H, m)

Preparation Example 45-2

Dimethyl 2-((N-acetyl)-(2,4-dichlorobenzyl)amino) terephthalate

A mixture of dimethyl 2-(2,4-dichlorobenzyl) aminoterephthalate (12.00 g), N,N-dimethylaniline (7.92 g) and acetyl chloride (5.5 ml) in toluene (140 ml) was heated at 50° C. for 15 hr. After cooling, ice and concentrated hydrochloric acid were added to acidify the reaction mixture and the toluene layer was separated. The toluene layer was washed successively with water and a saturated aqueous sodium hydrogencarbonate solution, dried over sodium sulfate and concentrated. The residue was crystallized from 2-propanol to give the objective compound (8.40 g) as white crystals.

$^1$H-NMR(CDCl$_3$, δ ppm): 3.88(3H, s), 3.90(3H, s), 7.19–7.27(4H, m), 7.42(1H, d, J=2.0 Hz), 7.99(1H, d, J=8.8 Hz), 8.20–8.28(1H, m)

Preparation Example 45-3

2-((N-Acetyl)-(2,4-dichlorobenzyl)amino) terephthalic acid

A mixture of dimethyl 2-((N-acetyl)-(2,4-dichlorobenzyl) amino)terephthalate (2.05 g) and 10% aqueous sodium hydroxide solution (8.00 g) in methanol (20 ml) was heated at 60° C. for 1 hr. After cooling, concentrated hydrochloric acid was added to acidify the reaction mixture and the precipitated solid was collected by filtration. The solid was washed with water (60 ml) and dried to give the objective compound (1.87 g) as white crystals.

$^1$H-NMR(DMSO-$d_6$, δ ppm): 1.73(3H, s), 4.30(1H, d, J=10.30 Hz), 5.28(1H, d, J=10.30 Hz), 7.37(1H, dd, J=8.3 and 2.0 Hz), 7.41(1H, d, J=8.4 Hz), 7.52(1H, d, J=2.0 Hz), 7.55(1H, s), 7.97–7.99(2H, m)

Preparation Example 45-4

2-((N-Acetyl)-(2,4-dichlorobenzyl)amino)-1,4-dicarbamoylbenzene

A mixture of 2-((N-acetyl)-(2,4-dichlorobenzyl)amino) terephthalic acid (1.80 g) and N,N'-carbonyldiimidazole (1.62 g) in tetrahydrofuran (10 ml) was stirred at room temperature for 1 hr. Thereto was added 25% ammonia water (50 ml). The mixture was stirred for 10 min and concentrated. The residue was washed with water and 2-propanol and dried to give the object compound (1.56 g) as white crystals.

$^1$H-NMR(DMSO-$d_6$, δ ppm): 1.80(3H, s), 4.27(1H, d, J=15.75 Hz), 5.28(1H, d, J=15.75 Hz), 7.37(1H, dd, J=8.4 and 2.1 Hz), 7.44(1H, d, J=8.4 Hz), 7.50(1H, brs), 7.54(1H, d, J=2.1 Hz), 7.55(1H, d, J=1.5 Hz), 7.59(1H, d, J=8.0 Hz), 7.66(1H, brs), 7.88(1H, d, J=7.9 Hz), 8.01(1H, brs), 8.04 (1H, brs)

Preparation Example 45-5

7-Carbamoyl-1-(2,4-dichlorobenzyl)-2-methylquinazoline-4-one 2-((N-Acetyl)-(2,4-dichlorobenzyl)amino)-1,4-dicarbamoylbenzene (1.50 g) in a mixture of concentrated hydrochloric acid (10 ml) and methanol (30 ml) was heated under reflux for 30 min. After concentration, the object compound (1.46 g) was obtained as white crystals.

$^1$H-NMR(DMSO-$d_6$, δ ppm): 2.70(3H, s), 5.70(2H, s), 7.16(1H, d, J=8.4 Hz), 7.35(1H, dd, J=8.4 and 2.1 Hz), 7.77(1H, brs), 7.86(1H, brs), 8.09(1H, d, J=8.2 Hz), 8.32 (1H, d, J=8.2 Hz), 8.37(1H, brs)

Preparation Example 45-6

7-Carboxy-1-(2,4-dichlorobenzyl)-2-methyl-4(1H)-quinazolinone

7-Carbamoyl-1-(2,4-dichlorobenzyl)-2-methyl-4(1H)-quinazolinone (1.40 g) in a mixture of concentrated sulfuric acid (6 ml) and water (6 ml) was heated at 100° C. for 1 hr. After cooling, the precipitated solid was collected by filtration, washed with water, dried and concentrated to give the object compound (1.46 g) as white crystals.

$^1$H-NMR(DMSO-$d_6$, δ ppm): 2.54(3H, s), 5.56 (2H, s), 6.94(1H, d, J=8.5 Hz), 7.32(1H, d, J=8.5 Hz), 7.74(1H, s), 7.81(1H, d, J=1.9 Hz), 7.96(1H, d, J=8.2 Hz), 8.20(1H, d, J=8.2 Hz).

Preparation Example 46-1

Methyl 4-bromomethyl-3-nitrobenzoate

A mixture of methyl 3-nitro-4-methylbenzoate (4.147 g), N-bromosuccinimide (7.12 g) and AIBN (0.40 g) in carbon tetrachloride (30 ml) was stirred at 70° C. for 42 hr. After cooling, the insoluble matter was filtered off and the filtrate was concentrated to give an oil (7.40 g) containing the object compound.

Preparation Example 46-2

2-((N-Acetyl)aminomethyl)-5-((N-acetyl)carbamoyl)-1-nitrobenzene

The crude methyl 4-bromomethyl-3-nitrobenzoate (7.40 g) obtained above in 25% aqueous ammonia water (140 ml) and methanol (70 ml) was stirred at 50° C. for 1 hr. The reaction mixture was concentrated, and acetic acid (50 ml) and acetic anhydride (50 ml) were added. After refluxing for 30 min, the reaction mixture was cooled and a saturated aqueous sodium hydrogencarbonate solution was added. The mixture was extracted with ethyl acetate, dried over magnesium sulfate and concentrated. The residue was washed with chloroform to give the object compound.

$^1$H-NMR(DMSO-$d_6$, δ ppm): 1.91(3H, s), 2.34(3H, s), 4.57(2H, d, J=5.9 Hz), 7.63(1H, d, J=8.3 Hz), 8.19(1H, d, J=8.2 Hz), 8.48–8.53(2H, m), 11.26(1H, brs)

Preparation Example 46-3

2-((N-Acetyl)aminomethyl)-5-((N-acetyl)carbamoyl) aniline 2-((N-Acetyl)aminomethyl)-5-((N-acetyl)carbamoyl)-1-nitrobenzene (1.00 g) and sodium hydrosulfite (7.0 g) in a mixture of tetrahydrofuran (5 ml), ethanol (5 ml) and water (20 ml) were heated under reflux for 1 hr. After cooling, the organic layer was separated, dried over sodium sulfate and concentrated. The residue was purified by silica gel column chromatography to give the objective compound (1.06 g).

Preparation Example 46-4

7-(Acetylcarbamoyl)-1-(2,4-dichlorobenzyl)-1,4-dihydro-2-methylquinazoline hydrochloride 5-(Acetylcarbamoyl)-2-(acetylaminomethyl)aniline (1.06 g), potassium carbonate (1.40 g), potassium iodide (0.8 g) and 2,4-dichlorobenzyl chloride (1.40 g) in a mixture of dimethylformamide (15 ml) and water (10 ml) were stirred at 90° C. for 15 hr. After concentration of the reaction mixture, water was added and the mixture was extracted with ethyl acetate. The extract was concentrated, and methanol (5 ml) and concentrated hydrochloric acid (5 ml) were added. The mixture was refluxed for 1 hr. The reaction mixture was concentrated and purified by thin-layer chromatography to give the objective compound (0.46 g).

Preparation Example 46-5

7-Carboxy-1-(2,4-dichlorobenzyl)-1,4-dihydro-2-methylquinazoline 1/2 sulfate

To 7-(acetylcarbamoyl)-1-(2,4-dichlorobenzyl)-1,4-dihydro-2-methylquinazoline hydrochloride (0.46 g) were added water (1.2 g) and concentrated sulfuric acid (1.0 g) and the mixture was heated at 70° C. for 90 min. After cooling, ice was added and the precipitated solid was collected by filtration. The precipitate was washed with water and 2-propanol and dried to give the objective compound (0.145 g).

$^1$H-NMR(DMSO-$d_6$, δ ppm): 2.24(3H, s), 4.67(2H, s), 5.14(2H, s), 7.14(1H, s), 7.23(2H, t, J=7.2 Hz), 7.38(1H, d, J=8.4 Hz), 7.65(1H, d, J=7.2 Hz), 7.75(1H, s)

Preparation Example 47-1

1-(2,4-Dichlorobenzyl)-7-(ethoxycarbonyl)-3-methyl-2(1H)-quinoxalinone

A mixture of ethyl 4-amino-3-(2,4-dichlorobenzylamino) benzoate (1.90 g) and methyl pyruvate (0.55 ml) in toluene (15 ml) was heated under reflux for 1 hr. The reaction mixture was concentrated. The residue was washed with methanol and dried to give the object compound (0.50 g) as yellow crystals.

$^1$H-NMR(DMSO-$d_6$, δ ppm): 1.28(3H, t, J=7.2 Hz), 2.53 (3H, s), 4.28(2H, quartet., J=7.1 Hz), 5.49(2H, s), 6.99(1H, d, J=8.6 Hz), 7.27 (1H, dd, J=8.4 and 2.1 Hz), 7.63(1H, s), 7.76(1H, d, J=2.1 Hz), 7.84–7.91(1H, m)

Preparation Example 47-2

7-Carboxy-1-(2,4-dichlorobenzyl)-3-methyl-2(1H)-quinoxalinone 1-(2,4-Dichlorobenzyl)-7-(ethoxycarbonyl)-3-methyl-2 (1H)-quinoxalinone (0.50 g) in a mixture of a 5% aqueous sodium hydroxide solution (3 g) and methanol (20 ml) was heated under reflux for 1 hr. After cooling, concentrated hydrochloric acid (4 ml) and water (10 ml) were added to the reaction mixture and the precipitate was collected by filtration. The precipitate was washed with water (30 g) and dried to give the object compound (0.36 g) as yellow crystals.

$^1$H-NMR(DMSO-$d_6$, δ ppm): 2.52(3H, s), 5.47(2H, s), 6.92(1H, d, J=8.4 Hz), 7.26(1H, dd, J=8.4 and 2.0 Hz), 7.62(1H, s), 7.76(1H, d, J=2.0 Hz), 7.84–7.89(1H, m)

Preparation Example 48-1

1-(2,4-Dichlorobenzyl)-7-(ethoxycarbonyl)-2,3(1H, 4H)-quinoxalinedione

To a solution of ethyl 4-amino3-(2,4-dichlorobenzylamino)benzoate (1.53 g) and dimethylaniline (0.71 g) in toluene was added oxalyl dichloride (0.51 ml). After stirring at room temperature for 1.5 hr, ice was added to the reaction mixture. The toluene layer was separated and washed with 6N hydrochloric acid. The toluene layer was concentrated, and the residue was washed with methyl t-butyl ether and dried to give the object compound (1.03 g) as white crystals.

$^1$H-NMR(DMSO-$d_6$, δ ppm): 1.24(3H, t, J=7.2 Hz), 4.21 (2H, quartet., J=7.1 Hz), 5.34(2H, s), 7.24–7.32 (3H, m), 7.30(1H, d, J=2.1 Hz), 7.73(1H, dd, J=8.3 and 1.7 Hz), 7.75(1H, d, J=2.1 Hz), 12.38(1H, brs)

Preparation Example 48-2

1-(2,4-Dichlorobenzyl)-7-(ethoxycarbonyl)-4-methyl-2,3(1H,4H)-quinoxalinedione

A mixture of 1-(2,4-dichlorobenzyl)-7-(ethoxycarbonyl) quinoxaline-2,3-dione (0.90 g), methyl iodide (0.49 g) and potassium carbonate (0.63 g) in acetone (20 ml) was heated under reflux for 2 hr. After cooling, the reaction mixture was concentrated. The residue was washed with water (150 ml) and methyl t-butyl ether (100 ml) and dried to give the object compound (0.84 g) as white crystals.

$^1$H-NMR(DMSO-$d_6$, δ ppm): 1.25(3H, t, J=7.1 Hz), 3.59 (3H, s), 4.23(2H, quartet., J=7.1 Hz), 5.37(2H, s), 7.24 (1H, d, 8.5 Hz), 7.30(1H, dd, J=8.5 and 2.1 Hz), 7.42(1H, d, J=1.6 Hz), 7.56(1H, d, J=8.6 Hz), 7.76(1H, d, J=2.1 Hz), 7.80(1H, dd, J=8.6 and 1.6 Hz).

Preparation Example 48-3

7-Carboxy-1-(2,4-dichlorobenzyl)-4-methyl-2,3(1H, 4H)-quinoxalinedione 1-(2,4-Dichlorobenzyl)-7-(ethoxycarbonyl)-4-methyl-2,4 (1H,4H)-quinoxalinedione (0.80 g) in a mixture of a 3% aqueous sodium hydroxide solution (10 g) and methanol (15 g) was heated under reflux for 1 hr. After cooling, concentrated hydrochloric acid (4 ml) and water (10 ml) were added to the reaction mixture and the precipitate was collected by filtration. The precipitate was washed with water (50 g) and methyl t-butyl ether (30 ml) and dried to give the object compound (0.56 g) as yellow crystals.

$^1$H-NMR(DMSO-$d_6$, δ ppm): 3.59 (3H, s), 5.35(2H, s), 7.20(1H, d, J=8.5 Hz), 7.29(1H, dd, J=8.5 and 2.2 Hz), 7.41(1H, d, J=1.6 Hz), 7.54(1H, d, J=8.7 Hz), 7.76(1H, d, J=2.2 Hz), 7.80(1H, dd, J=8.6 and 1.7 Hz).

IR(Nujol): 1716, 1681, 1659 cm$^{-1}$ mp: 320–322° C.

Preparation Example 49-1

4-(2,4-Dichlorobenzyl)-3-(ethoxycarbonyl)-5-ethylimidazo[1,2-b]pyrazole

To a solution of ethyl 3-(ethoxycarbonyl)-5-ethylimidazo [1,2-b]pyrazole (0.348 g), which was prepared by a method described in Japanese Patent Unexamined Publication No. 163267/1993, in N,N-dimethylformamide was added sodium hydride (60% in oil, 0.100 g) and the mixture was stirred at room temperature for 30 min. 2,4-Dichlorobenzyl chloride (0.870 g) was added to the reaction mixture and the mixture was stirred at room temperature for 6 hr. The reaction mixture was concentrated to dryness and the residue was dissolved in ethyl acetate. The organic layer was washed with water and dried. The solvent was evaporated and the residue was purified by silica gel column chromatography (eluent: chloroform/ethyl acetate=2/1) to give the object compound (0.510 g).

$^1$H-NMR(CDCl$_3$, δ ppm): 1.19–1.25(6H, m), 2.45(2H, q), 4.18(2H, q, J=7.1 Hz), 5.73(2H, s), 6.57(1H, d, J=8.4 Hz), 7.12(1H, dd, J=8.4 and 2.0 Hz), 7.18(1H, s), 7.41(1H, d, J=2.0 Hz), 8.02(1H, s)

Preparation Example 49-2

3-Carboxy-4-(2,4-dichlorobenzyl)-5-ethylimidazo[1, 2-b]pyrazole

The objective compound (0.445 g) was obtained from 4-(2,4-dichlorobenzyl)-3-(ethoxycarbonyl)-5-ethylimidazo [1,2-b]pyrazole (0.510 g).

$^1$H-NMR(DMSO-$d_6$, δ ppm): 1.13(3H, dt, J=7.3 and 1.7 Hz), 2.45(2H, q, J=7.3 Hz), 5.75(2H, s), 6.50(1H, d, J=8.3 Hz), 7.34(1H, d, J=8.4 Hz), 7.66(2H, d, J=8.3 Hz), 7.83(1H, s), 11.82(1H, brs)

Preparation Example 50-1

5-(4-Cyanophenylamino)methylidene-2,2-dimethyl-1,3-dioxane-4,6-dione

A mixture of p-aminobenzonitrile (2.00 g), Meldrum's acid (2.56 g), ethyl orthoformate (2.76 g) and ethanol (10 ml) was heated at 120° C. (bath temperature) to evaporate the ethanol. Ethyl acetate was added to the obtained orange solid. The solid was pulverized, collected by filtration and washed with ethyl acetate to give the object compound (3.28 g) as a white powder.

$^1$H-NMR(CDCl$_3$): 1.77 (6H, s), 7.34 (2H, d, J=8 Hz), 7.73 (2H, d, J=8 Hz), 8.67 (1H, d, J=15 Hz), 11.24 (1H, br)

Preparation Example 50-2

4-Hydroxy-6-quinolinecarbonitrile

A mixture of biphenyl (10 ml) and diphenyl ether (30 ml) was heated at 250° C. and 5-(4-cyanophenylamino) methylidene-2,2-dimethyl-1,3-dioxane-4,6-dione (3.28 g) was added thereto. The mixture was stirred for 1 hr. The reaction mixture was cooled to 80° C. while stirring and hexane (100 ml) was added. The mixture was stirred in an ice bath for 0.5 hr. The resulting solid was collected by filtration and washed with hexane to give the object compound (1.86 g) as a yellow-brown powder.

$^1$H-NMR(DMSO-$d_6$): 6.15 (1H, d, J=7 Hz), 7.67 (1H, d, J=8 Hz), 7.96–8.04 (2H, m), 8.42 (1H, d, J=4 Hz)

Preparation Example 50-3

4-Chloro-6-quinolinecarbonitrile

Phosphorus oxychloride (0.518 ml) was added to DMF (9 ml) at an inner temperature of 5–7° C. while stirring under ice-cooling, and the mixture was stirred at room temperature for 0.5 hr. 4-Hydroxy-6-quinolinecarbonitrile (860 mg) was added while stirring under ice-cooling and the mixture was stirred under ice-cooling for 1 hr. 1N aqueous sodium hydroxide solution (18 ml) was added and the mixture was stirred at room temperature for 10 min. The precipitate was collected by filtration and washed with water to give a pale brown powder. The obtained powder was purified by silica gel column chromatography (eluent: chloroform-methanol=50/1) to give the object compound (800 mg) as a pale yellow powder.

$^1$H-NMR(CDCl$_3$): 7.62 (1H, d, J=7 Hz), 7.93 (1H, d, J=8 Hz), 8.23 (1H, d, J=8 Hz), 8.65 (1H, d, J=4 Hz), 8.92 (1H, d, J=7 Hz)

Preparation Example 50-4

Methyl 4-methoxy-6-quinolinecarboxylate

To a suspension of 4-chloro-6-quinolinecarbonitrile (910 mg) in methanol (50 ml) was dropwise added slowly concentrated sulfuric acid (5 ml) while stirring under ice-cooling. The mixture was heated under reflux for 15 hr and concentrated sulfuric acid (10 ml) was added. The mixture was further heated under reflux for 24 hr. An aqueous sodium hydrogencarbonate solution was added thereto under ice-cooling to make the reaction mixture basic. The reaction mixture was extracted once with chloroform. The organic layer was washed once with water and saturated brine, respectively, and dried over magnesium sulfate. The organic layer was concentrated to dryness under reduced pressure to give a white solid. The solid was pulverized by IPE to give the object compound (910 mg) as a white powder.

$^1$H-NMR(CDCl$_3$): 3.98 (3H, s), 4.08 (3H, s), 6.80 (1H, d, J=7 Hz), 8.05 (1H, d, J=8 Hz), 8.29 (1H, d, J=8 Hz), 8.83 (1H, d, J=7 Hz), 8.97 (1H, d, J=4 Hz)

Preparation Example 50-5

Methyl 4-bromo-6-quinolinecarboxylate

To a solution of methyl 4-methoxy-6-quinolinecarboxylate (910 mg) in DMF (7 ml) was added phosphorus tribromide (1.57 ml) while stirring under ice-cooling. DMF (7 ml) was added and the mixture was heated at 80° C. for 3 hr. To the reaction mixture was added water (50 ml) and the reaction mixture was made weak basic with a 1N aqueous sodium hydroxide solution. The resulting precipitate was collected by filtration and purified by silica gel column chromatography (eluent: chloroform-methanol=100/0-100/1) to give the object compound (420 mg) as a yellow powder.

$^1$H-NMR(CDCl$_3$): 4.03 (s, 3H), 7.78 (1H, d, J=7 Hz), 8.15 (1H, d, J=8 Hz), 8.36 (1H, d, J=8 Hz), 8.77 (1H, d, J=7 Hz), 8.95 (1H, d, J=4 Hz)

Preparation Example 50-6

4-(4-Phenylphenyloxy)-6-quinolinecarboxylic acid

60% Sodium hydride (38 mg) was suspended in dimethylimidazolinone (1 ml). 4-Phenylphenol (160 mg) was added while stirring under water-cooling, and the mixture was stirred under water-cooling for 0.5 hr. Methyl 4-bromo-6-quinolinecarboxylate (100 mg) was added under water-cooling and the mixture was stirred at 100° C. for 5 hr, and then at 140° C. for 3 hr. Water (10 ml) was added to the reaction mixture and the mixture was extracted once with ethyl acetate. The aqueous layer was made adjusted to pH 4 with 1N hydrochloric acid and the resulting solid was collected by filtration to give the object compound (73 mg) as a pale brown powder.

$^1$H-NMR(DMSO-d$_6$): 6.78 (1H, d, J=7 Hz), 7.37–7.53 (5H, m), 7.72 (2H, d, J=8 Hz), 7.84 (2H, d, J=8 Hz), 8.11 (1H, d, J=8 Hz), 8.29 (1H, d, J=8 Hz), 8.82 (1H, d, J=7 Hz), 8.97 (1H, s)

Preparation Example 50-7

4-Bromo-6-quinolinecarboxylic acid

Methyl 4-bromo-6-quinolinecarboxylate (6.00 g) was dissolved in methanol (60 ml) and tetrahydrofuran (40 ml). A 1N aqueous sodium hydroxide solution (30 ml) was added to the solution while stiring at room temperature and the mixture was stirred at room temperature for 3 hr. A 1N aqueous sodium hydroxide solution (20 ml) was added and the mixture was heated under reflux for 2 hr. The reaction mixture was adjusted to pH 4 with 1N hydrochloric acid. The resulting solid was collected by filtration and washed with water and ether to give 4-bromo-6-quinolinecarboxylic acid (4.65 g) as a white powder.

$^1$H-NMR(DMSO-d$_6$): 8.06 (1H, d, J=7 Hz), 8.18 (1H, d, J=8 Hz), 8.30 (1H, d, J=8 Hz), 8.77 (1H, s), 8.83 (1H, d, J=7 Hz)

Preparation Example 50-8

4-(4-Phenylbenzyloxy)-6-quinolinecarboxylic acid

In the same manner as in Preparation Example 50-6, the object compound (1.04 g) was obtained as a white powder from 4-bromo-6-quinolinecarboxylic acid (731 mg).

$^1$H-NMR(DMSO-d$_6$): 5.49 (2H, s), 7.26 (1H, d, J=7 Hz), 7.35–7.51 (3H, m), 7.64–7.79 (6H, m), 8.04 (1H, d, J=8 Hz), 8.21 (1H, d, J=8 Hz), 8.80 (1H, s), 8.86 (1H, d, J=7 Hz)

Preparation Example 51-1

Methyl 3-(4-phenylbenzyl)-2-methylbenzo[b]thiophene-5-carboxylate

In the same manner as in Preparation Example 1-1, the object compound (263 mg) was obtained as pale yellow crystals from methyl 2-methylbenzo-[b]thiophene-5-carboxylate (200 mg).

$^1$H-NMR(CDCl$_3$): 2.52(3H, s), 3.87(3H, s), 7.39–7.51 (3H, m), 7.63–7.72(4H, m), 7.84(1H, d, J=8 Hz), 7.92–7.97 (2H, m), 8.00(1H, dd, J=2, 8 Hz), 8.30(1H, s)

Preparation Example 51-2

Methyl 3-((4-phenylphenyl)methyl)-2-methylbenzo[b]thiophene-5-carboxylate

In the same manner as in Preparation Example 1-2, the object compound (177 mg) was obtained as white crystals from methyl 3-(4-phenylbenzyl)-2-methylbenzo[b]thiophene-5-carboxylate (240 mg).

$^1$H-NMR(CDCl$_3$): 2.55(3H, s), 3.90(3H, s), 4.23(2H, s), 7.20–7.24(2H, m), 7.28–7.57(7H, m), 7.80(1H, d, J=8 Hz), 7.92(1H, dd, J=2, 8 Hz), 8.30(1H, s)

Preparation Example 51-3

3-((4-Phenylphenyl)methyl)-2-methylbenzo[b]thiophene-5-carboxylic acid

In the same manner as in Preparation Example 4-7, the object compound (134 mg) was obtained as pale yellow crystals from methyl 3-((4-phenylphenyl)methyl)-2-methylbenzo[b]thiophene-5-carboxylate (153 mg).

$^1$H-NMR(DMSO-d$_6$): 2.59(3H, s), 4.23(2H, s), 7.23–7.34 (3H, m), 7.42(2H, t, J=7 Hz), 7.52–7.61(4H, m), 7.83(1H, d, J=8 Hz), 7.92(1H, d, J=8 Hz), 8.20(1H, s)

Preparation Example 52-1

Methyl 3-(2-chlorobenzyl)-2-methylbenzo[b]thiophene-5-carboxylate

In the same manner as in Preparation Example 16-2, the object compound (220 mg) was obtained as pale yellow crystals from methyl 2-methylbenzo-[b]thiophene-5-carboxylate (200 mg).

$^1$H-NMR(CDCl$_3$): 2.40(3H, s), 3.89(3H, s), 7.38–7.52 (4H, m), 7.80(1H, d, J=8 Hz), 8.00(1H, d, J=8 Hz), 8.52(1H, s)

Preparation Example 52-2

Methyl 3-((2-chlorophenyl)hydroxymethyl)-2-methylbenzo[b]thiophene-5-carboxylate In the same manner as in Preparation Example 35-5, the object compound (189 mg) was obtained as pale yellow crystals from methyl 3-(2-chlorobenzoyl)-2-methylbenzo[b]thiophene-5-carboxylate (207 mg).

$^1$H-NMR(CDCl$_3$): 2.52(3H, s), 3.89(3H, s), 6.51(1H, s), 7.20–7.38(3H, m), 7.68(1H, dd, J=2, 8 Hz), 7.76(1H, dd, J=2, 8 Hz), 7.90(1H, s), 8.51(1H, s)

Preparation Example 52-3

Methyl 3-(2-chlorobenzyl)-2-methylbenzo[b]thiophene-5-carboxylate

In the same manner as in Preparation Example 35-6, the object compound (162 mg) was obtained as white crystals from methyl 3-((2-chlorophenyl)hydroxymethyl)-2-methylbenzo[b]thiophene-5-carboxylate (170 mg).

$^1$H-NMR(CDCl$_3$): 2.47(3H, s), 3.89(3H, s), 4.26(2H, s), 6.69(1H, d, J=7 Hz), 7.02(1H, t, J=7 Hz), 7.13(1H, t, J=7 Hz), 7.42(1H, d, J=7 Hz), 7.82(1H, d, J=8 Hz), 7.93(1H, d, J=8 Hz), 8.17(1H, s)

Preparation Example 52-4

3-(2-Chlorobenzyl)-2-methylbenzo[b]thiophene-5-carboxylic acid

In the same manner as in Preparation Example 4-7, the object compound (137 mg) was obtained as white crystals from methyl 3-(2-chlorobenzyl)-2-methylbenzo[b]thiophene-5-carboxylate (145 mg).

$^1$H-NMR(DMSO-d$_6$): 2.52(3H, s), 4.27(2H, s), 6.80(1H, d, J=7 Hz), 7.17(1H, t, J=7 Hz), 7.23(1H, t, J=7 Hz), 7.51(1H, d, J=8 Hz), 7.83(1H, dd, J=2, 8 Hz), 8.02(1H, d, J=8 Hz), 8.04(1H, s)

Preparation Example 53-1

3-Nitro-4-propylbenzoic acid

In the same manner as in Preparation Example 39-1, the object compound (31.0 g) was obtained as white crystals from 4-propylbenzoic acid (25.0 g) and fuming nitric acid (60 ml).

$^1$H-NMR(CDCl$_3$, δ ppm): 1.02(3H, t, J=7.4 Hz), 1.67–1.76(2H, m), 2.94(2H, t, J=7.8 Hz), 7.49(1H, d, J=8.0 Hz), 8.22(1H, dd, J=8.0 and 1.7 Hz), 8.59(1H, d, J=1.8 Hz)

Preparation Example 53-2

Methyl 3-amino-4-propylbenzoate

To 3-nitro-4-propylbenzoic acid (31.0 g) were added sulfuric acid (1.0 g) and methanol (300 ml) and the mixture was heated under reflux for 24 hr. After cooling, 5% Pd-C (0.60 g) was added to the reaction mixture and the mixture was stirred under a hydrogen atmosphere (normal pressure) for 6 hr. The reaction mixture was filtered through Celite and concentrated. To the residue was added a saturated aqueous sodium hydrogencarbonate solution, and the mixture was extracted with toluene. The toluene layer was dried over sodium sulfate and concentrated to give the object compound (28.7 g) as an brown oil.

$^1$H-NMR(CDCl$_3$, δ ppm): 1.00(3H, t, J=7.4 Hz), 1.62–1.71(2H, m), 2.50(2H, t, J=7.7 Hz), 3.72(2H, brs), 3.88(3H, s), 7.09(1H, d, J=7.8 Hz), 7.34(1H, d, J=1.7 Hz), 7.39(1H, dd, J=7.8 and 1.7 Hz)

Preparation Example 53-3

3-Ethyl-6-(methoxycarbonyl)-1H-indazole

To a solution of methyl 3-amino-4-propylbenzoate (5.07 g) in acetic acid (150 ml) was dropwise added a solution of sodium nitrite (2.07 g) in water (5 ml) for 5 min. After stirring for 20 min, the reaction mixture was concentrated, and then toluene and a saturated aqueous sodium hydrogencarbonate solution were added to the residue. The separated toluene layer was dried over sodium sulfate and concentrated. The residue was allowed to stand and partially solidified. The solid was washed with hexane and dried to give the object compound (2.44 g) as a brown solid.

$^1$H-NMR(CDCl$_3$, δ ppm): 1.43(3H, t, J=7.6 Hz), 3.04(2H, quartet, J=7.6 Hz), 3.97(3H, s), 7.75(1H, dd, J=8.4 and 0.8 Hz), 7.81(1H, dd, J=8.4 and 1.3 Hz), 8.19(1H, d, J=0.9 Hz)

Preparation Example 53-4

1-(2,4-Dichlorobenzyl)-3-ethyl-6-(methoxycarbonyl)-1H-indazole

In the same manner as in Preparation Example 39-5, a crude product of the object compound (3.73 g) was obtained from 3-ethyl-6-(methoxycarbonyl)-1H-indazole (1.84 g), 60% sodium hydride (0.36 g) and 2,4-dichlorobenzyl chloride. The crude product was used in the next step without purification.

$^1$H-NMR(CDCl$_3$, δ ppm): 1.42(3H, t, J=7.6 Hz), 3.04(2H, quartet, J=7.6 Hz), 3.94(3H, s), 5.65(2H, s), 6.56(1H, d, J=8.4 Hz), 7.07(1H, dd, J=8.4 and 2.0 Hz), 7.43(1H, d, J=2.1 Hz), 7.76(1H, d, J=8.4 Hz), 7.81(1H, dd, J=8.4 and 1.0 Hz), 8.05(1H, d, J=1.0 Hz)

Preparation Example 53-5

6-Carboxy-1-(2,4-dichlorobenzyl)-3-ethyl-1H-indazole

In the same manner as in Preparation Example 39-6, the object compound (2.10 g) was obtained as brown crystals from the unpurified 1-(2,4-dichlorobenzyl)-3-ethyl-6-(methoxycarbonyl)-1H-indazole (3.70 g).

$^1$H-NMR(DMSO-d$_6$, δ ppm): 1.29(3H, t, J=7.6 Hz), 2.94 (2H, quartet, J=7.5 Hz), 5.73(2H, s), 6.77(1H, d, J=8.4 Hz), 7.33(1H, dd, J=8.4 and 2.0 Hz), 7.65–7.69(2H, m), 7.87(1H, d, J=8.4 Hz), 8.23(1H, s)

Preparation Example 54-1

6-Carbamoyl-3-(2,4-dichlorobenzyl)-2-methylimidazo[1,2-a]pyridine

A mixture of 3-bromo-4-(2,4-dichlorophenyl)-2-butanone (2.14 g), which was synthesized according to a method described in GB205177A, and 6-aminonicotinamide (2.10 g) in dimethylformamide (5 ml) was stirred at 100° C. for 64 hr. After concentration of the reaction mixture, the residue was washed with water and toluene and dried to give a crude product of the object compound (2.00 g) as a brown solid. The crude product was used in the next step without further purification.

Preparation Example 54-2

6-Carboxy-3-(2,4-dichlorobenzyl)-2-methylimidazo[1,2-a]pyridine

The crude product of 6carbamoyl-3-(2,4-dichlorobenzyl)-2-methylimidazo[1,2-a]pyridine (2.00 g) in a mixture of concentrated sulfuric acid (8.0 g) and water (8.0 g) was stirred at 100° C. for 1 hr. After cooling of the reaction mixture, ice was added and the precipitate was collected by filtration. The precipitate was washed with water and dried to give a crude product of the object compound (1.50 g) as a brown solid. The crude product was used in the next step without further purification.

$^1$H-NMR(DMSO-d$_6$, δ ppm): 2.31(31H, s), 4.45(2H, s), 6.88(1H, d, J=8.4 Hz), 7.30(1H, dd, J=8.3 and 2.1 Hz), 7.56(1H, d, J=8.8 Hz), 7.61–7.66(1H, m), 7.67(1H, d, J=2.2 Hz), 8.63(1H, s)

Preparation Example 55

Methyl 2-methyl-3H-imidazo[4,5-b]pyridine-5-carboxylate

In the same manner as in Preparation Example 26-2, the object compound (330 mg) was obtained as white crystals from 5-bromo-2-methyl-3H-imidazo[4,5-b]pyridine (1.06 g).

$^1$H-NMR(CDCl$_3$): 2.80(3H, s), 4.03(3H, s), 8.07(2H, d, J=8 Hz)

Preparation Example 56-1

Methyl 3-(2,3-dichlorobenzyl)-2-methyl-3H-imidazo[4,5-b]pyridine-5-carboxylate

In the same manner as in Preparation Example 14-2, the object compound (70 mg) was obtained as white crystals from methyl 2-methyl-3H-imidazo[4,5-b]pyridine-5-carboxylate.

$^1$H-NMR(CDCl$_3$): 2.62(3H, s), 4.00(3H, s), 5.72(2H, s), 6.50(1H, d, J=8 Hz), 7.07(1H, t, J=8 Hz), 7.43(1H, d, J=8 Hz), 8.17(2H, q, J=8 Hz)

Preparation Example 56-2

Methyl 3-((3-chlorobenzo[b]thiophene-2-ylmethyl)-2-methyl-3H-imidazo[4,5-b]pyridine-5-carboxylate In the same manner as in Preparation Example 14-2, the object compound (111 mg) was obtained as white crystals from methyl 2-methyl-3H-imidazo[4,5-b]pyridine-5-carboxylate (106 mg).

$^1$H-NMR(CDCl$_3$): 2.68(3H, s), 4.03(3H, s), 5.88(2H, s), 7.35–7.48(2H, m), 7.68(1H, d, J=8 Hz), 7.83(1H, d, J=8 Hz), 8.04(1H, d, J=8 Hz), 8.16(1H, d, J=8 Hz)

Preparation Example 57-1

3-(2,3-Dichlorobenzyl)-2-methyl-3H-imidazo[4,5-b]pyridine-5-carboxylic acid

In the same manner as Preparation Example 4-7, the object compound (55 mg) was obtained as white crystals from methyl 3-(2,3-dichlorobenzyl)-2-methyl-3H-imidazo[4,5-b]pyridine-5-carboxylate (63 mg).

$^1$H-NMR(DMSO-d$_6$): 2.52(3H, s), 5.65(2H, s), 6.46(1H, d, J=8 Hz), 7.25(1H, t, J=8 Hz), 7.63(1H, d, J=8 Hz), 8.02(1H, d, J=8 Hz), 8.16(1H, d, J=8 Hz)

Preparation Example 57-2

3-((3-Chlorobenzo[b]thiophene-2-yl)methyl)-2-methyl-3H-imidazo[4,5-b]pyridine-5-carboxylic acid In the same manner as in Preparation Example 4-7, the object compound (82 mg) was obtained as white crystals from methyl 3-((3-chlorobenzo[b]-thiophene-2-yl)methyl)-2-methyl-3H-imidazo[4,5-b]pyridine-5-carboxylate (95 mg).

$^1$H-NMR(DMSO-d$_6$): 2.65(3H, s), 5.90(2H, s), 7.42–7.55 (2H, m), 7.81(1H, d, J=8 Hz), 7.93(1H, d, J=8 Hz), 8.02(1H, d, J=8 Hz), 8.13(1H, d, J=8 Hz)

Preparation Example 58-1

Methyl 3-((2-chloro-4-phenylphenyl)methyl)-2-methylbenzo[b]thiophene-5-carboxylate The object compound (288 mg) was obtained as white crystals from methyl 3-(4-bromo-2-chlorobenzyl)-2-methylbenzo[b]thiophene-5-carboxylate (484 mg).

Preparation Example 58-2

3-((2-Chloro-4-phenylphenyl)methyl)-2-methylbenzo[b]thiophene-5-carboxylic acid

In the same manner as in Preparation Example 4-7, the object compound (237 mg) was obtained as white crystals from methyl 3-((3-chloro-4-phenylphenyl)methyl)-2-methylbenzo[b]thiophene-5-carboxylate (273 mg).

$^1$H-NMR(DMSO-d$_6$): 2.55(3H, s), 4.31(2H, s), 6.84(1H, d, J=8 Hz), 7.32–7.48(4H, m), 7.62–7.66(2H, m), 7.81(1H, s), 7.83(1H, d, J=8 Hz), 8.04(1H, d, J=8 Hz), 8.08(1H, s)

Preparation Example 59

3-Chlorobenzo[b]thiophene-2-methylene chloride

In the same manner as in Preparation Example 14-1, the object compound (220 mg) was obtained as white crystals from 3-chlorobenzo[b]thiophene-2-methanol (200 mg).

$^1$H-NMR(CDCl$_3$): 4.92(2H, s), 7.39–7.50(2H, m), 7.78–7.83(2H, m)

Preparation Example 60-1

1-(2-Chloro-4-phenylbenzyl)-6-(methoxycarbonyl)-3-methyl-1H-indazole

In the same manner as in Preparation Example 39-5, a crude product of the object compound (1.10 g) was obtained from 6-(methoxycarbonyl)-3-methyl-1H-indazole (0.475 g), 60% sodium hydride (0.10 g) and 2-chloro-4-phenylbenzyl bromide (0.70 g). The crude product was used in the next step without purification.

$^1$H-NMR(CDCl$_3$, δ ppm): 2.64(3H, s), 3.94(3H, s), 5.73 (2H, s), 6.74(1H, d, J=8.1 Hz), 7.31(1H, dd, J=8.1 and 1.8 Hz), 7.33–7.38(1H, m), 7.42(2H, t, J=7.5 Hz), 7.50–7.53 (2H, m), 7.64–7.67(2H, m), 7.74(1H, d, J=8.4 Hz), 7.82(1H, dd, J=8.4 and 1.3 Hz), 8.13(1H, s)

Preparation Example 60-2

6-Carboxy-1-(2-chloro-4-phenylbenzyl)-3-methyl-1H-indazole

In the same manner as in Preparation Example 39-6, the object compound (0.85 g) was obtained from 1-(2-chloro-4-phenylbenzyl)-6-(methoxycarbonyl)-3-methyl-1H-indazole (1.10 g).

$^1$H-NMR(DMSO-$d_6$, δ ppm): 2.67(3H, s), 5.77(2H, s), 6.91(1H, d, J=8.1 Hz), 7.37(1H, t, J=7.3 Hz), 7.44(2H, t, J=7.5 Hz), 7.54(1H, dd, J=8.2 and 1.7 Hz), 7.65(2H, d, J=7.5 Hz), 7.67–7.71(1H, m), 7.77(1H, d, J=1.7 Hz), 7.84(1H, d, J=8.4 Hz), 8.28(1H, s)

Preparation Example 61-1

1-(4-Bromo-2-chlorobenzyl)-6-(methoxycarbonyl)-3-methyl-1H-indazole

In the same manner as in Preparation Example 39-5, a crude product of the object compound (2.00 g) was obtained from 6-(methoxycarbonyl)-3-methyl-1H-indazole (0.63 g), 60% sodium hydride (0.13 g) and 4-bromo-2-chlorobenzyl chloride (1.30 g). The crude product was used in the next step without purification.

Preparation Example 61-2

1-(4-Bromo-2-chlorobenzyl)-6-carboxy-3-methyl-1H-indazole

In the same manner as in Preparation Example 39-6, the object compound (1.00 g) was obtained from the unpurified 1-(4-bromo-2-chlorobenzyl)-6-(methoxycarbonyl)-3-methyl-1H-indazole (2.00 g).

$^1$H-NMR(DMSO-$d_6$, δ ppm): 2.50(3H, s), 5.70(2H, s), 6.77(1H, d, J=8.4 Hz), 7.46(1H, dd, J=8.3 and 2.0 Hz), 7.68(1H, dd, J=8.4 and 1.0 Hz), 7.77(1H, d, J=2.0 Hz), 7.82(1H, d, J=8.5 Hz), 8.24(1H, s)

Preparation Example 62-1

3-(4-Bromo-2-chlorobenzoyl)-5-(methoxycarbonyl)-2-methylbenzo[b]furan

In the same manner as in Preparation Example 31-2, the object compound (3.09 g) was obtained as pale yellow crystals from 5-(methoxycarbonyl)-2-methylbenzo[b]furan (1.90 g), 4-bromo-2-chlorobenzoyl chloride (2.80 g) and aluminum chloride (2.67 g).

$^1$H-NMR(CDCl$_3$, δ ppm): 2.43(3H, s), 3.924(3H, s), 7.31(1H, d, J=8.2 Hz), 7.49(1H, d, J=8.6 Hz),7.59(1H, d, J=8.1 Hz), 7.70(1H, d, J=1.4 Hz), 8.05(1H, d, J=8.5 Hz), 8.28(1H, s)

Preparation Example 62-2

3-(4-Bromo-2-chlorobenzyl)-5-(methoxycarbonyl)-2-methylbenzo[b]furan

In the same manner as in Preparation Example 31-3, a pale yellow oil (4.00 g) containing the object compound as a main component was obtained from 3-(4-bromo-2-chlorobenzoyl)-5-(methoxycarbonyl)-2-methylbenzo[b]furan (3.09 g). The oil was used in the next step without purification.

$^1$H-NMR(CDCl$_3$, δ ppm): 2.40(3H, s), 3.89(3H, s), 4.01 (2H, s), 6.89(1H, d, J=8.5 Hz), 7.25(1H, d, J=8.3 Hz), 7.42(1H, d, J=8.7 Hz), 7.57(1H, d, J=1.9 Hz), 7.94(1H, dd, J=8.5 and 1.5 Hz), 7.98(1H,s)

Preparation Example 62-3

3-(2-Chloro-4-phenylbenzyl)-5-(methoxycarbonyl)-2-methylbenzo[b]furan

To unpurified 3-(4-bromo-2-chlorobenzyl)-5-(methoxycarbonyl)-2-methylbenzo[b]furan (4.00 g) were added a solution of phenylboric acid (1.34 g) in ethanol (3 ml), tetrakis(triphenylphosphine)palladium (0.40 g), sodium carbonate (1.59 g), water (7.50 g) and toluene (30 ml) and the mixture was heated under reflux for 80 min. After cooling, the insoluble matter was removed by filtration through Celite and the filtrate was washed with ethyl acetate and water. Saturated brine was added to the filtrate. The organic layer was separated, dried over anhydrous magnesium sulfate and concentrated to give an oil (3.50 g) containing the object compound as main component. The oil was used in the next step without purification.

$^1$H-NMR(CDCl$_3$, δ ppm): 2.44(3H, s), 3.89(3H, s), 4.12(2H, s), 7.09–8.09(11H, m)

Preparation Example 62-4

5-Carboxy-3-(2-chloro-4-phenylbenzyl)-2-methylbenzo[b]furan

In the same manner as in Preparation Example 31-4, the object compound (1.22 g) was obtained as pale yellow crystals from the unpurified 3-(2-chloro-4-phenylbenzyl)-5-(methoxycarbonyl)-2-methylbenzo[b]furan (3.50 g).

$^1$H-NMR(DMSO-$d_6$, δ ppm): 2.48(3H, s), 4.15(2H, s), 7.30(1H, d, J=8.1 Hz), 7.36(1H, t, J=7.3 Hz), 7.44(2H, t, J=7.6 Hz), 7.56(1H, dd, J=8.0 and 1.9 Hz), 7.57(1H, d, J=8.6 Hz), 7.66(2H, d, J=7.4 Hz), 7.75(1H, d, J=1.9 Hz), 7.82(1H, dd, J=8.6 and 1.7 Hz), 7.95(1H, d, J=1.5 Hz)

Preparation Example 63

3-(4-Bromo-2-chlorobenzyl)-5-carboxy-2-methylbenzo[b]furan

In the same manner as in Preparation Example 31-4, the object compound (0.67 g) was obtained as pale yellow crystals from 3-(4-bromo-2-chlorobenzyl)-5-(methoxycarbonyl)-2-methylbenzo[b]furan (1.15 g).

$^1$H-NMR(DMSO-$d_6$, δ ppm): 2.44(3H, s), 4.08(2H, s), 7.18(1H, d, J=8.3 Hz), 7.47(1H, dd, J=8.3 and 2.0 Hz), 7.56(1H, d, J=8.5 Hz), 7.74(1H, d, J=2.1 Hz), 7.82(1H, dd, J=8.6 and 1.7 Hz), 7.89(1H, d, J=1.6 Hz)

Preparation Example 64-1

Methyl 3-(2,4-dichlorobenzyl)-2-methyl-3H-imidazo[4,5-b]pyridine-5-carboxylate and methyl 1-(2,4-dichlorobenzyl)-2-methyl-1H-imidazo[4,5-b]pyridine-5-carboxylate In the same manner as in Preparation Example 14-2, methyl 3-(2,4-dichlorobenzyl)-2-methyl-3H-imidazo[4,5-b]pyridine-5-carboxylate (2.20 g) and methyl 1-(2,4-dichlorobenzyl)-2-methyl-1H-imidazo[4,5-b]pyridine-5-carboxylate (2.00 g) were obtained as a pale yellow powder from methyl 2-methyl-1H-imidazo[4,5-b]pyridine-5-carboxylate (2.68 g) and 2,4-dichlorobenzyl chloride (3.29 g).

Methyl 3-(2,4-dichlorobenzyl)-2-methyl-3H-imidazo[4,5-b]pyridine-5-carboxylate $^1$H-NMR(CDCl$_3$): 2.53(3H, s), 3.99(3H, s), 5.63(2H, s), 6.60(1H, d, J=8 Hz), 7.10(1H, dd, J=8 and 2 Hz), 7.47(1H, d, J=2 Hz), 8.07(1H, d, J=8 Hz), 8.14(1H, d, J=8 Hz)

Mass(ESI): m/e 350 (M+H)$^+$

Methyl 1-(2,4-dichlorobenzyl)-2-methyl-1H-imidazo[4,5-b]pyridine-5-carboxylate $^1$H-NMR(CDCl$_3$): 2.64(3H, s), 4.02(3H, s), 5.41(2H, s), 6.43(1H, d, J=8 Hz), 7.14(1H, dd, J=8 and 2 Hz), 7.50(1H, d, J=2 Hz), 7.54(1H, d, J=8 Hz), 8.08(1H, d, J=8 Hz)

Mass(ESI): m/e 350 (M+H)$^+$

Preparation Example 64-2

3-(2,4-Dichlorobenzyl)-2-methyl-3H-imidazo[4,5-b]pyridine-5-carboxylic acid

In the same manner as in Preparation Example 4-7, the object compound (1.98 g) was obtained as a white powder from methyl 3-(2,4-dichlorobenzyl)-2-methyl-3H-imidazo[4,5-b]pyridine-5-carboxylate (2.17 g).

$^1$H-NMR(DMSO-d$_6$): 2.51(3H, s), 5.60(2H, s), 6.60(1H, d, J=8 Hz), 7.32(1H, d, J=8 Hz), 7.76(1H, s), 8.00(1H, d, J=8 Hz), 8.13(1H, d, J=8 Hz)

Mass(ESI): m/e 334 (M−H)$^-$

Preparation Example 65-1

2-Chloro-4-(thiophene-2-yl)benzyl alcohol

In the same manner as in Preparation Example 11-2, the object compound (196 mg) was obtained as a pale yellow oil from 4-bromo-2-chlorobenzyl alcohol (500 mg) and 2-thiopheneboronic acid (318 mg).

$^1$H-NMR(CDCl$_3$): 1.93(1H, t, J=8 Hz), 4.79(2H, d, J=8 Hz), 7.09(1H, t, J=3 Hz), 7.29–7.34(2H, m), 7.46–7.54(2H, m), 7.61(1H, s)

Preparation Example 65-2

2-Chloro-1-((methanesulfonyloxy)methyl)-4-(thiophen-2-yl)benzene

In the same manner as in Preparation Example 14-1, the object compound was obtained from 2-chloro-4-(thiophen-2-yl)benzyl alcohol (196 mg). This compound was used in the next step without purification.

Preparation Example 65-3

Methyl 3-[2-chloro-4-(thiophen-2-yl)benzyl]-2-methyl-3H-imidazo[4,5-b]pyridine-5-carboxylate and methyl 1-[2-chloro-4-(thiophen-2-yl)benzyl]-2-methyl-1H-imidazo[4,5-b]pyridine-5-carboxylate In the same manner as in Preparation Example 14-2, methyl 3-[2-chloro-4-(thiophen-2-yl)benzyl]-2-methyl-3H-imidazo[4,5-b]pyridine-5-carboxylate was obtained as an amorphous (120 mg), and methyl 1-[2-chloro-4-(thiophen-2-yl)benzyl]-2-methyl-1H-imidazo[4,5-b]pyridine-5-carboxylate was obtained as an amorphous (86 mg) from methyl 2-methyl-3H-imidazo[4,5-b]pyridine-5-carboxylate (148 mg) and 2-chloro-1-((methanesulfonyloxy)methyl)-4-(thiophen-2-yl)benzene (210 mg).

Methyl 3-[2-chloro-4-(thiophen-2-yl)benzyl]-2-methyl-3H-imidazo[4,5-b]pyridine-5-carboxylate $^1$H-NMR(CDCl$_3$): 2.58(3H, s), 4.00(2H, s), 5.69(2H, s), 6.65(1H, d, J=8 Hz), 7.08(1H, t, J=4 Hz), 7.25–7.36(3H, m), 7.69(1H, d, J=2 Hz), 8.08(1H, d, J=8 Hz), 8.16(1H, d, J=8 Hz)

Mass(ESI): m/z 398 (M+1)

Methyl 1-[2-chloro-4-(thiophen-2-yl)benzyl]-2-methyl-1H-imidazo[4,5-b]pyridine-5-carboxylate $^1$H-NMR(CDCl$_3$): 2.68(3H, s), 4.01(2H, s), 5.45(2H, s), 6.50(1H, d, J=8 Hz), 7.09(1H, t, J=4 Hz), 7.28–7.39(3H, m), 7.58(1H, d, J=8 Hz), 7.70(1H, br s), 8.08(1H, d, J=8 Hz)

Mass(ESI): m/z 398 (M+1)

Preparation Example 65-4

3-[2-Chloro-4-(thiophen-2-yl)benzyl]-2-methyl-3H-imidazo[4,5-b]pyridine-5-carboxylic acid In the same manner as in Preparation Example 4-2, the object compound (61 mg) was obtained as colorless crystals from methyl 3-[2-chloro-4-(thiophen-2-yl)benzyl]-2-methyl-3H-imidazo[4,5-b]pyridne-5-carboxylate (70 mg).

$^1$H-NMR(DMSO-d$_6$): 2.53(3H, s), 5.62(2H, s), 6.60(1H, d, J=8 Hz), 7.14(1H, t, J=4 Hz), 7.49(1H, d, J=8 Hz), 7.59(2H, d, J=4 Hz), 7.87(1H, d, J=2 Hz), 8.01(1H, d, J=8 Hz), 8.14(1H, d, J=8 Hz)

Mass(ESI): m/z 382 (M−1)

mp 247–248° C.

Preparation Example 66-1

Methyl 3-[2-chloro-4-(5-chlorothiophen-2-yl)benzyl]-2-methyl-3H-imidazo[4,5-b]pyridine-5-carboxylate To a suspension of methyl 3-[2-chloro-4-(thiophen-2-yl)benzyl]-2-methyl-3H-imidazo[4,5-b]pyridine-5-carboxylate (50 mg, 0.126 mmol) in acetic acid (1 ml) was added N-chlorosuccinimide (19 mg, 0.138 mmol) at room temperature. Thirty minutes later, dichloromethane (0.5 ml) was added to the reaction mixture to give a clear transparent solution. Four hours later, N-chlorosuccinimide (19 mg, 0.138 mmol) was further added. The reaction mixture was left standing overnight and concentrated. The residue was purified by p-TLC (chloroform/methanol=40/1) to give the object compound (52 mg, 95.7%) as a colorless oil.

$^1$H-NMR(CDCl$_3$): 2.56(3H, s), 3.99(2H, s), 5.69(2H, s), 6.64(1H, d, J=8 Hz), 6.89(1H, t, J=4 Hz), 7.06(1H, d, J=4 Hz), 7.22(1H, d, J=8 Hz), 7.58(1H, s), 8.08(1H, d, J=8 Hz), 8.16(1H, d, J=8 Hz)

Mass(ESI): m/z 432 (M+1)

Preparation Example 66-2

3-[2-Chloro-4-(5-chlorothiophen-2-yl)benzyl]-2-methyl-3H-imidazo[4,5-b]pyridine-5-carboxylic acid In the same manner as in Preparation Example 4-7, the object compound (33 mg) was obtained as colorless crystals from methyl 3-[2-chloro-4-(5-chlorothiophen-2-yl)benzyl]-2-methyl-3H-imidazo[4,5-b]pyridine-5-carboxylate (50 mg).

$^1$H-NMR(DMSO-d$_6$): 2.53(3H, s), 5.62(2H, s), 6.59(1H, d, J=8 Hz), 7.18(1H, d, J=4 Hz), 7.42(1H, d, J=8 Hz), 7.49(1H, d, J=4 Hz), 7.87(1H, s), 8.01(1H, d, J=8 Hz), 8.14(1H, d, J=8 Hz)

Mass(ESI): m/z 416 (M−1)

mp 242–243° C.

Preparation Example 67-1

2-Chloro-4-vinylbenzyl alcohol

In the same manner as in Preparation Example 11-1, the object compound (1.23 g) was obtained as a colorless solid from 4-bromo-2-chlorobenzyl alcohol (2.0 g) and tributyl(vinyl)tin (3.32 g).

$^1$H-NMR(CDCl$_3$): 1.91(1H, t, J=7 Hz), 4.78(2H, d, J=7 Hz), 5.30(1H, d, J=10 Hz), 5.76(1H, d, J=16 Hz), 6.65(1H, dd, J=16, 10 Hz), 7.30(1H, d, J=8 Hz), 7.39–7.47(2H, m)

Preparation Example 67-2

2-Chloro-1-((methanesulfonyloxy)methyl)-4-vinylbenzene

In the same manner as in Preparation Example 14-1, the object compound was obtained from 2-chloro-4-vinylbenzyl alcohol (600 mg). This compound was used in the next step without purification.

Preparation Example 67-3

Methyl 3-(2-chloro-4-vinylbenzyl)-2-methyl-3H-imidazo[4,5-b]pyridine-5-carboxylate and methyl 1-(2-chloro-4-vinylbenzyl)-2-methyl-1H-imidazo[4,5-b]pyridine-5-carboxylate In the same manner as in Preparation Example 14-2, methyl 3-(2-chloro-4-vinylbenzyl)-2-methyl-3H-imidazo[4,5-b]pyridine-5-carboxylate was obtained as pale yellow crystals (387 mg), and methyl 1-(2-chloro-4-vinylbenzyl)-2-methyl-1H-imidazo[4,5-b]pyridine-5-carboxylate was obtained as an amorphous (264 mg) from methyl 2-methyl-3H-imidazo[4,5-b]pyridine-5-carboxylate (478 mg) and 2-chloro-1-((methanesulfonyloxy)methyl)-4-vinylbenzene (678 mg).

Methyl 3-(2-chloro-4-vinylbenzyl)-2-methyl-3H-imidazo[4,5-b]pyridine-5-carboxylate $^1$H-NMR(CDCl$_3$): 2.53(3H, s), 4.00(2H, s), 5.30(1H, d, J=10 Hz), 5.67(2H, s), 5.73(1H, d, J=16 Hz), 6.56–6.67(2H, m), 7.13(1H, d, J=8 Hz), 7.47(1H, d, J=2 Hz), 8.07(1H, d, J=8 Hz), 8.16(1H, d, J=8 Hz)

Mass(ESI): m/z 342 (M+1)

mp 185–186° C.

Methyl 1-(2-chloro-4-vinylbenzyl)-2-methyl-1H-imidazo[4,5-b]pyridine-5-carboxylate $^1$H-NMR(CDCl$_3$): 2.66(3H, s), 4.01(2H, s), 5.34(1H, d, J=10 Hz), 5.43(2H, s), 5.76(1H, d, J=16 Hz), 6.47(1H, d, J=10 Hz), 6.61(1H, dd, J=16, 10 Hz), 7.15(1H, d, J=8 Hz), 7.50(1H, s), 7.56(1H, d, J=8 Hz), 8.08(1H, d, J=8 Hz)

Mass(ESI): m/z 342 (M+1)

Preparation Example 67-4

Methyl 3-(2-chloro-4-ethylbenzyl)-2-methyl-3H-imidazo[4,5-b]pyridine-5-carboxylate To a solution of methyl 3-(2-chloro-4-vinylbenzyl)-2-methyl-3H-imidazo[4,5-b]pyridine-5-carboxylate (230 mg, 0.67 mmol) in 1,4-dioxane (4.6 ml) was added platinum dioxide (23 mg) and the mixture was subjected to catalytic reduction at normal temperature. Six hours later, the reaction mixture was filtered through Celite and the filtrate was concentrated to give black crystals. The obtained crystals were subjected to flash silica gel chromatography (silica gel 40 ml, eluent: chloroform/ethyl acetate=5/1-4/1) and crystallized from diisopropyl ether to give the object compound (213 mg) as colorless crystals.

$^1$H-NMR(CDCl$_3$): 1.20(3H, d, J=8 Hz), 2.53(3H, s), 2.60(2H, q, J=8 Hz), 3.99(3H, s), 5.65(2H, s), 6.53(1H, d, J=8 Hz), 6.92(1H, d, J=8 Hz), 7.28(1H, s), 8.05(1H, d, J=8 Hz), 8.14(1H, d, J=8 Hz)

Mass(ESI): m/z 344 (M+1)

mp 172–173° C.

Preparation Example 67-5

3-(2-Chloro-4-ethylbenzyl)-2-methyl-3H-imidazo[4,5-b]pyridine-5-carboxylic acid

In the same manner as in Preparation Example 4-7, the object compound (61 mg) was obtained as pale yellow crystals from methyl 3-(2-chloro-4-ethylbenzyl)-2-methyl-3H-imidazo[4,5-b]pyridine-5-carboxylate (209 mg).

$^1$H-NMR(DMSO-d$_6$): 1.14(3H, d, J=8 Hz), 2.50(3H, s), 2.59(2H, q, J=8 Hz), 5.59(2H, s), 6.45(1H, d, J=8 Hz), 7.06(1H, d, J=8 Hz), 7.14(1H, s), 8.00(1H, d, J=8 Hz), 8.12(1H, d, J=8 Hz)

Mass(ESI): m/z 328 (M−1)

mp 194–196° C.

Preparation Example 68

3-(2-Chloro-4-vinylbenzyl)-2-methyl-3H-imidazo[4,5-b]pyridine-5-carboxylic acid

In the same manner as in Preparation Example 4-7, the object compound (128 mg) was obtained as colorless crystals from methyl 3-(2-chloro-4-vinylbenzyl)-2-methyl-3H-imidazo[4,5-b]pyridine-5-carboxylate (150 mg).

$^1$H-NMR(DMSO-d$_6$): 2.5(3H, s), 5.32(1H, d, J=10 Hz), 5.60(2H, s), 5.89(1H, d, J=16 Hz), 6.54(1H, d, J=8 Hz), 6.70(1H, dd, J=16, 10 Hz), 7.32(1H, d, J=8 Hz), 7.71(1H, s), 8.01(1H, d, J=8 Hz), 8.14(1H, d, J=8 Hz)

Mass(ESI): m/z 326 (M−1)

mp 229–230° C.

Preparation Example 69-1

2-Chloro-1-((methanesulfonyloxy)methyl)-4-methylbenzene

In the same manner as in Preparation Example 14-1, the objective compound (383 mg) was obtained as a colorless oil from 2-chloro-4-methylbenzyl alcohol (259 mg).

$^1$H-NMR(CDCl$_3$): 2.35(3H, s), 2.98(3H, s), 5.31(2H, s), 7.11(1H, d, J=8 Hz), 7.26(1H, s), 7.36(1H, d, J=8 Hz)

Preparation Example 69-2

Methyl 3-(2-chloro-4-methylbenzyl)-2-methyl-3H-imidazo[4,5-b]pyridine-5-carboxylate and methyl 1-(2-chloro-4-methylbenzyl)-2-methyl-1H-imidazo[4,5b]pyridine-5-carboxylate In the same manner as in Preparation Example 14-2, methyl 3-(2-chloro-4-methylbenzyl)-2-methyl-3H-imidazo[4,5-b]pyridine-5-carboxylate (74 mg) and methyl 1-(2-chloro-4-methylbenzyl)-2-methyl-1H-imidazo[4,5-b]pyridine-5-carboxylate (80 mg) were obtained as white powders from methyl 2-methyl-1H-imidazo[4,5-b]pyridine-5-carboxylate (152 mg) and 2-chloro-1-((methanesulfonyloxy)methyl)-4-methylbenzene (230 mg).

Methyl 3-(2-chloro-4-methylbenzyl)-2-methyl-3H-imidazo[4,5-b]pyridine-5-carboxylate $^1$H-NMR(CDCl$_3$): 2.29(3H, s), 2.51(3H, s), 3.99(3H, s), 5.64(2H, s), 6.51(1H, d, J=8 Hz), 6.90(1H, d, J=8 Hz), 7.24(1H, s), 8.05(1H, d, J=8 Hz), 8.13(1H, d, J=8 Hz).

Mass(ESI): m/E 330 (M+H)$^+$

Methyl 1-(2-chloro-4-methylbenzyl)-2-methyl-1H-imidazo[4,5-b]pyridine-5-carboxylate $^1$H-NMR(CDCl$_3$): 2.32(3H, s), 2.65(3H, s), 4.01(3H, s), 5.40(2H, s), 6.41(1H, d, J=8 Hz), 6.94(1H, d, J=8 Hz), 7.28(1H, s), 7.54(1H, d, J=8 Hz), 8.06(1H, d, J=8 Hz).

Mass(ESI): m/E 330 (M+H)$^+$

Preparation Example 69-3

3-(2-Chloro-4-methylbenzyl)-2-methyl-3H-imidazo[4,5-b]pyridine-5-carboxylic acid In the same manner as in Preparation Example 4-7, the objective compound (98 mg) was obtained as a white powder from methyl 3-(2-chloro-4-methylbenzyl)-2-methyl-3H-imidazo[4,5-b]pyridine-5-carboxylate (68 mg).

$^1$H-NMR(DMSO-d$_6$): 2.26(3H, s), 2.49(3H, s), 5.59(2H, s), 6.41(1H, d, J=8 Hz), 7.02(1H, d, J=8 Hz), 7.39(1H, s), 8.00(1H, d, J=8 Hz), 8.11(1H, d, J=8 Hz)

Mass(ESI): m/E 314 (M–H)$^-$

Preparation Example 70-1

4-Bromo-1-((tert-butyldiphenylsilyloxy)methyl)-2-chlorobenzene

To a solution of 4-bromo-2-chlorobenzyl alcohol (14.48 g) in N,N-dimethylformamide (72 ml) were added imidazole (5.34 g) and tert-butylchlorodiphenylsilane (19.8 g) under ice-cooling and the mixture was stirred for 1 hr. Water was added to the reaction mixture and the resulting product was extracted twice with hexane. The organic layers were combined, and washed successively with water, a saturated aqueous solution of sodium hydrogencarbonate and saturated brine and dried over anhydrous magnesium sulfate. The solvent was evaporated and the residue was subjected to silica gel column chromatography (hexane) to give the objective compound (29.22 g) as colorless oil.

$^1$H-NMR(CDCl$_3$): 1.10(9H, s), 4.75(2H, s), 7.32–7.50 (8H, m), 7.55–7.72(5H, m)

Preparation Example 70-2

1-((tert-Butyldiphenylsilyloxy)methyl)-2-chloro-4-(n-pentyl)benzene

Tetrahydrofuran (5 ml) was added to magnesium (438 mg, turnings) under a nitrogen atmosphere and a small amount of a solution of 4-bromo-((tert-butyldiphenylsilyloxy)methyl)-2-chlorobenzene (7.92 g) in tetrahydrofuran (10 ml) was dropwise added. Upon confirmation of the initiation of the reaction, the reaction mixture was diluted with tetrahydrofuran (6.5 ml) and heated to 60° C. The remaining starting material was dropwise added over 45 min. After completion of the dropwise addition, the reaction mixture was refluxed under heating for 30 min to give a solution (ca. 0.6 M) of 4-((tert-butyldiphenylsilyloxy)methyl)-3-chlorophenyl magnesium bromide in tetrahydrofuran.

Then, 1-iodopentane (910 mg) was added to a suspension of copper bromide-dimethyl sulfide complex (62 mg) in hexamethylphosphoric triamide (0.3 ml) under a nitrogen atmosphere, and the mixture was heated to 60° C. Thereto was dropwise added the above-mentioned solution (5 ml) of 4-((tert-butyldiphenylsilyloxy)methyl)-3-chlorophenyl magnesium bromide in tetrahydrofuran over 10 min after removal of unreacted magnesium. After completion of the dropwise addition, the reaction mixture was refluxed under heating for 2 hr. Aqueous ammonium chloride was added to the reaction mixture and the resulting product was extracted three times with hexane. The organic layers were combined, washed successively with water and saturated brine, and dried over anhydrous magnesium sulfate. The solvent was evaporated and the residue was subjected to silica gel column chromatography (hexane) to give the objective compound (914 mg) as a colorless oil.

$^1$H-NMR(CDCl$_3$): 0.89(3H, t, J=7 Hz), 1.11(9H, s), 1.22–1.40(4H, m), 1.52–1.68(2H, m), 2.52–2.62(2H, m), 4.80(2H, s), 7.07–7.16(2H, m), 7.31–7.48(6H, m), 7.6(1H, d, J=8 Hz), 7.64–7.74(4H, m), 7.64–7.74(4H, m).

Preparation Example 70-3

2-Chloro-4-(n-pentyl)benzyl alcohol

A solution (1.0 M, 2.4 ml) of tetrabutylammonium fluoride/tetrahydrofuran was added to a solution of 1-((tert-butyldiphenylsilyloxy)methyl)-2-chloro-4-(n-pentyl)benzene (890 mg) in tetrahydrofuran (4.5 ml) under ice-cooling, and the mixture was stirred for 2 hr. Water was added to the reaction mixture and the resulting product was extracted three times with ethyl acetate. The organic layers were combined and washed successively with diluted hydrochloric acid, a saturated aqueous solution of sodium hydrogencarbonate and saturated brine, and dried over anhydrous magnesium sulfate. The solvent was evaporated and the residue was purified by silica gel column chromatography (hexane/ethyl acetate=7/1) to give the objective compound (345 mg) as a colorless oil.

$^1$H-NMR(CDCl$_3$): 0.88(3H, t, J=7 Hz), 1.21–1.41(4H, m), 1.51–1.66(2H, m), 1.90(1H, br t, J=7 Hz), 2.51–2.63 (2H, m), 4.74(2H, d, J=7 Hz), 7.08(1H, d, J=8 Hz), 7.19(1H, s), 7.35(1H, d, J=8 Hz)

Preparation Example 70-4

2-Chloro-1-((methanesulfonyloxy)methyl)-4-(n-pentyl)benzene

In the same manner as in Preparation Example 14-1, the objective compound (530 mg) was obtained as a colorless oil from 2-chloro-4-(n-pentyl)benzyl alcohol (333 mg).

$^1$H-NMR(CDCl$_3$): 0.89(3H, t, J=7 Hz), 1.22–1.44(4H, m), 1.51–1.67(2H, m), 2.52–2.64(2H, m), 2.99(3H, s), 5.31 (2H, s), 7.12(1H, d, J=8 Hz), 7.25(1H, s), 7.38(1H, d, J=8 Hz), 7.38(1H, d, J=8 Hz)

Preparation Example 70-5

Methyl 3-(2-chloro-4-(n-pentyl)benzyl)-2-methyl-3H-imidazo[4,5-b]pyridine-5-carboxylate and methyl 1-(2-chloro-4-(n-pentyl)benzyl)-2-methyl-1H-imidazo[4,5-b]pyridine-5-carboxylate In the same manner as in Preparation Example 14-2, methyl 3-(2-chloro-(n-pentyl)benzyl)-2-methyl-3H-imidazo [4,5-b]pyridine-5-carboxylate (147 mg) and methyl 1-(2-chloro-4-(n-pentyl)benzyl)-2-methyl-1H-imidazo[4,5-b] pyridine-5-carboxylate (176 mg) were obtained as pale-yellow powders from methyl 2-methyl-1H-imidazo[4,5-b] pyridine-5-carboxylate (230 mg) and 2-chloro-1-((methanesulfonyloxy)methyl)-4-(n-pentyl)benzene (440 mg).

Methyl 3-(2-chloro-4-(n-pentyl)benzyl)-2-methyl-3H-imidazo[4,5-b]pyridine-5-carboxylate $^1$H-NMR(CDCl$_3$): 0.88(3H, t, J=7 Hz), 1.19–1.40(4H, m), 1.48–1.64(2H, m), 2.48–2.59(2H, m), 2.53(3H, s), 3.99

(3H, s), 5.65(2H, s), 6.52(1H, d, J=8Hz), 6.90(1H, d, J=8 Hz), 7.25(1H, s), 8.07(1H, d, J=8 Hz), 8.14(1H, d, J=8 Hz).

Mass(ESI): m/E 386 (M+H)$^+$

Methyl 1-(2-chloro-4-(n-pentyl)benzyl)-2-methyl-1H-imidazo[4,5-b]pyridine-5-carboxylate $^1$H-NMR(CDCl$_3$): 0.88(3H, t, J=7 Hz), 1.19–1.40(4H, m), 1.50–1.64(2H, m), 2.49–2.61(2H, m), 2.65(3H, s), 4.01 (3H, s), 5.40(2H, s), 6.42(1H, d, J=8 Hz), 6.93(1H, d, J=8 Hz), 7.29(1H, s), 7.55(1H, d, J=8 Hz), 8.07(1H, d, J=8 Hz)

Mass(ESI): m/E 386 (M+H)$^+$

Preparation Example 70-6

3-(2-Chloro-4-(n-pentyl)benzyl)-2-methyl-3H-imidazo[4,5-b]pyridine-5-carboxylic acid In the same manner as in Preparation Example 4-7, the objective compound (119 mg) was obtained as a white powder from methyl 3-(2-chloro-4-(n-pentyl)benzyl)-2-methyl-3H-imidazo[4,5-b]pyridine-5-carboxylate (135 mg).

$^1$H-NMR(DMSO-d$_6$): 0.84(3H, t, J=7 Hz), 1.13–1.37(4H, m), 1.43–1.60(2H, m), 2.44–2.60(2H, m), 2.50(3H, s), 5.58 (2H, s), 6.45(1H, d, J=8 Hz), 7.03(1H, d, J=8 Hz), 7.39(1H, s), 8.01(1H, d, J=8 Hz), 8.12(1H, d, J=8 Hz).

Mass(ESI): m/E 370 (M–H)$^-$

Preparation Example 71-1

1-((tert-Butyldiphenylsilyloxy)methyl)-2-chloro-4-isobutylbenzene

In the same manner as in Preparation Example 70-2, the objective compound (1.644 g, 76%) was obtained as a colorless oil from 4-bromo-1-((tert-butyldiphenylsilyloxy) methyl)-2-chlorobenzene and isobutyl iodide.

$^1$H-NMR(CDCl$_3$): 0.90(6H, d, J=7 Hz), 1.10(9H, s), 1.75–1.96(1H, m), 2.44(2H, d, J=7 Hz), 4.80(2H, s), 7.03–7.11(2H, m), 7.30–7.46(6H, m), 7.56–7.74(5H, m).

Preparation Example 71-2

2-Chloro-4-isobutylbenzyl alcohol

In the same manner as in Preparation Example 70-3, the objective compound (568 mg) was obtained as a colorless oil from 1-((tert-butyldiphenylsilyloxy)methyl)-2-chloro-4-isobutylbenzene (1.71 g).

$^1$H-NMR(CDCl$_3$): 0.90(6H, d, J=7 Hz), 1.74–1.95(1H, m), 1.18(1H, br t, J=7 Hz), 2.44(2H, d, J=7 Hz), 4.75(2H, d, J=7 Hz), 7.05(1H, d, J=8 Hz), 7.16(1H, s), 7.35(1H, d, J=8 Hz)

Preparation Example 71-3

2-Chloro-4-isobutyl-1-((methanesulfonyloxy)methyl)benzene

In the same manner as in Preparation Example 14-1, the objective compound (458 mg) was obtained as a colorless oil from 2-chloro-4-isobutylbenzyl alcohol (293 mg).

$^1$H-NMR(CDCl$_3$): 0.90(6H, d, J=7 Hz), 1.75–1.96(1H, m), 2.48(2H, d, J=7 Hz), 3.00(3H, s), 5.31(2H, s), 7.09(1H, d, J=8 Hz), 7.22(1H, s), 7.39(1H, d, J=8 Hz)

Preparation Example 71-4

Methyl 3-(2-chloro-4-isobutylbenzyl)-2-methyl-3H-imidazo[4,5-b]pyridine-5-carboxylate and methyl 1-(2-chloro-4-isobutylbenzyl)-2-methyl-1H-imidazo[4,5-b]pyridine-5-carboxylate In the same manner as in Preparation Example 14-2, methyl 3-(2-chloro-4-isobutylbenzyl)-2-methyl-3H-imidazo [4,5-b]pyridine-5-carboxylate (124 mg) and methyl 1-(2-chloro-4-isobutylbenzyl)-2-methyl-1H-imidazo[4,5-b] pyridine-5-carboxylate (152 mg) were obtained as pale-yellow powders from methyl 2-methyl-1H-imidazo[4,5-b] pyridine-5-carboxylate (212 mg) and 2-chloro-4-isobutyl-1-((methanesulfonyloxy)methyl)benzene (390 mg).

Methyl 3-(2-chloro-4-isobutylbenzyl)-2-methyl-3H-imidazo[4,5-b]pyridine-5-carboxylate $^1$H-NMR(CDCl$_3$): 0.88(6H, d, J=7 Hz), 1.71–1.90(1H, m), 2.40(2H, d, J=7 Hz), 2.52(3H, s), 3.99(3H, s), 5.64(2H, s), 6.53(1H, d, J=8 Hz), 6.87(1H, d, J=8 Hz), 7.21(1H, s), 8.05(1H, d, J=8 Hz), 8.13(1H, d, J=8 Hz)

Mass(ESI): m/E 372 (M+H)$^+$

Methyl 1-(2-chloro-4-isobutylbenzyl)-2-methyl-1H-imidazo[4,5-b]pyridine-5-carboxylate $^1$H-NMR(CDCl$_3$): 0.88(6H, d J=7 Hz), 1.71–1.92(1H, m), 2.42(2H, d J=7 Hz), 2.65(3H, s), 4.00(3H, s), 5.41(2H, s), 6.41(1H, d, J=8 Hz), 6.90(1H, d, J=8 Hz), 7.24(1H, s), 7.55(1H, d, J=8 Hz), 8.07(1H, d, J=8 Hz).

Mass(ESI): m/E 372 (M+H)$^+$

Preparation Example 71-5

3-(2-Chloro-4-isobutylbenzyl)-2-methyl-3H-imidazo [4,5-b]pyridine-5-carboxylic acid In the same manner as in Preparation Example 4-7, the objective compound (122 mg) was obtained as a white powder from methyl 3-(2-chloro-4-isobutylbenzyl)-2-methyl-3H-imidazo[4,5-b]pyridine-5-carboxylate (116 mg).

$^1$H-NMR(DMSO-d$_6$): 0.82(6H, d, J=7 Hz), 1.68–1.89 (1H, m), 2.42(2H, d, J=7 Hz), 2.50(3H, s), 5.59(2H, s), 6.44(1H, d, J=8 Hz), 7.01(1H, d, J=8 Hz), 7.36(1H, s), 8.00(1H, d, J=8 Hz), 8.12 d, J=8H).

Mass(ESI): m/E 356 (M–H)$^-$

Preparation Example 72-1

1-((tert-Butyldiphenylsilyloxy)methyl)-2-chloro-4-(cyclohexylmethyl)benzene

In the same manner as in Preparation Example 70-2, the objective compound (797 mg, 56%) was obtained as a colorless oil from 4-bromo-1-((tert-butyldiphenylsilyloxy) methyl)-2-chlorobenzene and cyclohexylmethyl iodide.

$^1$H-NMR(CDCl$_3$): 0.82–1.75(11H, m), 1.11(9H, s), 2.45 (2H, d, J=7 Hz), 4.79(2H, s), 7.03–7.11(2H, m), 7.31–7.48 (6H, m), 7.61(1H, d, J=8 Hz), 7.63–7.73(4H, m)

Preparation Example 72-2

2-Chloro-4-(cyclohexylmethyl)benzyl alcohol

In the same manner as in Preparation Example 70-3, the objective compound (378 mg) was obtained as a colorless oil from 1-((tert-butyldiphenylsilyloxy)methyl)-2-chloro-4-(cyclohexylmethyl)benzene (1.03 g).

$^1$H-NMR(CDCl$_3$): 0.82–1.74(11H, m), 1.87(1H, br t, J=7 Hz), 2.44(2H, d, J=7 Hz), 4.74(2H, d, J=7 Hz), 7.04(1H, d, J=8 Hz), 7.15(1H, s), 7.34(1H, d, J=8 Hz)

Preparation Example 72-3

2-Chloro-4-(cyclohexylmethyl)-1-((methanesulfonyloxy)methyl)benzene

In the same manner as in Preparation Example 14-1, the objective compound (543 mg) was obtained as a colorless oil from 2-chloro-4-(cyclohexylmethyl)benzylalcohol (365 mg).

$^1$H-NMR(CDCl$_3$): 0.80–1.75(11H, m), 2.46(2H, d, J=7 Hz), 2.99(3H, s), 5.30(2H, s), 7.08(1H, d, J=8 Hz), 7.20(1H, s), 7.38(1H, d, J=8 Hz)

Preparation Example 72-4

Methyl 3-(2-chloro-4-(cyclohexylmethyl)benzyl)-2-methyl-3H-imidazo[4,5-b]pyridine-5-carboxylate (170 mg) and methyl 1-(2-chloro-4-(cyclohexylmethyl)benzyl)-2-methyl-1H-imidazo[4,5-b]pyridine-5-carboxylate In the same manner as in Preparation Example 14-2, methyl 3-(2-chloro-4-(cyclohexylmethyl)benzyl)-2-methyl-3H-imidazo[4,5-b]pyridine-5-carboxylate (170 mg) and methyl 1-(2-chloro-4-(cyclohexylmethyl)benzyl)-2-methyl-1H-imidazo[4,5-b]pyridine-5-carboxylate (222 mg) were obtained as pale-yellow powders from methyl 2-methyl-1H-imidazo[4,5-b]pyridine-5-carboxylate (229 mg) and 2-chloro-4-(cyclohexylmethyl)-1-((methanesulfonyloxy)methyl)benzene (469 mg).

Methyl 3-(2-chloro-4-(cyclohexylmethyl)benzyl)-2-methyl-3H-imidazo[4,5-b]pyridine-5-carboxylate $^1$H-NMR(CDCl$_3$): 0.80–1.74(11H, m), 2.40(2H, d, J=7 Hz), 2.53(3H, s), 3.99(3H, s), 5.64(2H, s), 6.52(1H, d, J=8 Hz), 6.86(1H, d, J=8 Hz), 7.21(1H, s), 8.05(1H, d, J=8 Hz), 8.13(1H, d, J=8 Hz).

Mass(ESI): m/E 412 (M+H)$^+$

Methyl 1-(2-chloro-4-(cyclohexylmethyl)benzyl)-2-methyl-1H-imidazo[4,5-b]pyridine-5-carboxylate $^1$H-NMR(CDCl$_3$): 0.80–1.75(11H, m), 2.43(2H, d, J=7 Hz), 2.65(3H, s), 4.01(3H, s), 5.04(2H, s), 6.40(1H, d, J=8 Hz), 6.89(1H, d, J=8 Hz), 7.24(1H, s), 7.56(1H, d, J=8 Hz), 8.07(1H, d, J=8 Hz)

Mass(ESI): m/E 412 (M+H)$^+$

Preparation Example 72-5

3-(2-Chloro-4-(cyclohexylmethyl)benzyl)-2-methyl-3H-imidazo[4,5-b]pyridine-5-carboxylic acid In the same manner as in Preparation Example 4-7, the objective compound (180 mg) was obtained as a white powder from methyl 3-(2-chloro-4-(cyclohexylmethyl)benzyl)-2-methyl-3H-imidazo[4,5-b]pyridine-5-carboxylate (156 mg).

$^1$H-NMR(DMSO-d$_6$): 0.78–1.68(11H, m), 2.42(2H, d, J=7 Hz), 2.50(3H, s), 5.58(2H, s), 6.44(1H, d, J=8 Hz), 7.00(1H, d, J=8 Hz), 7.35(1H, s), 8.01(1H, d, J=8 Hz), 8.13(1H, d, J=8 Hz)

Mass(ESI): m/E 396 (M–H)$^-$

Preparation Example 73-1

4-Bromo-1-((tert-butyldimethylsilyloxy)methyl)-2-chlorobenzene

In the same manner as in Preparation Example 70-1, the objective compound (6.10 g) was obtained as a colorless oil from 4-bromo-2-chlorobenzyl alcohol (4.42 g).

$^1$H-NMR(CDCl$_3$): 0.12(6H, s), 0.95(9H, s), 4.71(2H, s), 7.37–7.50(3H, m).

Preparation Example 73-2

4-((tert-Butyldimethylsilyloxy)methyl)-3-chlorobenzaldehyde

A solution (1.6 M, 8.3 ml) of n-butyl lithium/hexane was added to a solution of 4-bromo-1-((tert-butyldimethylsilyloxy)methyl)-2-chlorobenzene (4.03 g) in tetrahydrofuran (10 ml) under a nitrogen atmosphere at –60° C. and the mixture was stirred for 45 min. The reaction mixture was once heated to 0° C. and then cooled to –40° C. and 1-formyl piperidine (1.63 g) was dropwise added over 3 min. Then, the reaction mixture was heated to 0° C. over 2 hr. Aqueous ammonium chloride was added to the reaction mixture and the resulting product was extracted twice with hexane. The organic layers were combined, washed successively with diluted hydrochloric acid, a saturated aqueous solution of sodium hydrogencarbonate and saturated brine, and dried over anhydrous magnesium sulfate. The solvent was evaporated and the residue was subjected to silica gel column chromatography (hexane/ethyl acetate=30/1) to give the objective compound (2.49 g) as a colorless oil.

$^1$H-NMR(CDCl$_3$): 0.16(6H, s), 0.98(9H, s), 4.83(2H, s), 7.70–7.86(3H, m), 9.96(1H, s).

Mass(ESI): m/E 283 (M–H)$^-$

Preparation Example 73-3

(E)-1-((tert-Butyldimethylsilyloxy)methyl)-2-chloro-4-(2-phenylethenyl)benzene

Sodium hydride (70% in mineral oil, 81 mg) was added to a mixture of 4-((tert-butyldimethylsilyloxy)methyl)-3-chlorobenzaldehyde (571 mg) and diethyl benzylphosphonate (502 mg) in N,N-dimethylformamide (2 ml) under a nitrogen atmosphere at room temperature and the mixture was stirred at 40° C. for 2 hr. Water was added to the reaction mixture and the resulting product was extracted three times with ether. The organic layers were combined, washed with water and saturated brine, and dried over anhydrous magnesium sulfate. The solvent was evaporated and the residue was subjected to silica gel column chromatography (hexane/ethyl acetate=50/1) to give the objective compound (448 mg) as a colorless oil.

$^1$H-NMR(CDCl$_3$): 0.14(6H, s), 0.97(9H, s), 4.80(2H, s), 7.03(1H, d, J=16 Hz), 7.10(1H, d, J=16 Hz), 7.26–7.58(8H, m).

Preparation Example 73-4

(E)-2-Chloro-4-(2-phenylethenyl)benzyl alcohol

In the same manner as in Preparation Example 70-3, the objective compound (422 mg) was obtained as a white powder from (E)-1-((tert-butyldimethylsilyloxy)methyl)-2-chloro-4-(2-phenylethenyl)benzene (745 mg).

$^1$H-NMR(CDCl$_3$): 1.91(1H, br t, J=7 Hz), 4.79(2H, d, J=7 Hz), 7.02(1H, d, J=16 Hz), 7.12(1H, d, J=16 Hz), 7.24–7.55 (8H, m).

Preparation Example 73-5

(E)-2-Chloro-1-((methanesulfonyloxy)methyl)-4-(2-phenylethenyl)benzene

In the same manner as in Preparation Example 14-1, the objective compound (583 mg) was obtained as a white solid from (E)-2-chloro-4-(2-phenylethenyl)benzyl alcohol (412 mg).

$^1$H-NMR(CDCl$_3$): 3.01(3H, s), 5.34(2H, s), 7.02(1H, d, J=16 Hz), 7.14(1H, d, J=16 Hz), 7.27–7.61(8H, m).

Preparation Example 73-6

Methyl (E)-3-(2-chloro-4-(2-phenylethenyl)benzyl)-2-methyl-3H-imidazo[4,5-b]pyridine-5-carboxylate and methyl (E)-1-(2-chloro-4-(2-phenylethenyl)benzyl)-2-methyl-1H-imidazo[4,5-b]pyridine-5-carboxylate In the same manner as in Preparation Example 14-2, methyl (E)-3-(2-chloro-4-(2-phenylethenyl)benzyl)-2- methyl-3H-imidazo[4,5-b]pyridine-5-carboxylate (163 mg) and methyl (E)-1-(2-chloro-4-(2-phenylethenyl)benzyl)-2-methyl-1H-imidazo[4,5-b]pyridine-5-carboxylate (194 mg) were obtained as white powders from methyl 2-methyl-1H-imidazo[4,5-b]pyridine-5-carboxylate (250 mg) and (E)-2-chloro-1-((methanesulfonyloxy)methyl)-4-(2-phenylethenyl)benzene (518 mg).

Methyl (E)-3-(2-chloro-4-(2-phenylethenyl)benzyl)-2-methyl-3H-imidazo[4,5-b]pyridine-5-carboxylate $^1$H-NMR(CDCl$_3$): 2.54(3H, s), 3.99(3H, s), 5.68(2H, s), 6.61(1H, d, J=8 Hz), 6.97(1H, d, J=16 Hz), 7.08(1H, d, J=16 Hz), 7.16–7.62(7H, m), 8.08(1H, d, J=8 Hz), 8.14(1H, d, J=8 Hz).

Mass(ESI): m/E 418 (M+H)$^+$

Methyl (E)-1-(2-chloro-4-(2-phenylethenyl)benzyl)-2-methyl-1H-imidazo[4,5-b]pyridine-5-carboxylate $^1$H-NMR(CDCl$_3$): 2.65(3H, s), 4.01(3H, s), 5.44(2H, s), 6.48(1H, d, J=8 Hz), 6.97(1H, d, J=16 Hz), 7.10(1H, d, J=16 Hz), 7.19–7.64(8H, m), 8.08(1H, d, J=8 Hz).

Mass(ESI): m/E 418 (M+H)$^+$

Preparation Example 73-7

(E)-3-(2-Chloro-4-(2-phenylethenyl)benzyl)-2-methyl-3H-imidazo[4,5-b]pyridine-5-carboxylic acid In the same manner as in Preparation Example 4-7, the objective compound (149 mg) was obtained as a white powder from methyl (E)-3-(2-chloro-4-(2-phenylethenyl)benzyl)-2-methyl-3H-imidazo[4,5-b]pyridine-5-carboxylate (158 mg).

$^1$H-NMR(DMSO-d$_6$): 2.52(3H, s), 5.63(2H, s), 6.59(1H, d, J=8 Hz), 7.16–7.48(6H, m), 7.53–7.63(2H, m), 7.84(1H, s), 8.01(1H, d, J=8 Hz), 8.14(1H, d, J=8 Hz).

Mass(ESI): m/E 402 (M–H)$^-$

Preparation Example 74-1

2-Chloro-4-hydroxybenzoic acid

4-Amino-2-chlorobenzoic acid (10.01 g) was homogeneously dissolved in 12.5% sulfuric acid (400 ml) by heating the mixture to 70° C. and cooled with ice. An aqueous solution of sodium nitrite (4.24 g/water 12 ml) was dropwise added to this suspension over 5 min at a temperature of not more than 8° C. Five minutes later, this solution was gradually poured into water (500 ml) at 80° C., upon which vigorous bubbling occurred and the solution turned red. The reaction mixture was further stirred at 80° C. for 1 hr. After cooling, the resulting product was extracted three times with ether. The organic layers were combined, washed successively with diluted hydrochloric acid, water and saturated brine, and dried over anhydrous magnesium sulfate. The solvent was evaporated and a small amount of diisopropyl ether was added to allow crystallization, whereby the objective compound (6.32 g) was obtained as an orange powder.

$^1$H-NMR(DMSO-d$_6$): 6.79(1H, dd, J=8 and 2 Hz), 6.88 (1H, d, J=2 Hz), 7.77(1H, d, J=8 Hz).

Mass(ESI): m/E 171 (M–H)$^-$

Preparation Example 74-2

Benzyl 4-benzyloxy-2-chlorobenzoate

Potassium carbonate (1.67 g) and benzyl bromide (1.73 g) were added to a solution of 2-chloro-4-hydroxybenzoic acid (695 mg) in N,N-dimethylformamide (3.5 ml) and the mixture was stirred for 14 hr at room temperature. To the reaction mixture was added 1N hydrochloric acid and the resulting product was extracted three times with ether. The organic layers were combined, washed successively with water, a saturated aqueous solution of sodium hydrogencarbonate and saturated brine, and dried over anhydrous magnesium sulfate. The solvent was evaporated and the residue was recrystallized from diisopropyl ether/hexane to give the objective compound (1.13 g) as a pale-yellow powder.

$^1$H-NMR(CDCl$_3$): 5.09(2H, s), 5.32(2H, s), 6.87(1H, dd, J=8 and 2 Hz), 7.05(1H, d, J=2 Hz), 7.29–7.50(10H, m), 7.91(1H, d, J=8 Hz).

Mass(ESI): m/E 353 (M+H)$^+$

Preparation Example 74-3

4-Benzyloxy-2-chlorobenzoic acid

Ethanol (8.8 ml), 1,4-dioxane (2.2 ml) and a 1N aqueous sodium hydroxide solution (4.7 ml) were added to benzyl 4-benzyloxy-2-chlorobenzoate (1.12 g). The mixture was stirred at 70° C. for 1.5 hr. The solvent was evaporated and water was added to the residue to dissolve the same. After washing with ether, the aqueous layer was acidified with 1N hydrochloric acid, and the resulting precipitate was collected by filtration to give the objective compound (810 mg) as a pale-yellow powder.

$^1$H-NMR(DMSO-d$_6$): 5.20(2H, s), 7.06(1H, dd, J=8 and 2 Hz), 7.18(1H, d, J=2 Hz), 7.29–7.50(5H, m), 7.82(1H, d, J=8 Hz).

Mass(ESI): m/E 261 (M–H)$^-$

Preparation Example 74-4

4-Benzyloxy-2-chlorobenzyl alcohol

To a solution of 4-benzyloxy-2-chlorobenzoic acid (788 mg) in tetrahydrofuran (7.9 ml) was dropwise added a boran-dimethyl sulfide complex (10.0 M, 0.6 ml) at room temperature under a nitrogen atmosphere, and the mixture was refluxed under heating for 2.5 hr. The reaction mixture was allowed to cool to room temperature and 1N hydrochloric acid (1.5 ml) was dropwise added carefully, which was followed by stirring for 30 min. Water was added to the reaction mixture and the resulting product was extracted three times with ethyl acetate. The organic layers were combined, washed successively with a saturated aqueous solution of sodium hydrogencarbonate and saturated brine, and dried over anhydrous magnesium sulfate. The solvent was evaporated to give the objective compound (778 mg) as a white powder.

$^1$H-NMR(CDCl$_3$): 1.83(1H, br t, J=7 Hz), 4.70(2H, d, J=7 Hz), 5.05(2H, s), 6.88(1H, dd, J=8 and 2 Hz), 7.01(1H, d, J=2 Hz), 7.28–7.46(6H, m).

Preparation Example 74-5

4-Benzyloxy-2-chlorobenzyl chloride

In the same manner as in Preparation Example 14-1, the objective compound (639 mg) was obtained as a colorless oil from 4-benzyloxy-2-chlorobenzyl alcohol (523 mg).

$^1$H-NMR(CDCl$_3$): 4.67(2H, s), 5.05(2H, s), 6.87(1H, dd, J=8 and 2 Hz), 7.02(1H, d, J=2 Hz), 7.28–7.44(6H, m).

Preparation Example 74-6

Methyl 3-(4-benzyloxy-2-chlorobenzyl)-2-methyl-3H-imidazo[4,5-b]pyridine-5-carboxylate and methyl 1-(4-benzyloxy-2-chlorobenzyl)-2-methyl-1H-imidazo[4,5-b]pyridine-5-carboxylate In the same manner as in Preparation Example 14-2, methyl 3-(4-benzyloxy-2-chlorobenzyl)-2-methyl-3H- imidazo[4,5-b]pyridine-5-carboxylate (130 mg) and methyl 1-(4-benzyloxy-2-chlorobenzyl)-2-methyl-1H-imidazo[4,5-b]pyridine-5-carboxylate (141 mg) were obtained as pale-yellow powders from methyl 2-methyl-1H-imidazo[4,5-b]pyridine-5-carboxylate (229 mg) and 4-benzyloxy-2-chlorobenzyl chloride (509 mg).

Methyl 3-(4-benzyloxy2-chlorobenzyl)-2-methyl-3H-imidazo[4,5-b]pyridine-5-carboxylate $^1$H-NMR(CDCl$_3$): 2.53(3H, s), 4.00(3H, s), 5.01(2H, s), 5.62(2H, s), 6.63(1H, d, J=8 Hz), 6.72(1H, dd, J=8 and 2 Hz), 7.06(1H, d, J=2 Hz), 7.30–7.42(5H, m), 8.04(1H, d, J=8 Hz), 8.13(1H, d, J=8 Hz).

Mass(ESI): m/E 422 (M+H)$^+$

Methyl 1-(4-benzyloxy-2-chlorobenzyl)-2-methyl-1H-imidazo[4,5-b]pyridine-5-carboxylate $^1$H-NMR(CDCl$_3$): 2.66(3H, s), 4.01(3H, s), 5.02(2H, s), 5.38(2H, s), 6.48(1H, d, J=8 Hz), 6.75(1H, dd, J=8 and 2 Hz), 7.08(1H, d, J=2 Hz), 7.28–7.47(5H, m), 7.54(1H, d, J=8 Hz), 8.06(1H, d, J=8 Hz).

Mass(ESI): m/E 422 (M+H)$^+$

Preparation Example 74-7

3-(4-Benzyloxy-2-chlorobenzyl)-2-methyl-3H-imidazo[4,5-b]pyridine-5-carboxylic acid In the same manner as in Preparation Example 4-7, the objective compound (110 mg) was obtained as a white powder from methyl 3-(4-benzyloxy-2-chlorobenzyl)-2-methyl-3H-imidazo[4,5-b]pyridine-5-carboxylate (116 mg).

$^1$H-NMR(DMSO-d$_6$): 2.39(3H, s), 5.08(2H, s), 5.51(2H, s), 6.41(1H, d, J=8 Hz), 6.88(1H, dd, J=8 and 2 Hz), 7.23(1H, d, J=2 Hz), 7.28–7.45(5H, m), 7.85(2H, s).

Mass(ESI): m/E 406 (M–H)$^-$

Preparation Example 75-1

Methyl 3-(2-chloro-4-methoxybenzyl)-2-methyl-3H-imidazo[4,5-b]pyridine-5-carboxylate (62 mg) and methyl 1-(2-chloro-4-methoxybenzyl)-2-methyl-1H-imidazo[4,5-b]pyridine-5-carboxylate In the same manner as in Preparation Example 14-2, methyl 3-(2-chloro-4-methoxybenzyl)-2-methyl-3H-imidazo[4,5-b]pyridine-5-carboxylate (62 mg) and methyl 1-(2-chloro-4-methoxybenzyl)-2-methyl-1H-imidazo[4,5-b]pyridine-5-carboxylate (62 mg) were obtained as white powders from methyl 2-methyl-1H-imidazo[4,5-b]pyridine-5-carboxylate (145 mg) and 2-chloro-4-methoxybenzyl bromide (215 mg).

Methyl 3-(2chloro-4-methoxybenzyl)-2-methyl-3H-imidazo[4,5-b]pyridine-5-carboxylate $^1$H-NMR(CDCl$_3$): 2.52(3H, s), 3.77(3H, s), 4.00(3H, s), 5.61(2H, s), 6.65(2H, s), 6.97(1H, s), 8.04(1H, d, J=8 Hz), 8.12(1H, d, J=8 Hz).

Mass(ESI): m/E 346 (M+H)$^+$

Methyl 1-(2-chloro-4-methoxybenzyl)-2-methyl-1H-imidazo[4,5-b]pyridine5-carboxylate $^1$H-NMR(CDCl$_3$): 2.65(3H, s), 3.78(3H, s), 4.01(3H, s), 5.38(2H, s), 6.51(1H, d, J=8 Hz), 6.68(1H, dd, J=8 and 2 Hz), 7.00(1H, d, J=2 Hz), 7.54(1H, d, J=8 Hz), 8.04(1H, d, J=8 Hz).

Mass(ESI): m/E 346 (M+H)$^+$

Preparation Example 75-2

3-(2-Chloro-4-methoxybenzyl)-2-methyl-3H-imidazo[4,5-b]pyridine-5-carboxylic acid In the same manner as in Preparation Example 4-7, the objective compound (83 mg) was obtained as a pale-yellow powder from methyl 3-(2-chloro-4-methoxybenzyl)-2-methyl-3H-imidazo[4,5-b]pyridine-5-carboxylate (78 mg).

$^1$H-NMR(DMSO-d$_6$): 2.50(3H, s), 3.55(3H, s), 5.53(2H, s), 6.58(1H, d, J=8 Hz), 6.81(1H, dd, J=8 and 2 Hz), 7.13(1H, d, J=2 Hz), 7.99(1H, d, J=8 Hz), 8.11(1H, d, J=8 Hz).

Mass(ESI): m/E 330 (M–H)$^-$

Preparation Example 76-1

Isopropyl 2-chloro-4-isopropoxy benzoate

In the same manner as in Preparation Example74-2, the objective compound (839 mg) was obtained as a pale-brown oil from 2-chloro-4-hydroxybenzoic acid (500 mg) and isopropyl iodide (1.18 g).

$^1$H-NMR(CDCl$_3$): 1.36(12H, m), 4.59(1H, m), 4.59(1H, m), 5.24(1H, m), 6.78(1H, d, J=8 Hz), 6.93(1H, s), 7.82(1H, d, J=8 Hz).

Preparation Example 76-2

2-Chloro-4-isopropoxybenzyl alcohol

Lithium aluminum hydride (100 mg) was added to a solution of isopropyl 2-chloro-4-isopropoxybenzoate (675 mg) in ether (6.8 ml) and the mixture was stirred for 2 hr. To the reaction mixture were dropwise added successively water (0.8 ml), a 1N aqueous sodium hydroxide solution (0.8 ml) and water (2.4 ml) under ice-cooing, and the mixture was stirred for 30 min at room temperature. Then ether and water were added and the organic layer was separated. The resulting product was extracted with ether from the aqueous layer. The organic layers were combined, washed with saturated brine, and dried over anhydrous magnesium sulfate. The solvent was evaporated to give the objective compound (513 mg) as a brown oil.

$^1$H-NMR(CDCl$_3$): 1.32(6H, d, J=6 Hz), 1.97(1H, t, J=6 Hz), 4.52(1H, m), 4.70(2H, d, J=6 Hz), 6.78(1H, dd, J=2 Hz), 6.92(1H, d, J=2 Hz), 7.33(1H, d, J=8 Hz).

Preparation Example 76-3

2-Chloro-4-isopropoxybenzyl chloride

Pyridine (0.5 ml) and thionyl chloride (0.18 mg) were successively added to a solution of 2-chloro-4-isopropoxybenzylalcohol (401 mg) in dichloromethane (2 ml) under ice-cooling, and the mixture was stirred for 1 hr. Water was added to the reaction mixture and the resulting product was extracted three times with hexane. The organic layers were combined, washed successively with 1N hydrochloric acid, a saturated aqueous solution of sodium hydrogencarbonate and saturated brine, and dried over anhydrous magnesium sulfate. The solvent was evaporated to give the objective compound (353 mg) as a yellow oil.

$^1$H-NMR(CDCl$_3$): 1.32(6H, d, J=7 Hz), 4.52(1H, sept, J=7 Hz), 4.65(2H, s), 6.76(1H, dd, J=8 and 2 Hz), 6.91(1H, d, J=2 Hz), 7.32(1H, d, J=8.5 Hz).

Preparation Example 76-4

Methyl 3-(2-chloro-4-isopropoxybenzyl)-2-methyl-3H-imidazo[4,5-b]pyridine-5-carboxylate and methyl 1-(2-chloro-4-isopropoxybenzyl)-2-methyl-1H-imidazo[4,5-b]pyridine-5-carboxylate In the same manner as in Preparation Example 14-2, methyl 3-(2-chloro-4-isopropoxybenzyl)-2-methyl-3H- imidazo[4,5-b]pyridine-5-carboxylate (73 mg) and methyl 1-(2-chloro-4-isopropoxybenzyl)-2-methyl-1H-imidazo[4,5-b]pyridine-5-carboxylate (80 mg) as white powders from methyl 2-methyl-1H-imidazo[4,5-b]pyridine-5-carboxylate (194 mg) and 2-chloro-4-isopropoxybenzyl chloride (340 mg).

Methyl 3-(2-chloro-4-isopropoxybenzyl)-2-methyl-3H-imidazo[4,5-b]pyridine-5-carboxylate $^1$H-NMR(CDCl$_3$): 1.29(6H, d, J=7 Hz), 2.54(3H, s), 4.00 (3H, s), 4.47(1H, sept, J=7 Hz), 5.61(2H, s), 6.62(2H, s), 6.95(1H, s), 8.05(1H, d, J=8 Hz), 8.13(1H, d, J=8 Hz).

Mass(ESI): m/E 374 (M+H)$^+$

Methyl 1-(2-chloro-4-isopropoxybenzyl)-2-methyl-1H-imidazo[4,5-b]pyridine-5-carboxylate $^1$H-NMR(CDCl$_3$): 1.30(6H, d, J=7 Hz), 2.65(3H, s), 4.00 (3H, s), 4.48(1H, sept, J=7 Hz), 5.35(2H, s), 6.47(1H, d, J=8 Hz), 6.64(1H, dd, J=8 and 2 Hz), 6.98(1H, d, J=2 Hz), 7.54(1H, d, J=8 Hz), 8.06(1H, d, J=8 Hz).

Mass(ESI): m/E 374 (M+H)$^+$

Preparation Example 76-5

3-(2-Chloro-4-isopropoxybenzyl)-2-methyl-3H-imidazo[4,5-b]pyridine-5-carboxylic acid In the same manner as in Preparation Example 4-7, the objective compound (66 mg) was obtained as a pale-yellow powder from methyl 3-(2-chloro-4-isopropoxybenzyl)-2-methyl-3H-imidazo[4,5-b]pyridine-5-carboxylate (67 mg).

$^1$H-NMR(DMSO-d$_6$): 1.23(6H, d, J=7 Hz), 2.50(3H, s), 4.60(1H, sept, J=7 Hz), 5.53(2H, s), 6.52(1H, d, J=8 Hz), 6.79(1H, dd, J=8 and 2 Hz), 7.11(1H, d, J=2 Hz), 8.01(1H, d, J=8 Hz), 8.12(1H, d, J=8 Hz).

Mass(ESI): m/E 358 (M−H)$^-$

Preparation Example 77-1 n-Butyl 4-(n-butoxy)-2-chlorobenzoate

In the same manner as in Preparation Example 74-2, the objective compound (839 mg) was obtained as a pale-brown oil from 2-chloro-4-hydroxybenzoic acid (500 mg) and n-butyl iodide (1.28 g).

$^1$H-NMR(CDCl$_3$): 0.98(6H, t, J=6 Hz), 1.48(4H, m), 1.76(4H, m), 3.99(2H, t, J=6 Hz), 4.30(2H, t, J=6 Hz), 6.80(1H, d, J=8 Hz), 6.95(1H, s), 7.86(1H, d, J=8 Hz).

Preparation Example 77-2

4-(n-Butoxy)-2-chlorobenzyl alcohol

In the same manner as in Preparation Example 80-2 to be mentioned later, the objective compound (513 mg) was obtained as a pale-brown oil from n-butyl 4-(n-butoxy)-2-chlorobenzoate (835 mg).

$^1$H-NMR(CDCl$_3$): 0.98(3H, t, J=6 Hz), 1.48(2H, m), 1.76(2H, m), 1.86(1 H, t, J=6 Hz), 3.95(2H, t, J=6 Hz), 4.71(2H, d, J=6 Hz), 6.80(1H, d, J=8 Hz), 6.93(1H, s), 7.34(1H, d, J=8 Hz).

Preparation Example 77-3

4-(n-Butoxy)-2-chlorobenzyl chloride

In the same manner as in Preparation Example 14-1, the objective compound (505 mg) was obtained as a colorless oil from 4-(n-butoxy)-2-chlorobenzyl alcohol (475 mg).

$^1$H-NMR(CDCl$_3$): 0.98(3H, t, J=7 Hz), 1.38–1.56(2H, m), 1.68–1.82(2H, m), 3.95(2H, t, J=7 Hz), 4.67(2H, s), 6.78(1H, dd, J=8 and 2 Hz), 6.92(1H, d, J=2 Hz), 7.33(1H, d, J=8 Hz).

Preparation Example 77-4

Methyl 3-(4-(n-butoxy)-2-chlorobenzyl)-2-methyl-3H-imidazo[4,5-b]pyridine-5-carboxylate and methyl 1-(4-(n-butoxy)-2-chlorobenzyl)-2-methyl-1H-imidazo[4,5-b]pyridine-5-carboxylate In the same manner as in Preparation Example 14-2, methyl 3-(4-(n-butoxy)-2-chlorobenzyl)-2-methyl-3H-imidazo[4,5-b]pyridine-5-carboxylate (105 mg) and methyl 1-(4-(n-butoxy)-2-chlorobenzyl)-2-methyl-1H-imidazo[4,5-b]pyridine-5-carboxylate (111 mg) were obtained as pale-yellow powders from methyl 2-methyl-1H-imidazo[4,5-b]pyridine-5-carboxylate (230 mg) and 4-(n-butoxy)-2-chlorobenzyl chloride (443 mg).

Methyl 3-(4-(n-butoxy)-2-chlorobenzyl)-2-methyl-3H-imidazo[4,5-b]pyridine-5-carboxylate $^1$H-NMR(CDCl$_3$): 0.96(3H, t, J=7 Hz), 1.38–1.54(2H, m), 1.65–1.81(2H, m), 2.52(3H, s), 3.90(2H, t, J=7 Hz), 4.00(3H, s), 5.60(2H, s), 6.63(2H, s), 6.95(1H, s), 8.04(1H, d, J=8 Hz), 8.13(1H, d, J=8 Hz).

Mass(ESI): m/E 388 (M+H)$^+$

Methyl 1-(4-(n-butoxy)-2-chlorobenzyl)-2-methyl-1H-imidazo[4,5-b]pyridine-5-carboxylate $^1$H-NMR(CDCl$_3$): 0.95(3H, t, J=7 Hz), 1.38–1.53(2H, m), 1.66–1.81(2H, m), 2.65(3H, s), 3.92(2H, t, J=7 Hz), 4.01(3H, s), 5.37(2H, s), 6.48(1H, d, J=8 Hz), 6.67(1H, dd, J=8 and 2 Hz), 6.99(1H, d, J=2 Hz), 7.55(1H, d, J=8 Hz), 8.06(1H, d, J=8 Hz).

Mass(ESI): m/E 388 (M+H)$^+$

Preparation Example 77-5

3-(4-(n-Butoxy)-2-chlorobenzyl)-2-methyl-3H-imidazo[4,5-b]pyridine-5-carboxylic acid In the same manner as in Preparation Example 4-7, the objective compound (90 mg) was obtained as a pale-yellow powder from methyl 3-(4-(n-butoxy)-2-chlorobenzyl)-2-methyl-3H-imidazo[4,5-b]pyridine-5-carboxylate (90 mg).

$^1$H-NMR(DMSO-d$_6$): 0.90(3H, t, J=7 Hz), 1.30–1.48(2H, m), 1.57–1.71(2H, m), 2.50(3H, s), 3.94(2H, t, J=7 Hz), 5.54(2H, s), 6.53(1H, d, J=8 Hz), 6.80(1H, dd, J=8 and 2 Hz), 7.13(1H, d, J=2 Hz), 8.00(1H, d, J=8 Hz), 8.11(1H, d, J=8 Hz).

Mass(ESI): m/E 372 (M−H)$^-$

Preparation Example 78-1

Cyclohexylmethyl 2-chloro-4-((cyclohexylmethyl)oxy)benzoate

In the same manner as in Preparation Example 74-2, the objective compound (1.14 g) was obtained as a pale-brown oil from 2-chloro-4-hydroxybenzoic acid (500 mg) and cyclohexylmethyl bromide (1.23 g).

$^1$H-NMR(CDCl$_3$): 1.08(4H, m), 1.26(6H, m), 1.78(12H, m), 3.78(2H, d, J=6 Hz), 4.12(2H, d, J=6 Hz), 6.80(1H, d, J=8 Hz), 6.96(1H, s), 7.88(1H, d, J=8 Hz).

Preparation Example 78-2

2-Chloro-4-((cyclohexylmethyl)oxy)benzyl alcohol

In the same manner as in Preparation Example 80-2 to be mentioned later, the objective compound (903 mg) was obtained as a pale-brown oil from cyclohexylmethyl 2-chloro-4-((cyclohexylmethyl)oxybenzoate (1.13 g).

$^1$H-NMR(CDCl$_3$): 0.85–1.90(11H, m), 3.44(1H, t, J=6 Hz), 3.73(2H, d, J=6 Hz), 4.70(2H, d, J=6 Hz), 6.79(1H, dd, J=8, 1 Hz), 6.92(1H, d, J=1 Hz), 7.33(1H, d, J=8 Hz).

Preparation Example 78-3

2-Chloro-4-((cyclohexyl)methyloxy)benzyl chloride

In the same manner as in Preparation Example 76-3, the objective compound (844 mg) was obtained as a colorless oil from 2-chloro-4-((cyclohexylmethyl)-oxy)benzyl alcohol (855 mg).

$^1$H-NMR(CDCl$_3$): 0.82–1.91(11H, m), 3.72(2H, d, J=7 Hz), 4.66(2H, s), 6.78(1H, dd, J=8 and 2 Hz), 6.92(1H, d, J=2 Hz), 7.32(1H, d, J=8 Hz).

Preparation Example 78-4

Methyl 3-(2-chloro-4-((cyclohexylmethyl)oxy) benzyl)-2-methyl-3H-imidazo[4,5-b]pyridine-5-carboxylate (58 mg) and methyl 1-(2-chloro-4-((cyclohexylmethyl)-oxy)benzyl)-2-methyl-1H-imidazo[4,5-b]pyridine-5-carboxylate In the same manner as in Preparation Example 14-2, methyl 3-(2-chloro-4-((cyclohexylmethyl)oxy)benzyl)-2-methyl-3H-imidazo[4,5-b]pyridine-5-carboxylate (58 mg) and methyl 1-(2-chloro-4-((cyclohexylmethyl)oxy)-benzyl)-2-methyl-1H-imidazo[4,5-b]pyridine-5-carboxylate (36 mg) were obtained as colorless oils from methyl 2-methyl-1H-imidazo[4,5-b]pyridine-5-carboxylate (194 mg) and 2-chloro-4-((cyclohexylmethyl)oxy)benzyl chloride (403 mg).

Methyl 3-(2-chloro-4-((cyclohexylmethyl)oxy) benzyl)-2-methyl-3H-imidazo[4,5-b]pyridine-5-carboxylate $^1$H-NMR(CDCl$_3$): 0.90–1.90(11H, m), 2.52(3H, s), 3.69 (2H, d, J=7 Hz), 3.99(3H, s), 5.61(2H, s), 6.62(2H, s), 6.95(1H, s), 8.04(1H, d, J=8 Hz), 8.13(1H, d, J=8 Hz).

Mass(ESI): m/E 428 (M+H)$^+$

Methyl 1-(2-chloro-4-((cyclohexylmethyl)oxy) benzyl)-2-methyl-1H-imidazo[4,5-b]pyridine-5-carboxylate $^1$H-NMR(CDCl$_3$): 0.92–1.92(11H, m), 2.64(3H, s), 3.69 (2H, d, J=7 Hz), 4.00(3H, s), 5.37(2H, s), 6.48(1H, d, J=8 Hz), 6.65(1H, dd, J=8 and 2 Hz), 6.98(1H, d, J=2 Hz), 7.53(1H, d, J=8 Hz), 8.04(1H, d, J=8 Hz).

Mass(ESI): m/E 428 (M+H)$^+$

Preparation Example 78-5

3-(2-Chloro-4-((cyclohexylmethyl)oxy)benzyl)-2-methyl-3H-imidazo[4,5-b]pyridine-5-carboxylic acid In the same manner as in Preparation Example 4-7, the objective compound (53 mg) was obtained as a pale-yellow powder from methyl 3-(2-chloro-4-((cyclohexylmethyl) oxy)benzyl)-2-methyl-3H-imidazo[4,5-b]pyridine-5-carboxylate (53 mg).

$^1$H-NMR(DMSO-d$_6$): 0.90–1.82(11H, m), 2.50(3H, s), 3.76(1H, d, J=7 Hz), 5.53(2H, s), 6.54(1H, d, J=8 Hz), 6.80(1H, dd, J=8 and 2 Hz), 7.12(1H, d, J=2 Hz), 8.00(1H, d, J=8 Hz), 8.11(1H, d, J=8 Hz).

Mass(ESI): m/E 412 (M−H)$^−$

Preparation Example 79-1

2-Chloro-4-((2-(N-methyl-N-(2-pyridinyl)amino) ethyl)oxy)benzaldehyde

To a solution of 2-[N-(2-hydroxyethyl)-N-methylamino] pyridine (3.87 g) in dry N,N-dimethylformamide (39 ml) was added sodium hydride (60% in oil, 1.12 g), and the reaction mixture was stirred at room temperature for 30 min. 2-Chloro-4-fluorobenzaldehyde (4.43 g) was added to the reaction mixture and the mixture was stirred for 3 days. The mixture was diluted with ethyl acetate and washed with water. The aqueous layer was extracted twice with ethyl acetate. The organic layers were combined, dried over magnesium sulfate and concentrated to dryness under reduced pressure. The residue was purified by silica gel column chromatography (hexane/ethyl acetate=9/1) to give the objective compound (3.30 g) as a pale-yellow oil.

$^1$H-NMR(CDCl$_3$): 3.13(3H, s), 4.01(2H, t, J=6 Hz), 4.28 (2H, t, J=6 Hz), 6.52(1H, d, J=8 Hz), 6.60(1H, dd, J=8, 5 Hz), 6.90(1H, dd, J=8, 2 Hz), 7.02(1H, d, J=8, 2 Hz), 7.48(1H, t, J=8 Hz), 7.87(1H, d, J=8 Hz), 8.18(1H, d, J=5 Hz), 10.00(1H, s).

Preparation Example 79-2

2-Chloro-4-((2-(N-methyl-N-(2-pyridinyl)amino) ethyl)oxy)benzyl alcohol

Sodium borohydride (58 mg) was added to a solution of 2-chloro-4-((2-(N-methyl-N-(2-pyridinyl)amino)ethyl)oxy) benzaldehyde (438 mg) in ethanol (3 ml) at room temperature and the mixture was stirred for 2 hr. 1N Hydrochloric acid (1.5 ml) was dropwise added to the reaction mixture to decompose the redundant reagent and the whole mixture was diluted with ethyl acetate. A saturated aqueous solution of sodium hydrogencarbonate was added to neutralize the mixture and the resulting product was extracted twice with ethyl acetate. The organic layers were combined, washed with saturated brine, and dried over anhydrous magnesium sulfate. The solvent was evaporated to give the objective compound (437 mg) as a colorless oil.

$^1$H-NMR(CDCl$_3$): 3.12(3H, s), 3.97(2H, t, J=5 Hz), 4.17 (2H, t, J=5 Hz), 4.70(2H, s), 6.51(1H, d, J=8 Hz), 6.58(1H, dd, J=8 and 5 Hz), 6.79(1H, dd, J=8 and 2 Hz), 6.97(1H, d, J=2 Hz), 7.32(1H, d, J=8 Hz), 7.46(1H, t, J=8 Hz), 8.16(1H, d, J=5 Hz).

Mass(ESI): m/E 293 (M+H)$^+$

Preparation Example 79-3

2-Chloro-4-((2-(N-methyl-N-(2-pyridinyl)amino) ethyl)oxy)benzyl chloride

In the same manner as in Preparation Example 76-3, the objective compound (662 mg) was obtained as a pale-yellow oil from 2-chloro-4-((2-(N-methyl-N-(2-pyridinyl)amino) ethyl)oxy)benzyl alcohol (557 mg).

$^1$H-NMR(CDCl$_3$): 3.13(3H, s), 3.99(2H, t, J=5 Hz), 4.19 (2H, t, J=5 Hz), 4.65(2H, s), 6.51(1H, d, J=8 Hz), 6.58(1H, dd, J=8 and 5 Hz), 6.79(1H, dd, J=8 and 2 Hz), 7.00(1H, d, J=2 Hz), 7.31(1H, d, J=8 Hz), 7.47(1H, t, J=8 Hz), 8.17(1H, d, J=5 Hz).

Preparation Example 79-4

Methyl 3-(2-chloro-4-((2-(N-methyl-N-(2-pyridinyl) amino)ethyl)oxy)benzyl)-2-methyl-3H-imidazo[4,5-b]pyridine-5-carboxylate and methyl 1-(2-chloro-4-((2-(N-methyl-N-(2-pyridinyl)amino)ethyl)oxy) benzyl)-2-methyl-1H-imidazo[4,5-b]pyridine-5-carboxylate In the same manner as in Preparation Example 14-2, methyl 3-(2-chloro-4-((2-(N-methyl-N-(2-pyridinyl)amino)

ethyl)oxy)benzyl)-2-methyl-3H-imidazo[4,5-b]pyridine-5-carboxylate (156 mg) and methyl 1-(2-chloro-4-((2-(N-methyl-N-(2-pyridinyl)amino)ethyl)oxy)benzyl)-2-methyl-1H-imidazo[4,5-b]pyridine-5-carboxylate (160 mg) were obtained as colorless oils from methyl 2-methyl-1H-imidazo[4,5-b]pyridine-5-carboxylate (290 mg) and 2-chloro-4-((2-(N-methyl-N-(2-pyridinyl)amino)ethyl)oxy)benzyl chloride (577 mg).

Methyl 3-(2-chloro-4-((2-(N-methyl-N-(2-pyridinyl)amino)ethyl)oxy)benzyl)-2-methyl-3H-imidazo[4,5-b]pyridine-5-carboxylate $^1$H-NMR(CDCl$_3$): 2.51(3H, s), 3.11(3H, s), 3.95(2H, t, J=5 Hz), 3.99(3H, s), 4.14(2H, t, J=5 Hz), 5.60(2H, s), 6.49(1H, d, J=8 Hz), 6.55(1H, dd, J=8 and 5 Hz), 6.63(2H, s), 7.02(1H, s), 7.44(1H, t, J=8 Hz), 8.04(1H, d, J=8 Hz), 8.13(1H, d, J=8 Hz), 8.15(1H, d, J=5 Hz).

Mass(ESI): m/E 466 (M+H)$^+$

Methyl 1-(2chloro-4-((2-(N-methyl-N-(2-pyridinyl)amino)ethyl)oxy)benzyl)-2-methyl-1H-imidazo[4,5-b]pyridine-5-carboxylate $^1$H-NMR(CDCl$_3$): 2.64(3H, s), 3.11(3H, s), 3.95(2H, t, J=5 Hz), 4.01(3H, s), 4.15(2H, t, J=5 Hz), 5.35(2H, s), 6.45–6.60(3H, m), 6.68(1H, dd, J=8 and 2 Hz), 7.08(1H, d, J=2 Hz), 7.44(1H, t, J=8 Hz), 7.52(1H, d, J=8 Hz), 8.01(1H, d, J=2 Hz), 8.04(1H, d, J=8 Hz).

Mass(ESI): m/E 466 (M+H)$^+$

Preparation Example 79-5

3-(2-Chloro-4-((2-(N-methyl-N-(2-pyridinyl)amino)ethyl)oxy)benzyl)-2-methyl-3H-imidazo[4,5-b]pyridine-5-carboxylic acid In the same manner as in Preparation Example 4-7, the objective compound (114 mg) was obtained as a white powder from methyl 3-(2-chloro-4-((2-(N-methyl-N-(2-pyridinyl)amino)ethyl)oxy)benzyl)-2-methyl-3H-imidazo[4,5-b]pyridine-5-carboxylate (143 mg).

$^1$H-NMR(DMSO-d$_6$): 2.50(3H, s), 3.03(3H, s), 3.87(2H, t, J=5 Hz), 4.13(2H, t, J=5 Hz), 5.53(2H, s), 6.50–6.65(3H, m), 6.82(1H, dd, J=8 and 2 Hz), 7.20(1H, d, J=2 Hz), 7.49(1H, t, J=8 Hz), 7.99(1H, d, J=8 Hz), 8.06(1H, d, J=5 Hz), 8.10(1H, d, J=8 Hz).

Mass(ESI): m/E 450 (M−H)$^-$

Preparation Example 80-1

Methyl 2-chloro-4-(methylthio)benzoate

Sodium thiomethoxide (459 mg) was added to a solution of methyl 4-bromo-2-chlorobenzoate (1.25 g) in N,N-dimethylformamide (10 ml) under ice-cooling, and the mixture was stirred for 2 hr. 1N Hydrochloric acid was added to the reaction mixture and the resulting product was extracted three times with ether. The organic layers were combined, washed successively with water and saturated brine, and dried over anhydrous magnesium sulfate. The solvent was evaporated and the residue was subjected to silica gel column chromatography (hexane/ethyl acetate=10/1) to give the objective compound (835 mg) as a colorless oil.

$^1$H-NMR(CDCl$_3$): 2.49(3H, s), 3.90(3H, s), 7.11(1H, d, J=8 Hz), 7.23(1H, s), 7.78(1H, d, J=8 Hz).

Preparation Example 80-2

2-Chloro-4-(methylthio)benzyl alcohol

Methyl 2-chloro-4-(methylthio)benzoate (806 mg) was dropwise added to a suspension of lithium aluminum hydride (139 mg) in tetrahydrofuran (8 ml) under ice-cooling, and the mixture was stirred for 1 hr. The reaction mixture was diluted with ether and 1N hydrochloric acid (10 ml) was dropwise added. The resulting product was extracted three times with ether. The organic layers were combined, washed successively with a saturated aqueous solution of sodium hydrogencarbonate and saturated brine, and dried over anhydrous magnesium sulfate. The solvent was evaporated to give the objective compound (725 mg) as a colorless oil.

$^1$H-NMR(CDCl$_3$): 1.92(1H, br t, J=7 Hz), 2.48(3H, s), 4.73(2H, d, J=7 Hz), 7.15(1H, d, J=8 Hz), 7.23(1H, s), 7.37(1H, d, J=8 Hz).

Preparation Example 80-3

2-Chloro-1-((methanesulfonyloxy)methyl)-4-(methylthio)benzene

In the same manner as in Preparation Example 14-1, the objective compound (1.02 g) was obtained as a colorless oil from 2-chloro-4-(methylthio)benzyl alcohol (687 mg).

$^1$H-NMR(CDCl$_3$) 2.48(3H, s), 3.00(3H, s), 5.30(2H, s), 7.15(1H, dd, J=8 and 2 Hz), 7.26(1H, d, J=2 Hz), 7.38(1H, d, J=8 Hz).

Preparation Example 80-4

Methyl 3-(2-chloro-4-(methylthio)benzyl)-2-methyl-3H-imidazo[4,5-b]pyridine-5-carboxylate and methyl 1-(2-chloro-4-(methylthio)benzyl)-2-methyl-1H-imidazo[4,5-b]pyridine-5-carboxylate In the same manner as in Preparation Example 14-2, methyl 3-(2-chloro-4-(methylthio)benzyl)-2-methyl-3H-imidazo[4,5-b]pyridine-5-carboxylate (457 mg) and methyl 1-(2-chloro-4-(methylthio)benzyl)-2-methyl-1H-imidazo[4,5-b]pyridine5-carboxylate (402 mg) were obtained as white powder from methyl 2-methyl-1H-imidazo[4,5-b]pyridine-5-carboxylate (573 mg) and 2-chloro-1-((methanesulfonyloxy)methyl)-4-(methylthio)benzene (955 mg).

Methyl 3-(2-chloro-4-(methylthio)benzyl)-2-methyl-3H-imidazo[4,5-b]pyridine-5-carboxylate $^1$H-NMR(CDCl$_3$): 2.44(3H, s), 2.53(3H, s), 4.00(3H, s), 5.63(2H, s), 6.58(1H, d, J=8 Hz), 6.96(1H, dd, J=8 and 2 Hz), 7.28(1H, d, J=2 Hz), 8.06(1H, d, J=8 Hz), 8.13(1H, d, J=8 Hz).

Mass(ESI): m/e 362 (M+H)$^+$

Methyl 1-(2-chloro-4-(methylthio)benzyl)-2-methyl-1H-imidazo[4,5-b]pyridine-5-carboxylate $^1$H-NMR(CDCl$_3$): 2.45(3H, s), 2.65(3H, s), 4.01(3H, s), 5.39(3H, s), 6.42(1H, d, J=8 Hz), 6.98(1H, dd, J=8 and 2 Hz), 7.30(1H, d, J=2 Hz), 7.54(1H, d, J=8 Hz), 8.08(1H, d, J=8 Hz).

Mass(ESI): m/e 362 (M+H)$^+$

Preparation Example 80-5

3-(2-Chloro-4-(methylthio)benzyl)-2-methyl-3H-imidazo[4,5-b]pyridine-5-carboxylic acid In the same manner as in Preparation Example 4-7, the objective compound (184 mg) was obtained as a white powder from methyl 3-(2-chloro-4-(methylthio)benzyl)-2-methyl-3H-imidazo[4,5-b]pyridine-5-carboxylate (146 mg).

$^1$H-NMR(DMSO-d$_6$): 2.45(3H, s), 2.50(3H, s), 5.60(2H, s), 6.44(1H, d, J=8 Hz), 7.10(1H, d, J=8 Hz), 7.42(1H, s), 8.00(1H, d, J=8 Hz), 8.10(1H, d, J=8 Hz).

Mass(ESI): m/e 346 (M−H)$^−$

Preparation Example 81-1

Methyl 3-(2-chloro-4-(methylsulfinyl)benzyl)-2-methyl-3H-imidazo[4,5-b]pyridine-5-carboxylate To a solution of methyl 3-(2-chloro-4-(methylthio)benzyl)-2-methyl-3H-imidazo[4,5-b]pyridine-5-carboxylate (148 mg) in dichloromethane (2.8 ml) was added m-chloroperbenzoic acid (81 mg) under ice-cooling, and the mixture was stirred for 1 hr. The reaction mixture was diluted with chloroform, washed successively with a saturated aqueous sodium hydrogencarbonate solution and saturated brine, and dried over anhydrous magnesium sulfate. The solvent was evaporated, and acetonitrile was added to the residue for crystallization, whereby the objective compound (118 mg) was obtained as a white powder.

$^1$H-NMR(CDCl$_3$): 2.55(3H, s), 2.71(3H, s), 3.99(3H, s), 5.71(2H, s), 6.78(1H, d, J=8 Hz), 7.32(1H, d, J=8 Hz), 7.80(1H, s), 8.09(1H, d, J=8 Hz), 8.16(1H, d, J=8 Hz).

Mass(ESI): m/e 378 (M+H)$^+$

Preparation Example 81-2

3-(2-Chloro-4-(methylsulfinyl)benzyl)-2-methyl-3H-imidazo[4,5-b]pyridine-5-carboxylic acid In the same manner as in Preparation Example 4-7, the objective compound (112 mg) was obtained as a white powder from methyl 3-(2-chloro-4-(methylsulfinyl)benzyl)-2-methyl-3H-imidazo[4,5-b]pyridine-5-carboxylate (112 mg).

$^1$H-NMR(DMSO-d$_6$): 2.54(3H, s), 2.76(3H, s), 5.67(2H, s), 6.75(1H, d, J=8 Hz), 7.52(1H, d, J=8 Hz), 7.88(1H, s), 8.01(1H, d, J=8 Hz), 8.14(1H, d, J=8 Hz).

Mass(ESI): m/e 362 (M−H)$^−$

Preparation Example 82-1

2-Chloro-4-(methanesulfonyl)-1-((methanesulfonyloxy)methyl)benzene

In the same manner as in Preparation Example 14-1, the objective compound (737 mg) was obtained as a white powder from 2-chloro-4-(methanesulfonyl)benzyl alcohol (457 mg) and methanesulfonyl chloride (261 mg).

$^1$H-NMR(DMSO-d$_6$): 3.31(3H, s), 3.33(3H, s), 5.42(2H, s), 7.85(1H, d, J=8 Hz), 7.79(1H, d, J=8 Hz), 8.07(1H, s).

Preparation Example 82-2

Methyl 3-(2-chloro-4-(methanesulfonyl)benzyl)-2-methyl-3H-imidazo[4,5-b]pyridine-5-carboxylate and methyl 1-(2-chloro-4-(methanesulfonyl)benzyl)-2-methyl-1H-imidazo[4,5-b]pyridine-5-carboxylate In the same manner as in Preparation Example 14-2, methyl 3-(2-chloro-4-(methanesulfonyl)benzyl)-2-methyl-3H-imidazo[4,5-b]pyridine-5-carboxylate (233 mg) was obtained as white crystals and methyl 1-(2-chloro-4-(methanesulfonyl)benzyl)-2-methyl-1H-imidazo[4,5-b]pyridine-5-carboxylmethylate (25 mg) was obtained as white crystals, from methyl 2-methyl-3H-imidazo[4,5-b]pyridine-5-carboxylate (200 mg) and 2-chloro-4-((methanesulfonyl)-1-((methanesulfonyloxy)methyl)benzene (344 mg).

Methyl 3-(2-chloro-4-(methanesulfonyl)benzyl)-2-methyl-3H-imidazo[4,5-b]pyridine-5-carboxylate $^1$H-NMR(CDCl$_3$): 2.56(3H, s), 3.03(3H, s), 3.99(3H, s), 5.72(2H, s), 6.80(1H, d, J=8 Hz), 7.08(1H, d, J=8 Hz), 8.05(1H, s), 8.10(1H, d, J=8 Hz), 8.16(1H, d, J=8 Hz).

Methyl 1-(2-chloro-4-(methanesulfonyl)benzyl)-2-methyl-1H-imidazo[4,5-b]pyridine-5-carboxylate $^1$H-NMR(CDCl$_3$): 2.70(3H, s), 3.10(3H, s), 4.03(3H, s), 5.62(2H, s), 6.62–6.70(1H, m), 7.75–8.12(4H, m).

Preparation Example 82-3

3-(2-Chloro-4-(methylsulfonyl)benzyl)-2-methyl-3H-imidazo[4,5-b]pyridine-5-carboxylic acid In the same manner as in Preparation Example 4-7, the objective compound (199 mg) was obtained as white crystals from methyl 3-(2-chloro-4-(methylsulfonyl)benzyl)-2-methyl-3H-imidazo[4,5-b]pyridine-5-carboxylate.

$^1$H-NMR(DMSO-d$_6$): 2.53(3H, s), 3.25(3H, s), 5.70(2H, s), 6.80(1H, d, J=8 Hz), 7.75(1H, d, J=8 Hz), 8.00(1H, d, J=8 Hz), 8.10(1H, s), 8.13(1H, d, J=8 Hz).

Preparation Example 83-1

2-Chloro-1-((methanesulfonyloxy)methyl)-4-nitrobenzene

In the same manner as in Preparation Example 14-1, the objective compound (3.56 g) was obtained as brown crystals from 2-chloro-4-nitrobenzyl alcohol (2.5 g) and methanesulfonyl chloride (1.68 g).

$^1$H-NMR(DMSO-d$_6$): 3.12(3H, s), 5.40(2H, s), 7.73(1H, d, J=8 Hz), 8.18(1H, dd, J=2, 8 Hz), 8.79(1H, d, J=2 Hz).

Preparation Example 83-2

Methyl 3-(2chloro-4-nitrobenzyl)-2-methyl-3H-imidazo[4,5-b]pyridine-5-carboxylate and methyl 1-(2-chloro-4-nitrobenzyl)-2-methyl-1H-imidazo[4,5-b]pyridine-5-carboxylate In the same manner as in Preparation Example 14-2, methyl 3-(2-chloro-4-nitrobenzyl)-2-methyl-3H-imidazo[4,5-b]pyridine-5-carboxylate (1.02 g) was obtained as white crystals, and methyl 1-(2-chloro-4-nitrobenzyl)-2-methyl-1H-imidazo[4,5-b]pyridine-5-carboxylate (330 mg) was obtained as pale-brown crystals, from methyl 2-methyl-3H-imidazo[4,5-b]pyridine-5-carboxylate (2.00 g) and 2-chloro-1-((methanesulfonyloxy)methyl)-4-nitrobenzene (3.06 g).

Methyl 3-(2-chloro-4-nitrobenzyl)-2-methyl-3H-imidazo[4,5-b]pyridine-5-carboxylate $^1$H-NMR(CDCl$_3$): 2.55(3H, s), 3.99(3H, s), 5.73(2H, s), 6.80(1H, d, J=8 Hz), 7.97(1H, d, J=8 Hz), 8.08(1H, d, J=8 Hz), 8.16(1H, d, J=8 Hz), 8.33(1H, s).

Methyl 1-(2-chloro-4-nitrobenzyl)-2-methyl-1H-imidazo[4,5-b]pyridine-5-carboxylate $^1$H-NMR(CDCl$_3$): 2.65(3H, s), 4.03(3H, s), 5.51(2H, s), 6.62(1H, d, J=8 Hz), 7.53(1H, d, J=8 Hz), 8.01(1H, dd, J=2, 8 Hz), 8.10(1H, d, J=8 Hz), 8.39(1H, d, J=2 Hz).

Preparation Example 83-3

Methyl 3-(4-amino-2-chlorobenzyl)-2-methyl-3H-imidazo[4,5-b]pyridine-5-carboxylate Methyl 3-(2-chloro-4-nitrobenzyl)-2-methyl-3H-imidazo[4,5-b]pyridine-5-carboxylate (705 mg) was suspended in ethanol (6 ml), and reduced iron (437 mg) and acetic acid (1.01 ml) were added. The mixture was refluxed under heating for 2 hr. Then, reduced iron (218 mg) and acetic acid (1.01 ml) were further added, and the mixture was refluxed under heating for 1 hr. The reaction mixture was filtered through Celite, the insoluble matter was washed with ethanol and the filtrate was concentrated under reduced pressure. To the concentrate were added a saturated aqueous sodium hydrogencarbonate solution and ethyl acetate to make the aqueous layer alkaline. At this stage, part of the objective compound was precipitated. The precipitate was collected by filtration and the filtrate was partitioned. The organic layer was washed successively with a saturated aqueous sodium hydrogencarbonate solution and saturated brine, dried over anhydrous magnesium sulfate, and filtrated. The objective compound that precipitated during neutrlization was dissolved in a mixed solvent of methanol/chloroform (1/4), and the mixture was filtered. Both filtrates were combined and concentrated under reduced pressure to give the objective compound (608 mg) as a white powder.

$^1$H-NMR(CDCl$_3$): 2.53(3H, s), 3.75(2H, s), 4.00(3H, s), 5.67(2H, s), 6.40(1H, dd, J=2, 8 Hz), 6.54(1H, dd, J=1, 8 Hz), 6.72(1H, d, J=1 Hz), 8.02(1H, d, J=8 Hz), 8.12(1H, d, J=8 Hz).

Preparation Example 83-4

Methyl 3-(4-(benzylamino)-2-chlorobenzyl)-2-methyl-3H-imidazo[4,5-b]pyridine-5-carboxylate Methyl 3-(4-amino-2-chlorobenzyl)-2-methyl-3H-imidazo[4,5-b]pyridine-5-carboxylate (100 mg) was dissolved in methanol (1 ml), and benzaldehyde (39 mg), zinc chloride (49 mg) and sodium cyanoborohydride (23 mg) were added. The mixture was stirred at room temperature for 2 hr and refluxed under heating for 15 min. Benzaldehyde (16 mg), zinc chloride (21 mg) and sodium cyanoborohydride (10 mg) were added and the mixture was stirred at room temperature for 1 hr. To the reaction mixture was added ice water, and then a saturated aqueous sodium hydrogencarbonate solution. The mixture was extracted with ethyl acetate, and the organic layer was washed successively with a saturated aqueous sodium hydrogencarbonate solution and saturated brine, dried over anhydrous magnesium sulfate, and filtrated. The filtrate was concentrated under reduced pressure. Hexane was added to the residue and the precipitated pale-yellow crystals were washed, collected by filtration and dried under reduced pressure to give the objective compound (120 mg).

$^1$H-NMR(CDCl$_3$): 2.52(3H, s),3.98(3H, s), 4.17(1H, t, J=7 Hz), 4.27(2H, d, J=6 Hz), 5.56(2H, s), 6.34(1H, dd, J=2, 8 Hz), 6.55(1H, d, J=8 Hz), 6.66(1H, d, J=2 Hz), 7.25–7.37 (5H, m), 8.02(1H, d, J=8 Hz), 8.10(1H, d, J=8 Hz).

Preparation Example 83-5

3-(4-(Benzylamino)-2-chlorobenzyl)-2-methyl-3H-imidazo[4,5-b]pyridine-5-carboxylic acid In the same manner as in Preparation Example 4-7, the objective compound (82 mg) was obtained as white crystals from methyl 3-(4-(benzylamino)-2-chlorobenzyl)-2-methyl-3H-imidazo[4,5-b]pyridine-5carboxylate.

$^1$H-NMR(DMSO-d$_6$): 2.48(3H, s), 4.22(2H, d, J=6 Hz), 5.44(2H, s), 6.43(2H, s), 6.58–6.63(1H, m), 6.68(1H, s), 7.17–7.25(1H, m), 7.27–7.30(4H, m), 7.98(1H, d, J=8 Hz), 8.08(1H, d, J=8 Hz).

Preparation Example 84-1

Methyl 3-(4-(n-butylamino)-2-chlorobenzyl)-2-methyl-3H-imidazo[4,5-b]pyridine-5-carboxylate In the same manner as in Preparation Example 84-4, the objective compound (87 mg) was obtained as pale-yellow crystals from methyl 3-(4-amino-2-chlorobenzyl)-2-methyl-3H-imidazo[4,5-b]pyridine-5-carboxylate (100 mg) and n-butyl aldehyde (37 mg).

$^1$H-NMR(CDCl$_3$): 0.93(3H, t, J=8 Hz), 1.37–1.48(2H, m), 1.52–1.62(2H, m), 2.55(3H, s), 4.00(2H, q, J=7 Hz), 3.72(1H, br s), 4.01(3H, s), 5.57(2H, s), 6.32(1H, dd, J=2, 8 Hz), 6.57(1H, d, J=8 Hz), 6.60(1H, d, J=2 Hz), 8.02(1H, d, J=8 Hz), 8.12(1H, d, J=8 Hz).

Preparation Example 84-2

3-(4-(n-Butylamino)-2-chlorobenzyl)-2-methyl-3H-imidazo[4,5-b]pyridine-5-carboxylic acid In the same manner as in Preparation Example 4-7, the objective compound (54 mg) was obtained as a white powder from methyl 3-(4-(n-butylamino)-2-chlorobenzyl)-2-methyl-3H-imidazo[4,5-b]pyridine-5-carboxylate (75 mg).

$^1$H-NMR(DMSO-d$_6$): 0.88(3H, t, J=8 Hz), 1.23–1.40(2H, m), 1.42–1.53(2H, m), 2.49(3H, s), 2.92(2H, q, J=7 Hz), 5.45(2H, s), 5.93(1H, t, J=7 Hz), 6.38(1H, d, J=8 Hz), 6.44(1H, d, J=8 Hz), 6.63(1H, s), 8.00(1H, d, J=8 Hz), 8.10(1H, d, J=8 Hz).

Preparation Example 85-1

Methyl 3-(2-chloro-4-(N,N-dimethylamino)benzyl)-2-methyl-3H-imidazo[4,5-b]pyridine-5-carboxylate Methyl 3-(4-amino-2-chlorobenzyl)-2-methyl-3H-imidazo[4,5-b]pyridine-5-carboxylate (100 mg) was dissolved in acetonitrile (1 ml), and a 37% aqueous formaldehyde solution (0.123 ml) and sodium cyanoborohydride (29 mg) were added, and the mixture was stirred at room temperature for 1 hr. Then, a 37% aqueous formaldehyde solution (0.123 ml) and sodium cyanoborohydride (29 mg) were added, and acetic acid was added to neutralize the reaction mixture, which was followed by stirring at room temperature overnight. The reaction mixture was concentrated under reduced pressure, and ice water was added to the residue. A saturated aqueous sodium hydrogencarbonate solution was added and the mixture was extracted with ethyl acetate. The organic layer was washed successively with an aqueous sodium hydrogencarbonate solution and saturated brine, dried over anhydrous magnesium sulfate, dried and filtrated. The filtrate was concentrated under reduced pressure. Hexane was added to the residue and the precipitated pale-yellow crystals were washed, filtered, and dried under reduced pressure to give the objective compound (97 mg).

$^1$H-NMR(CDCl$_3$): 2.52(3H, s), 2.90(6H, s), 4.00(3H, s), 5.59(2H, s), 6.42(1H, dd, J=2, 8 Hz), 6.62(1H, d, J=8 Hz), 6.70(1H, d, J=2 Hz), 8.03(1H, d, J=8Hz), 8.13(1H, d, J=8 Hz).

Preparation Example 85-2

3-(2-Chloro-4-(N,N-dimethylamino)benzyl)-2-methyl-3H-imidazo[4,5-b]pyridine-5-carboxylic acid In the same manner as in Preparation Example 4-7, the objective compound (65 mg) was obtained as white crystals from methyl 3-(2-chloro-4-(N,N-dimethylamino)benzyl)-2-methyl-3H-imidazo[4,5-b]pyridine-5-carboxylate (90 mg).

$^1$H-NMR(DMSO-d$_6$): 2.50(3H, s), 2.87(6H, s), 5.48(2H, s), 6.78(1H, s), 7.98(1H, d, J=8 Hz), 8.10(1H, d, J=8 Hz).

Preparation Example 86-1

Methyl 3-(4-(acetylamino)-2-chlorobenzyl)-2-methyl-3H-imidazo[4,5-b]pyridine-5-carboxylate Methyl 3-(4-amino-2-chlorobenzyl)-2-methyl-3H-imidazo[4,5-b]pyridine-5-carboxylate (150 mg) was dissolved in 1,2-dichloroethane (1.5 ml), and acetic anhydride (148 mg) and acetic acid (87 mg) were added at room temperature. The mixture was refluxed under heating for 1 hr. The reaction mixture was concentrated under reduced pressure, and ice water, a saturated aqueous sodium hydrogencarbonate solution were successively added to the residue. The precipitated white crystals were collected by filtration, washed with water, and dried under reduced pressure to give the objective compound (139 mg).

$^1$H-NMR(CDCl$_3$): 2.12(3H, s), 2.52(3H, s), 3.40(1H, s), 3.99(3H, s), 5.60(2H, s), 6.51(1H, d, J=8 Hz), 7.13(1H, d, J=8 Hz), 7.83(1H, s), 8.05(1H, d, J=8 Hz), 8.14(1H, d, J=8 Hz).

Preparation Example 86-2

3-(4-(Acetylamino)-2-chlorobenzyl)-2-methyl-3H-imidazo[4,5-b]pyridine-5-carboxylic acid In the same manner as in Preparation Example 4-7, the objective compound (116 mg) was obtained as white crystals from methyl 3-(4-(acetylamino)-2-chlorobenzyl)-2-methyl-3H-imidazo[4,5-b]pyridine5-carboxylate (123 mg).

$^1$H-NMR(DMSO-d$_6$): 2.03(3H, s), 2.50(3H, s), 5.55(2H, s), 6.57(1H, d, J=8 Hz), 7.23(1H, d, J=8 Hz), 7.95(1H, s), 7.98(1H, d, J=8 Hz), 8.11(1H, d, J=8 Hz).

Preparation Example 87-1

Methyl 3-(2-chloro-4-(methanesulfonylamino) benzyl)-2-methyl-3H-imidazo[4,5-b]pyridine-5-carboxylate Methyl 3-(4-amino-2-chlorobenzyl)-2-methyl-3H-imidazo[4,5-b]pyridine-5-carboxylate (150 mg) was dissolved in pyridine (1.5 ml), and a solution of methanesulfonyl chloride (114 mg) in pyridine (0.5 ml) was added at room temperature. The mixture was refluxed under heating for 1 hr. Thereto was added a solution of methanesulfonyl chloride (114 mg) in pyridine (0.5 ml) at room temperature, and the mixture was left standing overnight at room temperature. The reaction mixture was concentrated under reduced pressure and ice water was added to the residue. The resulting product was extracted with chloroform. The organic layer was washed successively with a saturated aqueous sodium hydrogencarbonate solution and saturated brine, dried over anhydrous magnesium sulfate, and filtrated. The filtrate was concentrated under reduced pressure. Ethanol was added to the residue, and the crystals were washed, filtrated and dried under reduced pressure to give the objective compound (101 mg) as pale-yellow crystals.

$^1$H-NMR(CDCl$_3$): 2.52(3H, s), 3.04(3H, s), 3.97(3H, s), 5.60(2H, s), 6.10(1H, d, J=8 Hz), 6.90(1H, d, J=8 Hz), 7.20(1H, d, J=3 Hz), 8.07(1H, d, J=8 Hz), 8.13(1H, d, J=8 Hz), 8.87(1H, s).

Preparation Example 87-2

3-(2-Chloro-4-(methanesulfonylamino)benzyl)-2-methyl-3H-imidazo[4,5-b]-pyridine-5-carboxylic acid In the same manner as in Preparation Example 4-7, the objective compound (88 mg) was obtained as pale-yellow crystals from methyl 3-(2-chloro-4-(methanesulfonylamino) benzyl)-2-methyl-3H-imidazo[4,5-b]pyridine-5-carboxylate.

$^1$H-NMR(DMSO-d$_6$): 2.48(3H, s), 3.01(3H, s), 5.55(2H, s), 6.60(1H, d, J=8 Hz), 7.03(1H, d, J=8 Hz), 7.33(1H, s), 7.97(1H, d, J=8 Hz), 8.11(1H, d, J=8 Hz).

Preparation Example 88

3-(2-Chloro-4-nitrobenzyl)-2-methyl-3H-imidazo[4,5-b]pyridine-5-carboxylic acid

In the same manner as in Preparation Example 4-7, the objective compound (258 mg) was obtained as white crystals from methyl 3-(2-chloro-4-nitrobenzyl)-2-methyl-3H-imidazo[4,5-b]pyridine-5-carboxylate (300 mg).

$^1$H-NMR(DMSO-d$_6$): 2.52(3H, s), 5.70(2H, s), 6.82(1H, d, J=8 Hz), 8.00(1H, d, J=8 Hz), 8.04(1H, dd, J=2, 8 Hz), 8.12(1H, d, J=8 Hz), 8.40(1H, s).

Preparation Example 89-1

3-Chloro-4-(hydroxymethyl)benzaldehyde

In the same manner as in Preparation Example 70-3, the objective compound (112 mg) was obtained as a pale-yellow powder from 4-((tert-butyldimethylsilyloxy)methyl)-3-chlorobenzaldehyde (228 mg).

$^1$H-NMR(CDCl$_3$): 2.04(1H, br.s), 4.88(2H, br.s), 7.76 (1H, d, J=8 Hz), 7.82(1H, d, J=8 Hz), 7.88(1H, s), 9.98(1H, s).

Preparation Example 89-2

3-Chloro-4-((methanesulfonyloxy)methyl) benzaldehyde

In the same manner as in Preparation Example 14-1, the objective compound (577 mg) was obtained as pale-yellow oil from 3-chloro-4-(hydroxymethyl)benzaldehyde (393 mg).

$^1$H-NMR(CDCl$_3$): 3.12(3H, s), 5.40(2H, s), 7.72(1H, d, J=8 Hz), 7.84(1H, d, J=8 Hz), 7.94(1H, s), 9.98(1H, s).

Preparation Example 89-3

Methyl 3-(2-chloro-4-formylbenzyl)-2-methyl-3H-imidazo[4,5-b]pyridine-5-carboxylate and methyl 1-(2-chloro-4-formylbenzyl)-2-methyl-1H-imidazo[4, 5-b]pyridine-5-carboxylate In the same manner as in Preparation Example 14-2, methyl 3-(2-chloro-4-formylbenzyl)-2-methyl-3H-imidazo [4,5-b]pyridine-5-carboxylate was obtained as colorless crystals (1.71 g) and methyl 1-(2-chloro-4-formylbenzyl)-2-methyl-1H-imidazo[4,5-b]pyridine5-carboxylate was obtained as amorphous (1.40 g), from methyl 2-methyl-3H-imidazo[4,5-b]pyridine-5-carboxylate (2.60 g) and 3-chloro-4-((methanesulfonyloxy)methyl)benzaldehyde (3.72 g).

Methyl 3-(2-chloro-4-formylbenzyl)-2-methyl-3H-imidazo[4,5-b]pyridine-5-carboxylate $^1$H-NMR(CDCl$_3$): 2.54(3H, s), 3.99(3H, s), 5.73(2H, s), 6.77(1H, d, J=8 Hz), 7.61(1H, d, J=8 Hz), 7.98(1H, s), 8.10(1H, d, J=8 Hz), 8.18(1H, d, J=8 Hz), 9.94(1H, s)

Mass(ESI): m/z 344 (M+1)

mp 189–191° C.

Methyl 1-(2-chloro-4-formylbenzyl)-2-methyl-1H-imidazo[4,5-b]pyridine-5-carboxylate $^1$H-NMR(CDCl$_3$): 2.64(3H, s), 4.00(3H, s), 5.50(2H, s), 6.61(1H, d, J=8 Hz), 7.55(1H, d, J=8 Hz), 7.64(1H, br d, J=8 Hz), 8.00(1H, s), 8.09(1H, d, J=8 Hz), 8.18(1H, d, J=8 Hz), 9.95(1H, s)

Mass(ESI): m/z 344 (M+1)

Preparation Example 89-4

3-(2-Chloro-4-formylbenzyl)-2-methyl-3H-imidazo[4,5-b]pyridine-5-carboxylic acid In the same manner as in Preparation Example 4-7, the objective compound (202 mg) was obtained as colorless crystals from methyl 3-(2-chloro-4-formylbenzyl)-2-methyl-3H-imidazo[4,5-b]pyridine-5carboxylate (200 mg).

$^1$H-NMR(DMSO-d$_6$): 2.53(3H, s), 5.70(2H, s), 6.78(1H, d, J=8 Hz), 7.75(1H, d, J=8 Hz), 8.01(1H, d, J=8 Hz), 8.09(1H, s), 8.16(1H, d, J=8 Hz), 9.96(1H, s).

Mass(ESI): m/z 328 (M−1)

mp 188–192° C.

Preparation Example 90-1

Methyl 3-[2-chloro-4-[(2,4-dioxo-1,3-thiazolidin-5-ylidene)methyl]-benzyl]-2-methyl-3H-imidazo[4,5-b]pyridine-5-carboxylate A suspension of methyl 3-(2-chloro-4-formylbenzyl)-2-methyl-3H-imidazo[4,5-b]pyridine-5-carboxylate (200 mg, 0.582 mmol), thiazolidine-2,4-dione (82 mg, 0.698 mmol) and piperidine (25 mg, 0.291 mmol) in ethanol (4 ml) was refluxed under heating overnight. The reaction mixture was cooled, and the precipitated crystals were filtrated to give the objective compound (189 mg) as pale-yellow crystals.

$^1$H-NMR(DMSO-d$_6$): 2.54(3H, s), 3.85(3H, s), 5.64(2H, s), 6.71(1H, d, J=8 Hz), 7.42(1H, d, J=8 Hz), 7.74(1H, s), 7.82(1H, s), 8.02(1H, d, J=8 Hz), 8.17(1H, d, J=8 Hz).

Mass(ESI): m/z 441 (M−1)

mp >300° C.

Preparation Example 90-2

3-[2-Chloro-4-[(2,4-dioxo-1,3-thiazolidin-5-ylidene)methyl]benzyl]-2-methyl-3H-imidazo[4,5-b]pyridine-5-carboxylic acid In the same manner as in Preparation Example 4-7, the objective compound (63 mg) was obtained from methyl 3-[2-chloro-4-[(thiazolidine-2,4-dione-5-ylidene)methyl]benzyl]-2-methyl-3H-imidazo[4,5-b]pyridine-5-carboxylate (80 mg).

$^1$H-NMR(DMSO-d$_6$): 2.51(3H, s), 5.67(2H, s), 6.70(1H, d, J=8 Hz), 7.42(1H, d, J=8 Hz), 7.75(1H, s), 7.84(1H, s), 8.01(1H, d, J=8 Hz), 8.16(1H, d, J=8 Hz).

Mass(ESI): m/z 427 (M−1)

mp >300° C.

Preparation Example 91-1

2-Chloro-4-fluorobenzyl alcohol

In the same manner as in Preparation Example 74-4, the objective compound (4.20 g) was obtained as white crystals from 2-chloro-4-fluorobenzoic acid (5.00 g).

$^1$H-NMR(CDCl$_3$): 1.92(1H, br s), 4.75(2H, br d), 6.99 (1H, dt, J=2, 8 Hz), 7.12(1H, dd, J=2, 8 Hz), 7.47(1H, t, J=7 Hz).

Preparation Example 91-2

2-Chloro-4-fluoro-1-((methanesulfonyloxy)methyl)benzene

In the same manner as in Preparation Example 14-1, the objective compound (572 mg) was obtained as a colorless oil from 2-chloro-4-fluorobenzyl alcohol (400 mg) and methanesulfonyl chloride (314 mg).

$^1$H-NMR(CDCl$_3$): 3.02(3H, s), 5.30(2H, s), 7.03(1H, dt, J=2, 8 Hz), 7.20(1H, dd, J=2, 8 Hz), 7.49(1H, t, J=8 Hz).

Preparation Example 91-3

Methyl 3-(2-chloro-4-fluorobenzyl)-2-methyl-3H-imidazo[4,5-b]pyridine-5-carboxylate and methyl 1-(2-chloro-4-fluorobenzyl)-2-methyl-1H-imidazo[4,5b]pyridine-5-carboxylate In the same manner as in Preparation Example 14-2, methyl 3-(2-chloro-4-fluorobenzyl)-2-methyl-3H-imidazo[4,5-b]pyridine-5-carboxylate (100 mg) was obtained as white crystals and methyl 1-(2-chloro-4-fluorobenzyl)-2-methyl-1H-imidazo[4,5-b]pyridine-5-carboxylate (55 mg) was obtained as pale-yellow crystals, from methyl 2-methyl-3H-imidazo[4,5-b]pyridine-5-carboxylate (150 mg) and 2-chloro-4-fluoro-1-((methanesulfonyloxy)methyl)benzene (206 mg).

Methyl 3-(2-chloro-4-fluorobenzyl)-2-methyl-3H-imidazo[4,5-b]pyridine-5-carboxylate $^1$H-NMR(CDCl$_3$): 2.53(3H, s), 4.00(3H, s), 5.62(2H, s), 6.70(1H, dt, J=1, 8 Hz), 6.85(1H, dt, J=2, 8 Hz), 7.20(1H, dd, J=2, 8 Hz), 8.05(1H, d, J=8 Hz), 8.14(1H, d, J=8 Hz).

Methyl 1-(2-chloro-4-fluorobenzyl)-2-methyl-1H-imidazo[4,5-b]pyridine-5-carboxylate $^1$H-NMR(CDCl$_3$): 2.65(3H, s), 4.02(3H, s), 5.40(2H, s), 6.50(1H, dt, J=1, 8 Hz), 6.87(1H, dt, J=2, 8 Hz), 7.23(1H, dd, J=2, 8 Hz), 7.53(1H, d, J=8 Hz), 8.08(1H, d, J=8 Hz).

Preparation Example 91-4

3-(2-Chloro-4-fluorobenzyl)-2-methyl-3H-imidazo[4,5-b]pyridine-5-carboxylic acid In the same manner as in Preparation Example 4-7, the objective compound (75 mg) was obtained as white crystals from methyl 3-(2-chloro-4-fluorobenzyl)-2-methyl-3H-imidazo[4,5-b]pyridine-5-carboxylate (90 mg).

$^1$H-NMR(DMSO-d$_6$): 2.51(3H, s), 5.59(2H, s), 6.67(1H, dt, J=1, 8 Hz), 7.11(1H, dt, J=1, 8 Hz), 7.60(1H, dd, J=2, 8 Hz), 8.01(1H, d, J=8 Hz), 8.13(1H, d, J=8 Hz).

Preparation Example 92-1

2,4,6-Trichlorobenzyl alcohol

In the same manner as in Preparation Example 74-4, the objective compound (4.14 g) was obtained as white crystals from 2,4,6-trichlorobenzoic acid (5.00 g).

$^1$H-NMR(CDCl$_3$): 2.04(1H, br s), 4.91(2H, s), 7.36(2H, s).

Preparation Example 92-2

2,4,6-Trichloro-1-((methanesulfonyloxy)methyl)benzene

In the same manner as in Preparation Example 14-1, the objective compound (407 mg) was obtained as white crystals from 2,4,6-trichlorobenzyl alcohol (300 mg) and methanesulfonyl chloride (179 mg).

$^1$H-NMR(CDCl$_3$): 3.08(3H, s), 5.48(2H, s), 7.42(2H, s).

Preparation Example 92-3

Methyl 2-methyl-3-(2,4,6-trichlorobenzyl)-3H-imidazo[4,5-b]pyridine-5-carboxylate and methyl 2-methyl-1-(2,4,6-trichlorobenzyl)-1H-imidazo[4,5-b]pyridine-5-carboxylate In the same manner as in Preparation Example 14-2, methyl 2-methyl-3-(2,4,6-trichlorobenzyl)-3H-imidazo[4,5- b]pyridine-5-carboxylate (129 mg) was obtained as white crystals and methyl 2-methyl-1-(2,4,6-trichlorobenzyl)-1H-imidazo[4,5-b]pyrdine-5-carboxylate (100 mg) was obtained as pale-yellow crystals, from methyl 2-methyl-3H-imidazo[4,5-b]pyridine-5-carboxylate (150 mg) and 2,4,6-trichloro-1-((methanesulfonyloxy)methyl)benzene (250 mg).

Methyl 2-methyl-3-(2,4,6-trichlorobenzyl)-3H-imidazo[4,5-b]pyridine-5-carboxylate $^1$H-NMR(CDCl$_3$): 2.46(3H, s), 4.00(3H, s), 5.79(2H, s), 7.39(2H, s), 7.97(1H, d, J=1, 8 Hz), 8.07(1H, d, J=1, 8 Hz).

Methyl 2-methyl-1-(2,4,6-trichlorobenzyl)-1H-imidazo[4,5-b]pyridine-5carboxylate $^1$H-NMR(CDCl$_3$): 2.73(3H, s), 4.00(3H, s), 5.56(2H, s), 7.34(1H, d, J=8 Hz), 7.44(2H, s), 7.98(1H, d, J=8 Hz).

Preparation Example 92-4

2-Methyl-3-(2,4,6-trichlorobenzyl)-3H-imidazo[4,5-b]pyridine-5-carboxylic acid

In the same manner as in Preparation Example 4-7, the objective compound (83 mg) was obtained as white crystals from 2-methyl-3-(2,4,6-trichlorobenzyl)-3H-imidazo[4,5-b]pyridine-5-carboxylate (94 mg).

$^1$H-NMR(DMSO-d$_6$): 2.50(3H, s), 5.71(2H, s), 7.72(2H, s), 7.92(1H, d, J=8 Hz), 8.03(1H, d, J=8 Hz).

Preparation Example 93-1

2,3,4-trichlorobenzyl-bromide 2,3,4-Trichlorotoluene (2.00 g) was dissolved in carbon tetrachloride (20 ml), and 2,2'-azobis(2,4-dimethyl-4-methoxyvaleronitrile) (158 mg) and N-bromosuccinimide (2.00 g) were added thereto. The mixture was refluxed under heating for 2 hr, and hexane was added, which was followed by stirring under cooling for 30 min. The mixture was filtrated and an insoluble matter on a filter paper was washed with small amounts of hexane. The filtrates were combined and concentrated under reduced pressure. Diisopropyl ether was added to the residue and the mixture was washed successively with a saturated aqueous sodium hydrogencarbonate solution and saturated brine, dried over anhydrous magnesium sulfate and filtrated. The filtrate was concentrated under reduced pressure to give a mixture (2.40 g) of the objective compound and 2,3,4-trichlorotoluene as brown crystals.

$^1$H-NMR(CDCl$_3$): 4.57(2H, s), 7.29(1H, d, J=8 Hz), 7.37 (1H, d, J=8 Hz).

Preparation Example 93-2

Methyl 2-methyl-3-(2,3,4-trichlorobenzyl)-3H-imidazo[4,5-b]pyridine-5-carboxylate and methyl 2-methyl-1-(2,3,4-trichlorobenzyl)-1H-imidazo[4,5-b]pyridine-5-carboxylate In the same manner as in Preparation Example 14-2, methyl 2-methyl-3-(2,3,4-trichlorobenzyl)-3H-imidazo[4,5-b]pyridine-5-carboxylate (196 mg) was obtained as white crystals and methyl 2-methyl-1-(2,3,4-trichlorobenzyl)-1H-imidazo[4,5-b]pyridine-5-carboxylate (82 mg) was obtained as pale-brown crystals, from methyl 2-methyl-3H-imidazo[4,5-b]pyridine-5-carboxylate (200 mg) and 2,3,4-trichlorobenzyl-bromide (1.44 g).

Methyl 2-methyl-3-(2,3,4-trichlorobenzyl)-3H-imidazo[4,5-b]pyridine-5-carboxylate $^1$H-NMR(CDCl$_3$): 2.54(3H, s), 3.98(3H, s), 5.65(2H, s), 6.43(1H, d, J=8 Hz), 7.23(1H, d, J=9 Hz), 8.07(1H, d, J=8 Hz), 8.15(1H, d, J=8 Hz).

Methyl 2-methyl-1-(2,3,4-trichlorobenzyl)-1H-imidazo[4,5-b]pyridine-5-carboxylate $^1$H-NMR(CDCl$_3$): 2.65(3H, s), 4.03(3H, s), 5.42(2H, s), 6.26(1H, d, J=8 Hz), 7.26(1H, d, J=8 Hz), 7.53(1H, d, J=8 Hz), 8.10(1H, d, J=8 Hz).

Preparation Example 93-3

2-Methyl-3-(2,3,4-trichlorobenzyl)-3H-imidazo[4,5-b]pyridine-5-carboxylic acid

In the same manner as in Preparation Example 4-7, the objective compound (156 mg) was obtained as white crystals from methyl 2-methyl-3-(2,3,4-trichlorobenzyl)-3H-imidazo[4,5-b]pyridine-5-carboxylate (185 mg).

$^1$H-NMR(DMSO-d$_6$): 2.53(3H, s), 5.62(2H, s), 6.52(1H, d, J=8 Hz), 7.52(1H, d, J=8 Hz), 8.00(1H, d, J=8 Hz), 8.13(1H, d, J=8 Hz).

Preparation Example 94-1

2,4-Dichloro-5-fluorobenzyl alcohol

In the same manner as in Preparation Example 74-4, the objective compound (1.00 g) was obtained as white crystals from 2,4-dichloro-5-fluorobenzoic acid (1.25 g).

$^1$H-NMR(CDCl$_3$): 1.96(1H, t, J=7 Hz), 4.73(2H, d, J=7 Hz), 7.35(1H, d, J=9 Hz), 7.40(1H, d, J=7 Hz).

Preparation Example 94-2

2,4-Dichloro-5-fluoro-1-((methanesulfonyloxy) methyl)benzene

In the same manner as in Preparation Example 14-1, the objective compound (404 mg) was obtained as a colorless oil from 2,4-dichloro-5-fluorobenzyl alcohol (300 mg) and methanesulfonyl chloride (194 mg).

$^1$H-NMR(CDCl$_3$): 3.08(3H, s), 5.27(2H, s), 7.32(1H, d, J=9 Hz), 7.49(1H, d, J=7 Hz).

Preparation Example 94-3

Methyl 3-(2,4-dichloro-5-fluorobenzyl)-2-methyl-3H-imidazo[4,5-b]pyridine-5-carboxylate (234 mg) and methyl 1-(2,4-dichloro-5-fluorobenzyl)-2-methyl-1H-imidazo[4,5-b]pyridine-5-carboxylate In the same manner as in Preparation Example 14-2, methyl 3-(2,4-dichloro-5-fluorobenzyl)-2-methyl-3H-imidazo[4,5-b]pyridine5-carboxylate (234 mg) was obtained as white crystals, and methyl 1-(2,4-dichloro-5-fluorobenzyl)-2-methyl-1H-imidazo[4,5-b]pyridine-5-carboxylate (86 mg) was obtained as pale-yellow crystals, from methyl 2-methyl-3H-imidazo[4,5-b]pyridine-5-carboxylate (200 mg) and 2,4-dichloro-5-fluoro-1-((methanesulfonyloxy)methyl)benzene (314 mg).

Methyl 3-(2,4-dichloro-5-fluorobenzyl)-2-methyl-3H-imidazo[4,5-b]pyridine-5-carboxylate $^1$H-NMR(CDCl$_3$): 2.57(3H, s), 4.00(3H, s), 5.60(2H, s), 6.53(1H, d, J=9 Hz), 7.52(1H, d, J=8 Hz), 8.08(1H, d, J=8 Hz), 8.17(1H, d, J=8 Hz).

Methyl 1-(2,4-dichloro-5-fluorobenzyl)-2-methyl-1H-imidazo[4,5-b]pyridine-5-carboxylate $^1$H-NMR(CDCl$_3$): 2.67(3H, s), 4.03(3H, s), 5.38(2H, s), 6.28(1H, d, J=9 Hz), 7.55(1H, d, J=8 Hz), 7.56(1H, d, J=8 Hz), 8.12(1H, d, J=8 Hz).

Preparation Example 94-4

3-(2,4-Dichloro-5-fluorobenzyl)-2-methyl-3H-imidazo[4,5-b]pyridine-5-carboxylic acid In the same manner as in Preparation Example 4-7, the objective compound (198 mg) was obtained as white crystals from methyl 3-(2,4-dichloro-5-fluorobenzyl)-2-methyl-3H-imidazo[4,5-b]pyridine-5-carboxylate (215 mg).

$^1$H-NMR(DMSO-d$_6$): 2.55(3H, s), 5.58(2H, s), 6.82(1H, d, J=9 Hz), 7.95(1H, d, J=8 Hz), 8.00(1H, d, J=8 Hz), 8.12(1H, dd, J=1, 8 Hz).

Preparation Example 95-1

2-Chloro-4-iodobenzyl-bromide

In the same manner as in Preparation Example 93-1, the the objective compound (5.83 g) was obtained as a pale-yellow oil from 2-chloro-4-iodotoluene (5.10 g).

$^1$H-NMR(CDCl$_3$): 4.52(2H, s), 7.17(1H, d, J=8 Hz), 7.60 (1H, d, J=8 Hz), 7.76(1H, s).

Preparation Example 95-2

Methyl 3-(2-chloro-4-iodobenzyl)-2-methyl-3H-imidazo[4,5-b]pyridine-5-carboxylate and methyl 1-(2-chloro-4-iodobenzyl)-2-methyl-1H-imidazo[4,5-b]pyridine-5-carboxylate In the same manner as in Preparation Example 14-2, methyl 3-(2-chloro-4-iodobenzyl)-2-methyl-3H-imidazo[4,5-b]pyridine-5-carboxylate (163 mg) and methyl 1-(2-chloro-4-iodobenzyl)-2-methyl-1H-imidazo[4,5-b]pyridine-5-carboxylate (108 mg) were obtained as pale-brown powder, from methyl 2-methyl-1H-imidazo[4,5-b]pyridine-5-carboxylate (150 mg) and 2-chloro-4-iodobenzyl bromide (780 mg).

Methyl 3-(2-chloro-4-iodobenzyl)-2-methyl-3H-imidazo[4,5-b]pyridine-5-carboxylate $^1$H-NMR(CDCl$_3$): 2.54(3H, s), 3.99(3H, s), 5.62(2H, s), 6.37(1H, d, J=8 Hz), 7.43(1H, d, J=8 Hz), 7.80(1H, s), 8.08(1H, d, J=8 Hz), 8.16(1H, d, J=8 Hz).

Methyl 1-(2-chloro-4-iodobenzyl)-2-methyl-1H-imidazo[4,5-b]pyridine-5-carboxylate $^1$H-NMR(CDCl$_3$): 2.65(3H, s), 4.03(3H, s), 5.38(2H, s), 6.20(1H, d, J=8 Hz), 7.48(1H, d, J=8 Hz), 7.53(1H, d, J=8 Hz), 7.83((1H, s), 8.09(1H, d, J=8 Hz).

Preparation Example 95-3

3-(2-Chloro-4-iodobenzyl)-2-methyl-3H-imidazo[4,5-b]pyridine-5-carboxylic acid

In the same manner as in Preparation Example 4-7, the objective compound (115 mg) was obtained as a white powder from methyl 3-(2-chloro-4-iodobenzyl)-2-methyl-3H-imidazo[4,5-b]pyridine-5-carboxylate (160 mg).

$^1$H-NMR(DMSO-d$_6$): 2.50(3H, s), 5.57(2H, s), 6.34(1H, d, J=8 Hz), 7.60(1H, d, J=8 Hz), 7.97(1H, s), 8.02(1H, d, J=8 Hz), 8.12(1H, d, J=8 Hz).

Preparation Example 96-1

2,5-Dichloro-3-(hydroxymethyl)thiophene

In the same manner as in Preparation Example76-2, the objective compound (718 mg) was obtained as a pale-yellow oil from methyl 2,5-dichlorothiophene-3-carboxylate (835 mg).

$^1$H-NMR(CDCl$_3$): 1.70 (1H, t, J=6 Hz), 4.58(2H, d, J=6 Hz), 6.88(1H, s).

Preparation Example 96-2

2,5-Dichloro-3-((methanesulfonyloxy)methyl)thiophene

In the same manner as in Preparation Example 14-1, the objective compound (384 mg) was obtained as a colorless oil from 2,5-dichloro-3-(hydroxymethyl)thiophene (300 mg) and methanesulfonyl chloride (206 mg).

$^1$H-NMR(CDCl$_3$): 3.02(3H, s), 5.12(2H, s), 6.90(1H, s).

Preparation Example 96-3

Methyl 3-((2,5-dichlorothiophen-3-yl)methyl)-2-methyl-3H-imidazo[4,5-b]pyridine-5-carboxylate and methyl 1-((2,5-dichlorothiophen-3-yl)methyl)-2-methyl-1H-imidazo[4,5-b]pyridine-5-carboxylate In the same manner as in Preparation Example 14-2, methyl 3-((2,5-dichlorothiophen-3-yl)methyl)-2-methyl-3H-imidazo[4,5-b]pyridine-5carboxylate (87 mg) was obtained as white crystals and methyl 1-((2,5-dichlorothiophene-3-yl)methyl)-2-methyl-1H-imidazo[4,5-b]pyridine-5-carboxylate (59 mg) was obtained as pale-yellow crystals, from methyl 2-methyl-3H-imidazo[4,5-b]pyridine-5-carboxylate (150 mg) and 2,5-dichloro-3-((methanesulfonyloxy)methyl)thiophene (225 mg).

Methyl 3-((2,5-dichlorothiophene-3-yl)methyl)-2-methyl-3H-imidazo[4,5-b]pyridine-5-carboxylate $^1$H-NMR(CDCl$_3$): 2.64(3H, s), 4.03(3H, s), 5.42(2H, s), 6.66(1H, s), 8.02(1H, d, J=8 Hz), 8.13(1H, d, J=8 Hz).

Methyl 1-((2,5-dichlorothiophene-3-yl)methyl)-2-methyl-1H-imidazo[4,5-b]pyridine-5-carboxylate $^1$H-NMR(CDCl$_3$): 2.70(3H, s), 4.02(3H, s), 5.20(2H, s), 6.30(1H, s), 7.64(1H, d, J=8 Hz), 8.12(1H, d, J=8 Hz).

Preparation Example 96-4

3-((2,5-Dichlorothiophen-3-yl)methyl)-2-methyl-3H-imidazo[4,5-b]pyridine-5-carboxylic acid In the same manner as in Preparation Example 4-7, the objective compound (67 mg) was obtained as white crystals from methyl 3-((2,5-dichlorothiophen-3-yl)methyl)-2-methyl-3H-imidazo[4,5-b]pyridine-5-carboxylate (77 mg).

$^1$H-NMR(DMSO-d$_6$): 2.60(3H, s), 5.43(2H, s), 6.94(1H, s), 7.99(1H, d, J=8 Hz), 8.07(1H, d, J=8 Hz).

Preparation Example 97-1

Methyl 3-(2-chloro-4,5-(methylenedioxy)benzyl)-2-methyl-3H-imidazo[4,5-b]pyridine-5-carboxylate and methyl 1-(2-chloro-4,5-(methylenedioxy)benzyl)-2-methyl-1H-imidazo[4,5-b]pyridine-5-carboxylate In the same manner as in Preparation Example 14-2, methyl 3-(2-chloro-4,5-(methylenedioxy)benzyl)-2-methyl- 3H-imidazo[4,5-b]pyridine-5-carboxylate (169 mg) was obtained as white crystals and methyl 1-(2-chloro-4,5-(methylenedioxy)benzyl)-2-methyl-1H-imidazo[4,5-b]pyridine-5-carboxylate (75 mg) was obtained as white crystals, from methyl 2-methyl-3H-imidazo[4,5-b]pyridine-5-carboxylate (200 mg) and 6-chloropiperonyl chloride (236 mg).

Methyl 3-(2-chloro-4,5-(methylenedioxy)benzyl)-2-methyl-3H-imidazo[4,5-b]pyridine-5-carboxylate $^1$H-NMR(CDCl$_3$): 2.56(3H, s), 4.00(3H, s), 5.59(2H, s), 5.91(2H, s), 6.23(1H, s), 6.89(1H, s), 8.04 (1H, d, J=8 Hz), 8.14(1H, d, J=8 Hz).

Methyl 1-(2-chloro-4,5-(methylenedioxy)benzyl)-2-methyl-1H-imidazo[4,5-b]pyridine 5-carboxylate $^1$H-NMR(CDCl$_3$): 2.67(3H, s), 4.02(3H, s), 5.33(2H, s), 5.94(2H, s), 5.99(1H, s), 6.92(1H, s), 7.57 (1H, d, J=8 Hz), 8.08(1H, d, J=8 Hz).

Preparation Example 97-2

3-(2-Chloro-4,5-(methylenedioxy)benzyl)-2-methyl-3H-imidazo[4,5-b]pyridine-5-carboxylic acid In the same manner as in Preparation Example 4-7, the objective compound (144 mg) was obtained as yellow crystals from methyl 3-(2-chloro-4,5-(methylenedioxy)benzyl)-2-methyl-3H-imidazo[4,5-b]pyridine-5-carboxylate (160 mg).

$^1$H-NMR(DMSO-d$_6$): 2.46(3H, s), 5.47(2H, s), 6.00(2H, s), 6.11(1H, s), 7.19(1H, s), 7.88(1H, d, J=8 Hz), 7.92(1H, d, J=8 Hz).

Preparation Example 98-1

In the same manner as in Preparation Example 14-1, a mixture (377 mg) of 2-chloro-3-((methanesulfonyloxy)methyl)quinoline and 2-chloro-3-(chloromethyl)quinoline was obtained as a pale-yellow powder from 2-chloro-3-(hydroxymethyl)quinoline (300 mg) and methanesulfonyl chloride (89 mg). This compound was used in the next reaction without purification.

Preparation Example 98-2

Methyl 3-((2-chloroquinolin-3-yl)methyl)-2-methyl-3H-imidazo[4,5-b]pyridine-5-carboxylate and methyl 1-((2-chloroquinolin-3-yl)methyl)-2-methyl-1H-imidazo[4,5-b]pyridine-5-carboxylate In the same manner as in Preparation Example 14-2, methyl 3-((2-chloroquinolin-3-yl)methyl)-2-methyl-3H-imidazo[4,5-b]pyridine-5-carboxylate (112 mg) was obtained as pale-yellow crystals and methyl 1-((2-chloroquinoline-3-yl)methyl)-2-methyl-1H-imidazo[4,5-b]pyridine-5-carboxylate (100 mg) was obtained as pale-yellow crystals, from methyl 2-methyl-3H-imidazo[4,5-b]pyridine-5-carboxylate (200 mg) and 2-chloro-3-((methanesulfonyloxy)methyl)quinoline (313 mg, mixture with 2-chloro-3-(chloromethyl)quinoline).

Methyl 3-((2-chloroquinolin-3-yl)methyl)-2-methyl-3H-imidazo[4,5-b]pyridine-5-carboxylate $^1$H-NMR(CDCl$_3$): 2.63(3H, s), 3.97(3H, s), 5.80(2H, s), 7.39(1H, s), 7.50(1H, t, J=7 Hz), 7.58(1H, d, J=8 Hz), 7.72(1H, t, J=8 Hz), 8.03(1H, d, J=8 Hz), 8.12(1H, d, J=8 Hz), 8.18(1H, dd, J=1, 8 Hz).

Methyl 1-((2-chloroquinolin-3-yl)methyl)-2-methyl-1H-imidazo[4,5-b]pyridine-5-carboxylate $^1$H-NMR(CDCl$_3$): 2.70(3H, s), 4.03(3H, s), 5.59(2H, s), 7.10(1H, s), 7.49–7.62(3H, m), 7.70–7.78(1H, m), 8.02–8.20(2H, m).

Preparation Example 98-3

3-((2-Chloroquinolin-3-yl)methyl)-2-methyl-3H-imidazo[4,5-b]pyridine-5-carboxylic acid In the same manner as in Preparation Example 4-7, the objective compound (90 mg) was obtained as white crystals from methyl 3-((2-chloroquinolin-3-yl)methyl)-2-methyl-3H-imidazo[4,5-b]pyridine-5-carboxylate (100 mg).

$^1$H-NMR(DMSO-d$_6$): 2.60(3H, s), 5.74(2H, s), 7.58(1H, t, J=7 Hz), 7.70(1H, s), 7.80(1H, t, J=8 Hz), 7.91(1H, d, J=8 Hz), 8.00(2H, t, J=8 Hz), 8.16(1H, d, J=8 Hz).

Preparation Example 99-1

Methyl 3-(2-chloro-4-(trifluoromethyl)benzyl)-2-methyl-3H-imidazo[4,5-b]pyridine-5-carboxylate and methyl 1-(2-chloro-4-(trifluoromethyl)benzyl)-2-methyl-1H-imidazo[4,5-b]pyridine-5-carboxylate In the same manner as in Preparation Example 14-2, methyl 3-(2-chloro-4-(trifluoromethyl)benzyl)-2-methyl-3H-imidazo[4,5-b]pyridine-5-carboxylate (129 mg) was obtained as white crystals and methyl 1-(2-chloro-4-(trifluoromethyl)benzyl)-2-methyl-1H-imidazo[4,5-b]pyridine-5-carboxylate (129 mg) was obtained as white crystals, from methyl 2-methyl-3H-imidazo[4,5-b]pyridine-5-carboxylate (150 mg) and 2-chloro-1-((methanesulfonyloxy)methyl)-4-(trifluoromethyl)benzene (226 mg).

Methyl 3-(2-chloro-4-(trifluoromethyl)benzyl)-2-methyl-3H-imidazo[4,5-b]pyridine-5-carboxylate $^1$H-NMR(CDCl$_3$): 2.54(3H, s), 3.99(3H, s), 5.71(2H, s), 6.73(1H, d, J=8 Hz), 7.38(1H, d, J=8 Hz), 7.72(1H, s), 8.08(1H, d, J=8 Hz), 8.17(1H, d, J=8 Hz).

Methyl 1-(2-chloro-4-(trifluoromethyl)benzyl)-2-methyl-1H-imidazo[4,5-b]pyridine-5-carboxylate $^1$H-NMR(CDCl$_3$): 2.67(3H, s), 4.03(3H, s), 5.49(2H, s), 6.57(1H, d, J=8 Hz), 7.40(1H, d, J=8 Hz), 7.53(1H, d, J=8 Hz), 7.76(1H, s), 8.10(1H, d, J=8 Hz).

Preparation Example 99-2

3-(2-Chloro-4-(trifluoromethyl)benzyl)-2-methyl-3H-imidazo[4,5-b]pyridine-5-carboxylic acid In the same manner as in Preparation Example 4-7, the objective compound (103 mg) was obtained as white crystals from methyl 3-(2-chloro-4-(trifluoromethyl)benzyl)-2-methyl-3H-imidazo[4,5-b]pyridine-5-carboxylate (119 mg).

$^1$H-NMR(DMSO-d$_6$): 2.53(3H, s), 5.69(2H, s), 6.75(1H, d, J=8 Hz), 7.60(1H, d, J=8 Hz), 8.02(1H, d, J=8 Hz), 8.03(1H, s), 8.15(1H, d, J=8 Hz).

Preparation Example 100-1

Methyl 3-(1-bromonaphthalen-2-ylmethyl)-2-methyl-3H-imidazo[4,5-b]pyridine-5-carboxylate and methyl 1-(1-bromonaphthalen-2-ylmethyl)-2-methyl-1H-imidazo[4,5-b]pyridine-5-carboxylate In the same manner as in Preparation Example 14-2, methyl 3-(1-bromonaphthalen-2-ylmethyl)-2-methyl-3H- imidazo[4,5-b]pyridine-5-carboxylate (1122 mg) was obtained as white crystals and methyl 1-(1-bromonaphthalen-2-ylmethyl)-2-methyl-1H-imidazo[4,5-b]pyridine-5-carboxylate (198 mg) was obtained as white crystals, from methyl 2-methyl-3H-imidazo[4,5-b]pyridine-5-carboxylate (150 mg) and 1-bromonaphthalen-2-ylmethyl bromide (259 mg).

Methyl 3-(1-bromonaphthalene-2-ylmethyl)-2-methyl-3H-imidazo[4,5-b]pyridine-5-carboxylate $^1$H-NMR(CDCl$_3$): 2.50(3H, s), 3.97(3H, s), 5.92(2H, s), 6.65(1H, d, J=8 Hz), 7.56(1H, t, J=8 Hz), 7.64(2H, dt, J=1, 8 Hz), 7.77(1H, d, J=8 Hz), 8.08(1H, d, J=8 Hz), 8.17(1H, d, J=8 Hz), 8.37(1H, d, J=8 Hz).

Methyl 1-(1-bromonaphthalene-2-ylmethyl)-2-methyl-1H-imidazo[4,5-b]pyridine-5-carboxylate $^1$H-NMR(CDCl$_3$): 2.68(3H, s), 4.02(3H, s), 5.67(2H, s), 6.52(1H, d, J=8 Hz), 7.53–7.60(2H, m), 7.68(2H, dt, J=2, 7 Hz), 7.81(1H, d), 8.07(1H, d), 8.36(1H, d, J=7 Hz).

Preparation Example 100-2

3-(1-Bromonaphthalen-2-ylmethyl)-2-methyl-3H-imidazo[4,5-b]pyridine-5-carboxylic acid In the same manner as in Preparation Example 4-7, the objective compound (81 mg) was obtained as white crystals from methyl 3-(1-bromonaphthalen-2-ylmethyl)-2-methyl-3H-imidazo[4,5-b]pyridine-5-carboxylate (105 mg).

$^1$H-NMR(DMSO-d$_6$): 2.51(3H, s), 5.83(2H, s), 6.62(1H, d, J=8 Hz), 7.62(1H, t, J=8 Hz), 7.75(1H, t, J=8 Hz), 7.86(1H, d, J=8 Hz), 7.96(1H, d, J=8 Hz), 8.03(1H, d, J=8 Hz), 7.17(1H, d, J=8 Hz), 8.31(1H, d, J=8 Hz).

Preparation Example 101

Methyl 3-(4-bromo-2-chlorobenzyl)-2-methyl-3H-imidazo[4,5-b]pyridine-5-carboxylate and methyl 1-(4-bromo-2-chlorobenzyl)-2-methyl-1H-imidazo[4,5-b]pyridine-5-carboxylate In the same manner as in Preparation Example 14-2, methyl 3-(4-bromo-2-chlorobenzyl)-2-methyl-3H-imidazo[4,5-b]pyridine-5-carboxylate (400 mg) was obtained as a white powder and methyl 1-(4-bromo-2-chlorobenzyl)-2-methyl-1H-imidazo[4,5-b]pyridine-5-carboxylate (250 mg) was obtained as a pale-yellow powder, from methyl 2-methylimidazo[4,5-b]pyridine-5-carboxylate (400 mg) and 4-bromo-2-chloro-1-((methanesulfonyloxy)methyl)benzene (689 mg).

Methyl 3-(4-bromo-2-chlorobenzyl)-2-methyl-3H-imidazo[4,5-b]pyridine-5-carboxylate $^1$H-NMR(CDCl$_3$): 2.54(3H, s), 4.00(3H, s), 5.62(2H, s), 6.53(1H, d, J=8 Hz), 7.25(1H, d, J=8 Hz), 7.61(1H, s), 8.08(1H, d, J=8 Hz), 8.16(1H, d, J=8 Hz).

Mass(ESI): m/z 396 (M+1)

Methyl 1-(4-bromo-2-chlorobenzyl)-2-methyl-1H-imidazo[4,5-b]pyridine-5-carboxylate $^1$H-NMR(CDCl$_3$): 2.64(3H, s), 4.01(3H, s), 5.49(2H, s), 6.36(1H, d, J=8 Hz), 7.29(1H, d, J=8 Hz), 7.53(1H, d, J=8 Hz), 7.65(1H, s), 8.09(1H, d, J=8 Hz).

Mass(ESI): m/z 396 (M+1)

Preparation Example 102-1

2,7-Dimethyl-1H-imidazo[4,5-b]pyridine-4-oxide

To a solution of 2,7-dimethyl-1H-imidazo[4,5-b]pyridine (4.29 g) in chloroform (43 ml) was added m-chloroperbenzoic acid (80%, 7.55 g) at room temperature, and the mixture was refluxed under heating for 1 hr. After cooling to room temperature, the reaction mixture was directly purified by silica gel column chromatography (chloroform/methanol=9/1) and pulverized in ethyl acetate to give the objective compound (4.61 g) as a brown powder.

$^1$H-NMR(DMSO-$_6$): 2.46(3H, s), 2.52(3H, s), 6.93(1H, d, J=5 Hz), 7.98(1H, d, J=5 Hz).

Preparation Example 102-2

5-Chloro-2,7-dimethyl-1H-imidazo[4,5-b]pyridine

A mixture of 2,7-dimethyl-1H-imidazo[4,5-b]pyridine-4-oxide (4.45 g) in chloroform (4.5 ml) and phosphorous oxychloride (25.4 ml) was stirred at 80° C. for 3 hr and concentrated to dryness under reduced pressure. The residue was poured to ice (75 g), and which was neutralized with aqueous ammonia under ice-cooling. The mixture was stirred at room temperature for 30 min and the precipitated solid was washed with water to give the objective compound (3.66 g) as a gray powder.

$^1$H-NMR(DMSO-d$_6$): 2.49(3H, s), 2.52(3H, s), 7.08(1H, s).

Preparation Example 102-3

5-Bromo-2,7-dimethyl-1H-imidazo[4,5-b]pyridine

In the same manner as in Preparation Example 9-1, the objective compound (4.07 g) was obtained as a brown solid from 6-chloro-2,7-dimethyl-1H-imidazo[4,5-b]pyridine (3.6 g).

$^1$H-NMR(DMSO-d$_6$): 2.44–2.57(6H, overlapped with DMSO-d 6), 7.20(1H, s).

Mass(ESI): m/z 226 (M−1)

Preparation Example 102-4

Methyl 2,7-dimethyl-1H-imidazo[4,5-b]pyridine-5-carboxylate

In the same manner as in Preparation Example 110-4 to be described later, the objective compound (2.44 g) was obtained as a white powder from 5-bromo-2,7-dimethyl-1H-imidazo[4,5-b]pyridine (4.02 g).

$^1$H-NMR(CDCl$_3$): 2.72(3H, s), 2.80(3H, s), 3.49(1H, br s), 4.02(3H, s), 7.91(1H, s).

Mass(ESI): m/e 206 (M+1)$^+$

Preparation Example 102-5

Methyl 3-(1-bromonaphthalen-2-ylmethyl)-2,7-dimethyl-3H-imidazo[4,5-b]pyridine-5-carboxylate To a suspension of methyl 2,7-dimethyl-1H-imidazo[4,5-b]pyridine-5-carboxylate (625 mg) in N,N-dimethylformamide (6 ml) was added sodium hydride (70% in mineral oil, 125 mg) under ice-cooling, and the mixture was stirred for 30 min. 1-Bromonaphthalen-2-ylmethyl bromide (1.05 g) was added to the reaction mixture, and the mixture was stirred under ice-cooling for 3 hr. Diisopropyl ether (12 ml) was added to the reaction mixture and the precipitate was collected by filtration to give the objective compound (1.35 g) as a white powder.

$^1$H-NMR(CDCl$_3$): 2.49(3H, s), 2.75(3H, s), 3.98(3H, s), 5.91(2H, s), 6.64(1H, d, J=8 Hz), 7.49–7.83(4H, m), 8.00 (1H, s), 8.38 (1H, d, J=8 Hz).

Mass(ESI): m/e 426 (M+1)$^+$

Preparation Example 102-6

3-(1-Bromonaphthalen-2-ylmethyl)-2,7-dimethyl-3H-imidazo[4,5-b]pyridine-5-carboxylic acid In the same manner as in Preparation Example 4-7, the objective compound (1.01 g) was obtained as a white powder from methyl 3-(1-bromonaphthalen-2-ylmethyl)-2,7-dimethyl-3H-imidazo[4,5-b]pyridine-5-carboxylate (1.34 g).

$^1$H-NMR(DMSO-d$_6$): 2.49(3H, s), 2.62(3H, s), 5.82(2H, s), 6.53(1H, d, J=8 Hz), 7.55–8.00(5H, m), 8.29(1H, d, J=8 Hz).

Mass(ESI): m/e 408, 410 (M−1)$^-$

Preparation Example 103-1

Methyl 3-(4-bromo-2-chlorobenzyl)-2,7-dimethyl-3H-imidazo[4,5-b]pyridine-5-carboxylate In the same manner as in Preparation Example 102-6, the objective compound (950 mg) was obtained as colorless crystals from methyl 2,7-dimethyl-3H-imidazo[4,5-b]pyridine-5-carboxylate (550 mg) and 4-bromo-2-chloro-1-((methanesulfonyloxy)methyl)benzene (963 mg).

$^1$H-NMR(CDCl$_3$): 2.52(3H, s), 2.73(3H, s), 3.98(3H, s), 5.59(2H, s), 6.49(1H, d, J=8 Hz), 7.22(1H, d, J=8 Hz), 7.60(1H, s), 7.99(1H, d, J=8 Hz).

Preparation Example 103-2

3-(4-Bromo-2-chlorobenzyl)-2,7-dimethyl-3H-imidazo[4,5-b]pyridine5-carboxylic acid In the same manner as in Preparation Example 4-7, the objective compound (870 mg) was obtained as colorless crystals from methyl 3-(4-bromo-2-chlorobenzyl)-2,7-dimethyl-3H-imidazo[4,5-b]pyridine-5carboxylate (950 mg).

$^1$H-NMR(DMSO-d$_6$): 2.49(3H, s), 2.62(3H, s), 5.55(2H, s), 6.47(1H, d, J=8 Hz), 7.43(1H, dd, J=8, 1 Hz), 7.85(1H, d, J=1 Hz).

Preparation Example 104

Methyl 3-(2,4-dichlorobenzyl)-2-methyl-3H-imidazo[4,5-b]pyridine-5-carboxylate

In the same manner as in Preparation Example 26-2, the objective compound was obtained as a pale-yellow powder from 5-bromo-3-(2,4-dichlorobenzyl)-2-methyl-3H-imidazo[4,5-b]pyridine.

$^1$H-NMR(CDCl$_3$): 2.53(3H, s), 3.99(3H, s), 5.63(2H, s), 6.60(1H, d, J=8 Hz), 7.10(1H, dd, J=8 and 2 Hz), 7.47(1H, d, J=2 Hz), 8.07(1H, d, J=8 Hz), 8.14(1H, d, J=8 Hz).

Mass(ESI): m/e 350 (M+H)$^+$

Preparation Example 105-1

Methyl 3-(2-chloro-4-nitrobenzyl)-2,7-dimethyl-3H-imidazo[4,5-b]pyridine-5-carboxylate In the same manner as in Preparation Example 102-6, the objective compound(759 mg) was obtained as a pale-brown powder from methyl 2,7-dimethylimidazo[4,5-b]pyridine-5-carboxylate (500 mg) and 2-chloro-1-((methanesulfonyloxy)methyl)-4-nitrobenzene (777 mg).

$^1$H-NMR(CDCl$_3$): 2.54(3H, s), 2.65(3H, s), 3.83(3H, s), 5.68(2H, s), 6.82(1H, d, J=8 Hz), 7.90(1H, s), 8.08(1H, dd, J=8, 2 Hz), 8.42(1H, d, J=2 Hz).

Preparation Example 105-2

3-(2-Chloro-4-nitrobenzyl)-2,7-dimethyl-3H-imidazo[4,5-b]pyridine-5-carboxylic acid In the same manner as in Preparation Example 4-7, the objective compound (681 mg) was obtained as a pale-brown powder from methyl 3-(2-chloro-4-nitrobenzyl)-2,7-dimethyl-3H-imidazo[4,5-b]pyridine-5-carboxylate (755 mg).

$^1$H-NMR(DMSO-d$_6$): 2.52(3H, s), 2.62(3H, s), 5.69(2H, s), 6.77(1H, d, J=8 Hz), 7.85(1H, s), 8.05(1H, dd, J=8, 2 Hz), 8.40(1H, d, J=2 Hz).

Preparation Example 106-1

2-Amino-6-bromo-3-nitropyridine

To a suspension of 2,6-dibromo-3-nitropyridine (5.00 g) in ethanol (10 ml) was added an ammonia/ethanol solution (6.8 M, 15 ml) at room temperature, and the mixture was placed in a closed reaction vessel and stirred at room temperature for 19 hr. To the reaction mixture was added water (25 ml), and the precipitate was collected by filtration. The precipitate was washed with ethanol, suspended in ethanol (55 ml), heated and cooled. The precipitate was collected by filtration to give the objective compound (3.19 g) as a yellow powder.

$^1$H-NMR(DMSO-d$_6$): 6.89(1H, d, J=8 Hz), 8.24(1H, d, J=8 Hz), 8.25(2H, br s).

Mass(ESI): m/e 216, 218 (M−H)$^-$

Preparation Example 106-2

2-(Acetamido)-6-bromo-3-nitropyridine

To a suspension of 2-amino-6-bromo-3-nitropyridine (23.9 g) in acetic acid (48 ml) were added acetic anhydride (48 ml) and sulfuric acid (2.9 ml), and the mixture was heated at 65° C. for 40 min. The mixture was uniform so that it quickly became a suspension containing a precipitate. After cooling, the reaction mixture was poured into cold water (480 ml) and the mixture was stirred for 30 min. The precipitate was collected by filtration and washed with water to give a crude product. The crude product was suspended in ether (60 ml) and collected by filtration to give the objective compound (27.2 g) as a pale-yellow powder.

$^1$H-NMR(CDCl$_3$): 2.54(3H, s), 7.33(1H, d, J=8 Hz), 8.33 (1H, d, J=8 Hz), 9.95(1H, br s).

Mass(ESI): m/e 258, 260 (M−H)$^-$

Preparation Example 106-3

6-Bromo-2-(N-(2-chloro-4-cyanobenzyl)acetamido)-3-nitropyridine 2-(Acetamido)-6-bromo-3-nitropyridine (3.21 g) was dissolved in dry N,N-dimethylformamide (16 ml), and sodium hydride (60% in oil, 326 mg) was added under ice-cooling. The mixture was stirred for 30 min. A solution of 2-chloro-4-cyanobenzyl bromide (2.34 g) in dry N,N-dimethylformamide (4 ml) was dropwise added at the same temperature, and the mixture was stirred at room temperature for 1 hr. The reaction mixture was poured into ice water and the mixture was extracted with ethyl acetate. The organic layer was dried over magnesium sulfate and concentrated to dryness under reduced pressure. The residue was purified by silica gel column chromatography (hexane/ethyl acetate=5/1) to give the objective compound (4.17 g) as a pale-yellow powder.

$^1$H-NMR(CDCl$_3$): 2.17(3H, s), 5.39(2H, s), 7.54(1H, d, J=8 Hz), 7.58(1H, d, J=8 Hz), 7.69(1H, s), 7.79(1H, d, J=8 Hz), 8.14(1H, d, J=8 Hz).

Preparation Example 106-4

5-Bromo-3-(2-chloro-4-cyanobenzyl)-2-methyl-3H-imidazo[4,5-b]pyridine

To a solution of 6-bromo-2-(N-(2-chloro-4-cyanobenzyl)acetamido)-3-nitropyridine (21.8 g) in ethanol (33 ml)-acetic acid (8.3 ml) was added iron powder (2.29 g) at room temperature, and the mixture was refluxed under heating for 2 hr. The reaction mixture was cooled, the insoluble matter was removed by filtration, and the solvent was evaporated. To the residue was added dichloromethane, and the product was extracted. The solvent was evaporated and the residue was purified by silica gel column chromatography (dichloromethane/methanol=30/1) to give the objective compound (1.90 g) as a pale-yellow powder.

$^1$H-NMR(CDCl$_3$): 2.49(3H, s), 5.58(2H, s), 6.67(1H, d, J=8 Hz), 7.41(1H, d, J=8 Hz), 7.44(1H, d, J=8 Hz), 7.75(1H, s), 7.87(1H, d, J=8 Hz).

Mass(ESI): m/e 361, 363 (M+H)$^+$

Preparation Example 106-5

Methyl 3-(2-chloro-4-cyanobenzyl)-2-methyl-3H-imidazo[4,5-b]pyridine-5-carboxylate In the same manner as in Preparation Example 26-2, the objective compound (482 mg) was obtained as a white powder from 5-bromo-3-(2-chloro-4-cyanobenzyl)-2-methyl-3H-imidazo[4,5-b]pyridine (546 mg).

$^1$H-NMR(CDCl$_3$): 2.54(3H, s), 3.98(3H, s), 5.70(2H, s), 6.73(1H, d, J=8 Hz), 7.42(1H, d, J=8 Hz), 7.76(1H, s), 8.09(1H, d, J=8 Hz), 8.16(1H, d, J=8 Hz).

Mass(ESI): m/e 341 (M+H)$^+$

Preparation Example 106-6

3-(2-Chloro-4-cyanobenzyl)-2-methyl-3H-imidazo[4,5-b]pyridine-5-carboxylic acid

In the same manner as in Preparation Example 4-7, the objective compound (39 mg) was obtained as a pale-brown powder from methyl 3-(2-chloro-4-cyanobenzyl)-2-methyl-3H-imidazo[4,5-b]pyridine-5-carboxylate (67 mg).

$^1$H-NMR(DMSO-d$_6$): 2.52(3H, s), 5.68(2H, s), 6.72(1H, d, J=8 Hz), 7.69(1H, d, J=8 Hz), 8.01(1H, d, J=8 Hz), 8.14(1H, d, J=8 Hz), 8.20(1H, s).

Mass(ESI): m/e 325 (M-H)$^-$

Preparation Example 107-1

2-Chloro-4-phenyltoluene

In the same manner as in Preparation Example 11-2, the objective compound (1.9 g) was obtained as a pale-brown oil from 2-chloro-4-iodotoluene (2.3 g).

$^1$H-NMR(CDCl$_3$): 2.40(3H, s), 7.23–7.60(8H, m).

Preparation Example 107-2

2-Chloro-4-phenylbenzyl-bromide

In the same manner as in Preparation Example 93-1, the objective compound (3.22 g) was obtained as colorless crystals from 2-chloro-4-phenyltoluene (3.6 g).

$^1$H-NMR(CDCl$_3$): 4.64(2H, s), 7.35–7.63(8H, m).

mp 73–74° C.

Preparation Example 107-3

6-Bromo-2-(N-(2-chloro-4-phenylbenzyl)acetamido)-3-nitropyridine

In the same manner as in Preparation Example 106-3, the objective compound (1.6 g) was obtained as amorphous from 2-(acetamido)-6-bromo-3-nitropyridine (1.0 g) and 2-chloro-4-phenylbenzyl bromide (1.1 g).

$^1$H-NMR(CDCl$_3$): 2.25(3H, br s), 5.42(2H, br s), 7.32–7.70(9H, m), 8.11(1H, d, J=8 Hz).

Mass(ESI): m/z 458 (M–H)

Preparation Example 107-4

5-Bromo-3-(2-chloro-4-phenylbenzyl)-2-methyl-3H-imidazo[4,5-b]pyridine

In the same manner as in Preparation Example 106-4, the objective compound (2.80 g) was obtained as pale-yellow crystals from 6-bromo-2-(N-(2-chloro-4-phenylbenzyl)acetamido)-3-nitropyridine (3.56 g).

$^1$H-NMR(CDCl$_3$) 2.61(3H, s), 5.62(2H, s), 6.71(1H, d, J=8 Hz), 7.32–7.55(7H, m), 7.68(1H, s), 7.92(1H, d, J=8 Hz).

Mass(ESI): m/z 414 (M+1)

Preparation Example 108-1

6-Bromo-2-(N-(2-chloro-4-(trifluoromethyl)benzyl)acetamido)-3-nitropyridine

In the same manner as in Preparation Example 106-3, the objective compound (2.60 g) was obtained from 2-(acetamido)-6-bromo-3-nitropyridine (2.00 g) and 2-chloro-1-((methanesulfonyloxy)methyl)-4-(trifluoromethyl)benzene (2.33 g).

$^1$H-NMR(CDCl$_3$): 2.20(3H, br s), 5.40(2H, br s), 7.53 (2H, d, J=8 Hz), 7.66(1H, br s), 7.78(1H, d, J=8 Hz), 8.12(1H, d, J=8 Hz).

Preparation Example 108-2

5-Bromo-3-(2-chloro-4-(trifluoromethyl)benzyl)-2-methyl-3H-imidazo[4,5-b]pyridine In the same manner as in Preparation Example 106-4, the objective compound (1.55 g) was obtained as pale-yellow crystals from 6-bromo-2-(N-(2-chloro-4-(trifluoromethyl)benzyl)acetamido)-3-nitropyridine (2.60 g).

$^1$H-NMR(CDCl$_3$): 2.51(3H, s), 5.59(2H, s), 6.68(1H, d, J=8 Hz), 7.39(1H, br d, J=8 Hz), 7.41(1H, d, J=8 Hz), 7.73(1H, br s), 7.88(1H, d, J=8 Hz).

Mass(ESI): m/z 406 (M+1)

mp 106–107° C.

Preparation Example 108-3

Methyl 3-(2-chloro-4-(trifluoromethyl)benzyl)-2-methyl-3H-imidazo[4,5-b]pyridine-5-carboxylate In the same manner as in Preparation Example 26-2, the objective compound (1.47 g) was obtained as pale-brown crystals from 5-bromo-3-(2-chloro-4-(trifluoromethyl)benzyl)-2-methyl-3H-imidazo[4,5-b]pyridine (1.50 g).

$^1$H-NMR(CDCl$_3$): 2.54(3H, s), 3.99(3H, s), 5.71(2H, s), 6.73(1H, d, J=8 Hz), 7.38(1H, d, J=8 Hz), 7.72(1H, s), 8.08(1H, d, J=8 Hz), 8.17(1H, d, J=8 Hz).

Preparation Example 109-1

2-Amino-6-bromo-3-nitropyridine hydrobromide

2-Amino-6-chloro-3-nitropyridine (20.2 g) was suspended in a 30% hydrobomide/acetic acid solution (100 ml), and the suspension was stirred at 90° C. After 4 hours, a 30% hydrobomide/acetic acid solution (100 ml) was added, and the mixture was stirred for another 1 hour at 90° C. Then, the reaction mixture was stirred at 100° C. for 8 hr while a hydrobromic acid gas was introduced little by little. The reaction mixture was cooled, and the precipitate was collected by filtration and washed with hexane to give the objective compound (33.0 g) as a pale-yellow powder.

$^1$H-NMR(DMSO-$d_6$): 7.63(1H, d, J=8 Hz), 8.01(1H, d, J=8 Hz).

Preparation Example 109-2

2-(Acetamido)-6-bromo-3-nitropyridine

In the same manner as in Preparation Example 106-2, the objective compound (40.7 g) was obtained as a pale-yellow powder from 2-amino-6-bromo-3-nitropyridine hydrobromide (50.0 g) and acetic anhydride (100 ml).

$^1$H-NMR(CDCl$_3$): 2.54(3H, s), 7.34(1H, d, J=8 Hz), 8.34 (1H, d, J=8 Hz), 9.98(1H, br s)

Mass(ESI): m/e 260 (M−1)$^-$

Preparation Example 109-3

5-Bromo-2-methyl-1H-imidazo[4,5-b]pyridine

In the same manner as in Preparation Example 106-4, the objective compound (2.48 g) was obtained as pale-yellow crystals from 2-(acetamido)-6-bromo-3-nitropyridine (4.0 g).

$^1$H-NMR(DMSO-$d_6$): 2.51(3H, s), 7.32(1H, d, J=8 Hz), 7.83(1H, d, J=8 Hz).

Mass(ESI): m/z 210(M−1)

mp 239–241° C.

Preparation Example 109-4

Methyl 2-methyl-1H-imidazo[4,5-b]pyridine-5-carboxylate

Palladium acetate (1.18 g), 1,3-bis(diphenylphosphino) propane (2.31 g) and 5-bromo-2-methyl-1H-imidazo[4,5-b] pyridine (3.72 g) were placed in an autoclave, and N,N-dimethylformamide (18.6 ml), methanol (14.9 ml) and triethylamine (5.4 ml) were added thereto. The mixture was stirred at 85° C. for 14 hr at 10 atm under a carbon monoxide atmosphere. The reaction mixture was cooled and the solvent was evaporated. To the residue was added methanol (60 ml), and the mixture was heated. The insoluble matter was filtered off while the mixture was hot. The filtrate was concentrated to give the objective compound (2.95 g) as a white powder.

$^1$H-NMR(CDCl$_3$) 2.82(3H, s), 4.05(3H, s), 8.04(1H, d, J=8 Hz), 8.10(1H, d, J=8 Hz).

Mass(ESI): m/e 192 (M+1)$^+$

Preparation Example 110-1

6-Bromo-2-(N-(2,4-dichlorobenzyl)acetamido)-3-nitropyridine

In the same manner as in Preparation Example 106-3, the objective compound (11.71 g) was obtained as a pale-yellow powder from 2-(acetmaido)-6-bromo-3-nitropyridine (10.0 g) and 2,4-dichlorobenzyl chloride (8.3 g).

$^1$H-NMR(CDCl$_3$): 2.20(3H, br s), 5.33(2H, br s), 7.24 (2H, d, J=8 Hz), 7.30–7.68(3H, m), 8.11(1H, d, J=8 Hz).

Preparation Example 110-2

5-Bromo-3-(2,4-dichlorobenzyl)-2-methyl-3H-imidazo[4,5-b]pyridine

In the same manner as in Preparation Example 106-4, the objective compound (4.27 g) was obtained as a pale-yellow powder from 6-bromo-2-(N-(2,4-dichlorobenzyl) acetamido)-3-nitropyridine (11.7 g).

$^1$H-NMR(CDCl$_3$): 2.48(3H, s), 5.50(2H, s), 6.54(1H, d, J=8 Hz), 7.12(1H, dd, J=8 and 2 Hz), 7.39(1H, d, J=8 Hz), 7.47(1H, d, J=2 Hz), 7.86(1H, d, J=8 Hz).

Mass(ESI): m/e 370, 372 (M+H)$^+$

Preparation Example 111-1

3-Chloro-4-methylbenzyl alcohol

In the same manner as in Preparation Example 74-4, the objective compound (23.0 g) was obtained as a colorless oil from 3-chloro-4-methylbenzoic acid (25.0 g).

$^1$H-NMR(CDCl$_3$): 2.36(3H, s), 4.65(2H, s), 7.14(1H, d, J=8 Hz), 7.23(1H, d, J=8 Hz), 7.36(1H, S)

Preparation Example 111-2

3-chloro-4-methylbenzaldehyde

To a solution of 3-chloro-4-methylbenzyl alcohol (2.00 g) and triethylamine (8.9 ml) in a dimethyl sulfoxide (10 ml) was added sulfur trioxide-pyridine complex (4.47 g) under ice-cooling, and the mixture was stirred at room temperature for 3 hr. The reaction mixture was poured into ice water, and extracted with ether. The organic layer was washed with 1N hydrochloric acid, saturated brine and a saturated aqueous sodium hydrogencarbonate solution, dried over magnesium sulfate, and concentrated to dryness under reduced pressure to give the objective compound (1.40 g) as a pale-yellow oil.

$^1$H-NMR(CDCl$_3$): 2.46(3H, s), 4.65(2H, s), 7.40(1H, d, J=8 Hz), 7.68(1H, d, J=8 Hz), 9.92(1H, s)

Preparation Example 111-3

2-Chloro-4-(E)-(2-phenylethenyl)toluene

In the same manner as in Preparation Example 73-3, the objective compound (1.55 g) was obtained as a white powder from 3-chloro-4-methylbenzaldehyde (1.40 g) and diethyl benzyl phosphonate(2.27 g).

$^1$H-NMR(CDCl$_3$): 2.38(3H, s), 7.00(1H, d, J=16 Hz), 7.08(1H, d, J=16 Hz), 7.18–7.53(8H)

Preparation Example 111-4

2-Chloro-4-(E)-(2-phenylethenyl)benzyl bromide

In the same manner as in Preparation Example 93-1, the objective compound (309 mg) was obtained as a white powder from 2-chloro-4-(E)-(2-phenylethenyl)toluene (1.35 g).

$^1$H-NMR(CDCl$_3$): 4.61(2H, s), 7.01(1H, d, J=16 Hz), 7.14(1H, d, J=16 Hz), 7.24–7.57(8H)

Preparation Example 112-1

Methyl 3-(2-chloro-4-(2-phenylethyl)benzyl)-2-methyl-3H-imidazo[4,5-b]pyridine-5-carboxylate Methyl 3-(2-chloro-4-(E)-(2-phenylethenyl)benzyl)-2-methyl-3H-imidazo[4,5-b]pyridine-5-carboxylate (2.37 g)

was dissolved in methanol/chloroform=1/4 (24 ml), and platinum(IV) oxide (169 mg) was added. The mixture was stirred under a hydrogen atmosphere at normal pressure for 4 hours. Platinum(IV) oxide (169 mg) was added, and the mixture was further stirred under a hydrogen atmosphere at normal pressure for 6 hr. The reaction mixture was filtered through Celite and the filtrate was concentrated to dryness under reduced pressure. The obtained residue was subjected to silica gel column chromatography (eluent: ethyl acetate/chloroform=1/3). The fraction containing the objective compound was concentrated under reduced pressure to give the objective compound (1.92 g) as a white powder.

¹H-NMR(CDCl₃): 2.53(3H, s), 2.88(4H, s), 4.01(3H, s), 5.64(2H, s), 6.53(1H, d, J=8 Hz), 6.89(1H, dd, J=2, 8 Hz), 7.12–7.30(6H, m), 8.04(1H, d, J=8 Hz), 8.15(1H, d, J=8 Hz)

Preparation Example 112-2

3-(2-Chloro-4-(2-phenylethyl)benzyl)-2-methyl-3H-imidazo[4,5-b]pyridine5-carboxylic acid In the same manner as in Preparation Example 4-7, the objective compound (1.79 g) was obtained as white crystals from methyl 3-(2-chloro-4-(2-phenylethyl)benzyl)-2-methyl-3H-imidazo[4,5-b]pyridine-5-carboxylate (1.89 g).

¹H-NMR(DMSO-d₆): 2.50(4H, s), 2.84(3H, s), 5.57(2H, s), 6.45(1H, d, J=8 Hz), 7.09(1H, dd, J=2, 8 Hz), 7.15–7.20 (5H, m), 7.43(1H, s) 7.99(1H, d, J=8 Hz), 8.12(1H, d, J=8 Hz)

Preparation Example 113-1

Ethyl 3-chloro-4-methylbenzoate

In the same manner as in Preparation Example 74-2, the objective compound (28.7 g) was obtained as a pale-yellow oil from 3-chloro-4-methylbenzoic acid (28.7 g).

¹H-NMR(CDCl₃): 1.39(3H, t, J=6 Hz), 2.43(3H, s), 4.38 (2H, q, J=6 Hz), 7.29(1H, d, J=8 Hz), 7.83(1H, d, J=8 Hz), 8.02(1H, s)

Preparation Example 113-2

Ethyl 4-bromomethyl-3-chlorobenzoate

In the same manner as in Preparation Example 93-1, the objective compound (39.9 g) was obtained as pale-yellow oil from ethyl 3-chloro-4-methylbenzoate (28.7 g).

¹H-NMR(CDCl₃): 1.40(3H, t, J=6 Hz), 4.39(2H, q, J=6 Hz), 4.60(2H, s), 7.52(1H, d, J=8 Hz), 7.92(1H, d, J=8 Hz), 8.06(1H, s)

Preparation Example 113-3

6-Bromo-2-(N-(4-carboethoxy-2-chlorobenzyl) acetamido)-3-nitropyridine

In the same manner as in Preparation Example 106-3, the objective compound (40.91 g) was obtained from 2-acetamido-6-bromo-3-nitropyridine (24.7 g) and ethyl 4-bromomethyl-3-chlorobenzoate (44.8 g).

¹H-NMR(CDCl₃): 1.40(3H, t, J=6 Hz), 2.20(3H, s), 4.40 (2H, q, J=6 Hz), 5.40(2H, s), 7.16–8.22(5H)

Preparation Example 113-4

5-Bromo-3-(2-chloro-4-(ethoxycarbonyl)benzyl)-2-methyl-3H-imidazo[4,5-b]pyridine In the same manner as in Preparation Example 106-4, the objective compound (32.0 g) was obtained as pale-yellow crystals from 2-[N-acetyl-N-(2-chloro-4-(ethoxycarbonyl) benzyl)]amino-6-bromo-3-nitropyridine (40.8 g).

¹H-NMR(CDCl₃): 1.38(3H, t, J=7.5 Hz), 4.36(2H, q, J=7.5 Hz), 5.57(2H, s), 6.61(1H, d, J=8 Hz), 7.40(1H, d, J=8 Hz), 7.77(1H, d, J=8 Hz),7.88(1H, d, J=8 Hz), 8.11(1H, s)

Preparation Example 113-5

3-(2-Chloro-4-(ethoxycarbonyl)benzyl)-2-methyl-3H-imidazo[4,5-b]pyridine-5-carboxylic acid In a sealed tube, 5-bromo-3-(2-chloro-4-(ethoxycarbonyl) benzyl)-2-methyl-3H-imidazo[4,5-b]pyridine (4.92 g) was dissolved in a mixture of N,N-dimethylformamide (27.6 ml) and t-butanol (21.7 ml), and triethylamine (2.84 g), 1,3-bis (diphenylphosphino)propane (1.59 g) and palladium acetate (II) (865 mg) were added. After sealing, the mixture was stirred under a carbon monoxide atmosphere at 10 atm and 85° C. for 24 hr. Triethylamine (1.42 g), 1,3-bis (diphenylphosphino)propane (795 mg) and palladium acetate (II) (433 mg) were successively added. After sealing, the mixture was stirred under a carbon monoxide atmosphere at 10 atm and 85° C. for 12 hr. The reaction mixture was filtrated, and the residue was washed with chloroform. The filtrate was concentrated under reduced pressure. The residue was subjected to silica gel column chromatography (eluent: methanol/chloroform=1/49). The fraction containing the objective compound was concentrated under reduced pressure. To the residue was added ethyl acetate (50 ml), and the mixture was warmed on a water bath. The reaction mixture was cooled with stirring at room temperature. The precipitated crystals were collected by filtration to give the objective compound (3.61 g) as pale-yellow crystals.

¹H-NMR(DMSO-d₆): 1.30(3H, t, J=7 Hz), 2.50(3H, s), 4.28(2H, q, J=7 Hz), 5.08(2H, s), 6.70(1H, d, J=8 Hz), 7.76(1H, d, J=8 Hz), 8.00–8.03(2H, m), 8.14(1H, d, J=8 Hz)

Preparation Example 114-1

5-Bromo-3-(2-chloro-4-(hydroxymethyl)benzyl)-2-methyl-3H-imidazo[4,5-b]pyridine

In the same manner as in Preparation Example 76-2, the objective compound (11.5 g) was obtained as pale-yellow crystals from 5-bromo-3-(2-chloro-4-(ethoxycarbonyl) benzyl)-2-methyl-3H-imidazo[4,5-b]pyridine (15.0 g).

¹H-NMR(DMSO-d₆): 2.46(3H, s), 4.47(2H, d, J=5 Hz), 5.32(1H, t, J=5 Hz), 5.50(2H, s), 6.55(1H, d, J=8 Hz), 7.16(1H, d, J=8 Hz), 7.44(1H, d, J=8 Hz),7.48(1H, s), 7.99(1H, d, J=8 Hz)

MS(ESI) m/e: 366, 368.

Preparation Example 114-2

Methyl 3-(2-chloro-4-(hydroxymethyl)benzyl)-2-methyl-3H-imidazo[4,5-b]pyridine-5-carboxylate In the same manner as in Preparation Example 26-2, the objective compound (9.95 g) was obtained as pale-yellow crystals from 5-bromo-3-(2-chloro-4-(hydroxymethyl) benzyl)-2-methyl-3H-imidazo[4,5-b]pyridine (12.7 g).

¹H-NMR(DMSO-d₆): 2.50(3H, s), 3.86(3H, s), 4.46(2H, d, J=5 Hz), 5.31(1H, t, J=3 Hz), 5.59(2H, s), 6.53(1H, d, J=8 Hz), 7.14(1H, d, J=8 Hz), 7.49(1H, s), 8.02(1H, d, J=8 Hz), 8.15(1H, d, J=8 Hz)

MS(ESI) m/e: 346(M+H), 691(2M+H), 713(2M+Na).

Preparation Example 114-3

Methyl 3-(2-chloro-4-((methanesulfonyloxy)methyl) benzyl)-2-methyl-3H-imidazo[4,5-b]pyridine-5-carboxylate In the same manner as in Preparation Example 14-1, the objective compound (4.2 g) was obtained as pale-yellow crystals from methyl 3-(2-chloro-4-(hydroxymethyl) benzyl)-2-methyl-3H-imidazo[4,5-b]pyridine-5-carboxylate (3.6 g) and methanesulfonyl chloride (1.43 g).

$^1$H-NMR(CDCl$_3$): 2.54(3H, s), 3.00(3H, s), 4.00(3H, s), 5.16(2H, s), 5.68(2H, s), 6.65(1H, d, J=8 Hz), 7.15(1H, d, J=8 Hz), 7.51(1H, s), 8.07(1H, d, J=8 Hz), 8.15(1H, d, J=8 Hz)

MS(ESI) m/e: 424(M+H), 446(M+Na).

Preparation Example 114-4

Methyl 3-(2-chloro-4-((phenyloxy)methyl)benzyl)-2-methyl-3H-imidazo[4,5-b]pyridine-5-carboxylate In the same manner as in Example 118 described later, the objective compound (1.94 g) was obtained as pale-yellow crystals from methyl 3-(2-chloro-4-((methanesulfonyloxy) methyl)benzyl)-2-methyl-3H-imidazo[4,5-b]pyridine-5-carboxylate (2.8 g).

$^1$H-NMR(CDCl$_3$): 2.54(3H, s), 4.00(3H, s), 5.01(2H, s), 5.69(2H, s), 6.63(1H, d, J=8 Hz), 6.91–7.01(3H, m), 7.16 (1H, d, J=8 Hz), 7.25–7.34(2H, m), 7.55(1H, s), 8.07(1H, d, J=8 Hz), 8.15(1H, d, J=8 Hz)

MS(ESI) m/e: 422(M+H).

Preparation Example 114-5

3-(2-Chloro-4-((phenyloxy)methyl)benzyl)-2-methyl-3H-imidazo[4,5-b]pyridine-5-carboxylic acid In the same manner as in Preparation Example 4-7, the objective compound (1.54 g) was obtained as pale-yellow crystals from methyl 3-(2-chloro-4-((phenyloxy)methyl) benzyl)-2-methyl-3H-imidazo[4,5-b]pyridine-5-carboxylate (1.94 g).

$^1$H-NMR(DMSO-d$_6$): 2.50(3H, s), 5.08(2H, s), 5.64(2H, s), 6.52(1H, br peak), 6.89–7.03(3H, m), 7.23–7.34(3H, m), 7.64(1H, s), 7.98(1H, d, J=8 Hz), 8.10(1H, d, J=8 Hz)

MS(ESI) m/e: 406(M–H).

Preparation Example 115-1

Methyl 3-(2-chloro-4-(dimethylaminomethyl) benzyl)-2-methyl-3H-imidazo[4,5-b]pyridine-5-carboxylate In the same manner as in Preparation Example 116-1 described later, the objective compound (128 mg) was obtained as pale-yellow crystals from methyl 3-(2-chloro-4-((methanesulfonyloxy)methyl)benzyl)-2-methyl-3H-imidazo[4,5-b]pyridine-5-carboxylate (200 mg) and dimethylamine hydrochloride (115 mg).

$^1$H-NMR(CDCl$_3$): 2.25(6H, s), 2.52(3H, s), 3.40(2H, s), 3.99(3H, s), 5.67(2H, s), 6.58(1H, d, J=8 Hz), 7.06(1H, d, J=8 Hz), 7.45(1H, s), 8.07(1H, d, J=8 Hz), 8.15(1H, d, J=8 Hz)

MS(ESI) m/e: 373(M+H)

Preparation Example 115-2

3-(2-Chloro-4-(dimethylaminomethyl)benzyl)-2-methyl-3H-imidazo[4,5-b]pyridine5-carboxylic acid In the same manner as in Preparation Example 4-7, the objective compound (116 mg) was obtained as pale-yellow crystals from methyl 3-(2-chloro-4-(dimethylaminomethyl) benzyl)-2-methyl-3H-imidazo[4,5-b]pyridine-5-carboxylate (120 mg).

$^1$H-NMR(DMSO-d$_6$): 2.45–2.61(9H, m), 4.04(2H, br peak), 5.63(2H, s), 6.62(1H, d, J=8 Hz), 7.33(1H, d, J=8 Hz), 7.74(1H, s), 8.01(1H, d, J=8 Hz), 8.15(1H, d, J=8 Hz)

MS(ESI) m/e: 357(M–H)

Preparation Example 116-1

Methyl 3-(2-chloro-4-((imidazol-1-yl)methyl) benzyl)-2-methyl-3H-imidazo[4,5-b]pyridine-5-carboxylate To a solution of methyl 3-(2-chloro-4-((methanesulfonyloxy)methyl)benzyl)-2-methyl-3H-imidazo[4,5-b]pyridine-5-carboxylate (300 mg) in dichloromethane (6.0 ml) was added imidazole (193 mg), and the mixture was stirred at room temperature overnight. The reaction mixture was poured into water and extracted with chloroform. The organic layer was washed with saturated brine, dried over magnesium sulfate and concentrated to dryness under reduced pressure. The residue was washed with diethyl ether, and collected by filtration to give the objective compound (213 mg) as a pale-yellow powder.

$^1$H-NMR(CDCl$_3$): 2.53(3H, s), 3.99(3H, s), 5.08(2H, s), 5.65(2H, s), 6.62(1H, d, J=8 Hz), 6.84–6.93(2H, m), 7.11 (1H, s), 7.21(1H, s), 7.53(1H, s), 8.06(1H, d, J=8 Hz), 8.15(1H, d, J=8 Hz)

MS(ESI) m/e: 396(M+H).

Preparation Example 116-2

3-(2-Chloro-4-((imidazol-1-yl)methyl)benzyl)-2-methyl-3H-imidazo[4,5-b]pyridine-5-carboxylic acid In the same manner as in Preparation Example 4-7, the objective compound (204 mg) was obtained as pale-yellow crystals from methyl 3-(2-chloro-4-((imidazol-1-yl)methyl) benzyl)-2-methyl-3H-imidazo[4,5-b]pyridine-5-carboxylate (235 mg).

$^1$H-NMR(DMSO-d$_6$): 2.50(3H, s), 5.21(2H, s), 5.58(2H, s), 6.65(1H, d, J=8 Hz), 7.00(1H, s), 7.10(1H, d, J=8 Hz), 7.26(1H, s), 7.47(1H, s), 7.93(1H, s), 7.99(1H, d, J=8 Hz), 8.13(1H, d, J=8 Hz)

MS(ESI) m/e: 380.1(M–H).

Preparation Example 117-1

Methyl 3-(2-chloro-4-((piperidin-1-yl)methyl) benzyl)-2-methyl-3H-imidazo[4,5-b]pyridine-5-carboxylate In the same manner as in Preparation Example 116-1, the objective compound (174 mg) was obtained as pale-yellow crystals from methyl 3-(2-chloro-4-((methanesulfonyloxy) methyl)benzyl)-2-methyl-3H-imidazo[4,5-b]pyridine-5-carboxylate (200 mg) and piperidine (80 mg).

$^1$H-NMR(CDCl$_3$): 1.36–1.48(2H, m), 1.48–1.64(4H, m), 2.27–2.40(4H, m), 2.54(3H, s), 3.40(2H, s), 4.00(3H, s), 5.66(2H, s), 6.54(1H, d, J=8 Hz), 7.04(1H, d, J=8 Hz), 7.43(1H, s), 8.06(1H, d, J=8 Hz), 8.15(1H, d, J=8 Hz)

MS(ESI) m/e: 413.2(M+H)

Preparation Example 117-2

3-(2-Chloro-4-((piperidin-1-yl)methyl)benzyl)-2-methyl-3H-imidazo[4,5-b]pyridine-5-carboxylic acid In the same manner as in Preparation Example 4-7, the objective compound (153 mg) was obtained as pale-yellow crystals from methyl 3-(2-chloro-4-((piperidin-1-yl)methyl) benzyl)-2-methyl-3H-imidazo[4,5-b]pyridine-5-carboxylate (169 mg).

$^1$H-NMR(DMSO-d$_6$): 1.45(2H, br peak), 1.64(4H, br peak), 2.54(3H, s), 2.79(4H, br peak), 4.02(2H, br peak), 5.62(2H, s), 6.60(1H, d, J=8 Hz), 7.31(1H, d, J=8 Hz), 7.73(1H, s), 8.00(1H, d, J=8 Hz), 8.15(1H, d, J=8 Hz)

MS(ESI) m/e: 399.3(M+H).

Preparation Example 118-1

Methyl 3-(2-chloro-4-(phenylthiomethyl)benzyl)-2-methyl-3H-imidazo[4,5-b]pyridine-5-carboxylate In the same manner as in Example 118 described later, the objective compound (182 mg) was obtained as pale-yellow crystals from methyl 3-(2-chloro-4-((methanesulfonyloxy) methyl)benzyl)-2-methyl-3H-imidazo[4,5-b]pyridine-5-carboxylate (200 mg) and thiophenol (62 mg).

$^1$H-NMR(CDCl$_3$): 2.50(3H, s), 4.00(3H, s), 4.01(2H, s), 5.63(2H, s), 6.51(1H, d, J=8 Hz), 6.98(1H, d, J=8 Hz), 7.15–7.30(5H, m), 7.36(1H, s), 8.04(1H, d, J=8 Hz), 8.14 (1H, d, J=8 Hz)

MS(ESI) m/e: 438

Preparation Example 118-2

3-(2-Chloro-4-(phenylthiomethyl)benzyl)-2-methyl-3H-imidazo[4,5-b]pyridine5-carboxylic acid The objective compound (191 mg) was obtained as pale-yellow crystals from methyl 3-(2-chloro-4-(phenylthiomethyl)benzyl)-2-methyl-3H-imidazo[4,5-b] pyridine-5-carboxylate (217 mg).

$^1$H-NMR(DMSO-d$_6$): 2.47(3H, s), 4.21(2H, s), 5.58(2H, s), 6.50(1H, d, J=8 Hz), 7.11–7.22(2H, m), 7.22–7.34(4H, m), 7.53(1H, s), 8.00(1H, d, J=8 Hz), 8.13(1H, d, J=8 Hz)

MS(ESI) m/e: 422(M−H)

Preparation Example 119-1

Methyl 3-(4-((benzyloxy)methyl)-2-chlorobenzyl)-2-methyl-3H-imidazo[4,5-b]pyridine-5-carboxylate To a suspension of methyl 3-(2-chloro-4-(hydroxymethyl) benzyl)-2-methyl-3H-imidazo[4,5-b]pyridine-5-carboxylate (400 mg) in dimethylformamide (8.0 ml) were added sodium hydride (51 mg) and benzyl bromide (277 mg) under ice-cooling, and the mixture was stirred at the same temperature for 4 hr. The reaction mixture was concentrated under reduced pressure. Chloroform and sodium hydrogencarbonate were added to the residue, and the mixture was partitioned. The organic layer was washed with saturated brine and dried over magnesium sulfate. The solvent was evaporated under reduced pressure. The residue was purified by silica gel column (eluent: chloroform:methanol=50:1) to give the objective compound (322 mg) as a pale-yellow powder.

$^1$H-NMR(CDCl$_3$): 2.53(3H, s), 3.99(3H, s), 4.48(2H, s), 4.55(2H, s), 5.66(2H, s), 6.59(1H, d, J=8 Hz), 7.08(1H, d, J=8 Hz), 7.26–7.41(5H, m), 7.46(1H, s), 8.06(1H, d, J=8 Hz), 8.15(1H, d, J=8 Hz)

MS(ESI) m/e: 436.

Preparation Example 119-2

3-(4-((Benzyloxy)methyl)-2-chlorobenzyl)-2-methyl-3H-imidazo[4,5-b]pyridine-5-carboxylic acid In the same manner as in Preparation Example 4-7, the objective compound (232 mg) was obtained as pale-yellow crystals from methyl 3-(4-((benzyloxy)methyl)-2-chlorobenzyl)-2-methyl-3H-imidazo[4,5-b]pyridine-5-carboxylate (352 mg).

$^1$H-NMR(DMSO-d$_6$): 4.51(4H, s-like), 5.62(2H, s), 6.55 (1H, d, J=8 Hz), 7.21(1H, d, J=8 Hz), 7.24–7.40(5H, m), 7.53(1H, s), 8.01(1H, d, J=8 Hz), 8.14(1H, d, J=8 Hz)

MS(ESI) m/e: 420(M−H)

Preparation Example 120-1

5-Bromo-3-(4-carboxy-2-chlorobenzyl)-2-methyl-3H-imidazo[4,5-b]pyridine

In the same manner as in Preparation Example 4-7, the objective compound (5.3 g) was obtained as pale-yellow crystals from 5-bromo-3-(2-chloro-4-(ethoxycarbonyl) benzyl)-2-methyl-3H-imidazo[4,5-b]pyridine (6.0 g).

$^1$H-NMR(DMSO-d$_6$): 2.50(3H, s), 5.57(2H, s), 6.70(1H, d, J=8 Hz), 7.45(1H, d, J=8 Hz), 7.79(1H, d, J=8 Hz), 7.95–8.09(2H, m)

MS(ESI) m/e: 378, 380, 382.

Preparation Example 120-2

5-Bromo-3-[4-(benzimidazol-2-yl)-2-chlorobenzyl]-2-methyl-3H-imidazo[4,5-b]pyridine To a solution of 5-bromo-3-(4-carboxy-2-chlorobenzyl)-2-methyl-3H-imidazo[4,5-b]pyridine (2.75 g) in N,N-dimethylformamide (30 ml) were added 1-ethyl-3-(3-dimethylaminopropyl)carbodiimide hydrochloride (1.66 g), 1-hydroxybenzotriazole (1.37 g) and 1,2-phenylenediamine (781 mg) at room temperature, and the mixture was stirred for 1 hr. The reaction mixture was allowed to stand under the same conditions overnight and concentrated to dryness under reduced pressure. The residue was partitioned between chloroform and a saturated aqueous sodium hydrogencarbonate solution. The partially precipitated solid was collected by filtration. The organic layer was dried over magnesium sulfate, and the solvent was evaporated under reduced pressure. The previously-collected solid and the residue were combined and washed with ether to give the amide compound (2.97 g).

To the suspension of the obtained amide compound (2.97 g) in ethanol (100 ml) was added p-toluenesulfonic acid monohydrate (150 mg), and the mixture was refluxed under heating for 48 hr. The residue was partitioned between chloroform and a saturated aqueous sodium hydrogencarbonate solution. The aqueous layer was further extracted with a mixture of chloroform and methanol (10:1). The combined organic layers were dried over magnesium sulfate, and the solvent was evaporated under reduced pressure. The residue was washed with ethyl acetate and collected by filtration to give the object compound (2.39 g) as a pale-yellow powder.

$^1$H-NMR(DMSO-d$_6$): 2.52(3H, s), 5.59(2H, s), 6.81(1H, d, J=8 Hz), 7.17–7.26(2H, m), 7.47(1H, d, J=8 Hz), 7.55–7.65(2H, m), 7.97–8.06(2H, m), 8.33(1H, s)

MS(ESI) m/e: 450, 452, 454

Preparation Example 120-3

Methyl 3-[4-(benzimidazol-2-yl)-2-chlorobenzyl]-2-methyl-3H-imidazo[4,5-b]pyridine-5-carboxylate In the same manner as in Preparation Example 26-2, the objective compound (1.38 g) was obtained as pale-yellow crystals from 5-bromo-3-[4-(benzimidazol-2-yl)-2-chlorobenzyl]-2-methyl-3H-imidazo[4,5-b]pyridine (1.85 g).

¹H-NMR(DMSO-d₆): 2.58(3H, s), 3.86(3H, s), 5.68(2H, s), 6.80(1H, d, J=8 Hz), 7.17–7.27(2H, m), 7.55–7.66(2H, m), 7.98–8.09(2H, m), 8.19(1H, d, J=8 Hz), 8.35(1H, s)

MS(ESI) m/e: 430(M–H).

Preparation Example 120-4

3-[4-(Benzimidazole-2-yl)-2-chlorobenzyl]-2-methyl-3H-imidazo[4,5-b]pyridine-5-carboxylic acid In the same manner as in Preparation Example 4-7, the objective compound (260 mg) was obtained as pale-yellow crystals from methyl 3-[4-(benzimidazol-2-yl)-2-chlorobenzyl]-2-methyl-3H-imidazo[4,5-b]pyridine-5-carboxylate (300 mg).

¹H-NMR(DMSO-d₆): 2.58(3H, s), 5.70(2H, s), 6.81(1H, d, J=8 Hz), 7.21–7.31(2H, m), 7.60–7.69(2H, m), 7.98–8.06 (2H, m), 8.16(1H, d, J=8 Hz), 8.37(1H, s)

MS(ESI) m/e: 416(M–H).

Preparation Example 121-1

Methyl 2-methyl-3-[4-(1-methylbenzimidazol-2-yl)-2-chlorobenzyl]-3H-imidazo[4,5-b]pyridine-5-carboxylate A mixture of 3-[4-(benzimidazol-2-yl)-2-chlorobenzyl]-2-methyl-3H-imidazo[4,5-b]pyridine-5-carboxylate (325 mg), methyl iodide (107 mg), potassium carbonate (198 mg) and dimethylformamide (10 ml) was stirred at room temperature overnight and concentrated to dryness under reduced pressure. The residue was suspended in chloroform and washed with a saturated aqueous sodium hydrogencarbonate solution and then with saturated brine. The organic layer was dried over magnesium sulfate and concentrated to dryness under reduced pressure. The residue was pulverized in ether to give the objective compound (282 mg) as a pale-yellow powder.

¹H-NMR(CDCl₃): 2.60(3H, s), 3.85(3H, s), 4.01(3H, s), 5.78(2H, s), 6.77(1H, d, J=8 Hz), 7.27–7.44(3H, m), 7.50 (1H, d, J=8 Hz), 7.76–7.84(1H, m), 7.95( 1H, s), 8.10(1H, d, J=8 Hz), 8.17(1H, d, J=8 Hz)

MS(ESI) m/e: 446(M+H)

Preparation Example 121-2

2-Methyl-3-[4-(1-methylbenzimidazol-2-yl)-2-chlorobenzyl]-3H-imidazo[4,5-b]pyridine-5-carboxylic acid In the same manner as in Preparation Example 4-7, the objective compound (215 mg) was obtained as pale-yellow crystals from methyl 2-methyl-3-[4-(1-methylbenzimidazol-2-yl)-2-chlorobenzyl]-3H-imidazo[4,5-b]pyridine-5-carboxylate (268 mg).

¹H-NMR(DMSO-d₆): 2.59(3H, s), 3.88(3H, s), 5.74(2H, s), 6.72(1H, d, J=8 Hz), 7.20–7.40(2H, m), 7.59–7.80(3H, m), 7.98–8.13(2H, m), 8.18(1H, d, J=8 Hz)

MS(ESI) m/e: 430(M–H).

Preparation Example 122-1

Methyl 3-((benzimidazol-2-yl)methyl)-2-methyl-3H-imidazo[4,5-b]pyridine5-carboxylate and methyl 1-((benzimidazol-2-yl)methyl)-2-methyl-1H-imidazo [4,5-b]pyridine-5-carboxylate In the same manner as in Preparation Example 14-2, methyl 3-((benzimidazol-2-yl)methyl)-2-methyl-3H-imidazo[4,5-b]pyridine-5-carboxylate (20 mg) and methyl 1-((benzimidazol-2-yl)methyl)-2-methyl-1H-imidazo[4,5-b]pyridine-5-carboxylate (20 mg) were obtained both as brown powder from methyl 2-methylimidazo[4,5-b] pyridine-5-carboxylate (100 mg).

Methyl 3-((benzimidazol-2-yl)methyl)-2-methyl-3H-imidazo[4,5-b]pyridine-5-carboxylate ¹H-NMR(CDCl₃): 2.88(3H, s), 4.10(3H, s), 5.69(2H, s), 7.20–7.80(4H), 8.03(1H, d, J=8 Hz), 8.12(1H, d, J=8 Hz)

Methyl 1-((benzimidazol-2-yl)methyl)-2-methyl-1H-imidazo[4,5-b]pyridine-5-carboxylate ¹H-NMR(CDCl₃): 2.30(3H, s), 3.83(3H, s), 5.66(2H, s), 7.18–7.88(6H)

Preparation Example 122-2

Methyl 3-[(1-ethylbenzimidazol-2-yl)methyl]-2-methyl-3H-imidazo[4,5-b]pyridine-5-carboxylate In the same manner as in Preparation Example 121-1, the objective compound (192 mg) was obtained as yellow crystals from methyl 3-[(benzimidazol-2-yl)methyl]-2-methyl-3H-imidazo[4,5-b]pyridine-5-carboxylate (380 mg) and ethyl iodide (194 mg).

¹H-NMR(CDCl₃): 1.08(3H, t, J=7.5 Hz), 2.85(3H, s), 4.04(3H, s), 4.51(2H, q, J=7.5 Hz), 5.83(2H, s), 7.23–7.38 (3H, m), 7.71–7.80(1H, m), 8.02(1H, d, J=8 Hz), 8.12(1H, d, J=8 Hz)

MS(ESI) m/e: 350(M+H).

Preparation Example 122-3

3-[(1-Ethylbenzimidazol-2-yl)methyl]-2-methyl-3H-imidazo[4,5-b]pyridine-5-carboxylic acid In the same manner as in Preparation Example 4-7, the objective compound (110 mg) was obtained as pale-yellow crystals from methyl 3-[(1-ethylbenzimidazol-2-yl)methyl]-2-methyl-3H-imidazo[4,5-b]pyridine-5-carboxylate (226 mg).

¹H-NMR(DMSO-d₆): 1.33(3H, t, J=7.5 Hz), 2.68(3H, s), 4.53(2H, q, J=7.5 Hz), 5.91(2H, s), 7.14(1H, t, J=8 Hz), 7.24(1H, t, J=8 Hz), 7.50(1H, d, J=8 Hz), 7.60(1H, d, J=8 Hz), 8.00(1H, d, J=8 Hz), 8.11(1H, d, J=8 Hz)

MS(ESI) m/e: 334(M–H)

Preparation Example 123-1

2-Chloro-4-(thiophen-2-yl)toluene

In the same manner as in Preparation Example 11-2, the objective compound (6.50 g) was obtained from 2-chloro-4-iodotoluene (7.89 g) and thiophene-2-boric acid (4.8 g).

¹H-NMR(CDCl₃): 2.38(3H, s), 7.07(1H, dd, J=5, 4 Hz), 7.22(1H, d, J=8 Hz), 7.24–7.30(2H), 7.39(1H, d, J=8 Hz), 7.60(1H, s)

Preparation Example 123-2

2-Chloro-4-(thiophen-2-yl)benzyl bromide

In the same manner as in Preparation Example 93-1, the objective compound (1.35 g) was obtained from 2-chloro-4-(thiophen-2-yl)toluene (1.00 g).

¹H-NMR(CDCl₃): 4.61(2H, s), 7.09(1H, t, J=4 Hz), 7.30–7.52(4H), 7.63(1H, s),

Preparation Example 123-3

6-Bromo-2-(N-(2-chloro-4-(thiophen-2-yl)benzyl)acetamido)-3-nitropyridine

In the same manner as in Preparation Example 106-3, the objective compound (1.60 g) was obtained from 2-acetamido-6-bromo-3-nitropyridine (1.24 g) and 2-chloro-4-(thiophen-2-yl)benzyl bromide (1.35 g).

$^1$H-NMR(CDCl$_3$): 2.24(3H, br. s), 5.39(2H, br. s), 7.09 (1H, t, J=4 Hz), 7.29–7.34(2H), 7.50(1H, br. d, J=8 Hz), 7.62(1H, br. d, J=8 Hz), 8.11(1H, d, J=8 Hz)

Preparation Example 123-4

5-Bromo-3-(2-chloro-4-(thiophen-2-yl)benzyl)-2-methyl-3H-imidazo[4,5-b]pyridine

In the same manner as in Preparation Example 106-4, the objective compound (647 mg) was obtained from 6-bromo-2-(N-(2-chloro-4-(thiophen-2-yl)benzyl)acetamido)-3-nitropyridine (836 mg).

$^1$H-NMR(CDCl$_3$): 2.52(3H, br. s), 5.56(2H, s), 6.60(1H, d, J=8 Hz), 7.08(1H, t, J=5 Hz), 7.26–7.42(4H), 7.67(1H, s), 7.87(1H, d, J=8 Hz)

Preparation Example 123-5

Methyl 3-(2-chloro-4-(thiophen-2-yl)benzyl)-2-methyl-3H-imidazo[4,5-b]pyridine-5-carboxylate In the same manner as in Preparation Example 26-2, the objective compound (4.0 g) was obtained as pale-yellow crystals from 5-bromo-3-(2-chloro-4-(thiophen-2-yl)benzyl)-2-methyl-3H-imidazo[4,5-b]pyridine (4.7 g).

$^1$H-NMR(CDCl$_3$): 2.56(3H, s), 4.00(3H, s), 5.69(3H, s), 6.64(1H, d, J=8 Hz), 7.07(1H, dd, J=5, 4 Hz), 7.22–7.37(3H, m), 7.67(1H, d, J=2 Hz), 8.07(1H, d, J=8 Hz), 8.15(1H, d, J=8 Hz)

MS(ESI) m/e: 398.0(M+H).

Preparation Example 124-1

Methyl 3-(2-chloro-4-phenylbenzyl)-2,7-dimethyl-3H-imidazo[4,5-b]pyridine-5-carboxylate In the same manner as in Preparation Example 102-5, the objective compound (1.48 g) was obtained as colorless crystals from methyl 2,7-dimethyl-3H-imidazo[4,5-b]pyridine-5-carboxylate (900 mg).

mp 202–204° C.

$^1$H-NMR(CDCl$_3$): 2.58(3H, s), 2.75(3H, s), 3.99(3H, s), 5.70(2H, s), 6.65(1H, d, J=8 Hz), 7.23–7.45(4H, m), 7.51 (2H, d, J=8 Hz), 7.66(1H, s), 7.99(1H, s)

MS(ESI) m/z: 406(M+1)

Preparation Example 124-2

Methyl 3-[2-chloro-4-(thiophen-2-yl)benzyl]-2,7-dimethyl-3H-imidazo[4,5-b]pyridine-5-carboxylate In the same manner as in Preparation Example 14-2, the objective compound (4.60 g) was obtained as colorless crystals from 2,7-dimethyl-3H-imidazo[4,5-b]pyridine-5-carboxylate (2.85 g).

mp 160–164° C.

$^1$H-NMR(CDCl$_3$): 2.57(3H, s), 2.75(3H, s), 4.00(3H, s), 5.67(2H, s), 6.61(1H, d, J=8 Hz), 7.07(1H, t, J=4 Hz), 7.25–7.35(3H, m), 7.67(1H, d, J=1 Hz), 7.99(1H, d, J=8 Hz), 8.16(1H, d, J=8 Hz)

MS(ESI) m/z: 412(M+1).

Preparation Example 125-1

3-(2-Chloro-4-phenylbenzyl)-2,7-dimethyl-3H-imidazo[4,5-b]pyridine-5-carboxylic acid In the same manner as in Preparation Example 4-7, the objective compound (1.33 g) was obtained as colorless crystals from methyl 3-(2-chloro-4-phenylbenzyl)-2,7-dimethyl-3H-imidazo[4,5-b]pyridine-5-carboxylate (1.45 g).

mp>250° C.

$^1$H-NMR(DMSO-d$_6$): 2.55(3H, s), 2.64(3H, s), 5.64(2H, s), 6.56(1H, d, J=8 Hz), 7.35–7.54(4H, m), 7.62–7.67(2H, m), 7.84–7.89(2H, m)

MS(ESI) m/z: 392(M+1).

Preparation Example 125-2

3-[2-Chloro-4-(thiophen-2-yl)benzyl]-2,7-dimethyl-3H-imidazo[4,5-b]pyridine-5-carboxylic acid In the same manner as in Preparation Example 4-7, the objective compound (1.81 g) was obtained as colorless crystals from methyl 3-[2-chloro-4-(thiophen-2-yl)benzyl]-2,7-dimethyl-3H-imidazo[4,5-b]pyridine-5-carboxylate (2.0 g).

mp>250° C.

$^1$H-NMR(DMSO-d$_6$): 2.53(3H, s), 2.64(3H, s), 5.61(2H, s), 6.55(1H, d, J=8 Hz), 7.14(1H, t, J=4 Hz), 7.49(1H, dd, J=8, 1 Hz), 7.58(1H, s), 7.60(1H, br s), 7.87(2H, s)

MS(ESI) m/z: 396(M–1)

Preparation Example 126-1

Methyl 3-[2-chloro-4-(5-chlorothiophen-2-yl)benzyl]-2,7-dimethyl-3H-imidazo[4,5-b]pyridine-5-carboxylate In the same manner as in Preparation Example 66-1, the objective compound (1.72 g) was obtained as colorless crystals from methyl 3-[2-chloro-4-(thiophen-2-yl)benzyl]-2,7-dimethyl-3H-imidazo[4,5-b]pyridine-5-carboxylate (2.55 g).

$^1$H-NMR(CDCl$_3$): 2.55(3H, s), 2.74(3H, s), 3.98(3H, s), 5.60(2H, s), 6.60(1H, d, J=8 Hz), 6.88(1H, d, J=4 Hz), 7.04(1H, d, J=4 Hz), 7.21(1H, dd, J=8, 1 Hz), 7.57(1H, d, J=1 Hz), 7.98(1H, s)

MS(ESI) m/z: 446(M+1)

Preparation Example 126-2

3-[2-Chloro-4-(5-chlorothiophen-2-yl)benzyl]-2,7-dimethyl-3H-imidazo[4,5-b]pyridine-5-carboxylic acid In the same manner as in Preparation Example 4-7, the objective compound (1.08 g) was obtained as colorless crystals from methyl 3-[2-chloro-4-(5-chlorothiophen-2-yl)benzyl]-2,7-dimethyl-3H-imidazo[4,5-b]pyridine-5-carboxylate (1.23 g).

mp>250° C.

$^1$H-NMR(DMSO-d$_6$): 2.53(3H, s), 2.63(3H, s), 5.60(2H, s), 6.54(1H, d, J=8 Hz), 7.17(1H, d, J=4 Hz), 7.42(1H, dd, J=8, 1 Hz), 7.49(1H, d, J=4 Hz), 7.84–7.88(2H, m)

MS(ESI) m/z: 430(M–1).

Preparation Example 127-1

Methyl 2-chloro-4-(n-pentanethio)benzoate

In the same manner as in Preparation Example 80-1, the objective compound (438 mg) was obtained as a colorless oil from methyl 4-bromo-2-chlorobenzoate (1 g).

¹H-NMR(CDCl₃): 0.90(3H, t, J=8 Hz), 1.29–1.51(4H, m), 1.64–1.76(2H, m), 2.96(2H, t, J=8 Hz), 3.90(3H, s), 7.14(1H, dd, J=8, 1 Hz), 7.29(1H, d, J=1 Hz)

Preparation Example 127-2

Methyl 4-benzylthio-2-chlorobenzoate

In the same manner as in Preparation Example 80-1, the objective compound (908 mg) was obtained as a colorless oil from methyl 4-bromo-2-chlorobenzoate (1 g).

¹H-NMR(CDCl₃): 3.91(3H, s), 4.19(2H, s), 7.15(1H, dd, J=8, 1 Hz), 7.23–7.43(6H, m), 7.75(1H, d, J=8 Hz)

Preparation Example 127-3

Methyl 2-chloro-4-ethylthiobenzoate

In the same manner as in Preparation Example 80-1, the objective compound (2.01 g) was obtained as a colorless oil from methyl 4-bromo-2-chlorobenzoate (3.65 g).

¹H-NMR(CDCl₃): 1.37(3H, t, J=7.5 Hz), 3.01(2H, q, J=7.5 Hz), 3.91(3H, s), 7.15(1H, dd, J=8, 1 Hz), 7.29(1H, d, J=1 Hz), 7.78(1H, d, J=8 Hz)

Preparation Example 128-1

2-Chloro-4-(n-pentanethio)benzyl alcohol

In the same manner as in Preparation Example 80-2, the objective compound (354 mg) was obtained as a colorless oil from methyl 2-chloro-4-(n-pentanethio)benzoate (430 mg).

¹H-NMR(CDCl₃): 0.90(3H, t, J=8 Hz), 1.29–1.49(4H, m), 1.60–1.72(2H, m), 1.89(1H, t, J=5 Hz), 2.91(2H, t, J=8 Hz), 4.74(2H, d, J=5 Hz), 7.20(1H, d, J=8 Hz), 7.29(1H, br s), 7.38(1H, d, J=8 Hz)

Preparation Example 128-2

4-Benzylthio-2-chlorobenzyl alcohol

In the same manner as in Preparation Example 80-2, the objective compound (787 mg) was obtained as a colorless oil from methyl 4-benzylthio-2-chlorobenzoate (900 mg).

¹H-NMR(CDCl₃): 1.88(1H, t, J=7 Hz), 4.11(3H, s), 4.73(2H, d, J=7 Hz), 4.19(2H, s), 7.19(1H, d, J=8 Hz), 7.21–7.32(6H, m), 7.36(1H, d, J=8 Hz)

Preparation Example 128-3

2-Chloro-4-ethylthiobenzyl alcohol

In the same manner as in Preparation Example 80-2, the objective compound (1.69 g) was obtained as a colorless oil from methyl 2-chloro-4-ethylthiobenzoate (2.0 g).

¹H-NMR(CDCl₃): 1.32(3H, t, J=7.5 Hz), 1.92(1H, t, J=7 Hz), 2.95(2H, q, J=7.5 Hz), 4.74(2H, d, J=7 Hz), 7.21(1H, dd, J=8, 1 Hz), 7.30(1H, d, J=1 Hz), 7.38(1H, d, J=8 Hz)

Preparation Example 129-1

2-Chloro-1-((methanesulfonyloxy)methyl)-4-(n-pentanethio)benzene

In the same manner as in Preparation Example 14-1, the objective compound was obtained from 2-chloro-4-(n-pentanethio)benzyl alcohol (350 mg). This compound was used in the next reaction without purification.

Preparation Example 129-2

4-Benzylthio-1-((methanesulfonyloxy)methyl)-2-chlorobenzene

In the same manner as in Preparation Example 14-1, the objective compound was obtained from 4-benzylthio-2-chlorobenzyl alcohol (350 mg). The compound was used in the next reaction without purification.

Preparation Example 129-3

2-Chloro-4-ethylthio-1-((methanesulfonyloxy)methyl)benzene

In the same manner as in Preparation Example 14-1, the objective compound was obtained from 2-chloro-4-ethylthiobenzyl alcohol (1.66 g). The compound was used in the next reaction without purification.

Preparation Example 130-1

Methyl 3-[2-chloro-4-(n-pentanethio)benzyl]-2-methyl-3H-imidazo[4,5-b]pyridine-5-carboxylate and methyl 1-[2-chloro-4-(n-pentanethio)benzyl]-2-methyl-3H-imidazo[4,5-b]pyridine-5-carboxylate In the same manner as in Preparation Example 14-2, methyl 3-[2-chloro-4-(n-pentanethio)benzyl]-2-methyl-3H-imidazo[4,5-b]pyridine-5-carboxylate (207 mg) was obtained as pale-yellow crystals and methyl 1-[2-chloro-4-(n-pentanethio)benzyl]-2-methyl-3H-imidazo[4,5-b]pyridine-5-carboxylate (293 mg) was obtained as an amorphous, from methyl 2-methyl-3H-imidazo[4,5-b]pyridine-5-carboxylate (273 mg).

Methyl 3-[2-chloro-4-(n-pentanethio)benzyl]-2-methyl-3H-imidazo[4,5-b]pyridine-5-carboxylate mp 64–65° C.

¹H-NMR(CDCl₃): 0.89(3H, t, J=7.5 Hz), 1.26–1.46(4H, m), 1.59–1.70(2H, m), 2.54(3H, s), 2.89(2H, t, J=7.5 Hz), 4.00(3H, s), 5.63(2H, s), 6.55(1H, d, J=8 Hz), 7.00(1H, d, J=8 Hz), 7.34(1H, d, J=1 Hz), 8.06(1H, d, J=8 Hz), 8.16(1H, d, J=8 Hz)

MS(ESI) m/z: 418(M+1).

Methyl 1-[2-chloro-4-(n-pentanethio)benzyl]-2-methyl-3H-imidazo[4,5-b]pyridine-5-carboxylate ¹H-NMR(CDCl₃): 0.89(H, t, J=7.5 Hz), 1.26–1.47(4H, m), 1.59–1.71(2H, m), 2.65(3H, s), 2.90(2H, t, J=7.5 Hz), 4.01(3H, s), 5.39(2H, s), 6.40(1H, d, J=8 Hz), 7.01(1H, dd, J=8, 1 Hz), 7.35(1H, br s), 7.56(1H, d, J=8 Hz), 8.09(1H, d, J=8 Hz)

MS(ESI) m/z: 418(M+1).

Preparation Example 130-2

Methyl 3-[4-(benzylthio)-2-chloro]benzyl-2-methyl-3H-imidazo[4,5-b]pyridine-5-carboxylate and methyl 1-[4-(benzylthio)-2-chloro]benzyl-2-methyl-3H-imidazo[4,5-b]pyridine-5-carboxylate In the same manner as in Preparation Example 14-2, methyl 3-[4-(benzylthio)-2-chloro]-benzyl-2-methyl-3H-imidazo[4,5-b]pyridine-5-carboxylate (592 mg) was obtained as pale-yellow crystals and methyl 1-[4-(benzylthio)-2-chloro]benzyl-2methyl-3H-imidazo[4,5-b]pyridine-5-carboxylate (495 mg) was obtained as an amorphous, from methyl 2-methyl-3H-imidazo[4,5-b]pyridine-5-carboxylate (554 mg).

Methyl 3-[4-(benzylthio)-2-chloro]-benzyl-2-methyl-3H-imidazo[4,5-b]pyridine-5-carboxylate mp 140–142° C.

¹H-NMR(CDCl₃): 2.51(3H, s), 4.00(3H, s), 4.09(2H, s), 5.61(2H, s), 6.51(1H, d, J=8 Hz), 6.99(1H, d, J=8 Hz), 7.23–7.31(5H, m), 7.34(1H, br s), 8.05(1H, d, J=8 Hz), 8.14(1H, d, J=8 Hz)

MS(ESI) m/z: 438(M+1).

Methyl 1-[4-(benzylthio)-2-chloro]benzyl-2-methyl-3H-imidazo[4,5-b]pyridine-5-carboxylate ¹H-NMR(CDCl₃): 2.64(3H, s), 4.00(3H, s), 4.10(2H, s), 5.38(2H, s), 6.38(1H, d, J=8 Hz), 7.01(1H, br d, J=8 Hz), 7.20–7.31(5H, m), 7.36(1H, br s), 7.51(1H, d, J=8 Hz), 8.07(1H, d, J=8 Hz)

MS(ESI) m/z: 438(M+1).

Preparation Example 130-3

Methyl 3-(2-chloro-4-ethylthiobenzyl)-2-methyl-3H-imidazo[4,5-b]pyridine-5-carboxylate and methyl 1-(2-chloro-4-ethylthiobenzyl)-2-methyl-3H-imidazo[4,5-b]pyridine-5-carboxylate In the same manner as in Preparation Example 14-2, methyl 3-(2-chloro-4-ethylthiobenzyl)-2-methyl-3H-imidazo[4,5-b]pyridine-5-carboxylate (1.21 g) was obtained as pale-yellow crystals and methyl 1-(2-chloro-4-ethylthiobenzyl)-2-methyl-3H-imidazo[4,5-b]pyridine-5-carboxylate (947 mg) was obtained as an amorphous, from methyl 2-methyl-3H-imidazo[4,5-b]pyridine-5-carboxylate (1.57 g).

Methyl 3-(2-chloro-4-ethylthiobenzyl)-2-methyl-3H-imidazo[4,5-b]pyridine-5-carboxylate mp 116–117° C.

¹H-NMR(CDCl₃): 1.31(3H, t, J=7.5 Hz), 2.54(3H, s), 2.92(2H, q, J=7.5 Hz), 4.00(3H, s), 5.63(2H, s), 6.55(1H, d, J=8 Hz), 7.01(1H, dd, J=8, 1 Hz), 7.34(1H, d, J=1 Hz), 8.05(1H, d, J=8 Hz), 8.14(1H, d, J=8 Hz)

MS(ESI) m/z: 376(M+1).

Methyl 1-(2-chloro-4-ethylthiobenzyl)-2-methyl-3H-imidazo[4,5-b]pyridine-5-carboxylate mp 150–151° C.

¹H-NMR(CDCl₃): 1.32(3H, t, J=7.5 Hz), 2.66(3H, s), 2.93(2H, q, J=7.5 Hz), 4.02(3H, s), 5.39(2H, s), 6.41(1H, d, J=8 Hz), 7.02(1H, dd, J=8, 1 Hz), 7.36(1H, d, J=1 Hz), 7.55(1H, d, J=8 Hz), 8.07(1H, d, J=8 Hz)

MS(ESI) m/z: 376(M+1).

Preparation Example 131-1

3-[2-Chloro-4-(n-pentanethio)benzyl]-2-methyl-3H-imidazo[4,5-b]pyridine-5-carboxylic acid In the same manner as in Preparation Example 4-7, the objective compound (182 mg) was obtained as colorless crystals from methyl 3-[2-chloro-4-(n-pentanethio)benzyl]-2-methyl-3H-imidazo[4,5-b]pyridine-5-carboxylate (200 mg).

mp 178–179° C.

¹H-NMR(DMSO-d₆): 0.83(3H, t, J=7.5 Hz), 1.19–1.41 (4H, m), 1.49–1.62(2H, m), 2.51(3H, s), 2.97(2H, t, J=7.5 Hz), 5.57(2H, s), 6.50(1H, d, J=8 Hz), 7.14(1H, dd, J=8, 1 Hz), 7.46(1H, d, J=1 Hz), 8.00(1H, d, J=8 Hz), 8.13(1H, d, J=8 Hz)

MS(ESI) m/z: 404(M+1).

Preparation Example 131-2

3-[4-(Benzylthio)-2-chloro]benzyl-2-methyl-3H-imidazo[4,5-b]pyridine-5carboxylic acid In the same manner as in Preparation Example 4-7, the objective compound (413 mg) was obtained as colorless crystals from methyl 3-[4-(benzylthio)-2-chloro]benzyl-2-methyl-3H-imidazo[4,5-b]pyridine-5-carboxylate (462 mg).

mp 177–185° C.

¹H-NMR(DMSO-d₆): 2.48(3H, s), 4.25(2H, s), 5.55(2H, s), 6.49(1H, d, J=8 Hz), 7.13–7.39(6H, m), 7.50(1H, d, J=1 Hz), 8.00(1H, d, J=8 Hz), 8.13(1H, d, J=8 Hz)

MS(ESI) m/e: 424(M+1).

Preparation Example 131-3

3-(2-Chloro-4-ethylthiobenzyl)-2-methyl-3H-imidazo[4,5-b]pyridine-5-carboxylic acid In the same manner as in Preparation Example 4-7, the objective compound (1.07 g) was obtained as colorless crystals from methyl 3-(2-chloro-4-ethylthiobenzyl)-2-methyl-3H-imidazo[4,5-b]pyridine-5-carboxylate (1.2 g).

mp 202–204° C.

¹H-NMR(DMSO-d₆): 1.21(3H, t, J=7.5 Hz), 2.52(3H, s), 2.99(2H, q, J=7.5 Hz), 5.57(2H, s), 6.50(1H, d, J=8 Hz), 7.15(1H, dd, J=8, 1 Hz), 7.47(1H, d, J=1 Hz), 8.00(1H, d, J=8 Hz), 8.13(1H, d, J=8 Hz)

MS(ESI) m/z: 360(M−1).

Preparation Example 132-1

Methyl 3-(2-chloro-4-((3-pyridyloxy)methyl)benzyl)-2-methyl-3H-imidazo[4,5-b]pyridine-5-carboxylate In the same manner as in the following Example 118, the objective compound (197 mg) was obtained as pale-yellow crystals from methyl 3-(2-chloro-4-((methanesulfonyloxy)methyl)benzyl)-2-methyl-3H-imidazo[4,5-b]pyridine-5-carboxylate (300 mg) and 3-hydroxypyridine (77 mg).

¹H-NMR(CDCl₃): 2.55(3H, s), 4.00(3H, s), 5.06(2H, s), 5.69(2H, s), 6.65(1H, d, J=8 Hz), 7.16(1H, d, J=8 Hz), 7.19–7.30(2H, m), 7.55(1H, s), 8.07(1H, d, J=8 Hz), 8.15 (1H, d, J=8 Hz), 8.21–8.19(1H, m), 8.36(1H, s)

MS(ESI) m/e: 423.1(M+H).

Preparation Example 132-2

3-(2-Chloro-4-((3-pyridyloxy)methyl)benzyl)-2-methyl-3H-imidazo[4,5-b]pyridine-5-carboxylic acid In the same manner as in Preparation Example 4-7, the objective compound (162 mg) was obtained as pale-yellow crystals from methyl 3-(2-chloro-4-((3-pyridyloxy)methyl)benzyl)-2-methyl-3H-imidazo[4,5-b]pyridine-5-carboxylate (210 mg).

¹H-NMR(DMSO-d₆): 2.52(3H, s), 5.17(2H, s), 5.63(2H, s), 6.59(1H, d, J=8 Hz), 7.26–7.36(2H, m), 7.43(1H, dd, J=8, 2 Hz), 7.68(1H, s), 8.01(1H, d, J=8 Hz), 8.10–8.20(2H, m), 8.34(1H, d, J=2 Hz)

MS(ESI) m/e: 407.2 (M−H).

Preparation Example 133-1

Methyl 3-(4-(N-butyrylamino)-2-chlorobenzyl)-2-methyl-3H-imidazo[4,5-b]pyridine-5-carboxylate In the same manner as in Preparation Example 133-2, the objective compound (510 mg) was obtained as colorless crystals from methyl 3-(4-amino2-chlorobenzyl)-2-methyl-3H-imidazo[4,5-b]pyridine-5-carboxylate (500 mg) and benzenesulfonyl chloride (191 mg).

$^1$H-NMR(CDCl$_3$): 0.94(3H, t, J=7 Hz), 1.64–1.78(2H, m), 2.32(2H, t, J=8 Hz), 2.48(3H, s), 3.98(3H, s), 5.48(2H, s), 6.17(1H, d, J=8 Hz), 7.04(1H, dd, J=8, 2 Hz), 7.86(1H, s), 8.07(1H, d, J=8 Hz), 8.15(1H, d, J=8 Hz), 8.67(1H, s)

Preparation Example 133-2

Methyl 3-(4-(N-benzoylamino)-2-chlorobenzyl)-2-methyl-3H-imidazo[4,5-b]pyridine-5-carboxylate To a solution of methyl 3-(4-amino-2-chlorobenzyl)-2-methyl-3H-imidazo[4,5-b]pyridine-5-carboxylate (300 mg) in dichloromethane (3 ml) was added triethylamine (110 mg). Benzoyl chloride (134 mg) was added under ice-cooling and the mixture was stirred at room temperature for 12 hr. Water was added to the reaction mixture and the mixture was extracted with chloroform. The organic layer was washed with saturated brine, dried over anhydrous magnesium sulfate and concentrated under reduced pressure. Hexane was added to the residue for crystallization, and the crystals were collected by filtration and dried under reduced pressure to give the objective compound (317 mg) as colorless crystals.

$^1$H-NMR(CDCl$_3$): 2.50(3H, s), 3.49(3H, s), 5.55(2H, s), 6.35(1H, d, J=8 Hz), 7.17(1H, d, J=8 Hz), 7.37–7.53(3H, m), 7.89(2H, d, J=8 Hz), 8.06–8.17(3H, m), 8.70(1H, s)

Preparation Example 134-1

3-(4-(N-Butyrylamino)-2-chlorobenzyl)-2-methyl-3H-imidazo[4,5-b]pyridine-5-carboxylic acid In the same manner as in Preparation Example 4-7, the objective compound (228 mg) was obtained as colorless crystals from methyl 3-(4-(N-butyrylamino)-2-chlorobenzyl)-2-methyl-3H-imidazo[4,5-b]pyridine-5-carboxylate (239 mg).

$^1$H-NMR(DMSO-d$_6$): 0.89(3H, t, J=7 Hz), 1.52–1.63(2H, m), 2.26(2H, t, J=7 Hz), 2.50(3H, s), 5.56(2H, s), 6.57(1H, d, J=8 Hz), 7.28(1H, dd, J=8, 2 Hz), 7.97–8.02(2H, m), 8.12(1H, d, J=8 Hz)

Preparation Example 134-2

3-(4-(N-Benzoylamino)-2-chlorobenzyl)-2-methyl-3H-imidazo[4,5-b]pyridine-5-carboxylic acid In the same manner as in Preparation Example 4-7, the objective compound (165 mg) was obtained as colorless crystals from methyl 3-(4-(N-benzoylamino)-2-chlorobenzyl)-2-methyl-3H-imidazo[4,5-b]pyridine-5-carboxylate (200 mg).

$^1$H-NMR(DMSO-d$_6$): 2.52(3H, s), 5.60(2H, s), 6.63(1H, d, J=8 Hz), 7.50–7.62(4H, m), 7.92–8.15(5H, m)

Preparation Example 135-1

Methyl 3-(4-(N-benzoyl-N-methylamino)-2-chlorobenzyl)-2-methyl-3H-imidazo[4,5-b]pyridine-5-carboxylate To a solution of methyl 3-(4-(N-benzoylamino)-2-chlorobenzyl)-2-methyl-3H-imidazo[4,5-b]pyridine-5-carboxylate (300 mg) in N,N-dimethylformamide (3 ml) was added 60% sodium hydride (in mineral oil, 30.4 mg) at room temperature. After 15 min, methyl iodide (108 mg) was added and the mixture was stirred at room temperature for 2 hr. Ice water was poured thereinto and the mixture was extracted with ethyl acetate. The organic layer was successively washed with a saturated aqueous solution of sodium hydrogencarbonate and saturated brine, dried over anhydrous magnesium sulfate and concentrated under reduced pressure to give the objective compound (305 mg) as a pale-yellow powder.

$^1$H-NMR(CDCl$_3$): 2.45(3H, s), 3.45(3H, s), 4.00(3H, s), 5.59(2H, s), 6.51(1H, d, J=8 Hz), 6.76(1H, d, J=8 Hz), 7.18–7.25(6H, m), 8.03(1H, d, J=8 Hz), 8.12(1H, d, J=8 Hz)

Preparation Example 135-2

3-(4-(N-Benzoyl-N-methylamino)-2-chlorobenzyl)-2-methyl-3H-imidazo[4,5-b]pyridine-5-carboxylic acid In the same manner as in Preparation Example 4-7, the objective compound (257 mg) was obtained as a pale-yellow powder from methyl 3-(4-(N-benzoyl-N-methylamino)-2-chlorobenzyl)-2-methyl-3H-imidazo[4,5-b]pyridine-5-carboxylate (288 mg).

$^1$H-NMR(DMSO-d$_6$): 2.40(3H, s), 2.50(3H, s), 5.55(2H, s), 6.51(1H, d, J=8 Hz), 7.01(1H, dd, J=8, 2 Hz), 7.22–7.32 (5H, m), 7.49(1H, s), 7.98(1H, d, J=8 Hz), 8.11(1H, d, J=8 Hz)

Preparation Example 136-1

Methyl 3-(4-(N-butyryl-N-methylamino)-2-chlorobenzyl)-2-methyl-3H-imidazo[4,5-b]pyridine-5-carboxylate In the same manner as in Preparation Example 135-1, the objective compound (107 mg) was obtained as colorless crystals from methyl 3-(4-(N-butyrylamino)-2-chlorobenzyl)-2-methyl-3H-imidazo[4,5-b]pyridine-5-carboxylate (250 mg) and methyl iodide (97 mg).

$^1$H-NMR (CDCl$_3$): 0.85(3H, t, J=7 Hz), 1.56–1.64(2H, m), 2.06(2H, br), 2.58(3H, s), 3.22(3H, s), 4.00(3H, s), 5.69(2H, s), 6.68(1H, d, J=8 Hz), 6.94(1H, dd, J=8, 2 Hz), 7.31(1H, s), 8.07(1H, d, J=8 Hz), 8.16(1H, d, J=8 Hz)

Preparation Example 136-2

3-(4-(N-Butyryl-N-methylamino)-2-chlorobenzyl)-2-methyl-3H-imidazo[4,5-b]pyridine-5-carboxylic acid In the same manner as in Preparation Example 4-7, the objective compound (99 mg) was obtained as a pale-yellow powder from methyl 3-(4-(N-butyryl-N-methylamino)-2-chlorobenzyl)-2-methyl-3H-imidazo[4,5-b]pyridine-5-carboxylate (102 mg).

$^1$H-NMR (DMSO-d$_6$): 0.77(3H, t, J=7 Hz), 1.39–1.51 (2H, m), 2.03(2H, br), 2.53(3H, s), 3.13(3H, s), 5.64(2H, s), 6.57(1H, d, J=8 Hz), 7.17(1H, d, J=8 Hz), 7.64(1H, s), 8.01(1H, d, J=8 Hz), 8.14(1H, d, J=8 Hz)

Preparation Example 137-1

Methyl 3-(2-chloro-4-(N-(n-pentyl)amino)benzyl)-2-methyl-3H-imidazo[4,5-b]pyridine-5-carboxylate In the same manner as in Preparation Example 83-4, the objective compound (481 mg) was obtained as pale-yellow crystals from methyl 3-(4amino-2-chlorobenzyl)-2-methyl-3H-imidazo[4,5-b]pyridine-5-carboxylate (500 mg) and valeraldehyde (169 mg).

¹H-NMR (CDCl₃): 0.91(3H, t, J=7 Hz), 1.30–1.40(4H, m), 1.55–1.63(2H, m), 2.55(3H, s), 3.00–3.06(2H, m), 3.73 (1H, br), 4.01(3H, s), 5.57(2H, s), 6.31(1H, d, J=8 Hz), 6.55–6.60(2H, m), 8.03(1H, d, J=8 Hz), 8.13(1H, d, J=8 Hz)

Preparation Example 137-2

3-(2-Chloro-4-(N-(n-pentyl)amino)benzyl)-2-methyl-3H-imidazo[4,5-b]pyridine-5-carboxylic acid In the same manner as in Preparation Example 4-7, the objective compound (186 mg) was obtained as a colorless powder from methyl 3-(2-chloro-4-(N-(n-pentyl)amino) benzyl)-2-methyl-3H-imidazo[4,5-b]pyridine-5-carboxylate (200 mg).

¹H-NMR (DMSO-d₆): 0.86(3H, t), 1.22–1.34(4H, m), 1.43–1.46(2H, m), 2.49(3H, s), 2.93(2H, m), 5.46(2H, s), 5.96(1H, br), 6.37–6.43(2H, m), 6.64(1H, d, J=2 Hz), 7.99 (1H, d, J=8 Hz), 8.09(1H, d, J=8 Hz)

Preparation Example 137-3

Methyl 3-(2-chloro-4-(N-methyl-N-(n-pentyl)amino) benzyl)-2-methyl-3H-imidazo[4,5-b]pyridine-5-carboxylate In the same manner as in Preparation Example 85-1, the objective compound (95 mg) was obtained as a pale-yellow powder from methyl 3-(2-chloro-4-(N-(n-pentyl)amino) benzyl)-2-methyl-3H-imidazo[4,5-b]pyridine-5-carboxylate (201 mg) and a 37% aqueous formaldehyde solution (151 mg).

¹H-NMR (CDCl₃): 0.89(3H, t, J=7 Hz), 1.20–1.38(4H, m), 1.46–1.56(2H, m), 2.85(3H, s), 2.91(3H, s), 3.26(2H, t, J=7 Hz), 4.05(3H, s), 5.72(2H, s), 6.43(1H, dd, J=8, 2 Hz), 6.63(1H, d, J=2 Hz), 6.91(1H, d, J=8 Hz), 8.32(1H, d, J=8 Hz), 8.38(1H, d, J=8 Hz)

Preparation Example 137-4

3-(2-Chloro-4-(N-methyl-N-(n-pentyl)amino) benzyl)-2-methyl-3H-imidazo[4,5-b]pyridine-5-carboxylic acid In the same manner as in Preparation Example 4-7, the objective compound (50 mg) was obtained as a pale-yellow powder from methyl 3-(2-chloro-4-(N-methyl-N-(n-pentyl) amino)benzyl)-2-methyl-3H-imidazo[4,5-b]pyridine-5-carboxylate (85 mg).

¹H-NMR (DMSO-d₆): 0.84(3H, t, J=7 Hz), 1.15–1.32 (4H, m), 1.38–1.48(2H, m), 2.77(3H, s), 2.86(3H, s), 5.66 (2H, s), 6.55(1H, dd, J=8, 2 Hz), 6.71(1H, d, J=2 Hz), 6.90(1H, d, J=8 Hz), 8.27(1H, d, J=8 Hz), 8.40(1H, d, J=8 Hz)

Preparation Example 138-1

Methyl 3-(4-(N-benzenesulfonylamino)-2-chlorobenzyl)-2-methyl-3H-imidazo[4,5-b]pyridine-5-carboxylate To a solution of methyl 3-(4-amino-2-chlorobenzyl)-2-methyl-3H-imidazo[4,5-b]pyridine-5-carboxylate (200 mg) in dichloromethane (2 ml) was added pyridine (95.7 mg). Benzenesulfonyl chloride (117 mg) was added under ice-cooling and the mixture was stirred at room temperature for 12 hr. Water was added to the reaction mixture and the mixture was extracted with chloroform. The organic layer was washed with saturated brine, dried over anhydrous magnesium sulfate and concentrated under reduced pressure. Methanol was added to the residue for crystallization, and the crystals were collected by filtration, dried under reduced pressure to give the objective compound (213 mg) as colorless crystals.

¹H-NMR (CDCl₃): 2.45(3H, s), 3.99(3H, s), 5.57(2H, s), 6.45(1H, d, J=8 Hz), 6.38(1H, dd, J=8, 2 Hz), 7.24(1H, d, J=2 Hz), 7.44(2H, t, J=7 Hz), 7.54(1H, t, J=7 Hz), 7.76–7.79 (2H, m), 8.04(1H, d, J=8 Hz),8.13(1H, d, J=8 Hz)

Preparation Example 138-2

3-(4-(N-Benzenesulfonylamino)-2-chlorobenzyl)-2-methyl-3H-imidazo[4,5-b]pyridine-5-carboxylic acid In the same manner as in Preparation Example 4-7, the objective compound (179 mg) was obtained as colorless crystals from methyl 3-(4-(N-benzenesulfonylamino)-2-chlorobenzyl)-2-methyl-3H-imidazo[4,5-b]pyridine-5-carboxylate (200 mg).

¹H-NMR (DMSO-d₆): 2.43(3H, s), 5.50(2H, s), 6.55(1H, d, J=8 Hz), 6.96(1H, dd, J=8, 2 Hz), 7.22(1H, d, J=2 Hz), 7.52–7.62(3H,m), 7.74–7.77(2H, m), 7.98(1H, d, J=8 Hz), 8.10(1H, d, J=8 Hz)

Preparation Example 139-1

5-Bromo-3-(2-chloro-4-(isopropoxylcarbonyl) benzyl)-2-methyl-3H-imidazo[4,5-b]pyridine To a solution of 5-bromo-3-(2-chloro-4-carboxybenzyl)-2-methyl-3H-imidazo[4,5-b]pyridine (400 mg) in N,N-dimethylformamide (4 ml) were successively added potassium carbonate (218 mg) and isopropyl iodide (197 mg), and the mixture was stirred at room temperature for 24 hr. Water and ethyl acetate were added for partitioning. The organic layer was successively washed with water and saturated brine, dried over anhydrous magnesium sulfate and concentrated under reduced pressure. Hexane was added to the residue and the mixture was heated and allowed to cool. The precipitated crystals were collected by filtration. The crystals were dried under reduced pressure and by heating to give the objective compound (394 mg) as gray-brown crystals.

¹H-NMR (CDCl₃): 1.34(3H, s), 1.36(3H, s), 2.48(3H, s), 5.17–5.39(1H, m), 5.58(2H, s), 6.60(1H, d, J=8 Hz), 7.40 (1H, d, J=8 Hz), 7.78(1H, d, J=8, 2 Hz), 7.87(1H, d, J=8 Hz), 8.10(1H, d, J=2 Hz)

Preparation Example 139-2

5-Bromo-3-(2-chloro-4-(cyclohexyloxycarbonyl) benzyl)-2-methyl-3H-imidazo[4,5-b]pyridine To a solution of 5-bromo-3-(2-chloro-4-carboxybenzyl)-2-methyl-3H-imidazo[4,5-b]pyridine (525 mg) in dichloromethane (5 ml) were added oxalyl chloride (0.36 ml) and N,N-dimethylformamide (0.03 ml), and the mixture was stirred at room temperature for 1 hr and concentrated under reduced pressure. Dichloromethane (5 ml) was added and dissolved, and trimethylamine (698 mg), 4-dimethylaminopyridine (10 mg) and cyclohexanol (1.38 g) were successively added under ice-cooling. The mixture was stirred under ice-cooling for 30 min and at room temperature for 30 min. The reaction mixture was concentrated under reduced pressure, and water and ethyl acetate were added for partitioning. The organic layer was successively washed with a saturated aqueous solution of sodium hydrogencarbonate and saturated brine, dried over anhydrous magnesium sulfate and concentrated under reduced pressure. Hexane (20 ml) was added to the residue and the mixture was heated. The black insoluble matter was removed by filtration and the filtrate was allowed to cool. The precipitated crystals were collected by filtration, dried under reduced pressure and by heating to give the objective compound (533 mg) as colorless crystals.

$^1$H-NMR (CDCl$_3$): 1.15–1.90(10H, m), 2.48(3H, s), 4.96–5.04(1H, m), 5.58(2H, s), 6.61(1H, d, J=8 Hz), 7.40 (1H, d, J=8 Hz), 7.79(1H, dd, J=8, 2 Hz), 7.86(1H, d, J=8 Hz), 8.10(1H, d, J=2 Hz)

Mass (ESI): m/z 464(M+H)$^+$

Preparation Example 140-1

3-(2-Chloro-4-(isopropoxylcarbonyl)benzyl)-2-methyl-3H-imidazo[4,5-b]pyridine-5-carboxylic acid In the same manner as in Preparation Example 113-5, the objective compound (282 mg) was obtained as a pale-yellow powder from 5-bromo-3-(2-chloro-4-(isopropoxylcarbonyl) benzyl)-2-methyl-3H-imidazo[4,5-b]pyridine (370 mg).

$^1$H-NMR (DMSO-d$_6$): 1.29(3H, s), 1.31(3H, s), 2.52,(3H, s), 5.06–5.18(1H, m), 5.69(2H, s), 6.72(1H, d, J=8 Hz), 7.78(1H, d, J=8, 2 Hz), 8.00–8.03(2H, m), 8.15(1H, d, J=8 Hz)

Preparation Example 140-2

3-(2-Chloro-4-(cyclohexyloxycarbonyl)benzyl)-2-methyl-3H-imidazo[4,5-b]pyridine-5-carboxylic acid In the same manner as in Preparation Example 113-5, the objective compound (317 mg) was obtained as colorless crystals from 5-bromo-3-(2-chloro-4-(cyclohexyloxycarbonyl)benzyl)-2-methyl-3H-imidazo[4,5-b]pyridine (514 mg).

$^1$H-NMR (DMSO-d$_6$): 1.28–1.58(6H, m), 1.69(2H, br s), 1.83(2H, br s), 2.52(3H, s), 4.87–4.95(1H, m), 5.69(2H, s), 6.71(1H, d, J=8 Hz), 7.80(1H, dd, J=8, 2 Hz), 8.01–8.03(2H, m), 8.05(1H, d, J=8 Hz)

Preparation Example 141-1

Methyl 3-(2-chloro-4-(3-phenylureido)benzyl)-2-methyl-3H-imidazo[4,5-b]pyridine-5-carboxylate Methyl 3-(4-amino-2-chlorobenzyl)-2-methyl-3H-imidazo[4,5-b]pyridine-5-carboxylate (275 mg) was suspended in toluene (10 ml), and phenyl isocyanate (218 mg) was added at room temperature. The mixture was refluxed under heating for 5 hr and concentrated under reduced pressure. Hexane (20 ml) was added, and the mixture was heated and allowed to cool. The precipitated crystals were collected by filtration. The crystals were suspended in ethyl acetate (10 ml), heated and allowed to cool. The precipitated crystals were collected by filtration and dried under reduced pressure and by heating to give the objective compound (328 mg) as colorless crystals.

$^1$H-NMR (CDCl$_3$): 2.49(3H, s), 4.01(3H, s), 5.46(2H, s), 5.78(1H, d, J=8 Hz), 6.75(1H, d, J=8 Hz), 6.99(1H, t, J=7 Hz), 7.20–7.26(2H, m), 7.31–7.37(3H, m), 8.05(1H, s), 8.15(1H, d, J=8 Hz), 8.21(1H, d, J=8 Hz), 8.34(1H, s)

Mass (ESI): m/z 448(M−H)$^-$

Preparation Example 141-2

3-(2-Chloro-4-(3-phenylureido)benzyl)-2-methyl-3H-imidazo[4,5-b]pyridine-5-carboxylic acid In the same manner as in Preparation Example 4-7, the objective compound (222 mg) was obtained as a pale-yellow powder from methyl 3-(2-chloro-4-(3-phenylureido) benzyl)-2-methyl-3H-imidazo[4,5-b]pyridine-5-carboxylate (300 mg).

$^1$H-NMR (DMSO-d$_6$): 2.52(3H, s),5.57(2H, s),5.66(1H, d, J=8 Hz),6.98(1H, t, J=7 Hz),7.01(1H, dd, J=8, 2 Hz),7.28 (2H, t, J=8 Hz),7.43(2H, d, J=8 Hz),7.89(1H, d, J=2 Hz), 8.01(1H, d, J=8 Hz),8.14(1H, d, J=8 Hz),8.72(1H, s),8.93 (1H, s)

Mass (ESI): m/z 434(M−H)$^-$

Preparation Example 142-1

4-Acetoxy-2-chlorotoluene

To a solution of 3-chloro-4-methylphenol (500 mg) in ether (5.0 ml) were added acetic anhydride (430 mg) and pyridine (416 mg), and the mixture was stirred at room temperature for 2 hr. The reaction mixture was washed with 1N hydrochloric acid (once) and saturated brine (twice), dried over magnesium sulfate and concentrated to dryness under reduced pressure to give the objective compound (645 mg) as a pale-yellow oil.

$^1$H-NMR (CDCl$_3$): 2.30(3H, s),2.36(3H, s),6.90(1H, dd, J=8, 2 Hz),7.12(1H, d, J=2 Hz),7.22(1H, d, J=8 Hz)

Preparation Example 142-2

2-Bromomethyl-5-acetoxychlorobenzene

In the same manner as in Preparation Example 93-1, the objective compound (18.4 g) was obtained as a pale-yellow oil from 4-acetoxy-2-chlorotoluene (13.4 g).

$^1$H-NMR (CDCl$_3$): 2.30(3H, s),4.58(2H, s),7.02(1H, dd, J=8, 2 Hz),7.18(1H, d, J=2 Hz),7.44(1H, d, J=8 Hz)

Preparation Example 142-3

Methyl 3-(4-acetoxy-2-chlorobenzyl)-2-methyl-3H-imidazo[4,5-b]pyridine-5-carboxylate In the same manner as in Preparation Example 14-2, the objective compound (4.64 g) was obtained as a pale-brown powder from methyl 2-methylimidazo[4,5-b]pyridine-5-carboxylate (5.00 g) and 2-bromomethyl-5-acetoxychlorobenzene (6.89 g).

$^1$H-NMR (CDCl$_3$): 2.28(3H, s), 2.56(3H, s), 4.00(3H, s), 5.64(2H, s), 6.64(1H, d, J=8 Hz), 6.86(1H, dd, J=8, 2 Hz), 7.24(1H, d, J=2 Hz), 8.06(1H, d, J=8 Hz), 8.16(1H, d, J=8 Hz)

A by-product, methyl 1-(4-acetoxy-2-chlorobenzyl)-2-methyl-1H-imidazo[4,5-b]pyridine-5-carboxylate (3.84 g), was obtained as a pale-brown powder.

$^1$H-NMR (CDCl$_3$): 2.30(3H, s), 2.68(3H, s), 4.02(3H, s), 5.43(2H, s), 6.48(1H, d, J=8 Hz), 6.88(1H, dd, J=8, 2 Hz), 7.28(1H, d, J=2 Hz), 7.56(1H, d, J=8 Hz), 8.10(1H, d, J=8 Hz)

Preparation Example 142-4

Methyl 3-(2-chloro-4-hydroxybenzyl)-2-methyl-3H-imidazo[4,5-b]pyridine-5-carboxylate To a mixture of methyl 3-(4-acetoxy-2-chlorobenzyl)-2-methyl-3H-imidazo[4,5-b]pyridine-5-carboxylate (2.87 g), methanol (29 ml), 1,4-dioxane (29 ml) and water (2.9 ml) was added sodium hydrogencarbonate (968 mg), and the mixture was stirred at room temperature for 2.5 hr. 1,4-Dioxane (29 ml) was added to dissolve the insoluble matter, and the mixture was stirred for 2 hr. Sodium hydrogencarbonate (968 mg) was added and the mixture was stirred at room temperature for 2 days and at 60° C. for 3 hr and stood overnight. The reaction mixture was partitioned between ethyl acetate and water, and the aqueous layer was again extracted with ethyl acetate. The organic layers were combined and concentrated to dryness under reduced pressure. The residue was pulverized in ether to give the objective compound (1.94 g) as a pale-yellow powder.

$^1$H-NMR (DMSO-d$_6$): 2.52(3H, s), 3.86(3H, s), 5.50(2H, s), 6.50(1H, d, J=8 Hz), 6.64(1H, dd, J=8, 2 Hz), 6.92(1H, d, J=2 Hz), 8.04(1H, d, J=8 Hz), 8.16(1H, d, J=8 Hz), 10.00(1H, br s)

Preparation Example 143-1

2-Methyl-5-ethoxychlorobenzene

In the same manner as in Preparation Example 74-2, the objective compound (3.56 g) was obtained as a pale-yellow oil from 3-chloro-4-methylphenol (3.0 g).

$^1$H-NMR (CDCl$_3$): 1.40(3H, t, J=6 Hz), 2.28(3H, s), 4.00(3H, q, J=6 Hz), 6.72(1H, dd, J=8, 2 Hz), 6.90(1H, d, J=2 Hz), 7.10(1H, d, J=8 Hz)

Preparation Example 143-2

2-Bromomethyl-5-ethoxychlorobenzene

In the same manner as in Preparation Example 93-1, the objective compound (3.99 g) was obtained as a pale-yellow oil from 2-methyl-5-ethoxychlorobenzene (3.56 g).

$^1$H-NMR (CDCl$_3$): 1.40(3H, t, J=6 Hz), 4.02(3H, q, J=6 Hz),4.59(2H, s),6.78(1H, dd, J=8, 2 Hz),6.92(1H, d, J=2 Hz),7.32(1H, d, J=8 Hz)

Preparation Example 144-1

Methyl 3-[2-chloro-4-propoxybenzyl]-2-methyl-3H-imidazo[4,5-b]pyridine-5-carboxylate In the same manner as in Preparation Example 74-2, the objective compound (220 mg) was obtained as colorless crystals from methyl 3-[2-chloro-4-hydroxybenzyl]-2-methyl-3H-imidazo[4,5-b]pyridine-5-carboxylate (240 mg).

$^1$H-NMR (CDCl$_3$): 1.01(3H, t, J=7 Hz), 1.70–1.85(2H, m), 2.53(3H, s), 3.86(2H, t, J=7 Hz), 4.00(3H, s), 5.61(2H, s), 6.63(2H, s), 6.96(1H, br s), 8.04(1H, d, J=8 Hz), 8.13(1H, d, J=8 Hz)

Mass (ESI):m/z 374(M+1).

Preparation Example 144-2

Methyl 3-[2-chloro-4-(n-pentoxy)benzyl]-2-methyl-3H-imidazo[4,5-b]pyridine-5-carboxylate In the same manner as in Preparation Example 74-1, the objective compound (247 mg) was obtained as colorless crystals from methyl 3-[2-chloro-4-hydroxybenzyl]-2-methyl-3H-imidazo[4,5-b]pyridine-5-carboxylate (240 mg).

$^1$H-NMR (CDCl$_3$): 0.92(3H, br t, J=7 Hz), 1.29–1.48(4H, m), 1.69–1.81(2H, m), 2.53(3H, s), 3.89(2H, t, J=7 Hz), 4.00(3H, s), 5.61(2H, s), 6.63(2H, s), 6.96(1H, br s), 8.04 (1H, d, J=8 Hz), 8.13(1H, d, J=8 Hz)

Mass (ESI):m/z 402(M+1)

Preparation Example 144-3

Methyl 3-(2-chloro-4-ethoxy)benzyl-2-methyl-3H-imidazo[4,5-b]pyridine-5-carboxylate and methyl 1-(2-chloro-4-ethoxy)benzyl-2-methyl-3H-imidazo[4,5-b]pyridine-5-carboxylate In the same manner as in Preparation Example 14-2, methyl 3-(2-chloro-4-ethoxy)benzyl-2-methyl-3H-imidazo[4,5-b]pyridine-5-carboxylate (380 mg) was obtained as pale-yellow crystals and methyl 1-(2-chloro-4-ethoxy)benzyl-2-methyl-3H-imidazo[4,5-b]pyridine-5-carboxylate (415 mg) was obtained an amorphous, from methyl 2-methyl-3H-imidazo[4,5-b]pyridine-5-carboxylate (554 mg).

Methyl 3-(2-chloro-4-ethoxy)benzyl-2-methyl-3H-imidazo[4,5-b]pyridine-5-carboxylate $^1$H-NMR (CDCl$_3$): 1.39(3H, t, J=7 Hz), 2.53(3H, s), 3.93–4.03(5H, m), 5.62(2H, s), 6.63(1H, s), 6.64(1H, s), 6.96(1H, br s), 8.05(1H, d, J=8 Hz), 8.14(1H, d, J=8 Hz)

Mass (ESI):m/z 360(M+1).

Methyl 1-(2-chloro-4-ethoxy)benzyl-2-methyl-3H-imidazo[4,5-b]pyridine5-carboxylate $^1$H-NMR (CDCl$_3$): 1.40(3H, t, J=7 Hz), 2.66(3H, s), 3.94–4.04(5H, m), 5.37(2H, s), 6.49(1H, d, J=8 Hz), 6.68 (1H, dd, J=8, 2 Hz), 6.99(1H, d, J=2 Hz), 7.54(1H, d, J=8 Hz), 8.06(1H, d, J=8 Hz)

Mass (ESI):m/z 360(M+1).

Preparation Example 144-4

Methyl 3-[2-chloro-4-(2-methoxyethoxy)benzyl]-2-methyl-3H-imidazo[4,5-b]pyridine-5-carboxylate In the same manner as in Preparation Example 74-1, the objective compound (216 mg) was obtained as colorless crystals from methyl 3-[2-chloro-4-hydroxybenzyl]-2-methyl-3H-imidazo[4,5-b]pyridine-5-carboxylate (240 mg).

$^1$H-NMR (CDCl$_3$): 2.53(3H, s), 3.43(3H, s), 3.69–3.74 (2H, m), 4.00(3H, s), 4.04–4.09(2H, m), 5.62(2H, s), 6.63 (1H, d, J=8 Hz), 6.69(1H, dd, J=8, 2 Hz), 7.01(1H, d, J=2 Hz), 8.05(1H, d, J=8 Hz), 8.14(1H, d, J=8 Hz)

Mass (ESI):m/z 390(M+1).

Preparation Example 144-5

Methyl 3-[2-chloro-4-[(thiophen-2-yl)methyl]oxybenzyl]-2-methyl-3H-imidazo[4,5-b]pyridine-5-carboxylate In the same manner as in Preparation Example 14-2, the objective compound (220 mg) was obtained as colorless crystals from methyl 3-[2-chloro-4-hydroxybenzyl]-2-methyl-3H-imidazo[4,5-b]pyridine-5-carboxylate (240 mg).

$^1$H-NMR (CDCl$_3$): 2.53(3H, s), 4.00(3H, s), 5.17(2H, s), 5.61(2H, s), 6.64(1H, d, J=8 Hz), 6.73(1H, dd, J=8, 2 Hz), 6.99(1H, dd, J=8, 5 Hz), 7.05–7.10(2H, m), 7.32(1H, d, J=5 Hz), 8.05(1H, d, J=8 Hz), 8.13(1H, d, J=8 Hz)

Mass (ESI):m/z 428(M+1).

Preparation Example 144-6

Methyl 3-[2-chloro-4-[(thiophene-3-yl)methyl]oxybenzyl]-2-methyl-3H-imidazo[4,5-b]pyridine-5-carboxylate To a suspension of methyl 3-[2-chloro-4-hydroxybenzyl]-2-methyl-3H-imidazo[4,5-b]pyridine-5-carboxylate (240 mg), 3-thiophenemethanol (68 mg) and triphenylphosphine (218 mg) in dry dichloromethane were added to diethyl azodicarboxylate (139 mg) under ice-cooling. After 2 hr, the reaction mixture was stirred at room temperature. After 6 hr, to a suspension of 3-thiophenemethanol (34 mg) and triphenylphosphine (109 mg) in dry dichloromethane was added diethyl azodicarboxylate (69 mg) under ice-cooling. After 20 hr, the reaction mixture was subjected to flash silica gel chromatography (silica gel 60 ml, eluent: chloroform). The eluate was recrystallized from ethyl acetate to give the objective compound (143 mg) as colorless crystals.

$^1$H-NMR (CDCl$_3$): 2.54(3H, s), 4.00(3H, s), 5.02(2H, s), 5.62(2H, s), 6.64(1H, d, J=8 Hz), 6.72(1H, dd, J=8, 2 Hz), 7.05(1H, d, J=2 Hz), 7.12(1H, br d, J=5 Hz), 7.26–7.38(2H, m), 8.05(1H, d, J=8 Hz), 8.14(1H, d, J=8 Hz)

Mass (ESI):m/z 428(M+1).

Preparation Example 144-7

Methyl 3-[2-chloro-4-cyclopentylmethyloxybenzyl]-2-methyl-3H-imidazo[4,5-b]pyridine-5-carboxylate In the same manner as in Preparation Example 74-2, the objective compound (83 mg) was obtained as a colorless amorphous from methyl 3-[2-chloro-4-hydroxybenzyl]-2-methyl-3H-imidazo[4,5-b]pyridine-5-carboxylate (240 mg).

$^1$H-NMR (CDCl$_3$): 1.22–1.41(2H, m), 1.50–1.70(3H, m), 1.75–1.90(2H, m), 2.33(1H, m), 2.53(3H, s), 3.77(2H, d, J=5 Hz), 4.00(3H, s), 5.62(2H, s), 6.64(2H, s), 6.97(1H, br s), 8.05(1H, d, J=8 Hz), 8.14(1H, d, J=8 Hz)

Mass (ESI):m/z 414(M+1).

Preparation Example 145-1

3-[2-Chloro-4-propoxybenzyl]-2-methyl-3H-imidazo[4,5-b]pyridine-5-carboxylic acid In the same manner as in Preparation Example 4-7, the objective compound (205 mg) was obtained as colorless crystals from methyl 3-[2-chloro-4-propoxybenzyl]-2-methyl-3H-imidazo[4,5-b]pyridine-5-carboxylate (247 mg).

$^1$H-NMR (DMSO-d$_6$): 0.93(3H, t, J=7 Hz), 1.62–1.76 (2H, m), 2.51(3H, s), 3.91(2H, t, J=7 Hz), 5.54(2H, s), 6.56(1H, d, J=8 Hz), 6.81(1H, dd, J=8, 2 Hz), 7.13(1H, d, J=2 Hz), 8.00(1H, d, J=8 Hz), 8.11(1H, d, J=8 Hz)

Mass (ESI):m/z 358(M−1).

Preparation Example 145-2

3-[2-Chloro-4-(n-pentoxy)benzyl]-2-methyl-3H-imidazo[4,5-b]pyridine-5-carboxylic acid In the same manner as in Preparation Example 4-7, the objective compound (208 mg) was obtained as colorless crystals from methyl 3-[2-chloro-4-(n-pentoxy)benzyl]-2-methyl-3H-imidazo[4,5-b]pyridine-5-carboxylate (247 mg).

$^1$H-NMR (DMSO-d$_6$): 0.87(3H, t, J=7 Hz), 1.27–1.41 (6H, m), 1.61–1.72(2H, m), 2.50(3H, s), 3.94(2H, t, J=7 Hz), 5.53(2H, s), 6.55(1H, d, J=8 Hz), 6.80(1H, dd, J=8, 2 Hz), 7.13(1H, d, J=2 Hz), 8.00(1H, d, J=8 Hz), 8.12(1H, d, J=8 Hz)

Mass (ESI):m/z 386(M−1).

Preparation Example 145-3

3-(2-Chloro-4-ethoxy)benzyl-2-methyl-3H-imidazo[4,5-b]pyridine-5-carboxylic acid In the same manner as in Preparation Example 4-7, the objective compound (380 mg) was obtained as colorless crystals from methyl 3-(2-chloro-4-ethoxy)benzyl-2-methyl-3H-imidazo[4,5-b]pyridine-5-carboxylate (376 mg).

$^1$H-NMR (DMSO-d$_6$): 1.21(3H, t, J=7.5 Hz), 2.52(3H, s), 2.99(2H, q, J=7.5 Hz), 5.57(2H, s), 6.50(1H, d, J=8 Hz), 7.15(1H, dd, J=8, 1 Hz), 7.47(1H, d, J=1 Hz), 8.00(1H, d, J=8 Hz), 8.13(1H, d, J=8 Hz)

Preparation Example 145-4

3-[2-Chloro-4-(2-methoxyethoxy)benzyl]-2-methyl-3H-imidazo[4,5-b]pyridine-5-carboxylic acid In the same manner as in Preparation Example 4-7, the objective compound (192 mg) was obtained as colorless crystals from methyl 3-[2-chloro-4-(2-methoxyethoxy)benzyl]-2-methyl-3H-imidazo[4,5-b]pyridine-5-carboxylate (216 mg).

$^1$H-NMR (CDCl$_3$): 2.63(3H, s), 3.43(3H, s), 3.69–3.76 (2H, m), 4.05–4.12(2H, m), 5.54(2H, s), 6.65(1H, d, J=8 Hz), 6.74(1H, dd, J=8, 2 Hz), 7.04(1H, d, J=2 Hz), 8.15(1H, d, J=8 Hz), 8.21(1H, d, J=8 Hz)

Mass (ESI):m/z 374(M−1).

Preparation Example 145-5

3-[2-Chloro-4-[(thiophen-2-yl)methyl]oxybenzyl]-2-methyl-3H-imidazo[4,5-b]pyridine-5-carboxylic acid In the same manner as in Preparation Example 4-7, the objective compound (195 mg) was obtained as colorless crystals from methyl 3-[2-chloro-4-[(thiophen-2-yl)methyl]oxybenzyl]-2-methyl-3H-imidazo[4,5-b]pyridine-5-carboxylate (243 mg).

$^1$H-NMR (DMSO-d$_6$): 2.50(3H, s), 5.29(2H, s), 5.55(2H, br s), 6.57(1H, d, J=8 Hz), 6.90(1H, dd, J=8, 2 Hz), 7.02(1H, dd, J=5, 3 Hz), 7.19(1H, d, J=3 Hz), 7.27(1H, d, J=2 Hz), 7.55(1H, d, J=5 Hz), 8.00(1H, d, J=8 Hz), 8.12(1H, d, J=8 Hz)

Mass (ESI):m/z 412(M−1).

Preparation Example 145-6

3-[2-Chloro-4-[(thiophen-3-yl)methyl]oxybenzyl]-2-methyl-3H-imidazo[4,5-b]pyridine-5-carboxylic acid In the same manner as in Preparation Example 4-7, the objective compound (118 mg) was obtained as colorless crystals from methyl 3-[2-chloro-4-[(thiophen-3-yl)methyl]oxybenzyl]-2-methyl-3H-imidazo[4,5-b]pyridine-5-carboxylate (140 mg).

$^1$H-NMR (DMSO-d$_6$) 2.50(3H, s), 5.09(2H, s), 5.55(2H, s), 6.57(1H, d, J=8 Hz), 6.89(1H, dd, J=8, 2 Hz), 7.15(1H, d, J=5 Hz), 7.24(1H, d, J=2 Hz), 7.51–7.60(2H, m), 8.00(1H, d, J=8 Hz), 8.12(1H, d, J=8 Hz)

Mass (ESI):m/z 412(M−1).

Preparation Example 145-7

3-[2-Chloro-4-(cyclopentylmethyloxy)benzyl]-2-methyl-3H-imidazo[4,5-b]pyridine-5-carboxylic acid In the same manner as in Preparation Example 4-7, the objective compound (72 mg) was obtained as colorless crystals from methyl 3-[2-chloro-4-(cyclopentylmethyloxy)benzyl]-2-methyl-3H-imidazo[4,5-b]pyridine-5-carboxylate (82 mg).

¹H-NMR (CDCl₃): 1.24–1.41(2H, m), 1.50–1.70(3H, m), 1.75–1.90(2H, m), 2.33(1H, m), 2.64(3H, s), 3.79(2H, d, J=5 Hz), 5.53(2H, s), 6,67(1H, d, J=8 Hz), 6.70(1H, dd, J=8, 2 Hz), 7.00(1H, d, J=2 Hz), 8.15(1H, d, J=8 Hz), 8.21(1H, d, J=8 Hz)

Mass (ESI):m/z 398(M−1).

Preparation Example 146-1

Methyl 3-(2-chloro-4-iodobenzyl)-2,7-dimethyl-3H-imidazo[4,5-b]pyridine-5-carboxylate In the same manner as in Preparation Example 14-2, the objective compound (6.42 g) was obtained as a white powder from methyl 2,7-dimethylimidazo[4,5-b]pyridine-5-carboxylate (3.00 g) and 2-chloro-4-iodobenzyl bromide (7.00 g).

¹H-NMR (DMSO): 2.51(3H, s), 2.63(3H, s), 3.85(3H, s), 5.50(2H, s), 6.30(1H, d, J=8 Hz), 7.58(1H, d, J=8 Hz), 7.88(1H, s), 7.95(1H, s)

Preparation Example 146-2

Methyl 3-(2-chloro-4-(2-phenylethynyl)benzyl)-2,7-dimethyl-3H-imidazo[4,5-b]pyridine-5carboxylate In the same manner as in the following Preparation Example 147-1, the objective compound (386 mg) was obtained as a white powder from methyl 3-(2-chloro-4-iodobenzyl)-2,7-dimethyl-3H-imidazo[4,5-b]pyridine-5-carboxylate (400 mg).

¹H-NMR (CDCl₃): 2.54(3H, s), 2.75(3H, s), 3.99(3H, s), 5.67(2H, s), 6.56(1H, d, J=8 Hz), 7.21–7.72(7H), 7.99(1H, s)

Preparation Example 146-3

3-(2-Chloro-4-(2-phenylethynyl)benzyl)-2,7-dimethyl-3H-imidazo[4,5-b]pyridine-5-carboxylic acid In the same manner as in Preparation Example 4-7, the objective compound (348 mg) was obtained as a white powder from methyl 3-(2-chloro-4-(2-phenylethynyl)benzyl)-2,7-dimethyl-3H-imidazo[4,5-b]pyridine-5-carboxylate (383 mg).

¹H-NMR (DMSO): 2.48(3H, s), 2.61(3H, s), 5.60(2H, s), 6.52(1H, d, J=8 Hz), 7.34–7.60(6H), 7.76(1H, s), 7.85(1H, s)

Preparation Example 147-1

Methyl 3-(2-chloro-4-(1-hexynyl)benzyl)-2-methyl-3H-imidazo[4,5-b]pyridine-5-carboxylate A mixture of methyl 3-(2-chloro-4-iodobenzyl)-2-methyl-3H-imidazo[4,5-b]pyridine-5-carboxylate (2.31 g), 1-hexyne (2.00 g), palladium(II) acetate (235 mg), triphenylphosphine (549 mg), copper(I) iodide (297 mg), tributylamine (2.91 g) and dimethylformamide (23 ml) was stirred under an nitrogen atmosphere at 60° C. for 1.5 hr. The reaction mixture was partitioned between ethyl acetate and water. The organic layer was washed with water, dried and concentrated under reduced pressure. The residue was purified by silica gel column chromatography (hexane:ethyl acetate=1:1-1:2) to give the objective compound (1.44 g) as a gray powder.

¹H-NMR (CDCl₃): 0.94(3H, t, J=6 Hz), 1.38–1.64(4H), 2.38(2H, t, J=6Hz), 2.52(3H, s), 4.00(3H, s), 5.65(2H, s), 6.52(1H, d, J=8 Hz), 7.10(1H, d, J=8 Hz), 7.47(1H, s), 8.06(1H, d, J=8 Hz), 8.15(1H, d, J=8 Hz)

Also, a by-product, methyl 3-(4-chloro-2-(1-hexynyl)benzyl)-2-methyl-3H-imidazo[4,5-b]pyridine-5-carboxylate (288 mg) was obtained as a gray powder.

¹H-NMR (CDCl₃): 0.94(3H, t, J=6 Hz), 1.35–1.65(4H), 2.38(2H, t, J=6Hz),2.65(3H, s), 4.00(3H,s), 5.67(2H, s), 6.56(1H, d, J=8 Hz), 7.12(1H, d, J=8 Hz), 7.47(1H, s), 8.15(1H, d, J=8 Hz), 8.35(1H, d, J=8 Hz)

Preparation Example 147-2

3-(2-Chloro-4-(1-hexynyl)benzyl)-2-methyl-3H-imidazo[4,5-b]pyridine-5-carboxylic acid In the same manner as in Preparation Example 4-7, the objective compound (872 mg) was obtained as a gray powder from methyl 3-(2-chloro-4-(1-hexynyl)benzyl)-2-methyl-3H-imidazo[4,5-b]pyridine-5-carboxylate (1.0 g).

¹H-NMR (DMSO): 0.86(3H, t, J=6 Hz), 1.30–1.54(4H), 2.38(2H, t, J=6 Hz), 2.48(3H, s), 5.58(2H, s), 6.47(1H, d, J=8 Hz), 7.20(1H, d, J=8 Hz), 7.54(1H, s), 7.98(1H, d, J=8 Hz),8.11(1H, d, J=8 Hz)

Preparation Example 148-1

Methyl 3-(2-chloro-4-cyclohexylmethyloxybenzyl)-2,7-dimethyl-3H-imidazo[4,5-b]pyridine-5-carboxylate In the same manner as in Preparation Example 102-5, the objective compound (954 mg) was obtained as colorless crystals from methyl 2,7-dimethyl-3H-imidazo[4,5-b]pyridine-5-carboxylate (513 mg) and 2-chloro-1-chloromethyl-4-cyclohexylmethyloxybenzene (751 mg).

¹H-NMR (CDCl₃): 0.95–1.34(5H, m), 1.68–1.84(6H, m), 2.52(3H, s), 2.72(3H, s), 3.68(2H, d, J=7 Hz), 3.99(3H, s), 5.59(2H, s), 6.56–6.63(2H, m), 6.95(1H, d, J=1 Hz), 7.96 (1H, s)

MS (ESI):m/z 442(M+1)

Preparation Example 148-2

3-(2-Chloro-4-cyclohexylmethyloxybenzyl)-2,7-dimethyl-3H-imidazo[4,5-b]pyridine-5-carboxylic acid In the same manner as in Preparation Example 4-7, the objective compound (797 mg) was obtained as colorless crystals from methyl 3-(2-chloro-4-cyclohexylmethyloxybenzyl)-2,7-dimethyl-3H-imidazo[4,5-b]pyridine-5-carboxylate (900 mg).

¹H-NMR (CDCl₃): 0.97–1.35(5H, m), 1.67–1.85(6H, m), 2.63(3H, s), 2.75(3H, s), 3.71(2H, d, J=7 Hz), 5.50(2H, s), 6.58–6.70(2H, m), 6.98–6.99(1H, m), 8.03(1H, s)

MS (ESI):m/z 426(M−1)

Preparation Example 149-1

Methyl 3-(2-chloro-4-vinylbenzyl)-2,7-dimethyl-3H-imidazo[4,5-b]pyridine-5-carboxylate In the same manner as in Preparation Example 11-1, the objective compound (786 mg) was obtained as colorless crystals from methyl 3-(4-bromo-2-chlorobenzyl)-2,7-dimethyl-3H-imidazo[4,5-b]pyridine-5-carboxylate (1.10 g) and vinyl tributyltin (853 mg).

¹H-NMR (CDCl₃): 2.53(3H, s), 2.73(3H, s), 3.98(3H, s), 5.29(1H, d, J=10 Hz), 5.64(2H, s), 5.72(1H, d, J=15 Hz), 6.54(1H, d, J=7 Hz), 6.60(1H, dd, J=10, 15 Hz), 7.11(1H, d, J=8 Hz), 7.47(1H, d, J=1 Hz), 7.97(1H, s)

MS (ESI):m/z 356(M+1)

Preparation Example 149-2

Methyl 3-(2-chloro-4-ethylbenzyl)-2,7-dimethyl-3H-imidazo[4,5-b]pyridine-5-carboxylate In the same manner as in Preparation Example 67-4, the objective compound (502 mg) was obtained as colorless crystals from methyl 3-(2-chloro-4-vinylbenzyl)-2,7-dimethyl-3H-imidazo[4,5-b]pyridine-5-carboxylate (750 mg).

$^1$H-NMR (CDCl$_3$): 1.19(3H, t, J=7 Hz), 2.53(3H, s), 2.59(2H, q, J=7 Hz), 2.73(3H, s), 3.98(3H, s), 5.63(2H, s), 6.50(1H, d, J=8 Hz), 6.91(1H, d, J=8 Hz), 7.26(1H, overlapped with CDCl$_3$), 7.97(1H, s)

MS (ESI):m/z 358(M+1)

Preparation Example 149-3

3-(2-Chloro-4-ethylbenzyl)-2,7-dimethyl-3H-imidazo[4,5-b]pyridine-5-carboxylic acid In the same manner as in Preparation Example 4-7, the objective compound (385 mg) was obtained as colorless crystals from methyl 3-(2-chloro-4-ethylbenzyl)-2,7-dimethyl-3H-imidazo[4,5-b]pyridine-5-carboxylate (490 mg).

$^1$H-NMR (CDCl$_3$): 1.21(3H, t, J=7 Hz), 2.61(2H, q, J=7 Hz), 2.62(3H, s), 3.76(3H, s), 5.54(2H, s), 6.54(1H, d, J=8 Hz), 6.96(1H, d, J=8 Hz), 7.30(1H,s), 8.04(1H,s)

MS (ESI):m/z 342(M−1)

Preparation Example 150-1

Methyl 3-(2-chloro-4-trifluoromethylbenzyl)-2,7-dimethyl-3H-imidazo[4,5-b]pyridine-5-carboxylate In the same manner as in Preparation Example 102-5, the objective compound (819 mg) was obtained as pale-yellow crystals from methyl 2,7-dimethyl-3H-imidazo[4,5-b]pyridine-5-carboxylate (467 mg) and 1-bromomethyl-2-chloro-4-trifluoromethylbenzene.

$^1$H-NMR (CDCl$_3$): 2.54(3H, s), 2.74(3H, s), 3.98(3H, s), 5.69(2H, s), 6.68(1H, d, J=8 Hz), 7.35(1H, br d, J=8 Hz), 7.70(1H, br s), 7.98(1H, s)

Preparation Example 150-2

3-(2-Chloro-4-trifluoromethylbenzyl)-2,7-dimethyl-3H-imidazo[4,5-b]pyridine-5-carboxylic acid In the same manner as in Preparation Example 4-7, the objective compound (566 mg) was obtained as pale-yellow crystals from methyl 3-(2-chloro-4-trifluoromethylbenzyl)-2,7-dimethyl-3H-imidazo[4,5-b]pyridine-5-carboxylate (767 mg).

$^1$H-NMR (CDCl$_3$): 2.61(3H, s), 2.78(3H, s), 5.61(2H, s), 6.67(1H, d, J=8 Hz), 7.41(1H, br d, J=8 Hz), 7.76(1H, br s), 8.08(1H, s)

Preparation Example 151-1

Methyl 3-(2-chloro-4-ethoxybenzyl)-2,7-dimethyl-3H-imidazo[4,5-b]pyridine-5-carboxylate In the same manner as in Preparation Example 102-5, the objective compound (631 mg) was obtained as beige crystals from methyl 2,7-dimethyl-3H-imidazo[4,5-b]pyridine-5-carboxylate (430 mg) and 1-bromomethyl-2-chloro-4-ethoxybenzene.

$^1$H-NMR (CDCl$_3$): 1.38(3H, t, J=7 Hz), 2.53(3H, s), 2.73(3H, s), 3.97(2H, q, J=7 Hz), 3.99(3H, s), 5.59(2H, s), 6.59(1H, d, J=8 Hz), 6.64(1H, dd, J=8,2 Hz), 6.95(1H, d, J=2 Hz), 7.97(1H, s)

Preparation Example 151-2

3-(2-Chloro-4-ethoxybenzyl)-2,7-dimethyl-3H-imidazo[4,5-b]pyridine-5-carboxylic acid In the same manner as in Preparation Example 4-7, the objective compound (530 mg) was obtained as colorless crystals from methyl 3-(2-chloro-4-ethoxybenzyl)-2,7-dimethyl-3H-imidazo[4,5-b]pyridine-5-carboxylate (621 mg).

$^1$H-NMR (CDCl$_3$): 1.40(3H, t, J=7 Hz), 2.62(3H, s), 2.75(3H, s), 3.99(2H, q, J=7 Hz), 5.51(2H, s), 6.61(1H, d, J=8 Hz), 6.68(1H, dd, J=8,2 Hz), 6.99(1H, d, J=2 Hz), 8.03(1H, s)

Preparation Example 152-1

2-(2-Chloro-4-phenylbenzyl)-6-(methoxycarbonyl)-3-methyl-2H-indazole

A mixture of 6-(methoxycarbonyl)-3-methyl-1H-indazole (1.90 g), 2-chloro-4-phenylbenzyl bromide (3.37 g), potassium carbonate (2.76 g), ethyl acetate(10 ml) and water (5 ml) was stirred for 14 hr at 70° C. Hexane and water were added, and the precipitated solid was collected by filtration and washed with a mixed solvent of ethyl acetate and hexane (2/3). This was dried under reduced pressure to give the objective compound (1.02 g).

$^1$H-NMR (CDCl$_3$, δ ppm): 2.61(3H, s), 3.96(3H, s), 5.77(2H, s), 6.66(1H, d, J=8.1 Hz), 7.33–7.39(2H, m), 7.43(2H, t, J=7.6 Hz), 7.51(2H, d, J=7.5 Hz), 7.62–7.66(2H, m), 7.69(1H, d, J=8.8 Hz), 8.49(1H, s)

Preparation Example 152-2

6-Carboxy-2-(2-chloro-4-phenylbenzyl)-3-methyl-2H-indazole

In the same manner as in Preparation Example 39-6, the objective compound (1.80 g) was obtained from 2-(2-chloro-4-phenylbenzyl)-6-(methoxycarbonyl)-3-methyl-2H-indazole (3.00 g). This was immediately used for the following reaction.

Preparation Example 153-1

Methyl 3-(2-chloro-4-methylthiobenzyl)-2,7-dimethyl-3H-imidazo[4,5-b]pyridine-5-carboxylate In the same manner as in Preparation Example 102-5, the objective compound (904 mg) was obtained as colorless crystals from methyl 2,7-dimethyl-3H-imidazo[4,5-b]pyridine-5-carboxylate (648 mg) and 2-chloro-1-chloromethyl-4-methylthiobenzene (767 mg).

$^1$H-NMR (CDCl$_3$): 2.45(3H, s), 2.53(3H, s), 2.73(3H, s), 3.99(3H, s), 5.61(2H, s), 6.53(1H, d, J=8 Hz), 6.95(1H, dd, J=1, 8 Hz), 7.28(1H, d, J=1 Hz), 7.97(1H, s),

MS (ESI):m/z 376(M+1)

Preparation Example 153-2

3-(2-Chloro-4-methylthiobenzyl)-2,7-dimethyl-3H-imidazo[4,5-b]pyridine-5-carboxylic acid In the same manner as in Preparation Example 4-7, the objective compound (797 mg) was obtained as colorless crystals from methyl 3-(2-chloro-4-methylthiobenzyl)-2,7-dimethyl-3H-imidazo[4,5-b]pyridine-5-carboxylate (879 mg).

$^1$H-NMR (CDCl$_3$): 2.46(3H, s), 2.62(3H, s), 2.76(3H, s), 5.52(2H, s), 6.55(1H, d, J=8 Hz), 6.99(1H, dd, J=1, 8 Hz), 7.30(1H, d, J=1 Hz), 8.04(1H, s)

MS (ESI):m/z 360(M−1)

Example 1

3-(3,4-Dichlorobenzyl)-2-methylbenzo[b]thiophene-5-carboxylic acid (160 mg) was dissolved in dry dimethylformamide (2 ml). Carbonyl-diimidazole (111 mg) was added and the mixture was stirred at room temperature for 1 hr. To the reaction mixture were added n-pentanesulfonamide (108 mg) and 1,8-diazabicyclo[5,4,0]undec-7-ene (122 mg) and the mixture was stirred at 100° C. for 1.5 hr. The reaction mixture was cooled in ice, and the pH thereof was adjusted to pH 4 with 1N hydrochloric acid. The mixture was partitioned between ethyl acetate and water. The organic layer was washed twice with water, dried over magnesium sulfate and concentrated to dryness under reduced pressure. The residue was eluted by silica gel column chromatography (hexane:ethyl acetate=1:1). The resulting residue was crystallized from hexane-ethyl acetate to give 3-(3,4-dichlorobenzyl)-2-methyl-5-(n-pentanesulfonylcarbamoyl)benzo[b]thiophene (118 mg).

$^1$H-NMR(CDCl$_3$): 0.88(3H, t, J=7 Hz), 1.20–1.51(4H, m), 1.75–1.93(2H, m), 2.52(3H, s), 3.47–3.63(2H, m), 4.16 (2H, s), 6.98(1H, d, J=8 Hz), 7.16(1H, s), 7.32(1H, d, J=8 Hz), 7.70(1H, d, J=8 Hz), 7.89(1H, d, J=8 Hz), 8.01(1H, s), 8.59(1H, br s)

Mass(ESI): m/e 482(M−H)$^-$ mp: 159–160° C.

Example 2

In the same manner as in Example 1, 3-(2,3-dichlorobenzyl)-2-methyl-5-(n-pentanesulfonylcarbamoyl)benzo[b]thiophene was obtained from 3-(2,3-dichlorobenzyl)-2-methylbenzo[b]thiophene-5-carboxylic acid.

$^1$H-NMR(CDCl$_3$): 0.86(3H, t, J=7 Hz), 1.22–1.49(4H, m), 1.74–1.92(2H, m) 2.48(3H, s), 3.48–3.61(2H, m), 4.27 (2H, s), 6.56(1H, d, J=8 Hz), 6.99(1H, t, J=8 Hz), 7.33(1H, d, J=8 Hz), 7.71(1H, d, J=8 Hz), 7.89(1H, d, J=8 Hz), 7.90(1H, s), 8.45(1H, br s)

Mass(ESI): m/e 482(M−H)$^-$ mp: 196–197° C.

Example 3

In the same manner as in Example 1, 3-(2,5-dichlorobenzyl)-2-methyl-5-(n-pentanesulfonylcarbamoyl)benzo[b]thiophene was obtained from 3-(2,5-dichlorobenzyl)-2-methylbenzo[b]thiophene-5-carboxylic acid.

$^1$H-NMR(CDCl$_3$): 0.88(3H, t, J=7 Hz), 1.22–1.48(4H, m), 1.76–1.92(2H, m), 2.49(3H, s), 3.48–3.62(2H, m), 4.21 (2H, s), 6.61(1H, d, J=2 Hz), 7.13(1H, dd, J=8 and 2 Hz), 7.37(1H, d, J=8 Hz), 7.72(1H, dd, J=8 and 2 Hz), 7.90(1H, d, J=8 Hz), 7.93(1H, d, J=2 Hz), 8.52(1H, br s)

Mass(ESI): m/e 482(M−H)$^-$ mp: 147–148° C.

Example 4-1

In the same manner as in Example 1, 3-(2,4-dichlorobenzyl)-2-methyl-5-(n-pentanesulfonylcarbamoyl)pyrazolo[1,5-a]pyridine (103 mg) was obtained as a yellow-green powder from 3-(2,4-dichlorobenzyl)-2-methylpyrazolo[1,5-a]pyridine-5-carboxylic acid (102 mg).

$^1$H-NMR(CDCl$_3$): 0.88(3H, t, J=7 Hz), 1.24–1.46(4H, m), 1.84(2H, m), 2.38(3H, s), 3.54(2H, t, J=7 Hz), 4.13(2H, s), 6.79(1H, d, J=8 Hz), 7.09(1H, t, J=8 Hz), 7.43(1H, s), 7.87(1H, s), 8.43(1H, d, J=8 Hz).

Example 4-2

In the same manner as in Example 1, 3-(2,4-dichlorobenzyl)-2-methyl-5-(benzenesulfonylcarbamoyl)pyrazolo[1,5-a]pyridine (139 mg) was obtained as a yellow powder from 3-(2,4-dichlorobenzyl)-2-methylpyrazolo[1,5-a]pyridine-5-carboxylic acid (101 mg).

$^1$H-NMR(CDCl$_3$): 2.32(3H, s), 4.06(2H, s), 6.70(1H, d, J=8 Hz), 7.00–7.07(2H), 7.37(1H, s), 7.56(2H, t, J=8 Hz), 7.67(1H, t, J=8 Hz), 7.84(1H, s), 8.12(2H, d, J=8 Hz), 8.37(1H, d, J=8 Hz).

Example 5-1

In the same manner as in Example 1, 1-(2,4-dichlorobenzyl)-2-methyl-7-(n-pentanesulfonylcarbamoyl)indolizine (208 mg) was obtained as a yellow-green powder from 1-(2,4-dichlorobenzyl)-2-methylindolizine-7-carboxylic acid (200 mg).

$^1$H-NMR(CDCl$_3$): 0.88(3H, t, J=6 Hz), 1.23–1.45(4H), 1.82(2H, m), 2.14(3H, s), 3.53(2H, t, J=6 Hz), 4.17(2H, s), 6.68(1H, d, J=8 Hz), 6.86(1H, d, J=8 Hz), 7.06(1H, d, J=8 Hz), 7.42(1H, s), 7.82(1H, s), 7.86(1H, d, J=8 Hz), 8.51(1H, s).

Example 5-2

In the same manner as in Example 1, 7-(n-butanesulfonylcarbamoyl)-1-(2,4-dichlorobenzyl)-2-methylindolizine (151 mg) was obtained as a yellow-green powder from 1-(2,4-dichlorobenzyl)-2-methylindolizine-7-carboxylic acid (200 mg).

$^1$H-NMR(CDCl$_3$): 0.92(3H, t, J=6 Hz), 1.46(2H, m), 1.82(2H, m), 2.14(3H, s), 3.53(2H, t, J=6 Hz), 4.17(2H, s), 6.68(1H, d, J=8 Hz), 6.86(1H, d, J=8 Hz), 7.06(1H, d, J=8 Hz), 7.41(1H, s), 7.82(1H, s), 7.86(1H, d, J=8 Hz), 8.54(1H, s).

Example 5-3

In the same manner as in Example 1, 1-(2,4-dichlorobenzyl)-2-methyl-7-(benzenesulfonylcarbamoyl)indolizine (208 mg) was obtained as a yellow-green powder from 1-(2,4-dichlorobenzyl)-2-methylindolizine-7-carboxylic acid (200 mg).

$^1$H-NMR(DMSO-d$_6$): 2.14(3H, s), 4.18(2H, s), 6.76(1H, d, J=8 Hz), 6.82(1H, d, J=8 Hz), 7.28(1H, d, J=8 Hz), 7.55–7.75(5H), 7.98(1H, d, J=8 Hz), 8.18(1H, d, J=8 Hz), 8.26(1H, s).

Example 6

In the same manner as in Example 1, 2-methyl-7-(n-pentanesulfonylcarbamoyl)-1-(4-phenylbenzyl)indolizine (329 mg) was obtained as a yellow-green powder from 2-methyl-1-(4-phenylbenzyl)indolizine-7-carboxylic acid (300 mg).

$^1$H-NMR(DMSO-d$_6$): 0.83(3H, t, J=6 Hz), 1.29(2H, m), 1.38(2H, m), 1.70(2H, m), 2.17(3H, s), 3.52(2H, t, J=6 Hz), 4.18(2H, s), 6.92(1H, d, J=8 Hz), 6.82(1H, d, J=8 Hz), 7.27(2H, d, J=8 Hz), 7.33(1H, t, J=8 Hz), 7.43(2H, t, J=8 Hz), 7.52–7.64(5H), 8.20(1H, d, J=8 Hz), 8.44(1H, s).

Example 7

In the same manner as in Example 1, 6-(n-pentanesulfonylcarbamoyl)-4-(4-phenylbenzyl)quinoline (68 mg) was obtained as a white powder from 4-(4-phenylbenzyl)quinoline-6-carboxylic acid (81 mg).

$^1$H-NMR(DMSO-d$_6$): 0.80 (3H, t, J=7 Hz), 1.19–1.42 (4H, br), 1.64–1.76 (2H, br), 3.50 (2H, br), 4.61 (2H, s), 7.30–7.47 (6H, m), 7.64 (4H, m), 8.10 (1H, d, J=8 Hz), 8.22 (1H, d, J=8 Hz), 8.89–8.96 (2H, m).

Example 8-1

In the same manner as in Example 1, 3-(2,4-dichlorobenzyl)-2-methyl-5-(n-pentanesulfonylcarbamoyl)-3H-imidazo[4,5-b]pyridine(98 mg) was obtained as a pale-yellow crystal from 3-(2,4-dichlorobenzyl)-2-methyl-3H-imidazo[4,5-b]pyridine-5-carboxylic acid (115 mg).

$^1$H-NMR(CDCl$_3$): 0.89(3H, t, J=7 Hz), 1.28–1.50(4H, m), 1.80–1.95(2H, m), 2.66(3H, s), 3.49–3.59(2H, m), 5.55 (2H, s), 6.69(1H, d, J=8 Hz), 7.20(1H, dd, J=8, 1 Hz), 7.51(1H, d, J=1 Hz), 8.17(1H, d, J=8 Hz), 8.22(1H, d, J=8 Hz), 9.77(1H, br s).

MASS(ESI): m/z 467(M−1)

mp 174–175° C.

Example 8-2

In the same manner as in Example 1, 5-(n-butanesulfonylcarbamoyl)-3-(2,4-dichlorobenzyl)-2-methyl-3H-imidazo[4,5-b]pyridine (132 mg) was obtained as colorless crystals from 3-(2,4-dichlorobenzyl)-2-methyl-3H-imidazo[4,5-b]pyridine-5-carboxylic acid (150 mg).

$^1$H-NMR(CDCl$_3$): 0.94(3H, t, J=7 Hz), 1.42–1.54(2H, m), 1.80–1.92(2H, m), 2.62(3H, s), 3.51–3.60(2H, m), 5.54 (2H, s), 6.67(1H, d, J=8 Hz), 7.19(1H, dd, J=8, 2 Hz), 7.51(1H, d, J=2 Hz), 8.13(1H, d, J=8 Hz), 8.21(1H, d, J=8 Hz), 9.79(1H, br s).

MASS(ESI): m/z 455(M+1)

mp 153–154° C.

Example 8-3

In the same manner as in Example 1, 5-benzenesulfonylcarbamoyl-3-(2,4-dichlorobenzyl)-2-methyl-3H-imidazo[4,5-b]pyridine (128 mg) was obtained as pale-yellow crystals from 3-(2,4-dichlorobenzyl)-2-methyl-3H-imidazo[4,5-b]pyridine-5-carboxylic acid (150 mg).

$^1$H-NMR(CDCl$_3$) 2.61(3H, s), 5.55(2H, s), 6.69(1H, d, J=8 Hz), 7.21(1H, dd, J=8, 2 Hz), 7.50–7.68(4H, m), 8.05 (1H, d, J=8 Hz), 8.10(1H, d, J=8 Hz), 8.17(2H, br d, J=8 Hz).

MASS(ESI): m/z 475(M+1)

mp 193–194° C.

Example 9

In the same manner as in Example 1, 3-(2-chloro-4-phenylbenzyl)-2-methyl-5-(n-pentanesulfonylcarbamoyl)-3H-imidazo[4,5-b]pyridine (34 mg) was obtained as pale-yellow crystals from 3-(2-chloro-4-phenylbenzyl)-2-methyl-3H-imidazo[4,5-b]pyridine-5-carboxylic acid (160 mg).

$^1$H-NMR(CDCl$_3$): 0.86(3H, t, J=7 Hz), 1.22–1.45(4H, m), 1.79–1.91(2H, m), 2.69(3H, s), 3.50–3.58(2H, m), 5.62 (2H, s), 6.80(1H, d, J=8 Hz), 7.34–7.48(4H, m), 7.50–7.58 (2H, m), 7.70(1H, br s), 8.14(1H, d, J=8 Hz), 8.20(1H, d, J=8 Hz), 9.83(1H, br s).

MASS(ESI): m/z 509(M−1)

mp 155–156° C.

Example 10

In the same manner as in Example 1, 3-(1-bromo-2-naphthyl)methyl-2-methyl-5-(n-pentanesulfonylcarbamoyl)-3H-imidazo[4,5-b]pyridine (40 mg) was obtained as pale-yellow crystals from 3-(1-bromo-2-naphthyl)methyl-2-methyl-3H-imidazo[4,5-b]pyridine-5-carboxylic acid (140 mg).

$^1$H-NMR(CDCl$_3$): 0.84(3H, t, J=7 Hz), 1.22–1.44(4H, m), 1.74–1.87(2H, m), 2.65(3H, s), 3.46–3.55(2H, m), 5.81 (2H, s), 6.81(1H, d, J=8 Hz), 7.57(1H, br t, J=8 Hz), 7.65(1H, br t, J=8 Hz), 7.74(1H, br d, J=8 Hz), 7.82(1H, br d, J=8 Hz), 8.13(1H, d, J=8 Hz), 8.20(1H, d, J=8 Hz), 8.39(1H, br d, J=8 Hz), 9.81(1H, br s).

MASS(ESI): m/z 527(M−1)

mp 200–201° C.

Example 11

In the same manner as in Example 1, 2-methyl-5-(n-pentanesulfonylcarbamoyl)-3-(4-phenylbenzyl)-3H-imidazo[4,5-b]pyridine (120 mg) was obtained as colorless crystals from 2-methyl-3-(4-phenylbenzyl)-3H-imidazo[4,5-b]pyridine-5-carboxylic acid (130 mg).

$^1$H-NMR(CDCl$_3$): 0.89(3H, t, J=7 Hz), 1.26–1.50(4H, m), 1.83–1.98(2H, m), 2.65(3H, s), 3.52–3.62(2H, m), 5.55 (2H, s), 7.20(2H, d, J=8 Hz), 7.30–7.48(3H, m), 7.51–7.61 (4H, m), 8.15(1H, d, J=8 Hz), 8.24(1H, d, J=8 Hz), 9.92(1H, br s).

MASS(ESI): m/z 475(M−1)

mp 170–171° C.

Example 12-1

In the same manner as in Example 1, 3-(4-bromo-2-chlorobenzyl)-2-methyl-5-(n-pentanesulfonylcarbamoyl)-3H-imidazo[4,5-b]pyridine (66 mg) was obtained as a white powder from 3-(4-bromo-2-chlorobenzyl)-2-methyl-3H-imidazo[4,5-b]pyridine-5-carboxylic acid (70 mg).

$^1$H-NMR(CDCl$_3$): 0.88(3H, t, J=7 Hz), 1.24–1.50(4H, m), 1.78–1.94(2H, m), 2.63(3H, s), 3.49–3.60(2H, m), 5.53 (2H, s), 6.60(1H, dd, J=8 and 2 Hz), 7.34(1H, d, J=8 Hz), 7.66(1H, d, J=2 Hz), 8.14(1H, d, J=8 Hz), 8.22(1H, d, J=8 Hz), 9.76(1H, br s)

Mass(ESI): m/e 511, 513 (M−H)$^-$ mp: 183–184° C.

Example 12-2

In the same manner as in Example 1, 3-(4-bromo-2-chlorobenzyl)-5-(n-butanesulfonylcarbamoyl)-2-methyl-3H-imidazo[4,5-b]pyridine (63 mg) was obtained as a white powder from 3-(4-bromo-2-chlorobenzyl)-2-methyl-3H-imidazo[4,5-b]pyridine-5-carboxylic acid (70 mg).

$^1$H-NMR(CDCl$_3$): 0.93(3H, t, J=7 Hz), 1.39–1.56(2H, m), 1.78–1.92(2H, m), 2.64(3H, s), 3.50–3.61(2H, m), 5.53 (2H, s), 6.61(1H, d, J=8 Hz), 7.34(1H, dd, J=8 and 2 Hz), 7.67(1H, d, J=2 Hz), 8.15(1H, d, J=8 Hz), 8.22(1H, d, J=8 Hz), 9.78(1H, br s)

Mass(ESI): m/e 497, 499 (M−H)$^-$ mp: 165–166° C.

Example 12-3

In the same manner as in Example 1, 5-(benzenesulfonylcarbamoyl)-3-(4-bromo-2- chlorobenzyl)-2-methyl-3H-imidazo[4,5-b]pyridine (68 mg) was obtained as a white powder from 3-(4-bromo-2-chlorobenzyl)-2-methyl-3H-imidazo[4,5-b]pyridine-5-carboxylic acid (70 mg).

$^1$H-NMR(CDCl$_3$): 2.62(3H, s), 5.53(2H, s), 6.65(1H, d, J=8 Hz), 7.37(1H, dd, J=8 and 2 Hz), 7.50–7.65(3H, m), 7.68(1H, d, J=2 Hz), 8.09(2H, s), 8.17(2H, m), 1H, br s)

Mass(ESI): m/e 517, 519 (M–H)$^-$ mp: 193–194° C.

Example 13-1

In the same manner as in Example 1, 3-(2-bromo-4-chlorobenzyl)-2-methyl-5-(n-pentanesulfonylcarbamoyl)-3H-imidazo[4,5-b]pyridine (70 mg) was obtained as a pale-yellow powder from 3-(2-bromo-4-chlorobenzyl)-2-methyl-3H-imidazo[4,5-b]pyridine-5-carboxylic acid (81 mg).

$^1$H-NMR(CDCl$_3$): 0.89(3H, t, J=7 Hz), 1.22–1.50(4H, m), 1.79–1.95(2H, m) 2.68(3H, s), 3.48–3.61(2H, m), 5.54 (2H, s), 6.62(1H, d, J=8 Hz), 7.23(1H, dd, J=8 and 2 Hz), 7.70(1H, d, J=2 Hz), 8.13–8.29(2H, m), 9.76(1H, br s)

Mass(ESI): m/e 511, 513 (M–H)$^-$ mp: 167–168° C.

Example 13-2

In the same manner as in Example 1, 5-(benzenesulfonylcarbamoyl)-3-(2bromo-4-chlorobenzyl)-2-methyl-3H-imidazo[4,5-b]pyridine (56 mg) was obtained as a pale-yellow powder from 3-(2-bromo-4-chlorobenzyl)-2-methyl-3H-imidazo[4,5-b]pyridine-5-carboxylic acid (79 mg).

$^1$H-NMR(CDCl$_3$): 2.67(3H, s), 5.56(2H, s), 6.67(1H, d, J=8 Hz), 7.27(1H, dd, J=8 and 2 Hz), 7.50–7.68(3H, m), 7.71(1H, d, J=2 Hz), 8.07–8.22(4H, m), 10.06(1H, br s)Mass (ESI): m/e 517, 519 (M–H)$^-$ mp: 189–190° C.

Example 13-3

In the same manner as in Example 1, 3-(2-bromo-4-chlorobenzyl)-5-(n-butanesulfonylcarbamoyl)-2-methyl-3H-imidazo[4,5-b]pyridine (27 mg) was obtained as a pale-yellow powder from 3-(2-bromo-4-chlorobenzyl)-2-methyl-3H-imidazo[4,5-b]pyridine-5-carboxylic acid (41 mg).

$^1$H-NMR(CDCl$_3$): 0.94(3H, t, J=7 Hz), 1.38–1.56(2H, m), 1.76–1.93(2H, m), 2.67(3H, s), 3.48–3.62(2H, m), 5.55 (2H, s), 6.62(1H, d, J=8 Hz), 7.24(1H, dd, J=8 and 2 Hz), 7.69(1H, d, J=2 Hz), 8.13–8.29(2H, m), 9.74(1H, br s)

Mass(ESI): m/e 497, 499 (M–H)$^-$ mp: 145–146° C.

Example 14-1

In the same manner as in Example 1, 3-(2,4-dichlorobenryl)-2-methyl-6-(n-pentanesulfonylcarbamoyl) indolizine (90 mg) was obtained as a yellow-green powder from 3-(2,4-dichlorobenzyl)-2-methylindolizie-6-carboxylic acid (150 mg).

$^1$H-NMR(DMSO-d$_6$): 0.82(3H, t, J=7 Hz), 1.21–1.35(4H, m), 1.53–1.62(2H, m), 2.19(3H, s), 3.12–3.18(2H, m), 4.32 (2H, s), 6.37(1H, s), 6.48(1H, d, J=8 Hz), 7.15(1H, d, J=8 Hz), 7.25(1H, dd, J=8 and 3 Hz), 7.32(1H, d, J=8 Hz), 7.66(1H, d, J=3 Hz), 8.34(1H, s)

Mass(ESI): m/e 465(M–H)$^-$

Example 14-2

In the same manner as in Example 1, 3-(2,4-dichlorobenzyl)-2-methyl-6-(n-butanesulfonylcarbamoyl) indolizine (88 mg) was obtained as a yellow-green powder from 3-(2,4-dichlorobenzyl)-2-methylindolizine-6-carboxylic acid (150 mg).

$^1$H-NMR(DMSO-d$_6$): 0.82(3H, t, J=8 Hz), 1.29–1.40(2H, m), 1.52–1.62(2H, m), 2.19(3H, s), 3.14–3.20(2H, m), 4.32 (2H, s), 6.38(1H, s), 6.50(1H, d, J=8 Hz), 7.15(1H, d, J=8 Hz), 7.25(1H, dd, J=8 and 3 Hz), 7.32(1H, d, J=8 Hz), 7.66(1H, d, J=3 Hz), 8.37(1H, s)

Mass(ESI): m/e 451(M–H)$^-$

Example 14-3

In the same manner as in Example 1, 3-(2,4-dichlorobenzyl)-2-methyl-6-(benzenesulfonylcarbamoyl) indolizine (68 mg) was obtained as a yellow-green powder from 3-(2,4-dichlorobenzyl)-2-methylindolizine-6-carboxylic acid (150 mg).

$^1$H-NMR(DMSO-d$_6$): 2.18(3H, s), 4.30(2H, s), 6.33(1H, s), 6.47(1H, d, J=8 Hz), 7.11(1H, d, J=8 Hz), 7.22–7.30(2H, m), 7.40–7.43(3H, m), 7.66(1H, s), 7.80–7.83(2H, m), 8.28 (1H, s)

Mass(ESI): m/e 471(M–H)$^-$

Example 15

In the same manner as in Example 1, 3-(2,4-dichlorobenzyl)-2-ethyl-7-methyl-5-(n-pentanesulfonylcarbamoyl)-3H-imidazo[4,5-b]pyridine (211 mg) was obtained as colorless crystals from 3-(2,4-dichlorobenzyl)-2-ethyl-7-methyl-3H-imidazo[4,5-b] pyridine-5-carboxylic acid (177 mg).

$^1$H-NMR(CDCl$_3$): 0.89(3H, t, J=7 Hz), 1.29–1.50(7H, m), 1.80–1.95(2H, m), 2.76(3H, s), 2.87(2H, q, J=7 Hz), 3.50–3.60(2H, m), 5.53(2H, s), 6.67(1H, d, J=8 Hz), 7.15 (1H, dd, J=8, 2 Hz), 7.51(1H, d, J=2 Hz), 8.02(1H, s), 9.82(1H, br s).

Mass(ESI): m/e 495(M–1)

mp: 178–180° C.

Example 16

In the same manner as in Example 1, 2-ethyl-7-methyl-5-(n-pentanesulfonylcarbamoyl)-3-(4-phenylbenzyl)-3H-imidazo[4,5-b]pyridine (138 mg) was obtained as colorless crystals from 2-ethyl-7-methyl-3-(4-phenylbenzyl)-3H-imidazo[4,5-b]pyridine-5-carboxylic acid (120 mg).

$^1$H-NMR(CDCl$_3$): 0.87(3H, t, J=7 Hz), 1.25–1.47(7H, m), 1.80–1.92(2H, m), 2.75(3H, s), 2.90(2H, q, J=7 Hz), 3.50–3.59(2H, m), 5.52(2H, s), 7.15(1H, d, J=8 Hz), 7.28–7.47(3H, m), 7.50–7.59(4H, m), 8.02(1H, s).

Mass(ESI): m/e 503(M–1)

mp: 210–211° C.

Example 17-1

In the same manner as in Example 1, 3-(2,4-dichlorobenzyl)-2-methyl-5-(benzenesulfonylcarbamoyl) benzo[b]thiophene (117 mg) was obtained as white crystals from 3-(2,4-dichlorobenzyl1)-2-methylbenzo[b]thiophene-5-carboxylic acid (150 mg).

$^1$H-NMR(DMSO-d$_6$): 2.42(3H, s), 4.25(2H, s), 6.71(1H, d, J=8 Hz), 7.24(1H, dd, J=2, 8 Hz), 7.60–7.78(5H, m), 7.97–8.04(3H, m), 8.11(1H, s)

Mass(ESI): 488(M–H)$^-$

Example 17-2

In the same manner as in Example 1, 3-(2,4-dichlorobenzyl)-2-methyl-5-(n-butanesulfonylcarbamoyl)

benzo[b]thiophene (117 mg) was obtained as white crystals from 3-(2,4-dichlorobenzyl)-2-methylbenzo[b]thiophene-5-carboxylic acid (150 mg).

$^1$H-NMR(DMSO-d$_6$): 0.83(3H, t, J=8 Hz), 1.33–1.46(2H, m), 1.60–1.71(2H, m), 2.45(3H, s), 3.50(2H, t, J=8 Hz), 4.27(2H, s), 6.73(1H, d, J=8 Hz), 7.25(1H, dd, J=2, 8 Hz), 7.67(1H, d, J=2 Hz), 7.83(1H, d, J=8 Hz), 8.08(1H, d, J=8 Hz), 8.18(1H, s)

Mass(ESI): 468(M−H)$^-$

Example 18

In the same manner as in Example 1, 3-(4-phenylbenzyl)-2-methyl-5-(n-pentanesulfonylcarbamoyl)benzo[b]thiophene (87 mg) was obtained as white crystals from 3-(4-phenylbenzyl)-2-methylbenzo[b]thiophene-5-carboxylic acid (112 mg).

$^1$H-NMR(DMSO-d$_6$): 0.79(3H, t, J=7 Hz), 1.20–1.38(4H, m), 1.60–1.70(2H, m), 2.57(3H, s), 3.33–3.40(2H, m), 4.26(2H, s), 7.25–7.34(3H, m), 7.41(2H, t, J=8 Hz), 7.54–7.60(4H, m), 7.83(1H, d, J=8 Hz), 7.97(1H, d, J=8 Hz), 8.33(1H, s)

Mass(ESI): 490(M−H)$^-$

Example 19

In the same manner as in Example 1, 3-(2-chlorobenzyl)-2-methyl-5-(n-pentanesulfonylcarbamoyl)benzo[b]thiophene (131 mg) was obtained as white crystals from 3-(2-chlorobenzyl)-2-methylbenzo[b]thiophene-5-carboxylic acid (120 mg).

$^1$H-NMR(DMSO-d$_6$): 0.80(3H, t, J=7 Hz), 1.20–1.42(4H, m), 1.63–1.73(2H, m), 2.47(3H, s), 3.48(2H, t, J=8 Hz), 4.29(2H, s), 6.74(1H, d, J=7 Hz), 7.17(1H, t, J=7 Hz), 7.24(1H, t, J=7 Hz), 7.51(1H, d, J=8 Hz), 7.83(1H, d, J=8 Hz), 8.06(1H, d, J=8 Hz), 8.18(1H, s)

Mass(ESI): 448(M−H)$^-$

Example 20

In the same manner as in Example 1, 3-(4-bromo-2-chlorobenzyl)-2-methyl-5-(n-pentanesulfonylcarbamoyl)benzo[b]thiophene (137 mg) was obtained as white crystals from 3-(4-bromo-2 chlorobenzyl)-2-methylbenzo[b]thiophene-5-carboxylic acid (212 mg).

$^1$H-NMR(DMSO-$_6$): 0.82(3H, t, J=7 Hz), 1.20–1.41(4H, m), 1.63–1.73(2H, m), 2.45(3H, s), 3.50(2H, t, J=8 Hz), 4.24(2H, s), 6.67(1H, d, J=8 Hz), 7.37(1H, dd, J=2, 8 Hz), 7.78(1H, s), 7.82(1H, d, J=8 Hz), 8.08(1H, d, J=8 Hz), 8.17(1H, s)

Mass(ESI): 528(M−H)$^-$

Example 21

In the same manner as in Example 1, 3-(2,4-dichloro-5-fluorobenzyl)-2-methyl-5-(n-pentanesulfonylcarbamoyl)benzo[b]thiophene (204 mg) was obtained as white crystals from 3-(2,4-dichloro-5-fluorobenzyl)-2-methylbenzo[b]thiophene-5-carboxylic acid (222 mg).

$^1$H-NMR(DMSO-d$_6$): 0.80(3H, t, J=8 Hz), 1.22–1.40(4H, m), 1.03–1.73(2H, m), 2.48(3H, s), 3.51(2H, t, J=8 Hz), 4.27(2H, s), 6.70(1H, d, J=8 Hz), 7.83(1H, d, J=8 Hz), 7.88(1H, d, J=7 Hz), 8.08(1H, d, J=8 Hz), 8.17(1H, s)

Mass(ESI): 500(M−H)$^-$

Example 22

In the same manner as in Example 1, 3-((3-chlorobenzo[b]thiophen-2-yl)methyl)-2-methyl-5-(n-pentanesulfonylcarbamoyl)benzo[b]thiophene (176 mg) was obtained as white crystals from 3-((3-chlorobenzo[b]thiophen-2-yl)methyl)-2-methylbenzo[b]thiophene-5-carboxylic acid (218 mg).

$^1$H-NMR(DMSO-d$_6$): 0.79(3H, t, J=7 Hz), 1.18–1.40(4H, m), 1.63–1.74(2H, m), 2.60(3H, s), 3.50(2H, t, J=8 Hz), 4.56(2H, s), 7.38(1H, t, J=7 Hz), 7.47(1H, t, J=7 Hz), 7.76(1H, d, J=8 Hz), 7.83(1H, d, J=8 Hz), 7.86(1H, d, J=7 Hz), 8.08(1H, d, J=8 Hz), 8.41(1H, s)

Mass(ESI): 504(M−H)$^-$

Example 23

In the same manner as in Example 1, 3-(1-bromonaphthalen-2-yl)methyl-2-methyl-5-(n-pentanesulfonylcarbamoyl)benzo[b]thiophene (207 mg) was obtained as white crystals from 3-(1-bromonaphthalen-2-yl)methyl-2-methylbenzo[b]thiophene-5-carboxylic acid (200 mg).

$^1$H-NMR(DMSO-d$_6$): 0.75(3H, t, J=7 Hz), 1.15–1.37(4H, m), 1.60–1.70(2H, m), 2.48(3H, s), 3.47(2H, t, J=8 Hz), 4.54(2H, s), 6.91(1H, d, J=8 Hz), 7.60(1H, t, J=7 Hz), 7.72(1H, t, J=7 Hz), 7.80(1H, d, J=8 Hz), 7.83(1H, d, J=8 Hz), 7.91(1H, d, J=8 Hz), 8.096(1H, d, J=8 Hz), 8.26(1H, s), 8.30(1H, d, J=8 Hz)

Mass(ESI): 544(M−H)$^-$

Example 24-1

In the same manner as in Example 1, 1-(2,4-dichlorobenzyl)-2-methyl-5-(n-pentanesulfonylcarbamoyl)-1H-thieno[2,3-d]imidazole (112 mg) was obtained as a pale-yellow powder from 1-(2,4-dichlorobenzyl)-2-methyl-1H-thieno[2,3-d]imidazole-5-carboxylic acid (120 mg).

$^1$H-NMR(CDCl$_3$): 0.88(3H, t, 7 Hz), 1.27–1.47(4H, m), 1.78–1.88(2H, m), 2.57(3H, s), 3.50–3.54(2H, m), 5.30(2H, s), 6.69(1H, d, 8 Hz), 7.18(1H, d, 8 Hz), 7.38(1H, s), 7.46(1H, d, 2 Hz)

Mass(ESI): 472(M−H)$^-$

Example 24-2

In the same manner as in Example 1, 3-(2,4-dichlorobenzyl)-2-methyl-5-(n-pentanesulfonylcarbamoyl)-3H-thieno[2,3-d]imidazole (77 mg) was obtained as a white powder from 3-(2,4-dichlorobenzyl)-2-methyl-3H-thieno[2,3-d]imidazole-5-carboxylic acid (90 mg).

$^1$H-NMR(CDCl$_3$): 0.87(3H, t, 8 Hz), 1.25–1.43(4H, m), 1.68–1.85(2H, m), 2.60(3H, s), 3.32–3.53(2H, m), 5.27(2H, s), 7.38(2H, s), 7.48(1H, s), 7.84(1H, s)

Mass(ESI): 472(M−H)$^-$

Example 25

In the same manner as in Example 1, 1-(2,4-dichlorobenzyl)-2-methyl-6-(n-pentanesulfonylcarbamoyl)-1H-imidazo[4,5-b]pyridine (151 mg) was obtained as colorless crystals from 1-(2,4-dichlorobenzyl)-2-methyl-1H-imidazo[4,5-b]pyridine-6-carboxylic acid (150 mg).

$^1$H-NMR (DMSO-d$_6$): 0.82(3H, t, J=7 Hz), 1.20–1.42 (4H, m), 1.64–1.78(2H, m), 2.55(3H, s), 3.51(2H, t, J=7 Hz), 5.65(2H, s), 6.60(1H, d, J=8 Hz), 7.34(1H, dd, J=8, 2 Hz), 7.76(1H,d, J=2 Hz), 8.44(1H, s), 8.90(1H, s).

MASS(ESI): m/z 467(M−1)

mp 103–106° C.

Example 26-1

In the same manner as in Example 1, 3-(2,4-dichlorobenzyl)-2-methyl-5-(n-pentanesulfonylcarbamoyl)

pyrrolo[3,2-b]pyridine (87 mg) was obtained as colorless crystals from 3-(2,4-dichlorobenzyl)-2-methylpyrrolo[3,2-b]pyridine-5-carboxylic acid (100 mg).

$^1$H-NMR(CDCl$_3$): 0.88(3H, t, J=7 Hz), 1.27–1.49(4H, m), 1.81–1.95(2H, m), 2.50(3H, s), 3.49–3.57(2H, m), 4.19 (2H, s), 7.14–7.22(2H, m), 7.39(1H, s), 7.65(1H, d, J=8 Hz), 7.94(1H, d, J=8 Hz), 8.32(1H, br s).

MASS(ESI): m/z 466(M−1)

mp 147–148° C.

Example 26-2

In the same manner as in Example 1, 3-(2,4-dichlorobenzyl)-2-methyl-5-(benzenesulfonylcarbamoyl)pyrrolo[3,2-b]pyridine (70 mg) was obtained as colorless crystals from 3-(2,4-dichlorobenzyl)-2-methylpyrrolo[3,2-b]pyridine-5-carboxylic acid (60 mg).

$^1$H-NMR(DMSO-d$_6$): 2.39(3H, s), 4.25(2H, s), 7.29(1H, d, J=8 Hz), 7.33(1H, d, J=8 Hz), 7.58–7.74(5H, m), 7.79(1H, d, J=8 Hz), 8.04(1H, d, J=8 Hz).

MASS(ESI): m/z 472(M−1)

mp >250° C.

Example 27

In the same manner as in Example 1, 3-(4-chloro-2-methoxybenzyl)-2-methyl-5-(n-pentanesulfonylcarbamoyl)-3H-imidazo[4,5-b]pyridine (47 mg) was obtained as colorless crystals from 3-(4-chloro-2-methoxybenzyl)-2-methyl-3H-imidazo[4,5-b]pyridine-5carboxylic acid (50 mg).

$^1$H-NMR (CDCl$_3$): 0.89(3H, t, J=7 Hz), 1.28–1.50(4H, m), 1.81–1.94(2H, m), 2.78(3H, s), 3.51–3.60(2H, m), 3.86 (3H, s), 5.47(2H, s), 6.84–6.95(3H, m), 8.19(1H, d, J=8 Hz), 8.23(1H, d, J=8 Hz), 9.79(1H, br s).

MASS(ESI):m/z 463(M−1)

mp 168–170° C.

Example 28-1

In the same manner as in Example 1, 3-(4-chloro-2-methylbenzyl)-2-methyl-5-(n-pentanesulfonylcarbamoyl)-3H-imidazo[4,5-b]pyridine (73 mg) was obtained as colorless crystals from 3-(4-chloro-2-methylbenzyl)-2-methyl-3H-imidazo[4,5-b]pyridine-5-carboxylic acid (70 mg).

$^1$H-NMR(CDCl$_3$): 0.89(3H, t, J=7 Hz), 1.28–1.49(4H, m), 1.79–1.95(2H, m), 2.42(3H, s), 2.69(3H, s), 3.51–3.60 (2H, m), 5.45(2H, s), 6.43(1H, d, J=8 Hz), 7.09(1H, br d, J=8 Hz), 7.28(1H, br s), 8.17(1H, d, J=8 Hz), 8.23(1H, d, J=8 Hz), 9.78(1H, br s).

MASS(ESI): m/z 447(M−1)

mp 155–157° C.

Example 28-2

In the same manner as in Example 1, 5-benzenesulfonylcarbamoyl-3-(4-chloro-2-methylbenzyl)-2-methyl-3H-imidazo[4,5-b]pyridine (85 mg) was obtained as colorless crystals from 3-(4-chloro-2-methylbenzyl)-2-methyl-3H-imidazo[4,5-b]pyridine-5-carboxylic acid (70 mg).

$^1$H-NMR(DMSO-d$_6$): 2.40(3H, s), 2.42(3H, s), 5.72(2H, s), 6.60(1H, d, J=8 Hz), 7.17(1H, br d, J=8 Hz), 7.39(1H, br s), 7.59–7.77(3H, m), 7.89(1H, d, J=8 Hz), 8.02(2H, br d, J=8 Hz), 8.12(1H, d, J=8 Hz).

MASS(ESI): m/z 453(M−1)

mp 235–237° C.

Example 29-1

In the same manner as in Example 1, 5-benzenesulfonylcarbamoyl-3-(2-chloro-4-phenylbenzyl)-2-methyl-3H-imidazo[4,5-b]pyridine (78 mg) was obtained as colorless crystals from 3-(2-chloro-4-phenylbenzyl)-2-methyl-3H-imidazo[4,5-b]pyridine-5-carboxylic acid (130 mg).

$^1$H-NMR(CDCl$_3$): 2.40(3H, s), 2.76(3H, s), 5.64(2H, s), 6.95(1H, d, J=8 Hz) 7.38–7.52(4H, m), 7.59(2H, d, J=8 Hz), 7.82(1H, br s), 8.07–8.16(3H, m).

MASS(ESI): m/z 515(M−1)

mp 204–214° C. [broad]

Example 29-2

In the same manner as in Example 1, 5-(n-butanesulfonylcarbamoyl)-3-(2-chloro-4-phenylbenzyl)-2-methyl-3H-imidazo[4,5-b]pyridine (106 mg) was obtained as colorless crystals from 3-(2-chloro-4-phenylbenzyl)-2-methyl-3H-imidazo[4,5-b]pyridine-5-carboxylic acid (130 mg).

$^1$H-NMR(CDCl$_3$): 0.90(3H, t, J=7 Hz), 1.38–1.51(2H, m), 1.77–1.89(2H, m), 2.75(3H, s), 3.50–3.59(2H, m), 5.65 (2H, s), 6.89(1H, brd, J=8 Hz), 7.35–7.49(4H, m), 7.55(2H, br d, J=8 Hz), 7.71(1H, br s), 8.20(1H, d, J=8 Hz), 8.26(1H, d, J=8 Hz), 9.80(1H, br s).

MASS(ESI): m/z 495(M−1)

mp 199–200° C.

Example 30-1

In the same manner as in Example 1, 3-(2,4-dichlorobenzyl)-2-methyl-5-(1-n-pentanesulfonylcarbamoyl)benzo[b]furan (260 mg, 62%) was obtained as colorless crystals from 5-carboxy-3-(2,4-dichlorobenzyl)-2-methylbenzo[b]furan (300 mg, 0.90 mmol), N,N'-carbonyldiimidazole (218 mg, 1.34 mmol), 1,8-diazabicyclo[5,4,0]-7-undecene (DBU, 204 mg, 1.34 mmol) and 1-n-pentanesulfonamide (203 mg, 1.34 mmol).

mp: 149.1–149.9° C.

$^1$H-NMR(DMSO-d$_6$, δ ppm): 11.94(1H, br s), 7.99(1H, d, J=1.3 Hz), 7.82(1H, dd, J=1.7 and 8.6 Hz), 7.63(1H, d, J=2.1 Hz), 7.61(1H, d, J=8.6 Hz), 7.33(1H, dd, J=2.1 and 8.3 Hz), 7.19(1H, d, J=8.4 Hz), 4.09(2H, s), 3.48(2H, m), 2.41(3H, s), 1.67(2H, quint., J=7.7 Hz), 1.35(2H, quint., J=7.4 Hz), 1.25(2H, sextet, J=7.6 Hz), 0.80(3H, t, J=7.3 Hz).

IR(Nujol): 1687 cm$^{-1}$

Mass(FD): m/e 467(M).

Example 30-2

In the same manner as in Example 1, 5-(benzenesulfonylcarbamoyl)-3-(2,4-dichlorobenzyl)-2-methylbenzo[b]furan (168 mg, 54 %) was obtained as colorless crystals from 5-carboxy-3-(2,4-dichlorobenzyl)-2-methylbenzo-[b]furan (220 mg, 0.66 mmol), N,N'-carbonyldiimidazole (160 mg, 0.66 mmol), DBU (150 mg, 0.98 mmol) and benzenesulfonamide (155 mg, 0.98 mmol).

mp: 208.5–209.5° C.

$^1$H-NMR(DMSO-d$_6$, δ ppm): 12.45(1H, br s), 7.97(2H, m), 7.93(1H, d, J=1.6 Hz), 7.75(1H, dd, J=1.8 and 8.6 Hz), 7.70(1H, m), 7.62(3H, m), 7.57(1H, d, J=8.6 Hz), 7.32(1H, dd, J=2.1 and 8.3 Hz), 7.16(1H, d, J=8.4 Hz), 4.06(2H, s), 2.38(3H, s).

IR(Nujol): 1702 cm$^{-1}$.

Mass(FD): m/e 473(M).

Example 31-1

In the same manner as in Example 1, 2-(2,4-dichlorobenzyl)-3,5-dimethyl-7-(1-n-pentanesulfonylcarbamoyl)benzo[b]furan (0.26 g) was obtained as white crystals from 7-carboxy-2-(2,4-dichlorobenzyl)-3,5-dimethylbenzo[b]furan (0.30 g), N,N'-carbonyldiimidazole (0.28 g), DBU (0.26 ml) and 1-n-pentanesulfonamide (0.26 g).

$^1$H-NMR(DMSO-d$_6$, δ ppm): 0.79(3H, t, J=7.2 Hz), 1.20–1.28(2H, m), 1.30–1.37(2H, m), 1.64–1.71(2H, m), 2.19(3H, s), 2.42(3H, s), 3.46(2H, t, J=7.7 Hz), 4.24(2H, s), 7.33–7.38(2H, m), 7.46(1H, s), 7.59(1H, s), 7.62(1H, s), 11.57(1H, br s).

IR(Nujol): 1691 cm$^{-1}$.
Mass(FD): m/e 481(M)
mp: 164–165.5° C.

Example 31-2

In the same manner as in Example 1, 7-(benzenesulfonylcarbamoyl)-2-(2,4-dichlorobenzyl)-3,5-dimethylbenzo[b]furan (0.29 g) was obtained as white crystals from 7-carboxy-2-(2,4-dichlorobenzyl)-3,5-dimethylbenzo-[b]furan (0.30 g), N,N'-carbonyldiimidazole (0.28 g), DBU (0.26 ml) and benzenesulfonamide (0.27 g).

$^1$H-NMR(DMSO-d$_6$,δ ppm): 2.17(3H, s), 2.38(3H, s), 4.23(2H, s), 7.33–7.41(3H, m), 7.56(1H, s), 7.58–7.64(3H, m), 7.72(1H, t, J=7.3 Hz), 7.97–8.00(2H, m), 12.09(1H, br s).

IR(Nujol): 1703 cm$^{-1}$.
Mass(FD): m/e 487(M)
mp: 214–215° C.

Example 32-1

In the same manner as in Example 1, 2-methyl-5-(1-n-pentanesulfonyl-carbamoyl)-3-(4-phenylbenzyl)benzo[b]furan (0.25 g) was obtained as white crystals from 5-carboxy-2-methyl-3-(4-phenylbenzyl)benzo[b]furan (0.30 g), N,N'-carbonyldiimidazole (0.28 g), DBU (0.26 ml) and 1-n-pentane-sulfonamide (0.27 g).

$^1$H-NMR(DMSO-d$_6$, δ ppm): 0.79(3H, t, J=7.3 Hz), 1.21–1.26(2H, m), 1.34(2H, quint., J=7.5 Hz), 1.67(2H, quint., J=7.7 Hz), 2.51(3H, s), 3.49(2H, t, J=7.7 Hz), 4.07 (2H, s), 7.32(1H, t, J=7.3 Hz), 7.36 (2H, d, J=8.1 Hz), 7.42(2H, t, J=7.6 Hz), 7.57–7.62(5H, m), 7.82(1H, dd, J=8.6 and 1.6 Hz), 8.15(1H, s), 11.99(1H, br s).

IR(Nujol): 1687 cm$^{-1}$
mp: 130.5–132° C.

Example 32-2

In the same manner as in Example 1, 5-(1-benzenesulfonylcarbamoyl)-2-methyl-3-(4-phenylbenzyl)benzo[b]furan (0.31 g) was obtained as white crystals from 5-carboxy-2-methyl-3-(4-phenylbenzyl)benzo[b]furan (0.30 g), N,N'-carbonyldiimidazole (0.28 g), DBU (0.26 ml) and benzenesulfonamide (0.28 g).

$^1$H-NMR(DMSO-d$_6$, δ ppm): 2.49(3H, s), 4.04(2H, s), 7.30–7.35(3H, m), 7.42(2H, t, J=7.7 Hz), 7.54–7.63(7H, m), 7.69(1H, t, J=7.4 Hz), 7.74(1H, dd, J=8.6 and 1.8 Hz), 7.97–7.99(2H, m), 8.07(1H, d, J=1.7 Hz), 12.5(1H, br s).

IR(Nujol): 1686 cm$^{-1}$
mp: 188–190° C.

Example 33-1

In the same manner as in Example 1, 5-(1-n-butanesulfonyl-carbamoyl)-3-(2,4-dichlorobenzyl)-2-methylbenzo[b]furan (0.26 g) was obtained as white crystals from 5-carboxy-3-(2,4-dichlorobenzyl)-2-methylbenzo[b]furan (0.335 g), N,N'-carbonyldiimidazole (0.32 g), DBU (0.30 ml) and 1-n-butanesulfonamide (0.275 g).

$^1$H-NMR(DMSO-d$_6$, δ ppm): 0.85(3H, t, J=7.4 Hz), 1.34–1.42(2H, m), 1.61–1.68(2H, m), 2.42(3H, s), 3.49(2H, t, J=8.3 Hz), 4.09(2H, s), 7.19(1H, d, J=8.4 Hz), 7.33 (1H, dd, J=8.3 and 2.2 Hz), 7.61(1H, d, J=8.6 Hz), 7.64(1H, d, J=2.3 Hz), 7.83(1H, dd, J=8.7 and 1.9 Hz), 7.99(1H, d, J=1.7 Hz), 11.95(1H, brs).

IR(Nujol): 1698 cm$^{-1}$
mp: 145.5–146° C.

Example 33-2

In the same manner as in Example 1, 3-(2,4-dichlorobenzyl)-5-(1-n-hexanesulfonylcarbamoyl)-2-methylbenzo[b]furan (0.22 g) was obtained as white crystals from 5-carboxy-3-(2,4-dichlorobenzyl)-2-methylbenzo[b]furan (0.335 g), N,N'-carbonyldiimidazole (0.32 g), DBU (0.30 ml) and 1-n-hexanesulfonamide (0.33 g).

$^1$H-NMR(DMSO-d$_6$, δ ppm): 0.81(3H, t, J=7.1 Hz), 1.18–1.23(4H, m), 1.33–1.40(2H, m), 1.62–1.68(2H, m), 2.42(3H, s), 3.48(2H, t, J=7.7 Hz), 4.09(2H, s), 7.14(1H, d, J=8.4 Hz), 7.33 (1H, dd, J=8.3 and 2.2 Hz), 7.61(1H, d, J=8.6 Hz) 7.64(1H, d, J=2.2 Hz), 7.82(1H, dd, J=8.7 and 1.8 Hz), 7.99(1H, d, J=1.7 Hz), 11.94(1H, brs).

IR(Nujol): 1688 cm$^{-1}$
mp: 139–139.5° C.

Example 33-3

In the same manner as in Example 1, 3-(2,4-dichlorobenzyl)-2-methyl-5-(2-thiophenesulfonylcarbamoyl)benzo[b]furan (0.33 g) was obtained as white crystals from 5-carboxy-3-(2,4-dichlorobenzyl)-2-methylbenzo[b]furan (0.335 g), N,N'-carbonyldiimidazole (0.32 g), DBU (0.30 ml) and 2-thiophene-sulfonamide (0.33 g).

$^1$H-NMR(DMSO-d$_6$, δ ppm): 2.39(3H, s), 4.07(2H, s), 7.15–7.21(2H, m), 7.32(1H, dd, J=8.3 and 2.3 Hz), 7.58(1H, d, J=8.6 Hz), 7.63(1H, d, J=2.2 Hz), 7.78(1H, dd, J=8.6 and 1.8 Hz), 7.83(1H, dd, J=3.7 and 1.1 Hz), 7.95(1H, d, J=1.6 Hz), 8.02(1H, dd, J=4.9 and 0.9 Hz), 12.57(1H, brs).

IR(Nujol): 1703 cm$^{-1}$
mp: 198–199° C.

Example 34-1

In the same manner as in Example 1, 3-(2,4-dichlorobenzyl)-2-ethyl-5-(1-n-pentanesulfonylcarbamoyl)benzo[b]furan (0.15 g) was obtained as white crystals from 5-carboxy-3-(2,4-dichlorobenzyl)-2-ethylbenzo[b]furan (0.30 g), N,N'-carbonyldiimidazole (0.26 g), DBU (0.26 ml) and 1-n-pentanesulfonamide (0.26 g).

$^1$H-NMR(DMSO-d$_6$, δ ppm): 0.81(3H, t, J=7.3 Hz), 1.18 (3H, t, J=7.5 Hz), 1.22–1.38(4H, m), 1.65–1.71(2H, m), 2.77(2H, quartet, J=7.5 Hz), 3.48(2H, t, J=7.8 Hz), 4.10(2H, s), 7.14(1H, d, J=8.4 Hz), 7.33 (1H, dd, J=8.4 and 2.1 Hz), 7.63–7.66(2 Hz, m), 7.83(1H, dd, J=8.8 and 1.9 Hz), 8.01 (1H, s), 11.95(1H, brs).

IR(Nujol): 1689 cm$^{-1}$
mp: 131–132° C.

Example 34-2

In the same manner as in Example 1, 5-(benzenesulfonylcarbamoyl)-3-(2,4-dichlorobenzyl)-2- ethylbenzo[b]furan (0.26 g) was obtained as white crystals from 5-carboxy-3-(2,4-dichlorobenzyl)-2-ethylbenzo[b]furan (0.335 g), N,N'-carbonyldiimidazole (0.32 g), DBU (0.30 ml) and benzenesulfonamide (0.33 g).

$^1$H-NMR(DMSO-$d_6$, δ ppm): 1.16(3H, t, J=7.6 Hz), 2.75 (2H, quartet, J=7.6 Hz), 4.08(2H, s), 7.12(1H, d, J=8.4 Hz), 7.32(1H, d, J=8.4 Hz), 7.58–7.65(4H, m), 7.70(1H, t, J=7.0 Hz), 7.76(1H, d, J=8.8 Hz), 7.96–7.99(3H, m), 12.46(1H, brs).

IR(Nujol): 1704 cm$^{-1}$ mp: 196–197° C.

Example 34-3

In the same manner as in Example 1, 3-(2,4-dichlorobenzyl)-2-ethyl-5-(8-quinolinesulfonylcarbamoyl)benzo[b]furan (0.39 g) was obtained as white crystals from 5-carboxy-3-(2,4-dichlorobenzyl)-2-ethylbenzo[b]furan (0.335 g), N,N'-carbonyldiimidazole (0.32 g), DBU (0.30 ml) and 8-quinolinesulfonamide (0.33 g).

$^1$H-NMR(DMSO-$d_6$, δ ppm): 1.15(3H, t, J=7.5 Hz), 2.74 (2H, quartet, J=7.5 Hz), 4.08(2H, s), 7.03(1H, d, J=8.4 Hz), 7.29(1H, dd, J=8.3 and 2.1 Hz), 7.54(1H, d, J=8.7 Hz), 7.59(1H, dd, J=8.3 and 4.3 Hz), 7.68(1H, d, J=2.1 Hz), 7.71(1H, dd, J=8.7 and 1.6 Hz), 7.82(1H, t, J=7.8 Hz), 7.99(1H, s), 8.34(1H, d, J=8.0 Hz), 8.51(2H, d, J=7.8 Hz), 8.80 (1H, dd, J=4.2 and 1.6 Hz).

IR(Nujol): 1687 cm$^{-1}$ m p: 232–233° C.

Example 34-4

In the same manner as in Example 1,3-(2,4-dichlorobenzyl)-2-ethyl-5-((2-methylbenzene)sulfonylcarbamoyl)benzo[b]furan (0.24 g) was obtained as white crystal from 5-carboxy-3-(2,4-dichlorobenzyl)-2-ethylbenzo[b]furan (0.36 g), N,N'-carbonyldiimidazole (0.32 g), DBU (0.30 ml) and 2-methylbenzenesulfonamide (0.31 g).

$^1$H-NMR(DMSO-$d_6$, δ ppm): 1.17(3H, t, J=7.6 Hz), 2.57 (3H, s), 2.77(2H, quartet, J=7.5 Hz), 4.08(2H, s), 7.15(1H, d, J=8.4 Hz), 7.32(1H, dd, J=8.3 and 2.2 Hz), 7.38(1H, d, J=7.6 Hz), 7.44(1H, t, J=7.4 Hz), 7.57(1H, t, J=7.5 Hz), 7.60(1H, d, J=8.7 Hz), 7.63(1H, d, J=2.2 Hz), 7.77(1H, d, J=8.8 Hz), 7.97(1H, s), 8.02(1H, d, J=8.1 Hz), 12.56(1H, brs).

IR(Nujol: 1694 cm$^{-1}$ mp: 182–183° C.

Example 35-1

In the same manner as in Example 1, 3-(2,4-dichlorobenzyl)-5-(1-n-pentanesulfonylcarbamoyl)-2-propylbenzo[b]furan (0.36 g) was obtained as white crystal from 5-carboxy-3-(2,4-dichlorobenzyl)-2-propylbenzo[b]furan (0.36 g), N,N'-carbonyldiimidazole (0.32 g), DBU (0.30 ml) and 1-n-pentanesulfonamide (0.30 g).

$^1$H-NMR(CDCl$_3$, δ ppm): 0.39(3H, t, J=7.3 Hz), 0.95(3H, t, J=7.4 Hz), 1.30–1.47(4H, m), 1.70–1.79(2H, m), 1.83–1.90(2H, m), 2.77(2H, t, J=7.5 Hz), 3.75(2H, t, J=8.0 Hz), 4.05(2H, s), 6.88(1H, d, J=8.4 Hz), 7.10 (1H, dd, J=8.3 and 2.2 Hz), 7.45(1H, d, J=2.1 Hz), 7.50(1H, d, J=8.6 Hz), 7.71(1H, dd, J=8.6 and 1.9 Hz), 7.76(1H, d, J=1.6 Hz), 8.36(1H, brs).

IR(Nujol): 1693 cm$^{-1}$ mp: 114–115° C.

Example 35-2

In the same manner as in Example 1, 5-(benzenesulfonylcarbamoyl)-3-(2,4-dichlorobenzyl)-2-propylbenzo[b]furan (0.24 g) was obtained as white crystal from 5-carboxy-3-(2,4-dichlorobenzyl)-2-propylbenzo[b]furan (0.36 g), N,N'-carbonyldiimidazole (0.32 g), DBU (0.30 ml) and benzenesulfonamide (0.31 g).

$^1$H-NMR(DMSO-$d_6$, δ ppm): 0.83(3H, t, J=7.4 Hz), 1.56–1.63(2H, m), 2.70(2H, t, J=7.4 Hz), 4.08(2H, s), 7.10 (1H, d, J=8.4 Hz), 7.32(1H, dd, J=8.3 and 2.2 Hz), 7.58–7.65 (4H, m), 7.70(1H, t, J=7.4 Hz), 7.76(1H, dd, J=8.7 and 1.8 Hz), 7.96–7.99(3H, m), 12.45(1H, brs)

IR(Nujol): 1708 cm$^{-1}$ mp: 197–197.5° C.

Example 35-3

In the same manner as in Example 1, 3-(2,4-dichlorobenzyl)-5-(2-nitrobenzenesulfonylcarbamoyl)-2-propylbenzo[b]furan (0.18 g) was obtained as white crystals from 5-carboxy-3-(2,4-dichlorobenzyl)-2-propylbenzo[b]furan (0.36 g), N,N'-carbonyldiimidazole (0.32 g), DBU (0.30 ml) and 2-nitrobenzenesulfonamide (0.40 g).

$^1$H-NMR(DMSO-$d_6$, δ ppm): 0.84(3H, t, J=7.3 Hz), 1.58–1.64(2H, m), 2.72(2H, t, J=7.4 Hz), 4.09(2H, s), 7.13 (1H, d, J=8.3 Hz), 7.32(1H, dd, J=8.4 and 2.2 Hz) 7.61(1H, d, J=8.7 Hz), 7.63(1H, d, J=2.0 Hz), 7.82(1H, dd, J=8.8 and 1.3 Hz), 7.85–8.00(3H, m), 8.03(1H, s), 8.22–8.25(1H, m)

IR(Nujol): 1692 cm$^{-1}$ mp: 219–220° C.

Example 36

In the same manner as in Example 1, 3-(2,4-dichlorobenzyl)-5-(1-n-pentanesulfonylcarbamoyl)benzo[b]furan (0.24 g) was obtained as a yellow oil from 5-carboxy-3-(2,4-dichlorobenzyl)benzo[b]furan (0.26 g), N,N'-carbonyldiimidazole (0.26 g), DBU (0.24 ml) and n-pentanesulfonamide (0.24 g).

hu 1H-NMR(DMSO-$d_6$, δ ppm): 0.82(3H, t, J=7.2 Hz), 1.23–1.40(4H, m), 1.65–1.73(2H, m), 3.51(2H, t, J=7.7 Hz), 4.14(2H, s), 7.37(2H, s), 7.64(1H, s), 7.70(1H, d, J=8.8 Hz), 7.87(1H, s), 7.91(1H, dd, J=8.7 and 1.6 Hz), 8.269(1H, s), 12.01(1H, brs)

IR(Nujol): 1682 cm$^{-1}$

Example 37

In the same manner as in Example 1, 5-carboxy-3-(2,4-dichlorobenzyl)-2-methylbenzo[b]thiophene (440 mg, 1.25 mmol) was suspended in dimethylformamide and carbonyldiimidazole (305 mg, 1.88 mmol) was added, which was followed by stirring at room temperature for 1 hr. Then, 1-n-pentanesulfonamide (284 mg, 1.88 mmol) and DBU (286 mg, 1.88 mmol) were added and the mixture was refluxed under heating at 100° C. for 15 hr. The reaction mixture was concentrated under reduced pressure and water and 3N hydrochloric acid were added to acidify the mixture. The mixture was extracted with ethyl acetate, and the organic layer was washed with saturated brine and dried over anhydrous magnesium sulfate. The desiccant was filtered off and the filtrate was concentrated under reduced pressure. The residual oil was purified by silica gel column chromatography (eluent: hexane/ethyl acetate=3/2) and recrystallized from 2-propanol-n-hexane to give 3-(2,4-dichlorobenzyl)-2-methyl-5-(1-n-pentanesulfonylcarbamoyl)benzo[b]thiophene (410 mg, 68%) as colorless crystals.

mp: 158.5–159.3° C.

$^1$H-NMR(DMSO-$d_6$, δ ppm): 12.01(1H, brs), 8.15(1H, d, J=1.4 Hz), 8.06(1H, d, J=8.4 Hz), 7.82(1H, dd, J=1.6 and 8.4

Hz), 7.66(1H, d, J=2.1 Hz), 7.25(1H, dd, J=2.1 and 8.4 Hz), 6.72(1H, d, J=8.4 Hz), 4.25(2H, s), 3.48(2H, m), 2.44(3H, s), 1.66(2H, quint., J=7.5 Hz), 1.34(2H, quint., J=7.7 Hz), 1.24(2H, sextet, J=7.6 Hz), 0.80(3H, t, J=7.3 Hz)

IR(Nujol): 1661 cm$^{-1}$

Mass(FD): m/e 483(M)

Example 38-1

In the same manner as in Example 1, 2-(2,4-dichlorobenzyl)-3-ethyl-7-(1-n-pentanesulfonylcarbamoyl) benzo[b]thiophene (0.17 g) was obtained as white crystals from 7-carboxy-2-(2,4-dichlorobenzyl)-3-ethylbenzo[b] thiophene (0.25 g), N,N'-carbonyldiimidazole (0.22 g), DBU (0.20 ml) and 1-n-pentanesulfonamide (0.21 g).

$^{1}$H-NMR(CDCl$_3$, δ ppm): 0.89(3H, t J=7.4 Hz), 1.20(3H, t, J=7.7 Hz), 1.30–1.38(2H, m), 1.41–1.48(2H, m), 1.85–1.93(2H, m), 2.89(2H, quartet, J=7.6 Hz), 3.62(2H, t, J=8.3 Hz), 4.31(2H, s), 7.13(1H, d, J=8.3 Hz), 7.16(1H, dd, J=8.4 and 2.0 Hz), 7.41(1H, d, J=2.2 Hz), 7.49(1H, t, J=7.8 Hz), 7.62(1H, d, J=7.5 Hz), 7.96(1H, d, J=7.9 Hz), 8.4(1H, brs)

IR(Nujol): 1667 cm$^{-1}$

Mass(FD): m/e 497(M)

mp: 176–178° C.

Example 38-2

In the same manner as in Example 1, 7-(benzenesulfonylcarbamoyl)-2(2,4-dichlorobenzyl)-3-ethylbenzo[b]thiophene (0.15 g) was obtained as white crystals from 7carboxy-2-(2,4-dichlorobenzyl)-3-ethylbenzo[b]thiophene (0.25 g), N,N'-carbonyldiimidazole (0.22 g), DBU (0.20 ml) and benzenesulfonamide (0.22 g).

$^{1}$H-NMR(CDCl$_3$, δ ppm): 1.14(3H, t, J=7.6 Hz), 2.84(2H, quartet, J=7.5 Hz), 4.24(2H, s), 7.04(1H, d, J=8.3 Hz), 7.12(1H, dd, J=8.3 and 2.0 Hz), 7.38(2H, d, J=2.0 Hz), 7.54(2H, t, J=7.7 Hz), 7.62(1H, t, J=7.4 Hz), 7.70(1H, d, J=7.5 Hz), 7.87(1H, d, J=7.9 Hz), 8.18(2H, d, J=7.9 Hz)

IR(Nujol): 1704 cm$^{-1}$

Mass(FD): m/e 503(M)

mp: 181–183° C.

Example 39

In the same manner as in Example 1, N,N'-carbonyldiimidazole (0.290 g) was added to a mixture of 6-carboxy-1-(2,4-dichlorobenzyl)-3-methyl-2-benzimidazolone (0.314 g) and N,N-dimethylformamide (9 ml), and the mixture was stirred at room temperature for 1 hr. 1-n-Butanesulfonamide (0.246 g) and DBU (0.273 g) were added and the mixture was stirred at 100° C. for 16 hr. The solvent was evaporated and the resulting mixture was extracted with chloroform and water. The organic layer was concentrated and the residue was purified by preparative thin layer chromatography to give 6-(1-n-butanesulfonylcarbamoyl)-1-(2,4-dichlorobenzyl)-3-methyl-2-benzimidazolone (0.123 g).

$^{1}$H-NMR(DMSOd$_6$, δ ppm): 0.81(3H, t, J=7.2 Hz), 1.29 (2H, m), 1.51(2H, m), 3.00(2H, m), 3.39(3H, s), 5.11(2H, s), 6.93(1H, d, J=8.3 Hz), 7.13(1H, d, J=8.2 Hz), 7.34(1H, d), 7.50(1H, s), 7.68(1H, s), 7.78(1H, d, J=8.1 Hz)

IR(Nujol): 1666 cm$^{-1}$ mp: 358–360° C.

Mass(FD): m/e 469(M)

Example 40

In the same manner as in Example 1, 6-(1-n-butanesulfonyl-carbamoyl)-1-(2,4-dichlorobenzyl) benzotriazole (0.13 g) was obtained from 6-carboxy-1-(2,4-dichlorobenzyl)-benzotriazole (0.12 g), N,N'-carbonyl-diimidazole (0.12 g), DBU (0.11 ml) and 1-n-butanesulfonamide (0.10 g).

$^{1}$H-NMR(CDCl$_3$, δ ppm): 0.90(3H, t,J=7.4 Hz), 1.40–1.48(2H, m), 1.76–1.82(2H, m), 3.57 (2H, t, J=8.4 Hz), 5.93(2H, s), 6.89(1H, d, J=8.4 Hz), 7.13(1H, dd, J=8.4 and 2.1 Hz), 7.38 (1H, d, J=2.0 Hz), 7.92(1H, d, J=8.9 Hz), 8.13(1H, d, J=8.7 Hz), 8.26(1H, s), 10.0(1H, brs)

IR(Nujol): 1688 cm$^{-1}$

Mass(FD): m/e 440 (M)

mp: 158–160° C.

Example 41-1

In the same manner as in Example 1, 6-carboxy-1-(2,4-dichlorobenzyl)-3-methyl-1H-indazole (0.44 g, 1.31 mmol) was dissolved in dimethylformamide (16 ml) and N,N'-carbonyldiimidazole (319 mg, 2.0 mmol) was added, which was followed by stirring at room temperature for 1 hr. Then, 1-n-butanesulfonamide (270 mg, 2.0 mmol) and DBU (300 mg, 2.0 mmol) were added and the mixture was refluxed under heating at 100° C. for 14 hr. Dimethylformamide was evaporated and the residue was adjusted to pH 3 with 1N hydrochloric acid. The precipitated oil was extracted with ethyl acetate. The organic layer was washed with saturated brine, and dried over anhydrous sodium sulfate. The desiccant was filtered off and the filtrate was concentrated under reduced pressure. The residual oil was purified by silica gel column chromatography (eluent: hexane/ethyl acetate=1/1) to give 6-(1-n-butanesulfonylcarbamoyl)-1-(2,4-dichlorobenzyl)-1H-3-methylindazole as a crystalline oil (0.53 g). This was recrystallized from ethyl acetate-hexane to give colorless crystals (0.36 g, 60%).

mp: 133.6–135.0° C.

$^{1}$H-NMR(CDCl$_3$, δ ppm): 8.82(1H, brs), 7.94(1H, s), 7.78(1H, d, J=8.4 Hz), 7.56(1H, d, J=8.4 Hz), 7.42(1H, d, J=1.7 Hz), 7.09(1H, dd, J=1.9 and 8.4 Hz), 6.63(1H, d, J=8.4 Hz), 5.64(2H, s), 3.58(2H, m), 2.62(3H, s), 1.83(2H, quint, J=7.4 Hz), 1.47(2H, sextet, J=7.4 Hz), 0.94(3H, t, J=7.4 Hz)

IR(Nujol): 1681 cm$^{-1}$

Mass(FD): m/e 453(M)

Example 41-2

In the same manner as in Example 1, 1-(2,4-dichlorobenzyl)-3-methyl-6-(1-pentanesulfonylcarbamoyl)-1H-indazole (0.39 g) was obtained as pale-yellow amorphous from 6-carboxy-1-(2,4-dichlorobenzyl)-3-methyl-1H-indazole (0.335 g), N,N'-carbonyldiimidazole (0.32 g), DBU (0.30 ml) and 1-pentanesulfonamide (0.30 g).

$^{1}$H-NMR(DMSO-d$_6$, δ ppm): 0.82(3H, t, J=7.2 Hz), 1.22–1.40(4H, m), 1.66–1.74(2H, m), 2.51(3H, s), 3.52(2H, t, J=7.7 Hz), 5.69(2H, s), 6.78(1H, d, J=8.4 Hz), 7.34(1H, dd, J=8.4 and 2.0 Hz), 7.64(1H, d, J=8.5 Hz), 7.67(1H, d, J=2.0 Hz), 7.87(1H, d, J=8.5 Hz), 8.33(1H, s), 12.07(1H, brs)

IR(Nujol): 1690 cm$^{-1}$

Example 41-3

In the same manner as in Example 1, 6-(benzenesulfonylcarbamoyl)-1-(2,4-dichlorobenzyl)-3-methyl-1H-indazole (0.36 g) was obtained as white crystals from 6-carboxy-1-(2,4-dichlorobenzyl)-3-methyl-1H-indazole (0.335 g), N,N'-carbonyldiimidazole (0.32 g), DBU (0.30 ml) and benzenesulfonamide (0.31 g).

¹H-NMR(DMSO-d₆, δ ppm): 2.50(3H, s), 5.68(2H, s), 6.75(1H, d, J=8.5 Hz),7.33(1H, dd, J=8.4 and 2.0 Hz), 7.56(1H, d, J=8.7 Hz), 7.64(2H, t, J=7.7 Hz), 7.67(1H, d, J=2.0 Hz), 7.72(1H, t, J=7.5 Hz), 7.83(1H, d, J=8.5 Hz), 8.02(2H, d, J=7.9 Hz), 8.31(1H, s), 12.60(1H, brs)

IR(Nujol): 1699 cm⁻¹ mp: 227.5–229° C.

Example 41-4

In the same manner as in Example 1, (E)-1-(2,4-dichlorobenzyl)-3-methyl-6-((2-phenylethenyl)sulfonylcarbamoyl)-1H-indazole (0.17 g) was obtained as white crystals from 6-carboxy-1-(2,4-dichlorobenzyl)-3-methyl-1H-indazole (0.335 g), N,N'-carbonyldiimidazole (0.32 g), DBU (0.30 ml) and (E)-(2-phenylethenyl)sulfonamide (0.37 g).

¹H-NMR(DMSO-d₆, δ ppm): 2.50(3H, s), 5.68(2H, s), 6.76(1H, d, J=8.4 Hz),7.33(1H, dd, J=8.4 and 2.2 Hz), 7.43–7.47(3H, m), 7.53(1H, d, J=15.4 Hz), 7.64(1H, d, J=8.5 Hz), 7.67(1H, d, J=15.5 Hz), 7.76–7.79(2H, m), 7.85(1H, d, J=8.4 Hz), 8.34(1H, s), 12.35(1H, brs)

IR(Nujol): 1694 cm⁻¹ mp: 209.5–210.5° C.

Example 42

In the same manner as in Example 1, 7-(1-n-butanesulfonyl-carbamoyl)-1-(2,4-dichlorobenzyl)-3-ethyl-2,4(1H,3H)-quinazolinedione (0.58 g) was obtained as white crystals from 7-carboxy-1-(2,4-dichlorobenzyl)-3-ethyl-2,4(1H,3H)-quinazolinedione (0.79 g), N,N'-carbonyldiimidazole (0.44 g), DBU (0.41 g) and 1-n-butanesulfonamide (0.37 g).

¹H-NMR(DMSO-d₆, δ ppm): 0.81(3H, t, J=7.4 Hz), 1.18 (3H, t, J=7.2 Hz), 1.32–1.40(2H, m), 1.61(2H, quint., J=8.0 Hz), 3.46(2H, t, J=7.1 Hz), 4.01(2H, quartet, J=7.2 Hz), 5.39(2H, s), 7.11(1H, d, J=8.5 Hz), 7.29(1H, d, J=8.4 Hz), 7.51(1H, s), 7.74(1H, d, J=2.0 Hz), 7.77(1H, d, J=8.1 Hz), 8.21(1H, d, J=8.7 Hz), 8.23(1H, s), 12.3(1H, brs)

IR(Nujol): 1712, 1693, 1658 cm⁻¹

Mass(FD): m/e 511(M)

mp: 212–214° C.

Example 43

In the same manner as in Example 1, 7-(1-n-butanesulfonyl-carbamoyl)-3-(2,4-dichlorobenzyl)-1-methyl-2,4(1H,3H)-quinazolinedione (0.65 g) was obtained as white crystals from 7-carboxy-3-(2,4-dichlorobenzyl)-1-methyl-2,4(1H,3H)-quinazolinedione (0.57 g), N,N'-carbonyldiimidazole (0.36 g), DBU (0.34 ml) and 1-n-butanesulfonamide (0.31 g).

¹H-NMR(DMSO-d₆, δ ppm): 0.88(3H, t, J=7.4 Hz), 1.39–1.46(2H, m), 1.70(2H, quint., J=7.7 Hz), 3.56(2H, t, J=7.9 Hz), 3.60(3H, s), 5.14(2H, s), 7.18(1H, d, J=8.4 Hz), 7.30(1H, dd, J=8.4 and 2.1 Hz), 7.65(1H, d, J=2.1 Hz), 7.80 (1H, d, J=8.2 Hz), 7.98(1H, s), 8.16(1H, d, J=8.2 Hz), 12.5(1H, brs)

IR(Nujol): 1712, 1693, 1658 cm⁻¹

Mass(FD): m/e 497(M)

mp: 212–214° C.

Example 44

In the same manner as in Example 1, 7-(1-n-butanesulfonyl-carbamoyl)-3-(2,4-dichlorobenzyl)-4(3H)-quinazolinone (0.38 g) was obtained as white crystals from 7-carboxy-3-(2,4-dichlorobenzyl)-4(3H)-quinazolinone (0.35 g), N,N'-carbonyldiimidazole (0.32 g), DBU (0.30 ml) and 1-n-butanesulfonamide (0.27 g).

¹H-NMR(DMSO-d₆, δ ppm): 0.87(3H, t, J=7.6 Hz), 1.38–1.46(2H, m), 1.66–1.73(2H, m), 3.54(2H, t, J=7.8 Hz), 5.25(2H, s), 7.21(1H, d, J=8.4 Hz), 7.38(1H, dd, J=8.4 and 2.1 Hz), 7.69 (1H, d, J=2.1 Hz), 7.99(1H, dd, J=8.3 and 1.7 Hz), 8.23(1H, d, J=8.3 Hz), 8.25(1H, d, J=1.7 Hz), 8.58(1H, s), 12.40(1H, brs)

IR(Nujol): 1694 cm⁻¹

Mass(FD): m/e 468 (M+1)

mp: 245–247° C.

Example 45

In the same manner as in Example 1, 7-(1-n-butanesulfonyl-carbamoyl)-2-(2,4-dichlorobenzyl)-3-methyl-4(3H)-quinazolinone (0.09 g) was obtained as white crystals from 7-carboxy-2-(2,4-dichlorobenzyl)-3-methyl-4(3H)-quinazolinone (0.19 g), N,N'-carbonyldiimidazole (0.21 g), DBU (0.20 ml) and 1-n-butanesulfonamide (0.20 g).

¹H-NMR(CDCl₆, δ ppm): 0.96(3H, t, J=7.4 Hz), 1.48–1.53(2H, m), 1.84–1.91(2H, m), 3.58–3.62(5H, m), 4.29(2H, s), 7.14(1H, d, J=8.3 Hz), 7.23–7.26(1H, m), 7.50 (1H, d, J=2.1 Hz), 7.89(1H, d, J=8.3 Hz), 7.97(1H, s), 8.36(1H, brs), 8.39(1H, d, J=8.3 Hz)

IR(Nujol): 1690, 1661 cm⁻¹

Mass(FD): m/e 482 (M+1)

mp: 244–246° C.

Example 46

In the same manner as in Example 1, except that pH was adjusted to 1 with 3N hydrochloric acid in a post-treatment step, 6-(1-n-butanesulfonylcarbamoyl)-3-(2,4-dichlorobenzyl)-3,4-dihydro-2-methylquinazoline hydrochloride (0.16 g) was obtained as pale-yellow crystals from 6-carboxy-3-(2,4-dichlorobenzyl)-3,4-dihydro-2-methylquinazoline hydrochloride (0.27 g), N,N'-carbonyldiimidazole (0.34 g), DBU (0.31 ml) and 1-n-butanesulfonamide (0.29 g).

¹H-NMR(DMSO-d₆, δ ppm): 0.82 (3H, t, J=7.4 Hz), 1.27–1.33(2H, m), 1.48–1.56(2H, m), 2.43(3H, s), 3.04(2H, t, J=7.7 Hz), 4.72(2H, s), 4.86(2H, s), 7.01(1H, d, J=8.3 Hz), 7.49(1H, dd, J=8.4 and 2.1 Hz), 7.59 (1H, d, J=8.4 Hz), 7.66(1H, s), 7.75(1H, d, J=2.1 Hz), 7.85(1H, d, J=8.4 Hz), 12.0(1H, brs)

IR(Nujol): 1642 cm⁻¹

Mass(FD): m/e 467 (M)

mp: 258° C. (decomposition)

Example 47-1

In the same manner as in Example 1, 1-(2,4-dichlorobenzyl)-2-methyl-7-(1-n-pentanesulfonylcarbamoyl)-4(1H)-quinazolinone (0.47 g) was obtained as white crystals from 7-carboxy-1-(2,4-dichlorobenzyl)-2-methyl-4(1H)-quinazolinone (0.36 g), N,N'-carbonyldiimidazole (0.32 g), DBU (0.30 ml) and 1-n-pentanesulfonamide (0.30 g).

¹H-NMR(DMSO-d₆, δ ppm): 0.80(3H, t, J=7.3 Hz), 1.18–1.26(2H, m), 1.29–1.35(2H, m), 1.60–1.67(2H, m), 2.67(3H, s), 3.48(2H, t, J=8.3 Hz), 5.70(2H, s), 7.14(1H, d, J=8.6 Hz), 7.33–7.36(1H, m), 7.83–7.86(2H, m), 8.07(1H, d, J=8.4 Hz), 8.33(1H, d, J=8.3 Hz)

Example 47-2

In the same manner as in Example 1, 7-(benzenesulfonylcarbamoyl)-1-(2,4-dichlorobenzyl)-2-methyl-4(1H)-quinazolinone (0.50 g) was obtained as white crystals from 7-carboxy-1-(2,4-dichlorobenzyl)-2-methyl-4(1H)-quinazolinone (0.36 g), N,N'-carbonyldiimidazole (0.32 g), DBU (0.30 ml) and benzenesulfonamide (0.31 g).

$^1$H-NMR(CDCl$_3$, δ ppm): 2.66(3H, s), 5.68(2H, s), 7.11 (1H, d, J=8.5 Hz), 7.3 1(1H, dd, J=8.4 and 2.1 Hz), 7.61(2H, t, J=7.9 Hz), 7.71(1H, t, J=7.5 Hz), 7.80(1H, s), 7.84(1H, d, J=2.1 Hz), 7.94(2H, d, J=7.9 Hz), 8.03(1H, d, J=8.2 Hz), 8.29(1H, d, J=8.3 Hz)

IR(Nujol): 1735, 1698 cm$^{-1}$

Mass(FD): m/e 502(M+1)

mp: 214–216° C.

Example 48

In the same manner as in Example 1, 1-(2,4-dichlorobenzyl)-1,4-dihydro-2-methyl-7-(1-n-pentanesulfonylcarbamoyl)quinazoline hydrochloride (0.075 g) was obtained as white crystals from 7-carboxy-1-(2,4-dichlorobenzyl)-1,4-dihydro-2-methylquinazoline 1/2 sulfate (0.100 g), N,N'-carbonyldiimidazole (0.122 g), DBU (0.11 ml) and benzenesulfonamide (0.113 g).

$^1$H-NMR(DMSO-d$_6$, δ ppm): 0.79(3H, t, J=7.3 Hz), 1.18–1.34(4H, m), 1.55–1.65(2H, m), 2.43(3H, s), 3.40–3.50(2H, m), 4.86(2H, s), 5.30(2H, s), 7.27(1H, s), 7.37 (1H, s), 7.38(1H, d, J=2.0 Hz), 7.41(1H, d, J=8.2 Hz), 7.79(1H, d, J=1.9 Hz), 7.81(1H, d, J=7.9 Hz), 11.4(1H,brs), 12.1(1H, brs)

IR(Nujol): 1685 cm$^{-1}$

Mass(FD) m/e 482(M+1)

mp: 184–186° C.

Example 49

In the same manner as in Example 1, 7-(1-n-butanesulfonyl-carbamoyl)-1-(2,4-dichlorobenzyl)-3-methyl-2(1H)-quinoxalinone (0.17 g) was obtained from 7-carboxy-1-(2,4-dichlorobenzyl)-3-methyl-2(1H)-quinoxalinone (0.28 g), N,N'-carbonyldiimidazole (0.23 g), DBU (0.21 ml) and 1-n-butanesulfonamide (0.19 g).

$^1$H-NMR(DMSO-d$_6$, δ ppm): 0.81(3H, t, J=7.4 Hz), 1.32–1.40(2H, m), 1.62(2H, quint., J=7.5 Hz), 2.51(3H, s), 3.47(2H, t, J=7.5 Hz), 5.48(2H, s), 6.88(1H, d, J=8.6 Hz), 7.25(1H, dd, J=8.5 and 2.3 Hz), 7.69 (1H, s), 7.75(1H, d, J=2.3 Hz), 7.86(1H, d, J=8.4 Hz), 7.90(1H, d, J=8.3 Hz), 12.2(1H, brs)

IR(Nujol): 1708, 1692 cm$^{-1}$

Mass(FD): m/e 481 (M)

mp: 223–225° C.

Example 50

In the same manner as in Example 1, 7-(1-n-butanesulfonyl-carbamoyl)-1-(2,4-dichlorobenzyl)-4-methyl-2,3-(1H,4H)-quinoxalinedione (0.32 g) was obtained from 7-carboxy-1-(2,4-dichlorobenzyl)-4-methyl-2,3-(1H,4H)-quinoxalinedione (0.28 g), N,N'-carbonyldiimidazole (0.22 g), DBU (0.20 ml) and 1-n-butanesulfonamide (0.18 g).

$^1$H-NMR(DMSO-d$_6$, δ ppm): 0.80(3H, t, J=7.3 Hz), 1.30–1.38(2H, m), 1.60(2H, quint., J=7.7 Hz), 3.46(2H, t, J=7.2 Hz), 3.59(3H, s), 5.37(2H, s), 7.17(1H, d, J=8.5 Hz), 7.28(1H, dd, J=8.5 and 2.2 Hz), 7.45 (1H, d, J=1.8 Hz), 7.58(1H, d, J=8.8 Hz), 7.75(1H, d, J=2.1 Hz), 7.86(1H, dd, J=7.2 and 1.8 Hz), 12.1(1H, brs)

IR(Nujol): 1682 cm$^{-1}$

Mass(FD): m/e 497 (M)

mp: 243–246° C.

Example 51

In the same manner as in Example 1, 4-(2,4-dichlorobenzyl)-5-ethyl-3-(1-n-pentanesulfonylcarbamoyl)imidazo[1,2-b]pyrazole (0.140 g) was obtained from 3-carboxy-4-(2,4-dichlorobenzyl)-5-ethylimidazo[1,2-b]pyrazole (0.546 g), N,N'-carbonyldiimidazole (0.524 g), 1-n-pentanesulfonamide (0.488 g) and DBU (0.491 g).

$^1$H-NMR(CD$_3$OD, δ ppm): 0.77(3H, t, J=7.1 Hz), 1.11–1.27(7H, m), 1.58(2H, m), 2.45(2H, m), 3.26(2H, m), 5.78(2H, s), 6.43(1H, d, J=8.4 Hz), 7.12(1H, dd, J=8.4 and 2.1 Hz), 7.36(1H, s), 7.43(1H, d, J=2.1 Hz), 8.01 (1H, s)

IR(Nujol): 1661 cm$^{-1}$

Mass(FD): m/e 470(M)

mp: 165–166.5° C.

Example 52

In the same manner as in Example 1, 3-(2,4-dichlorobenzyl)-2-methyl-6-(1-n-pentanesulfonylcarbamoyl)imidazo[1,2-a]pyridine (0.07 g) was obtained from a crude purification product of 6-carboxy-3-(2,4-dichlorobenzyl)-2-methylimidazo[1,2-a]pyridine (0.40 g), N,N'-carbonyldiimidazole (0.32 g), DBU (0.30 ml) and 1-n-pentanesulfonamide (0.31 g).

$^1$H-NMR(DMSO-d$_6$, δ ppm): 0.8(3H, t,J=7.2 Hz), 1.21–1.37(4H, m), 1.61–1.68(2H, m), 2.26(3H, s), 3.33(2H, m), 4.44(2H, s), 6.86(1H, d, J=8.1 Hz), 7.30(1H, dd. J=8.3 and 2.2 Hz), 7.62(1H, d, J=9.3 Hz), 7.69(1H, d, J=2.1 Hz), 7.77 (1H, brs), 8.84(1H, s)

IR(Nujol): 1659 cm$^{-1}$ mp: 264–267° C.

Example 53-1

In the same manner as in Example 1, 6-(n-pentanesulfonylcarbamoyl)-4-(4-phenylphenyloxy)quinoline (91 mg) was obtained as a brown powder from 4-(4-phenylphenyloxy)-6-quinolinecarboxylic acid (227 mg).

$^1$H-NMR(DMSO-d$_6$): 0.83 (3H, t, J=7 Hz), 1.19–1.39 (4H, br), 1.57–1.70 (2H, br), 3.20 (2H, br), 6.72 (1H, d, J=4 Hz), 7.38–7.53 (5H, m), 7.73 (2H, d, J=8 Hz), 7.85 (2H, d, J=8 Hz), 8.00 (1H, d, J=8 Hz), 8.32 (1H, d, J=8 Hz), 8.73 (1H, d, J=4 Hz), 8.98 (1H, s)

Example 53-2

In the same manner as in Example 1, 6-(n-pentanesulfonylcarbamoyl)-4-(4-phenylbenzyloxy)quinoline (814 mg) was obtained as a white powder from 4-(4-phenylbenzyloxy)-6-quinolinecarboxylic acid (600 mg).

$^1$H-NMR (DMSO-d$_6$): 0.80 (3H, t, J=7 Hz), 1.20–1.33 (4H, br), 1.52–1.64 (2H, br), 3.03–3.09 (2H, m), 5.49 (2H, s), 7.15 (1H, d, J=7 Hz), 7.38 (1H, m), 7.48 (2H, m), 7.64–7.75 (6H, m), 7.87 (1H, d, J=8 Hz), 8.26 (1H, d, J=8 Hz), 8.70 (1H, d, J=7 Hz), 8.80 (1H, s)

Example 54

In the same manner as in Example 1, 3-(2,4-dichlorobenzyl)-2-ethyl-5-(((E)-pentene-1-sulfonyl)carbamoyl)benzo[b]furan (0.24 g) was obtained as white crystals from 5-carboxy-3-(2,4-dichlorobenzyl)-2-ethylbenzo[b]furan (0.30 g), N,N'-carbonyldiimidazole (0.28 g), DBU (0.26 ml) and 1-pentene-1-sulfonamide (0.30 g).

$^1$H-NMR(DMSO-$d_6$, δ ppm): 0.86(3H, t, J=7.4 Hz), 1.18 (3H, t, J=7.5 Hz), 1.40–1.48(2H, m), 2.23(2H, quartet, J=7.0 Hz), 2.77(2H, quartet, J=7.5 Hz), 4.09(2H, s), 6.76(1H, d, J=15.2 Hz), 6.83–6.90(1H, m), 7.13(1H, d, J=8.4 Hz), 7.33 (1H, dd, J=8.4 and 2.2 Hz), 7.62(1H, d, J=8.7 Hz), 7.64(1H, d, J=2.1 Hz), 7.81(1H, dd, J=8.8 and 1.8 Hz), 7.99(1H, d, J=1.6 Hz), 12.05(1H, brs)

IR(Nujol): 1657 cm$^{-1}$ mp: 191–192° C.

Example 55-1

In the same manner as in Example 1, 1-(2,4-dichlorobenzyl)-3-ethyl-6-(1-n-pentanesulfonylcarbamoyl)-1H-indazole (0.47 g) was obtained from 6-carboxy-1-(2,4-dichlorobenzyl)-3-ethyl-1H-indazole (0.35 g), N,N'-carbonyldiimidazole (0.32 g), DBU (0.30 ml) and 1-n-pentanesulfonamide (0.30 g).

$^1$H-NMR(DMSO-$d_6$, δ ppm): 0.82(3H, t, J=7.2 Hz), 1.23–1.40(7H, m), 1.65–1.73(2H, m), 2.95(2H, quartet, J=7.6 Hz), 3.52(2H, t, J=7.8 Hz), 5.70(2H, s), 6.71(1H, d, J=8.4 Hz), 7.34(1H, dd, J=8.4 and 2.1 Hz), 7.64(1H, dd, J=8.5 and 1.3 Hz), 7.68(1H, d, J=2.1 Hz), 7.91(1H, d, J=8.5 Hz), 8.32(1H, s), 12.07(1H, brs)

IR(Nujol): 1690 cm$^{-1}$

Example 55-2

In the same manner as in Example 1, 6-(benzenesulfonylcarbamoyl)-1-(2,4-dichlorobenzyl)-3-ethyl-1H-indazole (0.38 g) was obtained as pale-yellow crystals from 6-carboxy-1-(2,4-dichlorobenzyl)-3-ethyl-1H-indazole (0.35 g), N,N'-carbonyldiimidazole (0.32 g), DBU (0.30 ml) and benzenesulfonamide (0.31 g).

$^1$H-NMR(DMSO-$d_6$, δ ppm): 1.27(3H, t, J=7.5 Hz), 2.93 (2H, quartet, J=7.6 Hz), 5.69(2H, s), 6.67(1H, d, J=8.4 Hz), 7.33(1H, dd, J=8.4 and 2.2 Hz), 7.55(1H, dd, J=8.5 and 1.3 Hz), 7.64(2H, t, J=7.4 Hz), 7.68(1H, d, J=2.1 Hz), 7.72(1H, t, J=7.4 Hz), 7.87(1H, d, J=8.5 Hz), 8.01(2H, d, J=7.8 Hz), 8.28(1H, s), 12.55(1H, brs)

IR(Nujol): 1697 cm$^{-1}$ mp: 208–209° C.

Example 56

In the same manner as in Example 1, 6-(benzenesulfonylcarbamoyl)-3-(2,4-dichlorobenzyl)-2-methylimidazo[1,2-a]pyridine (0.07 g) was obtained as a brown solid from a crude purification product of 6-carboxy-3-(2,4-dichlorobenzyl)-2-methylimidazo[1,2-a]pyridine (0.20 g), N,N'-carbonyldiimidazole (0.32 g), DBU (0.30 ml) and benzenesulfonamide (0.31 g).

mp: 308–310° C.

$^1$H-NMR(DMSO-$d_6$, δ ppm): 2.33(3H, s), 4.51(2H, s), 7.05(1H, d, J=8.3 Hz), 7.30(1H, dd, J=8.4 and 2.1 Hz), 7.56(2H, t, J=7.6 Hz), 7.60–7.63 (1H, m), 7.71(1H, d, J=2.2 Hz), 7.87(1H, d, J=8.4 Hz), 7.94(2H, d, J=7.2 Hz), 8.09–8.14(1H, m), 8.98(1H, brs)

IR(Nujol): 1664 cm$^{-1}$

Mass(FD): m/e 473(M)

Example 57-1

In the same manner as in Example 1, 3-((2,3-dichlorobenzyl)-2-methyl-5-(n-pentanesulfonylcarbamoyl)-3H-imidazo[4,5-b]pyridine (32 mg) was obtained as white crystals from 3-(2,3-dichlorobenzyl)-2-methyl-3H-imidazo[4,5-b]pyridine-5-carboxylic acid (45 mg).

$^1$H-NMR(DMSO-$d_6$): 0.79(3H, t, J=8 Hz), 1.19–1.40(4H, m), 1.65–1.75(2H, m), 2.51(3H, s), 3.52(2H, t, J=8 Hz), 5.86(2H, s), 6.60(1H, d, J=8 Hz), 7.27(1H, t, J=8 Hz), 7.62(1H, d, J=8 Hz), 8.01(1H, d, J=8 Hz), 8.22(1H, dd, J=8 Hz)

Mass(ESI): 467(M−H)$^-$

Example 57-2

In the same manner as in Example 1, 3-((3-chlorobenzo[b]thiophene-2-yl)methyl)-2-methyl-5-n-pentanesulfonylcarbamoyl-3H-imidazo[4,5-b]pyridine (47 mg) was obtained as pale-yellow crystals from 3-((3-chlorobenzo[b]thiophen-2-yl)methyl)-2-methyl-3H-imidazo[4,5-b]pyridine-5-carboxylic acid (78 mg).

$^1$H-NMR(DMSO-$d_6$): 0.79(3H, t, J=8 Hz), 1.22–1.41(4H, m), 1.68–1.78(2H, m), 2.63(3H, s), 3.57(2H, t, J=8 Hz), 6.13(2H, s), 7.43–7.58(2H, m), 7.80(1H, d, J=8 Hz), 7.92 (1H, d, J=8 Hz), 8.03(1H, d, J=8 Hz), 8.20(1H, dd, J=2.8 Hz)

Mass(ESI): 489(M−H)$^-$

Example 58

In the same manner as in Example 1, 3-(2-chloro-4-phenylbenzyl)-2-methyl-5-(n-pentanesulfonylcarbamoyl)benzo[b]thiophene (125 mg) was obtained as white crystals from 3-(2-chloro-4-phenylbenzyl)-2-methylbenzo[b]thiophene-5-carboxylic acid (130 mg).

$^1$H-NMR(DMSO-$d_6$): 0.78(3H, t, J=7 Hz), 1.17–1.38(4H, m), 1.60–1.72(2H, m), 2.47(3H, s), 3.49(2H, t, J=8 Hz), 6.81(1H, d, J=8 Hz), 7.32–7.48(4H, m), 7.65(2H, d, J=8 Hz), 7.80–7.86(2H, m), 8.08(1H, d, J=8 Hz), 8.23(1H, s)

Mass(ESI): 524(M−H)$^-$

Example 59

In the same manner as in Example 1, 3-(2-chloro-4-phenylbenzyl)-2-methyl-5-(((E)-1-pentene-1-sulfonyl)carbamoyl)-3H-imidazo[4,5-b]pyridine (47 mg) was obtained as pale-yellow crystals from 3-(2-chloro-4-phenylbenzyl)-2-methyl-3H-imidazo[4,5-b]pyridine-5-carboxylic acid (78 mg).

$^1$H-NMR(DMSO-$d_6$): 0.86(3H, t, J=7 Hz), 1.40–1.49(2H, m), 2.20–2.28(2H, m), 2.52(3H, s), 5.87(2H, s), 6.72–6.80 (2H, m), 6.87–6.97(1H, m), 7.35–7.48(3H, m), 7.53(1H, d, J=8 Hz), 7.67(1H, d, J=8 Hz), 7.85(1H, s), 7.98(1H, dd, J=2.8 Hz), 8.19(1H, d, J=8 Hz)

Mass(ESI): 507(M−H)$^-$

Example 60-1

In the same manner as in Example 1, 1-(2-chloro-4-phenylbenzyl)-3-methyl-6-(1-pentanesulfonylcarbamoyl)-1H-indazole (0.16 g) was obtained as pale-yellow crystals from 6-carboxy-1-(2-chloro-4-phenylbenzyl)-3-methyl-1H-indazole (0.28 g), N,N'-carbonyldiimidazole (0.32 g), DBU (0.31 ml) and 1-pentanesulfonamide (0.30 g).

$^1$H-NMR(DMSO-$d_6$, δ ppm): 0.81(3H, t, J=7.3 Hz), 1.22–1.30(2H, m), 1.32–1.39(2H, m), 1.66–1.73(2H, m), 2.53(3H, s), 3.52(2H, t, J=7.7 Hz), 5.75(2H, s), 6.84(1H, d, J=8.2 Hz), 7.36–7.40(1H, m), 7.45(2H, t, J=7.6 Hz), 7.54 (1H, dd, J=8.0 and 1.9 Hz), 7.64–7.67(3H, m), 7.78(1H, d, J=1.9 Hz), 7.88(1H, d, J=8.3 Hz), 8.38(1H, s), 12.09(1H, brs)

IR(Nujol): 1684 cm$^{-1}$ mp: 172–173° C.

Example 60-2

In the same manner as in Example 1, 6-(benzenesulfonylcarbamoyl)-1-(2-chloro-4-phenylbenzyl)-3-methyl-1H-indazole (0.17 g) was obtained as pale-yellow crystals from 6-carboxy-1-(2-chloro-4-phenylbenzyl)-3-methyl-1H-indazole (0.25 g), N,N'-carbonyldiimidazole (0.30 g), DBU (0.30 ml) and benzenesulfonamide (0.29 g).

$^1$H-NMR(DMSO-d$_6$, δ ppm): 2.51(3H, s), 5.73(2H, s), 6.80(1H, d, J=8.1 Hz), 7.36–7.40(1H, m), 7.45(2H, t, J=7.7 Hz), 7.53(1H, dd, J=8.2 and 1.9 Hz), 7.56(1H, dd, J=8.6 and 1.2 Hz), 7.60–7.68(3H, m), 7.69–7.74(1H, m), 7.78(1H, d, J=1.8 Hz), 7.84(1H, d, J=8.9 Hz), 7.99–8.02(2H, m), 8.34 (1H, s), 12.57(1H, brs)

IR(Nujol): 1702 cm$^{-1}$ mp: 211–212° C.

Example 60-3

In the same manner as in Example 1, (E)-1-(2-chloro-4-phenylbenzyl)-3-methyl-6-((2-phenylethenyl)sulfonylcarbamoyl)-1H-indazole (0.25 g) was obtained as pale-yellow crystals from 6-carboxy-1-(2-chloro-4-phenylbenzyl)-3-methyl-1H-indazole (0.27 g), N,N'-carbonyldiimidazole (0.32 g), DBU (0.31 ml) and (E)-(2-phenylethenyl)sulfonamide (0.37 g).

$^1$H-NMR(DMSO-d$_6$, δ ppm): 2.52(3H, s), 5.74(2H, s), 6.81(1H, d, J=8.2 Hz), 7.35–7.83(15H, m), 7.87(1H, d, J=9.0 Hz), 8.39(1H, s), 12.35(1H, brs).

IR(Nujol): 1687 cm$^{-1}$ mp: 241–242° C.

Example 60-4

In the same manner as in Example 1, 1-(2-chloro-4-phenylbenzyl)-3-methyl-6-(((E)-1-pentene-1-sulfonyl)carbamoyl)-1H-indazole (0.10 g) was obtained as pale-yellow crystals from 6-carboxy-1-(2-chloro-4-phenylbenzyl)-3-methyl-1H-indazole (0.22 g), N,N'-carbonyldiimidazole (0.16 g), DBU (0.15 ml) and 1-pentene-1-sulfonamide (0.15 g).

$^1$H-NMR(DMSO-d$_6$, δ ppm): 0.86(3H, t, J=7.4 Hz), 1.42–1.48(2H, m), 2.21–2.27(2H, m), 2.53(3H, s), 5.74(2H, s), 6.77–6.83(2H, m), 6.87–6.92(1H, m), 7.38(1H, t, J=7.3 Hz), 7.45(2H, t, J=7.6 Hz), 7.54(1H, dd, J=7.8 and 2.1 Hz), 7.61–7.67(3H, m), 7.79(1H, d, J=1.8 Hz), 7.87(1H, d, J=8.5 Hz), 8.35(1H, s), 12.20(1H, brs)

IR(Nujol): 1682 cm$^{-1}$ mp: 201–202° C.

Example 60-5

In the same manner as in Example 1, 1-(2-chloro-4-phenylbenzyl)-3-methyl-6-((4-vinylbenzene)sulfonylcarbamoyl)-1H-indazole (0.10 g) was obtained as a pale-yellow powder from 6-carboxy-1-(2-chloro-4-phenylbenzyl)-3-methyl-1H-indazole (0.25 g), N,N'-carbonyldiimidazole (0.18 g), DBU (0.18 ml) and (4-vinylbenzene)sulfonamide (0.22 g).

$^1$H-NMR(DMSO-d$_6$, δ ppm): 2.51(3H, s), 5.46(1H, d, J=11.0 Hz), 5.74(2H, s), 6.02(1H, d, J=17.7 Hz), 6.75–6.84 (2H, m), 7.34–7.85(11H, m), 7.97(2H, d, J=8.5 Hz), 8.33 (1H, s), 12.51(1H, brs)

IR(Nujol): 1694 cm$^{-1}$

Example 60-6

In the same manner as in Example 1, 1-(2-chloro-4-phenylbenzyl)-3-methyl-6-((4-methylbenzene)sulfonylcarbamoyl)-1H-indazole (0.10 g) was obtained as white crystals from 6-carboxy-1-(2-chloro-4-phenylbenzyl)-3-methyl-1H-indazole (0.25 g), N,N'-carbonyldiimidazole (0.18 g), DBU (0.18 ml) and (4-methylbenzene)sulfonamide (0.20 g).

$^1$H-NMR(DMSO-d$_6$, δ ppm): 2.36(3H, s), 2.50(3H, s), 5.72(2H, s), 6.02(1H, d, J=17.7 Hz), 6.79(1H, d, J=8.1 Hz), 7.37–7.48(5H, m), 7.52(1H, d, J=8.1 Hz), 7.58(1H, d, J=7.8 Hz), 7.80(1H, d, J=8.4 Hz), 7.86(2H, d, J=8.2 Hz), 8.27(1H, s), 12.50(1H, brs)

IR(Nujol): 1706 cm$^{-1}$ mp: 188–190° C.

Example 61-1

In the same manner as in Example 1, 1-(4-bromo-2-chlorobenzyl)-3-methyl-6-(1-pentanesulfonylcarbamoyl)-1H-indazole (0.25 g) was obtained as pale-yellow amorphous from 1-(4-bromo-2-chlorobenzyl)-6-carboxy-3-methyl-1H-indazole (0.25 g), N,N'-carbonyldiimidazole (0.21 g), DBU (0.20 ml) and 1-pentanesulfonamide (0.20 g).

$^1$H-NMR(DMSO-d$_6$, δ ppm): 0.82(3H, t, J=7.2 Hz), 1.24–1.40(4H, m), 1.67–1.73(2H, m), 2.51(3H, s), 3.52(2H, t, J=7.7 Hz), 5.67(2H, s), 6.71(1H, d, J=8.3 Hz), 7.46(1H, dd, J=8.3 and 1.9 Hz), 7.64(1H, d, J=8.4 Hz), 7.79(1H, d, J=2.0 Hz), 7.87(1H, d, J=8.4 Hz), 8.34(1H, s), 12.06(1H, brs)

IR(Nujol): 1694 cm$^{-1}$

Example 61-2

In the same manner as in Example 1, 6-(benzenesulfonylcarbamoyl)-1-(4-bromo-2-chlorobenzyl)-3-methyl-1H-indazole (0.19 g) was obtained as white crystals from 1-(4-bromo-2-chlorobenzyl)-6-carboxy-3-methyl-1H-indazole (0.25 g), N,N'-carbonyldiimidazole (0.21 g), DBU (0.20 ml) and benzenesulfonamide (0.21 g).

$^1$H-NMR(DMSO-d$_6$, δ ppm): 2.50(3H, s), 5.66(2H, s), 6.67(1H, d, J=8.3 Hz), 7.46(1H, dd, J=8.3 and 1.9 Hz), 7.56(1H, d, J=8.4 Hz), 7.64(2H, brt, J=6.6 Hz), 7.71(1H, brd, J=7.1 Hz), 7.78(1H, d, J=7.1 Hz), 7.80–7.84(1H, m), 8.01(2H, d, J=7.5 Hz), 8.29(1H, s), 12.58(1H, brs)

IR(Nujol): 1702 cm$^{-1}$ mp: 213–215° C.

Example 61-3

In the same manner as in Example 1, (E)-1-(4-bromo-2-chlorobenzyl)-3-methyl-6-((2-phenylethenyl)sulfonylcarbamoyl)-1H-indazole (0.18 g) was obtained as white crystals from 1-(4-bromo-2-chlorobenzyl)-6-carboxy-3-methyl-1H-indazole (0.25 g), N,N'-carbonyldiimidazole (0.21 g), DBU (0.20 ml) and (E)-(2-phenylethenyl)sulfonamide (0.24 g).

$^1$H-NMR(DMSO-d$_6$, δ ppm): 2.50(3H, s), 5.66(2H, s), 6.68(1H, d, J=8.4 Hz), 7.43–7.48(4H, m), 7.53(1H, d, J=15.6

Hz), 7.63(1H, dd, J=8.5 and 1.3 Hz), 7.67(1H, d, J=15.5 Hz), 7.77(1H, d, J=1.9 Hz), 7.78(2H, d, J=2.0 Hz), 7.85(1H, d, J=8.5 Hz), 8.34(1H, s), 12.35(1H, brs)

IR(Nujol): 1691 cm$^{-1}$ mp: 211.5–212.5° C.

Example 62-1

In the same manner as in Example 1, 3-(2,4-dichlorobenzyl)-2-methyl-5-(((E)-1-pentene-1-sulfonyl)carbamoyl)benzo[b]furan (0.095 g) was obtained as white crystals from 5-carboxy-3-(2,4-dichlorobenzyl)-2-methylbenzo[b]furan (0.27 g), N,N'-carbonyldiimidazole (0.26 g), DBU (0.26 ml) and 1-pentene-1-sulfonamide (0.26 g).

$^1$H-NMR(DMSO-d$_6$, δ ppm): 0.86(3H, t, J=7.4 Hz), 1.39–1.48(2H, m), 2.23(2H, quartet, J=7.3 Hz), 2.41(3H, s), 4.08(2H, s), 6.76(1H, d, J=15.1 Hz), 6.83–6.90(1H, m), 7.17(1H, d, J=8.4 Hz), 7.33(1H, dd, J=8.3 and 2.2 Hz), 7.60(1H, d, J=8.6 Hz), 7.64(1H, d, J=2.7 Hz), 7.80(1H, dd, J=8.6 and 1.8 Hz), 7.96(1H, d, J=1.7 Hz), 12.07(1H, brs)

IR(Nujol): 1659 cm$^{-1}$ mp: 158–159° C.

Example 62-2

In the same manner as in Example 1, (E)-3-(2,4-dichlorobenzyl)-2-methyl-5-((2-phenylethenyl)sulfonylcarbamoyl)benzo[b]furan (0.14 g) was obtained as pale-yellow crystals from 5-carboxy-3-(2,4-dichlorobenzyl)-2-methylbenzo[b]furan (0.27 g), N,N'-carbonyldiimidazole (0.26 g), DBU (0.26 ml) and (E)-(2-phenylethenyl)sulfonamide (0.31 g).

$^1$H-NMR(DMSO-d$_6$, δ ppm): 2.39(3H, s), 4.07(2H, s), 7.15(1H, d, J=8.4 Hz),7.31(1H, dd, J=8.4 and 2.1 Hz), 7.40–7.57(6H, m), 7.62(1H, d, J=2.2 Hz), 7.69–7.72(2H, m), 7.83(1H, dd, J=8.6 and 1.8 Hz), 7.97(1H, d, J=1.7 Hz)

IR(Nujol): 1685 cm$^{-1}$ mp: 184–185° C.

Example 62-3

In the same manner as in Example 1, 3-(2,4-dichlorobenzyl)-2-methyl-5-((4-vinylbenzene)sulfonylcarbamoyl)benzo[b]furan (0.23 g) was obtained as a pale-yellow powder from 5-carboxy-3-(2,4-dichlorobenzyl)-2-methylbenzo-[b]furan (0.27 g), N,N'-carbonyldiimidazole (0.26 g), DBU (0.26 ml) and 4-vinylbenzenesulfonamide (0.31 g).

$^1$H-NMR(DMSO-d$_6$, δ ppm): 2.39(3H, s), 4.07(2H, s), 5.46(1H, d, J=11.1 Hz), 6.01(1H, d, J=17.6 Hz), 6.82(1H, dd, J=17.7 and 11.1 Hz), 7.16(1H, d, J=8.4 Hz), 7.32(1H, dd, J=8.3 and 2.2 Hz), 7.57(1H, d, J=8.7 Hz), 7.62(1H, d, J=2.1 Hz), 7.70(2H, d, J=8.4 Hz), 7.75(1H, dd, J=8.6 and 1.8 Hz), 7.91–7.94(3H, m), 12.40(1H, brs)

IR(Nujol): 1684 cm$^{-1}$ mp: 210–211° C.

Example 63-1

In the same manner as in Example 1, 3-(2-chloro-4-phenylbenzyl)-2-methyl-5-(1-pentanesulfonylcarbamoyl)benzo[b]furan (0.20 g) was obtained as white crystals from 5-carboxy-3-(2-chloro-4-phenylbenzyl)-2-methylbenzo[b]furan (0.25 g), N,N'-carbonyldiimidazole (0.23 g), DBU (0.22 ml) and 1-pentane-sulfonamide (0.22 g).

$^1$H-NMR(DMSO-d$_6$, δ ppm): 0.77(3H, t, J=7.3 Hz), 1.19–1.35(4H, m), 1.61–1.67(2H, m), 2.45(3H, s), 3.45–3.55(2H, m), 4.14(2H, s), 7.25(1H, d, J=8.1 Hz), 7.36(1H, t, J=7.3 Hz), 7.44(2H, t, J=7.6 Hz), 7.54(1H, dd, J=8.0 and 1.8 Hz), 7.61(1H, d, J=8.7 Hz), 7.65(2H, d, J=7.3 Hz), 7.76(1H, d, J=1.8 Hz), 7.83(1H, dd, J=8.7 and 1.8 Hz), 8.05(1H, s), 12.01(1H, brs)

IR(Nujol): 1685 cm$^{-1}$ mp: 150–151° C.

Example 63-2

In the same manner as in Example 1, 5-(benzenesulfonylcarbamoyl)-3-(2-chloro-4-phenylbenzyl)-2-methylbenzo[b]furan (0.18 g) was obtained as white crystals from 5-carboxy-3-(2-chloro-4-phenylbenzyl)-2-methylbenzo-[b]furan (0.25 g), N,N'-carbonyldiimidazole (0.23 g), DBU (0.22 ml) and benzenesulfonamide (0.23 g).

$^1$H-NMR(DMSO-d$_6$, δ ppm): 2.43(3H, s), 4.12(2H, s), 7.22(1H, d, J=8.1 Hz), 7.37(1H, t, J=7.4 Hz), 7.45(2H, t, J=7.6 Hz), 7.53(1H, d, J=8.1 Hz), 7.57–7.62(3H, m), 7.63–7.69(3H, m), 7.74–7.77(2H, m), 7.95–8.00(3H, m), 12.45(1H, brs)

IR(Nujol): 1703 cm$^{-1}$ mp: 185–186° C.

Example 63-3

In the same manner as in Example 1, (E)-3-(2-chloro-4-phenylbenzyl)-2-methyl-5-((2-phenylethenyl)sulfonylcarbamoyl)benzo[b]furan (0.28 g) was obtained as white crystals from 5-carboxy-3-(2-chloro-4-phenylbenzyl)-2-methylbenzo[b]furan (0.25 g), N,N'-carbonyldiimidazole (0.23 g), DBU (0.22 ml) and (E)-(2-phenylethenyl)sulfonamide (0.27 g).

$^1$H-NMR(DMSO-d$_6$, δ ppm): 2.43(3H, s), 4.12(2H, s), 7.20(1H, d, J=7.8 Hz), 7.34–7.58(10H, m), 7.64(2H, d, J=7.4 Hz), 7.69(2H, brs), 7.75(1H, s), 8.04(1H, s)

IR(Nujol): 1698 cm$^{-1}$ mp: 218–219° C.

Example 63-4

In the same manner as in Example 1, 3-(2-chloro-4-phenylbenzyl)-2-methyl-5-(4-vinylbenzenesulfonylcarbamoyl)benzo[b]furan (0.28 g) was obtained as a white powder from 5-carboxy-3-(2-chloro-4-phenylbenzyl)-2-methylbenzo[b]furan (0.25 g), N,N'-carbonyldiimidazole (0.23 g), DBU (0.22 ml) and 4-vinylbenzenesulfonamide (0.27 g).

$^1$H-NMR(DMSO-d$_6$, δ ppm): 2.43(3H, s), 4.12(2H, s), 5.44(1H, d, J=11.0 Hz), 5.99(1H, d, J=17.7 Hz), 6.78(1H, dd, J=17.7 and 11.0 Hz), 7.22(1H, d, J=8.2 Hz), 7.37(1H, t, J=7.2 Hz), 7.44(2H, t, J=7.7 Hz), 7.54(1H, dd, J=8.1 and 1.8 Hz), 7.59(1H, d, J=8.7 Hz), 7.64–7.69(4H, m), 7.74–7.77(2H, m), 7.93(2H, d, J=8.4 Hz), 8.00(1H, d, J=1.7 Hz), 12.46(1H, brs)

IR(Nujol): 1706 cm$^{-1}$ mp: 176–178° C.

Example 63-5

In the same manner as in Example 1, 3-(2-chloro-4-phenylbenzyl)-2-methyl-5-(((E)-1-pentene-1-sulfonyl)carbamoyl)benzo[b]furan (0.28 g) was obtained as a white powder from 5-carboxy-3-(2-chloro-4-phenylbenzyl)-2-methylbenzo[b]furan (0.22 g), N,N'-carbonyldiimidazole (0.16 g), DBU (0.15 ml) and 1-pentene-1-sulfonamide (0.27 g).

¹H-NMR(DMSO-d₆, δ ppm): 0.84(3H, t, J=7.4 Hz), 1.37–1.45(2H, m), 2.18–2.24(2H, m), 2.45(3H, s), 4.14(2H, s), 6.75(1H, d, J=15.2 Hz), 6.82–6.89(1H, m), 7.23(1H, d, J=8.0 Hz), 7.37(1H, t, J=7.4 Hz), 7.44(2H, t, J=7.6 Hz), 7.77(1H, d, J=1.9 Hz), 7.81(1H, d, J=8.6 Hz), 8.04(1H, s), 12.07(1H, brs)

IR(Nujol): 1688 cm⁻¹ mp: 166–167° C.

Example 64-1

In the same manner as in Example 1, 3-(4-bromo-2-chlorobenzyl)-2-methyl-5-(1-pentanesulfonylcarbamoyl)benzo[b]furan (0.07 g) was obtained as white crystals from 3-(4-bromo-2-chlorobenzyl)-5-carboxy-2-methylbenzo-[b]furan (0.21 g), N,N'-carbonyldiimidazole (0.19 g), DBU (0.18 ml) and 1-pentanesulfonamide (0.18 g).

¹H-NMR(DMSO-d₆, δ ppm): 0.81(3H, t, J=7.3 Hz), 1.23–1.29(2H, m), 1.31–1.38(2H, m), 1.63–1.70(2H, m), 2.42(3H, s), 3.49(2H, t, J=7.8 Hz), 4.07(2H, s), 7.12(1H, d, J=8.4 Hz), 7.45(1H, dd, J=8.3 and 2.1 Hz), 7.61(1H, d, J=8.6 Hz), 7.75(1H, d, J=2.1 Hz), 7.82(1H, dd, J=8.6 and 1.9 Hz), 7.99(1H, d, J=1.7 Hz), 11.95(1H, brs)

IR(Nujol): 1688 cm⁻¹ mp: 133–134.5° C.

Example 64-2

In the same manner as in Example 1, 5-(benzenesulfonylcarbamoyl)-3-(4-bromo-2-chlorobenzyl)-2-methylbenzo[b]furan (0.21 g) was obtained as white crystals from 3-(4-bromo-2-chlorobenzyl)-5-carboxy-2-methylbenzo-[b]furan (0.21 g), N,N'-carbonyldiimidazole (0.19 g), DBU (0.18 ml) and benzenesulfonamide (0.18 g).

¹H-NMR(DMSO-d₆, δ ppm): 2.39(3H, s), 4.05(2H, s), 7.09(1H, d, J=8.3 Hz), 7.45(1H, dd, J=8.3 and 2.0 Hz), 7.58(1H, d, J=8.7 Hz), 7.62(2H, t, J=7.7 Hz), 7.68–7.72(1H, m), 7.74(1H, d, J=2.1 Hz), 7.75(1H, dd, J=8.7 and 1.8 Hz), 7.93(1H, d, J=1.7 Hz), 7.96–7.99(2H, m), 12.45(1H, brs)

IR(Nujol): 1703 cm⁻¹ mp: 176–177° C.

Example 64-3

In the same manner as in Example 1, (E)-3-(4-bromo-2-chlorobenzyl)-2-methyl-5-((2-phenylethenyl)sulfonylcarbamoyl)benzo[b]furan (0.13 g) was obtained as white crystals from 3-(4-bromo-2-chlorobenzyl)-5-carboxy-2-methylbenzo[b]furan (0.21 g), N,N'-carbonyldiimidazole (0.19 g), DBU (0.18 ml) and (E)-(2-phenylethenyl)sulfonamide (0.21 g).

¹H-NMR(DMSO-d₆, δ ppm) 2.40(3H, s), 4.05(2H, s), 7.09(1H, d, J=8.3 Hz), 7.42–7.47(5H, m), 7.49(1H, d, J=15.4 Hz), 7.59(1H, d, J=8.7 Hz), 7.64(1H, d, J=15.5 Hz), 7.73 (1H, d, J=2.1 Hz), 7.74–7.77(1H, m), 7.82(1H, dd, J=8.7 and 1.9 Hz), 7.00(1H, d, J=1.8 Hz), 12.20(1H, brs)

IR(Nujol): 1687 cm⁻¹ mp: 214–215° C.

Example 65-1

In the same manner as in Example 1, 3-(2,4-dichlorobenzyl)-2-methyl-5-[(4-methylbenzene)sulfonylcarbamoyl]-3H-imidazo[4,5-b]pyridine (84 mg) was obtained as colorless crystals from 3-(2,4-dichlorobenzyl)-2-methyl-3H-imidazo[4,5-b]pyridine-5-carboxylic acid (100 mg) and (4-methylbenzene)sulfonamide (76 mg).

¹H-NMR(CDCl₆): 2.42(3H, s), 2.62(3H, s), 5.55(2H, s), 6.70(1H, d, J=8 Hz), 7.21(1H, dd, J=8 and 1 Hz), 7.35(2H, d, J=8 Hz), 7.52(1H, d, J=1 Hz), 8.01–8.12(3H, m)

Mass(ESI): m/z 487 (M-1)

mp: 127–128° C.

Example 65-2

In the same manner as in Example 1, 3-(2,4-dichlorobenzyl)-2-methyl-5-[(4-vinylbenzene)sulfonylcarbamoyl]-3H-imidazo[4,5-b]pyridine (96 mg) was obtained as colorless crystals from 3-(2,4-dichlorobenzyl)-2-methyl-3H-imidazo[4,5-b]pyridine-5-carboxylic acid (100 mg) and (4-vinylbenzene)sulfonamide (82 mg).

¹H-NMR(CDCl₃): 2.60(3H, s), 5.42(1H, d, J=10 Hz), 5.54(2H, s), 5.89(1H, d, J=16 Hz), 6.65–6.80(2H, m), 7.21 (1H, dd, J=8 and 1 Hz), 7.50–7.59(3H, m), 8.04–8.14(4H, m)

Mass(ESI): m/z 499 (M-1)

mp: 194–195° C.

Example 65-3

In the same manner as in Example 1, (E)-3-(2,4-dichlorobenzyl)-2-methyl-5-[(2-phenylethenyl)sulfonylcarbamoyl]-3H-imidazo[4,5-b]pyridine (96 mg) was obtained as colorless crystals from 3-(2,4-dichlorobenzyl)-2-methyl-3H-imidazo[4,5-b]pyridine-5-carboxylic acid (100 mg) and (E)-(2-phenylethene)sulfonamide (82 mg).

¹H-NMR(CDCl₃): 2.61(3H, s), 5.56(2H, s), 6.62(1H, d, J=8 Hz), 7.10–7.21(2H, m), 7.37–7.46(2H, m), 7.50–7.58 (2H, m), 7.82(1H, d, J=15 Hz), 8.11(1H, d, J=8 Hz), 8.19 (1H, d, J=8 Hz), 10.0(1H, s)

Mass(ESI): m/z 499 (M−1)

mp: 192–194° C.

Example 65-4

In the same manner as in Example 1, 5-((5-chlorothiophene-2-yl)sulfonylcarbamoyl)-3-(2,4-dichlorobenzyl)-2-methyl-3H-imidazo[4,5-b]pyridine (150 mg) was obtained as a white powder from 3-(2,4-dichlorobenzyl)-2-methyl-3H-imidazo[4,5-b]pyridine-5-carboxylic acid (165 mg) and 5-chlorothiophene-2-sulfonamide (140 mg).

¹H-NMR(CDCl₃): 2.61(3H, s), 5.55(2H, s), 6.68(1H, d, J=8 Hz), 6.95(1H, d, J=4 Hz), 7.20(1H, dd, J=8 and 2 Hz), 7.52(1H, d, J=2 Hz), 7.76(1H, d, J=4 Hz), 8.11(1H, d, J=8 Hz), 8.15(1H, d, J=8 Hz), 10.05(1H, brs)

Mass(ESI): m/e 513 (M−H)⁻ mp: 206–207° C.

Example 65-5

In the same manner as in Example 1, 5-((5-bromothiophen-2-yl)sulfonylcarbamoyl)-3-(2,4-dichlorobenzyl)-2-methyl-3H-imidazo[4,5-b]pyridine (152 mg) was obtained as a white powder from 3-(2,4-dichlorobenzyl)-2-methyl-3H-imidazo[4,5-b]pyridine-5-carboxylic acid (166 mg) and 5-bromothiophene-2-sulfonamide (176 mg).

¹H-NMR(CDCl₃): 2.64(3H, s), 5.56(2H, s), 6.68(1H, d, J=8 Hz), 7.10(1H, d, J=4 Hz), 7.22(1H, d, J=8 Hz), 7.53(1H, s), 7.74(1H, d, J=4 Hz), 8.11(1H, d, J=8 Hz), 8.16(1H, d, J=8 Hz), 10.05(1H, brs)

Mass(ESI): m/e 557, 559 (M−H)⁻ mp: 168–169° C.

Example 66-1

In the same manner as in Example 1, (E)-3-(4-bromo-2-chlorobenzyl)-2-methyl-5-[(2-phenylethenyl)sulfonylcarbamoyl]-3H-imidazo[4,5-b]pyridine (77 mg) was obtained as colorless crystals from 3-(4-bromo-2-chlorobenzyl)-2-methyl-3H-imidazo[4,5-b]pyridine-5-carboxylic acid (100 mg) and (E)-(2-phenylethene)sulfonamide (72 mg).

¹H-NMR(CDCl₃): 2.61(3H, s), 5.56(2H, s), 6.62(1H, d, J=8 Hz), 7.15(1H, d, J=15 Hz), 7.33(1H, dd, J=8 and 1 Hz), 7.38–7.46(3H, m), 7.50–7.58(2H, m), 7.68(1H, brs), 7.81 (1H, d, J=15 Hz), 8.11 (1H, d, J=8 Hz), 8.19(1H, d, J=8 Hz), 10.0(1H, brs)

Mass(ESI): m/z 545 (M−1)

mp: 204–205° C.

Example 66-2

In the same manner as in Example 1, 3-(4-bromo-2-chlorobenzyl)-2-methyl-5-[(4-vinylbenzene)sulfonylcarbamoyl]-3H-imidazo[4,5-b]pyridine (96 mg) was obtained as colorless crystals from 3-(4-bromo-2-chlorobenzyl)-2-methyl-3H-imidazo[4,5-b]pyridine-5-carboxylic acid (100 mg) and (4-vinylbenzene)sulfonamide (72 mg).

¹H-NMR(CDCl₃ ): 2.61(3H, s), 5.44(1H, d, J=10 Hz), 5.52(2H, s), 5.89(1H, d, J=16 Hz), 6.61(1H, d, J=8 Hz), 6.75(1H, dd, J=16 and 10 Hz), 7.38(1H, d, J=8 Hz), 7.54(2H, d, J=8 Hz), 7.69(1H, brs), 8.03–8.15(4H, m)

Mass(ESI): m/z 545 (M−1)

mp: 208–210° C.

Example 67-1

In the same manner as in Example 1, 3-(2-chloro-4-phenylbenzyl)-2-methyl-5-[(4-vinylbenzene)sulfonylcarbamoyl]-3H-imidazo[4,5-b]pyridine (70 mg) was obtained as colorless crystals from 3-(2-chloro-4-phenylbenzyl)-2-methyl-3H-imidazo[4,5-b]pyridine-5-carboxylic acid (100 mg) and (4-vinylbenzene)sulfonamide (73 mg).

¹H-NMR(CDCl₃): 2.67(3H, s), 5.42(1H, d, J=10 Hz), 5.61(2H, s), 5.85(1H, d, J=16 Hz), 6.70(1H, dd, J=16 and 10 Hz), 6.89(1H, d, J=8 Hz), 7.38–7.52(6H, m), 7.59(2H, d, J=8 Hz), 7.73(1H, brs), 8.01–8.12(4H, m)

Mass(ESI): m/z 541 (M−1)

mp: 178–179° C.

Example 67-2

In the same manner as in Example 1, (E)-3-(2-chloro-4-phenylbenzyl)-2-methyl-5-[(2-phenylethenyl)sulfonylcarbamoyl]-3H-imidazo[4,5-b]pyridine (78 mg) was obtained as colorless crystals from 3-(2-chloro-4-phenylbenzyl)-2-methyl-3H-imidazo[4,5-b]pyridine-5-carboxylic acid (100 mg) and (E)-(2-phenylethene)sulfonamide (73 mg).

¹H-NMR(CDCl₃): 2.66(3H, s), 5.61(2H, s), 6.80(1H, d, J=8 Hz), 7.12(1H, d, J=15 Hz), 7.34–7.60(11H, m), 7.71(1H, d, J=2 Hz), 7.79(1H, d, J=15 Hz), 8.11(1H, d, 8 Hz), 8.19(1H, d, J=8 Hz), 10.6(1H, brs)

Mass(ESI): m/z 541 (M−1)

mp: 216–218° C.

Example 67-3

In the same manner as in Example 1, 3-(2-chloro-4-phenylbenzyl)-5-[(5-chlorothiophene-2-yl)sulfonylcarbamoyl]-2-methyl-3H-imidazo[4,5-b]pyridine (78 mg) was obtained as colorless crystals from 3-(2-chloro-4-phenylbenzyl)-2-methyl-3H-imidazo[4,5-b]pyridine-5-carboxylic acid (100 mg) and 5-chlorothiophene-2-sulfonamide (79 mg).

¹H-NMR(CDCl₃): 2.69(3H, s), 5.60(2H, s), 6.84–6.91 (2H, m), 7.34–7.50(4H, m), 7.52–7.60(2H, m), 7.67–7.74 (2H, m), 8.09(1H, d, J=8 Hz), 8.13(1H, d, J=8 Hz)

Mass(ESI): m/z 555 (M−1)

mp: 210–212° C.

Example 67-4

In the same manner as in Example 1, 3-(2-chloro-4-phenylbenzyl)-2-methyl-5-[(4-methylbenzene)sulfonylcarbamoyl]-3H-imidazo[4,5-b]pyridine (221 mg) was obtained as colorless crystals from 3-(2-chloro-4-phenylbenzyl)-2-methyl-3H-imidazo[4,5-b]pyridine-5-carboxylic acid (200 mg) and (4-methylbenzene)sulfonamide (136 mg).

¹H-NMR(CDCl₃): 2.39(3H, s), 2.67(3H, s), 5.62(2H, s), 6.87(1H, d, J=8 Hz), 7.27(2H, d, J=8 Hz), 7.36–7.50(4H, m), 7.58(2H, d, J=8 Hz), 7.72(1H, d, J=2 Hz), 7.99(2H, d, J=8 Hz), 8.05(1H, d, J=8 Hz), 8.10(1H, d, J=8 Hz)

Mass(ESI) m/z 529 (M−1)

mp: 171–173° C.

Example 67-5

In the same manner as in Example 1, 5-[(5-bromothiophen-2-yl)sulfonylcarbamoyl]-3-(2-chloro-4-phenylbenzyl)-2-methyl-3H-imidazo[4,5-b]pyridine (198 mg) was obtained as colorless crystals from 3-(2-chloro-4-phenylbenzyl)-2-methyl-3H-imidazo[4,5-b]pyridine-5-carboxylic acid (200 mg) and 5-bromotiophene-2-sulfonamide (192 mg) .

¹H-NMR(CDCl₃): 2.68(3H, s), 5.61(2H, s), 6.87(1H, d, J=8 Hz), 7.03(1H, d, J=5 Hz), 7.36–7.50(4H, m), 7.57(2H, d, J=8 Hz), 7.65(1H, d, J=5 Hz), 7.72(1H, s), 8.09(1H, d, J=8 Hz), 8.15(1H, d, J=8 Hz).

Mass(ESI): m/z 601 (M−1)

mp: 205–207° C.

Example 67-6

In the same manner as in Example 1, 3-(2-chloro-4-phenylbenzyl)-5-[(4-ethylbenzene)sulfonylcarbamoyl]-2-methyl-3H-imidazo[4,5-b]pyridine (213 mg) was obtained as colorless crystals from 3-(2-chloro-4-phenylbenzyl)-2-methyl-3H-imidazo[4,5-b]pyridine-5-carboxylic acid (200 mg) and (4-ethylbenzene)sulfonamide (147 mg).

¹H-NMR(CDCl₃): 1.22(3H, t, J=8 Hz), 2.63–2.75(5H, m), 5.62(2H, s), 6.88(1H, d, J=8 Hz), 7.29(2H, d, J=8 Hz), 7.36–7.50(4H, m), 7.60(2H, d, J=8 Hz), 7.73(1H, d, J=2 Hz), 8.01(2H, d, J=8 Hz), 8.07(1H, d, J=8 Hz), 8.11(1H, d, J=8 Hz).

Mass(ESI): m/z 529 (M−1)

mp: 205–206° C.

Example 68

In the same manner as in Example 1, 5-(benzenesulfonylcarbamoyl)-3-[2-chloro-4-(thiophen-2- yl)benzyl]-2-methyl-3H-imidazo[4,5-b]pyridine (53 mg) was obtained as colorless crystals from 3-[2-chloro-4-(thiophene-2-yl)benzyl]-2-methyl-3H-imidazo[4,5-b]pyridine-5-carboxylic acid (58 mg) and benzenesulfonamide (36 mg).

$^1$H-NMR(CDCl$_3$): 2.66(3H, s), 5.59(2H, s), 6.85(1H, d, J=8 Hz), 7.10(1H, t, J=4 Hz), 7.32–7.39(2H, m), 7.44–7.52 (3H, m), 7.59(2H, d, J=8 Hz), 7.72(1H, brs), 8.05–8.14(4H, m).

Mass(ESI) m/z 521 (M−1)

mp: 225–226° C.

Example 69

In the same manner as in Example 1, 5-(benzenesulfonylcarbamoyl)-3-[2-chloro-4-(5-chlorothiophene-2-yl)benzyl]-2-methyl-3H-imidazo[4,5-b]pyridine (27 mg) was obtained as colorless crystals from 3-[2-chloro-4-(5-chlorothiophene-2-yl)benzyl]-2-methyl-3H-imidazo[4,5-b]pyridine-5-carboxylic acid (30 mg) and benzenesulfonamide (17 mg).

$^1$H-NMR(CDCl$_3$): 2.66(3H, s), 5.59(2H, s), 6.82(1H, d, J=8 Hz), 6.91(1H, d, J=4 Hz), 7.12(1H, d, J=4 Hz), 7.38(1H, d, J=8 Hz), 7.46–7.54(2H, m), 7.59–7.65(2H, m), 8.04–8.19 (4H, m).

Mass(ESI): m/z 555 (M−1)

mp: 215–217° C.

Example 70-1

In the same manner as in Example 1, 3-(2-chloro-4-ethylbenzyl)-2-methyl-5-(1-pentanesulfonylcarbamoyl)-3H-imidazo[4,5-b]pyridine (42 mg) was obtained as pale-yellow crystals from 3-(2-chloro-4-ethylbenzyl)-2-methyl-3H-imidazo[4,5-b]pyridine-5-carboxylic acid (42 mg) and 1-pentanesulfonamide (29 mg).

$^1$H-NMR(CDCl$_3$): 0.89(3H, t, J=8 Hz), 1.22(3H, d, J=8 Hz), 1.28–1.50(4H, m), 1.81–1.95(2H, m), 2.58–2.68(5H, m), 3.51–3.59(2H, m), 5.55(2H, s), 6.65(1H, d, J=8 Hz), 7.02(1H, brd, J=8 Hz), 7.31(1H, brs), 8.12(1H, d, J=8 Hz), 8.20(1H, d, J=8 Hz), 9.81(1H, brs).

Mass(ESI): m/z 461 (M−1)

mp: 138–139° C.

Example 70-2

In the same manner as in Example 1, 5-(benzenesulfonylcarbamoyl)-3-(2-chloro-4-ethylbenzyl)-2-methyl-3H-imidazo[4,5-b]pyridine (30 mg) was obtained as pale-yellow crystals from 3-(2-chloro-4-ethylbenzyl)-2-methyl-3H-imidazo[4,5-b]pyridine-5-carboxylic acid (42 mg) and benzenesulfonamide (30 mg).

$^1$H-NMR(CDCl$_3$): 1.24(3H, t, J=8 Hz), 2.59–2.70(5H, m), 5.56(2H, s), 6.68(1H, d, J=8 Hz), 7.04(1H, brd, J=8 Hz), 7.33(1H, brs), 7.51–7.68(3H, m), 8.05(1H, d, 8.10(1H, d, J=8 Hz), 8.19(2H, d, J=8 Hz).

Mass(ESI): m/z 467 (M−1)

mp: 167–168° C.

Example 70-3

In the same manner as in Example 1, 3-(2-chloro-4-ethylbenzyl)-2-methyl-5-[(4-methylbenzene)sulfonylcarbamoyl]-3H-imidazo[4,5-b]pyridine (33 mg) was obtained as pale-yellow crystals from 3-(2-chloro-4-ethylbenzyl)-2-methyl-3H-imidazo[4,5-b]pyridine-5-carboxylic acid (42 mg) and (4-methylbenzene)sulfonamide (33 mg).

$^1$H-NMR(CDCl$_3$): 1.24(3H, t, J=8 Hz), 2.41(3H, s), 2.60–2.70(5H, m), 5.56(2H, s), 6.65(1H, d, J=8 Hz), 7.04 (1H, brd, J=8 Hz), 7.30–7.37(3H, m), 8.01–8.10(4H, m).

Mass(ESI): m/z 481 (M−1)

mp: 190–191° C.

Example 70-4

In the same manner as in Example 1, (E)-3-(2-chloro-4-ethylbenzyl)-2-methyl-5-[(2-phenylethenyl)sulfonylcarbamoyl]-3H-imidazo[4,5-b]pyridine (33 mg) was obtained as pale-yellow crystals from 3-(2-chloro-4-ethylbenzyl)-2-methyl-3H-imidazo[4,5-b]pyridine-5-carboxylic acid (42 mg) and (E)-(2-phenylethene)sulfonamide (35 mg).

$^1$H-NMR(CDCl$_3$): 1.23(3H, t, J=8 Hz), 2.57–2.68(5H, m), 5.55(2H, s), 6.61(1H, d, J=8 Hz), 7.02(1H, brd, J=8 Hz), 7.15(1H, d, J=15 Hz), 7.31(1H, brs), 7.36–7.46(3H, m), 7.55(2H, d, J=8 Hz), 7.81(1H, d, J=15 Hz), 8.09(1H, d, J=8 Hz), 8.18(1H, d, J=8 Hz).

Mass(ESI): m/z 493 (M−1)

mp: 184–185° C.

Example 71

In the same manner as in Example 1, 5-(benzenesulfonylcarbamoyl)-3-(2-chloro-4-vinylbenzyl)-2-methyl-3H-imidazo[4,5-b]pyridine (46 mg) was obtained as pale-yellow crystals from 3-(2-chloro-4-vinylbenzyl)-2-methyl-3H-imidazo[4,5-b]pyridine-5-carboxylic acid (125 mg) and benzenesulfonamide (69 mg).

$^1$H-NMR(CDCl$_3$): 2.62(3H, s), 5.37(1H, d, J=10 Hz), 5.57(2H, s), 5.80(1H, d, J=16 Hz), 6.68(1H, dd, J=16 and 10 Hz), 6.86(1H, d, J=8 Hz), 7.23–7.30(1H, overlapped with H$_2$O), 7.49–7.69(4H, m), 8.05(1H, d, J=8 Hz), 8.10(1H, d, J=8 Hz), 8.17(2H, d, J=8 Hz).

Mass(ESI): m/z 465 (M−1)

mp: 174–175° C.

Example 72

In the same manner as in Example 1, 5-(benzenesulfonylcarbamoyl)-3-(2-chloro-4-methylbenzyl)-2-methyl-3H-imidazo[4,5-b]pyridine (50 mg) was obtained as a white powder from 3-(2-chloro-4-methylbenzyl)-2-methyl-3H-imidazo[4,5-b]pyridine-5-carboxylic acid (60 mg) and benzenesulfonamide (49 mg).

$^1$H-NMR(CDCl$_3$): 2.35(3H, s), 2.61(3H, s), 5.54(2H, s), 6.66(1H, d, J=8 Hz), 7.02(1H, d), 7.31(1H, s), 7.48–7.69 (3H, m), 8.00–8.10(2H, m), 8.12–8.21(2H, m), 10.05(1H, brs).

Mass(ESI): m/e 453 (M−H)$^-$ mp:213–215° C.

Example 73

In the same manner as in Example 1, 5-(benzenesulfonylcarbamoyl)-3-(2-chloro-4-(n-pentyl)benzyl)-2-methyl-3H-imidazo[4,5-b]pyridine (81 mg) was obtained as a white powder from 3-(2-chloro-4-(n-pentyl)benzyl)-2-methyl-3H-imidazo[4,5-b]pyridine-5-carboxylic acid (110 mg) and benzene-sulfonamide (70 mg).

$^1$H-NMR(CDCl$_3$): 0.88(3H, t, J=7 Hz), 1.24–1.38(4H, m), 1.50–1.68(2H, m) 2.52–2.64(2H, m), 2.62(3H, s), 5.56 (2H, s), 6.64(1H, d, J=8 Hz), 7.02(1H, d, J=8 Hz), 7.31(1H, s), 7.48–7.68(3H, m), 8.01–8.12(2H, m), 8.14–8.22(2H, m), 10.05(1H, brs).

Mass(ESI): m/e 509 (M−H)⁻ mp: 174–175° C.

Example 74

In the same manner as in Example 1, 5-(benzenesulfonylcarbamoyl)-3-(2-chloro-4-isobutylbenzyl)-2-methyl-3H-imidazo[4,5-b]pyridine (99 mg) was obtained as a white powder from 3-(2-chloro-4-isobutylbenzyl)-2-methyl-3H-imidazo[4,5-b]pyridine-5-carboxylic acid (102 mg) and benzenesulfonamide (70 mg).

$^1$H-NMR(CDCl$_3$): 0.90(6H, d, J=7 Hz), 1.76–1.95(1H, m), 2.46(2H, d, J=7 Hz), 2.61(3H, s), 5.56(2H, s), 6.63(1H, d, J=8 Hz), 6.98(1H, d, J=8 Hz), 7.29(1H, s), 7.49–7.68(3H, m), 8.01–8.12(2H, m), 8.14–8.22(2H, m), 10.05(1H, brs).

Mass(ESI): m/e 495 (M−H)⁻ mp: 183–184° C.

Example 75

In the same manner as in Example 1, 5-(benzenesulfonylcarbamoyl)-3-(2-chloro-4-(cyclohexylmethyl)benzyl)-2-methyl-3H-imidazo[4,5-b]pyridine (120 mg) was obtained as a white powder from 3-(2-chloro-4-(cyclohexyl-methyl)benzyl)-2-methyl-3H-imidazo[4,5-b]pyridine-5-carboxylic acid (141 mg) and benzenesulfonamide (88 mg).

$^1$H-NMR(CDCl$_3$): 0.82–1.76(11H, m), 2.46(2H, d, J=7 Hz), 2.61(3H, s), 5.56(2H, s), 6.61(1H, d, J=8 Hz), 6.97(1H, d, J=8 Hz), 7.28(1H, s), 7.49–7.69(3H, 8.01–8.12(2H, m), 8.14–8.21(2H, m), 10.05(1H, brs).

Mass(ESI): m/e 535 (M−H)⁻ mp: 170–171° C.

Example 76

In the same manner as in Example 1, (E)-5-(benzenesulfonylcarbamoyl)-3-(2-chloro-4-(2-phenylethenyl)benzyl)-2-methyl-3H-imidazo[4,5-b]pyridine (128 mg) was obtained as a white powder from (E)-3-(2-chloro-4-(2-phenylethenyl)-benzyl)-2-methyl-3H-imidazo[4,5-b]pyridine-5-carboxylic acid (140 mg) and benzenesulfonamide (85 mg).

$^1$H-NMR(CDCl$_3$): 2.66(3H, s), 5.58(2H, s), 6.83(1H, d, J=8 Hz), 7.03(1H, d, J=16 Hz), 7.16(1H, d, J=16 Hz), 7.27–7.66(10H, m), 8.01–8.11(2H, m), 8.11–8.30(2H, m), 10.05(1H, brs).

Mass(ESI): m/e 541 (M−H)⁻ mp: 262–263° C.

Example 77

In the same manner as in Example 1, 5-(benzenesulfonylcarbamoyl)-3-(4-2benzyloxy-2-chlorobenzyl)-2-methyl-3H-imidazo[4,5-b]pyridine (8 mg) was obtained as a white powder from 3-(4-benzyloxy-2-chlorobenzyl)-2-methyl-3H-imidazo[4,5-b]pyridine-5-carboxylic acid (98 mg) and benzenesulfonamide (57 mg).

$^1$H-NMR(CDCl$_3$): 2.63(3H, s), 5.08(2H, s), 5.52(2H, s), 6.79(1H, d, J=8 Hz), 6.88(1H, dd, J=8 and 2 Hz), 7.12(1H, d, J=2 Hz), 7.30–7.45(5H, m), 7.48–7.66(3H, m), 8.00–8.10 (2H, m), 8.12–8.22(2H, m), 10.05(1H, brs).

Mass(ESI): m/e 545 (M−H)⁻ mp: 190–191° C.

Example 78

In the same manner as in Example 1, 5-(benzenesulfonylcarbamoyl)-3-(2-chloro-4-methoxybenzyl)-2-methyl-3H-imidazo[4,5-b]pyridine (51 mg) was obtained as a white powder from 3-(2-chloro-4-methoxybenzyl)-2-methyl-3H-imidazo[4,5-b]pyridine-5-carboxylic acid (65 mg) and benzenesulfonamide (50 mg).

$^1$H-NMR(CDCl$_3$): 2.63(3H, s), 3.81(3H, s), 5.51(2H, s), 6.80(2H, s), 7.02(1H, s), 7.49–7.68(3H, m), 7.99–8.10(2H, m), 8.12–8.22(2H, m), 10.50(1H, brs).

Mass(ESI): m/e 469 (M−H)⁻ mp: 151–152° C.

Example 79

In the same manner as in Example 1, 5-(benzenesulfonylcarbamoyl)-3-(2-chloro-4-isopropoxybenzyl)-2-methyl-3H-imidazo[4,5-b]pyridine (53 mg) was obtained as a white powder from 3-(2-chloro-4-isopropoxybenzyl)-2-methyl-3H-imidazo[4,5-b]pyridine-5-carboxylic acid (61 mg) and benzenesulfonamide (45 mg).

$^1$H-NMR(CDCl$_3$): 1.33(6H, d, J=7 Hz), 2.63(3H, s), 4.53 (1H, sept, J=7 Hz), 5.50(2H, s), 6.75(2H, s), 7.00(1H, s), 7.48–7.70(3H, m), 8.03(1H, d, J=8 Hz), 8.07(1H, d, J=8 Hz), 8.16(2H, d, J=8 Hz), 10.20(1H, brs).

Mass(ESI): m/e 497 (M−H)⁻ mp: 177–179° C.

Example 80

In the same manner as in Example 1, 5-(benzenesulfonylcarbamoyl)-3-(4-(n-butoxy)-2-chlorobenzyl)-2-methyl-3H-imidazo[4,5-b]pyridine (88 mg) was obtained as a white powder from 3-(4-(n-butoxy)-2-chlorobenzyl)-2-methyl-3H-imidazo[4,5-b]pyridine-5-carboxylic acid (75 mg) and benzenesulfonamide (51 mg).

$^1$H-NMR(CDCl$_3$): 0.98(3H, t, J=7 Hz), 1.39–1.57(2H, m), 1.69–1.82(2H, m), 2.63(3H, s), 3.97(2H, t, J=7 Hz), 5.51(2H, s), 6.78(2H, s), 7.02(1H, s), 7.49–7.68(3H, m), 7.99–8.10(2H, m), 8.13–8.20(2H, m), 10.05(1H, brs).

Mass(ESI): m/e 511 (M−H)⁻ mp: 181–182° C.

Example 81

In the same manner as in Example 1, 5-(benzenesulfonylcarbamoyl)-3-(2-chloro-4-((cyclohexylmethyl)oxy)benzyl)-2-methyl-3H-imidazo4,5-b]pyridine (46 mg) was obtained as a white powder from 3-(2-chloro-4-((cyclohexylmethyl)-oxy)benzyl)-2-methyl-3H-imidazo[4,5-b]pyridine-5-carboxylic acid (45 mg) and benzenesulfonamide (30 mg).

$^1$H-NMR(CDCl$_3$): 0.95–1.90(11H, m), 2.62(3H, s), 3.74 (2H, d, J=7 Hz), 5.51(2H, s), 6.78(2H, s), 7.01(11H, s), 7.48–7.68(3H, m), 7.99–8.09(2H, m), 8.12–8.21(2H, m), 10.05(1H, brs).

Mass(ESI): m/e 551 (M−H)⁻ mp: 122–125° C.

Example 82

In the same manner as in Example 1, 5-(benzenesulfonylcarbamoyl)-3-(2-chloro-4-((2-(N-methyl-N-(2-pyridinyl)amino)ethyl)oxy)benzyl)-2-methyl-3H-imidazo[4,5-b]pyridine (54 mg) was obtained as a white powder from 3-(2-chloro-4-((2-(N-methyl-N-(2-pyridinyl)amino)ethyl)oxy)benzyl)-2-methyl-3H-imidazo[4,5-b]pyridine-5-carboxylic acid (103 mg) and benzenesulfonamide (56 mg).

$^1$H-NMR(CDCl$_3$): 2.62(3H, s), 3.12(3H, s), 3.98(2H, t, J=5 Hz), 4.19(2H, t, J=5 Hz), 5.51(2H, s), 6.51(1H, d, J=8

Hz), 6.57(1H, dd, J=8 and 5 Hz), 6.78(2H, s),7.10(1H, s), 7.38–7.67(4H, m), 7.99–8.10(2H, m), 8.12–8.21(3H, m), 10.05(1H, brs).

Mass(ESI): m/e 591 (M+H)$^+$ mp: 104–105° C.

Example 83

In the same manner as in Example 1, 5-(benzenesulfonylcarbamoyl)-3-(2-chloro-4-(methylthio) benzyl)-2-methyl-3H-imidazo[4,5-b]pyridine (53 mg) was obtained as a white powder from 3-(2-chloro-4-(methylthio) benzyl)-2-methyl-3H-imidazo[4,5-b]pyridine-5-carboxylic acid (131 mg) and benzenesulfonamide (92 mg).

$^1$H-NMR(CDCl$_3$): 2.49(3H, s), 2.62(3H, s), 5.52(2H, s), 6.74(1H, d, J=8 Hz), 7.10(1H, d,J=8 Hz), 7.33(1H, s), 7.48–7.68(3H, m), 8.00–8.10(2H, m), 8.12–8.20(2H, m), 10.05(1H, brs).

Mass(ESI): m/e 485 (M–H)$^-$ mp: 165–166° C.

Example 84

In the same manner as in Example 1, 5-(benzenesulfonylcarbamoyl)-3-(2-chloro-4-(methylsulfinyl)benzyl)-2-methyl-3H-imidazo[4,5-b] pyridine (90 mg) was obtained as a pale-yellow powder from 3-(2-chloro-4-(methyl-sulfinyl)benzyl)-2-methyl-3H-imidazo[4,5-b]pyridine-5-carboxylic acid (99 mg) and benzenesulfonamide (64 mg).

$^1$H-NMR(CDCl$_3$): 2.63(3H, s), 2.78(3H, s), 5.63(2H, s), 6.82(1H, d, J=8 Hz), 7.43(1H, d, J=8 Hz), 7.50–7.71(3H, m), 7.88(1H, s), 8.05–8.15(2H, m), 8.15–8.22(2H, m), 10.05 (1H, brs).

Mass(ES): m/e 501 (M–H)$^-$ mp : 230–231° C.

Example 85

In the same manner as in Example 1, 5-(benzenesulfonylcarbamoyl)-3-(2-chloro-4-(methanesulfonyl)benzyl)-2-methyl-3H-imidazo[4,5-b] pyridine (118 mg) was obtained as white crystals from 3-(2-chloro-4-(methane-sulfonyl)benzyl)-2-methyl-3H-imidazo[4,5-b]pyridine-5-carboxylic acid (100 mg) and benzenesulfonamide (62 mg).

$^1$H-NMR(DMSO-d$_6$): 2.48(3H, s), 3.29(3H, s), 5.93(2H, s), 6.93(1H, d, J=8 Hz), 7.63(2H, t, J=8 Hz), 7.70–7.80(2H, m), 7.90(1H, d, J=8 Hz), 8.03(2H, d, J=8 Hz), 8.13–8.18(2H, m).

Mass(ESI): m/z 517 (M–H)$^-$

Example 86

In the same manner as in Example 1, 5-(benzenesulfonylcarbamoyl)-3-(4-(benzylamino)-2-chlorobenzyl)-2-methyl-3H-imidazo[4,5-b]pyridine (55 mg) was obtained as pale-yellow crystals from 3-(4-(benzylamino)-2-chlorobenzyl)-2-methyl-3H-imidazo[4,5-b]pyridine-5-carboxylic acid (70 mg) and benzenesulfonamide (41 mg).

$^1$H-NMR(DMSO-d$_6$): 2.45(3H, s), 4.23(2H, d, J=6 Hz), 5.62(2H, s), 6.49(1H, dd, J=2 and 8 Hz), 6.61–6.68(3H, m), 7.20–7.32(5H, m), 7.65(2H, t, J=8 Hz), 7.72(1H, t, J=7 Hz), 7.87(1H, dd, J=1 and 8 Hz), 8.03(2H, d, J=8 Hz), 8.07(1H, d, J=8 Hz).

Mass(ESI): m/z 544 (M–H)$^-$

Example 87

In the same manner as in Example 1, 5-(benzenesulfonylcarbamoyl)-3-(4-(n-butylamino)-2-chlorobenzyl)-2-methyl-3H-imidazo[4,5-b]pyridine (50 mg) was obtained as pale-yellow crystals from 3-(4-(n-butylamino)-2-chlorobenzyl)-2-methyl-3H-imidazo[4,5-b] pyridine-5-carboxylic acid (45 mg) and benzenesulfonamide (29 mg).

$^1$H-NMR(DMSO-d$_6$): 0.89(3H, t, J=8 Hz), 1.30–1.421 (2H, m), 1.43–1.55(2H, m), 2.47(3H, s), 2.93(2H, q, J=7 Hz), 5.63(2H, s), 5.97(1H, t, J=7 Hz), 6.45(1H, d, J=8 Hz), 6.63(1H, d, J=7 Hz), 6.67(1H, d, J=8 Hz), 7.65(2H, t, J=7 Hz), 7.73(1H, t, J=7 Hz), 7.87(1H, dd, J=1 and 8 Hz), 8.02(2H, d, J=8 Hz), 8.08(1H, d, J=8 Hz).

Mass(ESI) m/z 510 (M–H)$^-$

Example 88

In the same manner as in Example 1, 5-(benzenesulfonylcarbamoyl)-3-(2-chloro-4-(N,N-dimethylamino)benzyl)-2-methyl-3H-imidazo[4,5-b] pyridine (60 mg) was obtained as white crystals from 3-(2-chloro-4-(N,N-dimethyl-amino)benzyl)-2-methyl-3H-imidazo[4,5-b]pyridine-5-carboxylic acid (55 mg) and benzenesulfonamide (38 mg).

$^1$H-NMR(DMSO-d$_6$): 2.48(3H, s), 2.89(6H, s), 5.68(2H, s), 6.60(1H, dd, J=2 and 8 Hz), 6.74(1H, d, J=8 Hz), 6.77(1H, d, J=2 Hz), 7.64(2H, t, J=8 Hz), 7.73(1H, t, J=8 Hz), 7.86(1H, d, J=8 Hz), 8.03(2H, d, J=8 Hz), 8.08(1H, d, J=8 Hz).

Mass(ESI): m/z 482 (M–H)$^-$

Example 89

In the same manner as in Example 1, 3-(4-(acetamido)-2-chlorobenzyl)-5-(benzenesulfonylcarbamoyl)-2-methyl-3H-imidazo[4,5-b]pyridine (92 mg) was obtained as white crystals from 3-(4-(acetylamino)-2-chlorobenzyl)-2-methyl-3H-imidazo[4,5-b]pyridine-5-carboxylic acid (98 mg) and benzenesulfonamide (64 mg).

$^1$H-NMR(DMSO-d$_6$): 2.02(3H, s), 2.44(3H, s), 5.73(2H, s), 6.73(1H, d, J=8 Hz), 7.27(1H, d, J=8 Hz), 7.60(2H, t, J=7 Hz), 7.70(1H, t, J=7 Hz), 7.86(1H, d, J=8 Hz), 7.97–8.00 (3H, m), 8.10(1H, d, J=8 Hz).

Mass(ESI): m/z 496 (M–H)$^-$

Example 90

In the same manner as in Example 1, 5-(benzenesulfonylcarbamoyl)-3-(2-chloro-4-(methanesulfonylamino)benzyl)-2-methyl-3H-imidazo[4,5-b]pyridine (61 mg) was obtained as pale-yellow crystals from 3-(2-chloro-4-(methanesulfonylamino)benzyl)-2-methyl-3H-imidazo[4,5-b]pyridine-5-carboxylic acid (69 mg) and benzenesulfonamide (41 mg).

$^1$H-NMR(DMSO-d$_6$): 2.47(3H, s), 3.04(3H, s), 5.77(2H, s), 6.78(1H, d, J=8 Hz), 7.10(1H, d, J=8 Hz), 7.36(1H, s), 7.62(2H, t, J=7 Hz), 7.71(1H, t, J=7 Hz), 7.87(1H, d,

Example 91

In the same manner as in Example 1, 5-(benzenesulfonylcarbamoyl)-3-(2-chloro-4-nitrobenzyl)-2-methyl-3H-imidazo[4,5-b]pyridine (284 mg) was obtained as pale-brown crystals from 3-(2-chloro-4-nitrobenzyl)-2-methyl-3H-imidazo[4,5-b]pyridine-5-carboxylic acid (240 mg) and benzenesulfonamide (163 mg).

$^1$H-NMR(DMSO-d$_6$): 2.47(3H, s), 5.93(2H, s), 6.93(1H, d, J=8 Hz), 7.63(2H, t, J=7 Hz), 7.72(11H, t, J=7 Hz), 7.90(1H, d, J=8 Hz), 8.08(1H, dd, J=2 and 8 Hz), 8.15(1H, d, J=8 Hz), 8.43(1H, s).

Mass(ESI): m/z 484 (M–H)$^-$

Example 92

In the same manner as in Example 1, 5-(benzenesulfonylcarbamoyl)-3-(2-chloro-4-formylbenzyl)-2-methyl-3H-imidazo[4,5-b]pyridine (115 mg) was obtained as colorless crystals from 3-(2-chloro-4-formylbenzyl)-2-methyl-3H-imidazo[4,5-b]pyridine-5-carboxylic acid (199 mg) and benzenesulfonamide (142 mg).

$^1$H-NMR(DMSO-d$_6$): 2.48(3H, s), 5.92(2H, s), 6.91(1H, d, J=8 Hz), 7.60–7.69(2H, m), 7.71(1H, d, J=8 Hz), 7.79(1H, d, J=8 Hz), 7.90(1H, d, J=8 Hz), 8.02(2H, d, J=8 Hz), 8.10–8.19(2H, m), 9.99(1H, s), 12.25(1H, brs)

Mass(ESI): m/z 467 (M–1)

mp: 253–255° C.

Example 93

In the same manner as in Example 1, 5-(benzenesulfonylcarbamoyl)-3-[2-chloro-4-[(2,4-dioxo-1,3-thiazolidine-5-ylidene)methyl]benzyl]-2-methyl-3H-imidazo[4,5-b]pyridine (46 mg) was obtained as pale-yellow crystals from 3-[2-chloro-4-[(thiazolidine-2,4-dione-5-ylidene)methyl]benzyl]-2-methyl-3H-imidazo[4,5-b]pyridine-5-carboxylic acid (59 mg) and benzenesulfonamide (32 mg).

$^1$H-NMR(DMSO-d$_6$): 2.48(3H, s), 5.89(2H, s), 6.85(1H, d, J=8 Hz), 7.45(1H, brd, J=8 Hz), 7.60–7.75(3H, m), 7.79(1H, s), 7.86(1H, s), 7.90(1H, d, J=8 Hz), 8.00–8.05(2H, m), 8.15(1H, d, J=8 Hz).

Mass(ESI): m/z 566 (M–1)

mp: 271–274° C.

Example 94

In the same manner as in Example 1, 5-(benzenesulfonylcarbamoyl)-3-(2-chloro-4-fluorobenzyl)-2-methyl-3H-imidazo[4,5-b]pyridine (67 mg) was obtained as white crystals from 3-(2-chloro-4-fluorobenzyl)-2-methyl-3H-imidazo[4,5-b]pyridine-5-carboxylic acid (65 mg) and benzenesulfonamide (48 mg).

$^1$H-NMR(DMSO-d$_6$): 2.47(3H, s), 5.81(2H, s), 6.85(1H, dt, J=1 and 8 Hz), 7.15(1H, dt, J=2 and 8 Hz), 7.58–7.67(3H, m), 7.73(1H, t, J=8 Hz), 7.89(1H, d, J=8 Hz), 8.03(2H, d, J=8 Hz), 8.13(1H, d, J=8 Hz).

Mass(ESI): m/z 457 (M–H)$^-$

Example 95

In the same manner as in Example 1, 5-(benzenesulfonylcarbamoyl)-2-methyl-3-(2,4,6-trichlorobenzyl)-3H-imidazo[4,5-b]pyridine (82 mg) was obtained as white crystals from 2-methyl-3-(2,4,6-trichlorobenzyl)-3H-imidazo[4,5-b]pyridine-5-carboxylic acid (70 mg) and benzenesulfonamide (45 mg).

$^1$H-NMR(DMSO-d$_6$): 2.68(3H, s), 5.85(2H, s), 7.67(2H, t, J=8 Hz), 7.73–7.81(3H, m), 7.84(1H, d, J=8 Hz), 8.04(2H, d, J=8 Hz), 8.10(1H, d, J=8 Hz).

Mass(ESI): m/z 507 (M–H)$^-$

Example 96

In the same manner as in Example 1, 5-(benzenesulfonylcarbamoyl)-2-methyl-3-(2,3,4-trichlorobenzyl)-3H-imidazo[4,5-b]pyridine (141 mg) was obtained as white crystals from 2-methyl-3-(2,3,4-trichlorobenzyl)-3H-imidazo[4,5-b]pyridine-5-carboxylic acid (140 mg) and benzenesulfonamide (89 mg).

$^1$H-NMR(DMSO-d$_6$): 2.46(3H, s), 5.82(2H, s), 6.62(1H, d, J=8 Hz), 7.53(1H, d, J=8 Hz), 7.61(1H, t, J=8 Hz), 7.70(1H, t, J=8 Hz), 7.88(1H, d, J=8 Hz), 8.01(2H, d, J=8 Hz), 8.13(1H, d, J=8 Hz).

Mass(ESI): m/z 507 (M–H)$^-$

Example 97

In the same manner as in Example 1, 5-(benzenesulfonylcarbamoyl)-3-(2,4-dichloro-5-fluorobenzyl)-2-methyl-3H-imidazo[4,5-b]pyridine (108 mg) was obtained as white crystals from 3-(2,4-dichloro-5-fluorobenzyl)-2-methyl-3H-imidazo[4,5-b]pyridine-5-carboxylic acid (100 mg) and benzene-sulfonamide (67 mg).

$^1$H-NMR(DMSO-d$_6$): 2.50(3H, s), 5.80(2H, s), 6.97(1H, d, J=9 Hz), 7.65(2H, t, J=8 Hz), 7.73(1H, t, J=8 Hz), 7.88(1H, d, J=8 Hz), 7.98(1H, d, J=8 Hz), 8.03(2H, d, J=8 Hz), 8.13(1H, d, J=8 Hz).

Mass(ESI): m/z 491 (M–H)$^-$

Example 98

In the same manner as in Example 1, 5-(benzenesulfonylcarbamoyl)-3-(2-chloro-4-iodobenzyl)-2-methyl-3H-imidazo[4,5-b]pyridine (58 mg) was obtained as white crystals from 3-(2-chloro-4-iodobenzyl)-2-methyl-3H-imidazo[4,5-b]pyridine-5-carboxylic acid (70 mg) and benzenesulfonamide (39 mg).

$^1$H-NMR(DMSO-d$_6$): 2.47(3H, s), 5.78(2H, s), 6.50(1H, d, J=8 Hz), 7.60–7.67(3H, m), 7.72(1H, t, J=7 Hz), 7.88(1H, d, J=8 Hz), 7.98(1H, s), 8.03(2H, d, J=8 Hz), 8.13(2H, d, J=8 Hz).

Mass(ESI): m/z 565 (M–H)$^-$

Example 99

In the same manner as in Example 1, 5-(benzenesulfonylcarbamoyl)-3-((2,5-dichlorothiophen-3-yl)methyl)-2-methyl-3H-imidazo[4,5-b]pyridine (57 mg) was obtained as white crystals from 3-((2,5-dichlorothiophene-3-yl)methyl)-2-methyl-3H-imidazo[4,5-b]pyridine-5-carboxylic acid (55 mg) and benzenesulfonamide (38 mg).

$^1$H-NMR(DMSO-d$_6$): 2.57(3H, s), 5.63(2H, s), 6.95(1H, s), 7.65(2H, t, J=7 Hz), 7.73(1H, t, J=7 Hz), 7.88(1H, d, J=8 Hz), 8.05(2H, d, J=8 Hz), 8.10(1H, d, J=8 Hz).

Mass(ESI): m/z 479 (M–H)$^-$

Example 100

In the same manner as in Example 1, 5-(benzenesulfonylcarbamoyl)-3-(2-chloro-4,5-(methylenedioxy)benzyl)-2-methyl-3H-imidazo[4,5-b]pyridine (43 mg) was obtained as pale-yellow crystals from 3-(2-chloro-4,5-(methylenedioxy)-benzyl)-2-methyl-3H-imidazo[4,5-b]pyridine-5-carboxylic acid (80 mg) and benzenesulfonamide (55 mg).

$^1$H-NMR(DMSO-d$_6$): 2.49(3H, s), 5.72(2H, s), 6.03(2H, s), 6.42(1H, s), 7.20(1H, s), 7.63(2H, t, J=7 Hz), 7.72(1H, t, J=7 Hz), 7.87(1H, d, J=8 Hz), 8.03(2H, d, J=8 Hz), 8.10(1H, d, J=8 Hz).

Mass(ESI): m/z 483 (M–H)$^-$

Example 101

In the same manner as in Example 1, 5-(benzenesulfonylcarbamoyl)-3-((2-chloroquinolin-3-yl)

methyl)-2-methyl-3H-imidazo[4,5-b]pyridine (20 mg) was obtained as white crystals from 3-((2-chloroquinolin-3-yl) methyl)-2-methyl-3H-imidazo[4,5-b]pyridine-5-carboxylic acid (80 mg) and benzenesulfonamide (54 mg).

$^1$H-NMR(DMSO-$_6$): 2.53(3H, s), 5.92(2H, s), 7.56–7.72 (4H, m), 7.78–8.00(8H, m), 8.15(1H, d, J=8 Hz).

Mass(ESI): m/z 490 (M–H)$^-$

Example 102-1

In the same manner as in Example 1, 5-(benzenesulfonylcarbamoyl)-3-(2-chloro-4-(trifluoromethyl)benzyl)-2-methyl-3H-imidazo[4,5-b] pyridine (90 mg) was obtained as white crystals from 3-(2-chloro-4-(trifluoromethyl)-benzyl)-2-methyl-3H-imidazo[4,5-b]pyridine-5-carboxylic acid (90 mg) and benzenesulfonamide (57 mg).

$^1$H-NMR(DMSO-d$_6$): 2.48(3H, s), 5.92(2H, s), 6.90(1H, d, J=8 Hz), 7.61–7.67(3H, m), 7.90(1H, d, J=8 Hz), 8.01–8.03(3H, m), 8.17(1H, d, J=8 Hz).

Mass(ESI): m/z 507 (M–H)$^-$

Example 102-2

In the same manner as in Example 1, 3-[2-chloro-4-(trifluoromethyl)-benzyl]-2-methyl-5-(1-pentanesulfonylcarbamoyl)-3H-imidazo[4,5-b]pyridine (143 mg) was obtained as colorless crystals from 3-(2-chloro-4-(trifluoromethyl)benzyl)-2-methyl-3H-imidazo[4,5-b]pyridine-5-carboxylic acid (160 mg) and 1-pentanesulfonamide (98 mg).

$^1$H-NMR(CDCl$_3$): 0.88(3H, t, J=8 Hz), 1.27–1.52(4H, m), 1.81–1.95(2H, m), 2.62(3H, s), 3.51–3.59(2H, m), 5.63 (2H, s), 6.75(1H, d, J=8 Hz), 7.45(1H, brd, J=8 Hz), 7.79 (1H, brs), 8.16(1H, d, J=8 Hz), 8.24(1H, d, J=8 Hz), 9.75 (1H, brs).

Mass(ESI): m/z 501 (M–1)

mp: 154–155° C.

Example 102-3

In the same manner as in Example 1, 3-[2-chloro-4-(trifluoromethyl)-benzyl]-2-methyl-5-[(4-methylbenzene) sulfonylcarbamoyl]-3H-imidazo[4,5-b]pyridine (176 mg) was obtained as colorless crystals from 3-(2-chloro-4-(trifluoromethyl)benzyl)-2-methyl-3H-imidazo[4,5-b] pyridine-5-carboxylic acid (160 mg) and 4-(methylbenzene) sulfonamide (111 mg).

$^1$H-NMR(CDCl$_3$): 2.41(3H, s), 2.61(3H, s), 5.62(2H, s), 6.77(1H, d, J=8 Hz), 7.32(2H, d, J=8 Hz), 7.47(1H, brd, J=8 Hz), 7.80(1H, brs), 8.02(2H, d, J=8 Hz), 8.09(1H, d, J=8 Hz), 8.12(1H, d, J=8 Hz).

Mass(ESI): m/z 521 (M–1)

mp: 174–175° C.

Example 103

In the same manner as in Example 1, 5-(benzenesulfonylcarbamoyl)-3-(1-bromonaphthalen-2-ylmethyl)-2-methyl-3H-imidazo[4,5-b]pyridine (67 mg) was obtained as white crystals from 3-(1-bromonaphthalen-2-ylmethyl)-2-methyl-3H-imidazo[4,5-b]pyridine-5-carboxylic acid (65 mg) and benzenesulfonamide (42 mg).

$^1$H-NMR(DMSO-d$_6$): 2.45(3H, s), 6.06(2H, s), 6.80(1H, d, J=8 Hz), 7.60–7.80(5H, m), 7.89–7.94(2H, m), 7.99–8.03 (3H, m), 8.17(1H, d, J=8 Hz), 8.33(1H, d, J=8 Hz).

Mass(ESI): m/z 533 (M–H)$^-$

Example 104-1

In the same manner as in Example 1, 3-(1-bromonaphthalen-2-ylmethyl)-2,7-dimethyl-5-(pentanesulfonylcarbamoyl)-3H-imidazo[4,5-b]pyridine (184 mg) was obtained as a white powder from 3-(1-bromonaphthalen-2-ylmethyl)-2,7-dimethyl-3H-imidazo[4,5-b] pyridine-5-carboxylic acid (328 mg) and pentanesulfonamide (183 mg).

$^1$H-NMR(CDCl$_3$): 0.84(3H, t, J=7 Hz), 1.20–1.43(4H, m), 1.73–1.88(2H, m), 2.63(3H, s), 2.74(3H, s), 3.43–3.55 (2H, m), 5.79(2H, s), 6.78(1H, d, J=8 Hz), 7.52–7.86(4H, m), 8.02(1H, s), 8.38(1H, d, J=8 Hz), 9.85(1H, brs).

Mass(ESI): m/e 541, 543 (M–H)$^-$ mp: 210–211° C.

Example 104-2

In the same manner as in Example 1, 5-(benzenesulfonylcarbamoyl)-3-(1-bromonaphthalen-2-ylmethyl)-2,7-dimethyl-3H-imidazo[4,5-b]pyfldine (278 mg) was obtained as a white powder from 3-(1-bromonaphthalen-2-ylmethyl)-2,7-dimethyl-3H-imidazo[4, 5-b]pyridine-5-carboxylic acid (328 mg) and benzenesulfonamide (191 mg).

$^1$H-NMR(CDCl$_3$): 2.63(3H, s), 2.67(3H, s), 5.80(2H, s), 6.79(1H, d, J=8 Hz), 7.41–7.88(7H, m), 7.90(1H, s), 8.02–8.12(2H, m), 8.41(1H, d, J=8 Hz), 10.05(1H, brs).

Mass(ESI): m/e 547, 549 (M–H)$^-$ mp: 229–230° C.

Example 104-3

In the same manner as in Example 1, (E)-3-(1-bromonaphthalen-2-ylmethyl)-2,7-dimethyl-5-((2-phenylethenyl)sulfonylcarbamoyl)-3H-imidazo[4,5-b] pyridine (268 mg) was obtained as a white powder from 3-(1-bromonaphthalen-2-ylmethyl)-2,7-dimethyl-3H-imidazo[4,5-b]pyridine-5-carboxylic acid (337 mg) and (E)-(2-phenylethenyl)sulfonamide (228 mg).

$^1$H-NMR(CDCl$_3$): 2.62(3H, s), 2.73(3H, s), 5.80(2H, s), 6.73(1H, d, J=8 Hz), 7.09(1H, d, J=16 Hz), 7.32–7.72(8H, m), 7.77(1H, d, J=I6 Hz), 7.80–7.87(1H, m), 7.99(1H, s), 8.39(1H, d, J=8 Hz), 10.07(1H, brs).

Mass(ESI): m/e 573, 575 (M–H)$^-$ mp: 262–263° C.

Example 104-4

In the same manner as in Example 1, 3-(1-bromonaphthalen-2-ylmethyl)-2,7-dimethyl-5-((4-methylbenzene)sulfonylcarbamoyl)-3H-imidazo[4,5-b] pyridine (190 mg) was obtained as a white powder from 3-(1-bromonaphthalen-2-ylmethyl)-2,7-dimethyl-3H-imidazo[4,5-b]pyridine-5-carboxylic acid (248 mg) and (4-methylbenzene)sulfonamide (156 mg).

$^1$H-NMR(CDCl$_3$): 2.38(3H, s), 2.62(3H, s), 2.68(3H, s), 5.81(2H, s), 6.79(1H, d, J=8 Hz), 7.26(2H, d, J=8 Hz), 7.53–7.88(4H, m), 7.90(1H, s), 7.96(2H, d, J=8 Hz), 8.32 (1H, d, J=8 Hz), 10.05(1H, brs).

Mass(ESI): m/e 561, 563 (M–H)$^-$ mp: 227–228° C.

Example 104-5

In the same manner as in Example 1, 3-(1-bromonaphthalen-2-ylmethyl)-2,7-dimethyl-5-((4- vinylbenzene)sulfonylcarbamoyl)-3H-imidazo[4,5-b]pyridine (186 mg) was obtained as a white powder from 3-(1-bromonaphthalen-2-ylmethyl)-2,7-dimethyl-3H-imidazo[4,5-b]pyridine-5-carboxylic acid (250 mg) and (4-vinylbenzene)sulfonamide (165 mg).

$^1$H-NMR(CDCl$_3$): 2.62(3H, s), 2.68(3H, s), 5.42(1H, d, J=10 Hz), 5.80(2H, s), 5.85(1H, d, J=17 Hz), 6.71(1H, dd, J=17 and 10 Hz), 6.78(1H, d, J=8 Hz), 7.46(2H, d, J=8 Hz), 7.53–7.88(4H, m), 7.90(1H, s), 8.02(2H, d, J=8 Hz), 8.41(1H, d, J=8 Hz), 10.05(1H, brs).

Mass(ESI): m/e 573, 575 (M−H)$^-$ mp: 234–236° C.

Example 104-6

In the same manner as in Example 1, 3-(1-bromonaphthalen-2-ylmethyl)-2,7-dimethyl-5-((5-chlorothiophen-2-yl)sulfonylcarbamoyl)-3H-imidazo[4,5-b]pyridine (207 mg) was obtained as a white powder from 3-(1-bromonaphthalen-2-ylmethyl)-2,7-dimethyl-3H-imidazo[4,5-b]pyridine-5-carboxylic acid (249 mg) and 5-chlorothiophene-2-sulfonamide (180 mg).

$^1$H-NMR(CDCl$_3$): 2.63(3H, s), 2.70(3H, s), 5.80(2H, s), 6.79(1H, d, J=8 Hz), 6.89(1H, d, J=4 Hz), 7.53–7.88(5H, m), 7.95(1H, s), 8.40(1H, d, J=8 Hz), 10.05(1H, brs).

Mass(ESI: m/e 587, 589 (M−H)$^-$ mp: 213–214° C.

Example 105

In the same manner as in Example 1, 3-(4-bromo-2-chlorobenzyl)-2,7-dimethyl-5-(pentanesulfonylcarbamoyl)-3H-imidazo[4,5-b]pyridine (159 mg) was obtained as colorless crystals from 3-(4-bromo-2-chlorobenzyl)-2,7-dimethyl-3H-imidazo[4,5-b]pyridine-5-carboxylic acid (160 mg) and pentanesulfonamide (92 mg).

$^1$H-NMR(CDCl$_3$): 0.89(3H, t, J=8 Hz), 1.28–1.50(4H, m), 1.80–1.93(2H, m), 2.60(3H, s), 2.73(3H, s), 3.50–3.59(2H, m), 5.50(2H, s), 6.53(1H, d, J=8 Hz), 7.31(1H, brd, J=8 Hz), 7.66(1H, brs), 8.02(1H, s), 9.80(1H, brs).

Mass(ESI): m/z 527 (M−1)

mp: 148–149° C.

Example 106-1

In the same manner as in Example 1, 3-(4-bromo-2-chlorobenzyl)-2,7-dimethyl-5-[(4-methylbenzene)sulfonylcarbamoyl]-3H-imidazo[4,5-b]pyridine (161 mg) was obtained as colorless crystals from 3-(4-bromo-2-chlorobenzyl)-2,7-dimethyl-3H-imidazo[4,5-b]pyridine-5-carboxylic acid (160 mg) and (4-methylbenzene)sulfonamide (104 mg).

$^1$H-NMR(CDCl$_3$): 2.41(3H, s), 2.59(3H, s), 2.68(3H, s), 5.50(2H, s), 6.59(1H, d, J=8 Hz), 7.30–7.38(3H, m), 7.68(1H, d, J=2 Hz), 7.90(1H, brs), 8.04(2H, d, J=8 Hz).

Mass(ESI): m/z 547 (M−1)

mp: 206–208° C.

Example 106-2

In the same manner as in Example 1, (E)-3-(4-bromo-2-chlorobenzyl)-2,7-dimethyl-5-[(2-phenylethenyl)sulfonylcarbamoyl]-3H-imidazo[4,5-b]pyridine (162 mg) was obtained as colorless crystals from 3-(4-bromo-2-chlorobenzyl)-2,7-dimethyl-3H-imidazo[4,5-b]pyridine-5-carboxylic acid (160 mg) and (E)-(2-phenylethene)sulfonamide (111 mg).

$^1$H-NMR(CDCl$_3$): 2.60(3H, s), 2.72(3H, s), 5.50(2H, s), 6.51(1H, d, J=8 Hz), 7.15(1H, d, J=15 Hz), 7.31(1H, brd, J=8 Hz), 7.39–7.47(3H, m), 7.50–7.59(2H, m), 7.6(1H, brs), 7.81(1H, d, J=15 Hz), 8.00(1H, s), 10.01(1H, brs).

Mass(ESI): m/z 559 (M−1)

mp: 225–227° C.

Example 106-3

In the same manner as in Example 1, 3-(4-bromo-2-chlorobenzyl)-5-[(5-chlorothiophen-2-yl)sulfonylcarbamoyl]-2,7-dimethyl-3H-imidazo[4,5-b]pyridine (191 mg) was obtained as colorless crystals from 3-(4-bromo-2-chlorobenzyl)-2,7-dimethyl-3H-imidazo[4,5-b]pyridine-5 carboxylic acid (200 mg) and 5-chlorothiophene-2-sulfonamide (150 mg).

$^1$H-NMR(CDCl$_3$): 2.61(3H, s), 2.70(3H, s), 5.50(2H, s), 6.56(1H, d, J=8 Hz), 6.95(1H, d, J=4 Hz), 7.32(1H, dd, J=8 and 1 Hz), 7.67(1H, brs), 7.76(1H, d, J=4 Hz), 7.96(1H, s).

Mass(ESI): m/z 573 (M−1)

mp: 214–215° C.

Example 106-4

In the same manner as in Example 1, 3-(4-bromo-2-chlorobenzyl)-2,7-dimethyl-5-[(4-vinylbenzene)sulfonylcarbamoyl]-3H-imidazo[4,5-b]pyridine was obtained as colorless crystals (208 mg) from 3-(4-bromo-2-chlorobenzyl)-2,7-dimethyl-3H-imidazo[4,5-b]pyridine-5-carboxylic acid (200 mg) and (4-vinylbenzene)sulfonamide (139 mg).

$^1$H-NMR(CDCl$_3$): 2.60(3H, s), 2.68(3H, s), 5.43(1H, d, J=10 Hz), 5.50(2H, s), 5.88(1H, d, J=16 Hz), 6.57(1H, d, J=8 Hz), 6.73(1H, dd, J=16 and 10 Hz), 7.34(1H, dd, J=8 and 2 Hz), 7.55(2H, d, J=8 Hz), 7.68(1H, d, J=2 Hz), 7.90(1H, s), 8.10(2H, d, J=8 Hz).

Mass(ESI): m/z 559 (M−1)

mp: 204–205° C.

Example 106-5

In the same manner as in Example 1, 3-(4-bromo-2-chlorobenzyl)-5-[(5-bromothiophen-2-yl)sulfonylcarbamoyl]-2,7-dimethyl-3H-imidazo[4,5-b]pyridine (238 mg) was obtained as colorless crystals from 3-(4-bromo-2-chlorobenzyl)-2,7-dimethyl-3H-imidazo[4,5-b]pyridine-5-carboxylic acid (200 mg) and 5-bromothiophene-2-sulfonamide (184 mg).

$^1$H-NMR(DMSO-d$_6$) 2.46(3H, s), 2.62(3H, s), 5.74(2H, s), 6.60(1H, d, J=8 Hz), 7.39(1H, d, J=5 Hz), 7.46(1H, dd, J=8 and 2 Hz), 7.70(1H, d, J=5 Hz), 7.83(1H, s), 7.87(1H, d, J=2 Hz).

mp: 210–211° C.

Example 107-1

In the same manner as in Example 1, 5-(benzenesulfonylcarbamoyl)-3-(2-chloro-4-nitrobenzyl)-2,7-dimethyl-3H-imidazo[4,5-b]pyridine (81 mg) was obtained as a pale-brown powder from 3-(2-chloro-4-nitrobenzyl)-2,7-dimethyl-3H-imidazo[4,5-b]pyridine-5-carboxylic acid (135 mg) and benzenesulfonamide (88 mg).

$^1$H-NMR(DMSO-d$_6$): 2.46(3H, s), 2.58(3H, s), 5.89(2H, s), 6.88(1H, d, J=8 Hz), 7.55–7.76(4H, m), 7.98(1H, d, J=8 Hz), 8.07(1H, d, J=8 Hz), 8.23(1H, s), 8.43(1H, s).

Mass(ESI): m/e 498 (M−H)$^-$

Example 107-2

In the same manner as in Example 1, 3-(2-chloro-4-nitrobenzyl)-2,7-dimethyl-5-((4-methylbenzene)

sulfonylcarbamoyl)-3H-imidazo[4,5-b]pyridine (151 mg) was obtained as a yellow powder from 3-(2-chloro-4-nitrobenzyl)-2,7-dimethyl-3H-imidazo[4,5-b]pyridine-5carboxylic acid (180 mg) and (4-methylbenzene)sulfonamide (88 mg).

$^1$H-NMR(DMSO-d$_6$): 2.37(3H, s), 2.46(3H, s), 2.58(3H, s), 5.89(2H, s), 6.88(1H, d, J=8 Hz), 7.40(2H, d, J=8 Hz), 7.73(1H, s), 7.88(2H, d, J=8 Hz), 8.08(1H, dd, J=8 and 2 Hz), 8.43(1H, d, J=2 Hz).

Mass(ESI): m/e 512 (M–H)$^-$

Example 107-3

In the same manner as in Example 1, (E)-3-(2-chloro-4-nitrobenzyl)-2,7-dimethyl-5-((2-phenylethenyl)sulfonylcarbamoyl)-3H-imidazo[4,5-b]pyridine (183 mg) was obtained as a yellow powder from 3-(2-chloro-4-nitrobenzyl)-2,7-dimethyl-3H-imidazo[4,5-b]pyridine-5-carboxylic acid (180 mg) and (E)-(2-phenylethene)sulfonamide (137 mg).

$^1$H-NMR(DMSO-d$_6$): 2.46(3H, s), 2.62(3H, s), 5.90(2H, s), 6.84(1H, d, J=8 Hz), 7.38–7.47(3H, m), 7.49(1H, d, J=15 Hz), 7.65(1H, d, J=15 Hz), 7.70–7.80(2H, m), 7.84(1H, s), 8.07(1H, d, J=8 Hz), 8.42(1H, s).

Mass(ESI): m/e 524 (M–H)$^-$

Example 107-4

In the same manner as in Example 1, 3-(2-chloro-4-nitrobenzyl)-2,7-dimethyl-5-((4-vinylbenzene)sulfonylcarbamoyl)-3H-imidazo[4,5-b]pyridine (85 mg) was obtained as a yellow powder from 3-(2-chloro-4-nitrobenzyl)-2,7-dimethyl-3H-imidazo[4,5-b]pyridine-5-carboxylic acid (180 mg) and (4-vinylbenzene)sulfonamide (137 mg).

$^1$H-NMR(DMSO-d$_6$): 2.48(3H, s), 2.60(3H, s), 5.48(1H, d, J=12 Hz), 5.91(2H, s), 6.02(1H, d, J=18 Hz), 6.82(1H, dd, J=18 and 12 Hz), 6.92(1H, d, J=8 Hz), 7.67–7.78(3H, m), 7.97(2H, d, J=8 Hz), 8.09(1H, d, J=8 Hz), 8.44(1H, s).

Mass(ESI): m/e 524 (M–H)$^-$

Example 108

In the same manner as in Example 1, 5-(benzenesulfonylcarbamoyl)-3-(2-chloro-4-cyanobenzyl)-2-methyl-3H-imidazo[4,5-b]pyridine (24 mg) was obtained as a pale-yellow powder from 3-(2-chloro-4-cyanobenzyl)-2-methyl-3H-imidazo[4,5-b]pyridine-5-carboxylic acid (32 mg) and benzenesulfonamide (25 mg).

$^1$H-NMR(CDCl$_3$): 2.59(3H, s), 5.63(2H, s), 6.75(1H, d, J=8 Hz), 7.45–7.70(4H, m), 7.81(1H, s), 8.06–8.20(4H, m), 10.05(1H, brs).

Mass(ESI): m/e 464 (M–H)$^-$
mp: 242–243° C.

Example 109-1

In the same manner as in Example 1, (E)-3-(2-chloro-4-(trifluoromethyl)benzyl) -2-methyl-5-((2-phenylethenyl)sulfonylcarbamoyl)-3H-imidazo[4,5-b]pyridine (152 mg) was obtained as colorless crystals from 3-(2-chloro-4-(trifluoromethyl)benzyl)-2-methyl-3H-imidazo[4,5-b]pyridine-5-carboxylic acid (160 mg) and (E)-(2-phenylethene)sulfonamide (119 mg).

$^1$H-NMR(CDCl$_3$): 2.62(3H, s), 5.64(2H, s), 6.73(1H, d, J=8 Hz), 7.14(1H, d, J=15 Hz), 7.38–7.48(4H, m), 7.50–7.58 (2H, m), 7.78–7.85(2H, m), 8.14(1H, d, J=8 Hz), 8.21(1H, d, J=8 Hz), 9.97(1H, brs).

Mass(ESI): m/z 533 (M–1)
mp: 140–142° C.

Example 109-2

In the same manner as in Example 1, 3-(2-chloro-4-(trifluoromethyl)-benzyl)-2-methyl-5-((4-vinylbenzene)sulfonylcarbamoyl)-3H-imidazo[4,5-b]pyridine b]pyridine (41 mg) was obtained as colorless crystals from 3-(2-chloro-4-(trifluoromethyl)benzyl)-2-methyl-3H-imidazo[4,5-b]pyridine-5-carboxylic acid (160 mg) and (4-vinylbenzene)sulfonamide (119 mg).

$^1$H-NMR(CDCl$_3$): 2.62(3H, s), 5.44(1H, d, J=10 Hz), 5.63(2H, s), 5.88(1H, d, J=16 Hz), 6.68–6.80(2H, m), 7.47 (1H, brd, J=8 Hz), 7.54(2H, d, J=8 Hz), 7.80 (1H, s), 8.08–8.16(4H, m).

Mass(ESI): m/z 533 (M–1)
mp: 157–158° C.

Example 109-3

In the same manner as in Example 1, 3-(2-chloro-4-(trifluoromethyl)-benzyl)-5-((5-chlorothiophen-2-yl)sulfonylcarbamoyl)-2-methyl-3H-imidazo[4,5-b]pyridine (189 mg) was obtained as colorless crystals from 3-(2-chloro-4-(trifluoromethyl)benzyl)-2-methyl-3H-imidazo[4,5-b]pyridine-5-carboxylic acid (160 mg) and 5-chlorothiophene-2-sulfonamide (128 mg).

$^1$H-NMR(CDCl$_3$): 2.62(3H, s), 5.63(2H, s), 6.77(1H, d, J=8 Hz), 6.95(1H, d, J=4 Hz), 7.46(1H, brd, J=8 Hz), 7.75(1H, d, J=4 Hz), 7.80(1H, brs), 8.14(1H, d, J=8 Hz), 8.19(1H, d, J=8 Hz).

Mass(ESI): m/z 547 (M–1)
mp: 170–171° C.

Example 109-4

In the same manner as in Example 1, 5-((5-bromothiophen-2-yl)sulfonylcarbamoyl)-3-(2-chloro-4-(trifluoromethyl)benzyl)-2-methyl-3H-imidazo[4,5-b] pyridine was obtained as colorless crystals (203 mg) from 3-(2-chloro-4-(trifluoromethyl)benzyl)-2-methyl-3H-imidazo[4,5-b]pyridine-5-carboxylic acid (160 mg) and 5-bromothiophene-2-sulfonamide (157 mg).

$^1$H-NMR(CDCl$_3$): 2.62(3H, s), 5.63(2H, s), 6.76(1H, d, J=8 Hz), 7.09(1H, d, J=4 Hz), 7.46(1H, brd, J=8 Hz), 7.71(1H, d, J=4 Hz), 7.79(1H, brs), 8.14(1H, d, J=8 Hz), 8.19(1H, d, J=8 Hz).

Mass(ESI): m/z 593 (M–1)
mp: 172–173° C.

Example 110

In the same manner as in Example 1, 5-(benzenesulfonylcarbamoyl)-3-(2-chloro-4-phenylbenzyl)-2-methylbenzo[b]thiophene (65 mg) was obtained as white crystals from 3-(2-chloro-4-phenylbenzyl)-2-methylbenzo[b]-thiophene-5-carboxylic acid (90 mg) and benzenesulfonamide (54 mg).

$^1$H-NMR(DMSO-d$_6$): 2.46(3H, s), 4.30(2H, s), 6.78(1H, d, J=8 Hz), 7.35–7.45(4H, m), 7.58–7.70(5H, m), 7.76–7.80 (2H, m), 7.97(2H, d, J=8 Hz), 8.03(1H, d, J=8 Hz), 8.18(1H, s).

Mass(ESI): m/z 530 (M–H)$^-$

Example 111-1

In the same manner as in Example 1, 1-(2-chloro-4-phenylbenzyl)-6-((5-chlorothiophen-2-yl)

sulfonylcarbamoyl)-3-methyl-1H-indazole (39 mg) was obtained as white crystals from 6-carboxy-1-(2-chloro-4-phenylbenzyl)-3-methyl-1H-indazole (200 mg) and 5-chlorothiophene-2-sulfonamide (157 mg).

$^1$H-NMR(DMSO-d$_6$): 2.48(3H, s), 5.70(2H, s), 6.77(1H, d, J=8 Hz), 6.98(1H, d, J=3 Hz), 7.32(1H, d, J=3 Hz), 7.34–7.47(3H, m), 7.52(1H, d, J=8 Hz), 7.64–7.68(3H, m), 7.74–7.77(2H, m), 8.11(1H, s).

Mass(ESI): m/z 554 (M−H)$^−$

Example 111-2

In the same manner as in Example 1, 6-((5-bromothiophen-2-yl)sulfonylcarbamoyl)-1-(2-chloro-4-phenylbenzyl)-3-methyl-1H-indazole (197 mg) was obtained as white crystals from 6-carboxy-1-(2-chloro-4-phenylbenzyl)-3-methyl-1H-indazole (200 mg) and 5-bromothiophene-2-sulfonamide (193 mg).

$^1$H-NMR(DMSO-d$_6$): 2.50(3H, s), 5.70(2H, s), 6.77(1H, d, J=8 Hz), 7.07(1H, d, J=3 Hz), 7.28(1H, d, J=4 Hz), 7.35–7.48(3H, m), 7.52(1H, d, J=8 Hz), 7.63–7.67 (3H, m), 7.73–7.77(2H, m), 8.10(1H, s).

Mass(ESI): m/z 600 (M−H)$^−$

Example 112

In the same manner as in Example 1, 3-(1-bromonaphthalen-2-ylmethyl)-5-((5-bromothiophene-2-yl)sulfonylcarbamoyl)-2,7-dimethyl-3H-imidazo[4,5-b]pyridine (216 mg) was obtained as a white powder from 3-(1-bromonaphthalen-2-ylmethyl)-2,7-dimethyl-3H-imidazo[4,5-b]pyridine-5-carboxylic acid (209 mg) and 5-bromothiophene-2-sulfonamide (166 mg).

$^1$H-NMR(CDCl$_3$): 2.63(3H, s), 2.70(3H, s), 5.80(2H, s), 6.78(1H, d, J=8 Hz), 7.03(1H, d, J=4 Hz), 7.53–7.88(5H, m), 7.95(1H, s), 8.40(1H, d, J=8 Hz), 10.05(1H, brs).

Mass(ESI): m/e 631, 633, 635 (1:2:1, M−H)$^−$ mp: 247–248° C.

Example 113

(E)-5-(Benzenesulfonylcarbamoyl)-3-(2-chloro-4-(2-phenylethenyl)-benzyl)-2-methyl-3H-imidazo[4,5-b]pyridine (42 mg) was suspended in a mixed solvent of chloroform (4 ml), 1,4-dioxane (2 ml) and methanol (2 ml), and platinum oxide (2 mg) was added. The mixture was stirred at room temperature for 6.5 hr under a hydrogen atmosphere at 1 atm. The reaction mixture was filtrated and the solvent was evaporated. The resultant mixture was purified by silica gel column chromatography (chloroform/methanol=20/1) and crystallized from ethyl acetate/hexane to give 5-(benzenesulfonylcarbamoyl)-3-(2-chloro-4-(2-phenylethyl)benzyl)-2-methyl-3H-imidazo[4,5-b]pyridine (18 mg) as a white powder.

$^1$H-NMR(CDCl$_3$): 2.60(3H, s), 2.90(4H, s), 5.56(2H, s), 6.63(1H, d, J=8 Hz), 7.00(1H, d, J=8 Hz), 7.10–7.32(6H, m), 7.49–7.67(3H, m), 8.02–8.12(2H, m), 8.14–8.21(2H, m), 10.05(1H, brs).

Mass(ESI): m/e 543 (M−H)$^−$ mp: 180–181° C.

Example 114

5-(Benzenesulfonylcarbamoyl)-3-(2-chloro-4-nitrobenzyl)-2-methyl-3H-imidazo[4,5-b]pyridine (245 mg) was suspended in ethanol (3 ml) and reduced iron (141 mg) and acetic acid (0.289 ml) were added, and the mixture was refluxed under heating overnight. The reaction mixture was filtered through Celite, and the filtrate was washed with a mixed solvent of methanol/chloroform (1/4) and the filtrate was concentrated under reduced pressure. To the concentrated residue were added a saturated aqueous sodium hydrogen carbonate solution, water and a mixed solvent of methanol/chloroform (1/4) and the aqueous phase was made alkaline. The precipitated insoluble matter was filtered through Celite and the filtrate was washed with a mixed solvent of methanol/chloroform (1/9). The filtrate was partitioned and the organic layer was dried over anhydrous magnesium sulfate and filtrated. The filtrate was concentrated under reduced pressure to give a crude product as a pale-brown powder. The crude product (100 mg) was recrystallized from N,N-dimethylformamide-water to give 3-(4-amino-2-chlorobenzyl)-5-(benzenesulfonylcarbamoyl)-2-methyl-3H-imidazo[4,5-b]pyridine (75 mg) as brown crystals.

$^1$H-NMR(DMSO-d$_6$): 2.50(3H, s), 5.62(2H, s), 6.45(1H, d, J=8 Hz), 6.62(1H, d, J=8 Hz), 6.67(1H, s), 7.63(2H, t, J=7 Hz), 7.72(1H, t, J=7 Hz), 7.87(1H, d, J=8 Hz), 8.04(2H, d, J=8 Hz), 8.08(1H, d, J=8 Hz).

Mass(ESI): m/z 454(M−H)$^−$

Example 115

5-(Benzenesulfonylcarbamoyl)-3-(2-chloro-4-(hydroxymethyl)benzyl)-2-methyl-3H-imidazo[4,5-b]pyridine was obtained as colorless crystals (80 mg) from 5-(benzenesulfonylcarbamoyl)-3-(2-chloro-4-formylbenzyl)-2-methyl-3H-imidazo[4,5-b]pyridine (170 mg).

$^1$H-NMR(CDCl$_3$—CD$_3$OD): 2.64(3H, s), 4.68(2H, s), 5.59(2H, s), 6.80(1H, d, J=8 Hz), 7.22(1H, brd, J=8 Hz), 8.05(1H, d, J=8 Hz), 8.09(1H, d, J=8 Hz), 8.13–8.19(2H, m).

Mass(ESI): m/z 469 (M−1)

mp: 198–199° C.

Example 116

To a suspension of 5-(benzenesulfonylcarbamoyl)-3-(2-chloro-4-formylbenzyl)-2-methyl-3H-imidazo[4,5-b]pyridine (95 mg, 0.20 mmol) in tert-butyl alcohol (2 ml) and water (0.5 ml) were added 2-methyl-2-butene (63 mg, 0.90 mmol) and sodium dihydrogenphosphate (32 mg, 0.20 mmol) at room temperature. To the suspension was added sodium chlorite.(63 mg, 0.56 mmol) and the mixture was stirred at room temperature. One hour later, 2-methyl-2-butene (63 mg, 0.90 mmol) and sodium dihydrogenphosphate (32 mg, 0.20 mmol) were added. Two hours later, 1,4-dioxane (2 ml) was added and the mixture was heated to 60° C. When the solution became transparent, it was stirred at room temperature for 1 hr. Water was added to the reaction mixture and the mixture was adjusted to pH 4 with 1N hydrochloric acid. The mixture was stirred for 30 min under ice-cooling and filtrated to give a colorless powder (97 mg). The powder was suspended in acetone and the suspension was heated and stirred at room temperature for 30 min to give 5-(benzenesulfonylcarbamoyl)-3-(4-carboxy-2-chlorobenzyl)-2-methyl-3H-imidazo[4,5-b]pyridine (70 mg) as colorless crystals.

$^1$H-NMR(DMSO-d$_6$): 2.48(3H, s), 5.90(2H, s), 6.82(1H, d, J=8 Hz), 7.60–7.68(2H, m), 7.71(1H, d, J=8 Hz), 7.80(1H, d, J=8 Hz), 8.00–8.08(3H, m), 8.17(1H, d, J=8 Hz).

Mass(ESI): m/z 483 (M−1)

mp: 155–160° C.

Example 117

In the same manner as in Preparation Example 14-1, 5-(benzene-sulfonylcarbamoyl)-3-(2-chloro-4-

((methanesulfonyloxy)methyl)benzyl)-2-methyl-3H-imidazo[4,5-b]pyridine was obtained from 5-(benzenesulfonylcarbamoyl)-3-[2-chloro-4-(hydroxymethyl)benzyl]-2-methyl-3H-imidazo[4,5-b]pyridine (58 mg). This compound was used in the next reaction without purification.

Example 118

To a solution of phenol (12 mg, 0.13 mmol) in N,N-dimethylformamide (0.5 ml) was added sodium hydride (60% in mineral oil, 5.2 mg) under ice-cooling. Thirty minutes later, a solution of 5-(benzenesulfonylcarbamoyl)-3-(2-chloro-4-((methanesulfonyloxy)methyl)benzyl)-2-methyl-3H-imidazo[4,5-b]pyridine (68 mg, 0.12 mmol) in N,N-dimethylformamide (1 ml) was dropwise added, which was followed by stirring at room temperature for 3 hr. The reaction mixture was cooled with ice and water was added. Its pH was adjusted to 4 by dropwise addition of 1N hydrochloric acid. The resulting product was extracted with ethyl acetate, washed three times with water, dried over anhydrous magnesium sulfate, and concentrated. The residue was subjected to silica gel thin layer chromatography (eluent: chloroform/methanol=20/1) and crystallized from ethyl acetate to give 5-(benzenesulfonylcarbamoyl)-3-(2-chloro-4-((phenyloxy)methyl)benzyl)-2-methyl-3H-imidazo[4,5-b]pyridine (30 mg) as colorless crystals.

$^1$H-NMR(CDCl$_3$): 2.62(3H, s), 5.05(2H, s), 5.59(2H, s), 6.74(1H, d, J=8 Hz), 6.91–7.01(3H, m), 7.23–7.33(3H, m), 7.49–7.67(4H, m), 8.06(1H, d, J=8 Hz), 8.10(1H, d, J=8 Hz), 8.15–8.21(2H, m).

Mass(ESI): m/z 545 (M−1)

mp: 203–205° C.

Example 119

To a solution of 5-(benzenesulfonylcarbamoyl)-3-(4-carboxy-2-chlorobenzyl)-2-methyl-3H-imidazo[4,5-b]pyridine (25 mg, 0.052 mmol) in N,N-dimethylformamide (0.3 ml) were added ethanol (4 mg, 0.088 mmol), 1-ethyl-3-(3-dimethylaminopropyl)carbodiimide hydrochloride (12 mg, 0.062 mmol) and 1-hydroxybenzotriazole (10 mg, 0.075 mmol) at room temperature. Three hours later, ethyl acetate and water were added to the reaction mixture and the mixture was adjusted to pH 4 with 1N hydrochloric acid. The organic layer was washed with water four times, dried over anhydrous magnesium sulfate and concentrated. The residue was subjected to silica gel thin layer chromatography (eluent: chloroform/methanol=10/1) and crystallized from ethyl acetate to give 5-(benzenesulfonylcarbamoyl)-3-(2-chloro-4-(ethoxycarbonyl)benzyl)-2-methyl-3H-imidazo[4,5-b]pyridine (18 mg) as colorless crystals.

$^1$H-NMR(CDCl$_3$): 1.40(3H, t, J=8 Hz), 2.60(3H, s), 4.40 (2H, q, J=8 Hz), 5.63(2H, s), 6.72(1H, d, J=8 Hz), 7.50–7.59 (2H, m), 7.62(1H, d, J=8 Hz), 7.86(1H, d, J=8 Hz), 8.09(1H, d, J=8 Hz), 8.12(1H, d, J=8 Hz), 8.15–8.20(3H, m).

Mass(ESI): m/z 511 (M−1)

mp: 196–197° C.

Example 120

5-(Benzenesulfonylcarbamoyl)-3-(2-chloro-4-(methylcarbamoyl)benzyl)-2-methyl-3H-imidazo[4,5-b] pyridine was obtained as colorless crystals (18 mg) from 5-(benzenesulfonylcarbamoyl)-3-(4-carboxy-2-chlorobenzyl)-2-methyl-3H-imidazo[4,5-b]pyridine (29 mg) and methylamine/tetrahydrofuran solution (2M, 0.05 ml).

$^1$H-NMR(CDCl$_3$—CD$_3$OD): 2.67(3H, s), 3.99(3H, s), 5.60(2H, s), 6.99(1H, d, J=8 HZ), 7.50–7.69(4H, m), 7.96 (1H, brs), 8.05–8.15(4H, m).

Mass(ESI): m/z 496 (M−1)

mp: 257–260° C.

Example 121

5-(Benzenesulfonylcarbamoyl)-3-(4-bromo-2-chlorobenzyl)-2,7-dimethyl-3H-imidazo[4,5-b] pyridine In the same manner as in Preparation Example 4-7, the objective compound (139 mg) was obtained as colorless crystals from 3-(4-bromo-2-chlorobenzyl)-2,7-dimethyl-3H-imidazo[4,5-b]pyridine-5-carboxylic acid (160 mg) and benzenesulfonamide (96 mg).

$^1$H-NMR(CDCl$_3$): 2.60(3H, s), 2.68(3H, s), 5.51(2H, s), 6.59(1H, d, J=8 Hz), 7.35(1H, dd, J=8, 2 Hz), 7.51–7.69(4H, m), 7.91(1H, br s), 8.17 (2H, d, J=8 Hz).

Mass(ESI): m/z 533 (M−1)

mp 231–232° C.

Example 122

In the same manner as in Example 1, 3-(2-chloro-4-(E)-(2-phenyl-ethenyl)benzyl)-2-methyl-5-((4-methylbenzene)sulfonylcarbamoyl)-3H-imidazo[4,5-b]pyridine (221 mg) was obtained as white crystals from 3-(2-chloro-4-(E)-(2-phenylethenyl)benzyl)-2-methyl-3H-imidazo[4,5-b]pyridine-5-carboxylic acid (200 mg) and (4-methylbenzene)sulfonamide (126 mg).

$^1$H-NMR(CDCl$_3$): 2.36(3H, s), 2.64(3H, s), 5.58(2H, s), 6.92(1H, d, J=8 Hz), 7.03(1H, d, J=16 Hz), 7.15(1H, d, J=19 Hz), 7.25–7.38(6H, m), 7.50(2H, d, J=8 Hz), 7.63(1H, s), 8.00–8.09(4H, m)

Mass(ESI): m/z 555(M−H)⁻

Example 123

In the same manner as in Example 1, 3-(2-chloro-4-(E)-(2-phenyl-ethenyl)benzyl)-2-methyl-5-((4-vinylbenzene)sulfonylcarbamoyl)-3H-imidazo[4,5-b]pyridine (229 mg) was obtained as white crystals from 3-(2-chloro-4-(E)-(2-phenylethenyl)benzyl)-2-methyl-3H-imidazo[4,5-b]pyridine-5-carboxylic acid (200 mg) and (4-vinylbenzene)sulfonamide (135 mg).

$^1$H-NMR(CDCl$_3$): 2.65(3H, s), 5.37(1H, d, J=9 Hz), 5.57 (2H, s), 5.79(1H, d, J=16 Hz), 6.68(1H, dd, J=9, 17 Hz), 6.84(1H, d, J=8 Hz), 7.02–7.53(8H, m), 7.63(1H, s), 8.05–8.08(4H, m)

Mass(ESI): m/z 567(M−H)⁻

Example 124

In the same manner as in Example 1, 3-(2-chloro-4-(E)-(2-phenylethenyl)benzyl)-2-methyl-5-(E)-((2-phenylethenyl)sulfonylcarbamoyl)-3H-imidazo[4,5-b]pyridine (227 mg) was obtained as white crystals from 3-(2-chloro-4-(E)-(2-phenylethenyl)benzyl)-2-methyl-3H-imidazo[4,5-b]pyridine-5-carboxylic acid (200 mg) and (E)-(2-phenylethene)sulfonamide (135 mg).

$^1$H-NMR(CDCl$_3$): 2.66(3H, s), 5.58(2H, s), 6.77(1H, d, J=8 Hz), 6.98–7.17(3H, m), 7.29–7.53(11H, m), 7.63(1H, s), 7.77(1H, d, J=16 Hz), 8.10(1H, d, J=8 Hz), 8.15 (1H, d, J=8Hz)

Mass(ESI): m/z 567(M−H)⁻

Example 125

In the same manner as in Example 1, 3-(2-chloro-4-(E)-(2-phenyl-ethenyl)benzyl)-5-((5-chlorothiophen-2-yl)sulfonylcarbamoyl)-2-methyl-3H-imidazo[4,5-b]pyridine (227 mg) was obtained as white crystals from 3-(2-chloro-4-(E)-(2-phenylethenyl)benzyl)-2-methyl-3H-imidazo[4,5-b]pyridine-5-carboxylic acid (200 mg) and 5-chlorothiophene-2-sulfonamide (145 mg).

$^1$H-NMR(CDCl$_3$): 2.66(3H, s), 5.57(2H, s), 6.82(1H, d, J=8 Hz), 6.99(1H, d, J=3 Hz), 7.02(1H, d, J=16 Hz), 7.13(1H, d, J=16 Hz), 7.29–7.39(4H, m), 7.50(1H, d, J=7 Hz), 7.63(1H, s), 7.75(1H, d, J=3 Hz), 8.09(1H, d, J=8 Hz), 8.13(1H, d, J=8 Hz)

Mass(ESI): m/z 581 (M−H)$^-$

Example 126

In the same manner as in Example 1, 5-((5-bromothiophen-2-yl)sulfonylcarbamoyl)-3-(E)-(2-chloro-4-(2-phenylethenyl)benzyl)-2-methyl-3H-imidazo[4,5-b]pyridine (226 mg) was obtained as white crystals from 3-(2-chloro-4-(E)-(2-phenylethenyl)benzyl)-2-methyl-3H-imidazo[4,5-b]pyridine-5-carboxylic acid (200 mg) and 5-bromothiophene-2-sulfonamide (178 mg).

$^1$H-NMR(CDCl$_3$): 2.68(3H, s), 5.57(2H, s), 6.82(1H, d, J=8 Hz), 7.00–7.16(3H, m), 7.28–7.38(4H, m), 7.51(2H, d, J=8 Hz), 7.63(1H, s), 7.70(1H, d, J=3 Hz), 8.08(1H, d, J=8 Hz), 8.13(1H, d, J=8 Hz)

Mass(ESI): m/z 627(M−H)$^-$

Example 127

In the same manner as in Example 1, 3-(2-chloro-4-(E)-(2-phenylethenyl)benzyl)-2-methyl-5-(1-pentanesulfonylcarbamoyl)-3H-imidazo[4,5-b]pyridine (202 mg) was obtained as white crystals from 3-(2-chloro-4-(E)-(2-phenylethenyl)benzyl)-2-methyl-3H-imidazo[4,5-b]pyridine-5-carboxylic acid (200 mg) and 1-pentanesulfonamide(111 mg).

$^1$H-NMR(CDCl$_3$): 8.03(3H, t, J=7 Hz), 1.22–1.43(4H, m), 1.80–1.92(2H, m), 2.67(3H, s), 3.53(2H, t, J=8 Hz), 5.58(2H, s), 6.77(1H, d, J=8 Hz), 6.99(1H, d, J=16 Hz), 7.13(1H, d, J=17 Hz), 7.29–7.36(4H, m), 7.49(2H, d, J=8 Hz), 7.63(1H, s), 8.13(1H, d, J=8 Hz), 8.20(1H, d, J=8 Hz)

Mass(ESI): m/z 537(M+H)$^+$

Example 128

In the same manner as in Example 1, 3-(2-chloro-4-(2-phenylethyl)-benzyl)-2-methyl-5-((4-methylbenzene)sulfonylcarbamoyl)-3H-imidazo[4,5-b]pyridine (193 mg) was obtained as white crystals from 3-(2-chloro-4-(2-phenylethyl)benzyl)-2-methyl-3H-imidazo[4,5-b]pyridine-5-carboxylic acid (200 mg) and (4-methylbenzene)sulfonamide (127 mg).

$^1$H-NMR(CDCl$_3$): 2.42(3H, s), 2.02(3H, s), 2.86(4H, s), 5.56(2H, s), 6.62(1H, d, J=8 Hz), 7.00(1H, d, J=8 Hz), 7.13–7.33(8H, m), 8.02–8.09(4H, m)

Mass(ESI): m/z 557(M−H)$^-$

Example 129

In the same manner as in Example 1, 3-(2-chloro-4-(2-phenylethyl)-benzyl)-2-methyl-5-((4-vinylbenzene)sulfonylcarbamoyl)-3H-imidazo[4,5-b]pyridine (174 mg) was obtained as white crystals from 3-(2-chloro-4-(2-phenylethyl)benzyl)-2-methyl-3H-imidazo[4,5-b]pyridine-5-carboxylic acid (200 mg) and (4-vinylbenzene)sulfonamide (226 mg).

$^1$H-NMR(CDCl$_3$): 2.61(3H, s), 2.91(4H, s), 5.43(1H, d, J=10 Hz), 5.88(1H, d, J=16 Hz), 6.64(1H, d, J=8 Hz), 6.74(1H, dd, J=9,16 Hz), 7.00(1H, d, J=8 Hz), 7.16–7.33(6H, m), 7.64(2H, d, J=8 Hz), 8.04–8.14(4H, m) Mass(ESI): m/z 569(M−H)$^-$

Example 130

In the same manner as in Example 1, 3-(2-chloro-4-(2-phenylethyl)-benzyl)-2-methyl-5-(E)-((2-phenylethenyl)sulfonylcarbamoyl)-3H-imidazo[4,5-b]pyridine (242 mg) was obtained as white crystals from 3-(2-chloro-4-(2-phenylethyl)benzyl)-2-methyl-3H-imidazo[4,5-b]pyridine-5-carboxylic acid (200 mg) and (E)-(2-phenylethene)sulfonamide (226 mg).

$^1$H-NMR(CDCl$_3$): 2.61(3H, s), 2.91(4H, s), 5.57(2H, s), 6.62(1H, d, J=8 Hz), 7.00(1H, d, J=8 Hz), 7.14–7.32(7H, m), 7.42–7.45(3H, m), 7.53(2H, d, J=8 Hz), 7.83(1H, J=15 Hz), 8.08(1H, d, J=8 Hz), 8.17(1H, d, J=8 Hz)

Mass(ESI): m/z 569(M−H)$^-$

Example 131

In the same manner as in Example 1, 3-(2-chloro-4-(2-phenylethyl)-benzyl)-5-((5-chlorothiophen-2-yl)sulfonylcarbamoyl)-2-methyl-3H-imidazo[4,5-b]pyridine (199 mg) was obtained as white crystals from 3-(2-chloro-4-(2-phenylethyl)benzyl)-2-methyl-3H-imidazo[4,5-b]pyridine-5-carboxylic acid (200 mg) and 5-chlorothiophene-2-sulfonamide (243 mg).

$^1$H-NMR(CDCl$_3$): 2.63(3H, s), 2.92(3H, s), 5.56(2H, s), 6.64(1H, d, J=8 Hz), 6.96(1H, d, J=3 Hz), 7.01(1H, d, J=8 Hz), 7.16–7.32(6H, m), 7.78(1H, d, J=3 Hz), 8,08(1H, d, J=8 Hz), 8.14(1H, d, J=8 Hz)

Mass(ESI): m/z 583(M−H)$^-$

Example 132

In the same manner as in Example 1, 5-((5-bromothiophen-2-yl)sulfonylcarbamoyl)-3-(2-chloro-4-(2-phenylethyl)benzyl)-2-methyl-3H-imidazo[4,5-b]pyridine (263 mg) was obtained as white crystals from 3-(2-chloro-4-(2-phenylethyl)benzyl)-2-methyl-3H-imidazo[4,5-b]pyridine-5-carboxylic acid (200 mg) and 5-bromothiophene-2-sulfonamide (298 mg).

$^1$H-NMR(CDCl$_3$): 2.62(3H, s), 2.90(4H, s), 5.56(2H, s), 6.65(1H, d, J=8 Hz), 7.01(1H, d, J=8 Hz), 7.08(1H, d, J=3 Hz), 7.12–7.30(6H, m), 7.74(1H, d, J=4 Hz), 8.07(1H, d J=8 Hz), 8.13(1H, d, J=8 Hz)

Mass(ESI): m/z 629(M−H)$^-$

Example 133

In the same manner as in Example 1, 3-(2-chloro-4-(2-phenylethyl)-benzyl)-2-methyl-5-(1-pentanesulfonylcarbamoyl)-3H-imidazo[4,5-b]pyridine (166 mg) was obtained as white crystals from 3-(2-chloro-4-(2-phenylethyl)-benzyl)-2-methyl-3H-imidazo[4,5-b]pyridine-5-carboxylic acid (200 mg) and 1-pentanesulfonamide (186 mg).

$^1$H-NMR(CDCl$_3$): 0.88(3H, t, J=7 Hz), 1.28–1.47(4H, m), 1.83–1.94(2H, m), 2.62(3H, s), 2.90(4H, s), 3.56(2H, t, J=8 Hz), 5.56(2H, s), 6.63(1H, d, J=8 Hz), 6.97(1H, d, J=8 Hz), 7.13–7.80(6H, m), 8.13(1H, d, J=8 Hz), 8.20(1H, d, J=8 Hz)

Mass(ESI): m/z 537(M−H)$^-$

Example 134

In the same manner as in Example 1, 3-(4-benzyloxy-2-chlorobenzyl)-2-methyl-5-((4-methylbenzene)sulfonylcarbamoyl)-3H-imidazo[4,5-b]pyridine (259 mg) was obtained as white crystals from 3-(4-benzyloxy-2-chlorobenzyl)-2-methyl-3H-imidazo[4,5-b]pyridine-5-carboxylic acid (230 mg) and (4-methylbenzene)sulfonamide (145 mg).

$^1$H-NMR(CDCl$_3$): 2.41(3H, s), 2.64(3H, s), 5.06(2H, s), 5.52(2H, s), 6.78–6.88(2H, m), 7.12(1H, s), 7.29–7.43(7H, m), 8.03–8.07(4H, m)

Mass(ESI): m/z 559(M–H)$^-$

Example 135

In the same manner as in Example 1, 3-(4-benzyloxy-2-chlorobenzyl)-2-methyl-5-((4-vinylbenzene)sulfonylcarbamoyl)-3H-imidazo[4,5-b]pyridine (214 mg) was obtained as white crystals from 3-(4-benzyloxy-2-chlorobenzyl)-2-methyl-3H-imidazo[4,5-b]pyridine-5-carboxylic acid (200 mg) and (4-vinylbenzene)sulfonamide (135 mg).

$^1$H-NMR(CDCl$_3$): 2.63(3H, s), 5.07(2H, s), 5.42(1H, d, J=9 Hz), 5.51(2H, s), 5.86(1H, d, J=17 Hz), 6.67–6.90(3H, m), 7.12(1H, d, J=2 Hz), 7.32–7.43(5H, m), 7.52(2H, d, J=8 Hz), 8.02–8.13(4H, m)

Mass(ESI): m/z 571(M–H)$^-$

Example 136

In the same manner as in Example 1, 3-(4-benzyloxy-2-chlorobenzyl)-2-methyl-5-(E)-((2-phenylethenyl)sulfonylcarbamoyl)-3H-imidazo[4,5-b]pyridine (212 mg) was obtained as white crystals from 3-(4-benzyloxy-2-chlorobenzyl)-2-methyl-3H-imidazo[4,5-b]pyridine-5-carboxylic acid (200 mg) and (E)-(2-phenylethene)sulfonamide (135 mg).

$^1$H-NMR(CDCl$_3$): 2.13(3H, s), 5.06(2H, s), 5.53(2H, s), 6.73(1H, d, J=8 Hz), 6.84(1H, dd, J=2,8 Hz), 7.10–7.18(2H, m), 7.32–7.43(8H, m), 7.50–7.53(2H, m), 7.82(1H, d, J=15 Hz), 8.07(1H, d, J=8 Hz), 8.15(1H, d, J=8 Hz)

Mass(ESI): m/z 571(M–H)$^-$

Example 137

In the same manner as in Example 1, 3-(4-benzyloxy-2-chlorobenzyl)-5-((5-chlorothiophen-2-yl)sulfonylcarbamoyl)-2-methyl-3H-imidazo[4,5-b]pyridine (178 mg) was obtained as white crystals from 3-(4-benzyloxy-2-chlorobenzyl)-2-methyl-3H-imidazo[4,5-b]pyridine-5-carboxylic acid (200 mg) and 5-chlorothiophene-2-sulfonamide (145 mg).

$^1$H-NMR(CDCl$_3$): 2.67(3H, s), 5.06(2H, s), 5.51(2H, s), 6.78(1H, d, J=8 Hz), 6.85(1H, dd, J=2,8 Hz), 6.92(1H, d, J=3 Hz), 7.12(1H, d, J=2 Hz), 7.32–7.42(5H, m), 7.78(1H, d, J=7 Hz), 8.06(1H, d, J=8 Hz), 8.10(1H, d, J=8 Hz)

Mass(ESI): m/z 585(M–H)$^-$

Example 138

In the same manner as in Example 1, 3-(4-benzyloxy-2-chlorobenzyl)-5-((5-bromothiophen-2-yl)sulfonylcarbamoyl)-2-methyl-3H-imidazo[4,5-b]pyridine (227 mg) was obtained as white crystals from 3-(4-benzyloxy-2-chlorobenzyl)-2-methyl-3H-imidazo[4,5-b]pyridine-5-carboxylic acid (200 mg) and 5-bromothiophene-2-sulfonamide (178 mg).

$^1$H-NMR(CDCl$_3$): 2.63(3H, s), 5.05(2H, s), 5.52(2H, s), 6.80(1H, d, J=5 Hz), 6.84(1H, dd, J=2,8 Hz), 7.07(1H, d, J=7 Hz), 7.10(1H, d, J=3 Hz), 7.32–7.42(5H, m), 7.72(1H, d, J=3 Hz), 8.07(1H, d, J=8 Hz), 8.12(1H, d, J=8 Hz)

Mass(ESI): m/z 630(M–H)$^-$

Example 139

In the same manner as in Example 1, 3-(4-benzyloxy-2-chlorobenzyl)-2-methyl-5-(1-pentanesulfonylcarbamoyl)-3H-imidazo[4,5-b]pyridine (184 mg) was obtained as white crystals from 3-(4-benzyloxy-2-chlorobenzyl)-2-methyl-3H-imidazo[4,5-b]pyridine-5-carboxylic acid (200 mg) and 1-pentane-sulfonamide (111 mg).

$^1$H-NMR(CDCl$_3$): 0.87(3H, t, J=8 Hz), 1.30–1.48(4H, m), 1.83–1.93(2H, m), 2.64(3H, s), 3.53(2H, t, J=8 Hz), 5.04(2H, s), 5.51(2H, s), 6.74(1H, d, J=8 Hz), 6.82 (1H, dd, J=2,8 Hz), 7.10(1H, d, J=8 Hz), 7.30–7.40(5H, m), 8.10(1H, d, J=8 Hz), 8.17(1H, d, J=8 Hz)

Mass(ESI): m/z 539(M–H)$^-$

Example 140

In the same manner as in Example 1, 3-(2-chloro-4-((cyclohexylmethyl)-oxy)benzyl)-2-methyl-5-((4-methylbenzene)sulfonylcarbamoyl)-3H-imidazo-[4,5-b]pyridine (211 mg) was obtained as white crystals from 3-(2-chloro-4-((cyclohexylmethyl)oxy)benzyl)-2-methyl-3H-imidazo[4,5-b]pyridine-5-carboxylic acid (200 mg) and (4-methylbenzene)sulfonamide (124 mg).

$^1$H-NMR(CDCl$_3$): 0.97–1.36(5H, m), 1.67–1.87(6H, m), 2.41(3H, s), 2.63(3H, s), 3.74(2H, d, J=7 Hz), 5.51(2H, s), 6.77(2H, s), 7.01(1H, s), 7.32(2H, d, J=8 Hz), 8.02–8.07(4H, m)

Mass(ESI): m/z 565(M–H)$^-$

Example 141

In the same manner as in Example 1, 3-(2-chloro-4-((cyclohexylmethyl)-oxy)benzyl)-2-methyl-5-((4-vinylbenzene)sulfonylcarbamoyl)-3H-imidazo[4,5-b]pyridine (203 mg) was obtained as white crystals from 3-(2-chloro-4-((cyclohexylmethyl)oxy)benzyl)-2-methyl-3H-imidazo[4,5-b]pyridine-5-carboxylic acid (200 mg) and (4-vinylbenzene)sulfonamide (133 mg).

$^1$H-NMR(CDCl$_{13}$): 0.98–1.38(5H, m), 1.68–1.88(6H, m), 2.64(3H, s), 3.75(2H, d, J=7 Hz), 5.43(1H, d, J=11 Hz), 5.50(2H, s), 5.87(1 H, d, J=16 Hz), 6.69–6.78(3H, m), 7.00(1H, s), 7.53(2H, d, J=8 Hz), 8.00–8.12(4H, m)

Mass(ESI): m/z 577(M–H)$^-$

Example 142

In the same manner as in Example 1, 3-(2-chloro-4-((cyclohexylmethyl)-oxy)benzyl)-2-methyl-5-(E)-((2-phenylethenyl)sulfonylcarbamoyl)-3H-imidazo[4,5-b]pyridine (193 mg) was obtained as white crystals from 3-(2-chloro-4-((cyclohexylmethyl)oxy)benzyl)-2-methyl-3H-imidazo[4,5-b]pyridine-5-carboxylic acid (200 mg) and (E)-(2-phenylethene)sulfonamide (133 mg).

$^1$H-NMR(CDCl$_3$): 0.96–1.36(5H, m), 1.68–1.84(6H, m), 2.64(3H, s), 3.72(2H, d, J=7 Hz), 5.51(2H, s), 6.69–6.74(2H, m), 7.00(1H, d, J=2 Hz), 7.14(1H, d, J=15 Hz), 7.36–7.46 (3H, m), 7.52–7.56(2H, m), 7.81(1H, d, J=16 Hz), 8.08(1H, d, J=8 Hz), 8.13(1H, d, J=8 Hz)

Mass(ESI): m/z 577(M–H)$^-$

Example 143

In the same manner as in Example 1, 3-(2-chloro-4-((cyclohexylmethyl)-oxy)benzyl)-5-((5-chlorothiophen-2- yl)sulfonylcarbamoyl)-2-methyl-3H-imidazo[4,5-b]pyridine (155 mg) was obtained as white crystals from 3-(2-chloro-4-((cyclohexylmethyl)oxy)benzyl)-2-methyl-3H-imidazo[4,5-b]pyridine-5-carboxylic acid (200 mg) and 5-chlorothiophene-2-sulfonamide (143 mg).

$^1$H-NMR(CDCl$_3$): 0.97–1.36(5H, m), 1.37–1.87(6H, m), 2.65(3H, s), 3.73(2H, d, J=7 Hz), 5.50(2H, s), 6.73–6.82(2H, m), 6.94(1H, d, J=2 Hz), 7.00(1H, s), 7.76(1H, d, J=3 Hz), 8.06(1H, d, J=8 Hz), 8.10(1H, d, J=8 Hz)

Mass(ESI): m/z 591(M−H)$^-$

Example 144

In the same manner as in Example 1, 5-((5-bromothiophen-2-yl)sulfonylcarbamoyl)-3-(2-chloro-4-((cyclohexylmethyl)oxy)benzyl)-2-methyl-3H-imidazo[4,5-b]pyridine (178 mg) was obtained as white crystals from 3-(2-chloro-4-((cyclohexylmethyl)oxy)benzyl)-2-methyl-3H-imidazo[4,5-b]pyridine-5-carboxylic acid (200 mg) and 5-bromothiophene-2-sulfonamide (175 mg).

$^1$H-NMR(CDCl$_3$): 0.97–1.36(5H, m), 1.68–1.87(6H, m), 2.64(3H, s), 3.73(2H, d, J=7 Hz), 5.50(2H, s), 6.72–6.80(2H, m), 7.00(1H, s), 7.08(1H, d, J=3 Hz), 7.72(1H, d, J=3 Hz), 8.05(1H, d, J=8 Hz), 8.11(1H, d, J=8 Hz)

Mass(ESI): m/z 537(M−H)$^-$

Example 145

In the same manner as in Example 1, 3-(2-chloro-4-((cyclohexylmethyl)-oxy)benzyl)-2-methyl-5-(1-pentanesulfonylcarbamoyl)-3H-imidazo[4,5-b]pyridine (178 mg) was obtained as white crystals from 3-(2-chloro-4-((cyclohexylmethyl)oxy)benzyl)-2-methyl-3H-imidazo[4,5-b]pyridine-5-carboxylic acid (200 mg) and 1-pentanesulfonamide (110 mg).

$^1$H-NMR(CDCl$_3$): 0.88(3H, t, J=8 Hz), 0.96–1.48(9H, m), 1.68–1.92(8H, m), 2.64(3H, s), 3.53(2H, t, J=8 Hz), 3.72(2H, d, J=7 Hz), 5.46(2H, s), 6.70–6.76(2H, m), 6.78(1H, s), 8.09(1H, d, J=8 Hz), 8.16(1H, d, J=8 Hz)

Mass(ESI): m/z 545(M−H)$^-$

Example 146

In the same manner as in Example 1, 3-(2-chloro-4-(methylthio)benzyl)-2-methyl-5-[(4-methylbenzene)sulfonylcarbamoyl]-3H-imidazo[4,5-b]pyridine (181 mg) was obtained as colorless crystals from 3-(2-chloro-4-(methylthio)-benzyl)-2-methyl-3H-imidazo[4,5-b]pyridine-5-carboxylic acid (160 mg).

$^1$H-NMR(CDCl$_3$): 2.41(3H, s), 2.50(3H, s), 2.63(3H, s), 5.52(2H, s), 6.73(1H, d, J=8 Hz), 7.09(1H, d, J=8 Hz), 7.30–7.37(3H, m), 8.00–8.07(4H, m).

Mass(ESI): m/z 499(M−1)

mp 180–181° C.

Example 147

In the same manner as in Example 1, 3-(2-chloro-4-(methylthio)benzyl)-2-methyl-5-[(4-vinylbenzene)sulfonylcarbamoyl]-3H-imidazo[4,5-b]pyridine (174 mg) was obtained as colorless crystals from 3-(2-chloro-4-(methylthio)-benzyl)-2-methyl-3H-imidazo[4,5-b]pyridine-5-carboxylic acid (160 mg).

$^1$H-NMR(CDCl$_3$): 2.50(3H, s), 2.64(3H, s), 5.44(1H, d, J=11 Hz), 5.53(2H, s), 5.88(1H, d, J=18 Hz), 6.57(1H, d, J=8 Hz), 6.71(2H, dd, J=18,11 Hz), 7.08(1H, dd, J=8,2 Hz), 7.32(1H, d, J=2 Hz), 7.54(2H, d, J=8 Hz), 8.00–8.14(4H, m).

Mass(ESI): m/z 513(M+1)

mp 197–198° C.

Example 148

In the same manner as in Example 1, 3-(2-chloro-4-(methylthio)benzyl)-2-methyl-5-(E)-[(2-phenylethenyl)sulfonylcarbamoyl]-3H-imidazo[4,5-b]pyridine (174 mg) was obtained as colorless crystals from 3-(2-chloro-4-(methylthio)benzyl)-2-methyl-3H-imidazo[4,5-b]pyridine-5-carboxylic acid (160 mg).

$^1$H-NMR(CDCl$_3$): 2.48(3H, s), 2.63(3H, s), 5.53(2H, s), 6.67(1H, d, J=8Hz), 7.06(1H, dd, J=8,1 Hz), 7.14(1H, d, J=15 Hz), 7.23–7.33(1H, overlapped with H$_2$O), 7.36–7.47 (3H, m), 7.50–7.59(2H, m), 7.81(1H, d, J=15 Hz), 8.09(1H, d, J=8 Hz), 8.17(1H, d, J=8 Hz), 10.01(1H, br s).

Mass(ESI): m/z 513(M+1).

mp 175–176° C.

Example 149

In the same manner as in Example 1, 3-(2-chloro-4-(methylthio)benzyl)-5-[(5-chlorothiophen-2-yl)sulfonylcarbamoyl]-2-methyl-3H-imidazo[4,5-b]pyridine (186 mg) was obtained as colorless crystals from 3-(2-chloro-4-(methylthio)-benzyl)-2-methyl-3H-imidazo[4,5-b]pyridine-5-carboxylic acid (160 mg).

$^1$H-NMR(CDCl$_3$): 2.40(3H, s), 2.65(3H, s), 5.53(2H, s), 6.73(1H, d, J=8Hz), 6.95(1H, d, J=5 Hz), 7.08(1H, dd, J=8,2 Hz), 7.31(1H, d, J=2 Hz), 7.77(1H, d, J=5 Hz), 7.70(1H, d, J=8 Hz), 8.12(1H, d, J=8 Hz).

Mass(ESI): m/z 528(M+1)

mp 170–171° C.

Example 150

In the same manner as in Example 1, 3-[2-chloro-4-(methylthio)benzyl-5-[(5-bromothiophen-2-yl)sulfonylcarbamoyl]-2-methyl-3H-imidazo[4,5-b]pyridine (211 mg) was obtained as colorless crystals from 3-(2-chloro-4-(methylthio)-benzyl)-2-methyl-3H-imidazo[4,5-b]pyridine-5-carboxylic acid (160 mg).

$^1$H-NMR(CDCl$_3$): 2.49(3H, s), 2.65(3H, s), 5.52(2H, s), 6.73(1H, d, J=8 Hz), 7.02–7.13(2H, m), 7.31(1H, br s), 7.72(1H, d, J=5 Hz), 8.08(1H, d, J=8 Hz), 8.12(1H, d, J=8 Hz).

Mass(ESI): m/z 572(M+1)

mp 169–170° C.

Example 151

In the same manner as in Example 1, 3-(2-chloro-4-(methylthio)benzyl)-2-methyl-5-(1-pentanesulfonylcarbamoyl)-3H-imidazo[4,5-b]pyridine (169 mg) was obtained as colorless crystals from 3-(2-chloro-4-(methylthio)benzyl)-2-methyl-3H-imidazo[4,5-b]pyridine-5-carboxylic acid (160 mg).

$^1$H-NMR(CDCl$_3$): 0.90(3H, t, J=8 Hz), 1.26–1.49(4H, m), 1.81–1.95(2H, m), 2.47(3H, s), 2.64(3H, s), 3.50–3.60 (2H, m), 5.52(2H, s), 6.70(1H, d, J=8 Hz), 7.05(1H, dd, J=8,1 Hz), 7.30(1H, d, J=1 Hz), 8.12(1H, d, J=8 Hz), 8.19(1H, d, J=8 Hz), 9.81(1H, br s).

Mass(ESI): m/z 481(M+1)

mp 184–185° C.

Example 152

In the same manner as in Example 1, 3-(2-chloro-4-(ethoxycarbonyl)-benzyl)-2-methyl-5-((4-methylbenzene)

sulfonylcarbamoyl)-3H-imidazo[4,5-b]pyridine (173 mg) was obtained as white crystals from 3-(2-chloro-4-(ethoxycarbonyl)benzyl)-2-methyl-3H-imidazo[4,5-b]pyridine-5-carboxylic acid (150 mg) and (4-methylbenzene)sulfonamide (103 mg).

$^1$H-NMR(CDCl$_3$): 1.40(3H, t, J=7 Hz), 2.42(3H, s), 2.59 (3H, s), 4.39(2H, q, J=7 Hz), 5.63(2H, s), 6.70(1H, d, J=8 Hz), 7.27–7.33(2H, m), 7.83(1H, d, J=8 Hz), 8.00–8.07(5H, m)

Mass(ESI): m/z 525(M–H)$^-$

Example 153

In the same manner as in Example 1, 3-(2-chloro-4-(ethoxycarbonyl)-benzyl)-2-methyl-5-((4-vinylbenzene)sulfonylcarbamoyl)-3H-imidazo[4,5-b]pyridine (212 mg) was obtained as white crystals from 3-(2-chloro-4-(ethoxycarbonyl)benzyl)-2-methyl-3H-imidazo[4,5-b]pyridine-5-carboxylic acid (200 mg) and (4-vinylbenzene)sulfonamide (147 mg).

$^1$H-NMR(CDCl$_3$): 1.40(3H, t, J=7 Hz), 2.59(3H, s), 4.40 (2H, q, J=7 Hz), 5.43(1H, d, J=9 Hz), 5.64(2H, s), 5.88(1H, d, J=16 Hz), 6.68–6.77(2H, m), 7.52(1H, d, J=8 Hz), 7.83 (1H, dd, J=2,8 Hz), 8.05–8.16(5H, m)

Mass(ESI): m/z 537(M–H)$^-$

Example 154

In the same manner as in Example 1, 3-(2-chloro-4-(ethoxycarbonyl)-benzyl)-2-methyl-5-(E)-((2-phenylethenyl)sulfonylcarbamoyl)-3H-imidazo[4,5-b]pyridine (237 mg) was obtained as white crystals from 3-(2-chloro-4-(ethoxycarbonyl)benzyl)-2-methyl-3H-imidazo[4,5-b]pyridine-5-carboxylic acid (200 mg) and (E)-(2-phenylethene)sulfonamide (147 mg).

$^1$H-NMR(CDCl$_3$): 11.38(3H, t, J=7 Hz), 2.60(3H, s), 4.37(2H, q, J=7 Hz), 5.65(2H, s), 6.65(1H, d, J=8 Hz), 7.14(1H, d, J=15 Hz), 7.36–7.53(5H, m), 7.77–7.85(2H, m), 8.12–8.20(3H, m)

Mass(ESI): m/z 537(M–H)$^-$

Example 155

In the same manner as in Example 1, 3-(2-chloro-4-(ethoxycarbonyl)-benzyl)-5-((5-chlorothiophen-2-yl)sulfonylcarbamoyl)-2-methyl-3H-imidazo[4,5-b]pyridine (210 mg) was obtained as white crystals from 3-(2-chloro-4-(ethoxycarbonyl)benzyl)-2-methyl-3H-imidazo[4,5-b]pyridine-5-carboxylic acid (200 mg) and 5-chlorothiophene-2-sulfonamide (159 mg).

$^1$H-NMR(CDCl$_3$): 1.39(3H, t, J=7 Hz), 2.60(3H, s), 4.38 (2H, q, J=7 Hz), 5.62(2H, s,) 6.70(1H, d, J=8 Hz), 6.93(1H, d, J=3 Hz), 7.26(1H, s), 7.73(1H, d, J=4 Hz), 7.83(1H, dd, J=2,8 Hz), 8.11–8.17(3H, m)

Mass(ESI): m/z 551(M–H)$^-$

Example 156

In the same manner as in Example 1, 5-((5-bromothiophen-2-yl)sulfonylcarbamoyl-3-(2-chloro-4-(ethoxycarbonyl)benzyl)-2-methyl-3H-imidazo[4,5-b]pyridine (229 mg) was obtained as white crystals from 3-(2-chloro-4-(ethoxycarbonyl)benzyl)-2-methyl-3H-imidazo[4,5-b]pyridine-5-carboxylic acid (200 mg) and 5-bromothiophene-2-sulfonamide (194 mg).

$^1$H-NMR(CDCl$_3$): 1.19(3H, t, J=7 Hz), 2.62(3H, s), 4.38 (2H, q, J=8 Hz), 5.63(2H, s), 6.71(1H, d, J=8 Hz), 7.07(1H, d, J=4 Hz), 7.71(1H, d, J=3 Hz), 7.83(1H, dd, J=2,8 Hz), 8.09–8.15(3H, m)

Mass(ESI): m/z 597(M–H)$^-$

Example 157

In the same manner as in Example 1, 3-(2-chloro-4-(ethoxycarbonyl)-benzyl)-2-methyl-5-(1-pentanesulfonylcarbamoyl)-3H-imidazo[4,5-b]pyridine (197 mg) was obtained as white crystals from 3-(2-chloro-4-(ethoxycarbonyl)-benzyl)-2-methyl-3H-imidazo[4,5-b]pyridine-5-carboxylic acid (200 mg) and 1-pentanesulfonamide (121 mg).

$^1$H-NMR(CDCl$_3$): 0.88(3H, t, J=7 Hz), 1.27–1.47(7H, m), 1.82–1.92(2H, m), 2.60(3H, s), 3.53(2H, t, J=8 Hz), 4.38(2H, q, J=7 Hz), 5.62(2H, s), 6.67(1H, d, J=8 Hz), 7.83(1H, dd, J=2,8 Hz), 8.14–8.24(3H, m)

Mass(ESI): m/z 505(M–H)$^-$

Example 158

In the same manner as in Example 1, 3-(2-chloro-4-((phenyloxy)methyl)benzyl)-2-methyl-5-[(4-methylbenzene)sulfonylcarbamoyl]-3H-imidazo[4,5-b]pyridine (182 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and (4-methylbenzene)sulfonamide (127 mg).

$^1$H-NMR(300 MHz, DMSO-d$_6$) δ: 2.38(s, 3H), 2.48(s, 3H), 5.12(s, 2H), 5.83(s, 3H), 6.76(d, J=8 Hz, 1H), 6.90–7.04(m, 3H), 7.24–7.38(m, 3H), 7.42(d, J=8 Hz, 2H), 7.66(s, 1H), 7.83–7.95(m, 3H), 8.14(d, J=8 Hz, 1H)

MS(ESI): m/e 559(M–H)

Example 159

In the same manner as in Example 1, 3-(2-chloro-4-((phenyloxy)methyl)benzyl)-2-methyl-5-[(4-vinylbenzene)sulfonylcarbamoyl]-3H-imidazo[4,5-b]pyridine (135 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and (4-vinylbenzene)sulfonamide (135 mg).

$^1$H-NMR(300MHz, DMSO-d$_6$) δ: 2.46(s, 3H), 5.11(s, 2H), 5.46(d, J=11 Hz, 1H), 5.83(s, 2H), 6.01(d, J=18 Hz, 1H), 6.74(d, J=8 Hz, 1 H), 6.81(dd, J=11,18 Hz, 1H), 6.90–7.03(m, 3H), 7.24–7.36(m, 3H), 7.64–7.75(m, 3H), 7.90(d, J=8 Hz, 1H), 7.98(d, J=8 Hz, 2H), 8.13(d, J=8 Hz, 1H)

MS(ESI): m/e 571(M–H)

Example 160

In the same manner as in Example 1, 3-(2-chloro-4-((phenyloxy)methyl)benzyl)-2-methyl-5-[(E) -(2-phenylethenyl)sulfonylcarbamoyl]-3H-imidazo[4,5-b]pyridine (152 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and (E)-(2-phenylethene)sulfonamide (135 mg).

$^1$H-NMR(300 MHz, DMSO-d$_6$) δ: 2.46(s, 3H), 5.60(s, 2H), 5.84(s, 2H), 6.68(d, J=8 Hz, 1H), 6.90–7.02(m, 3H), 7.24–7.36(m, 3H), 7.40–7.59(m, 4H), 7.66(s-like, 2H), 7.73–7.82(m, 2H), 7.98(d, J=8 Hz, 1H), 8.18(d, J=8 Hz, 1H)

MS(ESI): m/e 571(M–H)

Example 161

In the same manner as in Example 1, 3-(2-chloro-4-((phenyloxy)methyl)benzyl)-5-[(5-chlorothiophen-2-yl)

sulfonylcarbamoyl]-2-methyl-3H-imidazo-[4,5-b]pyridine (120 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and 5-chlorothiophene-2-sulfonamide (178 mg).

$^1$H-NMR(300MHz, DMSO-d$_6$) δ: 2.45(s, 3H), 5.61(s, 2H), 5.83(s, 2H), 6.70(d, J=8 Hz, 1H), 6.90–7.02(m, 3H), 7.24–7.35(m, 4H), 7.65(s, 1H), 7.76(d, J=4 Hz, 1H), 7.97(d, J=8 Hz, 1H), 8.18(d, J=8 Hz, 1H)

MS(ESI): m/e 585,587

Example 162

In the same manner as in Example 1, 5-[(5-bromothiophen-2-yl)sulfonylcarbamoyl]-3-(2-chloro-4-((phenyloxy)methyl)benzyl)-2-methyl-3H-imidazo[4,5-b]pyridine (153 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and 5-bromothiophene-2-sulfonamide (178 mg).

$^1$H-NMR(300 MHz, DMSO-$_6$) δ: 2.45(s, 3H), 5.10(s, 2H), 5.81(s, 2H), 6.69(d, J=8 Hz, 1H), 6.90–7.02(m, 3H), 7.24–7.35(m, 3H), 7.39(d, J=4 Hz, 1H), 7.65(s, 1H), 7.70(d, J=4 Hz, 1H), 7.97(d, J=8 Hz, 1H), 8.17(d, J=8 Hz, 1H)

MS(ESI): m/e 629,630,633

Example 163

In the same manner as in Example 1, 3-(2-chloro-4-((phenyloxy)methyl)benzyl)-2-methyl-5-(1-pentanesulfonylcarbamoyl)-3H-imidazo[4,5-b]pyridine (180 mg) was obtained as pale-yellow crystals from 3-(2-chloro-4-((phenyloxy)methyl)benzyl)-2-methyl-3H-imidazo[4,5-b]pyridine-5-carboxylic acid (200 mg) and 1-pentanesulfonamide (111 mg).

$^1$H-NMR(300MHz, DMSO-d$_6$) δ: 0.80(t, J=7.5 Hz, 3H), 1.17–1.43(m, 4H), 1.63–1.77(m, 2H), 2.48(s, 3H), 3.53(t, J=7.5 Hz, 2H), 5.51(s, 2H), 5.83(s, 2H), 6.74(d, J=8 Hz, 1H), 6.90–7.04(m, 3H), 7.23–7.48(m, 3H), 7.65(s, 1H), 8.02(d, J=8Hz, 1H), 8.20(d, J=8 Hz, 1H)

MS(ESI): m/e 539(M–1)

Example 164

In the same manner as in Example 1, 3-[2-chloro-4-(dimethylamino-methyl)benzyl]-2-methyl-5-[(4-methylbenzene)sulfonylcarbamoyl]-3H-imidazo[4,5-b]pyridine (80 mg) was obtained as pale-yellow crystals from 3-(2-chloro-4-(dimethylaminomethyl)benzyl)-2-methyl-3H-imidazo[4,5-b]pyridine-5-carboxylic acid (115 mg) and 4-methylbenzene)sulfonamide (83 mg).

$^1$H-NMR(300 MHz, DMSO-$_6$) δ: 2.34(s, 3H), 2.40(s, 6H), 2.46(s, 3H), 3.78(s, 2H), 5.70(s, 2H), 6.60(d, J=8 Hz, 1H), 7.23(d, J=8 Hz, 1H), 7.30(d, J=8 Hz, 2H), 7.60(s, 1H), 7.80(d, J=8 Hz, 1H), 7.93(d, J=8 Hz, 1H), 8.03(d, J=8 Hz, 1H)

MS(ESI): m/e 512(M+H)

Example 165

In the same manner as in Example 1, 3-[2-chloro-4-((imidazol-1-yl)methyl)benzyl]-2-methyl-5-[(4-methylbenzene)sulfonylcarbamoyl]-3H-imidazol4,5-b]pyridine (180 mg) was obtained as pale-yellow crystals from 3-(2-chloro4-((imidazol-1-yl)methyl)benzyl)-2-methyl-3H-imidazo[4,5-b]pyridine-5-carboxylic acid (184 mg) and (4-methylbenzene)sulfonamide (125 mg).

$^1$H-NMR(300 MHz, DMSO-d$_6$) δ: 2.39(s, 3H), 2.45(s, 3H), 5.22(s, 2H), 5.77(s, 2H), 6.67(d, J=8 Hz, 1H), 6.98(s, 1H), 7.14(d, J=8 Hz, 1H), 7.25(s, 1H), 7.40(d, J=8 Hz, 2H), 7.48(s, 1H), 7.84–7.93(m, 4H), 8.10(d, J=8 Hz, 1H)

MS(ESI): m/e 533(M–H)

Example 166

In the same manner as in Example 1, 3-[2-chloro-4-((piperidin-1-yl)methyl)benzyl]-2-methyl-5-[(4-methylbenzene)sulfonylcarbamoyl]-3H-imidazol4,5-b]pyridine (57 mg) was obtained as pale-yellow crystals from 3-(2-chloro4-((piperidin-1-yl)methyl)benzyl)-2-methyl-3H-imidazo[4,5-b]pyridine-5-carboxylic acid (148 mg) and (4-methylbenzene)sulfonamide (96 mg).

$^1$H-NMR(300 MHz, DMSO-d$_6$) δ: 1.43(br peak, 2H), 1.55(br peak, 4H), 2.34(s, 3H), 2.46(s, 3H), 2.66(br peak, 4H), 3.79(br peak, 2H), 5.69(s, 2H), 6.56(d, J=8 Hz, 1H), 7.23(d, J=8 Hz, 1H), 7.29(d, J=8 Hz, 2H), 7.58(s, 1H), 7.80(d, J=8 Hz, 2H), 7.90(d, J=8 Hz, 1H), 8.03(d, J=8 Hz, 1H)

MS(ESI): m/e 552.2(M+H)

Example 167

In the same manner as in Example 1, 3-[2-chloro-4-(phenylthiomethyl)-benzyl]-2-methyl-5-[(4-methylbenzene)sulfonylcarbamoyl]-3H-imidazo[4,5-b]pyridine (119 mg) was obtained as pale-yellow crystals from 3-(2-chloro-4-(phenylthiomethyl)benzyl)-2-methyl-3H-imidazo[4,5-b]pyridine-5-carboxylic acid (175 mg) and (4-methylbenzene)sulfonamide (107 mg).

$^1$H-NMR(300 MHz, DMSO-d$_6$) δ: 2.38(s, 3H), 2.41(s, 3H), 4.24(s, 2H), 5.79(s, 2H), 6.68(d, J=8 Hz, 1H), 7.12–7.35(m, 6H), 7.43(d, J=8 Hz, 1H), 7.54(s, 1H), 7.85–7.98(m, 3H), 8.13(d, J=8 Hz, 1H)

Mass (ESI) m/e 575.0 (M–H)

Example 168

In the same manner as in Example 1, 3-(4-((benzyloxy)methyl)-2-chlorobenzyl)-2-methyl-5-[(4-methylbenzene)sulfonylcarbamoyl]-3H-imidazo[4,5-b]pyridine was obtained as pale-yellow crystals (195 mg) from 3-(4-((benzyloxy)methyl)-2-chlorobenzyl)-2-methyl-3H-imidazo[4,5-b]pyridine-5-carboxylic acid (200 mg) and (4-methylbenzene)sulfonamide (123 mg).

$^1$H-NMR (300 MHz, DMSO-d$_6$) δ: 2.38(s, 3H), 2.46(s, 3H), 4.53(s, 4H), 5.82(s, 2H), 6.73(d, J=8 Hz, 1H), 7.20–7.38(m, 6H), 7.42(d, J=8 Hz, 2H), 7.56(s, 1H), 7.85–7.94(m, 3H), 8.13(d, J=8 Hz, 1H)

Mass (ESI) m/e 573 (M–H)

Example 169

In the same manner as in Example 1, 3-[4-(benzimidazol-2-yl)-2-chlorobenzyl]-2-methyl-5-[(4-methylbenzene)sulfonylcarbamoyl]-3H-imidazo[4,5-b]pyridine was obtained as pale-yellow crystals (140 mg) from 3-[4-(benzimidazol-2-yl)-2-chlorobenzyl]-2-methyl-3H-imidazo[4,5-b]pyridine-5-carboxylic acid (200 mg) and (4-methylbenzene)sulfonamide (124 mg).

$^1$H-NMR(300 MHz, DMSO-d$_6$) δ: 2.34(s, 3H), 2.50(s, 3H), 5.90(s, 2H), 6.98(d, J=8 Hz, 1H), 7.20–7.30(m, 2H), 7.38(d, J=8 Hz, 2H), 7.57–7.69(m, 2H), 7.86–7.94(m, 3H), 8.06(d, J=8 Hz, 1H), 8.16(d, J=8 Hz, 1H), 8.37(s, 1H)

Mass (ESI) m/e 569 (M–H)

Example 170

In the same manner as in Example 1, 2-methyl-5-[(4-methylbenzene)-sulfonylcarbamoyl]-3-[4-(1- methylbenzimidazol-2-yl)-2-chlorobenzyl]-3H-imidazo[4,5-b]pyridine was obtained as pale-yellow crystals (81 mg) from 2-methyl-3-[4-(1-methylbenzimidazol-2-yl)-2-chlorobenzyl]-3H-imidazo[4,5-b]pyridine-5-carboxylic acid (200 mg) and (4-methylbenzene)sulfonamide (120 mg).

$^1$H-NMR(300 MHz, DMSO-d$_6$) δ: 2.37(s, 3H), 2.53(s, 3H), 3.89(s, 3H), 5.94(s, 2H), 6.90(d, J=8 Hz, 1H), 7.21–7.37(m, 3H), 7.42(d, J=8 Hz, 2H), 7.65(d, J=8 Hz, 1H), 7.70(d, J=8 Hz, 1H), 7.78(d, J=8 Hz, 1H), 7.90(d, J=8 Hz, 2H), 8.09(s, 1H), 8.17(d, J=8 Hz, 1H)

Mass (ESI) m/e 585 (M+H)

Example 171

In the same manner as in Example 1, 3-[(1-ethylbenzimidazol-2-yl)methyl]-2-methyl-5-[(4-methylbenzene)sulfonylcarbamoyl]-3H-imidazo[4,5-b]pyridine was obtained as pale-yellow crystals (167 mg) from 3-[(1-ethylbenzimidazol-2-yl)methyl]-2-methyl-3H-imidazo[4,5-b]pyridine-5-carboxylic acid (180 mg) and (4-methylbenzene)sulfonamide (139 mg).

$^1$H-NMR(300 MHz, DMSO-d$_6$) δ: 1.20(t, J=7.5 Hz, 3H), 2.37(s, 3H), 2.65(s, 3H), 4.53(q, J=7.5 Hz, 2H), 6.10(s, 2H), 7.17(t, J=8 Hz, 1H), 7.26(t, J=8 Hz, 1H), 7.42(d, J=8 Hz, 2H), 7.53(d, J=8 Hz, 1H), 7.60(d, J=8 Hz, 1H), 7.87(d, J=8 Hz, 1H), 7.90(d, J=8 Hz, 1H), 8.12(d, J=8 Hz, 1H)

Mass (ESI) m/e 487.2 (M–H)

Example 172

In the same manner as in Example 1, 3-(2-chloro-4-(thiophen-2-yl)benzyl)-2-methyl-5-(1-pentanesulfonylcarbamoyl)-3H-imidazo[4,5-b]pyridine was obtained as pale-yellow crystals (174 mg) from 3-(2-chloro-4-(thiophen-2-yl)benzyl)-2-methyl-3H-imidazol[4,5-b]pyridine-5-carboxylic acid (180 mg) and 1-pentanesulfonamide (106 mg).

$^1$H-NMR(300 MHz, DMSO-d$_6$) δ: 0.79(t, J=7.5 Hz, 3H), 1.10–1.45(m, 4H), 1.56–1.81(m, 2H), 2.50(s, 3H), 3.43–3.63(m, 2H), 5.83(s, 2H), 6.80(d, J=8 Hz, 1H), 7.13(t, J=5 Hz, 1H), 7.50(d, J=8 Hz, 1H), 7.55–7.70(m, 2H), 7.86(s-like, 1H), 8.03(d, J=8 Hz, 1H), 8.21(d, J=8 Hz, 1H)

Mass (ESI) m/e 515.2 (M–H)

Example 173

In the same manner as in Example 1, 3-(2-chloro-4-(thiophen-2-yl)benzyl)-2-methyl-5-[(4-methylbenzene)sulfonylcarbamoyl]-3H-imidazo[4,5-b]pyridine was obtained as pale-yellow crystals (199 mg) from 3-(2-chloro-4-(thiophen-2-yl)benzyl)-2-methyl-3H-imidazo[4,5-b]pyridine-5 carboxylic acid (180 mg) and (4-methylbenzene)sulfonamide (120 mg).

$^1$H-NMR(300 MHz, DMSO-d$_6$) δ: 2.37(s, 3H), 2.50(s, 3H), 5.84(s, 2H), 6.80(d, J=8 Hz, 1H), 7.16(t, J=5 Hz, 1H), 7.40(d, J=8 Hz, 2H), 7.53(dd, J=8, 2 Hz, 7.58–7.65(m, 2H), 7.82–7.94(m, 4H), 8.13(d, J=8 Hz, 1H)

Mass (ESI) m/e 535.1 (M–H)

Example 174

In the same manner as in Example 1, 3-(2-chloro-4-(thiophen-2-yl)benzyl)-5-[(5-chlorothiophen-2-yl)sulfonylcarbamoyl]-2-methyl-3H-imidazo[4,5-b]pyridine was obtained as pale-yellow crystals (194 mg) from 3-(2-chloro-4-(thiophen-2-yl)benzyl)-2-methyl-3H-imidazo[4,5-b]pyridine-5-carboxylic acid (180 mg) and 5-chlorothiophene-2-sulfonamide (139 mg).

$^1$H-NMR(300 MHz, DMSO-d$_6$) δ: 2.50(s, 3H), 5.83(s, 2H), 6.75(d, J=8 Hz, 1H), 7.15(t, J=5 Hz, 1H), 7.28(d, J=4 Hz, 1H), 7.51(dd, J=8, 2 Hz, 1H), 7.56–7.65(m, 2H), 7.74(d, J=4 Hz, 1H), 7.88(d, J=2 Hz, 1H), 7.98(d, J=8 Hz, 1H), 8.17(d, J=8 Hz, 1H)

Mass (ESI) m/e 561.0

Example 175

In the same manner as in Example 1, 5-[(5-bromothiophen-2-yl)sulfonylcarbamoyl]-3-(2-chloro-4-(thiophen-2-yl)benzyl)-2-methyl-3H-imidazo[4,5-b]pyridine was obtained as pale-yellow crystals (228 mg) from 3-(2-chloro-4-(thiophen-2-yl)benzyl)-2-methyl-3H-imidazo[4,5-b]pyridine-5-carboxylic acid (180 mg) and 5-bromothiophene-2-sulfonamide (170 mg).

$^1$H-NMR(300 MHz, DMSO-d$_6$) δ: 2.50(s, 3H), 5.83(s, 2H), 6.75(d, J=8 Hz, 1H), 7.14(t, J=5 Hz, 1H), 7.37(d, J=4 Hz, 1H), 7.52(dd, J=8, 2 Hz, 1H), 7.57–7.64(m, 2H), 7.70(d, J=4 Hz, 1H), 7.87(d, J=2 Hz, 1H), 7.98(d, J=8 Hz, 1H), 8.17(d, J=8 Hz, 1H)

Mass (ESI) m/e 606.7

Example 176

In the same manner as in Example 1, 3-(2-chloro-4-(thiophen-2-yl)benzyl)-2-methyl-5-[(E)-(2-phenylethene)sulfonylcarbamoyl]-3H-imidazo[4,5-b]pyridine was obtained as pale-yellow crystals (199 mg) from 3-(2-chloro-4-(thiophen-2-yl)benzyl)-2-methyl-3H-imidazo[4,5-b]pyridine-5-carboxylic acid (180 mg) and ((E)-(2-phenylethene)sulfonamide (129 mg).

$^1$H-NMR(300 MHz, DMSO-d$_6$) δ: 2.50(s, 3H), 5.85(s, 2H), 6.71(d, J=8 Hz, 1H), 7.15(t, J=5 Hz, 1H), 7.36–7.82(m, 10H), 7.88(d, J=2 Hz, 1H), 7.98(d, J=8 Hz, 1H), 8.18(d, J=8 Hz, 1H)

Mass (ESI) m/e 547.1 (M–H)

Example 177

In the same manner as in Example 1, 3-(2-chloro-4-(thiophen-2-yl)benzyl)-2-methyl-5-[(4-vinylbenzene)sulfonylcarbamoyl]-3H-imidazo[4,5-b]pyridine was obtained as pale-yellow crystals (194 mg) from 3-(2-chloro-4-(thiophen-2-yl)benzyl)-2-methyl-3H-imidazo[4,5-b]pyridine-5-carboxylic acid (180 mg) and (4-vinylbenzene)sulfonamide (129 mg).

$^1$H-NMR(300 MHz, DMSO-d$_6$) δ: 2.58(s, 3H), 5.45(d, J=11 Hz, 1H), 5.83(s, 2H), 6.01(d, J=19 Hz, 1H), 6.72–6.90(m, 2H), 7.16(t, J=5 Hz, 3H), 7.55(dd, J=8, 2 Hz, 1H), 7.58–7.65(m, 2H), 7.69(d, J=8 Hz, 1H), 7.84–7.92(m, 2H), 7.97(d, J=8 Hz, 2H), 8.14(d, J=8 Hz, 1H)

Mass (ESI) m/e 547.1 (M–H)

Example 178

In the same manner as in Example 1, 3-(2-chloro-4-(5-chlorothiophen-2-yl)benzyl)-2-methyl-5-(1-pentanesulfonylcarbamoyl)-3H-imidazo[4,5-b]pyridine was obtained as pale-yellow crystals (177 mg) from 3-(2-chloro-4-(5-chlorothiophen-2-yl)benzyl)-2-methyl-3H-imidazo[4,5-b]pyridine-5-carboxylic acid (180 mg) and 1-pentanesulfonamide (98 mg).

$^1$H-NMR(300 MHz, DMSO-d$_6$) δ: 0.79(t, J=7.5 Hz, 3H), 1.14–1.41(m, 4H), 1.60–1.75(m, 2H), 2.51(s, 3H), 3.51(t, J=7.5 Hz, 2H), 5.83(s, 2H), 6.78(d, J=8 Hz, 1), 7.18(d, J=4 Hz, 1H), 7.41(dd, J=8, 2 Hz, 1H), 7.50(d, J=4 Hz, 1H), 7.85(d, J=2 Hz, 1H), 8.01(d, J=8 Hz, 1H), 8.19(d, J=8 Hz, 1H)

Mass (ESI) m/e 549.0

Example 179

In the same manner as in Example 1, 3-(2-chloro-4-(5-chlorothiophen-2-yl)benzyl)-2-methyl-5-[(4-methylbenzene)sulfonylcarbamoyl]-3H-imidazo[4,5-b]pyridine was obtained as pale-yellow crystals (179 mg) from 3-(2-chloro-4-(5-chlorothiophen-2-yl)benzyl)-2-methyl-3H-imidazo[4,5-b]pyridine-5-carboxylic acid (180 mg) and (4-methylbenzene)sulfonamide (111 mg).

$^1$H-NMR(300 MHz, DMSO-d$_6$) δ: 2.37(s, 3H), 2.50(s, 3H), 5.83(s, 2H), 6.78(d, J=8 Hz, 1H), 7.20(d, J=4 Hz, 1H), 7.40(d, J=8 Hz, 2H), 7.48(dd, J=8, 2 Hz, 1H), 7.52(d, J=4 Hz, 1H), 7.83–7.95(m, 4H), 8.15(d, J=8 Hz, 1H)

Mass (ESI) m/e 569.2

Example 180

In the same manner as in Example 1, 3-(2-chloro-4-(5-chlorothiophen-2-yl)benzyl)-5-[(5-chlorothiophen-2-yl)sulfonylcarbamoyl]-2-methyl-3H-imidazo[4,5-b]pyridine was obtained as pale-yellow crystals (182 mg) from 3-(2-chloro-4-(5-chlorothiophen-2-yl)benzyl)-2-methyl-3H-imidazo[4,5-b]pyridine-5-carboxylic acid (180 mg) and 5-chlorothiophene-2-sulfonamide (128 mg).

$^1$H-NMR(300 MHz, DMSO-d$_6$) δ: 2.50(s, 3H), 5.82(s, 2H), 6.73(d, J=8 Hz, 1H), 7.18(d, J=4 Hz, 1H), 7.29(d, J=8 Hz, 1H), 7.45(dd, J=8, 2 Hz, 1H), 7.51(d, J=4 Hz, 1H), 7.76(d, J=4 Hz, 1H), 7.86(d, J=2 Hz, 1H), 7.98(d, J=8 Hz, 1H), 8.17(d, J=8 Hz, 1H)

Mass (ESI) m/e 595.1, 597.0, 599.0

Example 181

In the same manner as in Example 1, 5-[(5-bromothiophen-2-yl)sulfonylcarbamoyl]-3-(2-chloro-4-(5-chlorothiophen-2-yl)benzyl)-2-methyl-3H-imidazo[4,5-b]pyridine was obtained as pale-yellow crystals (207 mg) from 3-(2-chloro-4-(5-chlorothiophen-2-yl)benzyl)-2-methyl-3H-imidazo[4,5-b]pyridine-5-carboxylic acid (180 mg) and 5-bromothiophene-2-sulfonamide (156 mg).

$^1$H-NMR(300 MHz, DMSO-d$_6$) δ: 2.50(s, 3H), 5.82(s, 2H), 6.74(d, J=8 Hz, 1H), 7.19(d, J=4 Hz, 1H), 7.38(d, J=4 Hz, 1H), 7.47(dd, J=8, 2 Hz, 1H), 7.51(d, J=4 Hz, 1H), 7.70(d, J=4 Hz, 1H), 7.87(d, J=2 Hz, 1H), 7.98(d, J=8 Hz, 1H), 8.18(d, J=8 Hz, 1H)

Mass (ESI) m/e 639.1, 641.3, 643.5

Example 182

In the same manner as in Example 1, 3-(2-chloro-4-(5-chlorothiophen-2-yl)benzyl)-2-methyl-5-[(E)-(2-phenylethene)sulfonylcarbamoyl]-3H-imidazo[4,5-b]pyridine was obtained as pale-yellow crystals (182 mg) from 3-(2-chloro-4-(5-chlorothiophen-2-yl)benzyl)-2-methyl-3H-imidazo[4,5-b]pyridine-5-carboxylic acid (180 mg) and (E)-(2-phenylethene)sulfonamide (118 mg).

$^1$H-NMR(300 MHz, DMSO-d$_6$) δ: 2.50(s, 3H), 5.84(s, 2H), 6.72(d, J=8 Hz, 1H), 7.18(d, J=4 Hz, 1H), 7.35–7.60(m, 6H), 7.60–7.84(m, 3H), 7.86(d, J=2 Hz, 1H), 7.98(d, J=8 Hz, 1H), 8.17(d, J=8 Hz, 1H)

Mass (ESI) m/e 581.0, 583.2

Example 183

In the same manner as in Example 1, 3-(2-chloro-4-(5-chlorothiophen-2-yl)benzyl)-2-methyl-5-[(4-vinylbenzene)sulfonylcarbamoyl]-3H-imidazo[4,5-b]pyridine was obtained as pale-yellow crystals (180 mg) from 3-(2chloro-4-(5-chlorothiophen-2-yl)benzyl)-2-methyl-3H-imidazo[4,5-b]pyridine-5-carboxylic acid (180 mg) and (4-vinylbenzene)sulfonamide (118 mg).

$^1$H-NMR(300 MHz, DMSO-d$_6$) δ: 2.49(s, 3H), 5.46(d, J=11 Hz, 1H), 5.83(s, 2H), 6.01(d, J=18 Hz, 1H), 6.70–6.98 (m, 2H), 7.20(d, J=4 Hz, 1H), 7.46(dd, J=8, 2 Hz, 1), 7.52(d, J=4 Hz, 1H), 7.70(d, J=8 Hz, 2H), 7.83–7.92(m, 2H), 7.96(d, J=8 Hz, 2H), 8.14(d, J=8 Hz, 1H)

Mass (ESI) m/e 581.2

Example 184

In the same manner as in Example 1, 3-(2-chloro-4-phenylbenzyl)-2,7-dimethyl-5-(1-pentanesulfonylcarbamoyl)-3H-imidazo[4,5-b]pyridine was obtained as colorless crystals (165 mg) from 3-(2-chloro-4-phenylbenzyl)-2,7-dimethyl-3H-imidazo[4,5-b]pyridine-5-carboxylic acid (160 mg).

mp 227–228° C.

$^1$H-NMR(CDCl$_3$): 0.85(3H, t, J=8 Hz), 1.21–1.44(4H, m), 1.78–1.90(2H, m), 2.67(3H, s), 2.75(3H, s), 3.49–3.56 (2H, m), 5.60(2H, s), 6.76(1H, d, J=8 Hz), 7.33–7.47(3H, m), 7.52–7.57(2H, m), 7.70(1H, d, J=1 Hz), 8.01(1H, s), 9.87(1H, br s)

Mass (ESI) m/z 523 (M−1)

Example 185

In the same manner as in Example 1, 3-(2-chloro-4-phenylbenzyl)-5-[(5-chlorothiophen-2-yl)sulfonylcarbamoyl]-2,7-dimethyl-3H-imidazo[4,5-b]pyridine was obtained as colorless crystals (177 mg) from 3-(2-chloro-4-phenylbenzyl)-2,7-dimethyl-3H-imidazo[4,5-b]pyridine-5-carboxylic acid (160 mg).

mp 241–242° C.

$^1$H-NMR(CDCl$_3$): 2.67(3H, s), 2.72(3H, s), 5.59(2H, s), 6.81(1H, d, J=8 Hz), 6.90(1H, d, J=5 Hz), 7.35–7.49(4H, m), 7.54–7.58(2H, m), 7.67–7.72(2H, m), 7.96(1H, s)

Mass (ESI) m/z 571 (M+)

Example 186

In the same manner as in Example 1, 5-[(5-bromothiophen-2-yl)sulfonylcarbamoyl]-3-(2-chloro-4-phenylbenzyl)-2,7-dimethyl-3H-imidazo[4,5-b]pyridine was obtained as colorless crystals (175 mg) from 3-(2-chloro-4-phenylbenzyl)-2,7-dimethyl-3H-imidazo[4,5-b]pyridine-5-carboxylic acid (160 mg).

mp 243–244° C.

$^1$H-NMR(CDCl$_3$): 2.67(3H, s), 2.71(3H, s), 5.59(2H, s), 6.81(1H, d, J=8 Hz), 7.03(1H, d, J=5 Hz), 7.35–7.49(4H, m), 7.56(2H, d, J=8 Hz), 7.65(1H, d, J=5 Hz), 7.71(1H, d, J=1 Hz), 7.95(1H, s)

Mass (ESI) m/z 615 (M−1)

Example 187

In the same manner as in Example 1, 3-(2-chloro-4-phenylbenzyl)-2,7-dimethyl-5-[(4-vinylbenzene)sulfonylcarbamoyl]-3H-imidazo[4,5-b]pyridine was obtained as colorless crystals (180 mg) from 3-(2-chloro4-phenylbenzyl)-2,7-dimethyl-3H-imidazol[4,5-b]pyridine-5carboxylic acid (160 mg).

mp 220–221° C.

$^1$H-NMR(CDCl$_3$): 2.66(3H, s), 2.68(3H, s), 5.41(1H, d, J=10 Hz), 5.60(2H, s), 5.83(1H, d, J=18 Hz), 6.65(2H, dd,

J=18, 10 Hz), 6.81(1H, d, J=8 Hz), 7.35–7.50(6H, m), 7.57(2H, d, J=8 Hz), 7.72(1H, d, J=1 Hz), 7.90(1H, s), 8.04(2H, d, J=8 Hz)

Mass (ESI) m/z 555 (M−1)

Example 188

In the same manner as in Example 1, 3-[2-chloro-4-(thiophen-2-yl)benzyl]-2,7-dimethyl-5-(1-pentanesulfonylcarbamoyl)-3H-imidazo[4,5-b]pyridine was obtained as colorless crystals (165 mg) from 3-[2-chloro-4-(thiophen-2-yl)benzyl]-2,7-dimethyl-3H-imidazo[4,5-b]pyridine-5-carboxylic acid (160 mg).

mp 220–224° C.

$^1$H-NMR(CDCl$_3$): 0.85(3H, t, J=8 Hz), 1.20–1.44(4H, m), 1.75–1.90(2H, m), 2.65(3H, s), 2.74(3H, s), 3.47–3.56 (2H, m), 5.56(2H, s), 6.73(1H, d, J=8 Hz), 7.08(1H, t J=4 Hz), 7.28–7.34(2H, m), 7.40(1H, brd, J=8 Hz), 7.70(1H, s), 8.01(1H, s), 9.85(1H, br s)

Mass (ESI) m/z 529 (M−1)

Example 189

In the same manner as in Example 1, 3-[2-chloro-4-(thiophen-2-yl)benzyl]-2,7-dimethyl-5-[(4-methylbenzene)sulfonylcarbamoyl]-3H-imidazo[4,5-b]pyridine was obtained as colorless crystals (187 mg) from 3-[2-chloro-4-(thiophen-2-yl)benzyl]-2,7-dimethyl-3H-imidazo[4,5-b]pyridine-5-carboxylic acid (180 mg).

mp 224–226° C.

$^1$H-NMR(CDCl$_3$): 2.39(3H, s), 2.69(3H, s), 2.68(3H, s), 5.56(2H, s), 6.79(1H, d, J=8 Hz), 7.10(1H, t, J=4 Hz), 7.20–7.38(3H, m), 7.45(1H, br d, J=8 Hz), 7.72(1H, d, J=1 Hz), 7.89(1H, s), 7.95–8.02(2H, m), 10.10(1H, br s)

Mass (ESI) m/z 549 (M−1)

Example 190

In the same manner as in Example 1, 5-[(5-bromothiophen-2-yl)sulfonylcarbamoyl]-3-[2-chloro-4-(thiophen-2-yl)benzyl]-2,7-dimethyl-3H-imidazo[4,5-b]pyridine was obtained as colorless crystals (199 mg) from 3-[2-chloro-4-(thiophen-2-yl)benzyl]-2,7-dimethyl-3H-imidazo[4,5-b]pyridine-5-carboxylic acid (180 mg).

mp 246–248° C.

$^1$H-NMR(CDCl$_3$): 2.66(3H, s), 2.70(3H, s), 5.55(2H, s), 6.79(1H, d, J=8 Hz), 7.03(1H, d, J=4 Hz), 7.10(1H, t, J=4 Hz), 7.33–7.36(2H, m), 7.45(1H, dd, J=8, 1 Hz), 7.65(1H, d, J=4 Hz), 7.71(1H, s), 7.94(1H, s), 10.19(1H, br s)

Mass (ESI) m/z 620 (M−1)

Example 191

In the same manner as in Example 1, 3-[2-chloro-4-(thiophen-2-yl)benzyl]-2,7-dimethyl-5-[(E)-(2-phenylethenyl)sulfonylcarbamoyl]-3H-imidazo[4,5-b]pyridine was obtained as colorless crystals (196 mg) from 3-[2-chloro-4-(thiophen-2-yl)benzyl]-2,7-dimethyl-3H-imidazo[4,5-b]pyridine-5-carboxylic acid (180 mg).

mp 216–217° C.

$^1$H-NMR(CDCl$_3$): 2.64(3H, s), 2.72(3H, s), 5.57(2H, s), 6.72(1H, d, J=8 Hz), 7.08–7.11(2H, m), 7.30–7.52(8H, m), 7.71(1H, d, J=1 Hz), 7.77(1H, d, J=15 Hz), 7.98(1H, s), 10.06(1H, br s)

Mass (ESI) m/z 561 (M+1)

Example 192

In the same manner as in Example 1, 3-[2-chloro-4-(thiophen-2-yl)benzyl]-2,7-dimethyl-5-[(4-vinylbenzene)sulfonylcarbamoyl]-3H-imidazo[4,5-b]pyridine was obtained as colorless crystals (187 mg) from 3-[2-chloro-4-(thiophen-2-yl)benzyl]-2,7-dimethyl-3H-imidazo[4,5-b]pyridine-5-carboxylic acid (180 mg).

mp 220–222° C.

$^1$H-NMR(CDCl$_3$): 2.65(3H, s), 2.68(3H, s), 5.41(1H, d, J=11 Hz), 5.56(2H, s), 5.84(1H, d, J=18Hz), 6.70(2H, dd, J=18, 11Hz), 6.79(1H, d, J=8Hz), 7.11(1H, t J=4 Hz), 7.32–7.37(2H, m), 7.42–7.48(3H, m), 7.72(1H, d, J=1 Hz), 7.89(1H, s), 8.04(2H, d, J=8 Hz), 10.13(1H, s)

Example 193

In the same manner as in Example 1, 3-[2-chloro-4-(5-chlorothiophen-2-yl)benzyl]-2,7-dimethyl-5-(1-pentanesulfonylcarbamoyl)-3H-imidazo[4,5-b]pyridine was obtained as colorless crystals (187 mg) from 3-[2-chloro-4-(5-chlorothiophen-2-yl)benzyl]-2,7-dimethyl-3H-imidazo[4,5-b]pyridine-5-carboxylic acid (180 mg).

mp 215–217° C.

$^1$H-NMR(CDCl$_3$): 0.86(3H, t, J=8 Hz), 1.23–1.45(4H, m), 1.77–1.90(2H, m), 2.65(3H, s), 2.74(3H, s), 3.47–3.56 (2H, m), 5.55(2H, s), 6.74(1H, d, J=8 Hz), 6.89(1H, t, J=4 Hz), 7.09(1H, d, J=4 Hz), 7.31(1H, dd, J=8, 1 Hz), 7.59(1H, d, J=1 Hz), 8.01(1H, s), 9.82(1H, br s)

Mass (ESI m/z 563 (M−1)

Example 194

In the same manner as in Example 1, 3-[2-chloro-4-(5-chlorothiophen-2-yl)benzyl]-2,7-dimethyl-5-[(4-methylbenzene)sulfonylcarbamoyl]-3H-imidazo[4,5-b]pyridine was obtained as colorless crystals (178 mg) from 3-[2-chloro-4-(5-chlorothiophen-2-yl)benzyl]-2,7-dimethyl-3H-idazo[4,5-b]pyridine-5-carboxylic acid (180 mg).

mp 240–241° C.

$^1$H-NMR(CDCl$_3$): 2.40(3H, s), 2.64(3H, s), 2.68(3H, s), 5.55(2H, s), 6.76(1H, d, J=8 Hz), 6.91(1H, d, J=4 Hz), 7.12(1H, d, J=4 Hz), 7.23–7.37(3H, m), 7.61(1H, d, J=1 Hz), 7.89(1H, s), 7.99(2H, d, J=8 Hz), 10.08(1H, br s)

Mass (ESI) m/z 583 (M−1)

Example 195

In the same manner as in Example 1, 5-[(5-bromothiophen-2-yl)sulfonylcarbamoyl]-3-[2-chloro-4-(5-chlorothiophen-2-yl)benzyl]-2,7-dimethyl-3H-imidazo[4,5-b]pyridine was obtained as colorless crystals (175 mg) from 3-[2-chloro-4-(5-chlorothiophen-2-yl)benzyl]-2,7-dimethyl-3H-imidazo[4,5-b]pyridine-5-carboxylic acid (180 mg).

mp 252–253° C.

$^1$H-NMR(CDCl$_3$): 2.66(3H, s), 2.70(3H, s), 5.54(2H, s), 6.78(1H, d, J=8Hz), 6.91(1H, d, J=4 Hz), 7.04(1H, d, J=4Hz), 7.11 (1H, d, J=4 Hz), 7.33(1H, dd, J=8, 1 Hz), 7.60(1H, br s), 7.67(1H, d, J=4 Hz), 7.94(1H, s), 10.18(1H, br s)

Mass (ESI) m/z 654 (M−1)

Example 196

In the same manner as in Example 1, 3-[2-chloro-4-(5-chlorothiophen-2-yl)benzyl]-2,7-dimethyl-5-[(E)-(2-phenylethenyl)sulfonylcarbamoyl]-3H-imidazo[4,5-b]pyridine was obtained as colorless crystals (208 mg) from 3-[2-chloro 4-(5-chlorothiophen-2-yl)benzyl]-2,7-dimethyl-3H-imidazo[4,5-b]pyridine-5-carboxylic acid (180 mg).

mp 224–225° C.

¹H-NMR(CDCl₃): 2.64(3H, s), 2.72(3H, s), 5.55(2H, s), 6.72(1H, d, J=8 Hz), 6.90(1H, d, J=4 Hz), 7.09(1H, d, J=4 Hz), 7.12(1H, d, J=8 Hz), 7.32(1H, dd, J=8, 1 Hz), 7.35–7.44 (3H, m), 7.47–7.52(2H, m), 7.60(1H, d, J=1 Hz), 7.77(1H, d, J=15 Hz), 7.98(1H, s), 10.03(1H, br s)

Mass (ESI) m/z 595 (M−1)

Example 197

In the same manner as in Example 1, 3-[2-chloro-4-(5-chlorothiophen-2-yl)benzyl]-2,7-dimethyl-5-[(4-vinylbenzene)sulfonylcarbamoyl]-3H-imidazo[4,5-b]pyridine was obtained as colorless crystals (184 mg) from 3-[2-chloro-4-(5-chlorothiophen-2-yl)benzyl]-2,7-dimethyl-3H-imidazo[4,5-b]pyridine-5-carboxylic acid (180 mg).

mp 217–218° C.

¹H-NMR(CDCl₃): 2.65(3H, s), 2.68(3H, s), 5.42(1H, d, J=11 Hz), 5.55(2H, s), 5.86(1H, d, J=18 Hz), 6.65–6.80(2H, m), 6.92(2H, d, J=4 Hz), 7.12(1H, d, J=4 Hz), 7.33(1H, dd, J=8, 1 Hz), 7.28(2H, d, J=8 Hz), 7.62(1H, d, J=1 Hz), 7.89(1H, s), 8.05(2H, d, J=8 Hz), 10.10(1H, s)

Mass (ESI) m/z 595 (M−1)

Example 198

In the same manner as in Example 1, 3-[2-chloro-4-(n-pentanethio)benzyl]-2-methyl-5-[(4-methylbenzene)sulfonylcarbamoyl]-3H-imidazo[4,5-b]pyridine (186 mg) was obtained as colorless crystals from 3-[2-chloro-4-(n-pentanethio)benzyl]-2-methyl-3H-imidazo[4,5-b]pyridine-5-carboxylic acid (170 mg).

mp 153–155° C.

¹H-NMR (CDCl₃): 0.91(3H, t, J=7.5 Hz), 1.25–1.48(4H, m), 1.55–1.73(2H, m), 2.42(3H, s), 2.63(3H, s), 2.94(2H, t, J=7.5 Hz), 5.53(2H, s), 6.68(1H, d, J=8 Hz), 7.12(1H, dd, J=8, 1 Hz), 7.27–7.40(3H, m), 8.00–8.10(4H, m)

Mass (ESI) m/z 557 (M+1)

Example 199

In the same manner as in Example 1, 3-[4-(benzylthio)-2-chloro]benzyl-2-methyl-5-[(4-methylbenzene)sulfonylcarbamoyl]-3H-imidazo[4,5-b]pyridine (156 mg) was obtained as colorless crystals from 3-[4-(benzylthio)-2-chloro]benzyl-2,7-dimethyl-3H-imidazo[4,5-b]pyridine-5-carboxylic acid (180 mg).

mp 165–166° C.

¹H-NMR (CDCl₃): 2.42(3H, s), 2.60(3H, s), 4.15(2H, s), 5.52(2H, s), 6.65(1H, d, J=8 Hz), 7.12(1H, dd, J=8, 1 Hz), 7.21–7.36(7H, m), 7.39(1H, d, J=1 Hz), 8.01–8.10(4H, m)

Mass (ESI) m/z 577 (M+1)

Example 200

In the same manner as in Example 1, 3-(2-chloro-4-((3-pyridyloxy)methyl)benzyl)-2-methyl-5-[(4-methylbenzene)sulfonylcarbamoyl]-3H-imidazo[4,5-b]pyridine (159 mg) was obtained as pale-yellow crystals from 3-(2-chloro-4-((3-pyridyloxy)methyl)benzyl)-2-methyl-3H-imidazo[4,5-b]pyridine-5-carboxylic acid (160 mg) and (4-methylbenzene)sulfonamide (101 mg).

¹H-NMR (300 MHz, DMSO-d₆) δ: 2.38(s, 3H), 2.46(s, 3H), 5.19(s, 2H), 5.84(s, 2H), 6.75(d, J=8 Hz, 1H), 7.23–7.38(m, 2H), 7.38–7.49(m, 3H), 7.70(s, 1H), 7.84–7.49(m, 3H), 8.13(d, J=8 Hz, 1H), 8.18(dd, J=5, 2 Hz, 1H), 8.35(d, J=2 Hz, 1H)

Mass (ESI) m/e 562.1 (M+H)

Example 201

In the same manner as in Example 1, 3-(2-chloro-4-ethylthiobenzyl)-2-methyl-5-[(4-methylbenzene)sulfonylcarbamoyl]-3H-imidazo[4,5-b]pyridine (156 mg) was obtained as colorless crystals from 3-(2-chloro-4-ethylthio-benzyl)-2-methyl-3H-imidazo[4,5-b]pyridine-5-carboxylic acid (180 mg).

mp 162–163° C.

¹H-NMR (CDCl₃): 1.35(3H, t, J=7.5 Hz), 2.42(3H, s), 2.63(3H, s), 2.97(2H, q, J=7.5Hz), 5.53(2H, s), 6.69(1H, d, J=8 Hz), 7.13(1H, dd, J=8, 1 Hz), 7.33(2H, d, J=8 Hz), 7.39(1H, d, J=1 Hz), 8.01–8.10(4H, m)

Mass (ESI) m/z 360 (M−1)

Example 202

In the same manner as in Example 1, 3-(4-(N-butyrylamino)-2-chlorobenzyl)-2-methyl-5-((4-methylbenzene) sulfonylcarbamoyl)-3H-imidazo[4,5-b]pyridine (225 mg) was obtained as colorless crystals from 3-(4-(N-butyrylamino)-2-chlorobenzyl)-2-methyl-3H-imidazo[4,5-b]pyridine-5-carboxylic acid (210 mg) and (4-methylbenzene)sulfonamide (232 mg).

¹H-NMR (CDCl₃): 1.00(3H, t, J=7 Hz), 1.69–1.81(2H, m), 2.35(2H, t, J=7 Hz), 2.42(3H, s), 2.64(3H, s), 5.51(2H, s), 6.84(1H, d, J=8 Hz), 7.25(1H, d, J=7 Hz), 7.33(1H, d, J=7 Hz), 7.40(1H, s), 7.97–8.03(5H, m)

Mass (ESI) m/z 538 (M−H)⁻ mp 242–246° C.

Example 203

In the same manner as in Example 1, 3-(4-(N-benzoylamino)-2-chlorobenzyl)-2-methyl-5-((4-methylbenzene)sulfonylcarbamoyl)-3H-imidazo[4,5-b]pyridine (139 mg) was obtained as colorless crystals from 3-(4-(N-benzoylamino)-2-chlorobenzyl)-2-methyl-3H-imidazo[4,5-b]pyridine-5-carboxylic acid (150 mg) and (4-methylbenzene)sulfonamide (153 mg).

¹H-NMR (CDCl₃): 2.40(3H, s), 2.69(3H, s), 5.57(2H, s), 6.97(1H, d, J=8 Hz), 7.31(2H, d, J=7 Hz), 7.46–7.58(4H, m), 7.90(2H, d, J=8 Hz), 7.98–8.11(4H, m)

Mass (ESI) m/z 572 (M−H)⁻ mp 270–274° C.

Example 204

In the same manner as in Example 1, 3-(4-(N-benzoyl-N-methylamino)-2-chlorobenzyl)-2-methyl-5-((4-methylbenzene)sulfonylcarbamoyl)-3H-imidazo[4,5-b]pyridine (227 mg) was obtained as a pale-yellow powder from 3-(4-(N-benzoyl-N-methylamino)-2-chlorobenzyl)-2-methyl-3H-imidazo[4,5-b]pyridine-5-carboxylic acid (225 mg) and (4-methylbenzene)sulfonamide (221 mg).

¹H-NMR (CDCl₃): 2.43(3H, s), 2.53(3H, s), 3.49(3H, s), 5.52(2H, s), 6.54(1H, d, J=8 Hz), 6.85(1H, d, J=8 Hz), 7.18–7.37(8H, m), 8.03–8.10(4H, m)

Mass (ESI) m/z 586 (M−H)⁻

Example 205

5-(Benzenesulfonylcarbamoyl)-3-(2-chloro-4-phenylbenzyl)-2-methyl-3H-imidazo[4,5-b]pyridine sodium salt N,N-Dimethylformamide (33 ml) was added to 5-(benzenesulfonylcarbamoyl)-3-(2-chloro-4- phenylbenzyl)-2-methyl-3H-imidazo[4,5-b]pyridine (1.0 g) and the mixture was heated to 80° C. The undissolved crystals were filtered off, washed with N,N-dimethylformamide (3 ml) and stirred at room temperature. A 1N aqueous solution (12 ml) of sodium hydroxide was added at room temperature and the mixture was stirred for 30 min. The precipitated crystals were collected by filtration, washed with N,N-dimethylformamide/water=3/1 and water and dried under reduced pressure at 60° C. for 8 hr to give the objective compound (600 mg) as colorless crystals.

$^1$H-NMR (DMSO-d$_6$): 2.49(3H, s), 5.59(2H, s), 6.49(1H, d, J=8 Hz), 7.32–7.51(7H, m), 7.65(2H, d, J=8 Hz), 7.80–7.86(3H, m), 7.94(1H, d, J=8 Hz), 8.01(1H, d, J=8 Hz)

Mass (ESI m/z 515

Example 206

In the same manner as in Example 205, 5-[(4-vinylbenzene)sulfonylcarbamoyl]-3-(2-chloro-4-phenylbenzyl)-2-methyl-3H-imidazo[4,5-b]pyridine sodium (532 mg) was obtained as colorless crystals from 5-[(4-vinylbenzene)sulfonylcarbamoyl]-3-(2-chloro-4-phenylbenzyl)-2-methyl-3H-imidazo[4,5-b]pyridine (1 g).

$^1$H-NMR (DMSO-d$_6$): 2.49(3H, s), 5.30(1H, d, J=10 Hz), 5.59(2H, s), 5.86(1H, d, J=17 Hz), 6.50(1H, d, J=8 Hz), 6.74(1H, dd, J=17, 10 Hz), 7.34–7.52(6H, m), 7.64(2H, d, J=8 Hz), 7.75–7.85(3H, m), 7.93(1H, d, J=8 Hz), 8.00(1H, d, J=8 Hz)

Mass (ESI) m/z 541 (M−1)

mp >300° C.

Example 207

In the same manner as in Example 205, 5-[(5-bromothiophen-2-yl)sulfonylcarbamoyl]-3-(2-chloro-4-phenylbenzyl)-2-methyl-3H-imidazo[4,5-b]pyridine sodium (1.02 g) was obtained as colorless crystals from 5-[(5-bromothiophen-2-yl)sulfonylcarbamoyl]-3-(2-chloro-4-phenylbenzyl)-2-methyl-3H-imidazo[4,5-b]pyridine (1.2 g).

$^1$H-NMR (DMSO-$_6$): 2.49(3H, s), 5.62(2H, s), 6.51(1H, d, J=8 Hz), 7.08(1H, d, J=5 Hz), 7.29(1H, d, J=3 Hz), 7.34–7.53(4H, m), 7.67(2H, d, J=8 Hz), 7.85(1H, s), 7.96 (1H, d, J=8 Hz), 8.01(1H, d, J=8 Hz)

mp >250° C.

Example 208

In the same manner as in Example 205, 3-(4-bromo-2-chlorobenzyl)-2,7-dimethyl-5-[(4-methylbenzene)sulfonylcarbamoyl]-3H-imidazo[4,5-b]pyridine sodium (972 mg) was obtained as colorless crystals from 3-(4-bromo-2-chlorobenzyl)-2,7-dimethyl-5-[(4-methylbenzene)-sulfonyl-carbamoyl]-3H-imidazo[4,5-b]pyridine (1 g).

$^1$H-NMR (DMSO-d$_6$): 2.30(3H, s), 2.43(3H, s), 2.56(3H, s), 5.48(2H, s), 6.35(1H, d, J=8 Hz), 7.17(2H, d, J=8 Hz), 7.40(1H, d, J=8 Hz), 7.71(2H, d, J=8 Hz), 7.83(2H, s)

mp >250° C.

Example 209

In the same manner as in Example 1, 3-(4-(N-butyryl-N-methylamino)-2-chlorobenzyl)-2-methyl-5-((4-methylbenzene)sulfonylcarbamoyl)-3H-imidazo[4,5-b]pyridine (58 mg) was obtained as a pale-yellow powder from 3-(4-(N-butyryl-N-methylamino)-2-chlorobenzyl)-2-methyl-3H-imidazo[4,5-b]pyridine-5-carboxylic acid (90 mg) and (4-methylbenzene)sulfonamide (96 mg).

$^1$H-NMR (CDCl$_3$): 0.87(3H, t, J=7 Hz), 1.56–1.69(2H, m), 2.12(2H, br), 2.43(3H, s), 2.63(3H, s), 3.27(3H, s), 5.61(2H, s), 6.68(1H, d, J=8 Hz), 7.03(1H, dd, J=8, 2 Hz), 7.30–7.39(3H, m), 8.04–8.13(4H, m), 10.09(1H, s)

Mass(ESI): m/z 552(M−H)$^-$

Example 210

In the same manner as in Example 1, 3-(2-chloro-4-(N-(n-pentyl)-amino)benzyl)-2-methyl-5-((4-methylbenzene)sulfonylcarbamoyl)-3H-imidazo[4,5-b]pyridine (189 mg) was obtained as colorless crystals from 3-(2-chloro-4-(N-(n-pentyl)amino)benzyl)-2-methyl-3H-imidazo[4,5-b]pyridine-5-carboxylic acid (170 mg) and (4-methylbenzene)sulfonamide (188 mg).

$^1$H-NMR (CDCl$_3$): 0.91(3H, t, J=7 Hz), 1.34–1.42(4H, m), 1.57–1.62(2H, m), 2.42(3H, s), 2.66(3H, s), 3.05–3.13 (2H, m), 3.83(1H, br), 5.45(2H, s), 6.48(1H, dd, J=8, 2 Hz), 6.65(1H, d, J=2 Hz), 6.79(1H, d, J=8 Hz), 7.33(2H, d, J=8 Hz), 7.97–8.05(4H, m), 10.14(1H, s)

Mass(ESI): m/z 538(M−H)$^-$ mp 222–223° C.

Example 211

In the same manner as in Example 1, 3-(2-chloro-4-(N-methyl-N-(n-pentyl)amino)benzyl)-2-methyl-5-((4-methylbenzene)sulfonylcarbamoyl)-3H-imidazo[4,5-b]pyridine (12 mg) was obtained as colorless crystals from 3-(2-chloro-4-(N-methyl-N-(n-pentyl)amino)benzyl)-2-methyl-3H-imidazo[4,5-b]pyridine-5-carboxylic acid (45 mg) and (4-methylbenzene)sulfonamide (48 mg).

$^1$H-NMR (CDCl$_3$): 0.90(3H, t, J=7 Hz), 1.15–1.45(4H, m), 1.55–1.65(2H, m), 2.42(3H, s), 2.67(3H, s), 2.94(3H, s), 5.47(2H, s), 6.53(1H, d, J=8 Hz), 6.70(1H, s), 6.81(1H, d, J=8 Hz), 7.27–7.35(2H, m), 7.98–8.04(4H, m), 10.18(1H, s)

Mass(ESI): m/z 552(M−H)$^-$ mp 175–177° C.

Example 212

In the same manner as in Example 1, 3-(4-(N-benzenesulfonylamino)-2-chlorobenzyl)-2-methyl-5-((4-methylbenzene)sulfonylcarbamoyl)-3H-imidazo[4,5-b]pyridine (157 mg) was obtained as colorless crystals from 3-(4-(N-benzenesulfonylamino)-2-chlorobenzyl)-2-methyl-3H-imidazo[4,5-b]pyridine-5-carboxylic acid (165 mg) and (4-methylbenzene)sulfonamide (155 mg).

$^1$H-NMR (DMSO-d$_6$): 2.37(3H, s), 2.39(3H, s), 5.70(2H, s), 6.72(1H, d, J=8 Hz), 7.00(1H, d, J=8 Hz), 7.24(1H, s), 7.42(2H, d, J=8 Hz), 7.55–7.65(3H, m), 7.77(2H, d, J=8 Hz), 7.83–7.92(3H, m), 8.09(1H, d, J=8 Hz)

Mass(ESI): m/z 608(M−H)$^-$ mp 234–236° C.

Example 213

In the same manner as in Example 1, 3-(2-chloro-4-(isopropoxylcarbonyl)benzyl)-2-methyl-5-((4-methylbenzene)sulfonylcarbamoyl)-3H-imidazo[4,5-b]pyridine (133 mg) was obtained as colorless crystals from 3-(2-chloro-4-(isopropoxylcarbonyl)benzyl)-2-methyl-3H-imidazo[4,5-b]pyridine-5-carboxylic acid (250 mg) and (4-methylbenzene)sulfonamide (331 mg).

$^1$H-NMR (CDCl$_3$): 1.36(3H, s), 1.38(3H, s), 2.42(3H, s), 2.59(3H, s), 5.20–5.32(1H, m), 5.64(2H, s), 6.71(1H, d, J=8 Hz), 7.33(2H, d, J=8 Hz), 7.85(1H, dd, J=8, 2 Hz), 8.02–8.16 (5H, m), 10.07(1H, s)

Example 214

In the same manner as in Example 1, 3-(2-chloro-4-(cyclohexyloxycarbonyl)benzyl)-2-methyl-5-((4-methylbenzene)sulfonylcarbamoyl)-3H-imidazo[4,5-b]pyridine (312 mg) was obtained as colorless crystals from 3-(2-chloro-4-(cyclohexyloxycarbonyl)benzyl)-2-methyl-3H-imidazo[4,5-b]pyridine-5-carboxylic acid (289 mg) and (4-methylbenzene)sulfonamide (231 mg).

$^1$H-NMR (CDCl$_3$): 1.32–1.65(6H, m), 1.78(2H, br s), 1.92(2H, br s), 2.42(3H, s), 2.59(3H, s), 4.99–5.06(1H, m), 5.64(2H, s), 6.71(1H, d, J=8 Hz), 7.73(2H, d, J=8 Hz), 7.86(1H, d, J=8 Hz), 8.02–8.16(5H, m), 10.09(1H, s)

Mass(ESI): m/z 579(M−H)$^−$

Example 215

In the same manner as in Example 1, 3-(2-chloro-4-(3-phenylureido)benzyl)-2-methyl-5-((4-methylbenzene)sulfonylcarbamoyl)-3H-imidazo[4,5-b]pyridine (60 mg) was obtained as colorless crystals from 3-(2-chloro-4-(3-phenylureido)benzyl)-2-methyl-3H-imidazo[4,5-b]pyridine-5-carboxylic acid (207 mg) and (4-methylbenzene)sulfonamide (244 mg).

$^1$H-NMR (CDCl$_3$): 2.38(3H, s), 2.68(3H, s), 5.52(2H, s), 6.93(1H, d, J=8 Hz), 7.05(1H, t, J=7 Hz), 7.22(1H, dd, J=8, 2 Hz), 7.27–7.33(4H, m), 7.42(2H, d, J=8 Hz), 7.87(1H, d, J=2 Hz), 7.98–8.02(5H, m), 8.28(1H, s)

Mass(ESI): m/z 587(M−H)$^−$

Example 216

In the same manner as in Example 1, 3-[2-chloro-4-propoxybenzyl]-2-methyl-5-[(4-methylbenzene)sulfonylcarbamoyl]-3H-imidazo[4,5-b]pyridine (213 mg) was obtained as colorless crystals from 3-[2-chloro-4-propoxy-benzyl]-2-methyl-3H-imidazo[4,5-b]pyridine-5-carboxylic acid (200 mg).

$^1$H-NMR (CDCl$_3$): 1.04(3H, t, J=7 Hz), 1.74–1.88(2H, m), 2.42(3H, s), 2.63(3H, s), 3.93(2H, t, J=7 Hz), 5.51(2H, s), 6.78(2H, s), 7.02(1H, s), 7.32(1H, s), 7.35(1H, s), 8.00–8.10(4H, m), 10.12(1H, br s)

Mass(ESI): m/z 511(M−1).

mp 144–146° C.

Example 217

In the same manner as in Example 1, 3-[2-chloro-4-(n-pentoxy)benzyl]-2-methyl-5-[(4-methylbenzene)sulfonylcarbamoyl]-3H-imidazo[4,5-b]pyridine (231 mg) was obtained as colorless crystals from 3-[2-chloro-4-(n-pentoxy)-benzyl]-2-methyl-3H-imidazo[4,5-b]pyridine-5-carboxylic acid (200 mg).

$^1$H-NMR (CDCl$_3$): 0.93(3H, t, J=7 Hz), 1.30–1.50(6H, m), 1.73–1.85(2H, m), 2.42(3H, s), 2.64(3H, s), 3.95(2H, t, J=7 Hz), 5.51(2H, s), 6.78(2H, s), 7.02(1H, s), 7.32(1H, s), 7.35(1H, s), 8.00–8.10(4H, m), 10.12(1H, br s)

Mass(ESI): m/z 539(M−1)

mp 162–163° C.

Example 218

In the same manner as in Example 1, 3-(2-chloro-4-ethoxy)benzyl-2-methyl-5-[(4-methylbenzene)sulfonylcarbamoyl]-3H-imidazo[4,5-b]pyridine (318 mg) was obtained as colorless crystals from 3-(2-chloro-4-ethoxy)-benzyl-2-methyl-3H-imidazo[4,5-b]pyridine-5-carboxylic acid (280 mg).

$^1$H-NMR (CDCl$_3$): 1.42(3H, t, J=7.5 Hz), 2.43(3H, s), 2.64(3H, s), 4.04(2H, q, J=7 Hz), 5.51(2H, s), 6.78(1H, s), 6.79(1H, s), 7.02(1H, br s), 7.34(1H, d, J=8 Hz), 8.00–8.09 (4H, m), 10.11(1H, br s)

Mass(ESI): m/z 497(M−1)

mp 190–191° C.

Example 219

In the same manner as in Example 1, 3-[2-chloro-4-(2-methoxyethoxy)benzyl]-2-methyl-5-[(4-methylbenzene)sulfonylcarbamoyl]-3H-imidazo[4,5-b]pyridine (203 mg) was obtained as colorless crystals from 3-[2-chloro-4-(2-methoxyethoxy)benzyl]-2-methyl-3H-imidazo[4,5-b]pyridine-5-carboxylic acid (189 mg).

$^1$H-NMR (CDCl$_3$): 2.43(3H, s), 2.64(3H, s), 3.46(3H, s), 3.70–3.80(2H, m), 4.08–4.18(2H, m), 5.52(2H, s), 6.74–6.87(2H, m), 7.07(1H, br s), 7.35(2H, d, J=8 Hz), 7.99–8.10(4H, m)

Mass(ESI): m/z 527(M−1)

mp 156–158° C.

Example 220

In the same manner as in Example 1, 3-[2-chloro-4-[(thiophen-2-yl)methyloxy]benzyl]-2-methyl-5-[(4-methylbenzene)sulfonylcarbamoyl]-3H-imidazo[4,5-b]pyridine (215 mg) was obtained as colorless crystals from 3-[2-chloro-4-[(thiophen-2-yl)methyloxy]benzyl]-2-methyl-3H-imidazo[4,5-b]pyridine-5-carboxylic acid (180 mg).

$^1$H-NMR (CDCl$_3$): 2.42(3H, s), 2.64(3H, s), 5.23(2H, s), 5.52(2H, s), 6.81(1H, d, J=8 Hz), 6.88(1H, dd, J=8, 2 Hz), 7.02(1H, dd, J=5, 3 Hz), 7.10–7.14(2H, m), 7.30–7.36(3H, m), 8.00–8.10(4H, m), 10.09(1H, br s)

Mass(ESI): m/z 565(M−1)

mp 184–185° C.

Example 221

In the same manner as in Example 1, 3-[2-chloro-4-[(thiophen-3-yl)methyloxy]benzyl]-2-methyl-5-[(4-methylbenzene)sulfonylcarbamoyl]-3H-imidazo[4,5-b]pyridine (126 mg) was obtained as colorless crystals from 3-[2-chloro-4-[(thiophen-3-yl)methyloxy]benzyl]-2-methyl-3H-imidazo[4,5-b]pyridine-5-carboxylic acid (115 mg).

$^1$H-NMR (CDCl$_3$): 2.42(3H, s), 2.64(3H, s), 5.08(2H, s), 5.52(2H, s), 6.81(1H, d, J=8 Hz), 6.87(1H, dd, J=8, 2 Hz), 7.11(1H, d, J=2 Hz), 7.14(1H, br d, J=5 Hz), 7.28–7.39(4H, m), 8.00–8.09(4H, d, J=8 Hz)

Mass(ESI): m/z 565(M−1)

mp 198–200° C.

Example 222

In the same manner as in Example 1, 3-(2-chloro-4-phenylethynyl)benzyl-2,7-dimethyl-5-[(4-methylbenzene)sulfonylcarbamoyl]-3H-imidazo[4,5-b]pyridine (123 mg) was obtained as colorless crystals from 3-(2-chloro-4-phenylethynyl)benzyl-2,7-dimethyl-3H-imidazo[4,5-b]pyridine-5-carboxylic acid (125 mg).

$^1$H-NMR (CDCl$_3$): 2.39(3H, s), 2.62(3H, s), 2.69(3H, s), 5.58(2H, s), 6.70(1H, br d, J=8 Hz), 7.12(1H, dd, J=8, 1 Hz), 7.23–7.43(6H, m), 7.48–7.58(2H, m), 7.65(1H, br s), 7.91 (1H, br s), 8.00–8.01(2H, m), 10.10(1H, br s)

Mass(ESI): m/z 567(M−1)

mp 221–222° C.

Example 223

In the same manner as in Example 1, 3-[2-chloro-4-(cyclopentylmethyloxy)benzyl]-2-methyl-5-[(4-methylbenzene)sulfonylcarbamoyl]-3H-imidazo[4,5-b]pyridine (66 mg) was obtained as colorless crystals from 3-[2-chloro-4-(cyclopentylmethyloxy)benzyl-2-methyl-3H-imidazo[4,5-b]pyridine-5-carboxylic acid (69 mg).

$^1$H-NMR (CDCl$_3$): 1.36–1.44(2H, m), 1.50–1.71(3H, m), 1.75–1.91(2H, m), 2.35(1H, m), 2.42(3H, s), 2.64(3H, s), 3.83(2H, d, J=5 Hz), 5.51(2H, s), 6.78(2H, s), 6.02(1H, br s), 7.33(2H, d, J=8 Hz), 7.98–8.10(4H, m)

Mass(ESI): m/z 551(M−1)

mp 177–178° C.

Example 224

In the same manner as in Example 1, 3-(2-chloro-4-phenylethynyl)benzyl-2,7dimethyl-5-(1-pentanesulfonylcarbamoyl)-3H-imidazo[4,5-b]pyridine (204 mg) was obtained as colorless crystals from 3-(2-chloro-4-phenylethynyl)benzyl-2,7-dimethyl-3H-imidazo[4,5-b]pyridine-5-carboxylic acid (200 mg).

$^1$H-NMR (CDCl$_3$):0.86(3H, t, J=8 Hz), 1.25–1.48(4H, m), 1.81–1.96(2H, m), 2.62(3H, s), 2.75(3H, s), 3.49–3.61 (2H, m), 5.57(2H, s), 6.65(1H, d, J=8 Hz), 7.29–7.41(4H, m), 7.48–7.56(2H, m), 7.65(1H, br s), 8.03(1H, s), 9.85(1H, br s)

Mass(ESI): m/z 547(M−1)

mp 201–203° C.

Example 225

In the same manner as in Example 1, 3-(2-chloro-4-(1-hexynyl)benzyl-2-methyl-5-(N-(4-methylphenylsulfonyl)carbamoyl-3H-imidazo[4,5-b]pyridine (448 mg) was obtained as colorless crystals from 3-(2-chloro-4-(1-hexynyl)-benzyl-2-methyl-3H-imidazo[4,5-b]pyridine-5-carboxylic acid (400 mg).

$^1$H-NMR (CDCl$_3$): 0.95(3H, t, J=6 Hz), 1.40–1.65(4H), 2.35–2.48(5H), 2.60(3H, s), 5.57(2H, s), 6.65(1H, d, J=8 Hz), 7.22(1H, d, J=8 Hz), 7.34(2H, d, J=8 Hz), 7.52(1H, s), 8.02–8.12(4H)

mp 175–176° C.

Example 226

In the same manner as in Example 1, 3-(2-chloro-4-(cyclohexylmethyloxy)benzyl)-2,7-dimethyl-5-((1-pentanesulfonylcarbamoyl)-3H-imidazo[4,5-b]pyridine (240 mg) was obtained as colorless crystals from 3-(2-chloro-4-(cyclohexylmethyloxy)benzyl)-2,7-dimethyl-3H-imidazo[4,5-b]pyridine-5-carboxylic acid (254 mg) and 1-pentanesulfonamide (135 mg).

$^1$H-NMR (CDCl$_3$): 0.89(3H, t, J=7 Hz), 0.96–1.93(17H, m), 2.64(3H, s), 2.73(3H, s), 3.55(2H, m), 3.72(2H, d, J=7 Hz), 5.48(2H, s), 6.71(2H, br s), 6.98(1H, d, J=1 Hz), 7.99(1H, s)

Mass(ESI): m/z 559(M−1)

Example 227

In the same manner as in Example 1, 3-(2-chloro-4-(cyclohexylmethyloxy)benzyl)-2,7-dimethyl-5-[(4-methylbenzene)sulfonylcarbamoyl]-3H-imidazo[4,5-b]pyridine (252 mg) was obtained as colorless crystals from 3-(2-chloro-4-(cyclohexylmethyloxy)benzyl)-2,7-dimethyl-3H-imidazo[4,5-b]pyridine-5-carboxylic acid (247 mg) and (4-methylbenzene)sulfonamide (148 mg).

$^1$H-NMR (CDCl$_3$): 0.98–1.87(11H, m), 2.42(3H, s), 2.62 (3H, s), 2.66(3H, s), 3.74(2H, d, J=7 Hz), 5.49 (2H, s), 6.71(2H, br s), 7.00(1H, d, J=1 Hz), 7.33(2H, d, J=8 Hz), 7.88(1H, s), 8.03(2H, d, J=8 Hz)

Mass (ESI) m/z 579(M−1)

Example 228

In the same manner as in Example 1, 3-(2-chloro-4-ethylbenzyl)-2,7-dimethyl-5-(1-pentanesulfonylcarbamoyl)-3H-imidazo[4,5-b]pyridine (178 mg) was obtained as colorless crystals from 3-(2-chloro-4-ethylbenzyl)-2,7-dimethyl-3H-imidazo[4,5-b]pyridine-5-carboxylic acid (190 mg) and 1-pentanesulfonamide (125 mg).

$^1$H-NMR (CDCl$_3$) 0.88(3H, t, J=7 Hz), 1.22(3H, t, J=7 Hz), 1.28–1.48(4H, m), 1.88–1.93(2H, m), 2.62(3H, s), 2.62(2H, q, J=7 Hz), 2.74(3H, s), 3.52–3.57(2H, m), 5.52 (2H, s), 6.60(1H, d, J=8 Hz), 7.00(1H, d, J=8 Hz), 7.31(1H, s), 8.01(1H, s)

Example 229

In the same manner as in Example 1, 3-(2-chloro-4-ethylbenzyl)-2,7-dimethyl-5-[(4-methylbenzene)sulfonylcarbamoyl]-3H-imidazo[4,5-b]pyridine (173 mg) was obtained as colorless crystals from 3-(2-chloro-4-ethylbenzyl)-2,7-dimethyl-3H-imidazo[4,5-b]pyridine-5-carboxylic acid (190 mg) and (4-methylbenzene)sulfonamide (142 mg).

$^1$H-NMR (CDCl$_3$): 1.24(3H, t, J=7 Hz), 2.42(3H, s), 2.61(3H, s), 2.64(2H, q, J=7 Hz), 2.68(3H, s), 5.53 (2H, s), 6.61(1H, d, J=8 Hz), 7.01(1H, d, J=8 Hz), 7.30–7.34(3H, m), 7.90(1H, s), 8.04(2H, d, J=8 Hz)

Example 230

In the same manner as in Example 1, 3-(2-chloro-4-(trifluoromethyl)-benzyl)-2,7-dimethyl-5-(1-pentanesulfonylcarbamoyl)-3H-imidazo[4,5-b]pyridine (210 mg) was obtained as pale-yellow crystals from 3-(2-chloro-4-(trifluoromethyl)benzyl)-2,7-dimethyl-3H-imidazo[4,5-b]pyridine-5-carboxylic acid (248 mg) and 1-pentanesulfonamide (135 mg).

$^1$H-NMR (CDCl$_3$): 0.88(3H, t, J=8 Hz), 1.25–1.48(4H, m), 1.80–1.94(2H, m), 2.61(3H, s), 2.76(3H, s), 3.50–3.58 (2H, m), 5.60 (2H, s), 6.72(1H, d, J=8 Hz), 7.44(1H, br d, J=8 Hz), 7.77(1H, br s), 8.05(1H, s), 9.78(1H, br s)

Example 231

In the same manner as in Example 1, 3-(2-chloro-4-(trifluoromethyl)-benzyl)-2,7-dimethyl-5-[(4-methylbenzene)sulfonylcarbamoyl]-3H-imidazo[4,5-b]pyridine (178 mg) was obtained as colorless crystals from 3-(2-chloro-4-(trifluoromethyl)benzyl)-2,7-dimethyl-3H-imidazo[4,5-b]pyridine-5-carboxylic acid (238 mg) and (4-methylbenzene)sulfonamide (159 mg).

$^1$H-NMR (CDCl$_3$): 2.42(3H, s), 2.60(3H, s), 2.69(3H, s), 5.61(2H, s), 6.73(1H, d, J=8 Hz), 7.33(2H, d, J=8 Hz), 7.44(1H, br d, J=8 Hz), 7.78(1H, br s), 7.93(1H, s), 8.02(1H, s), 10.05(1H, br s)

Example 232

In the same manner as in Example 1, 3-(2-chloro-4-ethoxybenzyl)-2,7-dimethyl-5-(1- pentanesulfonylcarbamoyl)-3H-imidazo[4,5-b]pyridine was obtained as colorless crystals from 3-(2-chloro-4-ethoxybenzyl)-2,7-dimethyl-3H-imidazo[4,5-b]pyridine-5-carboxylic acid (260 mg) and 1-pentanesulfonamide (164 mg).

$^1$H-NMR (CDCl$_3$): 0.89(3H, t, J=7 Hz), 1.26–1.51(7H, m), 1.80–1.94(2H, m), 2.64(3H, s), 2.73(3H, s), 3.52–3.57 (2H, m), 4.01(2H, q, J=7 Hz), 5.49(2H, s), 6.72(2H, s), 6.99(1H, s), 7.99(1H, s), 9.89(1H, br s)

Example 233

In the same manner as in Example 1, 3-(2-chloro-4-ethoxybenzyl)-2,7-dimethyl-5-[(4-methylbenzene) sulfonylcarbamoyl]-3H-imidazo[4,5-b]pyridine was obtained as colorless crystals from 3-(2-chloro-4-ethoxybenzyl)-2,7-dimethyl-3H-imidazo[4,5-b]pyridine-5-carboxylic acid (250 mg) and (4-methylbenzene) sulfonamide (178 mg).

$^1$H-NMR (CDCl$_3$): 1.42(3H, t, J=7 Hz), 2.42(3H, s), 2.62(3H, s), 2.66(3H, s), 4.03(2H, q, J=7 Hz), 5.49(2H, s), 6.72(1H, d, J=8 Hz), 6.77(1H, d, J=8 Hz), 7.01(1H, d, J=1 Hz), 7.33(2H, d, J=8 Hz), 7.88(1H, s), 8.03(2H, d, J=8 Hz), 10.14(1H, br s)

Example 234

In the same manner as in Example 1, 3-(2,4-dichlorobenzyl)-2-methyl-5-(p-toluenesulfonylcarbamoyl) benzo[b]furan (90 mg) was obtained as white crystals from 5-carboxy-3-(2,4-dichlorobenzyl)-2-methylbenzo[b]furan (300 mg), N,N'-carbonyldiimidazole (218 mg), DBU (0.20 ml) and (4-methyl-benzene)sulfonamide (230 mg).

$^1$H-NMR (DMSO-d$_6$, δ ppm): 2.37(3H, s), 4.06(2H, s), 7.16(1H, d, J=8.4 Hz), 7.32(1H, dd, J=8.2 and 2.0 Hz), 7.38(2H, d, J=8.0 Hz), 7.54(1H, d, J=8.7 Hz), 7.62(1H, d, J=1.9 Hz), 7.75(1H, d, J=8.9 Hz), 7.83(2H, d, J=8.2 Hz), 7.90(1H, s), 12.35(1H, br s)

IR(Nujol): 1700 cm$^{-1}$ mp: 120–121° C.

Example 235

In the same manner as in Example 1, 5-((5-bromothiophen-2-yl)sulfonylcarbamoyl)-3-(2,4-dichlorobenzyl)-2-methylbenzo[b]furan (350 mg) was obtained as white crystals from 5-carboxy-3-(2,4-dichlorobenzyl)-2-methylbenzo-[b]furan (280 mg), N,N'-carbonyldiimidazole (190 mg), DBU (0.18 ml) and (5-bromothiophen-2-yl)sulfonamide (280 mg).

$^1$H-NMR (DMSO-d$_6$, δ ppm): 2.40(3H, s), 4.08(2H, s), 7.17(1H, d, J=8.4 Hz), 7.33(1H, dd, J=8.4 and 2.2 Hz), 7.35(1H, d, J=4.1 Hz), 7.58(1H, d, J=8.7 Hz), 7.63(1H, d, J=2.1 Hz), 7.64(1H, d, J=4.0 Hz), 7.79(1H, d, J=8.7 Hz), 7.96(1H, s)

IR(Nujol): 1699 cm$^{-1}$ mp: 165–167° C.

Example 236

In the same manner as in Example 1, 5-((5-chlorothiophen-2-yl)sulfonylcarbamoyl)-3-(2,4-dichlorobenzyl)-2-methylbenzo[b]furan (210 mg) was obtained as white crystals from 5-carboxy-3-(2,4-dichlorobenzyl)-2-methylbenzo-[b]furan (230 mg), N,N'-carbonyldiimidazole (170 mg), DBU (0.16 ml) and (5-chlorothiophen-2-yl)sulfonamide (210 mg).

$^1$H-NMR (DMSO-d$_6$, δ ppm): 2.40(3H, s), 4.07(2H, s), 7.16(1H, d, J=8.4 Hz), 7.20(1H, d, J=4.0), 7.32(1H, dd, J=8.3 and 2.3 Hz), 7.55(1H, d, J=8.6 Hz), 7.60–7.64(2H, m), 7.81(1H, dd, J=8.7 and 1.8 Hz), 7.94(1H, d, J=1.5 Hz)

IR(Nujol): 1700 cm$^{-1}$ mp: 181–183° C.

Example 237

In the same manner as in Example 1, 3-(2-chloro-4-phenylbenzyl)-2-methyl-5-(4-pentene)sulfonylcarbamoyl)-3H-imidazo[4,5-b]pyridine (91 mg) was obtained as white crystals from 3-(2-chloro-4-phenylbenzyl)-2-methyl-3H-imidazo[4,5-b]pyridine-5-carboxylic acid (150 mg), N,N'-carbonyldi-imidazole (84 mg), DBU (79 mg) and 4-pentene-1-sulfonamide (77 mg).

$^1$H-NMR (DMSO-d$_6$, δ ppm): 1.75–1.83(2H, m), 2.10–2.16(2H, m), 2.49(3H, s), 3.52(2H, t, J=7.7 Hz), 4.94 (1H, d, J=11.3 Hz), 4.98(1H, dd, J=17.1 and 2.6 Hz), 5.70–5.76(1H, m), 5.86(2H, s), 6.89(1H, d, J=8.1 Hz), 7.38(1H, t, J=7.3 Hz), 7.45(2H, t, J=7.3 Hz), 7.54(1H, dd, J=8.1 and 1.7 Hz), 7.66(2H, d, J=7.4 Hz), 7.84(1H, d, J=1.8 Hz), 8.01(1H, d, J=8.3 Hz), 8.20(1H, d, J=8.2 Hz), 11.76 (1H, br s)

mp: 152–155° C.

Example 238

In the same manner as in Example 1, 2-(2-chloro-4-phenylbenzyl)-3-methyl-6-(p-toluenesulfonylcarbamoyl)-2H-indazole (1.00 g) was obtained as white crystals from 6-carboxy-2-(2-chloro-4-phenylbenzyl)-3-methyl-2H-indazole (1.131 g), N,N'-carbonyldiimidazole (0.63 g), DBU (0.58 ml) and p-toluenesulfonamide (0.67 g). $^1$H-NMR (DMSO-d$_6$, δ ppm): 2.39(3H, s), 2.65(3H, s), 5.77(2H, s), 6.80(1H, d, J=8.1 Hz), 7.34–7.47(6H, m), 7.56(1H, d, J=8.2 Hz), 7.66(2H, d, J=7.8 Hz), 7.78–7.81(2H, m), 7.89(2H, d, J=8.2 Hz), 8.22(1H, s), 12.42(1H, br s)

mp: 236–237° C.

Example 239

3-(2-Chloro-4-(1-hexynyl)benzyl)-2-methyl-5-(N-(4-methylphenylsulfonyl)carbamoyl-3H-imidazo[4,5-b] pyridine (240 mg) was reduced in dioxane using platinum oxide as a catalyst to give 3-(2-chloro-4-hexylbenzyl)-2-methyl-5-(N-(4-methylphenylsulfonyl)carbamoyl-3H-imidazo[4,5-b]pyridine (181 mg) as colorless crystals.

$^1$H-NMR (CDCl$_3$): 0.88(3H, t, J=6 Hz), 1.22–1.66(8H), 2.43(3H, s), 2.59(2H, t, J=6 Hz), 2.62(3H, s), 5.55(2H, s), 6.65(1H, d, J=8 Hz), 7.02(1H, d, J=8 Hz), 7.28–7.37(3H), 8.01–8.11(4H)

mp: 162–163° C.

Example 240

To a solution (5 ml) of 3-(4-bromo-2-chlorobenzyl)-2,7-dimethyl-5-((4-methylbenzene)sulfonylcarbamoyl)-3H-imidazo[4,5-b]pyridine (500 mg) in toluene were successively added sodium tert-butoxide (123 mg), piperidine (109 mg), (R)-(+)-BINAP (8 mg) and tris(dibenzylideneacetone) dipalladium(0) (4 mg) under a nitrogen atmosphere, and the mixture was stirred at 90° C. for 30 hr. The reaction mixture was concentrated under reduced pressure and water was added. 1N Hydrochloric acid was added to adjust to pH 7, and the mixture was extracted with a mixed solvent of chloroform and methanol (chloroform:methanol=4:1) The organic layer was washed with saturated brine, dried over anhydrous magnesium sulfate and concentrated under reduced pressure. Ethanol was added to the residue and the mixture was heated and allowed to cool. The precipitated crystals were collected by filtration. The crystals were dissolved in N,N-dimethylformamide (12 ml) and hot water (8.5 ml) was gradually added on an oil bath at 80° C. The mixture was allowed to cool with stirring and the precipitated crystals were collected by filtration. The crystals were washed with water, and dried under reduced pressure with heating to give 3-(2-chloro-4-piperidinobenzyl)-2,7-dimethyl-5-((4-methylbenzene)sulfonylcarbamoyl)-3H-imidazo[4,5-b]pyridine (391 mg) as pale-pink crystals.

$^1$H-NMR (CDCl$_3$): 1.65–1.70(6H, m), 2.42(3H, s), 2.64 (3H, s), 2.65(3H, s), 3.19(4H, t, J=7 Hz), 5.45(2H, s), 6.75(2H, s), 6.95(1H, s), 7.32(2H, d, J=8 Hz), 7.86(1H, s), 8.04(2H, d, J=8 Hz), 10.18(1H, s)

Mass(ESI): m/z 550(M−H)$^-$ mp: 190–192° C.

Example 241

In the same manner as in Example 240, 3-(2-chloro-4-morpholino-benzyl)-2,7-dimethyl-5-((4-methylbenzene)sulfonylcarbamoyl)-3H-imidazo[4,5-b]pyridine (78 mg) was obtained as colorless crystals from 3-(4-bromo-2-chlorobenzyl)-2,7-dimethyl-5-((4-methylbenzyl)sulfonylcarbamoyl)-3H-imidazo[4,5-b]pyridine (500 mg) and morpholine (191 mg).

$^1$H-NMR (CDCl$_3$): 2.42(3H, s), 2.65(3H, s), 2.66(3H, s), 3.18(4H, t, J=7 Hz), 3.85(4H, t, J=7 Hz), 5.46(2H, s), 6.73–6.82(2H, m), 6.95(1H, d, J=2 Hz), 7.33(2H, d, J=8 Hz), 7.86(1H, s), 8.05(2H, d, J=8 Hz), 10.14(1H, s)

Mass(ESI): m/z 552(M−H)$^-$ mp: 235–237° C.

Example 242

In the same manner as in Example 240, 3-(2-chloro-4-(hexamethylene-imino)benzyl)-2,7-dimethyl-5-((4-methylbenzene)sulfonylcarbamoyl)-3H-imidazo[4,5-b]pyridine (142 mg) was obtained as colorless crystals from 3-(4-bromo-2-chlorobenzyl)-2,7-dimethyl-5-((4-methylbenzene)-sulfonyl-carbamoyl)-3H-imidazo[4,5-b]pyridine (600 mg) and hexamethylene-imine (206 mg).

$^1$H-NMR (CDCl$_3$): 1.50–1.60(4H, m), 1.80(4H, br), 2.42 (3H, s), 2.65(3H, s), 2.66(3H, s), 3.43(4H, t, J=7 Hz), 5.44(2H, s), 6.53(1H, dd, J=8, 2 Hz), 6.70(1H, d, J=2 Hz), 6.76(1H, d, J=8 Hz), 7.32(2H, d, J=8 Hz), 7.85(1H, s), 8.04(2H, d, J=8 Hz)

Mass(ESI): m/z 564(M−H)$^-$ mp: 210–212° C.

Example 243

In the same manner as in Example 240, 3-(2-chloro-4-(1-pyrrolidinyl)-benzyl)-2,7-dimethyl-5-((4-methylbenzene)sulfonylcarbamoyl)-3H-imidazo-[4,5-b]pyridine (195 mg) was obtained as colorless crystals from 3-(4-bromo-2-chlorobenzyl)-2,7-dimethyl-5-((4-methylbenzene)sulfonylcarbamoyl)-3H-imidazo[4,5-b]pyridine (600 mg) and pyrrolidine (148 mg).

$^1$H-NMR (CDCl$_3$): 1.98–2.04(4H, m), 2.42(3H, s), 2.65 (3H, s), 2.66(3H, s), 3.27(4H, t, J=7 Hz), 5.45(2H, s), 6.43(1H, dd, J=8, 2 Hz), 6.59(1H, d, J=2 Hz), 6.83(1H, d, J=8 Hz), 7.32(2H, d, J=8 Hz), 7.84(1H, s), 8.03(2H, d, J=8 Hz), 10.21(1H, s)

Mass(ESI): m/z 536(M−H)$^-$ mp: 212–214° C.

Example 244

In the same manner as in Example 240, 3-(2-chloro-4-(4-methyl-piperazin-1-yl)benzyl)-2,7-dimethyl-5-((4-methylbenzene)sulfonylcarbamoyl)-3H-imidazo[4,5-b]pyridine (411 mg) was obtained as colorless crystals from 3-(4-bromo-2-chlorobenzyl)-2,7-dimethyl-5-((4-methylbenzene)-sulfonylcarbamoyl)-3H-imidazo[4,5-b]pyridine (600 mg) and 1-methyl-piperazine(154 mg).

$^1$H-NMR (CDCl$_3$): 2.35(3H, s), 2.42(3H, s), 2.55(4H, t, J=7 Hz), 2.64(3H, s), 2.65(3H, s), 3.24(4H, t, J=7 Hz), 5.46(2H, s), 6.77(2H, s), 6.96(1H, s), 7.33(2H, d, J=8 Hz), 7.86(1H, s), 8.03(2H, d, J=8 Hz)

Mass(ESI): m/z 568(M+H)$^+$ mp: 149–151° C.

Example 245

In the same manner as in Example 1, 3-(2-chloro-4-methylthiobenzyl)-2,7-dimethyl-5-[(4-methylbenzene)sulfonylcarbamoyl]-3H-imidazo[4,5-b]pyridine (234 mg) was obtained as colorless crystals from 3-(2-chloro-4-methylthiobenzyl)-2,7-dimethyl-3H-imidazo[4,5-b]pyridine-5-carboxylic acid (250 mg) and (4-methylbenzene)sulfonamide (356 mg).

$^1$H-NMR (CDCl$_3$): 2.42(3H, s), 2.50(3H, s), 2.62(3H, s), 2.67(3H, s), 5.51(2H, s), 6.69(1H, d, J=8 Hz), 7.08(1H, dd, J=1, 8 Hz), 7.32–7.35(3H, m), 7.88(1H, s), 8.04(2H, d, J=8 Hz)

Example 246

In the same manner as in Example 1, 3-(2-chloro-4-methylthiobenzyl)-2,7-dimethyl-5-(1-pentanesulfonylcarbamoyl-3H-imidazo[4,5-b]pyridine (188 mg) was obtained as colorless crystals from 3-(2-chloro-4-methylthiobenzyl)-2,7-dimethyl-3H-imidazo[4,5-b]pyridine-5-carboxylic acid (260 mg) and 1-pentanesulfonamide (326 mg).

$^1$H-NMR (CDCl3): 0.88(3H, t, J=7 Hz), 1.28–1.48(4H, m), 1.83–1.93(2H, m), 2.48(3H, s), 2.63(3H, s), 2.74(3H, s), 3.55(2H, m), 5.51(2H, s), 6.66(1H, d, J=8 Hz), 7.03(1H, dd, J=1, 8 Hz), 7.31(1H, d, J=1 Hz), 8.00(1H, s)

The above-mentioned sulfonamide compounds and pharmaceutically acceptable salts thereof of the present invention are useful as pharmaceutical preparations that can be used for the prophylaxis and treatment of impaired glucose tolerance disorder, diabetes (e.g., type II diabetes), diabetic complications (e.g., diabetic gangrene, diabetic arthropathy, diabetic bone resorption, diabetic glomerulosclerosis, diabetic nephropathy, diabetic dermatopathy, diabetic neuropathy, diabetic cataract, diabetic retinopathy and the like), insulin resistant syndrome (e.g., insulin receptor disorders, Rabson-Mendenhall syndrome, leprechaunism, Kobberling-Dunnigan syndrome, Seip syndrome, Lawrence syndrome, Cushing syndrome, acromegaly and the like), polycystic ovary syndrome, hyperlipidemia, atherosclerosis, cardiovascular disorders (e.g., stenocardia, cardiac failure and the like), hyperglycemia (e.g., those characterized by abnormal saccharometabolism such as feeding disorders), hypertension and the like, based on their blood sugar level-depressing activity, as well as angina pectoris, hypertension, pulmonary hypertension, congestive heart failure, glomerulopathy (e.g., diabetic glomerulosclerosis), tubulointerstitial disorders (e.g., kidney diseases induced by FK506, cyclosporin and the like), renal failure, atherosclerosis, angiostenosis (e.g., after percutaneous arterioplasty), distal angiopathy, cerebral apoplexy, chronic reversible obstructions (e.g., bronchitis, asthma inclusive of chronic asthma and allergic asthma), autoimmune diseases, allergic rhinitis, urticaria, glaucoma, diseases characterized by enteromotility (e.g., hypersensitive enteropathy), impotence (e.g., organic impotence, psychic impotence and the like), nephritis, cancer cachexia or restenosis after PTCA, pancreatitis, cachexia (e.g., progressive weight loss due to lipolysis, myolysis, anemia, edema, anorexia and the like in chronic diseases such as cancer, tuberculosis, endocrine diseases and AIDS, and the like, based on their cGMP-PDE (especially PDE-V)-inhibiting activity, smooth muscle relaxing activity, bronchodilating activity, vasodilating activity, smooth muscle cell suppressing activity and antiallergic activity.

This application is based on application Nos. 208295/1997 and 114718/1998 filed in Japan, the contents of which are incorporated hereinto by reference.

What is claimed is:

1. A sulfonamide compound of the formula (I):

$$R^1\text{—}SO_2NHCO\text{—}A\text{—}X\text{—}R^2 \qquad (I)$$

wherein:

$R^1$ is an optionally substituted alkyl, an optionally substituted alkenyl, an optionally substituted alkynyl, an optionally substituted cyclo(lower)alkyl, an optionally substituted aryl or an optionally substituted heterocyclic group;

A is imidazopyridyl, pyrrolopyridyl, pyrazolopyridyl, or indolizinyl, each of which is optionally substituted by one or two lower alkyl;

X is an alkylene, an oxa, an oxa(lower)alkylene, a lower alkylene-oxa, a carbonyl, a lower alkenylene, an optionally substituted imino, an optionally N-substituted imino(lower)alkylene, an optionally N-substituted lower alkyleneimino, a thioxa(lower) alkylene or a lower alkylenethioxa, and $R^2$ is an optionally substituted aryl, an optionally substituted heterocyclic group or a substituted biphenylyl, wherein, when these groups are substituted, the substituent is at least one member selected from the group consisting of alkyl, cyclo(lower)alkyl, alkenyl, alkynyl, lower alkanoyl, lower alkoxy, aryl, heterocycle(lower) alkyl, halogen, amino, substituted amino, lower alkylsulfonyl, lower alkylsulfinyl, lower alkylthio, cyano, carboxy, protected carboxy, carbamoyl, mono (lower)alkylcarbamoyl, di(lower)alkylcarbamoyl, nitro, halo(lower)alkyl, aryl(lower)alkyl, aryl(lower) alkenyl, aryl(lower)alkoxy, lower alkoxy substituted by substituted amino, cyclo(lower)alkyl(lower)alkoxy, cyclo(lower)alkyl(lower)alkyl, aryloxy(lower)alkyl, acyloxy(lower)alkyl, hydroxy(lower)alkyl, mono- or di(lower)alkylamino(lower)alkyl, aryl(lower)alkoxy (lower)alkyl, arylthio(lower)alkyl, heterocycle(lower) alkoxy, heterocycleoxy(lower)alkyl, aryl(lower) alkylthio, arylureido, lower alkoxy(lower)alkoxy, aryl (lower)alkynyl, lower alkyl substituted by optionally substituted divalent heterocyclic group, and heterocyclic group other than tetrazolyl, which is optionally substituted by lower alkyl or halogen, or a salt thereof.

2. The sulfonamide compound of claim 1, wherein, $R^2$ is an optionally substituted alkyl, an optionally substituted alkenyl, an optionally substituted alkynyl, an optionally substituted cyclo(lower)alkyl, an optionally substituted aryl or an optionally substituted heterocyclic group, wherein, when these groups are substituted, the substituent is at least one member selected from the group consisting of alkyl, cyclo(lower)alkyl, alkenyl, alkynyl, lower alkanoyl, lower alkoxy, aryl, heterocycle(lower)alkyl, halogen, amino, substituted amino, lower alkylsulfonyl, lower alkylsulfinyl, lower alkylthio, cyano, carboxy, protected carboxy, carbamoyl, mono(lower)alkylcarbamoyl, di(lower) alkylcarbamoyl, nitro, halo(lower)alkyl, aryl(lower) alkyl, aryl(lower)alkenyl, aryl(lower)alkoxy, lower alkoxy substituted by substituted amino, cyclo(lower) alkyl(lower)alkoxy, cyclo(lower)alkyl(lower)alkyl, aryloxy(lower)alkyl, acyloxy(lower)alkyl, hydroxy (lower)alkyl, mono- or di(lower)alkylamino(lower) alkyl, aryl(lower)alkoxy(lower)alkyl, arylthio(lower) alkyl, heterocycle(lower)alkoxy, heterocycleoxy (lower)alkyl, aryl(lower)alkylthio, arylureido, lower alkoxy(lower)alkoxy, aryl(lower)alkynyl, lower alkyl substituted by optionally substituted divalent heterocyclic group and optionally substituted heterocyclic group; and $R^2$ is an optionally substituted aryl, an optionally substituted heterocyclic group or a substituted biphenylyl, wherein, when these groups are substituted, the substituent is at least one member selected from the group consisting of alkyl, cyclo(lower)alkyl, alkenyl, alkynyl, lower alkanoyl, lower alkoxy, aryl, heterocycle(lower) alkyl, halogen, amino, substituted amino, lower alkylsulfonyl, lower alkylsulfinyl, lower alkylthio, cyano, carboxy, protected carboxy, carbamoyl, mono (lower)alkylcarbamoyl, di(lower)alkylcarbamoyl, nitro, halo(lower)alkyl, aryl(lower)alkyl, aryl(lower) alkenyl, aryl(lower)alkoxy, lower alkoxy substituted by substituted amino, cyclo(lower)alkyl(lower)alkoxy, cyclo(lower)alkyl(lower)alkyl, aryloxy(lower)alkyl, acyloxy(lower)alkyl, hydroxy(lower)alkyl, mono- or di(lower)alkylamino(lower)alkyl, aryl(lower)alkoxy (lower)alkyl, arylthio(lower)alkyl, heterocycle(lower) alkoxy, heterocycleoxy(lower)alkyl, aryl(lower) alkylthio, arylureido, lower alkoxy(lower)alkoxy, aryl (lower)alkynyl, lower alkyl substituted by optionally substituted divalent heterocyclic group, and heterocyclic group other than tetrazolyl, which is optionally substituted by lower alkyl or halogen, or a salt thereof.

3. The sulfonamide compound of claim 2, wherein, $R^1$ is an optionally substituted alkyl, an optionally substituted alkenyl, an optionally substituted alkynyl, an optionally substituted cyclo(lower)alkyl, an optionally substituted phenyl or an optionally substituted heterocyclic group, wherein, when these groups are substituted, the substituent is at least one member selected from the group consisting of alkyl, cyclo (lower)alkyl, alkenyl, alkynyl, lower alkanoyl, lower alkoxy, phenyl, heterocycle(lower)alkyl, halogen, amino, lower alkanoylamino, mono(lower)alkylamino, di(lower)alkylamino, N-(lower)alkyl-N-acylamino, lower alkylsulfonylamino, aryl(lower)alkylamino, N-heterocycle-N-(lower)alkylamino, arylsulfonylamino, arylcarbonylamino, lower alkylsulfonyl, lower alkylsulfinyl, lower alkylthio, cyano, carboxy, protected carboxy, carbamoyl, mono (lower)alkylcarbamoyl, di(lower)alkylcarbamoyl, nitro, halo(lower)alkyl, aryl(lower)alkyl, aryl(lower) alkenyl, aryl(lower)alkoxy, lower alkanoylamino (lower)alkoxy, mono(lower)alkylamino(lower)alkoxy, di(lower)alkylamino(lower)alkoxy, N-(lower)alkyl-N-acylamino(lower)alkoxy, lower alkylsulfonylamino (lower)alkoxy, aryl(lower)alkylamino(lower)alkoxy, N-heterocycle-N-(lower)alkylamino(lower)alkoxy, arylsulfonylamino(lower)alkoxy, arylcarbonylamino (lower)alkoxy, cyclo(lower)alkyl(lower)alkoxy, cyclo (lower)alkyl(lower)alkyl, aryloxy(lower)alkyl, acyloxy (lower)alkyl, hydroxy(lower)alkyl, mono- or di(lower) alkylamino(lower)alkyl, aryl(lower)alkoxy(lower)

alkyl, arylthio(lower)alkyl, heterocycle(lower)alkoxy, heterocycleoxy(lower)alkyl, aryl(lower)alkylthio, arylureido, lower alkoxy(lower)alkoxy, aryl(lower)alkynyl, lower alkyl substituted by optionally substituted divalent heterocyclic group and optionally substituted heterocyclic group or a salt thereof.

4. The sulfonamide compound of claim 3, wherein, $R^1$ is an alkyl, an alkenyl, a phenyl(lower)alkenyl, a quinolyl, a phenyl optionally substituted by a substituent selected from the group consisting of nitro, alkyl and alkenyl or a thienyl optionally substituted by halogen;

X is a lower alkylene, an oxa(lower)alkylene or an oxa; and $R^2$ is a phenyl optionally substituted by a substituent selected from the group consisting of alkyl, alkenyl, alkynyl, lower alkanoyl, lower alkoxy, phenyl, imidazolyl(lower)alkyl, piperidinyl(lower)alkyl, halogen, amino, lower alkanoylamino, mono(lower) alkylamino, di(lower)alkylamino, N-(lower)alkyl-N-(lower)alkanoylamino, N-(lower)alkyl-N-benzoylamino, lower alkylsulfonylamino, phenyl (lower)alkylamino, phenylsulfonylamino, benzoylamino, lower alkylsulfonyl, lower alkylsulfinyl, lower alkylthio, cyano, carboxy, lower alkoxycarbonyl, cyclo(lower)alkyloxycarbonyl, mono(lower)alkylcarbamoyl, nitro, halo(lower)alkyl, phenyl(lower)alkyl, phenyl(lower)alkenyl, phenyl(lower)alkoxy, (N-pyridyl-N(lower)alkylamino)(lower)alkoxy, cyclo(lower)alkyl(lower)alkoxy, cyclo(lower)alkyl(lower)alkyl, phenoxy(lower)alkyl, lower alkylsulfonyloxy(lower)alkyl, hydroxy(lower)alkyl, di(lower)alkylamino(lower)alkyl, phenyl(lower)alkoxy(lower)alkyl, phenylthio(lower)alkyl, thienyl(lower)alkoxy, pyridyloxy(lower)alkyl, phenyl(lower)alkylthio, phenylureido, lower alkoxy(lower)alkoxy, phenyl(lower)alkynyl, dioxothiazolidylidene(lower)alkyl and thienyl optionally substituted by halogen; naphthyl optionally substituted by halogen; a 4-phenylphenyl substituted by halogen; a thienyl optionally substituted by halogen; a benzothienyl optionally substituted by halogen; a quinolyl optionally substituted by halogen; or a benzooxolanyl optionally substituted by halogen, or a salt thereof.

5. The sulfonamide compound of claim 4, wherein, $R^1$ is an alkyl, an alkenyl, a phenyl(lower)alkenyl, a phenyl optionally substituted by a substituent selected from the group consisting of alkyl and alkenyl or a thienyl optionally substituted by halogen;

A is 3H-imidazo[4,5-b]pyridyl, pyrazolo[1,5-a]pyridyl, or indolizinyl, each of which is optionally substituted by one or two lower alkyl;

X is an alkylene; and $R^2$ is a phenyl optionally substituted by a substituent selected from the group consisting of alkyl, alkenyl, alkynyl, lower alkoxy, phenyl, halogen, di(lower)alkylamino, lower alkylthio, lower alkoxycarbonyl, nitro, halo(lower)alkyl, phenyl(lower)alkyl, phenyl(lower)alkenyl, phenyl(lower)alkoxy, cyclo(lower)alkyl(lower)alkoxy, phenoxy(lower)alkyl, phenyl(lower)alkoxy(lower)alkyl, phenyl(lower)alkynyl and thienyl optionally substituted by halogen; a naphthyl optionally substituted by halogen; or a 4-phenylphenyl substituted by halogen, or a salt thereof.

6. The sulfonamide compound of claim 5, wherein,

A is a 3H-imidazo[4,5-b]pyridyl, which is optionally substituted by lower alkyl; and $R^2$ is a phenyl substituted by halogen, said phenyl being optionally substituted by a substituent selected from the group consisting of alkyl, alkenyl, alkynyl, lower alkoxy, phenyl, halogen, di(lower)alkylamino, lower alkylthio, lower alkoxycarbonyl, nitro, halo(lower)alkyl, phenyl(lower)alkyl, phenyl(lower)alkenyl, phenyl(lower)alkoxy, cyclo(lower)alkyl(lower)alkoxy, phenoxy(lower)alkyl, phenyl(lower)alkoxy(lower)alkyl, phenyl(lower)alkynyl and thienyl optionally substituted by halogen, or a naphthyl substituted by halogen, or a salt thereof.

7. The sulfonamide compound of claim 6, wherein A is 3H-imidazo[4,5-b]pyridyl substituted by 1 or 2 lower alkyl, or a salt thereof.

8. A method for producing a compound of the formula (I)

$$R^1—SO_2NHCO—A—X—R^2 \qquad (I)$$

wherein:

$R^1$ is an optionally substituted alkyl, an optionally substituted alkenyl, an optionally substituted alkynyl, an optionally substituted cyclo(lower)alkyl, an optionally substituted aryl or an optionally substituted heterocyclic group;

A is imidazopyridyl, pyrrolopyridyl, pyrazolopyridyl or indolizinyl, each of which is optionally substituted by one or two lower alkyl;

X is an alkylene, an oxa, an oxa(lower)alkylene, a lower alkylene oxa, a carbonyl, a lower alkenylene, an optionally substituted imino, an optionally N-substituted imino(lower)alkylene, an N-substituted lower alkyleneimino, a thioxa(lower)alkylene or a lower alkylenethioxa; and $R^2$ is an optionally substituted aryl, an optionally substituted heterocyclic group or a substituted biphenylyl;

wherein, when these groups are substituted, the substituent is at least one member selected from the group consisting of alkyl, cyclo(lower)alkyl, alkenyl, alkynyl, lower alkanoyl, lower alkoxy, aryl, heterocycle(lower)alkyl, halogen, amino, substituted amino, lower alkylsulfonyl, lower alkylsulfinyl, lower alkylthio, cyano, carboxy, protected carboxy, carbamoyl, mono(lower)alkylcarbamoyl, di(lower)alkylcarbamoyl, nitro, halo(lower)alkyl, aryl(lower)alkyl, aryl(lower)alkenyl, aryl(lower)alkoxy, lower alkoxy substituted by substituted amino, cyclo(lower)alkyl(lower)alkoxy, cyclo(lower)alkyl(lower)alkyl, aryloxy(lower)alkyl, acyloxy(lower)alkyl, hydroxy(lower)alkyl, mono- or di(lower)alkylamino(lower)alkyl, aryl(lower)alkoxy(lower)alkyl, arylthio(lower)alkyl, heterocycle(lower)alkoxy, heterocycleoxy(lower)alkyl, aryl(lower)alkylthio, arylureido, lower alkoxy(lower)alkoxy, aryl(lower)alkynyl, lower alkyl substituted by optionally substituted divalent heterocyclic group, and heterocyclic group other than tetrazolyl, which is optionally substituted by lower alkyl or halogen, or a salt thereof, comprising (1) reacting a compound of the formula (II)

$$R^1—SO_2NH_2 \qquad (II)$$

wherein each symbol is as defined above, or a salt thereof, and a compound of the formula (III)

$$HOOC—A—X—R^2 \qquad (III)$$

wherein each symbol is as defined above, or a reactive derivative thereof at carboxy or a salt thereof, to give a compound of the formula (I)

$R^1-SO_2NHCO-A-X-R^2$ (I)

wherein each symbol is as defined above, or a salt thereof; or (2) reducing a compound of the formula (I-1)

$R^1-SO_2NHCO-A-X-R^{201}$ (I-1)

wherein $R^{201}$ is an optionally substituted aryl, an optionally substituted heterocyclic group or a substituted biphenylyl, all of which having at least alkynyl, aryl(lower)alkenyl, terminal nitro or terminal formyl and other symbols are as defined above, or a salt thereof, to give a compound of the formula (I-2)

$R^1-SO_2NHCO-A-X-R^{202}$ (I-2)

wherein $R^{202}$ is an optionally substituted aryl, an optionally substituted heterocyclic group or a substituted biphenylyl, all of which having at least alkyl, aryl(lower)alkyl, terminal amino or hydroxymethyl, and other symbols are as defined above, or a salt thereof; or (3) oxidizing a compound of the formula (I-3)

$R^1-SO_2NHCO-A-X-R^{203}$ (I-3)

wherein $R^{203}$ is an optionally substituted aryl, an optionally substituted heterocyclic group or a substituted biphenylyl, all of which having at least terminal formyl, and other symbols are as defined above, or a salt thereof, to give a compound of the formula (I-4)

$R^1-SO_2NHCO-A-X-R^{204}$ (I-4)

wherein $R^{204}$ is an optionally substituted aryl, an optionally substituted heterocyclic group or a substituted biphenylyl, all of which having at least carboxy, and other symbols are as defined above, or a salt thereof; or (4) acylating a compound of the formula (I-5)

$R^1-SO_2NHCO-A-X-R^{205}$ (I-5)

wherein $R^{205}$ is an optionally substituted aryl, an optionally substituted heterocyclic group or a substituted biphenylyl, all of which having at least hydroxy(lower)alkyl, and other symbols are as defined above, or a salt thereof, to give a compound of the formula (I-6)

$R^1-SO_2NHCO-A-X-R^{206}$ (I-6)

wherein $R^{206}$ is an optionally substituted aryl, an optionally substituted heterocyclic group or a substituted biphenylyl, all of which having at least acyloxy(lower)alkyl, and other symbols are as defined above, or a salt thereof; or (5) introducing an aryloxy group into a compound of the formula (I-6)

$R^1-SO_2NHCO-A-X-R^{206}$ (I-6)

wherein each symbol is as defined above, or a salt thereof, to give a compound of the formula (I-7)

$R^1-SO_2NHCO-A-X-R^{207}$ wherein $R^{207}$ is an optionally substituted aryl, an optionally substituted heterocyclic group or a substituted biphenylyl, all of which having at least aryloxy(lower)alkyl, and other symbols are as defined above, or a salt thereof; or (6) introducing a carboxy-protecting group into a compound of the formula (I-4)

$R^1-SO_2-NHCO-A-X-R^{204}$ (I-4)

wherein each symbol is as defined above, or a reactive derivative thereof, to give a compound of the formula (I-8)

$R^1-SO_2NHCO-A-X-R^{208}$ (I-8)

wherein $R^{208}$ is an optionally substituted aryl, an optionally substituted heterocyclic group or a substituted biphenylyl, all of which having at least protected carboxy, and other symbols are as defined above, or a salt thereof; or (7) amidating a compound of the formula (I-4)

$R^1-SO_2NHCO-A-X-R^{204}$ (I-4)

wherein each symbol is as defined above, or a reactive derivative thereof, to give a compound of the formula (I-9)

$R^1-SO_2NHCO-A-X-R^{209}$ (I-9)

wherein $R^{209}$ is an optionally substituted aryl, an optionally substituted heterocyclic group or a substituted biphenylyl, all of which having at least optionally substituted amide, and other symbols are as defined above, or a salt thereof; or (8) adding a nitrogen-containing heterocyclic group to a compound of the formula (I-10)

$R^1-SO_2NHCO-A-X-R^{210}$ (I-10)

wherein $R^{210}$ is an optionally substituted aryl having at least a halogen atom, and other symbols are as defined above, or a salt thereof, to give a compound of the formula (I-11)

$R^1-SO_2NHCO-A-X-R^{211}$ (I-11)

wherein $R^{211}$ is an aryl substituted by at least a heterocyclic group having nitrogen, and other symbols are as defined above, or a salt thereof.

9. A pharmaceutical composition comprising the sulfonamide compound of claim 1 or a pharmaceutically acceptable salt thereof.

10. A method for treating a disease treatable based on a blood sugar level-depressing activity or a disease treatable based on a cGMP-PDE inhibiting activity, smooth muscle relaxing activity, bronchodilating activity, vasodilating activity, smooth muscle cell suppressing activity or anti-allergic activity, comprising administering an effective amount of the sulfonamide compound of claim 1 or a pharmaceutically acceptable salt thereof to a subject in need thereof.

11. A method for producing a therapeutic agent comprising admixing the sulfonamide compound of claim 1 or a pharmaceutically acceptable salt thereof with a pharmaceutically acceptable excipient or carrier.

* * * * *